(12) United States Patent
Chandrasekhar et al.

(10) Patent No.: US 8,445,684 B2
(45) Date of Patent: May 21, 2013

(54) NICOTINIC ACETYLCHOLINE RECEPTOR LIGANDS AND THE USES THEREOF

(75) Inventors: Jayaraman Chandrasekhar, Trumbull, CT (US); Alan P. Kozikowski, Chicago, IL (US); Jianhua Liu, Chicago, IL (US); Werner Tueckmantel, Yorktown Heights, NY (US); Joel R. Walker, Schenectady, NY (US); Po-wai Yuen, Ann Arbor, MI (US)

(73) Assignees: PsycoGenics Inc., Tarrytown, NY (US); The Board of Trustee of the University of IL, Urbana, IL (US)

( * ) Notice: Subject to any disclaimer, the term of this patent is extended or adjusted under 35 U.S.C. 154(b) by 544 days.

(21) Appl. No.: 12/578,020

(22) Filed: Oct. 13, 2009

(65) Prior Publication Data

US 2010/0152450 A1     Jun. 17, 2010

Related U.S. Application Data

(60) Provisional application No. 61/105,167, filed on Oct. 14, 2008.

(51) Int. Cl.
| | |
|---|---|
| C07D 409/00 | (2006.01) |
| C07D 411/00 | (2006.01) |
| C07D 413/00 | (2006.01) |
| C07D 417/00 | (2006.01) |
| C07D 401/00 | (2006.01) |
| C07D 421/00 | (2006.01) |

(52) U.S. Cl.
USPC .......................... 546/256; 546/268.1

(58) Field of Classification Search .................. 546/256, 546/268.1
See application file for complete search history.

(56) References Cited

U.S. PATENT DOCUMENTS

| | | | |
|---|---|---|---|
| 5,371,188 A | 12/1994 | Heinemann et al. | |
| 5,629,325 A * | 5/1997 | Lin et al. | 514/318 |
| 5,914,328 A | 6/1999 | Lin et al. | |
| 5,948,793 A | 9/1999 | Abreo et al. | |
| 6,127,386 A * | 10/2000 | Lin et al. | 514/318 |
| 6,277,855 B1 | 8/2001 | Yerxa | |
| 6,437,138 B1 * | 8/2002 | Lin et al. | 546/268.1 |
| 8,030,300 B2 | 10/2011 | Kozikowski et al. | |
| 2007/0184490 A1 | 8/2007 | Verlinden et al. | |
| 2008/0132486 A1 | 6/2008 | Kozikowski et al. | |
| 2008/0176826 A1 | 7/2008 | Puhl et al. | |
| 2009/0221423 A1 | 9/2009 | Puhl et al. | |
| 2010/0129291 A1 | 5/2010 | Xiao et al. | |
| 2011/0269733 A1 | 11/2011 | Brown et al. | |
| 2011/0281836 A1 | 11/2011 | Walker et al. | |

FOREIGN PATENT DOCUMENTS

| | | |
|---|---|---|
| WO | 9010648 A1 | 9/1990 |
| WO | 9640682 A1 | 12/1996 |
| WO | 9746554 A1 | 12/1997 |
| WO | 98/25920 A1 | 6/1998 |
| WO | 9932480 A1 | 7/1999 |
| WO | 01/16107 A1 | 3/2001 |
| WO | 01/80844 A2 | 11/2001 |
| WO | 2005000806 A2 | 1/2005 |
| WO | 2006125641 A2 | 11/2006 |
| WO | 2007084535 A2 | 7/2007 |
| WO | 2007085565 A1 | 8/2007 |
| WO | 2008011484 A2 | 1/2008 |
| WO | 2009143507 * | 11/2009 |
| WO | 2009143507 A2 | 11/2009 |
| WO | 2010045212 A2 | 4/2010 |
| WO | 2010045212 A3 | 4/2010 |

OTHER PUBLICATIONS

Holladay et al., Bioorganic & Medicinal Chemistry Letters (1998), 8(19), 2797-2802.*
Chandrasekhar, Jayaraman et al., Nicotinic Acetylcholine Receptor Ligands and the Uses Thereof, WO 2010045212—International Preliminary Report on Patentability, published Apr. 19, 2011.
Chandrasekhar, Jayaraman et al., Nicotinic Acetylcholine Receptor Ligands and the Uses Thereof, EP 098211043.8—Supplementary Search Report and Opinion, published Apr. 3, 2012.
Kozikowski, A. P., et al., Chemistry and pharmacology of nicotinic ligands based on 6-[5-(azetidin-2-ylmethoxy) pyridin-3-yl]hex-5-yn-1-ol (AMOP-H-OH) for possible use in depression, ChemMedChem., 2009, 4(8): 1279-1291.
Kozikowski, A. P., et al., Chemical Medicine: Novel 10-Substituted Cytisine Derivatives with Increased Selectivity for ? 4?2 Nicotinic Acetylcholine Receptors, ChemMedChem., 2007, 2(8):1157-1161.
Yuan, H. et al., Computational evidence for the ligand selectivity to the alpha4beta2 and alpha3beta4 nicotinic acetylcholine receptors, Bioorg. Med. Chern., 2006, 14:7936-42.
Kozikowski, A. P., et al., Acetylenic Pyridines for Use in PET Imaging of Nicotinic Receptors, ChemMedChem, 2007, 2(1):54-57.
Xiao, Y., et al., Sazetidine-A, a novel ligand that desensitizes alpha4beta2 nicotinic acetylcholine receptors without activating them, Mol. Pharmacol., 2006, 70(4):1454-60.
Chellappan, S. K., et al., Synthesis and pharmacological evaluation of novel 9- and 10-substituted cytisine derivatives. Nicotinic ligands of enhanced subtype selectivity, J. Med. Chern., 2006, 49(9):2673-76.
Wei, Z. L. et al., Novel Pyridyl Ring C5 Substituted Analogues of Epibatidine and 3-(1-Methyl-2(S)pyrrolidinylmethoxy) pyridine (A-84543) as Highly Selective Agents for Neuronal Nicotinic Acetylcholine Receptors Containing b2 Subunits, J. Med. Chern., 2005, 48:1721-1724.
Wei, Z. L. et al., Synthesis and pharmacological characterization of bivalent ligauds of epibatidine at neuronal nicotinic acetylcholine receptors, Bioorg. Med. Chern. Lett., 2004, 14:1855-1858.
Wei, Z. L. et al., Synthesis, Nicotinic Acetylcholine Receptor Binding Affinities, and Molecular Modeling of Constrained Epibatidine Analogues, J. Med. Chern., 2003, 46:921-924.

(Continued)

*Primary Examiner* — Niloofar Rahmani
(74) *Attorney, Agent, or Firm* — Dennis A. Bennett; Michael Sertic

(57) ABSTRACT

The invention relates to pyridinyl nicotinic acetylcholine receptor ligands, compositions comprising an effective amount of a pyridinyl nicotinic acetylcholine receptor ligand and methods to treat or prevent a condition, such as depression and nicotine dependence, comprising administering to an animal in need thereof an effective amount of a pyridinyl nicotinic acetylcholine receptor ligand.

19 Claims, No Drawings

OTHER PUBLICATIONS

Wei, Z. L. et al., Synthesis of 5-endo-, 5-exo-, 6-endo- and 6-exo-hydroxylated analogues of epibatidine, Tetrahedron Letters, 2003, 44(19):3847-3850.

Brown, Milton et al., Design and Synthesis of New Neuronal NACHR Silent Desensitizers for Drug Abuse, U.S. Appl. No. 61/128,721, filed May 23, 2008, published Nov. 1, 2009.

Chandrasekhar, Jayaraman et al., Nicotinic Acetylcholine Receptor Ligands and the Uses Thereof, NZ 591936—New Zealand examination report.

Guandalini et al., Synthesis and pharmacological evaluation of some (pyridyl)cyclopropylmethyl amines and their methiodides as nicotinic receptor ligands, II Farmaco, 2001, 57, 487-496.

Zwart et al., Sazetidine-A is a Potent and Selective Agonist at Native and Recombinant Alpha4Beta2 Nicotinic Acetylcholine Receptors, Mol. Pharmacol., 2008, 73, 1838-1843.

* cited by examiner

NICOTINIC ACETYLCHOLINE RECEPTOR LIGANDS AND THE USES THEREOF

This application claims the benefit of priority of U.S. provisional application No. 61/105,167, filed Oct. 14, 2008, the disclosure of which is hereby incorporated by reference as if written herein in its entirety.

This invention was made with support from the U.S. Government under Contract No. NIH R01DA017980 and Contract No. NIH U19MH085193. The U.S. Government has certain rights to this invention.

FIELD OF THE INVENTION

The present invention relates to pyridinyl compounds that bind to nicotinic acetylcholine receptors, compositions comprising an effective amount of a pyridinyl nicotinic acetylcholine receptor ligand and methods for treating or preventing a neurological or psychiatric condition or for aiding smoking cessation, comprising administering to an animal in need thereof an effective amount of a pyridinyl nicotinic acetylcholine receptor ligand.

BACKGROUND OF THE INVENTION

Nicotinic acetylcholine receptors ("nAChRs") are ligand-gated ion channels found in cell plasma membranes in various tissues, including skeletal muscle at the neuromuscular junction, the peripheral nervous system, and the central nervous system. Nicotinic ligands have traditionally been classified as agonists (or partial agonists) that activate channel function, or competitive or noncompetitive antagonists, that block channel function. Ligands such as acetylcholine and nicotine are agonists, which act by binding to and effecting opening of nAChRs, and allowing the influx of cations into a cell to produce an excitatory response. nAChRs can also exist in a desensitized state, in which channel function is blocked in the presence of an agonist. Chronic nicotine exposure is associated with desensitization and inactivation of nAChRs.

nAChRs are potential therapeutic targets for the treatment of central and peripheral nervous system disorders, including neurodegenerative disorders (e.g., Alzheimer's disease and Parkinson's disease), age-related or disease-related cognitive impairment, dyskinesias, Tourette's syndrome, schizophrenia, attention-deficit hyperactivity disorder, depression, anxiety, mood disorders, pain, and methamphetamine addiction. In addition, nAChRs are the biological substrate through which nicotine acts in the body. Studies have shown that tobacco use is driven by nicotine addiction, in part because of nicotine's beneficial effects on cerebral functions, such as stabilizing mood and emotion and producing pro-cognitive and pro-attentive effects. Epidemiological studies have shown that people with cognitive or mood disorders are often nicotine dependents, which strongly suggests that nicotine use is a form of self-medication to treat such disorders. Thus, nAChRs are potential targets for treating or preventing nicotine addiction. Moreover, nicotinic acetylcholine receptors in the brain are thought to play a role not only in cholinergic neurotransmission at selected loci, but more globally in the modulation of neurotransmission by other chemical messengers (e.g., dopamine, norepinephrine or serotonin), and therefore, may play a role in central and peripheral nervous system disorders that do not result directly from irregularities in cholinergic neurotransmission.

Nicotinic acetylcholine receptor channels exist as a family of subtypes, and each subtype is composed of a homo- or hetero-pentamer of protein subunits encoded by one of 16 mammalian genes. Each nAChR subtype has a distinctive biophysical, physiological and pharmacological signature. In addition, each nAChR subtype has a unique tissue, regional, cellular and subcellular localization pattern. For example, the predominant nAChR subtype in the central nervous system is the $\alpha 4\beta 2$ subtype, which is composed of $\alpha 4$ and $\beta 2$ protein subunits that are known to assemble in a 2:3 ratio. The $\alpha 4\beta 2$ nAChR binds nicotine with high affinity.

The discovery of the subunit composition, characteristics and localization patterns of particular nAChR subtypes presents an opportunity in drug discovery for novel compounds that can be administered to treat central and peripheral nervous system disorders, or to aid in smoking cessation, by selectively modulating the activity of particular receptor subtypes found predominantly in the targeted tissues. Subtype-selective drugs also have the potential to reduce side effects, and to be critical tools to help identify and distinguish functions and responses mediated by particular receptor subtypes.

The publication "Neuronal nicotinic acetylcholine receptors as targets for drug discovery," of Holladay et al. (*J. Med. Chem.* 40(26):4169-4194 (1997)) describes the characteristics of different nAChR subtypes and discusses the potential development of selective agonists and antagonists of nAChRs.

U.S. Pat. Nos. 5,629,325, 6,127,386 and 6,437,138 and International PCT Publication No. WO 97/46554 to Lin et al. describe 3-pyridyloxymethyl heterocyclic ether compounds useful for controlling chemical synaptic transmission.

International PCT Publication No. WO 2005/000806 A2 describes ligands for nicotinic acetylcholine receptors and methods of making and using them.

U.S. Pat. No. 6,277,855 to Yerxa describes methods of treating dry eye disease with nicotinic acetylcholine receptor agonists.

International PCT Publication Nos. WO 2006/125641 A2 and WO 07/085565 A1 describe methods of using 3-pyridyl derivatives as pesticides.

International PCT Publication No. WO 2008/132486 to Kozikowski et al. describes ligands for nicotinic acetylcholine receptors, and methods of making and using them.

International PCT Publication No. WO 2008/011484 A2 to Xiao and Kellar describes nicotinic acetylcholine receptor desensitizers and methods of selecting, testing, and using them.

The publication "Synthesis and pharmacological evaluation of some (pyridyl)cyclopropylmethyl amines and their methiodides as nicotinic receptor ligands" of Guandalini et al. (*Il Farmaco* 57: 487-496 (2001)) describes the synthesis of a number of pyridyl cyclopropylamine compounds and their activities at nicotinic acetylcholine receptors.

The publication "Sazetidine-A is a potent and selective agonist at native and recombinant $\alpha 4\beta 2$ nicotinic acetylcholine receptors" of Zwart et al. (*Molecular Pharmacol.* 73:1838-1848 (2008)) describes the agonist activity of sazetidine-A at $\alpha 4\beta 2$ nicotinic acetylcholine receptors.

Citation of any reference in this section of the application is not to be construed as an admission that such reference is prior art to the present application.

SUMMARY OF THE INVENTION

In one aspect, the invention provides new compounds that exhibit affinity for a nicotinic acetylcholine receptor.

In certain embodiments of the invention, such new compounds desensitize the nicotinic acetylcholine receptor.

In certain embodiments of the invention, such new compounds activate or partially activate a nicotinic acetylcholine receptor.

In certain embodiments of the invention, such new compounds exhibit higher affinity for a nicotinic acetylcholine receptor of the α4β2 subtype than for other nicotinic acetylcholine receptor subtypes.

Certain new compounds of the invention can be used to treat an animal suffering a condition, which includes, but is not limited to, a neurological or psychiatric condition.

In certain embodiments of the invention, such new compounds can be used to treat a neurogenerative disorder, such as Alzheimer's disease or Parkinson's disease.

In certain embodiments of the invention, such new compounds can be used to treat age-related or disease-related cognitive impairment.

Certain new compounds of the invention can be used to treat an animal suffering from dyskinesias.

In certain embodiments of the invention, such new compounds can be used to treat an animal suffering from attention-deficit hyperactivity disorder.

Certain new compounds of the invention can be used to treat an animal suffering from Tourette's syndrome.

In certain embodiments of the invention, such new compounds can be used to treat an animal suffering from depression.

In certain embodiments of the invention, such new compounds can be used to treat an animal suffering from schizophrenia.

Certain new compounds of the invention can be used to treat an animal suffering from nicotine addiction.

In certain embodiments of the invention, such new compounds can be used to treat an animal suffering from pain.

In certain embodiments of the invention, the compounds of the invention can be used to treat an animal suffering from anxiety.

Certain new compounds of the invention can be used to treat an animal suffering from a mood disorder.

In certain embodiments of the invention, the compounds of the invention can be used to treat an animal suffering from methamphetamine addiction.

In a further aspect, the invention provides methods of treating or preventing a condition in an animal by administering one or more of the new compounds ("pyridinyl nicotinic acetylcholine receptor ligands") of the invention to an animal in need of such treatment. In certain embodiments, such new pyridinyl nicotinic acetylcholine receptor ligands effectively treat a neurological condition or a psychiatric condition in the animal, while producing fewer or reduced side effects compared to previously available compounds.

In yet another aspect, the invention provides methods of treating nicotine dependence by administering one or more pyridinyl nicotinic acetylcholine receptor ligands of the invention. In certain embodiments, such new pyridinyl nicotinic acetylcholine receptor ligands effectively treat nicotine addiction while producing fewer or reduced side effects compared to previously available medications for treating nicotine addiction.

In another aspect, the invention provides methods of treating depression by administering one or more pyridinyl nicotinic acetylcholine receptor ligands of the invention. In certain embodiments, such new pyridinyl nicotinic acetylcholine receptor ligands effectively treat depression while producing fewer or reduced side effects compared to previously available antidepressants.

Another aspect of the invention is to provide novel intermediates for the synthesis of such new pyridinyl nicotinic acetylcholine receptor ligands.

The invention encompasses compounds of formula I:

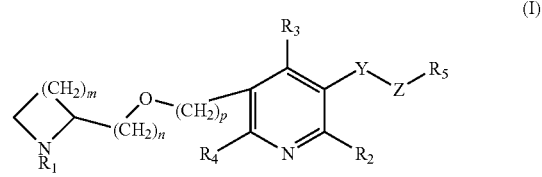

(I)

wherein $R_1$ is hydrogen, $C_1$-$C_6$ straight chain alkyl, $C_3$-$C_6$ branched chain alkyl, allyl, or $C_3$-$C_6$ cycloalkyl;

$R_2$, $R_3$ and $R_4$ are each independently hydrogen, $C_1$-$C_6$ straight chain alkyl, $C_3$-$C_6$ branched chain alkyl, $C_3$-$C_6$ cycloalkyl or $C_1$-$C_6$ alkyl substituted with one or more fluorine atoms;

Y is a bond, or —$(CH_2)_q$—, optionally substituted with one or two groups independently selected from methyl, ethyl, propyl, isopropyl, and cyclopropyl;

Z is $C_3$-$C_6$ cycloalkyl or a $C_4$-$C_6$ partially-unsaturated carbocycle, and wherein Z is optionally substituted with one or two $C_1$-$C_3$ alkyl groups;

$R_5$ is $C_1$-$C_6$ straight chain alkyl; $C_3$-$C_6$ branched chain alkyl; $C_1$-$C_6$ hydroxyalkyl; alkoxyalkyl in which the alkoxy and alkyl portions each independently contain from 1 to 6 carbon atoms; $C_1$-$C_6$ fluoroalkyl; arylalkyl in which the alkyl portion contains from 1 to 6 carbon atoms; arylalkoxy in which the alkoxy portion contains from 1 to 6 carbon atoms; aryl; biaryl; heteroarylalkyl in which the alkyl portion contains from 1 to 6 carbon atoms; heteroarylalkoxy in which the alkoxy portion contains from 1 to 6 carbon atoms; —$(CH_2)_{1-6}$—O—$(CH_2)_{0-6}$-aryl; —$(CH_2)_{1-6}$—O—$(CH_2)_{0-6}$-heteroaryl; —$(CH_2)_{0-6}$—O—$(CH_2)_{0-6}$—$C_3$-$C_6$ cycloalkyl; heteroaryl; or a four- to six-membered saturated heterocycle, with the proviso that $R_5$ is not arylalkoxy or heteroarylalkoxy when Z is $C_3$-cycloalkyl;

wherein $R_5$ is optionally substituted with one or two substituents independently selected from $C_1$-$C_6$ straight chain alkyl; $C_3$-$C_6$ branched chain alkyl; $C_1$-$C_6$ fluoroalkyl; $C_1$-$C_6$ hydroxyalkyl; aryloxy; heteroaryloxy; $C_3$-$C_6$ cycloalkyloxy; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —$NH_2$; $C_1$-$C_6$ alkylthio; —$CF_3$; $C_1$-$C_6$ monoalkylamino; $C_1$-$C_6$ dialkylamino; carboxyl; and $C_2$-$C_6$ alkoxycarbonyl;

and wherein if $R_5$ comprises an aryl group or a heteroaryl group, then $R_5$ is optionally substituted with one or two substituents selected from $C_1$-$C_6$ straight chain alkyl; $C_3$-$C_6$ branched chain alkyl; $C_1$-$C_6$ fluoroalkyl; $C_1$-$C_6$ hydroxyalkyl; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —$NH_2$; $C_1$-$C_6$ alkylthio; —$CF_3$; $C_1$-$C_6$ monoalkylamino; $C_1$-$C_6$ dialkylamino; carboxyl; $C_2$-$C_6$ alkoxycarbonyl; Cl and $OCF_3$;

or $R_5$ is —$(CH_2)_rNR'R^{vi}$; —$(CH_2)_rC(O)NR'R^{vi}$; —$(CH_2)_r$ $C(O)OR^{ix}$; —$(CH_2)_rSR^{viii}$; —$(CH_2)_rSO_2R^{ix}$ or —$(CH_2)_rSOR^{ix}$;

wherein:

$R^v$ and $R^{vi}$ are each independently hydrogen, $C_1$-$C_6$ straight chain alkyl; $C_3$-$C_6$ branched chain alkyl; $C_3$-$C_6$ cycloalkyl; aryl; arylalkyl in which the alkyl portion contains 1 to 6 carbon atoms; —(CO)$R^{vii}$; —(CO)O$R^{vii}$; —SO$_2R^{vii}$; or $R^v$ and $R^{vi}$ form a four- to six-membered saturated heterocyclic ring having a single nitrogen atom; wherein if one of $R^v$ and $R^{vi}$ is —(CO)$R^{vii}$ or —SO$_2R^{vii}$, the other is not —(CO)$R^{vii}$ or —SO$_2R^{vii}$;

$R^{vii}$ is $C_1$-$C_6$ straight chain alkyl which is optionally substituted with one or two hydroxyl groups; $C_3$-$C_6$ branched chain alkyl which is optionally substituted with one or two hydroxyl groups; $C_3$-$C_6$ cycloalkyl, wherein when the cycloalkyl group contains more than 3 carbon atoms, it is optionally substituted with one or two hydroxyl groups; aryl which is optionally substituted with 1 or 2 fluorine atoms, one hydroxyl group, one hydroxyl group and one fluorine atom, $C_1$-$C_6$ straight chain alkyl, $C_3$-$C_6$ branched chain alkyl or $C_3$-$C_6$ cycloalkyl, and wherein if the $C_1$-$C_6$ straight chain alkyl group, the $C_3$-$C_6$ branched chain alkyl group or the $C_3$-$C_6$ cycloalkyl group is substituted, then no more than one heteroatom selected from the oxygen atom in the hydroxyl group and the sulfur atom in —SO$_2R^{vii}$ is bound to any single carbon atom; arylalkyl in which the alkyl portion contains from 1 to 6 carbon atoms; heteroaryl; or heteroarylalkyl in which the alkyl portion contains from 1 to 6 carbon atoms; or when $R^v$ is not H and $R^{vi}$ is either —(CO)$R^{vii}$ or —SO$_2R^{vii}$, $R^v$ and $R^{vii}$ can be taken together to form a 4- to 7-membered ring;

$R^{viii}$ is hydrogen, $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —(CH$_2$)$_r$S$R^{viii}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; or $R^{viii}$ is —C(O)$R^x$;

$R^{ix}$ is $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —(CH$_2$)$_r$SO$_2R^{ix}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, one hydroxyl group and one fluorine atom, or $C_1$-$C_6$ hydroxyalkyl; heteroaryl that is optionally substituted with 1 or 2 fluorine atoms, one hydroxyl group, one hydroxyl group and one fluorine atom, or $C_1$-$C_6$ hydroxyalkyl, wherein the number of substituents does not exceed the number of available C—H and N—H bonds; or arylalkyl in which the alkyl portion contains from 1 to 6 carbon atoms and the aryl portion is optionally substituted with 1 or 2 fluorine atoms, one hydroxyl group, one hydroxyl group and one fluorine atom, or $C_1$-$C_6$ hydroxyalkyl;

$R^x$ is $C_1$-$C_6$ straight chain alkyl optionally substituted with one or two hydroxyl groups or $C_1$-$C_6$ alkoxy groups, wherein if the $C_1$-$C_6$ alkyl group is substituted, then no more than one heteroatom selected from the oxygen atom in the hydroxyl group and the oxygen atom in the alkoxy group is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; arylalkyl in which the alkyl portion contains from 1 to 6 carbon atoms and in which the aryl portion is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; $C_1$-$C_6$ monoalkylamino; or $C_1$-$C_6$ dialkylamino;

wherein if $R_5$ contains at least one saturated carbon atom and said $R_5$ is substituted with two substituents independently selected from $C_1$-$C_6$ alkoxy, alkoxyalkoxy in which the alkoxy portions each independently contain from 1 to 6 carbon atoms, F, —OH, —NH$_2$, $C_1$-$C_6$ monoalkylamino, $C_1$-$C_6$ dialkylamino, and $C_1$-$C_6$ alkylthio, then said two substituents are not bound to the same saturated carbon atom;

m is an integer ranging from 1 to 3;

n is an integer ranging from 1 to 2;

p is an integer ranging from 0 to 2;

wherein when n is 2 or p is 2, the carbon atom linked to the oxygen atom can be substituted with a $C_1$-$C_6$ straight chain alkyl group or a $C_3$-$C_6$ branched chain alkyl group;

q is an integer ranging from 1 to 5;

r is an integer ranging from 0 to 5;

and pharmaceutically acceptable derivatives thereof.

In another embodiment, the invention encompasses compounds of formula I, wherein all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —(CH$_2$)$_r$N$R^vR^{vi}$ wherein $R^v$ and $R^{vi}$ are each independently hydrogen, $C_1$-$C_6$ straight chain alkyl, $C_3$-$C_6$ branched chain alkyl or $C_3$-$C_6$ cycloalkyl; —(CH$_2$)$_r$S$R^{viii}$ when $R^{viii}$ is $C_1$-$C_6$ straight chain alkyl, $C_3$-$C_6$ branched chain alkyl, or $C_3$-$C_6$ cycloalkyl; —(CH$_2$)$_r$SO$_2R^{ix}$, —(CH$_2$)$_r$SO$R^{ix}$ or —(CH$_2$)$_r$C(O)O$R^{ix}$ when $R^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —(CH$_2$)$_r$N$R^vR^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl.

The invention encompasses compounds of formula II:

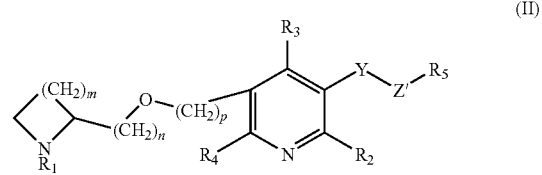

(II)

wherein

Z' is a four- to six-membered saturated heterocycle; a five- or six-membered partially-unsaturated heterocycle; or a saturated azabicycle having 4 to 8 carbon atoms; and wherein Z' is linked to Y through a carbon atom or a nitrogen atom in the Z' ring, and all other variables have the same meanings as set forth above for the compounds of the formula I, except $R_5$ may be hydrogen when Z' is a saturated azabicycle having 4 to 8 carbon atoms, and pharmaceutically acceptable derivatives thereof.

In another embodiment, the invention encompasses compounds of formula II, wherein all variables have the same meanings as set forth above, except $R_5$ may be hydrogen when Z' is a 5- or 6-membered partially unsaturated heterocycle or saturated azabicycle having 4 to 8 carbon atoms, or $R_5$ may be hydrogen when m is 1 and Z' is a four- to six-membered saturated heterocycle and with the proviso that when Z' is a 4- to 6-membered saturated heterocycle or a 5 to 6-membered partially unsaturated heterocycle, m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r NR^v R^{vi}$ when one of $R^v$ and $R^{vi}$ is hydrogen, and the other of $R^v$ and $R^{vi}$ is $C_1$-$C_6$ straight chain alkyl, $C_3$-$C_6$ branched chain alkyl or $C_3$-$C_6$ cycloalkyl or when both $R^v$ and $R^{vi}$ are independently $C_1$-$C_6$ straight chain alkyl, $C_3$-$C_6$ branched chain alkyl or $C_3$-$C_6$ cycloalkyl; —$(CH_2)_r SR^{viii}$ when $R^{viii}$ is $C_1$-$C_6$ straight chain alkyl, $C_3$-$C_6$ branched chain alkyl, or $C_3$-$C_6$ cycloalkyl; —$(CH_2)_r SO_2 R^{ix}$, —$(CH_2)_r SOR^{ix}$ or —$(CH_2)_r C(O)OR^{ix}$ when $R^{ix}$ is $C_1$-$C_6$ straight chain alkyl, $C_3$-$C_6$ branched chain alkyl or $C_3$-$C_6$ cycloalkyl.

The invention encompasses compounds of the formula III:

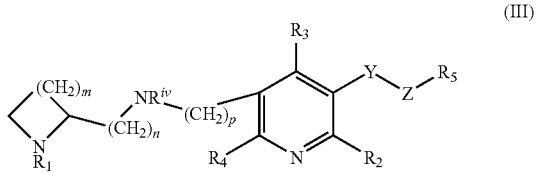

(III)

wherein $R^{iv}$ is hydrogen, $C_1$-$C_6$ straight chain alkyl, $C_3$-$C_6$ branched chain alkyl, $C_3$-$C_6$ cycloalkyl, or an acyl group having the formula:

wherein $R^i$ is a $C_1$-$C_6$ straight chain alkyl group, a $C_3$-$C_6$ branched chain alkyl group or a $C_3$-$C_6$ cycloalkyl group, and all other variables have the same meanings as set forth above for the compounds of the formula I, except $R_5$ may be hydrogen when Z is any one of the defined Z substituents, and pharmaceutically acceptable derivatives thereof.

The present invention encompasses compounds of formula IV:

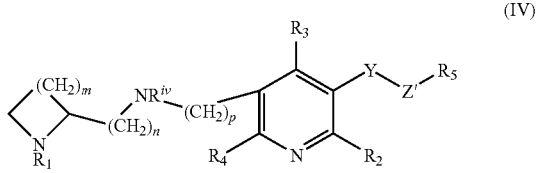

(IV)

wherein $R^{iv}$ is hydrogen, $C_1$-$C_6$ straight chain alkyl, $C_3$-$C_6$ branched chain alkyl, $C_3$-$C_6$ cycloalkyl, or an acyl group having the formula:

wherein $R^i$ is a $C_1$-$C_6$ straight chain alkyl group, a $C_3$-$C_6$ branched chain alkyl group or a $C_3$-$C_6$ cycloalkyl group, and all other variables have the same meanings as set forth above for the compounds of the formula II, except $R_5$ may be hydrogen when Z' is any one of the defined Z' substituents, and pharmaceutically acceptable derivatives thereof.

The invention encompasses compounds of the formula V:

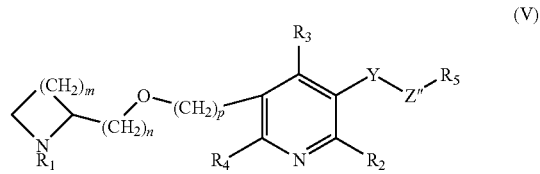

(V)

wherein $R_1$ is hydrogen, $C_1$-$C_6$ straight chain alkyl, $C_3$-$C_6$ branched chain alkyl, allyl, or $C_3$-$C_6$ cycloalkyl;

$R_2$, $R_3$ and $R_4$ are each independently hydrogen, $C_1$-$C_6$ straight chain alkyl, $C_3$-$C_6$ branched chain alkyl, $C_3$-$C_6$ cycloalkyl and $C_1$-$C_6$ alkyl substituted with one or more fluorine atoms;

Y is a bond, or —$(CH_2)_q$—, optionally substituted with one or two groups independently selected from methyl, ethyl, propyl, isopropyl, and cyclopropyl;

Z" is an aryl group; or a partially saturated $C_9$-$C_{16}$ carbocyclic group having a least one aromatic ring;

$R_5$ is $C_1$-$C_6$ hydroxyalkyl; alkoxyalkyl in which the alkoxy and alkyl portions each independently contain from 1 to 6 carbon atoms, provided that when Z" is an aryl group the alkoxyalkyl is substituted with one or two substituents which are members of the optional $R_5$ substituents described in formula I, other than a substituent which is straight or branched chain alkyl; or $R_5$ is arylalkyl in which the alkyl portion contains from 1 to 6 carbon atoms; arylalkoxy in which the alkoxy portion contains from 1 to 6 carbon atoms; aryl; biaryl; heteroarylalkyl in which the alkyl portion contains from 1 to 6 carbon atoms; heteroarylalkoxy in which the alkoxy portion contains from 1 to 6 carbon atoms; —$(CH_2)_{1-6}$—O—$(CH_2)_{0-6}$-aryl; —$(CH_2)_{1-6}$—O—$(CH_2)_{0-6}$-heteroaryl; —$(CH_2)_{0-6}$—O—$(CH_2)_{0-6}$—$C_3$-$C_6$ cycloalkyl; heteroaryl; or a four- to six-membered saturated heterocycle;

or $R_5$ may be hydrogen when Z" is a partially saturated $C_9$-$C_{16}$ carbocyclic group having at least one aromatic ring;

wherein Z" and $R_5$ are each independently optionally substituted with one or two substituents selected from $C_1$-$C_6$ straight chain alkyl; $C_3$-$C_6$ branched chain alkyl; $C_1$-$C_6$ fluoroalkyl; $C_1$-$C_6$ hydroxyalkyl; aryloxy; heteroaryloxy; $C_3$-$C_6$ cycloalkyloxy; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —$NH_2$; $C_1$-$C_6$ alkylthio; $CF_3$; $C_1$-$C_6$ monoalkylamino; $C_1$-$C_6$ dialkylamino; carboxyl; and $C_2$-$C_6$ alkoxycarbonyl; and wherein if $R_5$ comprises an aryl group or a heteroaryl group, then $R_5$ is optionally substituted with one or two substituents selected from $C_1$-$C_6$ straight chain alkyl; $C_3$-$C_6$ branched chain alkyl; $C_1$-$C_6$ fluoroalkyl; $C_1$-$C_6$ hydroxyalkyl; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —NH$_2$; $C_1$-$C_6$ alkylthio; —CF$_3$; $C_1$-$C_6$ monoalkylamino; $C_1$-$C_6$ dialkylamino; carboxyl; $C_2$-$C_6$ alkoxycarbonyl; Cl and OCF$_3$;

or $R_5$ is —(CH$_2$)$_r$NR'R$^{vi}$; —(CH$_2$)$_r$C(O)NR'R$^{vi}$; —(CH$_2$)$_r$C(O)OR$^{ix}$; —(CH$_2$)$_r$SR$^{viii}$; —(CH$_2$)$_r$SO$_2$R$^{ix}$; or —(CH$_2$)$_r$SOR$^{ix}$, wherein:

R$^v$ and R$^{vi}$ are each independently hydrogen, $C_1$-$C_6$ straight chain alkyl, $C_3$-$C_6$ branched chain alkyl; $C_3$-$C_6$ cycloalkyl; aryl; arylalkyl in which the alkyl portion contains 1 to 6 carbon atoms; —(CO)R$^{vii}$; —(CO)OR$^{vii}$; —SO$_2$R$^{vii}$, or R$^v$ and R$^{vi}$ form a four- to six-membered saturated heterocyclic ring having a single nitrogen atom; wherein if one of R$^v$ and R$^{vi}$ is —(CO)R$^{vii}$ or —SO$_2$R$^{vii}$, the other is not —(CO)R$^{vii}$ or —SO$_2$R$^{vii}$;

R$^{vii}$ is $C_1$-$C_6$ straight chain alkyl which is optionally substituted with one or two hydroxyl groups; $C_3$-$C_6$ branched chain alkyl which is optionally substituted with one or two hydroxyl groups; $C_3$-$C_6$ cycloalkyl, wherein when the cycloalkyl group contains more than 3 carbon atoms, it is optionally substituted with one or two hydroxyl groups; aryl which is optionally substituted with 1 or 2 fluorine atoms, one hydroxyl group, one hydroxyl group and one fluorine atom, $C_1$-$C_6$ straight chain alkyl, $C_3$-$C_6$ branched chain alkyl or $C_3$-$C_6$ cycloalkyl, and wherein if the $C_1$-$C_6$ straight chain alkyl group, the $C_3$-$C_6$ branched chain alkyl group or the $C_3$-$C_6$ cycloalkyl group is substituted, then no more than one heteroatom selected from the oxygen atom in the hydroxyl group and the sulfur atom in —SO$_2$R$^{vii}$ is bound to any single carbon atom; arylalkyl in which the alkyl portion contains from 1 to 6 carbon atoms; heteroaryl; or heteroarylalkyl in which the alkyl portion contains from 1 to 6 carbon atoms; or when R$^v$ is not H and R$^{vi}$ is either —(CO)R$^{vii}$ or —SO$_2$R$^{vii}$, R$^v$ and R$^{vii}$ can be taken together to form a 4- to 7-membered ring;

R$^{viii}$ is hydrogen, $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —(CH$_2$)$_r$SR$^{viii}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; or R$^{viii}$ is —C(O)R$^x$;

R$^{ix}$ is $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —(CH$_2$)$_r$SO$_2$R$^{ix}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, one hydroxyl group and one fluorine atom, or $C_1$-$C_6$ hydroxyalkyl; heteroaryl that is optionally substituted with 1 or 2 fluorine atoms, one hydroxyl group, one hydroxyl group and one fluorine atom, or $C_1$-$C_6$ hydroxyalkyl, wherein the number of substituents does not exceed the number of available C—H and N—H bonds; or arylalkyl in which the alkyl portion contains from 1 to 6 carbon atoms and the aryl portion is optionally substituted with 1 or 2 fluorine atoms, one hydroxyl group, one hydroxyl group and one fluorine atom, or $C_1$-$C_6$ hydroxyalkyl;

R$^x$ is $C_1$-$C_6$ straight chain alkyl optionally substituted with one or two hydroxyl groups or $C_1$-$C_6$ alkoxy groups, wherein if the $C_1$-$C_6$ alkyl group is substituted, then no more than one heteroatom selected from the oxygen atom in the hydroxyl group and the oxygen atom in the alkoxy group is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; arylalkyl in which the alkyl portion contains from 1 to 6 carbon atoms and in which the aryl portion is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; $C_1$-$C_6$ monoalkylamino; or $C_1$-$C_6$ dialkylamino;

wherein if $R_5$ contains at least one saturated carbon atom and said $R_5$ is substituted with two substituents selected from $C_1$-$C_6$ alkoxy, alkoxyalkoxy in which the alkoxy portions each independently contain from 1 to 6 carbon atoms, F, —OH, —NH$_2$, $C_1$-$C_6$ monoalkylamino, $C_1$-$C_6$ dialkylamino, and $C_1$-$C_6$ alkylthio, said two substituents are not bound to the same saturated carbon atom;

m is an integer ranging from 1 to 3;

n is an integer ranging from 1 to 2;

p is an integer ranging from 0 to 2;

wherein when n is 2 or p is 2, the carbon atom linked to the oxygen atom can be substituted with a $C_1$-$C_6$ straight chain alkyl group or a $C_3$-$C_6$ branched chain alkyl group;

q is an integer ranging from 1 to 5;

r is an integer ranging from 0 to 5; and pharmaceutically acceptable derivatives thereof.

In another embodiment, the invention encompasses compounds of formula V, wherein all variables have the same meanings as set forth above for the compounds of formula V, and with the proviso that when Z" is an aryl group, m is 2 and Y is a bond, $R_5$ is not phenylalkyl in which the alkyl portion contains from 1 to 6 carbon atoms; —(CH$_2$)$_r$NR'R$^{vi}$ when R$^v$ and R$^{vi}$ are each independently hydrogen, $C_1$-$C_6$ straight chain alkyl, $C_3$-$C_6$ branched chain alkyl or $C_3$-$C_6$ cycloalkyl; —(CH$_2$)$_r$SR$^{viii}$ when R$^{viii}$ is $C_1$-$C_6$ straight chain alkyl, $C_3$-$C_6$ branched chain alkyl, or $C_3$-$C_6$ cycloalkyl; —(CH$_2$)$_r$SO$_2$R$^{ix}$, —(CH$_2$)$_r$SOR$^{ix}$ or —(CH$_2$)$_r$C(O)OR$^{ix}$ when R$^{ix}$ is $C_1$-$C_6$ straight chain alkyl, $C_3$-$C_6$ branched chain alkyl or $C_3$-$C_6$ cycloalkyl; and with the proviso that when Z" is an aryl group, m is 1 or 3 and Y is a bond, $R_5$ is not —(CH$_2$)$_r$NR'R$^{vi}$ when both R$^v$ and R$^{vi}$ are hydrogen, or when one of R$^v$ and R$^{vi}$ is hydrogen and the other of R$^v$ and R$^{vi}$ is $C_1$-$C_6$ straight chain alkyl, $C_3$-$C_6$ branched chain alkyl or $C_3$-$C_6$ cycloalkyl.

The invention encompasses the compounds of formula VI:

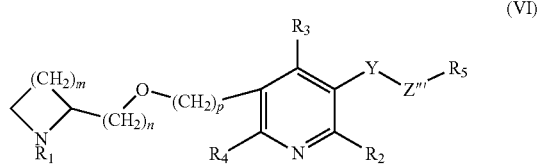

(VI)

wherein $R_1$ is hydrogen, $C_1$-$C_6$ straight chain alkyl, $C_3$-$C_6$ branched chain alkyl, allyl, or $C_3$-$C_6$ cycloalkyl;

$R_2$, $R_3$ and $R_4$ are each independently hydrogen, $C_1$-$C_6$ straight chain alkyl, $C_3$-$C_6$ branched chain alkyl, $C_3$-$C_6$ cycloalkyl and $C_1$-$C_6$ alkyl substituted with one or more fluorine atoms;

Y is a bond, or —$(CH_2)_q$—, optionally substituted with one or two groups independently selected from methyl, ethyl, propyl, isopropyl, and cyclopropyl;

Z''' is a heteroaryl group or a $C_8$-$C_9$ partially saturated bicyclic heteroaryl group;

$R_5$ is $C_1$-$C_6$ hydroxyalkyl; alkoxyalkyl in which the alkoxy and alkyl portions each independently contain from 1 to 6 carbon atoms, provided that when Z''' is a heteroaryl group the alkoxyalkyl is substituted with one or two substituents which are members of the optional $R_5$ substituents described in formula I, other than a substituent which is straight or branched chain alkyl; or $R_5$ is arylalkyl in which the alkyl portion contains from 1 to 6 carbon atoms; arylalkoxy in which the alkoxy portion contains from 1 to 6 carbon atoms; aryl; biaryl; heteroarylalkyl in which the alkyl portion contains from 1 to 6 carbon atoms; heteroarylalkoxy in which the alkoxy portion contains from 1 to 6 carbon atoms; —$(CH_2)_{1-6}$—O—$(CH_2)_{0-6}$-aryl; —$(CH_2)_{1-6}$—O—$(CH_2)_{0-6}$-heteroaryl; —$(CH_2)_{0-6}$—O—$(CH_2)_{0-6}$—$C_3$-$C_6$ cycloalkyl; heteroaryl; or a four- to six-membered saturated heterocycle;

or $R_5$ may be hydrogen when Z''' is a $C_8$-$C_9$ partially saturated bicyclic heteroaryl group;

wherein Z''' and $R_5$ are each independently optionally substituted with one or two substituents selected from $C_1$-$C_6$ straight chain alkyl; $C_3$-$C_6$ branched chain alkyl; $C_1$-$C_6$ fluoroalkyl; $C_1$-$C_6$ hydroxyalkyl; aryloxy; heteroaryloxy; $C_3$-$C_6$ cycloalkyloxy; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —$NH_2$; $C_1$-$C_6$ alkylthio; $CF_3$; $C_1$-$C_6$ monoalkylamino; $C_1$-$C_6$ dialkylamino; carboxyl; and $C_2$-$C_6$ alkoxycarbonyl; and wherein if $R_5$ comprises an aryl group or a heteroaryl group, then $R_5$ is optionally substituted with one or two substituents selected from $C_1$-$C_6$ straight chain alkyl; $C_3$-$C_6$ branched chain alkyl; $C_1$-$C_6$ fluoroalkyl; $C_1$-$C_6$ hydroxyalkyl; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —$NH_2$; $C_1$-$C_6$ alkylthio; —$CF_3$; $C_1$-$C_6$ monoalkylamino; $C_1$-$C_6$ dialkylamino; carboxyl; $C_2$-$C_6$ alkoxycarbonyl; Cl and $OCF_3$;

or $R_5$ is —$(CH_2)_rNR'R^{vi}$; —$(CH_2)_rC(O)NR'R^{vi}$; —$(CH_2)_r$ $C(O)OR^{ix}$; —$(CH_2)_rSR^{viii}$; —$(CH_2)_rSO_2R^{ix}$; or —$(CH_2)_r SOR^{ix}$, wherein:

$R^v$ and $R^{vi}$ are each independently hydrogen, $C_1$-$C_6$ straight chain alkyl, $C_3$-$C_6$ branched chain alkyl; $C_3$-$C_6$ cycloalkyl; aryl; arylalkyl in which the alkyl portion contains 1 to 6 carbon atoms; —$(CO)R^{vii}$; —$(CO)OR^{vii}$; —$SO_2R^{vii}$, or $R^v$ and $R^{vi}$ form a four- or six-membered saturated heterocyclic ring having a single nitrogen atom; wherein if one of $R^v$ and $R^{vi}$ is —$(CO)R^{vii}$ or —$SO_2R^{vii}$, the other is not —$(CO)R^{vii}$ or —$SO_2R^{vii}$;

$R^{vii}$ is $C_1$-$C_6$ straight chain alkyl which is optionally substituted with one or two hydroxyl groups; $C_3$-$C_6$ branched chain alkyl which is optionally substituted with one or two hydroxyl groups; $C_3$-$C_6$ cycloalkyl, wherein when the cycloalkyl group contains more than 3 carbon atoms, it is optionally substituted with one or two hydroxyl groups; aryl which is optionally substituted with 1 or 2 fluorine atoms, one hydroxyl group, one hydroxyl group and one fluorine atom, $C_1$-$C_6$ straight chain alkyl, $C_3$-$C_6$ branched chain alkyl or $C_3$-$C_6$ cycloalkyl, and wherein if the $C_1$-$C_6$ straight chain alkyl group, the $C_3$-$C_6$ branched chain alkyl group or the $C_3$-$C_6$ cycloalkyl group is substituted, then no more than one heteroatom selected from the oxygen atom in the hydroxyl group and the sulfur atom in —$SO_2R^{vii}$ is bound to any single carbon atom; arylalkyl in which the alkyl portion contains from 1 to 6 carbon atoms; heteroaryl; or heteroarylalkyl in which the alkyl portion contains from 1 to 6 carbon atoms; or when $R^v$ is not H and $R^{vi}$ is either —$(CO)R^{vii}$ or —$SO_2R^{vii}$, $R^v$ and $R^{vii}$ can be taken together to form a 4- to 7-membered ring;

$R^{viii}$ is hydrogen, $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —$(CH_2)_rSR^{viii}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; or $R^{viii}$ is $C(O)R^x$;

$R^{ix}$ is $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —$(CH_2)_rSO_2R^{ix}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, one hydroxyl group and one fluorine atom, or $C_1$-$C_6$ hydroxyalkyl; heteroaryl that is optionally substituted with 1 or 2 fluorine atoms, one hydroxyl group, one hydroxyl group and one fluorine atom, or $C_1$-$C_6$ hydroxyalkyl, wherein the number of substituents does not exceed the number of available C—H and N—H bonds; or arylalkyl in which the alkyl portion contains from 1 to 6 carbon atoms and the aryl portion is optionally substituted with 1 or 2 fluorine atoms, one hydroxyl group, one hydroxyl group and one fluorine atom, or $C_1$-$C_6$ hydroxyalkyl;

$R^x$ is $C_1$-$C_6$ straight chain alkyl optionally substituted with one or two hydroxyl groups or $C_1$-$C_6$ alkoxy groups, wherein if the $C_1$-$C_6$ alkyl group is substituted, then no more than one heteroatom selected from the oxygen atom in the hydroxyl group and the oxygen atom in the alkoxy group is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; arylalkyl in which the alkyl portion contains from 1 to 6 carbon atoms and in which the aryl portion is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; $C_1$-$C_6$ monoalkylamino; or $C_1$-$C_6$ dialkylamino;

wherein if $R_5$ contains at least one saturated carbon atom and said $R_5$ is substituted with two substituents selected from $C_1$-$C_6$ alkoxy, alkoxyalkoxy in which the alkoxy portions each independently contain from 1 to 6 carbon atoms, F, —OH, —$NH_2$, $C_1$-$C_6$ monoalkylamino, $C_1$-$C_6$ dialkylamino, and $C_1$-$C_6$ alkylthio, said two substituents are not bound to the same saturated carbon atom;

wherein the heteroatoms of $Z'''$ and $R_5$ are not directly connected to each other through a bond, or separated by a single saturated carbon atom, or connected to each other through a C=C double bond; with the exception that if $R_5$ is $SO_2R^{ix}$ and $Z'''$ is a nitrogen containing heteroaryl group, the sulfur atom in said $R_5$ can be directly attached to a nitrogen atom in $Z'''$;

m is an integer ranging from 1 to 3;

n is an integer ranging from 1 to 2;

p is an integer ranging from 0 to 2;

wherein when n is 2 or p is 2, the carbon atom linked to the oxygen atom can be substituted with a $C_1$-$C_6$ straight chain alkyl group or a $C_3$-$C_6$ branched chain alkyl group;

q is an integer ranging from 1 to 5;

r is an integer ranging from 0 to 5; and pharmaceutically acceptable derivatives thereof.

In another embodiment, the invention encompasses compounds of formula VI, wherein all variables have the same meanings as set forth above for the compounds of formula VI, and with the proviso that when $Z'''$ is a heteroaryl group, m is 2 and Y is a bond, $R_5$ is not phenylalkyl in which the alkyl portion contains from 1 to 6 carbon atoms; —$(CH_2)_rNR^vR^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl; —$(CH_2)_rSR^{viii}$ when $R^{viii}$ is $C_1$-$C_6$ straight chain alkyl, $C_3$-$C_6$ branched chain alkyl or $C_3$-$C_6$ cycloalkyl; —$(CH_2)_rSO_2R^{ix}$, —$(CH_2)_rSOR^{ix}$ or —$(CH_2)_rC(O)OR^{ix}$ when $R^{ix}$ is $C_1$-$C_6$ straight chain alkyl, $C_3$-$C_6$ branched chain alkyl, or $C_3$-$C_6$ cycloalkyl;

with the proviso that when $Z'''$ is pyridine, m is 2, and Y is a bond, $R_5$ is not —$CH_2OH$; and with the proviso that when $Z'''$ is a heteroaryl group, m is 1 or 3 and Y is a bond, $R_5$ is not —$(CH_2)_rNR^vR^{vi}$ when both $R^v$ and $R^{vi}$ are hydrogen, or when one of $R^v$ and $R^{vi}$ is hydrogen and the other of $R^v$ and $R^{vi}$ is $C_1$-$C_6$ straight chain alkyl, $C_3$-$C_6$ branched chain alkyl or $C_3$-$C_6$ cycloalkyl.

The invention encompasses compounds of the formula VII:

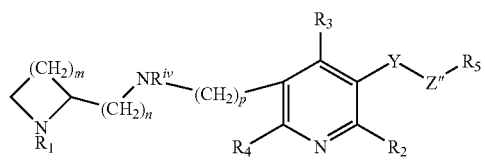

(VII)

wherein $R^{iv}$ is $C_1$-$C_6$ straight chain alkyl, $C_3$-$C_6$ branched chain alkyl, $C_3$-$C_6$ cycloalkyl, or an acyl group having the formula:

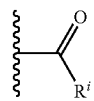

wherein $R^i$ is hydrogen, $C_1$-$C_6$ straight chain alkyl group, a $C_3$-$C_6$ branched chain alkyl group, or a $C_3$-$C_6$ cycloalkyl group, and all other variables have the same meanings as set forth above for the compounds of the formula V, except that $R_5$ may also be hydrogen, and pharmaceutically acceptable derivatives thereof.

The invention encompasses compounds of formula VIII:

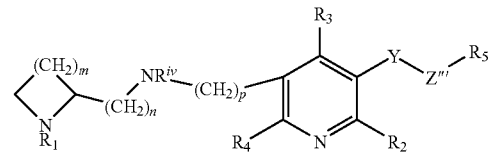

(VIII)

wherein $R^{iv}$ is hydrogen, a $C_1$-$C_6$ straight chain alkyl, $C_3$-$C_6$ branched chain alkyl, $C_3$-$C_6$ cycloalkyl, or an acyl group having the formula:

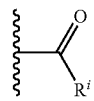

wherein $R^i$ is a $C_1$-$C_6$ straight chain alkyl group, a $C_3$-$C_6$ branched chain alkyl group, or a $C_3$-$C_6$ cycloalkyl group, and all other variables have the same meanings as set forth above for the compounds of the formula VI, except that $R_5$ may also be hydrogen, and pharmaceutically acceptable derivatives thereof.

DETAILED DESCRIPTION OF THE INVENTION

Definitions

As used in connection with the pyridinyl nicotinic acetylcholine receptor ligands herein, the terms used herein having the following meanings:

The term "agonist" refers to a compound that binds to a particular receptor and triggers a response in the cell. It mimics the activity of the endogenous ligand (e.g., acetylcholine) that binds to the same receptor.

The term "antagonist" refers to a compound that binds to a receptor site but does not cause any physiological changes unless another receptor ligand is present.

The term "partial agonist" refers to a compound that binds to a receptor site but does not produce the maximal effect, regardless of its concentration.

The term "competitive antagonist" refers to a compound that binds to a receptor site, the effect of which can be overcome by increasing the concentration of the agonist.

The term "ligand" refers to a compound that binds at a receptor site.

"$C_1$-$C_6$ straight chain alkyl" means a straight chain hydrocarbon radical having from 1 to 6 carbon atoms. Representative straight chain $C_1$-$C_6$ alkyls include methyl, ethyl, n-propyl, n-butyl, n-pentyl, and n-hexyl.

"$C_1$-$C_3$ alkyl" means a hydrocarbon radical having from 1 to 3 carbon atoms. Representative $C_1$-$C_3$ alkyls include methyl, ethyl, n-propyl, and isopropyl.

"$C_1$-$C_6$ fluoroalkyl" means a straight chain hydrocarbon radical having from 1 to 6 carbon atoms, in which between 1 and 4 hydrogen atoms are substituted by a fluorine atom.

"$C_1$-$C_6$ hydroxyalkyl" means a straight chain hydrocarbon radical having from 1 to 6 carbon atoms, in which 1 hydrogen atom bound to a carbon atom is substituted by one hydroxyl group, or 2 hydrogen atoms that are bound to different carbon atoms are each substituted by one hydroxyl group.

"$C_3$-$C_6$ branched chain alkyl" means a branched non-cyclic hydrocarbon radical having from 3 to 6 carbon atoms. Representative branched $C_3$-$C_6$ branched chain alkyls include iso-propyl, sec-butyl, iso-butyl, tert-butyl, iso-pentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl. A branched non-cyclic hydrocarbon means that one or more straight chain alkyl groups, such as methyl, ethyl or propyl, replace one or both hydrogens in a —$CH_2$— group of a straight chain non-cyclic hydrocarbon.

The term "allyl" refers to the chemical group having the structure:

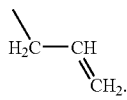

"$C_3$-$C_6$ cycloalkyl" means a saturated monocyclic hydrocarbon radical having from 3 to 6 carbon atoms. Representative $C_3$-$C_6$ cycloalkyls are cyclopropyl, cyclobutyl, cyclopentyl, and cyclohexyl.

"$C_4$-$C_6$ partially-unsaturated carbocycle" means a monocyclic hydrocarbon having from 4 to 6 carbon atoms which contains one double bond. Representative $C_4$-$C_6$ partially-unsaturated carbocycles include cyclobutenyl, cyclopentenyl and cyclohexenyl.

"A four- to six-membered saturated heterocycle" means saturated 4- to 6-membered ring structures containing 1 or 2 heteroatoms, which are preferably nitrogen, oxygen or sulfur. Heterocycles can also be polycycles, which means that they are optionally fused to a cycloalkyl, a partially-unsaturated carbocycle, an aryl group, a partially-unsaturated heterocycle or a heteroaryl group. Representative $C_4$-$C_6$ saturated heterocycles include oxetane, thietane, azetidine, tetrahydrofuran, tetrahydrothiophene, pyrrolidine, tetrahydropyran, tetrahydrothiopyran, piperidine, morpholine, thiomorpholine, piperazine, cis- and trans-perhydroindole, cis- and trans-2,3,3a, 4,7,7a-hexahydroindole, 7-oxabicyclo[2.2.1]heptane, 7-oxabicyclo[2.2.1]hept-2-ene, quinuclidine, 2,3-dihydroindole, 1,2,3,4-tetrahydroquinoline, 1,2,3,4-tetrahydroisoquinoline, 2,3-dihydro-4-, -5-, -6-, and -7-azaindole, chroman, isochroman, 2,3-dihydrobenzofuran, 2,3-dihydrobenzothiophene, 1,3-dihydroisobenzofuran, 1,3-dihydroisobenzothiophene, and 2,3-dihydro-1H-isoindole.

"Saturated azabicyclic ring," "saturated azabicyclic," or "saturated azabicycle" means a nitrogen-containing saturated bicyclic ring having 4 to 8 ring carbon atoms and one carbon to carbon bridge with 0 to 2 carbons in the bridge. Representative saturated azabicyclic rings include 2-azabicyclo[3.1.0] hexane, 3-azabicyclo[3.1.0]hexane, 2-azabicyclo[2.2.0]hexane, 3-azabicyclo[3.1.1]heptane and 2-azabicyclo[2.1.0] pentane.

"A five- or six-membered partially-unsaturated heterocycle" means non-aromatic 5- or 6-membered ring structures containing 1 or 2 heteroatoms, which are preferably nitrogen, oxygen or sulfur, and containing one carbon-carbon or carbon-nitrogen double bond. Partially-unsaturated heterocycles can also be polycycles, which means that they are optionally fused to a cycloalkyl, a partially-unsaturated carbocycle, an aryl group, a partially-unsaturated heterocycle or a heteroaryl group. Representative partially-unsaturated heterocycles include 2,5-dihydro-1H-pyrrole, 2,5-dihydrofuran, 2,5-dihydrothiophene, 4,5-dihydrooxazole, 4,5-dihydrothiazole, 4,5-dihydro-1H-imidazole, 4,5-dihydro-1H-1,2,3-triazole, 1,2,5,6-tetrahydropyridine, 1,4,5,6-tetrahydropyrimidine, 2,5,6,7-tetrahydro-1H-azepine, 1,3,4,5,6,7-hexahydroisobenzofuran, and 2H-chromene.

"Partially saturated $C_9$-$C_{16}$ carbocyclic group having at least one aromatic ring" means a bi- or tri-carbocyclic ring system having from 9 to 16 carbon atoms and wherein the ring closest to the pyridine group in Formula V is an aromatic ring and one ring is a five- or six-membered alicyclic ring which is saturated except for the carbon atoms shared with the aromatic ring.

"$C_8$-$C_9$ partially saturated bicyclic heteroaryl" means a single five- or six-membered heterocyclic ring containing either a single nitrogen or oxygen atom wherein the heterocyclic ring is fully saturated except those carbon atoms shared with a fused benzene ring and wherein either the benzene ring or the heterocyclic ring is linked to Y. Examples include 2,3-dihydro-1H-isoindole, 1,2,3,4-tetrahydroquinoline, 2,3-dihydro-1H-indole, 1,2,3,4-tetrahydroisoquinoline, 2,3-dihydrobenzofuran, chroman and isochroman.

"Aryl" means a monocyclic or fused bicyclic aromatic ring that contains only carbon atoms. Representative aryl groups include phenyl and naphthyl.

"Heteroaryl" means a monocyclic or fused bicyclic aromatic ring containing a total of 1 to 4 heteroatoms, which are preferably selected from oxygen, sulfur and nitrogen. In the case of fused bicyclic aromatic rings, there is no more than one oxygen atom or sulfur atom per ring. Representative heteroaryl groups include furyl, thienyl, pyridinyl (also named pyridyl), pyrazinyl, pyridazinyl, pyrimidinyl, pyrrolyl, pyrazolyl, imidazolyl, indolyl, thiazolyl, isothiazolyl, oxazolyl, isoxazolyl, thiadiazolyl, oxadiazolyl, triazolyl, tetrazolyl, benzoxazolyl, benzisoxazolyl, benzothiazolyl, benzisothiazolyl, benzimidazolyl, indazolyl, quinolinyl, isoquinolinyl, cinnolinyl, quinazolinyl, quinoxalinyl, phthalazinyl, azaindolyl, and naphthyridinyl.

"Biaryl" means a group containing two aromatic rings that contain only carbon atoms, and in which the two aromatic rings are connected by a single bond. Representative biaryl groups include biphenyl.

A "condition" refers to a disease or disorder that can be treated or prevented by administering an effective amount of a pyridinyl nicotinic acetylcholine receptor ligand. Such conditions include, but are not limited to, cognitive dysfunction associated with neurodegenerative disorders (e.g., Alzheimer's disease and Parkinson's disease), dyskinesias, Tourette's syndrome, schizophrenia, cognitive disorders associated with attention-deficit hyperactivity disorder, depression, anxiety, mood disorders, pain, addiction and nicotine dependence.

The phrases "treatment of," "treating", and the like include the amelioration or cessation of a condition or a symptom thereof. In one embodiment, treating includes inhibiting, for example, decreasing the overall frequency of episodes of a condition or a symptom thereof.

The phrases "prevention of," "preventing", and the like include the avoidance of the onset of a condition or a symptom thereof.

The term "animal" includes, but is not limited to, a human or a non-human animal, such as a companion animal, beast of burden, or livestock, e.g., a cow, buffalo, monkey, baboon, chimpanzee, horse, donkey, mule, camel, llama, elephant, goat, sheep, pig, chicken, turkey, duck, goose, ostrich, quail, cat, dog, mouse, rat, rabbit or guinea pig.

The phrase "pharmaceutically acceptable derivative," as used herein, includes any pharmaceutically acceptable salt, prodrug, radiolabeled form, stereoisomer, enantiomer, diastereomer, other stereoisomeric form, racemic mixture, geometric isomer, tautomer, solvate (e. g., hydrate, or addition compounds that contain acid in excess of the number of their basic nitrogen atoms due to hydrogen bonding), amorphous solid form and crystalline solid form, e.g., of a pyridinyl nicotinic acetylcholine receptor ligand of the invention. In one embodiment, the pharmaceutically acceptable derivative is a pharmaceutically acceptable salt, radiolabeled form, stereoisomer, enantiomer, diastereomer, other stereoisomeric form, racemic mixture, geometric isomer, and/or tautomer, e.g., of a pyridinyl nicotinic acetylcholine receptor ligand of the invention. In another embodiment, the pharmaceutically acceptable derivative is a pharmaceutically acceptable salt, e.g., of a pyridinyl nicotinic acetylcholine receptor ligand of the invention.

The phrase "pharmaceutically acceptable salt," as used herein, is any pharmaceutically acceptable salt that can be prepared from a pyridinyl nicotinic acetylcholine receptor ligand including a salt formed from an acid and a basic functional group, such as a nitrogen group, of a pyridinyl nicotinic acetylcholine receptor ligand. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, malate, maleate, gentisinate, fumarate, gluconate, glucuronate, saccharate, formate, benzoate, glutamate, methanesulfonate, ethanesulfonate, benzenesulfonate, p-toluenesulfonate, trifluoroacetate, and pamoate (i.e., 1,1'-methylene-bis-(2-hydroxy-3-naphthoate)) salts. One skilled in the art will recognize that acid addition salts of a pyridinyl nicotinic acetylcholine receptor ligand can be prepared by reaction of the compounds with the appropriate acid via a variety of known methods, or by reacting another salt of the compound with an anion exchanger containing the anion of the desired acid.

The invention disclosed herein is also meant to encompass all prodrugs of the pyridinyl nicotinic acetylcholine receptor ligands. "Prodrugs" are known in the art and, while not necessarily possessing any pharmaceutical activity as such, are considered to be any covalently bonded carrier(s) that releases the active parent drug in vivo. In general, such prodrugs will be a functional derivative of a pyridinyl nicotinic acetylcholine receptor ligand of formulas I-VIII which is readily convertible in vivo, e.g., by being metabolized, into the required pyridinyl nicotinic acetylcholine receptor ligand of formulas I-VIII. Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984).

In addition, one or more hydrogen, carbon or other atoms of a pyridinyl nicotinic acetylcholine receptor ligand can be replaced by an isotope of the hydrogen, carbon or other atoms. Such a "labeled" or "radiolabeled" form of a pyridinyl nicotinic acetylcholine receptor ligand, each of which is encompassed by the invention, is useful as a research tool in metabolism, pharmacokinetic studies, and in binding assays, and/or as a diagnostic tool. Examples of isotopes that can be incorporated into a pyridinyl nicotinic acetylcholine receptor ligand of the invention include isotopes of hydrogen, carbon, nitrogen, oxygen, phosphorus, sulfur, fluorine and chlorine, such as $^2H$, $^3H$, $^{11}C$, $^{13}C$, $^{14}C$, $^{15}N$, $^{18}O$, $^{17}O$, $^{35}S$, $^{18}F$, $^{32}P$, and $^{36}Cl$, respectively. Labeled compounds of the invention can be prepared by methods known in the art. For example, tritiated compounds of Formula (I) can be prepared by introducing tritium into the particular compound of Formula (I), for example, by catalytic dehalogenation with tritium. This method can include reacting a suitably halogen-substituted precursor of a compound of Formula (I) with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol.* 1, *Labeled Compounds (Part A)*, Chapter 6 (1987). $^{14}C$-labeled compounds can be prepared by employing starting materials having a $^{14}C$ carbon.

A pyridinyl nicotinic acetylcholine receptor ligand can contain one or more asymmetric centers and may thus give rise to enantiomers, diastereomers, and other stereoisomeric forms. The invention is also meant to encompass all such possible forms as well as their racemic and resolved forms or any mixture thereof. All "tautomers," e.g., amide-imidic acid, lactam-lactim, and enamine-imine tautomers, are intended to be encompassed by the invention as well.

As used herein, the terms "stereoisomer," "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposable on its mirror image and hence optically active where one enantiomer rotates the plane of polarized light in one direction and its minor image rotates the plane of polarized light in the opposite direction. In rare cases, and then typically dependent on the choice of solvent, pH, and concentration, the extent to which an enantiomer rotates the plane of polarized light may be too small to be measured.

The term "racemic" refers to a mixture of equal parts of enantiomers which by mutual cancellation of each other's contribution to the mixture's optical rotation is optically inactive.

The term "resolution" refers to the separation or concentration or depletion of one of the two enantiomeric forms of a molecule.

Optical isomers of a pyridinyl nicotinic acetylcholine receptor ligand can be obtained by known techniques such as chiral chromatography or formation of diastereomeric salts from an optically active acid or base.

The nicotinic acetylcholine receptor ligands of the invention may exist in solid form, which may be an amorphous form or crystalline form. The present invention encompasses all such amorphous and crystalline solid forms of the compounds of formulas I-VIII. By "crystalline form" is meant that the molecules are in a crystal lattice—a regular, three-dimensional arrangement of points in space at which the molecules are located. The unit cell is the smallest building block of a crystal whose geometric arrangement defines the characteristic symmetry of a crystal and whose repetition in three dimensions produces a crystal lattice. Small molecules often crystallize in more than one crystal lattice, which are known as polymorphs. Solvent molecules may also be incorporated into a crystal lattice and may be ordered (e.g., occurring at the same place in every unit cell) or disordered (e.g., filling a channel in the crystal). A crystal with solvent incorporated into the lattice is called a solvate. If the solvent is water, then the crystal form is a hydrate. Hydrates and solvates are sometimes known as pseudopolymorphs. The crystalline form obtained for a particular substance may depend on any number of factors, including temperature, solvent, time for crystallization, and the addition to the solution of the substance of seeding crystals of one of its polymorphs or pseudopolymorphs.

The phrase "effective amount," when used in connection with a pyridinyl nicotinic acetylcholine receptor ligand, means an amount effective for: (a) treating or preventing a Condition; (b) detectably inhibiting nicotinic acetylcholine receptor function in a cell; or (c) detectably activating nicotinic acetylcholine receptor function in a cell.

The phrase "effective amount," when used in connection with a second therapeutic agent means an amount for providing the therapeutic effect of the second therapeutic agent.

The terms "modulate," "modulating", and the like as used herein with respect to nicotinic acetylcholine receptors mean the mediation of a pharmacologic response (e.g., antidepressant) in an animal from (i) inhibiting or activating the receptor, or (ii) directly or indirectly affecting the normal regulation of the receptor activity. Compounds that modulate the receptor activity include agonists, antagonists, mixed agonists/antagonists and compounds which directly or indirectly affect regulation of the receptor activity.

The term "nicotinic acetylcholine receptor" and the abbreviation "nAChR" refer to a functional ligand-gated ion channel that is a homo- or hetero-pentamer of protein subunits designated as α1-α10, β1-β4, δ, γ and ε, the opening of which is triggered by acetylcholine or nicotine. nAChR subtypes are identified by their known subunit compositions, which includes an asterisk ("*") when other unknown subunits are or could be present in the pentamer, e.g., the α3* nAChR subtype found in the brain is composed of at least one α3 subunit and other subunits that have not yet been identified, whereas the α4β2 nAChR subtype found in the vertebrate central nervous system is composed only of α4 and β2 subunits.

The term "HPLC" means high performance liquid chromatography.

The term "TLC" means thin layer chromatography.
The term "CC" means column chromatography.
The term "CDCl$_3$" means deuterated chloroform.
The term "PPh$_3$" means triphenylphosphine.
The term "THF" means tetrahydrofuran.
The term "SiO$_2$" means chromatographic grade silica gel.
The term "EtOAc" means ethyl acetate.
The term "DME" means 1,2-dimethoxyethane.
The term "DMF" means N,N-dimethylformamide.
The term "MeOH" means methanol, i.e., methyl alcohol.

The term "EtOH" means ethanol, i.e., ethyl alcohol.
The term "NH$_4$Cl" means ammonium chloride.
The term "Na$_2$SO$_4$" means sodium sulfate.
The terms "DCM" and "CH$_2$Cl$_2$" mean dichloromethane, also referred to as methylene chloride or methylene dichloride.
The term "Et$_2$Zn" means diethylzinc.
The term "NaHCO$_3$" means sodium bicarbonate.
The term "HCl" means hydrogen chloride. If a solvent other than water is specified, "HCl" specifically means a solution of anhydrous (gaseous) hydrogen chloride in that solvent.
The term "Na$_2$SO$_3$" means sodium sulfite.
The terms "CF$_3$CO$_2$H" and "CF$_3$COOH" mean trifluoroacetic acid.
The term "CH$_3$CN" means acetonitrile.
The term "NaOH" means sodium hydroxide.
The term "p-TsCl" means para-toluenesulfonyl chloride, also known as tosyl chloride.
The term "DMSO" means dimethyl sulfoxide, i.e., methylsulfinylmethane.
The term "Et$_3$N" means triethylamine.
The term "LiCl" means lithium chloride.
The term "NaBH$_4$" means sodium borohydride.
The term "(c-Hex)$_2$BH" means dicyclohexylborane.
The term "2,6-lutidine" means the compound having the chemical structure:

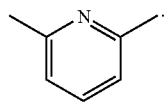

The term "H$_2$O$_2$" means hydrogen peroxide.
The term "OsO$_4$" means osmium tetroxide.
The term "MgSO$_4$" means magnesium sulfate.
The term "KMnO$_4$" means potassium permanganate.
The term "BH$_3$.SMe$_2$" means borane:dimethyl sulfide.
The term "DIBAL-H" means diisobutylaluminum hydride.
The term "CsF" means cesium fluoride.
The term "CuI" means copper (I) iodide.
The term "PdCl$_2$" means palladium (II) chloride.
The term "PtO$_2$" means platinum oxide.
The term "Pd(OH)$_2$/C" means palladium hydroxide on carbon, or Pearlman's Catalyst.
The term "Red-Al®", alternatively "Vitride®", means a solution of sodium bis(2-methoxyethoxy)aluminum hydride in toluene.
The term "DMPU" means N,N'-dimethylpropyleneurea, or 1,3-dimethyl-3,4,5,6-tetrahydro-2(1H)-pyrimidinone.

Nicotinic Acetylcholine Receptor Ligands of the Formula I

As stated above, the invention encompasses pyridinyl nicotinic acetylcholine receptor ligands of the formula I:

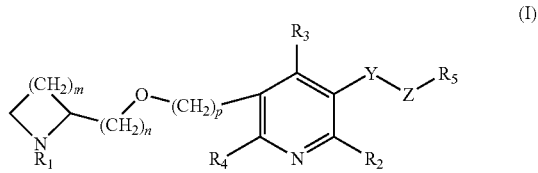
(I)

and pharmaceutically acceptable derivatives thereof, wherein all variables are as defined above for the pyridinyl nicotinic acetylcholine receptor ligands of the formula I.

In another embodiment, the invention encompasses compounds of formula I, wherein all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r NR^v R^{vi}$ wherein $R^v$ and $R^{vi}$ are each independently hydrogen, $C_1$-$C_6$ straight chain alkyl, $C_3$-$C_6$ branched chain alkyl or $C_3$-$C_6$ cycloalkyl; —$(CH_2)_r SR^{viii}$ when $R^{viii}$ is $C_1$-$C_6$ straight chain alkyl, $C_3$-$C_6$ branched chain alkyl, or $C_3$-$C_6$ cycloalkyl; —$(CH_2)_r SO_2 R^{ix}$, —$(CH_2)_r SOR^{ix}$ or —$(CH_2)_r C(O)OR^{ix}$ when $R^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_r NR^v R^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl.

In another embodiment, $R_1$ is H.
In another embodiment, $R_1$ is $C_1$-$C_6$ straight chain alkyl.
In another embodiment, $R_1$ is $C_3$-$C_6$ branched chain alkyl.
In another embodiment, $R_1$ is allyl.
In another embodiment, $R_1$ is $C_3$-$C_6$ cycloalkyl.
In another embodiment, $R_2$ is H.
In another embodiment, $R_3$ is H.
In another embodiment, $R_4$ is H.
In another embodiment, $R_2$, $R_3$ and $R_4$ are each H.
In another embodiment, m is 1.
In another embodiment, m is 2.
In another embodiment, m is 3.
In another embodiment, n is 1.
In another embodiment, n is 2.
In another embodiment, p is 0.
In another embodiment, p is 1.
In another embodiment, p is 2.
In another embodiment, n is 1 and p is 0.
In one embodiment, Y is —$CH_2$— and Z is $C_3$-$C_6$ cycloalkyl.
In another embodiment, Y is —$CH_2$— and Z is a $C_4$-$C_6$ partially unsaturated carbocycle.
In another embodiment, Y is —$CH_2CH_2$— and Z is $C_3$-$C_6$ cycloalkyl.
In another embodiment, Y is —$CH_2CH_2$— and Z is a $C_4$-$C_6$ partially unsaturated carbocycle.
In another embodiment, Y is —$CH_2CH_2CH_2$— and Z is $C_3$-$C_6$ cycloalkyl.
In another embodiment, Y is —$CH_2CH_2CH_2$— and Z is a $C_4$-$C_6$ partially unsaturated carbocycle.
In another embodiment, Y is —$(CH_2)_4$— and Z is $C_3$-$C_6$ cycloalkyl.
In another embodiment, Y is —$(CH_2)_4$— and Z is a $C_4$-$C_6$ partially unsaturated carbocycle.
In another embodiment, Y is —$(CH_2)_5$— and Z is $C_3$-$C_6$ cycloalkyl.
In another embodiment, Y is —$(CH_2)_5$— and Z is a $C_4$-$C_6$ partially unsaturated carbocycle.
In another embodiment, Y is unsubstituted —$(CH_2)_q$— and q is an integer ranging from 1 to 5.

In another embodiment, Y is —$(CH_2)_q$—, q is an integer ranging from 1 to 5, and Y is substituted with one or two groups independently selected from methyl, ethyl, propyl, isopropyl, and cyclopropyl.

In another embodiment, m is 1, Y is a bond, Z is $C_3$-$C_6$ cycloalkyl, p is 0, $R_1$, $R_2$, $R_3$, and $R_4$ are each hydrogen, $R_5$ is alkoxyalkyl, in which the alkoxy and alkyl portions each independently contain between 1 to 6 carbon atoms, and said alkoxylalkyl is substituted with either aryloxy; heteroaryloxy; or $C_3$-$C_6$ cycloalkyloxy.

In another embodiment, m is 1, Y is a bond, Z is 1,2-disubstututed cyclopropyl, p is 0, $R_1$, $R_2$, $R_3$, and $R_4$ are each hydrogen, $R_5$ is alkoxyalkyl, in which the alkoxy and alkyl portions each independently contain between 1 to 6 carbon atoms, and said alkoxylalkyl is substituted with either aryloxy; heteroaryloxy; or $C_3$-$C_6$ cycloalkyloxy.

In another embodiment, m is 1, Y is a bond and Z is $C_3$-$C_6$ cycloalkyl.
In another embodiment, m is 1, Y is a bond and Z is a $C_4$-$C_6$ partially unsaturated carbocycle.
In another embodiment, m is 3, Y is a bond and Z is $C_3$-$C_6$ cycloalkyl.
In another embodiment, m is 3, Y is a bond and Z is a $C_4$-$C_6$ partially unsaturated carbocycle.
In another embodiment, m is 1 or 3, Y is a bond, Z is $C_3$-$C_6$ cycloalkyl or a $C_4$-$C_6$ partially unsaturated carbocycle, and if Z is a six-membered ring, $R_5$ is in the meta position on said ring with respect to the pyridine ring.
In another embodiment, m is 1 or 3, Y is a bond, Z is $C_3$-$C_6$ cycloalkyl or a $C_4$-$C_6$ partially unsaturated carbocycle, and if Z is a six-membered ring, $R_5$ is in the para position on said ring with respect to the pyridine ring.
In another embodiment, m is 1 or 3, Y is a bond, Z is $C_3$-$C_6$ cycloalkyl or a $C_4$-$C_6$ partially unsaturated, and if Z is a six-membered ring, $R_5$ is in the ortho position on said ring with respect to the pyridine ring.

In one embodiment, Z is a 1,2-disubstituted cyclopropyl group.
In another embodiment, Z is a 1,2-disubstituted cyclobutyl group.
In another embodiment, Z is a 1,3-disubstituted cyclobutyl group.
In another embodiment, Z is a 1,2- or 1,3-disubstituted cyclopentyl group.
In another embodiment, Z is a 1,2-, 1,3- or 1,4-disubstituted cyclohexyl group.
In another embodiment, $R_5$ is $C_1$-$C_6$ hydroxyalkyl.
In another embodiment, $R_5$ is alkoxyalkyl with one or two hydroxyl substituents and in which the alkoxy and alkyl portions each independently contain from 1 to 6 carbon atoms.
In another embodiment, $R_5$ is hydroxyalkoxyalkyl in which the alkoxy and alkyl portions each independently contain from 1 to 6 carbon atoms.
In another embodiment, $R_5$ is arylalkoxy in which the alkoxy portion contains from 1 to 6 carbon atoms.
In another embodiment, $R_5$ is aryl.
In another embodiment, $R_5$ is biaryl.
In another embodiment, $R_5$ is heteroarylalkyl in which the alkyl portion contains from 1 to 6 carbon atoms.
In another embodiment, $R_5$ is —$(CH_2)_{1-6}$—O—$(CH_2)_{0-6}$-aryl.
In another embodiment, $R_5$ is —$(CH_2)_{1-6}$—O—$(CH_2)_{0-6}$-heteroaryl.
In another embodiment, $R_5$ is —$(CH_2)_{0-6}$—O—$(CH_2)_{0-6}$—$C_3$-$C_6$ cycloalkyl.
In another embodiment, $R_5$ is heteroaryl.

In another embodiment, $R_5$ is —$(CH_2)_rNR'R^{vi}$, wherein one of $R^v$ and $R^{vi}$ is hydrogen, $C_1$-$C_6$ straight chain alkyl, $C_3$-$C_6$ branched chain alkyl or $C_3$-$C_6$ cycloalkyl and the other of $R^v$ and $R^{vi}$ is —$(CO)R^{vii}$ or —$SO_2R^{vii}$, and r and $R^{vii}$ are as described above for the pyridinyl nicotinic acetylcholine receptor ligands of the formula I.

In another embodiment, $R_5$ is —$(CH_2)_rC(O)NR'R^{vi}$, and r, $R^v$ and $R^{vi}$ are as described above for the pyridinyl nicotinic acetylcholine receptor ligands of the formula I.

In another embodiment, $R_5$ is —$(CH_2)_rSR^{viii}$, wherein $R^{viii}$ is hydrogen or —$C(O)R^x$, and r and $R^x$ are as defined above for the pyridinyl nicotinic acetylcholine receptor ligands of the formula I.

In another embodiment, $R_5$ is —$(CH_2)_rSO_2R^{ix}$, wherein r is an integer ranging from 0 to 5 and $R^{ix}$ is as defined above for the compounds of formula I.

In another embodiment, $R_5$ is —$(CH_2)_2SOR^{ix}$, wherein r is an integer ranging from 0 to 5 and $R^{ix}$ is as defined above for the compounds of formula I.

In another embodiment $R_5$ is —$(CH_2)_rC(O)OR^{ix}$, wherein r is an integer ranging from 0 to 5 and $R^{ix}$ is as defined above for the compounds of formula I.

In another embodiment, Y is a bond, Z is a 1,2-disubstituted cyclopropyl ring and $R_5$ is $C_1$-$C_6$ hydroxyalkyl.

In another embodiment, Y is —$CH_2$—, Z is a 1,2-disubstituted cyclopropyl ring and $R_5$ is —$CH_2OH$.

In another embodiment, Y is —$(CH_2)_2$—, Z is a 1,2-disubstituted cyclopropyl ring and $R_5$ is —$(CH_2)_2OH$.

In another embodiment, m is 1 or 2, Y is a bond, n is 1, p is 0, $R_2$, $R_3$ and $R_4$ are each hydrogen, Z is a 1,2-disubstituted cyclopropyl ring and $R_5$ is $C_1$-$C_6$ hydroxyalkyl.

In another embodiment, m is 1, Y is a bond, n is 1, p is 0, $R_2$, $R_3$ and $R_4$ are each hydrogen, Z is a 1,2-disubstituted cyclopropyl ring and $R_5$ is —$(CH_2)_4OH$.

In another embodiment, m is 1, Y is a bond, n is 1, p is 0, $R_2$, $R_3$ and $R_4$ are each hydrogen, Z is a 1,2-disubstituted cyclopropyl ring and $R_5$ is —$CH_2CH_2OH$.

In another embodiment, m is 1, Y is a bond, n is 1, p is 0, $R_2$, $R_3$ and $R_4$ are each hydrogen, Z is a 1,2-disubstituted cyclopropyl ring and $R_5$ is —$CH_2OH$.

In another embodiment, m is 1, Y is a bond, n is 1, p is 0, $R_2$, $R_3$ and $R_4$ are each hydrogen, Z is a 1,2-disubstituted cyclopropyl ring and $R_5$ is $C_1$-$C_6$ fluoroalkyl.

In another embodiment, m is 1, Y is a bond, n is 1, p is 0, $R_2$, $R_3$ and $R_4$ are each hydrogen, Z is a 1,2-disubstituted cyclopropyl ring and $R_5$ is —$CH_2CH_2F$.

In another embodiment, m is 1, Y is a bond, n is 1, p is 0, $R_2$, $R_3$ and $R_4$ are each hydrogen, Z is a 1,2-disubstituted cyclopropyl ring and $R_5$ is —$CH_2F$.

In another embodiment, Y is a bond, n is 1, p is 0, $R_2$, $R_3$ and $R_4$ are each hydrogen, Z is a 1,2-disubstituted cyclopropyl ring and $R_5$ is —$(CH_2)_{1-6}$—O—$(CH_2)_{0-6}$-aryl, wherein the aryl is optionally substituted with 1 or 2 fluorine atoms, one hydroxyl group, one hydroxyl group and one fluorine atom, Cl or $OCF_3$.

In another embodiment, Y is a bond, n is 1, p is 0, $R_2$, $R_3$ and $R_4$ are each hydrogen, Z is a 1,2-disubstituted cyclopropyl ring and $R_5$ is —$(CH_2)_{1-6}$—O—$(CH_2)_{0-6}$-heteroaryl, wherein the heteroaryl is optionally substituted with 1 or 2 fluorine atoms, one hydroxyl group, one hydroxyl group and one fluorine atom, Cl or $OCF_3$.

In another embodiment, Y is a bond, n is 1, p is 0, $R_2$, $R_3$ and $R_4$ are each hydrogen, Z is a 1,2-disubstituted cyclopropyl ring and $R_5$ is —$(CH_2)_{0-6}$—O—$(CH_2)_{0-6}$—$C_3$-$C_6$ cycloalkyl, wherein the heteroaryl is optionally substituted with 1 or 2 fluorine atoms, one hydroxyl group, one hydroxyl group and one fluorine atom, Cl or $OCF_3$.

In another embodiment, m is 1, Y is a bond, Z is a 1,2-disubstituted cyclopropyl ring and $R_5$ is —$(CH_2)_rNR'R^{vi}$, wherein r is 1 or 2 and each of $R^v$ and $R^{vi}$ is H.

In another embodiment, m is 1, Y is a bond, Z is a 1,2-disubstituted cyclopropyl ring and $R_5$ is —$(CH_2)_rNR'R^{vi}$, wherein r is 2, and one of $R^v$ and $R^{vi}$ is H and the other of $R^v$ and $R^{vi}$ is —$(CO)R^{vii}$ wherein $R^{vii}$ is $C_1$-$C_6$ straight chain alkyl, $C_3$-$C_6$ branched chain alkyl, aryl that is optionally substituted with 1 or 2 fluorine atoms, one hydroxyl group, or one hydroxyl group and one fluorine atom, or $R_5$ is heteroaryl optionally substituted with 1 or 2 fluorine atoms, one hydroxyl group, or one hydroxyl group and one fluorine atom, wherein the number of substituents does not exceed the number of available C—H and N—H bonds.

In another embodiment, m is 1, Y is a bond, Z is a 1,2-disubstituted cyclopropyl ring and $R_5$ is —$(CH_2)_rNR'R^{vi}$, wherein r is 2, and one of $R^v$ and $R^{vi}$ is H and the other of $R^v$ and $R^{vi}$ is —$SO_2R^{vii}$, wherein $R^{vii}$ is $C_1$-$C_6$ straight chain alkyl, aryl that is optionally substituted with 1 or 2 fluorine atoms, one hydroxyl group, or one hydroxyl group and one fluorine atom, or $R_5$ is heteroaryl optionally substituted with 1 or 2 fluorine atoms, one hydroxyl group, or one hydroxyl group and one fluorine atom, wherein the number of substituents does not exceed the number of available C—H and N—H bonds.

In another embodiment, m is 1, Y is a bond, Z is a 1,2-disubstituted cyclopropyl ring, and $R_5$ is —$CH_2OCH_3$, —$CH_2CH_2OCH_3$ or —$CH_2CH_2OCH_2CF_3$.

In another embodiment, m is 1, Y is a bond, Z is a 1,2-disubstituted cyclopropyl ring and $R_5$ is $(CH_2)_rSR^{viii}$, wherein r is 1 or 2 and $R^{viii}$ is —$CH_3$.

In another embodiment, m is 1, Y is a bond, Z is a 1,2-disubstituted cyclopropyl ring and $R_5$ is $(CH_2)_rSR^{viii}$, wherein r is 1 or 2 and $R^{viii}$ is phenyl.

In another embodiment, m is 1, Y is a bond, Z is a 1,2-disubstituted cyclopropyl ring and $R_5$ is —$(CH_2)_rSOR^{ix}$, wherein r is 1 or 2 and $R^{ix}$ is —$CH_3$, $C_3$-$C_6$ branched chain alkyl, aryl that is optionally substituted with 1 or 2 fluorine atoms, one hydroxyl group, one hydroxyl group and one fluorine atom, or $C_1$-$C_6$ hydroxyalkyl, or $R^{ix}$ is arylalkyl optionally substituted with 1 or 2 fluorine atoms, one hydroxyl group, one hydroxyl group and one fluorine atom, or $C_1$-$C_6$ hydroxyalkyl, wherein the number of substituents does not exceed the number of available C—H and N—H bonds.

In another embodiment, m is 1, Y is a bond, Z is a 1,2-disubstituted cyclopropyl ring, and $R_5$ is —$(CH_2)_rSO_2R^{ix}$, wherein r and $R^{ix}$ are as defined above for the pyridinyl nicotinic acetylcholine receptor ligands of the formula I.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is selected from the group consisting of $C_1$-$C_6$ hydroxyalkyl, $C_1$-$C_6$ fluoroalkyl, alkoxyalkyl in which the alkoxy and alkyl portions each independently contain from 1 to 6 carbon atoms, —$(CH_2)_{1-6}$—O—$(CH_2)_{0-6}$-heteroaryl, and $R_5$ is optionally substituted by the optional substituents defined in formula I.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is $C_1$-$C_6$ hydroxyalkyl.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is alkoxyalkyl in which the alkoxy and the alkyl portions each independently contain from 1 to 6 carbon atoms and said alkoxyalkyl is optionally substituted by the optional substituents defined in formula I.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is —$CH_2CH_2OH$.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is $C_1$-$C_6$ fluoroalkyl.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is —$(CH_2)_{1-6}$—O—$(CH_2)_{0-6}$-aryl which is optionally substituted by the optional substituents defined in formula I.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is —$(CH_2)_{1-6}$—O—$(CH_2)_{0-6}$-heteroaryl which is optionally substituted by the optional substituents defined in formula I.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is —$(CH_2)_{1-6}$—O—$(CH_2)_{0-6}$-phenyl, wherein the phenyl group is optionally substituted with substitutents selected from one or two fluoro atoms, one hydroxyl, one fluoro and one hydroxyl, —$CF_3$, and —$OCF_3$.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is —$(CH_2)_{1-6}$—O—$(CH_2)_{0-6}$-heteroaryl, wherein the heteroaryl group is optionally substituted with substitutents selected from one or two fluoro atoms, one hydroxyl, one fluoro and one hydroxyl, —$CF_3$, and —$OCF_3$.

In another embodiment of formula I, m is 1 or 2, Y is a bond, n is 1, p is 0, $R_1$, $R_2$, $R_3$, and $R_4$ are each hydrogen, Z is a 1,2-disubstituted cyclopropyl ring, and $R_5$ is —$(CH_2)_{1-6}$—O—$(CH_2)_{0-6}$-pyridinyl, and wherein the pyridinyl group is optionally substituted by the optional substituents defined in formula I.

In another embodiment of formula I, m is 1 or 2, Y is a bond, n is 1, p is 0, $R_5$ is alkoxyalkyl in which the alkoxy and alkyl portions each independently contain from 1 to 6 carbon atoms and said alkoxyalkyl is optionally substituted by the optional substituents defined in formula I.

In another embodiment of formula I, m is 1 or 2, Y is a bond, n is 1, p is 0, $R_1$, $R_2$, $R_3$, and $R_4$ are each hydrogen, $R_5$ is alkoxyalkyl in which the alkoxy and alkyl portions each independently contain from 1 to 6 carbon atoms and said alkoxyalkyl is substituted with one hydroxyl substituent.

The present invention encompasses compounds of the formula I-1:

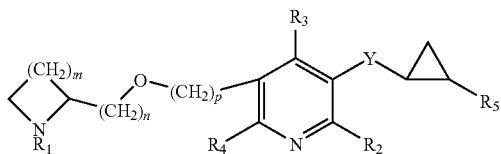

(I-1)

and pharmaceutically acceptable derivatives thereof, wherein all variables are as defined above for the pyridinyl nicotinic acetylcholine receptor ligands of the formula I.

In another embodiment, the invention encompasses the compounds of formula I-1, wherein all variables are as defined above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r NR'R^{vi}$ wherein $R^v$ and $R^{vi}$ are each independently hydrogen, $C_1$-$C_6$ straight chain alkyl, $C_3$-$C_6$ branched chain alkyl or $C_3$-$C_6$ cycloalkyl; —$(CH_2)_r SR^{viii}$ when $R^{viii}$ is $C_1$-$C_6$ straight chain alkyl, $C_3$-$C_6$ branched chain alkyl, or $C_3$-$C_6$ cycloalkyl; —$(CH_2)_r SO_2 R^{ix}$, —$(CH_2)_r SOR^{ix}$ or —$(CH_2)_r C(O)OR^{ix}$ when $R^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_r NR'R^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl.

In another embodiment, the present invention encompasses the compounds of formula I-1, and pharmaceutically acceptable derivatives thereof, wherein each of $R_1$, $R_2$ and $R_3$ is hydrogen, and all other variables have the same meanings as set forth above for the compounds of formula I.

In another embodiment, the present invention encompasses the compounds of formula I-1, and pharmaceutically acceptable derivatives thereof, wherein each of $R_1$, $R_2$ and $R_3$ is hydrogen, and all other variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r NR'R^{vi}$ wherein $R^v$ and $R^{vi}$ are each independently hydrogen, $C_1$-$C_6$ straight chain alkyl, $C_3$-$C_6$ branched chain alkyl or $C_3$-$C_6$ cycloalkyl; —$(CH_2)_r SR^{viii}$ when $R^{viii}$ is $C_1$-$C_6$ straight chain alkyl, $C_3$-$C_6$ branched chain alkyl, or $C_3$-$C_6$ cycloalkyl; —$(CH_2)_r SO_2 R^{ix}$, —$(CH_2)_r SOR^{ix}$ or —$(CH_2)_r C(O)OR^{ix}$ when $R^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_r NR'R^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl.

In another embodiment, the present invention encompasses compounds of formula I-1, and pharmaceutically acceptable derivatives thereof, wherein n is 1, p is 0, and all other variables have the same meanings as set forth above for the compounds of formula I.

In yet another embodiment, the present invention encompasses compounds of formula I-1, and pharmaceutically acceptable derivatives thereof, wherein Y is a bond and all other variables have the same meanings as set forth above for the compounds of formula I.

In another embodiment, the present invention encompasses compounds of formula I-1, and pharmaceutically acceptable derivatives thereof, wherein Y is —$CH_2$— and all other variables have the same meanings as set forth above for the compounds of formula I.

In another embodiment, the present invention encompasses compounds of formula I-1, and pharmaceutically acceptable derivatives thereof, wherein Y is —$(CH_2)_2$— and all other variables have the same meanings as set forth above for the compounds of formula I.

In another embodiment, the present invention encompasses compounds of formula I-1, and pharmaceutically acceptable derivatives thereof, wherein Y is —(CH$_2$)$_3$— and all other variables have the same meanings as set forth above for the compounds of formula I.

In another embodiment, the present invention encompasses compounds of formula I-1, and pharmaceutically acceptable derivatives thereof, wherein Y is —(CH$_2$)$_4$— and all other variables have the same meanings as set forth above for the compounds of formula I.

In another embodiment, the present invention encompasses compounds of formula I-1, and pharmaceutically acceptable derivatives thereof, wherein Y is —(CH$_2$)$_5$— and all other variables have the same meanings as set forth above for the compounds of formula I.

In another embodiment, the invention encompasses the compounds of formula I-1, and pharmaceutically acceptable derivatives thereof, wherein R$_5$ is C$_1$-C$_6$ hydroxyalkyl, and all other variables have the same meanings as defined above for the compounds of formula I.

In another embodiment, the invention encompasses the compounds of formula I-1 and pharmaceutically acceptable derivatives thereof, wherein R$_5$ is —(CH$_2$)$_r$NR$^v$R$^{vi}$, wherein R$^v$ and R$^{vi}$ are each independently C$_3$-C$_6$ cycloalkyl, —(CO)R$^{vii}$ or —SO$_2$R$^{vii}$, wherein if one of R$^v$ and R$^{vi}$ is —(CO)R$^{vii}$ or —SO$_2$R$^{vii}$, the other is not —(CO)R$^{vii}$ or —SO$_2$R$^{vii}$, or when R$^{vi}$ is either —(CO)R$^{vii}$ or —SO$_2$R$^{vii}$, R$^v$ and R$^{vii}$ are taken together to form a 4- to 7-membered ring, and all other variables have the same meanings as set forth above for the compounds of formula I.

In another embodiment, the invention encompasses the compounds of formula I-1 and pharmaceutically acceptable derivatives thereof, wherein R$_5$ is —(CH$_2$)$_r$NR$^v$R$^{vi}$, wherein R$^v$ and R$^{vi}$ are each independently hydrogen, C$_1$-C$_6$ straight chain alkyl, C$_3$-C$_6$ branched chain alkyl, C$_3$-C$_6$ cycloalkyl, —(CO)R$^{vii}$ or —SO$_2$R$^{vii}$, wherein if one of R$^v$ and R$^{vi}$ is —(CO)R$^{vii}$ or —SO$_2$R$^{vii}$, the other is not —(CO)R$^{vii}$ or —SO$_2$R$^{vii}$, or when R$^{vi}$ is either —(CO)R$^{vii}$ or —SO$_2$R$^{vii}$, R$^v$ and R$^{vii}$ are taken together to form a 4- to 7-membered ring, and all other variables have the same meanings as set forth above for the compounds of formula I.

In another embodiment, the invention encompasses the compounds of formula I-1, and pharmaceutically acceptable derivatives thereof, wherein R$_5$ is —(CH$_2$)$_r$C(O)NR$^v$R$^{vi}$, and all other variables have the same meanings as set forth above for the compounds of formula I.

In another embodiment, the invention encompasses the compounds of formula I-1, and pharmaceutically acceptable derivatives thereof, wherein R$_5$ is —(CH$_2$)$_r$SOR$^{ix}$, and all other variables have the same meanings as set forth above for the compounds of formula I.

In another embodiment, the invention encompasses the compounds of formula I-1, and pharmaceutically acceptable derivatives thereof, wherein R$_5$ is —(CH$_2$)$_r$C(O)OR$^{ix}$, and all other variables have the same meanings as set forth above for the compounds of formula I.

In another embodiment, the invention encompasses the compounds of formula I-1, and pharmaceutically acceptable derivatives thereof, wherein R$_5$ is —(CH$_2$)$_{1-6}$—O—(CH$_2$)$_{0-6}$-aryl, and all other variables have the same meanings as set forth above for the compounds of formula I.

In another embodiment, the invention encompasses the compounds of formula I-1, and pharmaceutically acceptable derivatives thereof, wherein R$^5$ is —(CH$_2$)$_r$SR$^{viii}$, wherein R$^{viii}$ is aryl or —C(O)R$^x$, and all other variables have the same meanings as set forth above for the compounds of formula I.

In another embodiment, the present invention encompasses compounds of formula I-2:

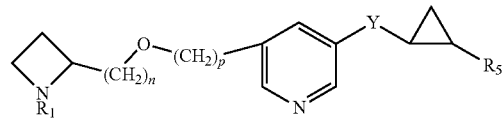

(I-2)

and pharmaceutically acceptable derivatives thereof, wherein all variables have the same meanings as set forth above for the pyridinyl nicotinic acetylcholine receptor ligands of the formula I.

In another embodiment, the present invention encompasses compounds of formula I-2, and pharmaceutically acceptable derivatives thereof, wherein n is 1, p is 0, and all other variables have the same meanings as set forth above for the compounds of formula I, with the proviso that when Y is a bond, R$_5$ is not —(CH$_2$)$_r$NR$^v$R$^{vi}$ when R$^v$ and R$^{vi}$ are each independently hydrogen, C$_1$-C$_6$ straight chain alkyl, C$_3$-C$_6$ branched chain alkyl or C$_3$-C$_6$ cycloalkyl.

In yet another embodiment, the present invention encompasses compounds of formula I-2, and pharmaceutically acceptable derivatives thereof, wherein Y is a bond and all other variables have the same meanings as set forth above for the compounds of formula I.

In another embodiment, the present invention encompasses compounds of formula I-2, and pharmaceutically acceptable derivatives thereof, wherein Y is —CH$_2$— and all other variables have the same meanings as set forth above for the compounds of formula I.

In another embodiment, the present invention encompasses compounds of formula I-2, and pharmaceutically acceptable derivatives thereof, wherein Y is —(CH$_2$)$_2$— and all other variables have the same meanings as set forth above for the compounds of formula I.

In another embodiment, the present invention encompasses compounds of formula I-2, and pharmaceutically acceptable derivatives thereof, wherein Y is —(CH$_2$)$_3$— and all other variables have the same meanings as set forth above for the compounds of formula I.

In another embodiment, the present invention encompasses compounds of formula I-2, and pharmaceutically acceptable derivatives thereof, wherein Y is —(CH$_2$)$_4$— and all other variables have the same meanings as set forth above for the compounds of formula I.

In another embodiment, the present invention encompasses compounds of formula I-2, and pharmaceutically acceptable derivatives thereof, wherein Y is —(CH$_2$)$_5$— and all other variables have the same meanings as set forth above for the compounds of formula I.

In another embodiment, the present invention encompasses compounds of formula I-2, and pharmaceutically acceptable derivatives thereof, wherein R$_5$ is C$_1$-C$_6$ hydroxyalkyl or alkoxyalkyl, in which the alkoxy and alkyl portions each independently contain between 1 to 6 carbon atoms, and all other variables have the same meanings as set forth above for the compounds of formula I.

In another embodiment, the invention encompasses the compounds of formula I-2 and pharmaceutically acceptable derivatives thereof, wherein R$_5$ is —(CH$_2$)$_r$NR$^v$R$^{vi}$, wherein R$^v$ and R$^{vi}$ are each independently C$_3$-C$_6$ cycloalkyl, —(CO)R$^{vii}$ or —SO$_2$R$^{vii}$, wherein if one of R$^v$ and R$^{vi}$ is —(CO)R$^{vii}$ or —SO$_2$R$^{vii}$, the other is not —(CO)R$^{vii}$ or —SO$_2$R$^{vii}$, or when $R^{vi}$ is either —(CO)$R^{vii}$ or —SO$_2$$R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-2 and pharmaceutically acceptable derivatives thereof, wherein $R_5$ is —(CH$_2$)$_r$NR$^v$R$^{vi}$, wherein $R^v$ and $R^{vi}$ are each independently hydrogen, $C_1$-$C_6$ straight chain alkyl, $C_3$-$C_6$ branched chain alkyl, $C_3$-$C_6$ cycloalkyl, —(CO)$R^{vii}$ or —SO$_2$$R^{vii}$, wherein if one of $R^v$ and $R^{vi}$ is —(CO)$R^{vii}$ or —SO$_2$$R^{vii}$, the other is not —(CO)$R^{vii}$ or —SO$_2$$R^{vii}$, or when $R^{vi}$ is either —(CO)$R^{vii}$ or —SO$_2$$R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-2, and pharmaceutically acceptable derivatives thereof, wherein $R_5$ is —(CH$_2$)$_r$C(O)NR$^v$R$^{vi}$, and all other variables have the same meanings as set forth above for the compounds of formula I.

In another embodiment, the invention encompasses the compounds of formula I-2, and pharmaceutically acceptable derivatives thereof, wherein $R_5$ is —(CH$_2$)$_r$SOR$^{ix}$, and all other variables have the same meanings as set forth above for the compounds of formula I.

In another embodiment, the invention encompasses the compounds of formula I-2, and pharmaceutically acceptable derivatives thereof, wherein $R_5$ is —(CH$_2$)$_r$C(O)OR$^{ix}$, and all other variables have the same meanings as set forth above for the compounds of formula I.

In another embodiment, the invention encompasses the compounds of formula I-2, and pharmaceutically acceptable derivatives thereof, wherein $R_5$ is —(CH$_2$)$_{1-6}$—O—(CH$_2$)$_{0-6}$-aryl, and all other variables have the same meanings as set forth above for the compounds of formula I.

In another embodiment, the invention encompasses the compounds of formula I-2, and pharmaceutically acceptable derivatives thereof, wherein $R^5$ is —(CH$_2$)$_r$SR$^{viii}$, wherein $R^{viii}$ is aryl or —C(O)R$^x$, and all other variables have the same meanings as set forth above for the compounds of formula I.

In another embodiment, the present invention encompasses compounds of formula I-3:

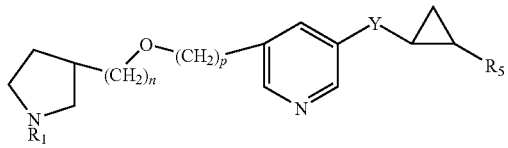

(I-3)

and pharmaceutically acceptable derivatives thereof, wherein all variables have the same meanings as set forth above for the compounds of formula I.

In another embodiment, the invention encompasses the compounds of formula I-3, wherein $R_1$, $R_5$, Y, n and p have the same meanings as set forth above for the compounds of formula I, and with the proviso that when Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —(CH$_2$)$_r$NR$^v$R$^{vi}$ wherein $R^v$ and $R^{vi}$ are each independently hydrogen, $C_1$-$C_6$ straight chain alkyl, $C_3$-$C_6$ branched chain alkyl or $C_3$-$C_6$ cycloalkyl; —(CH$_2$)$_r$SR$^{viii}$ when $R^{viii}$ is $C_1$-$C_6$ straight chain alkyl, $C_3$-$C_6$ branched chain alkyl, or $C_3$-$C_6$ cycloalkyl; —(CH$_2$)$_r$SO$_2$R$^{ix}$, —(CH$_2$)$_r$SOR$^{ix}$ or —(CH$_2$)$_r$C(O)OR$^{ix}$ when R$^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms.

In another embodiment, the present invention encompasses compounds of formula I-3, and pharmaceutically acceptable derivatives thereof, wherein Y is —CH$_2$— and all other variables have the same meanings as set forth above for the compounds of formula I.

In another embodiment, the present invention encompasses compounds of formula I-3, and pharmaceutically acceptable derivatives thereof, wherein Y is —(CH$_2$)$_2$— and all other variables have the same meanings as set forth above for the compounds of formula I.

In another embodiment, the present invention encompasses compounds of formula I-3, and pharmaceutically acceptable derivatives thereof, wherein Y is —(CH$_2$)$_3$— and all other variables have the same meanings as set forth above for the compounds of formula I.

In another embodiment, the present invention encompasses compounds of formula I-3, and pharmaceutically acceptable derivatives thereof, wherein Y is —(CH$_2$)$_4$— and all other variables have the same meanings as set forth above for the compounds of formula I.

In another embodiment, the present invention encompasses compounds of formula I-3, and pharmaceutically acceptable derivatives thereof, wherein Y is —(CH$_2$)$_5$— and all other variables have the same meanings as set forth above for the compounds of formula I.

In another embodiment, the present invention encompasses compounds of formula I-3, and pharmaceutically acceptable derivatives thereof, wherein $R_5$ is $C_1$-$C_6$ hydroxyalkyl and all other variables have the same meanings as set forth above for the compounds of formula I.

In another embodiment, the invention encompasses the compounds of formula I-3 and pharmaceutically acceptable derivatives thereof, wherein $R_5$ is —(CH$_2$)$_r$NR$^v$R$^{vi}$, wherein $R^v$ and $R^{vi}$ are each independently $C_3$-$C_6$ cycloalkyl, —(CO)$R^{vii}$ or —SO$_2$$R^{vii}$, wherein if one of $R^v$ and $R^{vi}$ is —(CO)$R^{vii}$ or —SO$_2$$R^{vii}$, the other is not —(CO)$R^{vii}$ or —SO$_2$$R^{vii}$, or when $R^{vi}$ is either —(CO)$R^{vii}$ or —SO$_2$$R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-3 and pharmaceutically acceptable derivatives thereof, wherein $R_5$ is —(CH$_2$)$_r$NR$^v$R$^{vi}$, wherein $R^v$ and $R^{vi}$ are each independently hydrogen, $C_1$-$C_6$ straight chain alkyl, $C_3$-$C_6$ branched chain alkyl, $C_3$-$C_6$ cycloalkyl, —(CO)$R^{vii}$ or —SO$_2$$R^{vii}$, wherein if one of $R^v$ and $R^{vi}$ is —(CO)$R^{vii}$ or —SO$_2$$R^{vii}$, the other is not —(CO)$R^{vii}$ or —SO$_2$$R^{vii}$, or when $R^{vi}$ is either —(CO)$R^{vii}$ or —SO$_2$$R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-3, and pharmaceutically acceptable derivatives thereof, wherein $R_5$ is —(CH$_2$)$_r$C(O)NR$^v$R$^{vi}$, and all other variables have the same meanings as set forth above for the compounds of formula I.

In another embodiment, the invention encompasses the compounds of formula I-3, and pharmaceutically acceptable derivatives thereof, wherein $R_5$ is —(CH$_2$)$_r$SOR$^{ix}$, and all other variables have the same meanings as set forth above for the compounds of formula I.

In another embodiment, the invention encompasses the compounds of formula I-3, and pharmaceutically acceptable derivatives thereof, wherein $R_5$ is $-(CH_2)_{1-6}-O-(CH_2)_{0-6}$-aryl or $-(CH_2)_{1-6}-O-(CH_2)_{0-6}$-heteroaryl, and all other variables have the same meanings as set forth above for the compounds of formula I.

In another embodiment, the invention encompasses the compounds of formula I-1 through I-3 and pharmaceutically acceptable derivatives thereof, wherein $R_5$ is $-(CH_2)_{1-6}-O-(CH_2)_{0-6}$-heteroaryl and all other variables have the same meaning set forth above for the compounds of formula I.

In another embodiment, the invention encompasses the compounds of formula I-3, and pharmaceutically acceptable derivatives thereof, wherein $R^5$ is $-(CH_2)_rSR^{viii}$, wherein $R^{viii}$ is aryl or $-C(O)R^x$, and all other variables have the same meanings as set forth above for the compounds of formula I.

In another embodiment, the invention encompasses the compounds of formula I-4:

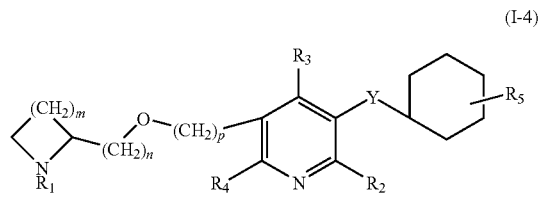

(I-4)

and pharmaceutically acceptable derivatives thereof, wherein all variables have the same meanings as set forth above for the compounds of formula I.

In another embodiment, the invention encompasses the compounds of formula I-4, wherein all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; $-(CH_2)_rNR^vR^{vi}$ wherein $R^v$ and $R^{vi}$ are each independently hydrogen, $C_1$-$C_6$ straight chain alkyl, $C_3$-$C_6$ branched chain alkyl or $C_3$-$C_6$ cycloalkyl; $-(CH_2)_rSR^{viii}$ when $R^{viii}$ is $C_1$-$C_6$ straight chain alkyl, $C_3$-$C_6$ branched chain alkyl, or $C_3$-$C_6$ cycloalkyl; $-(CH_2)_rSO_2R^{ix}$, $-(CH_2)_rSOR^{ix}$ or $-(CH_2)_rC(O)OR^{ix}$ when $R^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not $-(CH_2)_rNR^vR^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl.

In one embodiment, $R_5$ is in the ortho position on the cyclohexyl ring with respect to Y.

In another embodiment, $R_5$ is in the meta position on the cyclohexyl ring with respect to Y.

In another embodiment, $R_5$ is in the para position on the cyclohexyl ring with respect to Y.

In yet another embodiment, the present invention encompasses compounds of formula I-4, and pharmaceutically acceptable derivatives thereof, wherein Y is a bond and all other variables have the same meanings as set forth above for the compounds of formula I.

In another embodiment, the present invention encompasses compounds of formula I-4, and pharmaceutically acceptable derivatives thereof, wherein Y is $-CH_2-$ and all other variables have the same meanings as set forth above for the compounds of formula I.

In another embodiment, the present invention encompasses compounds of formula I-4, and pharmaceutically acceptable derivatives thereof, wherein Y is $-(CH_2)_2-$ and all other variables have the same meanings as set forth above for the compounds of formula I.

In another embodiment, the present invention encompasses compounds of formula I-4, and pharmaceutically acceptable derivatives thereof, wherein Y is $-(CH_2)_3-$ and all other variables have the same meanings as set forth above for the compounds of formula I.

In another embodiment, the present invention encompasses compounds of formula I-4, and pharmaceutically acceptable derivatives thereof, wherein Y is $-(CH_2)_4-$ and all other variables have the same meanings as set forth above for the compounds of formula I.

In another embodiment, the present invention encompasses compounds of formula I-4, and pharmaceutically acceptable derivatives thereof, wherein Y is $-(CH_2)_5-$ and all other variables have the same meanings as set forth above for the compounds of formula I.

In another embodiment, the present invention encompasses compounds of formula I-4, and pharmaceutically acceptable derivatives thereof, wherein $R_5$ is $C_1$-$C_6$ hydroxyalkyl and all other variables have the same meanings as set forth above for the compounds of formula I.

In another embodiment, the invention encompasses the compounds of formula I-4 and pharmaceutically acceptable derivatives thereof, wherein $R_5$ is $-(CH_2)_rNR^vR^{vi}$, wherein $R^v$ and $R^{vi}$ are each independently $C_3$-$C_6$ cycloalkyl, $-(CO)R^{vii}$ or $-SO_2R^{vii}$, wherein if one of $R^v$ and $R^{vi}$ is $-(CO)R^{vii}$ or $-SO_2R^{vii}$, the other is not $-(CO)R^{vii}$ or $-SO_2R^{vii}$, or when $R^{vi}$ is either $-(CO)R^{vii}$ or $-SO_2R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-4 and pharmaceutically acceptable derivatives thereof, wherein $R_5$ is $-(CH_2)_rNR^vR^{vi}$, wherein $R^v$ and $R^{vi}$ are each independently hydrogen, $C_1$-$C_6$ straight chain alkyl, $C_3$-$C_6$ branched chain alkyl, $C_3$-$C_6$ cycloalkyl, $-(CO)R^{vii}$ or $-SO_2R^{vii}$, wherein if one of $R^v$ and $R^{vi}$ is $-(CO)R^{vii}$ or $-SO_2R^{vii}$, the other is not $-(CO)R^{vii}$ or $-SO_2R^{vii}$, or when $R^{vi}$ is either $-(CO)R^{vii}$ or $-SO_2R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-4, and pharmaceutically acceptable derivatives thereof, wherein $R_5$ is $-(CH_2)_rC(O)NR^vR^{vi}$, and all other variables have the same meanings as set forth above for the compounds of formula I.

In another embodiment, the invention encompasses the compounds of formula I-4, and pharmaceutically acceptable derivatives thereof, wherein $R_5$ is $-(CH_2)_rSOR^{ix}$, and all other variables have the same meanings as set forth above for the compounds of formula I.

In another embodiment, the invention encompasses the compounds of formula I-4, and pharmaceutically acceptable derivatives thereof, wherein $R_5$ is $-(CH_2)_rSOR^{ix}$, $R^{ix}$ is arylalkyl in which the alkyl portion contains from 1 to 6 carbon atoms, and the aryl group is substituted with $C_1$-$C_6$ hydroxyalkyl, and all other variables have the same meanings as set forth above for the compounds of formula I.

In another embodiment, the invention encompasses the compounds of formula I-4, and pharmaceutically acceptable derivatives thereof, wherein $R_5$ is —$(CH_2)_rC(O)OR^{ix}$, and all other variables have the same meanings as set forth above for the compounds of formula I.

In another embodiment, the invention encompasses the compounds of formula I-4, and pharmaceutically acceptable derivatives thereof, wherein $R_5$ is —$(CH_2)_{1-6}$—O—$(CH_2)_{0-6}$-aryl, and all other variables have the same meanings as set forth above for the compounds of formula I.

In another embodiment, the invention encompasses the compounds of formula I-4, and pharmaceutically acceptable derivatives thereof, wherein $R^5$ is —$(CH_2)_rSR^{viii}$, wherein $R^{viii}$ is aryl or —$C(O)R^x$, and all other variables have the same meanings as set forth above for the compounds of formula I.

In another embodiment, the compounds of the invention encompass the compounds of formula I-5:

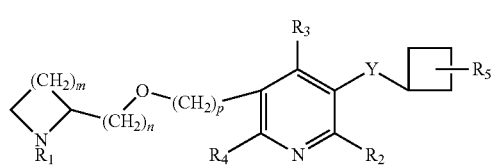

(I-5)

and pharmaceutically acceptable derivatives thereof, wherein all variables have the same meanings as set forth above for the compounds of formula I.

In other embodiments, the invention encompasses the compounds of formula I-5, wherein Z is a cyclobutyl group, and all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r$NR$^v$R$^{vi}$ wherein R$^v$ and R$^{vi}$ are each independently hydrogen, $C_1$-$C_6$ straight chain alkyl, $C_3$-$C_6$ branched chain alkyl or $C_3$-$C_6$ cycloalkyl; —$(CH_2)_rSR^{viii}$ when R$^{viii}$ is $C_1$-$C_6$ straight chain alkyl, $C_3$-$C_6$ branched chain alkyl, or $C_3$-$C_6$ cycloalkyl; —$(CH_2)_rSO_2R^{ix}$, —$(CH_2)_rSOR^{ix}$ or —$(CH_2)_rC(O)OR^{ix}$ when R$^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_r$NR$^v$R$^{vi}$ when R$^v$ and R$^{vi}$ are each independently hydrogen, $C_1$-$C_6$ straight chain alkyl, $C_3$-$C_6$ branched chain alkyl or $C_3$-$C_6$ cycloalkyl.

In some embodiments, the compound of formula I-5 have the formula:

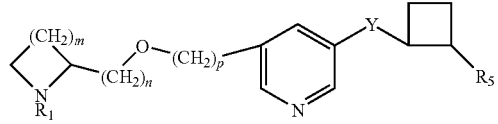

and pharmaceutically acceptable derivatives thereof, wherein all variables have the same meanings as set forth above for the compounds of formula I.

In other embodiments, the invention encompasses the compounds of formula I-5 having the formula:

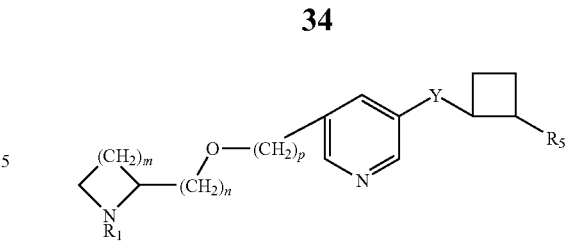

and pharmaceutically acceptable derivatives thereof, wherein all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r$NR$^v$R$^{vi}$ wherein R$^v$ and R$^{vi}$ are each independently hydrogen, $C_1$-$C_6$ straight chain alkyl, $C_3$-$C_6$ branched chain alkyl or $C_3$-$C_6$ cycloalkyl; —$(CH_2)_rSR^{viii}$ when R$^{viii}$ is $C_1$-$C_6$ straight chain alkyl, $C_3$-$C_6$ branched chain alkyl, or $C_3$-$C_6$ cycloalkyl; —$(CH_2)_rSO_2R^{ix}$, —$(CH_2)_rSOR^{ix}$ or —$(CH_2)_rC(O)OR^{ix}$ when R$^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_r$NR$^v$R$^{vi}$ when R$^v$ and R$^{vi}$ are each independently hydrogen, $C_1$-$C_6$ straight chain alkyl, $C_3$-$C_6$ branched chain alkyl or $C_3$-$C_6$ cycloalkyl.

In other embodiments, the compounds of formula I-5 have the formula:

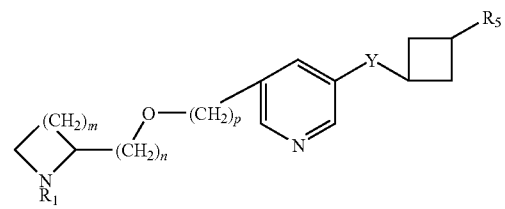

and pharmaceutically acceptable derivatives thereof, wherein all variables have the same meanings as set forth above for the compounds of formula I.

In other embodiments, the invention encompasses the compounds of I-5 having the formula:

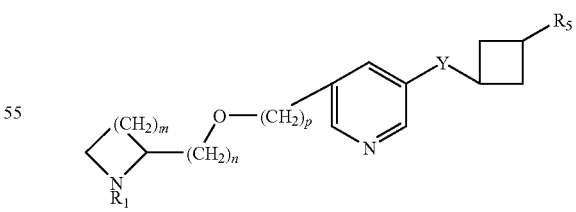

and pharmaceutically acceptable derivatives thereof, wherein all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r$-$NR'R^{vi}$ wherein $R^v$ and $R^{vi}$ are each independently hydrogen, $C_1$-$C_6$ straight chain alkyl, $C_3$-$C_6$ branched chain alkyl or $C_3$-$C_6$ cycloalkyl; —$(CH_2)_rSR^{viii}$ when $R^{viii}$ is $C_1$-$C_6$ straight chain alkyl, $C_3$-$C_6$ branched chain alkyl, or $C_3$-$C_6$ cycloalkyl; —$(CH_2)_rSO_2R^{ix}$, —$(CH_2)_rSOR^{ix}$ or —$(CH_2)_rC(O)OR^{ix}$ when $R^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_rNR'R^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl.

In yet another embodiment, the present invention encompasses compounds of formula I-5, and pharmaceutically acceptable derivatives thereof, wherein Y is a bond and all other variables have the same meanings as set forth above for the compounds of formula I.

In another embodiment, the present invention encompasses compounds of formula I-5, and pharmaceutically acceptable derivatives thereof, wherein Y is —$CH_2$— and all other variables have the same meanings as set forth above for the compounds of formula I.

In another embodiment, the present invention encompasses compounds of formula I-5, and pharmaceutically acceptable derivatives thereof, wherein Y is —$(CH_2)_2$— and all other variables have the same meanings as set forth above for the compounds of formula I.

In another embodiment, the present invention encompasses compounds of formula I-5, and pharmaceutically acceptable derivatives thereof, wherein Y is —$(CH_2)_3$— and all other variables have the same meanings as set forth above for the compounds of formula I.

In another embodiment, the present invention encompasses compounds of formula I-5, and pharmaceutically acceptable derivatives thereof, wherein Y is —$(CH_2)_4$— and all other variables have the same meanings as set forth above for the compounds of formula I.

In another embodiment, the present invention encompasses compounds of formula I-5, and pharmaceutically acceptable derivatives thereof, wherein Y is —$(CH_2)_5$— and all other variables have the same meanings as set forth above for the compounds of formula I.

In another embodiment, the present invention encompasses compounds of formula I-5, and pharmaceutically acceptable derivatives thereof, wherein $R_5$ is $C_1$-$C_6$ hydroxyalkyl and all other variables have the same meanings as set forth above for the compounds of formula I.

In another embodiment, the invention encompasses the compounds of formula I-5 and pharmaceutically acceptable derivatives thereof, wherein $R_5$ is —$(CH_2)_rNR'R^{vi}$, wherein $R^v$ and $R^{vi}$ are each independently $C_3$-$C_6$ cycloalkyl, —(CO)$R^{vii}$ or —$SO_2R^{vii}$, wherein if one of $R^v$ and $R^{vi}$ is —(CO)$R^{vii}$ or —$SO_2R^{vii}$, the other is not —(CO)$R^{vii}$ or —$SO_2R^{vii}$, or when $R^{vi}$ is either —(CO)$R^{vii}$ or —$SO_2R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-5 and pharmaceutically acceptable derivatives thereof, wherein $R_5$ is —$(CH_2)_rNR'R^{vi}$, wherein $R^v$ and $R^{vi}$ are each independently hydrogen, $C_1$-$C_6$ straight chain alkyl, $C_3$-$C_6$ branched chain alkyl, $C_3$-$C_6$ cycloalkyl, —(CO)$R^{vii}$ or —$SO_2R^{vii}$, wherein if one of $R^v$ and $R^{vi}$ is —(CO)$R^{vii}$ or —$SO_2R^{vii}$, the other is not —(CO)$R^{vii}$ or —$SO_2R^{vii}$, or when $R^{vi}$ is either —(CO)$R^{vii}$ or —$SO_2R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-5, and pharmaceutically acceptable derivatives thereof, wherein $R_5$ is —$(CH_2)_rC(O)NR'R^{vi}$, and all other variables have the same meanings as set forth above for the compounds of formula I.

In another embodiment, the invention encompasses the compounds of formula I-5, and pharmaceutically acceptable derivatives thereof, wherein $R_5$ is —$(CH_2)_rSOR^{ix}$, and all other variables have the same meanings as set forth above for the compounds of formula I.

In another embodiment, the invention encompasses the compounds of formula I-5, and pharmaceutically acceptable derivatives thereof, wherein $R_5$ is —$(CH_2)_rC(O)OR^{ix}$, and all other variables have the same meanings as set forth above for the compounds of formula I.

In another embodiment, the invention encompasses the compounds of formula I-5, and pharmaceutically acceptable derivatives thereof, wherein $R_5$ is —$(CH_2)_{1-6}$—O—$(CH_2)_{0-6}$-aryl, and all other variables have the same meanings as set forth above for the compounds of formula I.

In another embodiment, the invention encompasses the compounds of formula I-5, and pharmaceutically acceptable derivatives thereof, wherein $R^5$ is —$(CH_2)_rSR^{viii}$, wherein $R^{viii}$ is aryl or —C(O)$R^x$, and all other variables have the same meanings as set forth above for the compounds of formula I.

In some embodiments, the present invention encompasses compounds of formula I-6:

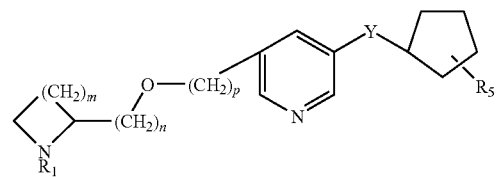

(I-6)

and pharmaceutically acceptable derivatives thereof, wherein all variables have the same meanings as set forth above for the compounds of formula I.

In other embodiments, the invention encompasses the compounds of formula I-6, wherein all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_rNR'R^{vi}$ wherein $R^v$ and $R^{vi}$ are each independently hydrogen, $C_1$-$C_6$ straight chain alkyl, $C_3$-$C_6$ branched chain alkyl or $C_3$-$C_6$ cycloalkyl; —$(CH_2)_rSR^{viii}$ when $R^{viii}$ is $C_1$-$C_6$ straight chain alkyl, $C_3$-$C_6$ branched chain alkyl, or $C_3$-$C_6$ cycloalkyl; —$(CH_2)_rSO_2R^{ix}$, —$(CH_2)_rSOR^{ix}$ or —$(CH_2)_rC(O)OR^{ix}$ when $R^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_rNR'R^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl.

In certain embodiments, the compounds of formula I-6 have the formula:

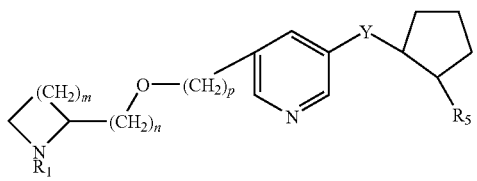

and pharmaceutically acceptable derivatives thereof, wherein all variables have the same meanings as set forth above for the compounds of formula I.

In other embodiments, the invention encompasses the compounds of formula I-6 have the formula:

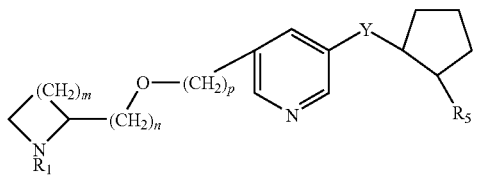

and pharmaceutically acceptable derivatives thereof, wherein all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r$NR$^v$R$^{vi}$ wherein R$^v$ and R$^{vi}$ are each independently hydrogen, $C_1$-$C_6$ straight chain alkyl, $C_3$-$C_6$ branched chain alkyl or $C_3$-$C_6$ cycloalkyl; —$(CH_2)_r$SR$^{viii}$ when R$^{viii}$ is $C_1$-$C_6$ straight chain alkyl, $C_3$-$C_6$ branched chain alkyl, or $C_3$-$C_6$ cycloalkyl; —$(CH_2)_r$SO$_2$R$^{ix}$, —$(CH_2)_r$SOR$^{ix}$ or —$(CH_2)_r$C(O)OR$^{ix}$ when R$^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_r$NR$^v$R$^{vi}$ when R$^v$ and R$^{vi}$ are each independently hydrogen, $C_1$-$C_6$ straight chain alkyl, $C_3$-$C_6$ branched chain alkyl or $C_3$-$C_6$ cycloalkyl.

In other embodiments, the compounds of formula I-6 have the formula:

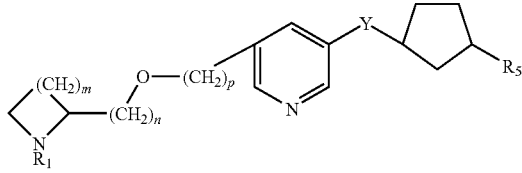

and pharmaceutically acceptable derivatives thereof, wherein all variables have the same meanings as set forth above for the compounds of formula I.

In other embodiments, the invention encompasses compounds of formula I-6 have the formula:

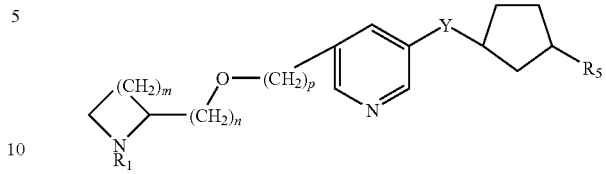

and pharmaceutically acceptable derivatives thereof, wherein all variables have the same meanings as set forth above for the compounds of formula I, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r$NR$^v$R$^{vi}$ wherein R$^v$ and R$^{vi}$ are each independently hydrogen, $C_1$-$C_6$ straight chain alkyl, $C_3$-$C_6$ branched chain alkyl or $C_3$-$C_6$ cycloalkyl; —$(CH_2)_r$SR$^{viii}$ when R$^{viii}$ is $C_1$-$C_6$ straight chain alkyl, $C_3$-$C_6$ branched chain alkyl, or $C_3$-$C_6$ cycloalkyl; —$(CH_2)_r$SO$_2$R$^{ix}$, —$(CH_2)_r$SOR$^{ix}$ or —$(CH_2)_r$C(O)OR$^{ix}$ when R$^{ix}$ is $C_1$-$C_6$ straight chain alkyl, $C_3$-$C_6$ branched chain alkyl, $C_3$-$C_6$ cycloalkyl or phenylalkyl in which the alkyl portion contains from 1 to 6 carbon atoms; and with the proviso that when m is 1 or 3 and Y is a bond, $R_5$ is not —$(CH_2)_r$NR$^v$R$^{vi}$ when R$^v$ and R$^{vi}$ are each independently hydrogen, $C_1$-$C_6$ straight chain alkyl, $C_3$-$C_6$ branched chain alkyl or $C_3$-$C_6$ cycloalkyl.

In yet another embodiment, the present invention encompasses compounds of formula I-6, and pharmaceutically acceptable derivatives thereof, wherein Y is a bond and all other variables have the same meanings as set forth above for the compounds of formula I.

In another embodiment, the present invention encompasses compounds of formula I-6, and pharmaceutically acceptable derivatives thereof, wherein Y is —$CH_2$— and all other variables have the same meanings as set forth above for the compounds of formula I.

In another embodiment, the present invention encompasses compounds of formula I-6, and pharmaceutically acceptable derivatives thereof, wherein Y is —$(CH_2)_2$— and all other variables have the same meanings as set forth above for the compounds of formula I.

In another embodiment, the present invention encompasses compounds of formula I-6, and pharmaceutically acceptable derivatives thereof, wherein Y is —$(CH_2)_3$— and all other variables have the same meanings as set forth above for the compounds of formula I.

In another embodiment, the present invention encompasses compounds of formula I-6, and pharmaceutically acceptable derivatives thereof, wherein Y is —$(CH_2)_4$— and all other variables have the same meanings as set forth above for the compounds of formula I.

In another embodiment, the present invention encompasses compounds of formula I-6, and pharmaceutically acceptable derivatives thereof, wherein Y is —$(CH_2)_5$— and all other variables have the same meanings as set forth above for the compounds of formula I.

In another embodiment, the present invention encompasses compounds of formula I-6, and pharmaceutically acceptable derivatives thereof, wherein $R_5$ is $C_1$-$C_6$ hydroxyalkyl and all other variables have the same meanings as set forth above for the compounds of formula I.

In another embodiment, the invention encompasses the compounds of formula I-6 and pharmaceutically acceptable derivatives thereof, wherein $R_5$ is —$(CH_2)_rNR'R^{vi}$, wherein $R^v$ and $R^{vi}$ are each independently $C_3$-$C_6$ cycloalkyl, —(CO)$R^{vii}$ or —$SO_2R^{vii}$, wherein if one of $R^v$ and $R^{vi}$ is —(CO)$R^{vii}$ or —$SO_2R^{vii}$, the other is not —(CO)$R^{vii}$ or —$SO_2R^{vii}$, or when $R^{vi}$ is either —(CO)$R^{vii}$ or —$SO_2R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-6 and pharmaceutically acceptable derivatives thereof, wherein $R_5$ is —$(CH_2)_rNR'R^{vi}$, wherein $R^v$ and $R^{vi}$ are each independently hydrogen, $C_1$-$C_6$ straight chain alkyl, $C_3$-$C_6$ branched chain alkyl, $C_3$-$C_6$ cycloalkyl, —(CO)$R^{vii}$ or —$SO_2R^{vii}$, wherein if one of $R^v$ and $R^{vi}$ is —(CO)$R^{vii}$ or —$SO_2R^{vii}$, the other is not —(CO)$R^{vii}$ or —$SO_2R^{vii}$, or when $R^{vi}$ is either —(CO)$R^{vii}$ or —$SO_2R^{vii}$, $R^v$ and $R^{vii}$ are taken together to form a 4- to 7-membered ring, and all other variables have the same meanings as set forth above for the compounds of formula I.

In another embodiment, the invention encompasses the compounds of formula I-6, and pharmaceutically acceptable derivatives thereof, wherein $R_5$ is —$(CH_2)_rC(O)NR'R^{vi}$, and all other variables have the same meanings as set forth above for the compounds of formula I.

In another embodiment, the invention encompasses the compounds of formula I-6, and pharmaceutically acceptable derivatives thereof, wherein $R_5$ is —$(CH_2)_rSOR^{ix}$, and all other variables have the same meanings as set forth above for the compounds of formula I.

In another embodiment, the invention encompasses the compounds of formula I-6, and pharmaceutically acceptable derivatives thereof, wherein $R_5$ is —$(CH_2)_rC(O)OR^{ix}$, and all other variables have the same meanings as set forth above for the compounds of formula I.

In another embodiment, the invention encompasses the compounds of formula I-6, and pharmaceutically acceptable derivatives thereof, wherein $R_5$ is —$(CH_2)_{1-6}$—O—$(CH_2)_{0-6}$-aryl, and all other variables have the same meanings as set forth above for the compounds of formula I.

In another embodiment, the invention encompasses the compounds of formula I-1 through I-6 and pharmaceutically acceptable derivatives thereof, wherein $R_5$ is —$(CH_2)_{1-6}$—O—$(CH_2)_{0-6}$-heteroaryl and all other variables have the same meaning set forth above for the compounds of formula I.

In another embodiment, the invention encompasses the compounds of formula I-6, and pharmaceutically acceptable derivatives thereof, wherein $R^5$ is —$(CH_2)_rSR^{viii}$, wherein $R^{viii}$ is aryl or —C(O)$R^x$, and all other variables have the same meanings as set forth above for the compounds of formula I.

In another embodiment, the pyridinyl nicotinic acetylcholine receptor ligand of the formula I is selected from:

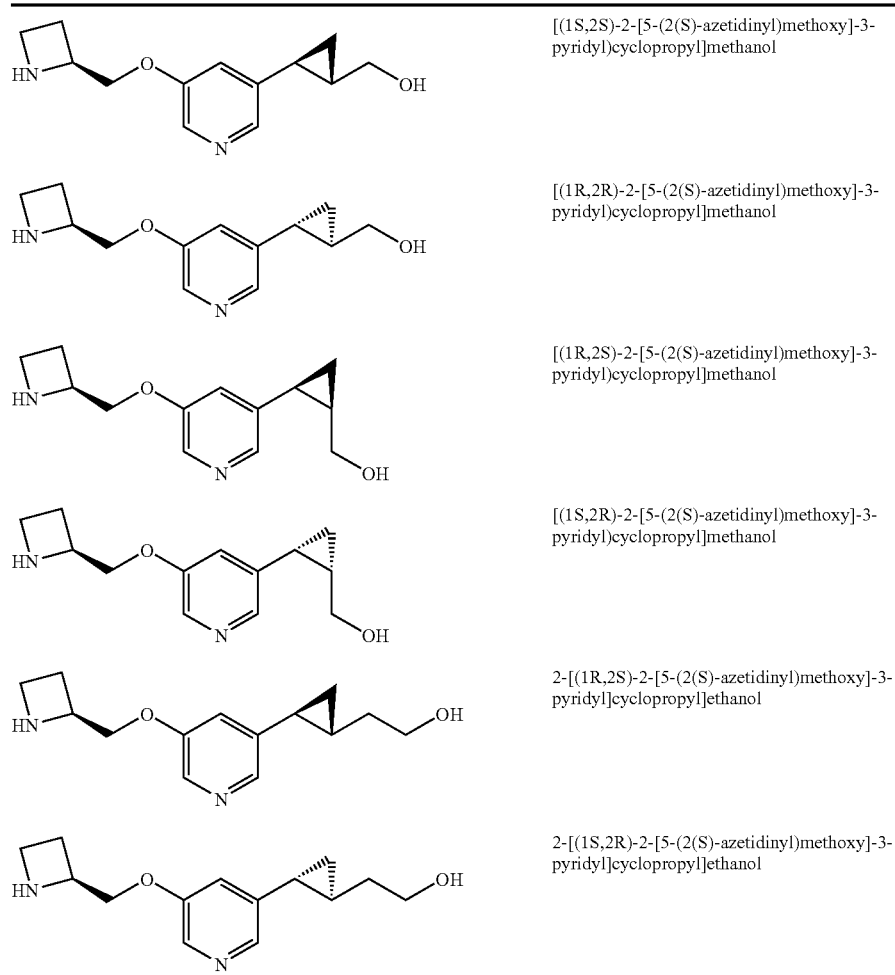

[(1S,2S)-2-[5-(2(S)-azetidinyl)methoxy]-3-pyridyl)cyclopropyl]methanol

[(1R,2R)-2-[5-(2(S)-azetidinyl)methoxy]-3-pyridyl)cyclopropyl]methanol

[(1R,2S)-2-[5-(2(S)-azetidinyl)methoxy]-3-pyridyl)cyclopropyl]methanol

[(1S,2R)-2-[5-(2(S)-azetidinyl)methoxy]-3-pyridyl)cyclopropyl]methanol

2-[(1R,2S)-2-[5-(2(S)-azetidinyl)methoxy]-3-pyridyl]cyclopropyl]ethanol

2-[(1S,2R)-2-[5-(2(S)-azetidinyl)methoxy]-3-pyridyl]cyclopropyl]ethanol

-continued

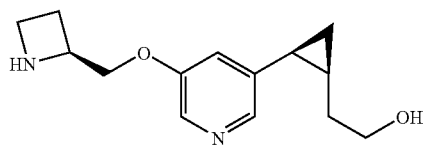 [SMILES: OCC[C@@H]1C[C@@H]1c1cncc(OC[C@@H]2CCN2)c1] 2-[(1S,2S)-2-[5-(2(S)-azetidinyl)methoxy]-3-pyridyl]cyclopropyl]ethanol

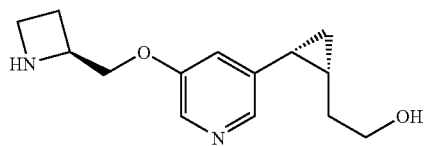 2-[(1R,2R)-2-[5-(2(S)-azetidinyl)methoxy]-3-pyridyl]cyclopropyl]ethanol

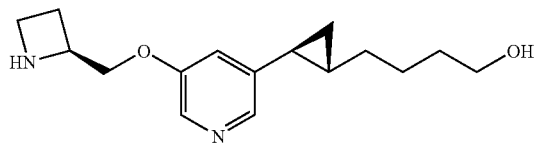 4-[(1S,2S)-2-[5-(2(S)-azetidinyl)methoxy]-3-pyridyl]cyclopropyl]-1-butanol

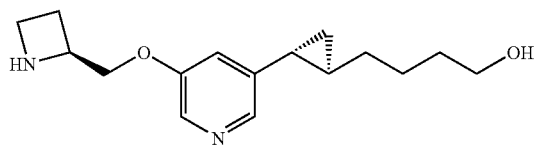 [SMILES: OCCCC[C@@H]1C[C@H]1c1cncc(OC[C@@H]2CCN2)c1] 4-[(1R,2R)-2-[5-(2(S)-azetidinyl)methoxy]-3-pyridyl]cyclopropyl]-1-butanol

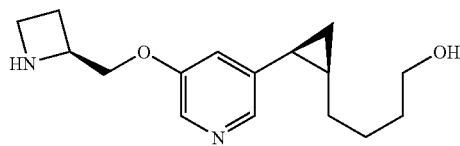 [SMILES: OCCCC[C@@H]1C[C@@H]1c1cncc(OC[C@@H]2CCN2)c1] 4-[(1R,2S)-2-[5-(2(S)-azetidinyl)methoxy]-3-pyridyl]cyclopropyl]-1-butanol

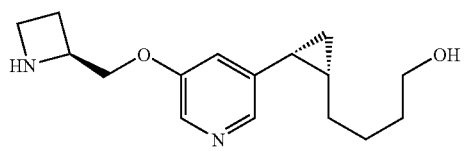 [SMILES: OCCCC[C@H]1C[C@H]1c1cncc(OC[C@@H]2CCN2)c1] 4-[(1S,2R)-2-[5-(2(S)-azetidinyl)methoxy]-3-pyridyl]cyclopropyl]-1-butanol

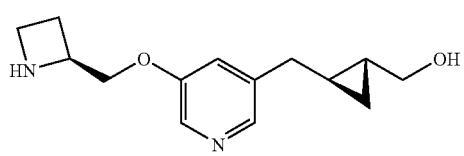 [SMILES: OC[C@@H]1C[C@H]1Cc1cncc(OC[C@@H]2CCN2)c1] [(1R,2S)-2-[[5-[(2(S)-azetidinyl)methoxy]-3-pyridyl]methyl]cyclopropyl]methanol

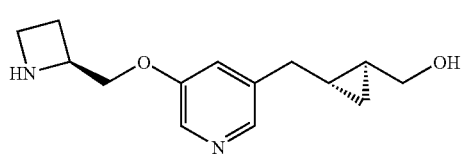 [SMILES: OC[C@H]1C[C@@H]1Cc1cncc(OC[C@@H]2CCN2)c1] [(1S,2R)-2-[[5-[(2(S)-azetidinyl)methoxy]-3-pyridyl]methyl]cyclopropyl]methanol

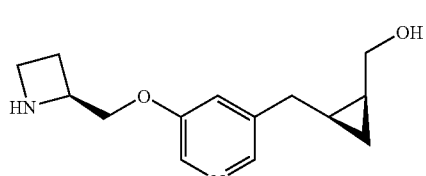 [(1S,2S)-2-[[5-[(2(S)-azetidinyl)methoxy]-3-pyridyl]methyl]cyclopropyl]methanol

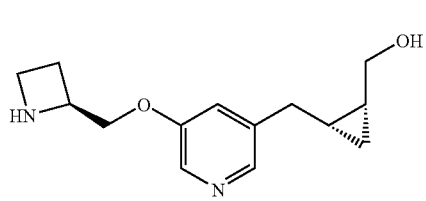 [SMILES: OC[C@@H]1C[C@@H]1Cc1cncc(OC[C@@H]2CCN2)c1] [(1R,2R)-2-[[5-[(2(S)-azetidinyl)methoxy]-3-pyridyl]methyl]cyclopropyl]methanol

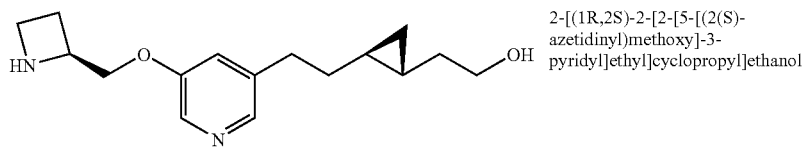
2-[(1R,2S)-2-[2-[5-[(2(S)-azetidinyl)methoxy]-3-pyridyl]ethyl]cyclopropyl]ethanol

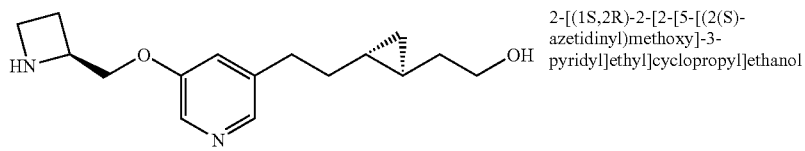
2-[(1S,2R)-2-[2-[5-[(2(S)-azetidinyl)methoxy]-3-pyridyl]ethyl]cyclopropyl]ethanol

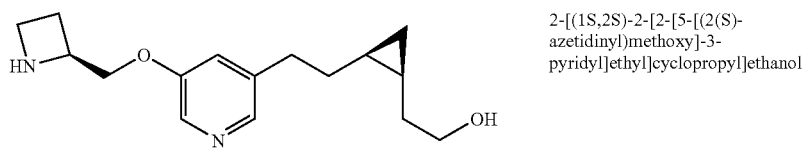
2-[(1S,2S)-2-[2-[5-[(2(S)-azetidinyl)methoxy]-3-pyridyl]ethyl]cyclopropyl]ethanol

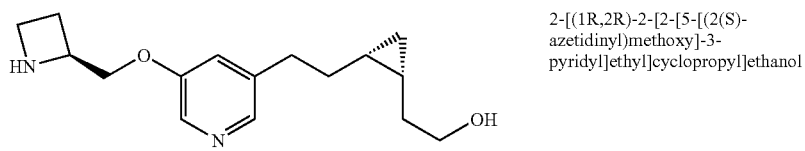
2-[(1R,2R)-2-[2-[5-[(2(S)-azetidinyl)methoxy]-3-pyridyl]ethyl]cyclopropyl]ethanol

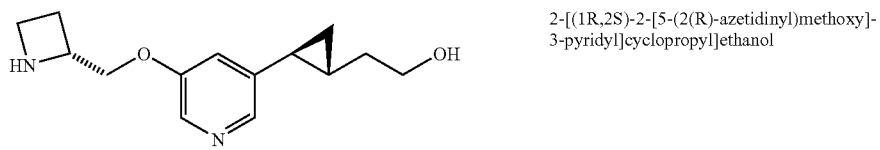
2-[(1R,2S)-2-[5-(2(R)-azetidinyl)methoxy]-3-pyridyl]cyclopropyl]ethanol

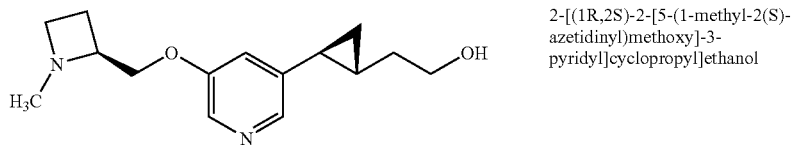
2-[(1R,2S)-2-[5-(1-methyl-2(S)-azetidinyl)methoxy]-3-pyridyl]cyclopropyl]ethanol

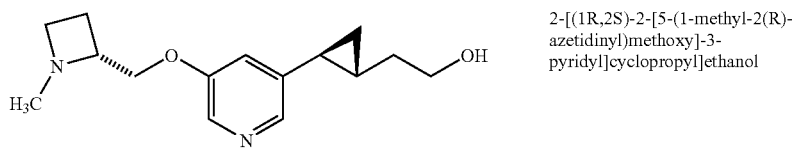
2-[(1R,2S)-2-[5-(1-methyl-2(R)-azetidinyl)methoxy]-3-pyridyl]cyclopropyl]ethanol

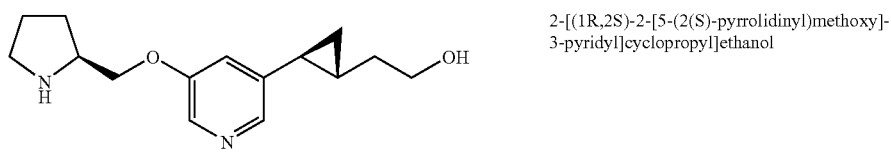
2-[(1R,2S)-2-[5-(2(S)-pyrrolidinyl)methoxy]-3-pyridyl]cyclopropyl]ethanol

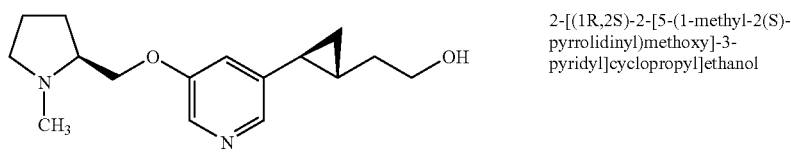
2-[(1R,2S)-2-[5-(1-methyl-2(S)-pyrrolidinyl)methoxy]-3-pyridyl]cyclopropyl]ethanol In another embodiment, the pyridinyl nicotinic acetylcholine receptor ligand of the formula I is selected from:

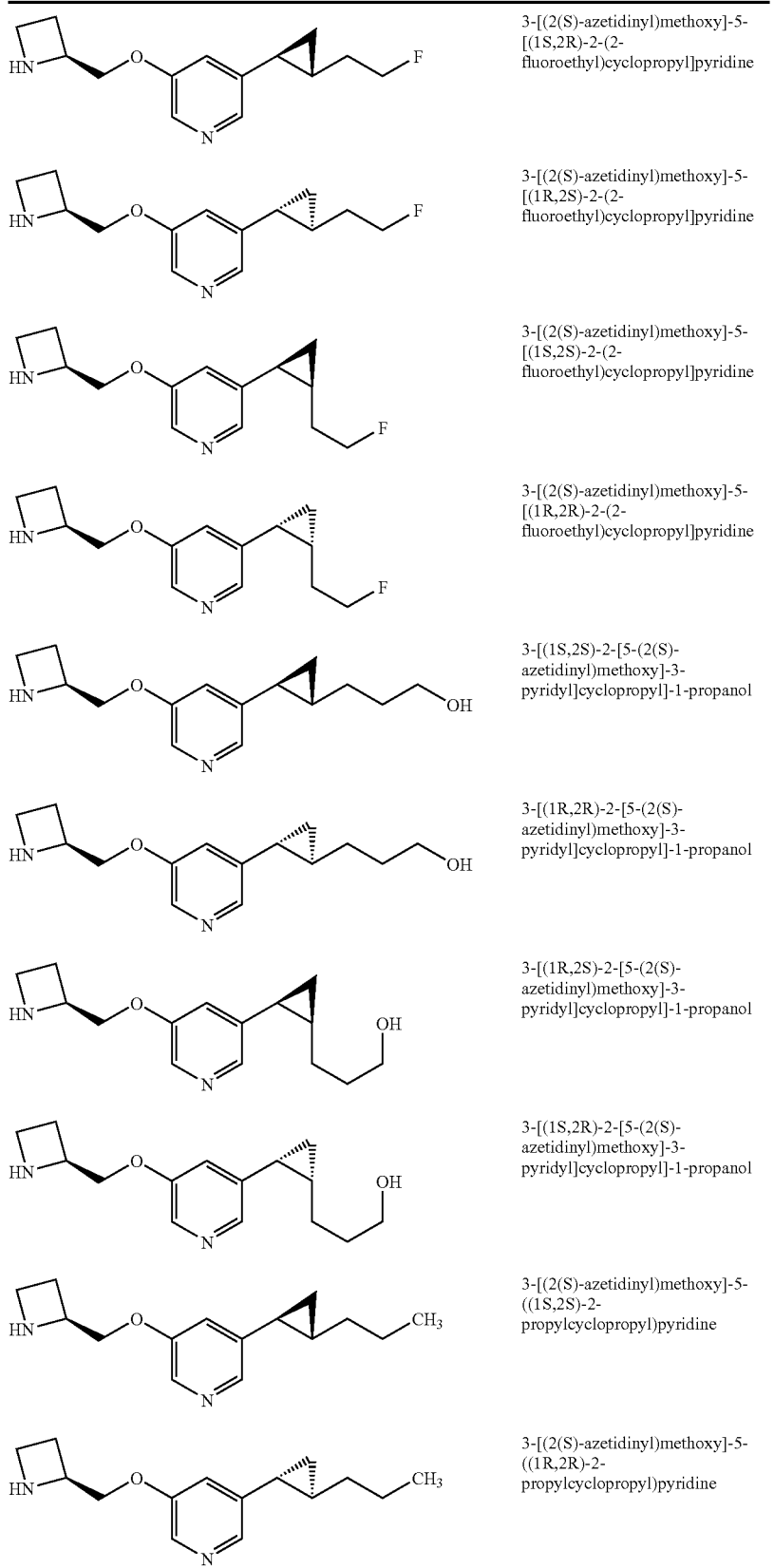

3-[(2(S)-azetidinyl)methoxy]-5-[(1S,2R)-2-(2-fluoroethyl)cyclopropyl]pyridine

3-[(2(S)-azetidinyl)methoxy]-5-[(1R,2S)-2-(2-fluoroethyl)cyclopropyl]pyridine

3-[(2(S)-azetidinyl)methoxy]-5-[(1S,2S)-2-(2-fluoroethyl)cyclopropyl]pyridine

3-[(2(S)-azetidinyl)methoxy]-5-[(1R,2R)-2-(2-fluoroethyl)cyclopropyl]pyridine

3-[(1S,2S)-2-[5-(2(S)-azetidinyl)methoxy]-3-pyridyl]cyclopropyl]-1-propanol

3-[(1R,2R)-2-[5-(2(S)-azetidinyl)methoxy]-3-pyridyl]cyclopropyl]-1-propanol

3-[(1R,2S)-2-[5-(2(S)-azetidinyl)methoxy]-3-pyridyl]cyclopropyl]-1-propanol

3-[(1S,2R)-2-[5-(2(S)-azetidinyl)methoxy]-3-pyridyl]cyclopropyl]-1-propanol

3-[(2(S)-azetidinyl)methoxy]-5-((1S,2S)-2-propylcyclopropyl)pyridine

3-[(2(S)-azetidinyl)methoxy]-5-((1R,2R)-2-propylcyclopropyl)pyridine

| | |
|---|---|
| 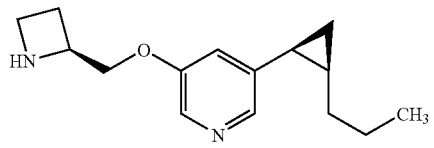 [SMILES: CCC[C@@H]1C[C@@H]1c1cncc(OC[C@@H]2CCN2)c1] | 3-[(2(S)-azetidinyl)methoxy]-5-((1S,2R)-2-propylcyclopropyl)pyridine |
| 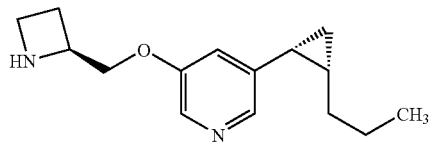 [SMILES: CCC[C@H]1C[C@H]1c1cncc(OC[C@@H]2CCN2)c1] | 3-[(2(S)-azetidinyl)methoxy]-5-((1R,2S)-2-propylcyclopropyl)pyridine |
| 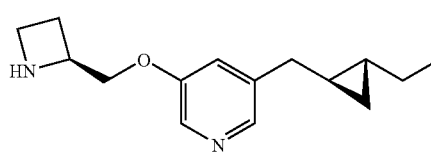 | 3-[(1R,2S)-2-[[5-[(2(S)-azetidinyl)methoxy]-3-pyridyl]methyl]cyclopropyl]-1-propanol |
| 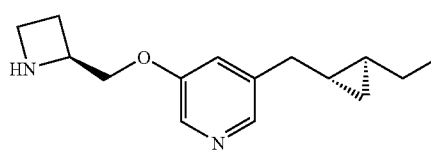 | 3-[(1S,2R)-2-[[5-[(2(S)-azetidinyl)methoxy]-3-pyridyl]methyl]cyclopropyl]-1-propanol |
| 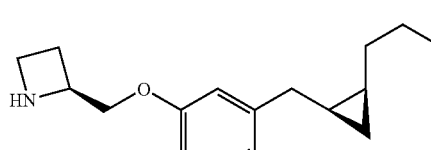 | 3-[(1S,2S)-2-[[5-[(2(S)-azetidinyl)methoxy]-3-pyridyl]methyl]cyclopropyl]-1-propanol |
| 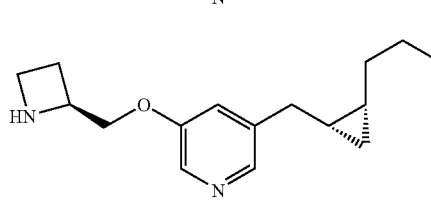 | 3-[(1R,2R)-2-[[5-[(2(S)-azetidinyl)methoxy]-3-pyridyl]methyl]cyclopropyl]-1-propanol |

In another embodiment, the pyridinyl nicotinic acetylcholine receptor ligand of the formula I is selected from:

| | |
|---|---|
| 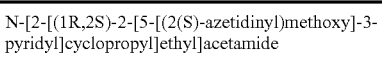 | N-[2-[(1R,2S)-2-[5-[(2(S)-azetidinyl)methoxy]-3-pyridyl]cyclopropyl]ethyl]acetamide |
| 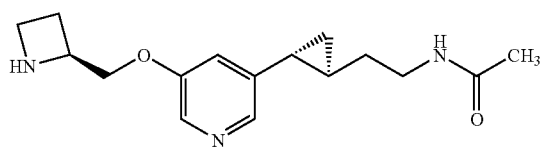 [SMILES: CC(=O)NCC[C@@H]1C[C@H]1c1cncc(OC[C@@H]2CCN2)c1] | N-[2-[(1S,2R)-2-[5-[(2(S)-azetidinyl)methoxy]-3-pyridyl]cyclopropyl]ethyl]acetamide |

-continued

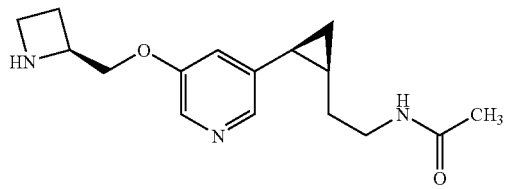 [SMILES: CC(=O)NCC[C@@H]1C[C@@H]1c1cncc(OC[C@@H]2CCN2)c1]
N-[2-[(1S,2S)-2-[5-[(2(S)-azetidinyl)methoxy]-3-pyridyl]cyclopropyl]ethyl]acetamide

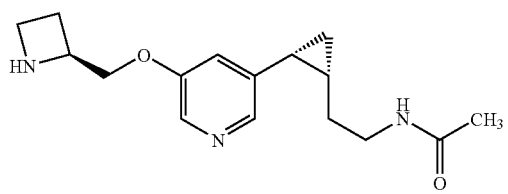 [SMILES: CC(=O)NCC[C@H]1C[C@H]1c1cncc(OC[C@@H]2CCN2)c1]
N-[2-[(1R,2R)-2-[5-[(2(S)-azetidinyl)methoxy]-3-pyridyl]cyclopropyl]ethyl]acetamide

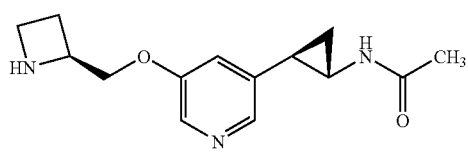 [SMILES: CC(=O)N[C@H]1C[C@@H]1c1cncc(OC[C@@H]2CCN2)c1]
N-[(1S,2R)-2-[5-[(2(S)-azetidinyl)methoxy]-3-pyridyl]cyclopropyl]acetamide

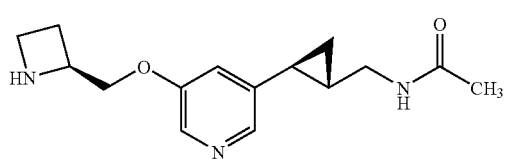 [SMILES: CC(=O)NC[C@H]1C[C@@H]1c1cncc(OC[C@@H]2CCN2)c1]
N-[[(1S,2S)-2-[5-[(2(S)-azetidinyl)methoxy]-3-pyridyl]cyclopropyl]methyl]acetamide

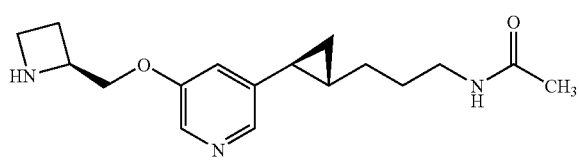 [SMILES: CC(=O)NCCC[C@H]1C[C@@H]1c1cncc(OC[C@@H]2CCN2)c1]
N-[3-[(1S,2S)-2-[5-[(2(S)-azetidinyl)methoxy]-3-pyridyl]cyclopropyl]propyl]acetamide

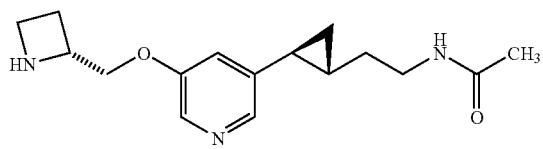
N-[2-[(1R,2S)-2-[5-[(2(R)-azetidinyl)methoxy]-3-pyridyl]cyclopropyl]ethyl]acetamide

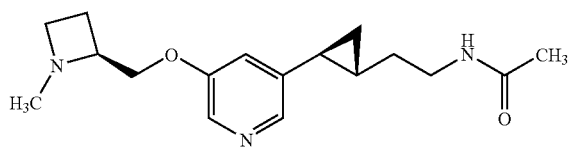 [SMILES: CC(=O)NCC[C@H]1C[C@@H]1c1cncc(OC[C@@H]2CCN2C)c1]
N-[2-[(1R,2S)-2-[5-[(1-methyl-2(S)-azetidinyl)methoxy]-3-pyridyl]cyclopropyl]ethyl]acetamide

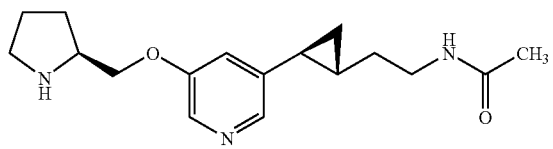 [SMILES: CC(=O)NCC[C@H]1C[C@@H]1c1cncc(OC[C@@H]2CCCN2)c1]
N-[2-[(1R,2S)-2-[5-[(2(S)-pyrrolidinyl)methoxy]-3-pyridyl]cyclopropyl]ethyl]acetamide

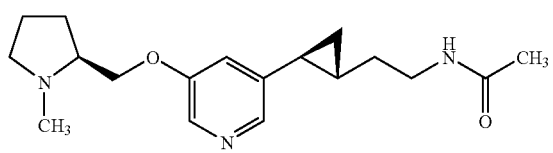 [SMILES: CC(=O)NCC[C@H]1C[C@@H]1c1cncc(OC[C@@H]2CCCN2C)c1]
N-[2-[(1R,2S)-2-[5-[(1-methyl-2(S)-pyrrolidinyl)methoxy]-3-pyridyl]cyclopropyl]ethyl]acetamide

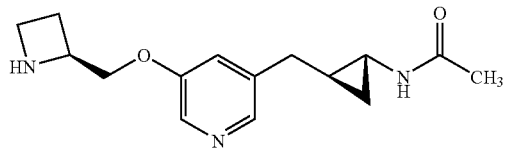 [SMILES: CC(=O)N[C@@H]1C[C@H]1Cc1cncc(OC[C@@H]2CCN2)c1] N-[(1R,2R)-2-[[5-[2(S)-pyrrolidinyl)methoxy]-3-pyridyl]methyl]cyclopropyl]acetamide

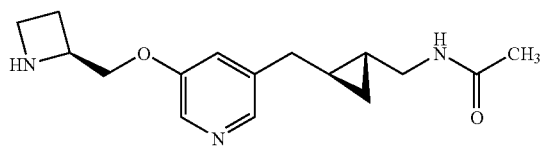 [SMILES: CC(=O)NC[C@@H]1C[C@H]1Cc1cncc(OC[C@@H]2CCN2)c1] N-[[(1R,2S)-2-[[5-[(2(S)-azetidinyl)methoxy]-3-pyridyl]methyl]cyclopropyl]methyl]acetamide

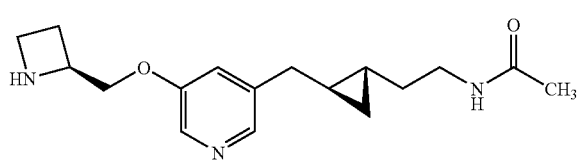 [SMILES: CC(=O)NCC[C@@H]1C[C@H]1Cc1cncc(OC[C@@H]2CCN2)c1] N-[2-[(1S,2S)-2-[[5-[(2(S)-azetidinyl)methoxy]-3-pyridyl]methyl]cyclopropyl]ethyl]acetamide

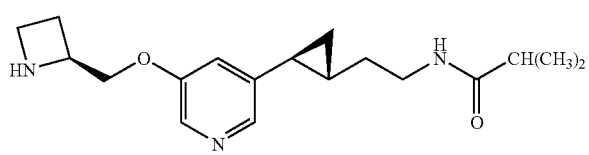 [SMILES: CC(C)C(=O)NCC[C@H]1C[C@@H]1c1cncc(OC[C@@H]2CCN2)c1] N-[2-[(1R,2S)-2-[5-[(2(S)-azetidinyl)methoxy]-3-pyridyl]cyclopropyl]ethyl]isobutyramide

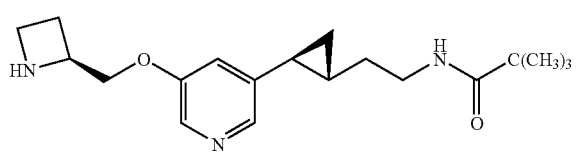 N-[2-[(1R,2S)-2-[5-[(2(S)-azetidinyl)methoxy]-3-pyridyl]cyclopropyl]ethyl]pivalamide

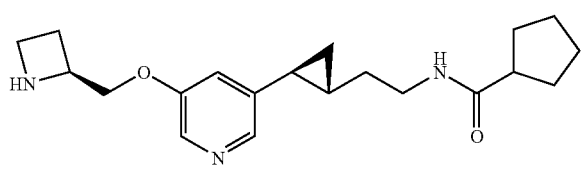 [SMILES: O=C(NCC[C@H]1C[C@@H]1c1cncc(OC[C@@H]2CCN2)c1)C1CCCC1] N-[2-[(1R,2S)-2-[5-[(2(S)-azetidinyl)methoxy]-3-pyridyl]cyclopropyl]ethyl]cyclopentanecarboxamide

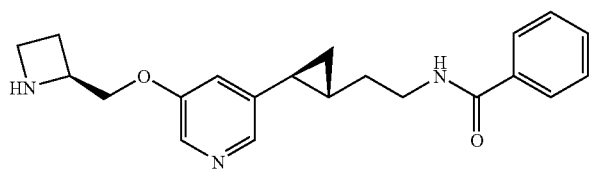 [SMILES: O=C(NCC[C@H]1C[C@@H]1c1cncc(OC[C@@H]2CCN2)c1)c1ccccc1] N-[2-[(1R,2S)-2-[5-[(2(S)-azetidinyl)methoxy]-3-pyridyl]cyclopropyl]ethyl]benzamide

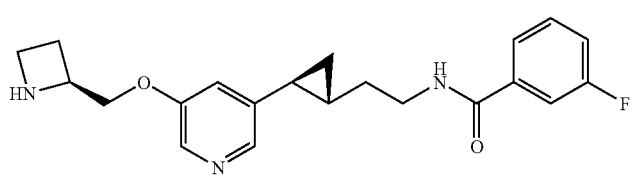 [SMILES: O=C(NCC[C@H]1C[C@@H]1c1cncc(OC[C@@H]2CCN2)c1)c1cccc(F)c1] N-[2-[(1R,2S)-2-[5-[(2(S)-azetidinyl)methoxy]-3-pyridyl]cyclopropyl]ethyl]-3-fluorobenzamide

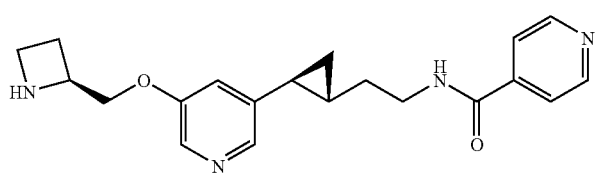 [SMILES: O=C(NCC[C@H]1C[C@@H]1c1cncc(OC[C@@H]2CCN2)c1)c1ccncc1] N-[2-[(1R,2S)-2-[5-[(2(S)-azetidinyl)methoxy]-3-pyridyl]cyclopropyl]ethyl]isonicotinamide -continued

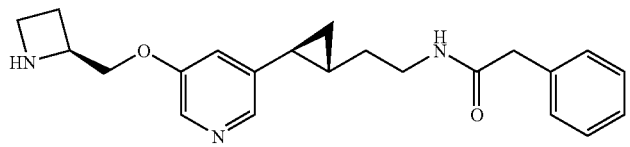 [SMILES: O=C(Cc1ccccc1)NCC[C@H]1C[C@@H]1c1cncc(OC[C@@H]2CCN2)c1]
N-[2-[(1R,2S)-2-[5-[(2(S)-azetidinyl)methoxy]-3-pyridyl]cyclopropyl]ethyl]-2-phenylacetamide

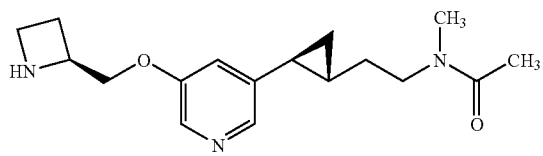 [SMILES: CC(=O)N(C)CC[C@H]1C[C@@H]1c1cncc(OC[C@@H]2CCN2)c1]
N-[2-[(1R,2S)-2-[5-[(2(S)-azetidinyl)methoxy]-3-pyridyl]cyclopropyl]ethyl]-N-methylacetamide

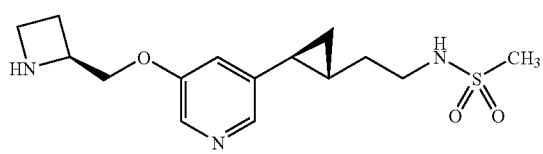 [SMILES: CS(=O)(=O)NCC[C@H]1C[C@@H]1c1cncc(OC[C@@H]2CCN2)c1]
N-[2-[(1R,2S)-2-[5-[(2(S)-azetidinyl)methoxy]-3-pyridyl]cyclopropyl]ethyl]methanesulfonamide

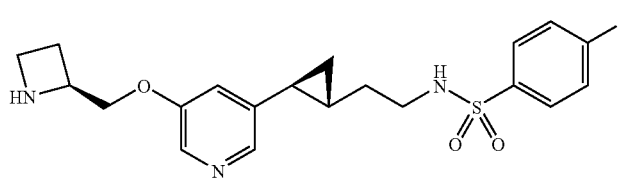
N-[2-[(1R,2S)-2-[5-[(2(S)-azetidinyl)methoxy]-3-pyridyl]cyclopropyl]ethyl]-4-methylbenzenesulfonamide In another embodiment, the compound of formula I is selected from:

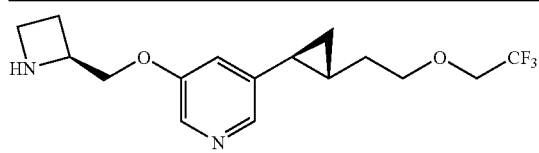
3-[(2(S)-azetidinyl)methoxy]-5-[(1S,2R)-2-[2-(2,2,2-trifluoroethoxy)ethyl]cyclopropyl]pyridine

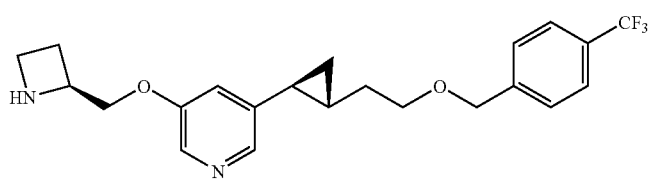
3-[(2(S)-azetidinyl)methoxy]-5-[(1S,2R)-2-[2-[4-(trifluoromethyl)benzyloxy]ethyl]cyclopropyl]pyridine

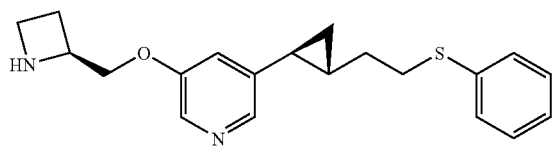
3-[(2(S)-azetidinyl)methoxy]-5-[(1S,2R)-2-[2-(phenylthio)ethyl]cyclopropyl]pyridine

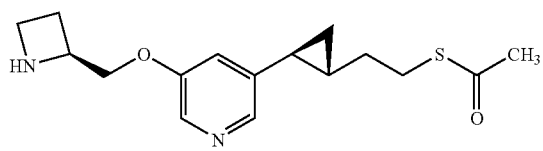 [SMILES: CC(=O)SCC[C@H]1C[C@@H]1c1cncc(OC[C@@H]2CCN2)c1]
S-2-[(1R,2S)-2-[5-[(2(S)-azetidinyl)methoxy]-3-pyridyl]cyclopropyl]ethyl ethanethioate

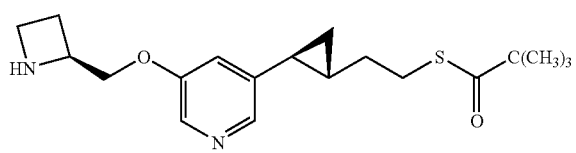 [SMILES: CC(C)(C)C(=O)SCC[C@H]1C[C@@H]1c1cncc(OC[C@@H]2CCN2)c1]
S-2-[(1R,2S)-2-[5-[(2(S)-azetidinyl)methoxy]-3-pyridyl]cyclopropyl]ethyl 2,2-dimethylpropanethioate -continued

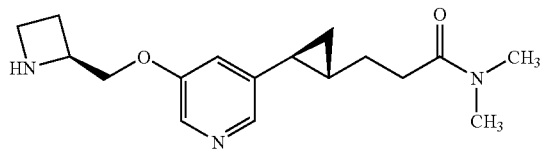 [SMILES: CN(C)C(=O)CC[C@H]1C[C@@H]1c1cncc(OC[C@@H]2CCN2)c1]
3-[(1S,2S)-2-[5-[(2(S)-azetidinyl)methoxy]-3-pyridyl]cyclopropyl]-N,N-dimethylpropionamide

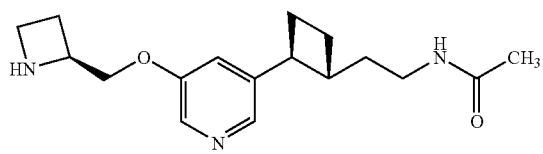 [SMILES: CC(=O)NCC[C@H]1CC[C@@H]1c1cncc(OC[C@@H]2CCN2)c1]
N-[2-[(1R,2S)-2-[5-[(2(S)-azetidinyl)methoxy]-3-pyridyl]cyclobutyl]ethyl]acetamide

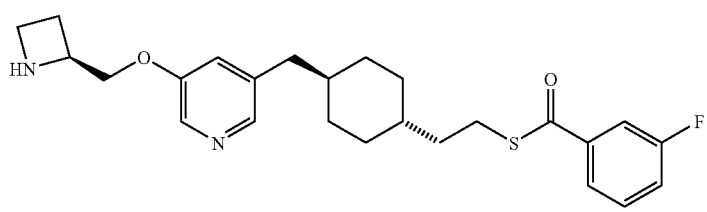 [SMILES: O=C(SCC[C@H]1CC[C@H](Cc2cncc(OC[C@@H]3CCN3)c2)CC1)c1cccc(F)c1]
S-2-[trans-4-[[5-[(2(S)-azetidinyl)methoxy]-3-pyridyl]methyl]cyclohexyl]ethyl 3-fluorobenzothioate

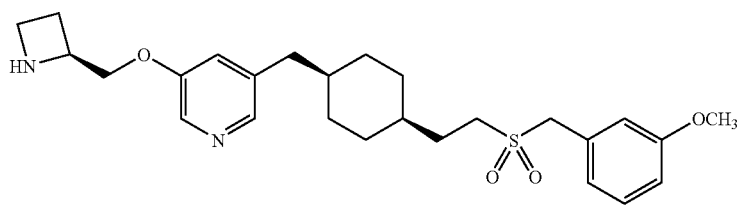 [SMILES: COc1cccc(CS(=O)(=O)CC[C@H]2CC[C@@H](Cc3cncc(OC[C@@H]4CCN4)c3)CC2)c1]
3-[(2(S)-azetidinyl)methoxy]-5-[[cis-4-[2-[3-methoxybenzylsulfonyl]ethyl]cyclohexyl]methyl]-pyridine

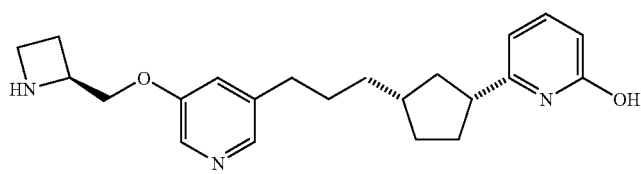 [SMILES: Oc1cccc([C@@H]2CC[C@H](CCCc3cncc(OC[C@@H]4CCN4)c3)C2)n1]
6-[(1R,3S)-3-[3-[5-[(2(S)-azetidinyl)methoxy]-3-pyridyl]propyl]cyclopentyl]pyridin-2-ol

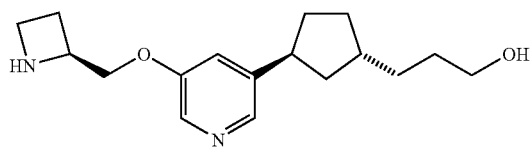 [SMILES: OCCC[C@H]1CC[C@H](c2cncc(OC[C@@H]3CCN3)c2)C1]
3-[(1R,3S)-3-[5-[(2(S)-azetidinyl)methoxy]-3-pyridyl]cyclopentyl]-1-propanol

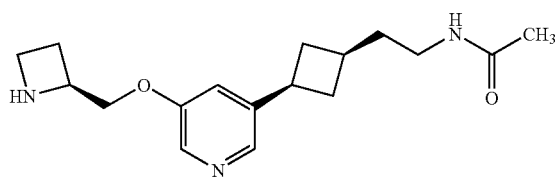 [SMILES: CC(=O)NCC[C@H]1C[C@@H](c2cncc(OC[C@@H]3CCN3)c2)C1]
N-[2-[cis-3-[5-[(2(S)-azetidinyl)methoxy]-3-pyridyl]cyclobutyl]ethyl]acetamide

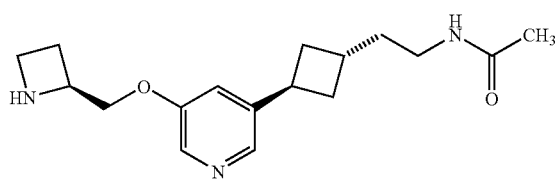 [SMILES: CC(=O)NCC[C@H]1C[C@H](c2cncc(OC[C@@H]3CCN3)c2)C1]
N-[2-[trans-3-[5-[(2(S)-azetidinyl)methoxy]-3-pyridyl]cyclobutyl]ethyl]acetamide In another embodiment, the pyridinyl nicotinic acetylcholine receptor ligand of the formula I is selected from:

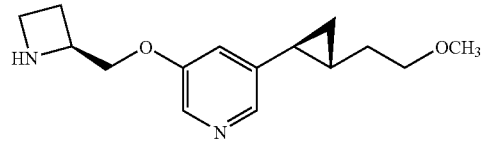 [SMILES: COCC[C@H]1C[C@@H]1c1cncc(OC[C@@H]2CCN2)c1]

3-[(2(S)-azetidinyl)methoxy]-5-[(1S,2R)-2-(2-methoxyethyl)cyclopropyl]pyridine

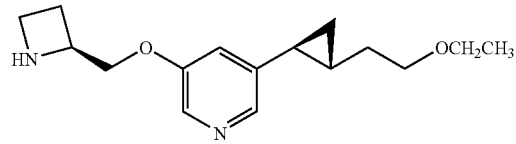 [SMILES: CCOCC[C@H]1C[C@@H]1c1cncc(OC[C@@H]2CCN2)c1]

3-[(2(S)-azetidinyl)methoxy]-5-[(1S,2R)-2-(2-ethoxyethyl)cyclopropyl]pyridine

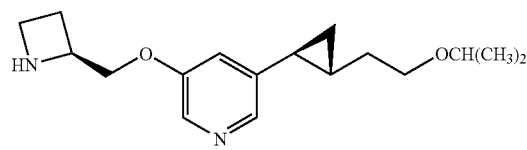

3-[(2(S)-azetidinyl)methoxy]-5-[(1S,2R)-2-(2-isopropoxyethyl)cyclopropyl]pyridine

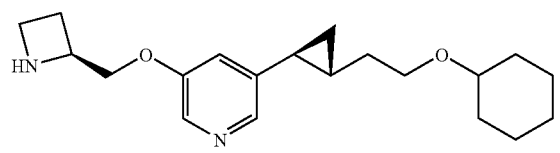

3-[(2(S)-azetidinyl)methoxy]-5-[(1S,2R)-2-[2-(cyclohexyloxy)ethyl]cyclopropyl]pyridine

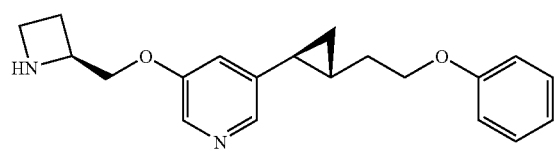 [SMILES: c1ccc(OCC[C@H]2C[C@@H]2c2cncc(OC[C@@H]3CCN3)c2)cc1]

3-[(2(S)-azetidinyl)methoxy]-5-[(1S,2R)-2-(2-phenoxyethyl)cyclopropyl]pyridine

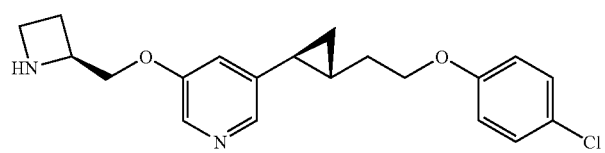 [SMILES: Clc1ccc(OCC[C@H]2C[C@@H]2c2cncc(OC[C@@H]3CCN3)c2)cc1]

3-[(2(S)-azetidinyl)methoxy]-5-[(1S,2R)-2-[2-(4-chlorophenoxy)ethyl]cyclopropyl]pyridine

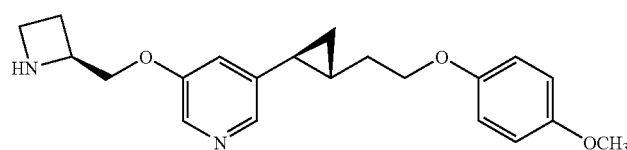

3-[(2(S)-azetidinyl)methoxy]-5-[(1S,2R)-2-[2-(4-methoxyphenoxy)ethyl]cyclopropyl]pyridine

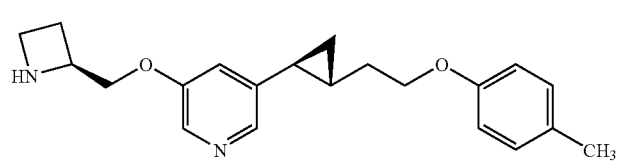 [SMILES: Cc1ccc(OCC[C@H]2C[C@@H]2c2cncc(OC[C@@H]3CCN3)c2)cc1]

3-[(2(S)-azetidinyl)methoxy]-5-[(1S,2R)-2-[2-(4-methylphenoxy)ethyl]cyclopropyl]pyridine

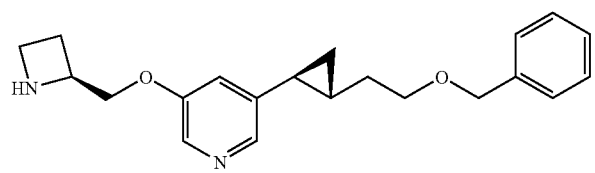 [SMILES: c1ccc(COCC[C@H]2C[C@@H]2c2cncc(OC[C@@H]3CCN3)c2)cc1]

3-[(2(S)-azetidinyl)methoxy]-5-[(1S,2R)-2-[2-(benzyloxy)ethyl]cyclopropyl]pyridine

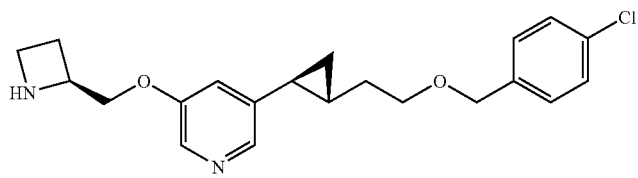 [SMILES: Clc1ccc(COCC[C@H]2C[C@@H]2c2cncc(OC[C@@H]3CCN3)c2)cc1]
3-[(2(S)-azetidinyl)methoxy]-5-[(1S,2R)-2-[2-(4-chlorobenzyloxy)ethyl]cyclopropyl]pyridine

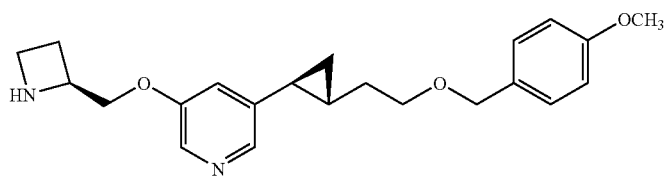 [SMILES: COc1ccc(COCC[C@H]2C[C@@H]2c2cncc(OC[C@@H]3CCN3)c2)cc1]
3-[(2(S)-azetidinyl)methoxy]-5-[(1S,2R)-2-[2-(4-methoxybenzyloxy)ethyl]cyclopropyl]pyridine

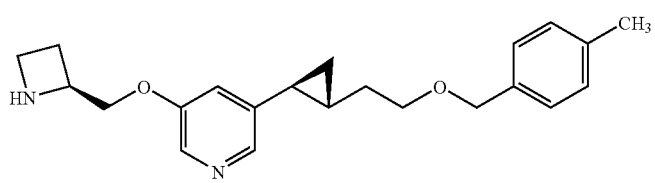 [SMILES: Cc1ccc(COCC[C@H]2C[C@@H]2c2cncc(OC[C@@H]3CCN3)c2)cc1]
3-[(2(S)-azetidinyl)methoxy]-5-[(1S,2R)-2-[2-(4-methylbenzyloxy)ethyl]cyclopropyl]pyridine

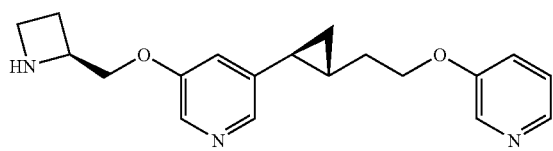 [SMILES: c1cncc(OCC[C@H]2C[C@@H]2c2cncc(OC[C@@H]3CCN3)c2)c1]
3-[(2(S)-azetidinyl)methoxy]-5-[(1S,2R)-2-[2-(3-pyridyloxy)ethyl]cyclopropyl]pyridine

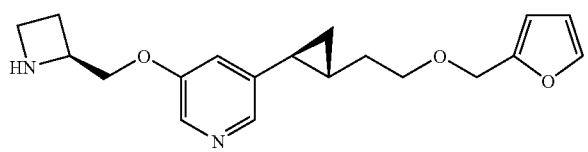 [SMILES: c1coc(COCC[C@H]2C[C@@H]2c2cncc(OC[C@@H]3CCN3)c2)c1]
3-[(2(S)-azetidinyl)methoxy]-5-[(1S,2R)-2-[2-[(2-furyl)methoxy]ethyl]cyclopropyl]pyridine

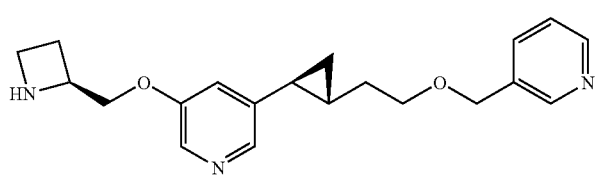 [SMILES: c1cncc(COCC[C@H]2C[C@@H]2c2cncc(OC[C@@H]3CCN3)c2)c1]
3-[(2(S)-azetidinyl)methoxy]-5-[(1S,2R)-2-[2-[(3-pyridyl)methoxy]ethyl]cyclopropyl]pyridine

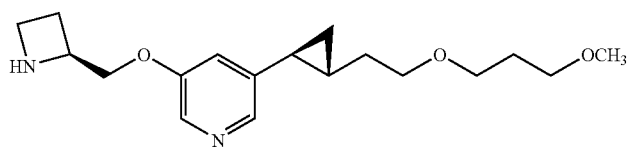 [SMILES: COCCCOCC[C@H]1C[C@@H]1c1cncc(OC[C@@H]2CCN2)c1]
3-[(2(S)-azetidinyl)methoxy]-5-[(1S,2R)-2-[2-(3-methoxypropoxy)ethyl]cyclopropyl]pyridine

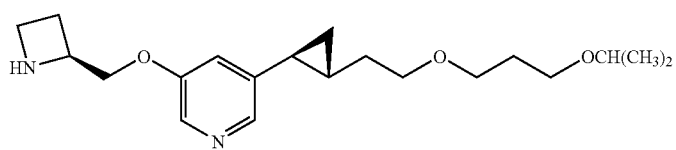
3-[(2(S)-azetidinyl)methoxy]-5-[(1S,2R)-2-[2-(3-isopropoxypropoxy)ethyl]cyclopropyl]pyridine

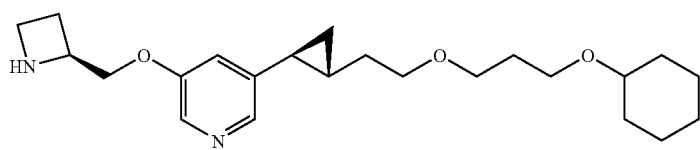 [SMILES: c1ncc([C@H]2C[C@@H]2CCOCCCOC2CCCCC2)cc1OC[C@@H]1CCN1]
3-[(2(S)-azetidinyl)methoxy]-5-[(1S,2R)-2-[2-[3-(cyclohexyloxy)propoxy]ethyl]cyclopropyl]pyridine -continued

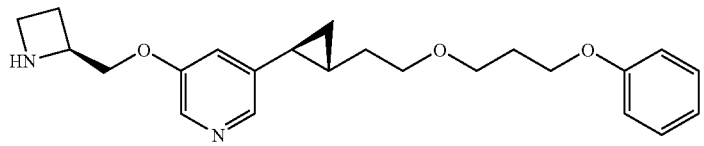 [SMILES: c1ccc(OCCCOCC[C@H]2C[C@@H]2c2cncc(OC[C@@H]3CCN3)c2)cc1]

3-[(2(S)-azetidinyl)methoxy]-5-[(1S,2R)-2-[2-(3-phenoxypropoxy)ethyl]cyclopropyl]pyridine

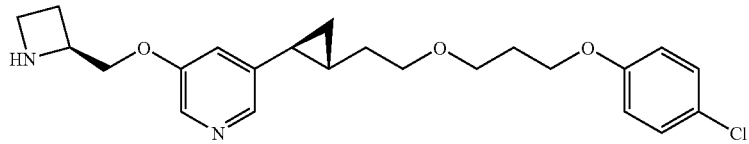 [SMILES: Clc1ccc(OCCCOCC[C@H]2C[C@@H]2c2cncc(OC[C@@H]3CCN3)c2)cc1]

3-[(2(S)-azetidinyl)methoxy]-5-[(1S,2R)-2-[2-[3-(4-chlorophenoxy)propoxy)ethyl]-cyclopropyl]pyridine

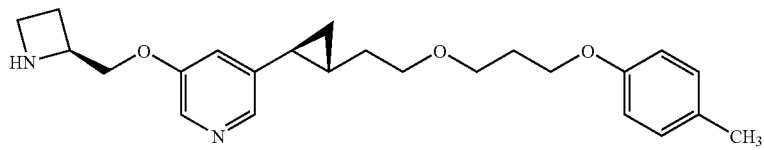 [SMILES: Cc1ccc(OCCCOCC[C@H]2C[C@@H]2c2cncc(OC[C@@H]3CCN3)c2)cc1]

3-[(2(S)-azetidinyl)methoxy]-5-[(1S,2R)-2-[2-[3-(4-methylphenoxy)propoxy]ethyl]cyclopropyl]-pyridine

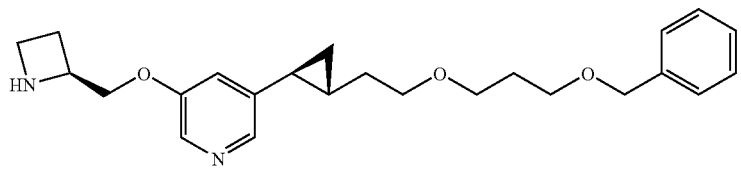 [SMILES: c1ccc(COCCCOCC[C@H]2C[C@@H]2c2cncc(OC[C@@H]3CCN3)c2)cc1]

3-[(2(S)-azetidinyl)methoxy]-5-[(1S,2R)-2-[2-[3-(benzyloxy)propoxy]ethyl]cyclopropyl]pyridine

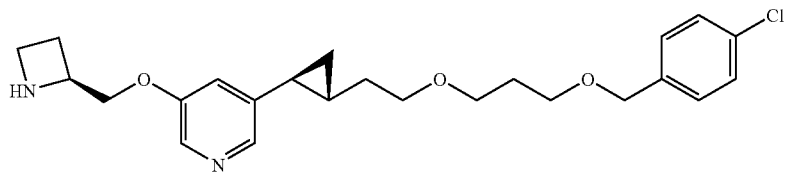 [SMILES: Clc1ccc(COCCCOCC[C@H]2C[C@@H]2c2cncc(OC[C@@H]3CCN3)c2)cc1]

3-[(2(S)-azetidinyl)methoxy]-5-[(1S,2R)-2-[2-[3-(4-chlorobenzyloxy)propoxy]ethyl]cyclopropyl]pyridine

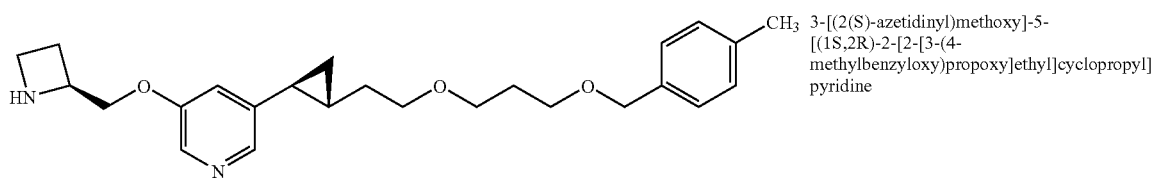

3-[(2(S)-azetidinyl)methoxy]-5-[(1S,2R)-2-[2-[3-(4-methylbenzyloxy)propoxy]ethyl]cyclopropyl]pyridine In another embodiment, the pyridinyl nicotinic acetylcholine receptor ligand of the formula I is selected from:

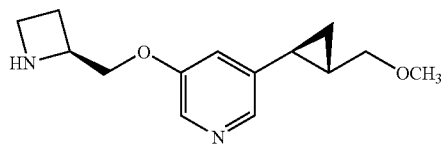 [SMILES: COC[C@H]1C[C@@H]1c1cncc(OC[C@@H]2CCN2)c1]

3-[(2(S)-azetidinyl)methoxy]-5-[(1S,2S)-2-(methoxymethyl)cyclopropyl]pyridine

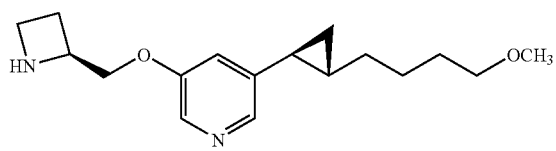 [SMILES: COCCCC[C@H]1C[C@@H]1c1cncc(OC[C@@H]2CCN2)c1]

3-[(2(S)-azetidinyl)methoxy]-5-[(1S,2S)-2-(4-methoxybutyl)cyclopropyl]pyridine

-continued

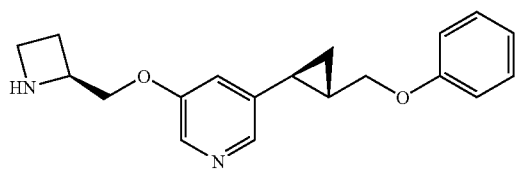 [SMILES: c1ccc(OC[C@H]2C[C@@H]2c2cncc(OC[C@@H]3CCN3)c2)cc1]
3-[(2(S)-azetidinyl)methoxy]-5-[(1S,2S)-2-(phenoxymethyl)cyclopropyl]pyridine

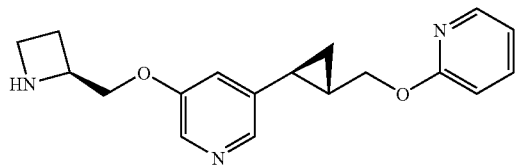 [SMILES: c1ccc(OC[C@H]2C[C@@H]2c2cncc(OC[C@@H]3CCN3)c2)nc1]
3-[(2(S)-azetidinyl)methoxy]-5-[(1S,2S)-2-[(2-pyridyloxy)methyl]cyclopropyl]pyridine

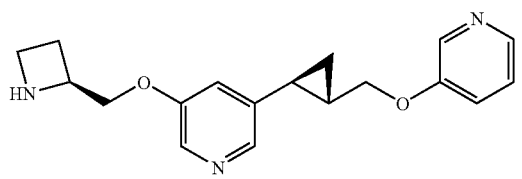 [SMILES: c1cncc(OC[C@H]2C[C@@H]2c2cncc(OC[C@@H]3CCN3)c2)c1]
3-[(2(S)-azetidinyl)methoxy]-5-[(1S,2S)-2-[(3-pyridyloxy)methyl]cyclopropyl]pyridine

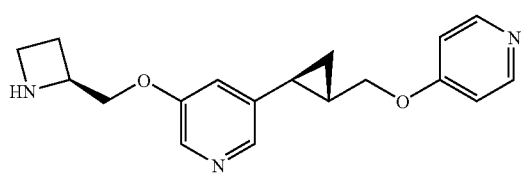 [SMILES: c1cc(OC[C@H]2C[C@@H]2c2cncc(OC[C@@H]3CCN3)c2)ccn1]
3-[(2(S)-azetidinyl)methoxy]-5-[(1S,2S)-2-[(4-pyridyloxy)methyl]cyclopropyl]pyridine

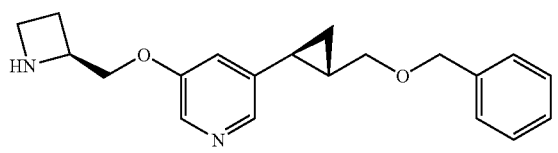
3-[(2(S)-azetidinyl)methoxy]-5-[(1S,2S)-2-[(benzyloxy)methyl]cyclopropyl]pyridine

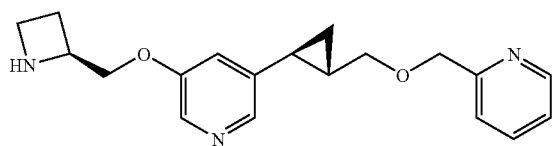 [SMILES: c1ccc(COC[C@H]2C[C@@H]2c2cncc(OC[C@@H]3CCN3)c2)nc1]
3-[(2(S)-azetidinyl)methoxy]-5-[(1S,2S)-2-[[(2-pyridyl)methoxy]methyl]cyclopropyl]pyridine

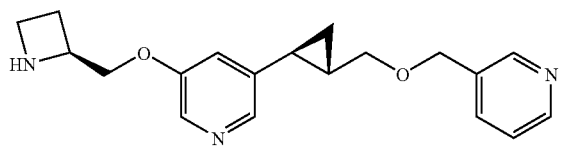 [SMILES: c1cncc(COC[C@H]2C[C@@H]2c2cncc(OC[C@@H]3CCN3)c2)c1]
3-[(2(S)-azetidinyl)methoxy]-5-[(1S,2S)-2-[[(3-pyridyl)methoxy]methyl]cyclopropyl]pyridine

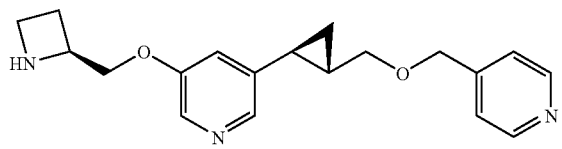 [SMILES: c1cc(COC[C@H]2C[C@@H]2c2cncc(OC[C@@H]3CCN3)c2)ccn1]
3-[(2(S)-azetidinyl)methoxy]-5-[(1S,2S)-2-[[(4-pyridyl)methoxy]methyl]cyclopropyl]pyridine

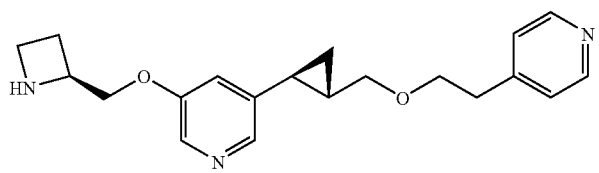 [SMILES: c1cc(CCOC[C@H]2C[C@@H]2c2cncc(OC[C@@H]3CCN3)c2)ccn1]
3-[(2(S)-azetidinyl)methoxy]-5-[(1S,2S)-2-[[2-(4-pyridyl)ethoxy]methyl]cyclopropyl]pyridine -continued

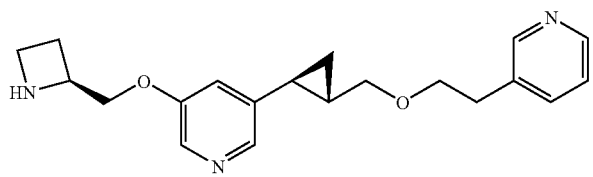 [SMILES: c1cncc(CCOC[C@H]2C[C@@H]2c2cncc(OC[C@@H]3CCN3)c2)c1]
3-[(2(S)-azetidinyl)methoxy]-5-[(1S,2S)-2-[[2-(3-pyridyl)ethoxy]methyl]cyclopropyl]pyridine

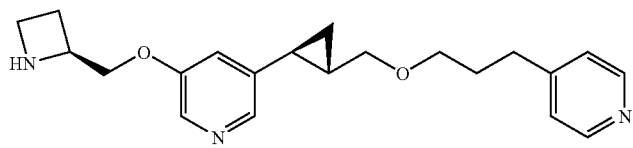 [SMILES: c1cc(CCCOC[C@H]2C[C@@H]2c2cncc(OC[C@@H]3CCN3)c2)ccn1]
3-[(2(S)-azetidinyl)methoxy]-5-[(1S,2S)-2-[[3-(4-pyridyl)ethoxy]methyl]cyclopropyl]pyridine

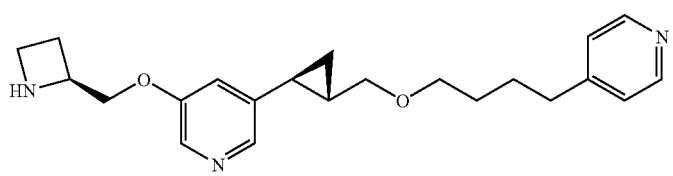 [SMILES: c1cc(CCCCOC[C@H]2C[C@@H]2c2cncc(OC[C@@H]3CCN3)c2)ccn1]
3-[(2(S)-azetidinyl)methoxy]-5-[(1S,2S)-2-[[4-(4-pyridyl)butoxy]methyl]cyclopropyl]pyridine

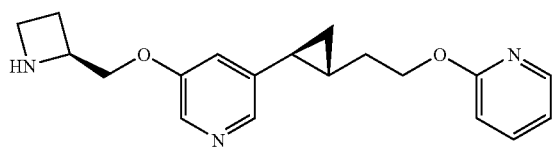 [SMILES: c1ccc(OCC[C@H]2C[C@@H]2c2cncc(OC[C@@H]3CCN3)c2)nc1]
3-[(2(S)-azetidinyl)methoxy]-5-[(1S,2R)-2-[2-(2-pyridyloxy)ethyl]cyclopropyl]pyridine

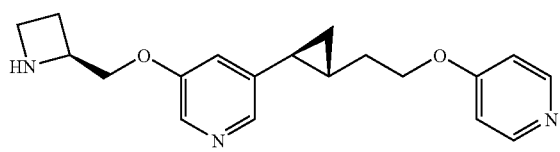 [SMILES: c1cc(OCC[C@H]2C[C@@H]2c2cncc(OC[C@@H]3CCN3)c2)ccn1]
3-[(2(S)-azetidinyl)methoxy]-5-[(1S,2R)-2-[2-(4-pyridyloxy)ethyl]cyclopropyl]pyridine

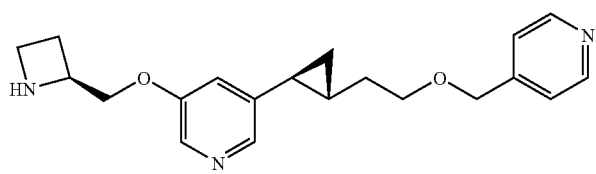 [SMILES: c1cc(COCC[C@H]2C[C@@H]2c2cncc(OC[C@@H]3CCN3)c2)ccn1]
3-[(2(S)-azetidinyl)methoxy]-5-[(1S,2R)-2-[2-[(4-pyridyl)methoxy]ethyl]cyclopropyl]pyridine

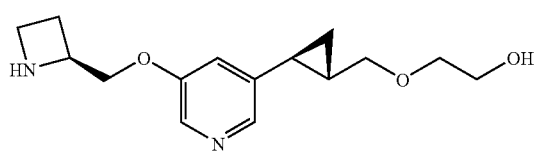
3-[(2(S)-azetidinyl)methoxy]-5-[(1S,2S)-2-[(2-hydroxyethoxy)methyl]cyclopropyl]pyridine

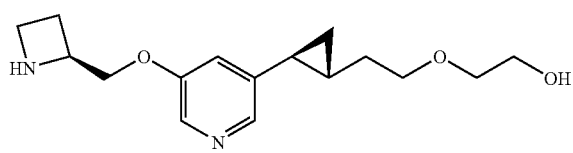 [SMILES: OCCOCC[C@H]1C[C@@H]1c1cncc(OC[C@@H]2CCN2)c1]
3-[(2(S)-azetidinyl)methoxy]-5-[(1S,2R)-2-[2-(2-hydroxyethoxy)ethyl]cyclopropyl]pyridine

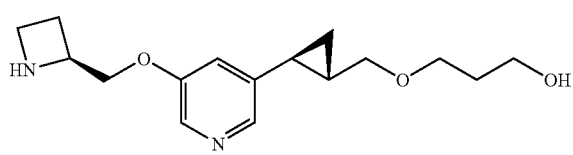 [SMILES: OCCCOC[C@H]1C[C@@H]1c1cncc(OC[C@@H]2CCN2)c1]
3-[(2(S)-azetidinyl)methoxy]-5-[(1S,2S)-2-[(3-hydroxypropoxy)methyl]cyclopropyl]pyridine

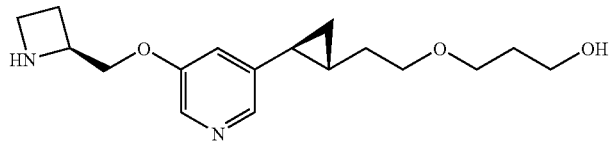 [SMILES: OCCCOCC[C@H]1C[C@@H]1c1cncc(OC[C@@H]2CCN2)c1]

3-[(2(S)-azetidinyl)methoxy]-5-[(1S,2R)-2-[2-(3-hydroxypropoxy)ethyl]cyclopropyl]pyridine

Nicotinic Acetylcholine Receptor Ligands of the Formula II

As stated above, the invention encompasses pyridinyl nicotinic acetylcholine receptor ligands of the formula II:

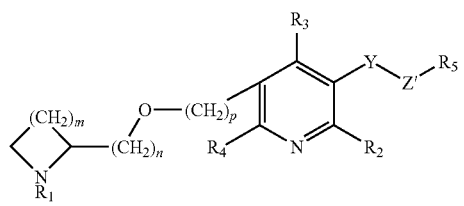

and pharmaceutically acceptable derivatives thereof, wherein all variables are as defined above for the pyridinyl nicotinic acetylcholine receptor ligands of the formula II.

In another embodiment, the invention encompasses compounds of formula II, wherein all variables have the same meanings as set forth above for the compounds of formula II, and with the proviso that when Z' is a 4- to 6-membered saturated heterocycle, m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —(CH$_2$)$_r$NR'R$^{vi}$ when one of R$^v$ and R$^{vi}$ is hydrogen, and the other of R$^v$ and R$^{vi}$ is $C_1$-$C_6$ straight chain alkyl, $C_3$-$C_6$ branched chain alkyl or $C_3$-$C_6$ cycloalkyl or when R$^v$ and R$^{vi}$ are independently $C_1$-$C_6$ straight chain alkyl, $C_3$-$C_6$ branched chain alkyl or $C_3$-$C_6$ cycloalkyl; —(CH$_2$)$_r$SR$^{viii}$ when R$^{viii}$ is $C_1$-$C_6$ straight chain alkyl, $C_3$-$C_6$ branched chain alkyl, or $C_3$-$C_6$ cycloalkyl; —(CH$_2$)$_r$SO$_2$R$^{ix}$, —(CH$_2$)$_r$SOR$^{ix}$ or —(CH$_2$)$_r$C(O)OR$^{ix}$ when R$^{ix}$ is $C_1$-$C_6$ straight chain alkyl, $C_3$-$C_6$ branched chain alkyl or $C_3$-$C_6$ cycloalkyl.

In another embodiment, $R_1$ is H.
In another embodiment, $R_1$ is $C_1$-$C_6$ straight chain alkyl.
In another embodiment, $R_1$ is $C_3$-$C_6$ branched chain alkyl.
In another embodiment, $R_1$ is allyl.
In another embodiment, $R_1$ is $C_3$-$C_6$ cycloalkyl.
In another embodiment, $R_2$ is H.
In another embodiment, $R_3$ is H.
In another embodiment, $R_4$ is H.
In another embodiment, $R_2$, $R_3$ and $R_4$ are each H.
In another embodiment, m is 1.
In another embodiment, m is 2.
In another embodiment, m is 3.
In another embodiment, n is 1.
In another embodiment, n is 2.
In another embodiment, p is 0.
In another embodiment, p is 1.
In another embodiment, p is 2.
In another embodiment, n is 1 and p is 0.
In one embodiment, Y is —CH$_2$— and Z' is a four- to six-membered saturated heterocycle.

In another embodiment, Y is —CH$_2$— and Z' is a five- or six-membered partially unsaturated heterocycle.
In another embodiment, Y is —CH$_2$CH$_2$— and Z' is a four- to six-membered saturated heterocycle.
In another embodiment, Y is —CH$_2$CH$_2$— and Z' is a five- or six-membered partially unsaturated heterocycle.
In another embodiment, Y is —CH$_2$CH$_2$CH$_2$— and Z' is a four- to six-membered saturated heterocycle.
In another embodiment, Y is —CH$_2$CH$_2$CH$_2$— and Z' is a five- or six-membered partially unsaturated heterocycle.
In another embodiment, Y is —(CH$_2$)$_4$— and Z' is a four- to six-membered saturated heterocycle.
In another embodiment, Y is —(CH$_2$)$_4$— and Z' is a five- or six-membered partially unsaturated heterocycle.
In another embodiment, Y is —(CH$_2$)$_5$— and Z' is a four- to six-membered saturated heterocycle.
In another embodiment, Y is —(CH$_2$)$_5$— and Z' is a five- or six-membered partially unsaturated heterocycle.
In another embodiment, Y is unsubstituted —(CH$_2$)$_q$— and q is an integer ranging from 1 to 5.
In another embodiment, Y is —(CH$_2$)$_q$—, q is an integer ranging from 1 to 5, and Y is substituted with one or two groups independently selected from methyl, ethyl, propyl, isopropyl, and cyclopropyl.
In another embodiment, m is 1, Y is a bond and Z' is a four- to six-membered saturated heterocycle.
In another embodiment, m is 1, Y is a bond and Z' is a five- or six-membered partially-unsaturated heterocycle.
In another embodiment, m is 3, Y is a bond and Z' is a four- to six-membered saturated heterocycle.
In another embodiment, m is 3, Y is a bond and Z' is a five- or six-membered partially-unsaturated heterocycle.
In another embodiment, m is 1 or 3, Y is a bond, Z' is a four- to six-membered saturated heterocycle or a five- or six-membered partially-unsaturated heterocycle having at least 3 carbon atoms and if Z' is a six-membered ring, $R_5$ is in the meta position on said ring with respect to the pyridine ring.
In another embodiment, m is 1 or 3, Y is a bond, Z' is a four- to six-membered saturated heterocycle or a five- or six-membered partially-unsaturated heterocycle having at least 3 carbon atoms and if Z' is a six-membered ring, $R_5$ is the para position on said ring with respect to the pyridine ring.
In another embodiment, m is 1 or 3, Y is a bond, Z' is a four- to six-membered saturated heterocycle or a five- or six-membered partially-unsaturated heterocycle having at least 3 carbon atoms and if Z' is a six-membered ring, $R_5$ is the ortho position on said ring with respect to the pyridine ring.
In another embodiment, Z' is a 2,5-disubstituted tetrahydrofuryl group.
In another embodiment, Z' is a 2,4-disubstituted azetidinyl group.
In another embodiment, $R_5$ is $C_1$-$C_6$ hydroxyalkyl.
In another embodiment, $R_5$ is alkoxyalkyl with one or two hydroxyl substitutents and in which the alkoxy and alkyl portions each independently contain from 1 to 6 carbon atoms.

In another embodiment, $R_5$ is hydroxyalkoxyalkyl in which the alkoxy and alkyl portions each independently contain from 1 to 6 carbon atoms.

In another embodiment, $R_5$ is arylalkoxy in which the alkoxy portion contains from 1 to 6 carbon atoms.

In another embodiment, $R_5$ is aryl.

In another embodiment, $R_5$ is biaryl.

In another embodiment, $R_5$ is heteroarylalkyl in which the alkyl portion contains from 1 to 6 carbon atoms.

In another embodiment, $R_5$ is $-(CH_2)_{1-6}-O-(CH_2)_{0-6}$-aryl.

In another embodiment, $R_5$ is $-(CH_2)_{1-6}-O-(CH_2)_{0-6}$-heteroaryl.

In another embodiment, $R_5$ is heteroaryl.

In another embodiment, $R_5$ is $-(CH_2)_r NR'R^{vi}$, wherein one of $R^v$ and $R^{vi}$ is hydrogen, $C_1$-$C_6$ straight chain alkyl, $C_3$-$C_6$ branched chain alkyl or $C_3$-$C_6$ cycloalkyl and the other of $R^v$ and $R^{vi}$ is $-(CO)R^{vii}$ or $-SO_2 R^{vii}$, and r and $R^{vii}$ are as described above for the pyridinyl nicotinic acetylcholine receptor ligands of the formula II.

In another embodiment, $R_5$ is $-(CH_2)_r C(O)NR'R^{vi}$, and r, $R^v$ and $R^{vi}$ are as described above for the pyridinyl nicotinic acetylcholine receptor ligands of the formula II.

In another embodiment, $R_5$ is $-(CH_2)_r C(O)OR^{ix}$, and r and $R^{ix}$ have the same meanings as set forth above for the compounds of formula II.

In another embodiment, $R_5$ is $-(CH_2)_r SR^{viii}$, wherein $R^{viii}$ is hydrogen or $-C(O)R^x$, and r and $R^x$ are as defined above for the pyridinyl nicotinic acetylcholine receptor ligands of the formula II.

In another embodiment, $R_5$ is $-(CH_2)_r SO_2 R^{ix}$, wherein r is an integer ranging from 0 to 5 and $R^{ix}$ is as defined above for the compounds of formula II.

In another embodiment, $R_5$ is $-(CH_2)_r SOR^{ix}$, wherein r is an integer ranging from 0 to 5 and $R^{ix}$ is as defined above for the compounds of formula II.

In one embodiment, m is 1 or 2, Y is a bond, and Z is a piperidine ring.

In another embodiment, m is 1 or 2, Y is a bond, and Z' is a piperidine ring linked to the pyridine ring by its nitrogen atom.

In another embodiment, m is 1 or 2, Y is a bond, and Z' is a piperidine ring linked to the pyridine ring by one of its carbon atoms.

In another embodiment, m is 1 or 2, Y is a bond, Z' is a piperidine ring, and $R_5$ is in the para position on said piperidine ring with respect to the pyridine ring.

In another embodiment, m is 1 or 2, Y is a bond, Z' is a piperidine ring, and $R_5$ is in the meta position on said piperidine ring with respect to the pyridine ring.

In another embodiment, m is 1 or 2, Y is a bond, Z' is a piperidine ring, and $R_5$ is in the ortho position on said piperidine ring with respect to the pyridine ring.

In another embodiment, m is 1 or 2, Y is a bond, Z' is a piperidine ring, and $R_5$ is alkoxyalkyl in which the alkoxy and alkyl portions each independently contain from 1 to 6 carbon atoms; arylalkyl in which the alkyl portion contains from 1 to 6 carbon atoms; arylalkoxy in which the alkoxy portion contains from 1 to 6 carbon atoms; $-(CH_2)_{1-6}-O-(CH_2)_{0-6}$-aryl; or $-(CH_2)_{0-6}-O-(CH_2)_{0-6}-C_3$-$C_6$ cycloalkyl.

In another embodiment, m is 2, Y is a bond, Z' is a piperidine ring that is bound to the pyridine ring by its nitrogen atom, $R_5$ is alkoxyalkyl in which the alkoxy and alkyl portions each independently contain from 1 to 6 carbon atoms; arylalkyl in which the alkyl portion contains from 1 to 6 carbon atoms; arylalkoxy in which the alkoxy portion contains from 1 to 6 carbon atoms; $-(CH_2)_{1-6}-O-(CH_2)_{0-6}$-aryl; or $-(CH_2)_{0-6}-O-(CH_2)_{0-6}-C_3$-$C_6$ cycloalkyl, $R_5$ is in the para position on said piperidine ring with respect to the pyridine ring.

In another embodiment, m is 1 or 2, Y is a bond, Z' is a piperidine ring and $R_5$ is arylalkyl in which the alkyl portion contains from 1 to 6 carbon atoms; arylalkoxy in which the alkoxy portion contains from 1 to 6 carbon atoms; or $-(CH_2)_{1-6}-O-(CH_2)_{0-6}$-aryl, wherein said aryl portion of $R_5$ is unsubstituted.

In another embodiment, m is 1 or 2, Y is a bond, Z' is a piperidine ring and $R_5$ is arylalkyl in which the alkyl portion contains from 1 to 6 carbon atoms; arylalkoxy in which the alkoxy portion contains from 1 to 6 carbon atoms; or $-(CH_2)_{1-6}-O-(CH_2)_{0-6}$-aryl, wherein said aryl portion of $R_5$ is substituted with one or two substituents selected from $C_1$-$C_6$ hydroxyalkyl; $C_1$-$C_6$ alkoxy; alkoxyalkyl in which the alkoxy and alkyl portions each independently contain from 1 to 6 carbon atoms; and —OH.

In another embodiment, m is 1 or 2, Y is a bond and Z' is a piperazine ring.

In another embodiment, m is 1 or 2, Y is a bond, and Z' is a piperazine ring linked to the pyridine ring by a nitrogen atom.

In another embodiment, m is 1 or 2, Y is a bond, and Z' is a piperazine ring linked to the pyridine ring by one of its carbon atoms.

In another embodiment, m is 1 or 2, Y is a bond, Z' is a piperazine ring, and $R_5$ is in the para position on said piperazine ring with respect to the pyridine ring.

In another embodiment, m is 1 or 2, Y is a bond, Z' is a piperazine ring and $R_5$ is in the meta position on said piperazine ring with respect to the pyridine ring.

In another embodiment, m is 1 or 2, Y is a bond, Z' is a piperazine ring and $R_5$ is in the ortho position on said piperazine ring with respect to the pyridine ring.

In another embodiment, m is 1 or 2, Y is a bond, Z' is a piperazine ring and $R_5$ is alkoxyalkyl in which the alkoxy and alkyl portions each independently contain from 1 to 6 carbon atoms; arylalkyl in which the alkyl portion contains from 1 to 6 carbon atoms; arylalkoxy in which the alkoxy portion contains from 1 to 6 carbon atoms; $-(CH_2)_{1-6}-O-(CH_2)_{0-6}$-aryl; or $-(CH_2)_{0-6}-O-(CH_2)_{0-6}-C_3$-$C_6$ cycloalkyl.

In another embodiment, m is 2, Y is a bond, Z' is a piperazine ring that is bound to the pyridine ring by its nitrogen atom, $R_5$ is alkoxyalkyl in which the alkoxy and alkyl portions each independently contain from 1 to 6 carbon atoms; arylalkyl in which the alkyl portion contains from 1 to 6 carbon atoms; arylalkoxy in which the alkoxy portion contains from 1 to 6 carbon atoms; $-(CH_2)_{1-6}-O-(CH_2)_{0-6}$-aryl; or $-(CH_2)_{0-6}-O-(CH_2)_{0-6}-C_3$-$C_6$ cycloalkyl, and $R_5$ is in the para position on said piperidine ring with respect to the pyridine ring.

In another embodiment, m is 1 or 2, Y is a bond, Z' is a piperazine ring and $R_5$ is arylalkyl in which the alkyl portion contains from 1 to 6 carbon atoms; arylalkoxy in which the alkoxy portion contains from 1 to 6 carbon atoms; or $-(CH_2)_{1-6}-O-(CH_2)_{0-6}$-aryl, wherein said aryl portion of $R_5$ is unsubstituted.

In another embodiment, m is 1 or 2, Y is a bond, Z' is a piperazine ring and $R_5$ is arylalkyl in which the alkyl portion contains from 1 to 6 carbon atoms; arylalkoxy in which the alkoxy portion contains from 1 to 6 carbon atoms; or $-(CH_2)_{1-6}-O-(CH_2)_{0-6}$-aryl, wherein said aryl portion of $R_5$ is substituted with one or two substituents selected from $C_1$-$C_6$ hydroxyalkyl; $C_1$-$C_6$ alkoxy; alkoxyalkyl in which the alkoxy and alkyl portions each independently contain from 1 to 6 carbon atoms; and —OH.

In another embodiment of formula II, m is 1 or 2, Y is a bond, n is 1, p is 0, $R_1$, $R_2$, $R_3$, and $R_4$ are each hydrogen and Z' is a monocyclic saturated five- or six-membered heterocycle having at least one nitrogen atom which is linked to the pyridine ring through a nitrogen atom.

In another embodiment of formula II, m is 1 or 2, Y is a bond, n is 1, p is 0, $R_1$, $R_2$, $R_3$, and $R_4$ are each hydrogen and Z' is a saturated azabicycle having 4 to 8 ring carbon atoms and one carbon to carbon bridge with 0-2 carbon atoms in the bridge and wherein said saturated azabicycle is linked through its nitrogen atom to the pyridine ring.

In another embodiment of formula II, m is 1 or 2, Y is a bond, n is 1, p is 0, $R_1$, $R_2$, $R_3$, and $R_4$ are each hydrogen and Z' is piperidine linked to the pyridine ring through its nitrogen atom and $R_5$ is on said piperidine ring in the meta or para position with respect to the pyridine ring and wherein $R_5$ is optionally substituted as defined in formula I.

In another embodiment of formula II, m is 1 or 2, Y is a bond, n is 1, p is 0, $R_1$, $R_2$, $R_3$, and $R_4$ are each hydrogen and Z' is a polycyclic heterocycle having as the only hetero atom a single nitrogen atom in a 5- or 6-membered ring that is saturated except for its positions of fusion to the aryl ring, and one aryl ring fused to said heterocycle and said heterocycle is linked to the pyridine ring through its nitrogen and wherein said $R_5$ is optionally substituted by the optional substituents defined in formula I.

In another embodiment of formula II, m is 1 or 2, Y is a bond, n is 1, p is 0, $R_1$, $R_2$, $R_3$, and $R_4$ are each hydrogen and Z' is piperidine linked to the pyridine ring through its nitrogen atom and $R_5$ is on said piperidine ring in the meta or para position with respect to the pyridine ring and $R_5$ is selected from the group consisting of $C_1$-$C_6$ hydroxyalkyl, $C_1$-$C_6$ fluoroalkyl, arylalkoxy in which the alkoxy portion has 1 to 6 carbon atoms, and alkoxyalkyl in which the alkoxy and alkyl portions each independently contain from 1 to 6 carbon atoms, and wherein said $R_5$ is optionally substituted by the optional substituents defined in formula I.

In another embodiment of formula II, m is 1 or 2, Y is a bond, n is 1, p is 0, $R_1$, $R_2$, $R_3$, and $R_4$ are each hydrogen, Z' is piperidine linked to the pyridine ring through its nitrogen atom and $R_5$ is $C_1$-$C_6$ hydroxyalkyl and wherein said $R_5$ is on the piperidine ring in the meta or para position with respect to the pyridine ring.

In another embodiment of formula II, m is 1 or 2, Y is a bond, n is 1, p is 0, $R_1$, $R_2$, $R_3$, and $R_4$ are each hydrogen, Z' is linked to the pyridine ring through its nitrogen and $R_5$ is $C_1$-$C_6$ hydroxyalkyl or alkoxyalkyl in which the alkoxy and alkyl portions each independently contain from 1 to 6 carbon atoms and wherein said $R_5$ is on the Z' ring in the meta or para position with respect to the pyridine ring and wherein said alkoxyalkyl is optionally substituted with one or two hydroxyl substituents.

In another embodiment of formula II, m is 1 or 2, Y is a bond, n is 1, p is 0, Z' is piperidine linked to the pyridine ring through its nitrogen atom and $R_5$ is alkoxyalkyl in which the alkoxy and alkyl portions each independently contain from 1 to 6 carbon atoms and said alkoxyalkyl is optionally substituted with one or two hydroxyl substituents and wherein $R_5$ is on the piperidine ring in the meta or para position with respect to the pyridine ring.

In some embodiments, the present invention encompasses the compounds of formula II-1:

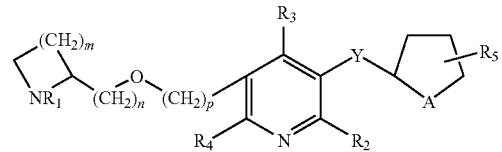

(II-1)

and pharmaceutically acceptable derivatives thereof, wherein A is O or S, and all other variables have the same meanings as set forth above for the compounds of formula II.

In other embodiments, the present invention encompasses the compounds of formula II-1, wherein A is O or S, and all other variables have the same meanings as set forth above for the compounds of formula II, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —(CH$_2$)$_r$NR$^v$R$^{vi}$ when one of R$^v$ and R$^{vi}$ is hydrogen, and the other of R$^v$ and R$^{vi}$ is $C_1$-$C_6$ straight chain alkyl, $C_3$-$C_6$ branched chain alkyl or $C_3$-$C_6$ cycloalkyl or when R$^v$ and R$^{vi}$ are independently $C_1$-$C_6$ straight chain alkyl, $C_3$-$C_6$ branched chain alkyl or $C_3$-$C_6$ cycloalkyl; —(CH$_2$)$_r$SR$^{viii}$ when R$^{viii}$ is $C_1$-$C_6$ straight chain alkyl, $C_3$-$C_6$ branched chain alkyl, or $C_3$-$C_6$ cycloalkyl; —(CH$_2$)$_r$SO$_2$R$^{ix}$, —(CH$_2$)$_r$SOR$^{ix}$ or —(CH$_2$)$_r$C(O)OR$^{ix}$ when R$^{ix}$ is $C_1$-$C_6$ straight chain alkyl, $C_3$-$C_6$ branched chain alkyl or $C_3$-$C_6$ cycloalkyl.

In other embodiments, the present invention encompasses the compounds of formula II-2:

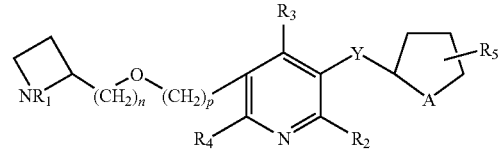

(II-2)

and pharmaceutically acceptable derivatives thereof, wherein A is O or S, and all other variables have the same meanings as set forth above for the compounds of formula II.

In other embodiments, the present invention encompasses the compounds of formula II-3:

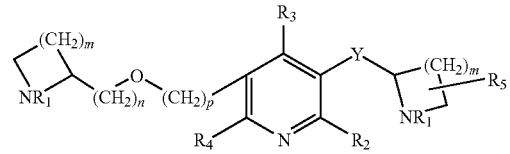

(II-3)

and pharmaceutically acceptable derivatives thereof, wherein all variables have the same meanings as described above for the compounds of formula II.

In other embodiments, the present invention encompasses the compounds of formula II-3, and pharmaceutically acceptable derivatives thereof, wherein all variables have the same meanings as described above for the compounds of formula II, and with the proviso that when m is 2 and Y is a bond, $R_5$ is not $C_1$-$C_6$ straight chain alkyl; $C_3$-$C_6$ branched chain alkyl; alkoxyalkyl in which the alkoxy and alkyl portions each independently contain from 1 to 6 carbon atoms; $C_1$-$C_6$ fluoroalkyl; phenylalkyl in which the alkyl portion contains from 1 to 6 carbon atoms; —$(CH_2)_r NR^v R^{vi}$ when one of $R^v$ and $R^{vi}$ is hydrogen, and the other of $R^v$ and $R^{vi}$ is $C_1$-$C_6$ straight chain alkyl, $C_3$-$C_6$ branched chain alkyl or $C_3$-$C_6$ cycloalkyl or when $R^v$ and $R^{vi}$ are independently $C_1$-$C_6$ straight chain alkyl, $C_3$-$C_6$ branched chain alkyl or $C_3$-$C_6$ cycloalkyl; —$(CH_2)_r SR^{viii}$ when $R^{viii}$ is $C_1$-$C_6$ straight chain alkyl, $C_3$-$C_6$ branched chain alkyl, or $C_3$-$C_6$ cycloalkyl; —$(CH_2)_r SO_2 R^{ix}$, —$(CH_2)_r SOR^{ix}$ or —$(CH_2)_r C(O)OR^{ix}$ when $R^{ix}$ is $C_1$-$C_6$ straight chain alkyl, $C_3$-$C_6$ branched chain alkyl or $C_3$-$C_6$ cycloalkyl.

In other embodiments, the present invention encompasses the compounds of formula II-4:

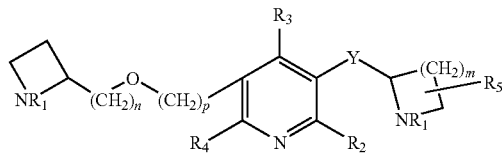

(II-4)

and pharmaceutically acceptable derivatives thereof, wherein all variables have the same meanings as described above for the compounds of formula II.

In another embodiment, the pyridinyl nicotinic acetylcholine receptor ligand of the formula II is selected from:

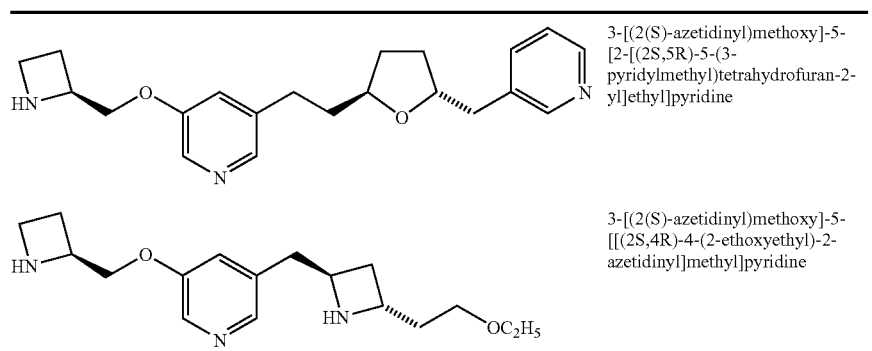

| | |
|---|---|
| | 3-[(2(S)-azetidinyl)methoxy]-5-[2-[(2S,5R)-5-(3-pyridylmethyl)tetrahydrofuran-2-yl]ethyl]pyridine |
| | 3-[(2(S)-azetidinyl)methoxy]-5-[[(2S,4R)-4-(2-ethoxyethyl)-2-azetidinyl]methyl]pyridine |

In another embodiment, the pyridinyl nicotinic acetylcholine receptor ligand of the formula II is selected from:

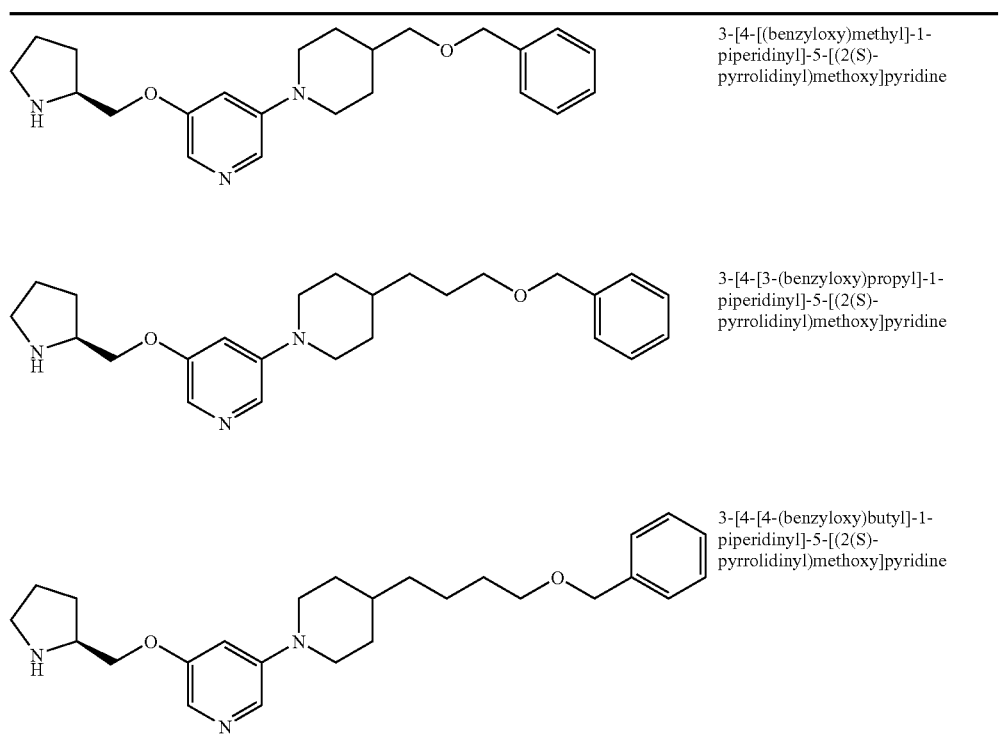

| | |
|---|---|
| | 3-[4-[(benzyloxy)methyl]-1-piperidinyl]-5-[(2(S)-pyrrolidinyl)methoxy]pyridine |
| | 3-[4-[3-(benzyloxy)propyl]-1-piperidinyl]-5-[(2(S)-pyrrolidinyl)methoxy]pyridine |
| | 3-[4-[4-(benzyloxy)butyl]-1-piperidinyl]-5-[(2(S)-pyrrolidinyl)methoxy]pyridine |

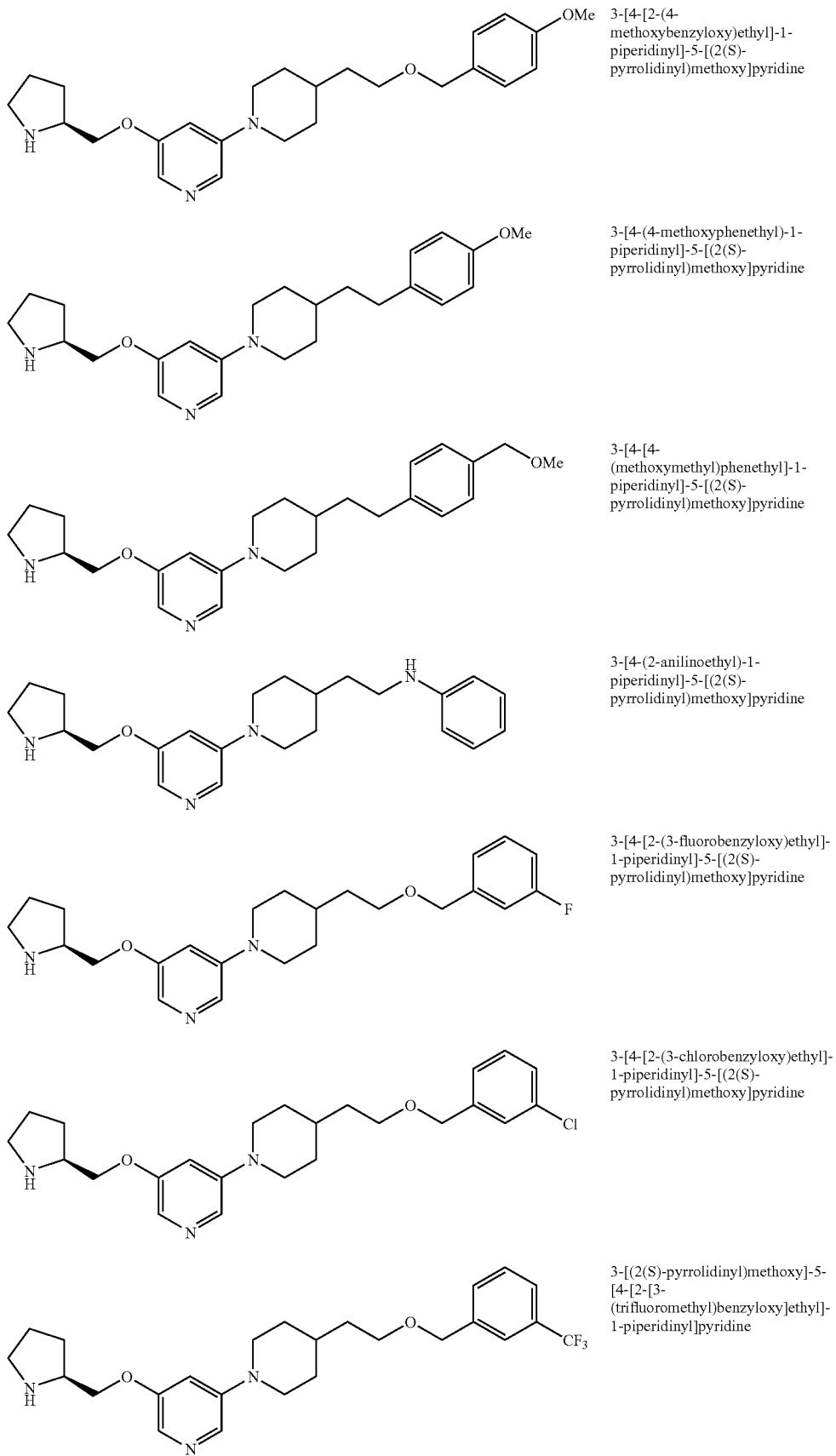

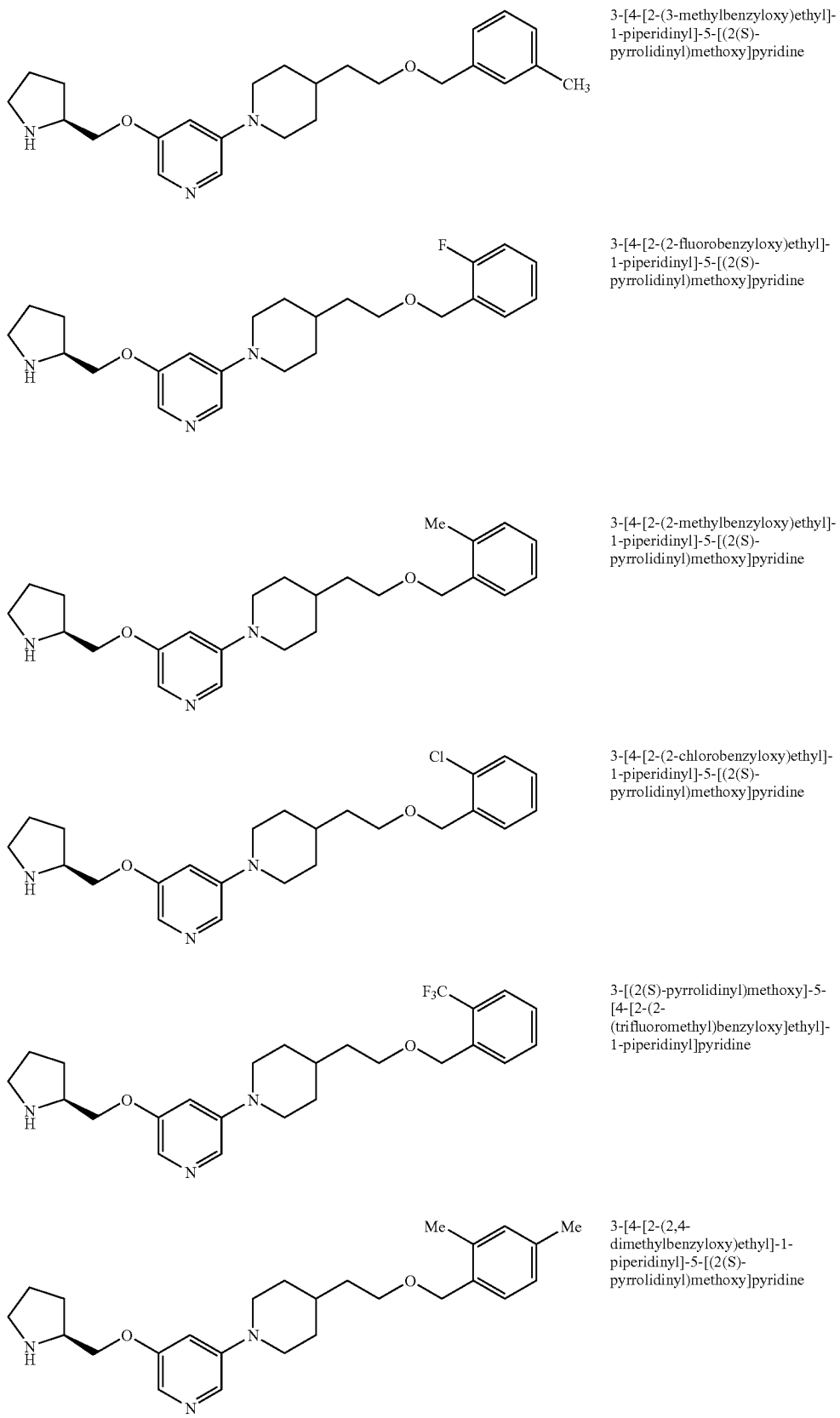

| | |
|---|---|
| | 3-[4-[2-(3-methylbenzyloxy)ethyl]-1-piperidinyl]-5-[(2(S)-pyrrolidinyl)methoxy]pyridine |
| | 3-[4-[2-(2-fluorobenzyloxy)ethyl]-1-piperidinyl]-5-[(2(S)-pyrrolidinyl)methoxy]pyridine |
| | 3-[4-[2-(2-methylbenzyloxy)ethyl]-1-piperidinyl]-5-[(2(S)-pyrrolidinyl)methoxy]pyridine |
| | 3-[4-[2-(2-chlorobenzyloxy)ethyl]-1-piperidinyl]-5-[(2(S)-pyrrolidinyl)methoxy]pyridine |
| | 3-[(2(S)-pyrrolidinyl)methoxy]-5-[4-[2-(2-(trifluoromethyl)benzyloxy]ethyl]-1-piperidinyl]pyridine |
| | 3-[4-[2-(2,4-dimethylbenzyloxy)ethyl]-1-piperidinyl]-5-[(2(S)-pyrrolidinyl)methoxy]pyridine |

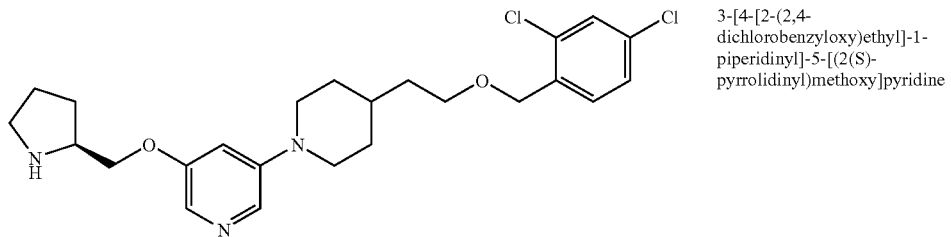

3-[4-[2-(2,4-dichlorobenzyloxy)ethyl]-1-piperidinyl]-5-[(2(S)-pyrrolidinyl)methoxy]pyridine

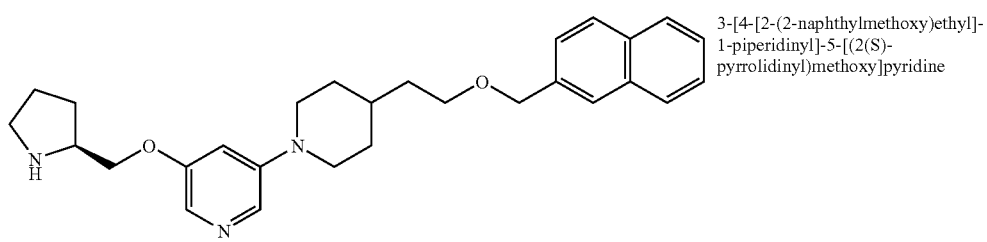

3-[4-[2-(2-naphthylmethoxy)ethyl]-1-piperidinyl]-5-[(2(S)-pyrrolidinyl)methoxy]pyridine

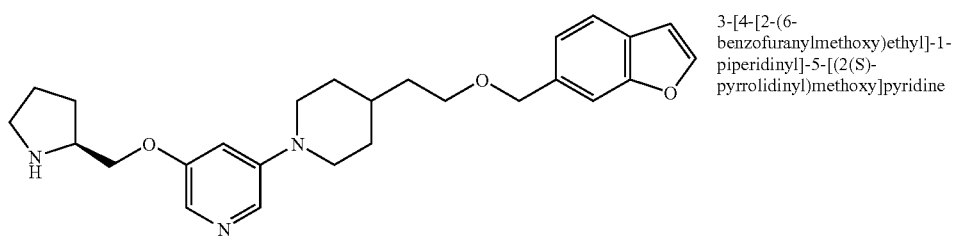

3-[4-[2-(6-benzofuranylmethoxy)ethyl]-1-piperidinyl]-5-[(2(S)-pyrrolidinyl)methoxy]pyridine

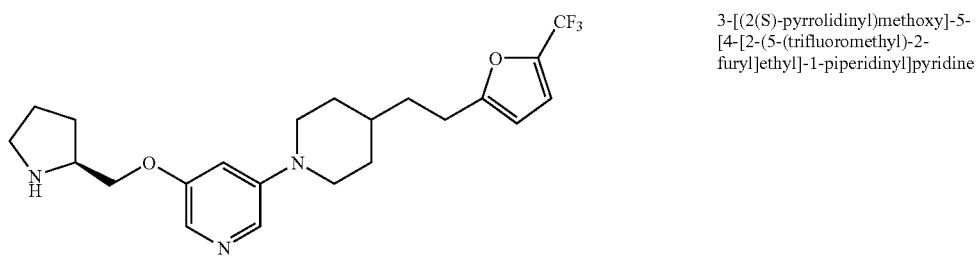

3-[(2(S)-pyrrolidinyl)methoxy]-5-[4-[2-(5-(trifluoromethyl)-2-furyl]ethyl]-1-piperidinyl]pyridine

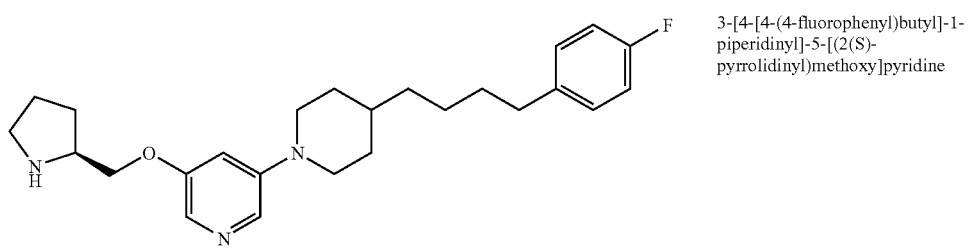

3-[4-[4-(4-fluorophenyl)butyl]-1-piperidinyl]-5-[(2(S)-pyrrolidinyl)methoxy]pyridine

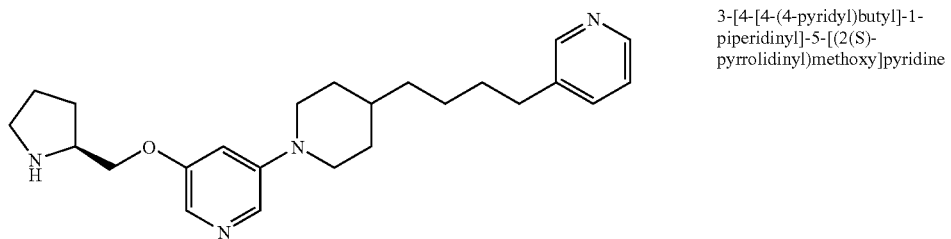

3-[4-[4-(4-pyridyl)butyl]-1-piperidinyl]-5-[(2(S)-pyrrolidinyl)methoxy]pyridine

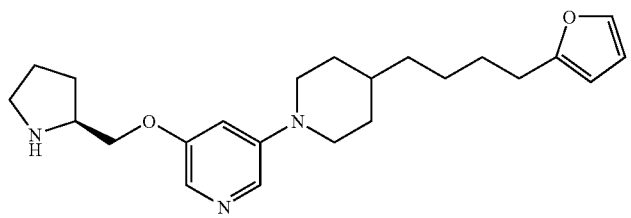 [SMILES: c1coc(CCCCC2CCN(c3cncc(OC[C@@H]4CCCN4)c3)CC2)c1]
3-[4-[4-(2-furyl)butyl]-1-piperidinyl]-5-[(2(S)-pyrrolidinyl)methoxy]pyridine

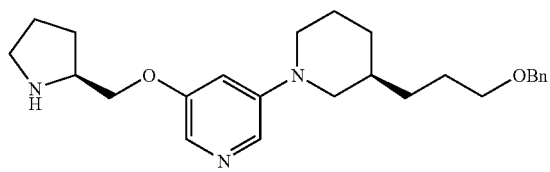 [SMILES: c1ccc(COCCC[C@@H]2CCCN(c3cncc(OC[C@@H]4CCCN4)c3)C2)cc1]
3-[3(S)-[3-(benzyloxy)propyl]-1-piperidinyl]-5-[(2(S)-pyrrolidinyl)methoxy]pyridine

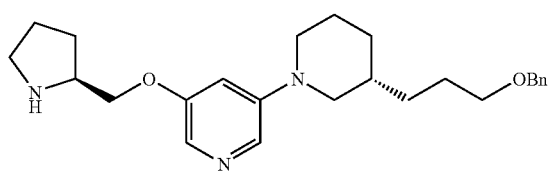 [SMILES: c1ccc(COCCC[C@H]2CCCN(c3cncc(OC[C@@H]4CCCN4)c3)C2)cc1]
3-[3(R)-[3-(benzyloxy)propyl]-1-piperidinyl]-5-[(2(S)-pyrrolidinyl)methoxy]pyridine

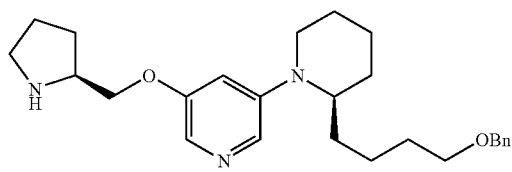 [SMILES: c1ccc(COCCCC[C@@H]2CCCCN2c2cncc(OC[C@@H]3CCCN3)c2)cc1]
3-[2(S)-[4-(benzyloxy)butyl]-1-piperidinyl]-5-[(2(S)-pyrrolidinyl)methoxy]pyridine

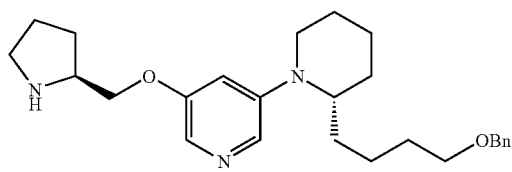 [SMILES: c1ccc(COCCCC[C@H]2CCCCN2c2cncc(OC[C@@H]3CCCN3)c2)cc1]
3-[2(R)-[4-(benzyloxy)butyl]-1-piperidinyl]-5-[(2(S)-pyrrolidinyl)methoxy]pyridine

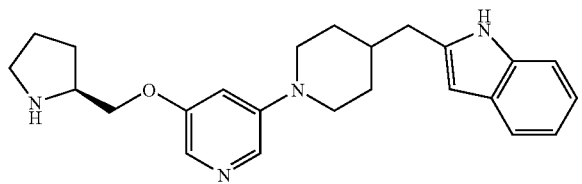 [SMILES: c1ccc2[nH]c(CC3CCN(c4cncc(OC[C@@H]5CCCN5)c4)CC3)cc2c1]
3-[4-(2[1H]-indolylmethyl)-1-piperidinyl]-5-[(2(S)-pyrrolidinyl)methoxy]pyridine

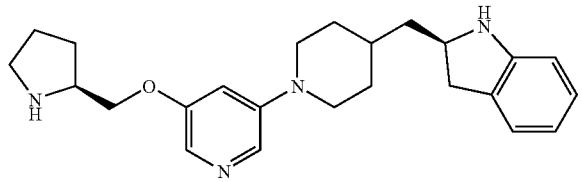 [SMILES: c1ccc2c(c1)C[C@@H](CC1CCN(c3cncc(OC[C@@H]4CCCN4)c3)CC1)N2]
3-[4-(2(R)-indolinylmethyl)-1-piperidinyl]-5-[(2(S)-pyrrolidinyl)methoxy]pyridine

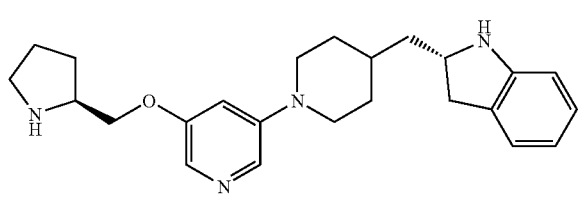
3-[4-(2(S)-indolinylmethyl)-1-piperidinyl]-5-[(2(S)-pyrrolidinyl)methoxy]pyridine -continued

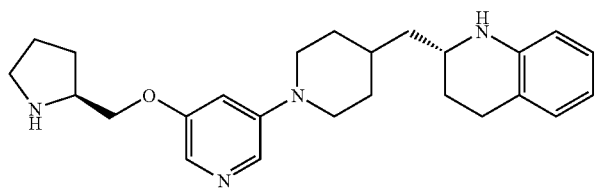 [SMILES: c1ccc2c(c1)CC[C@H](CC1CCN(c3cncc(OC[C@@H]4CCCN4)c3)CC1)N2]

2(R)-[[1-[5-[(2(S)-pyrrolidinyl)methoxy]-3-pyridyl]-4-piperidinyl]methyl]-1,2,3,4-tetrahydroquinoline

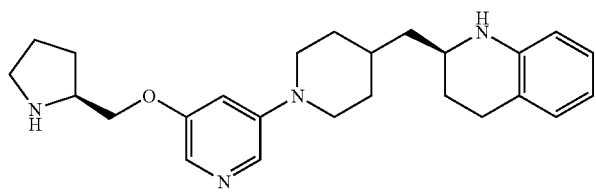 [SMILES: c1ccc2c(c1)CC[C@@H](CC1CCN(c3cncc(OC[C@@H]4CCCN4)c3)CC1)N2]

2(S)-[[1-[5-[(2(S)-pyrrolidinyl)methoxy]-3-pyridyl]-4-piperidinyl]methyl]-1,2,3,4-tetrahydroquinoline In another embodiment, the pyridinyl nicotinic acetylcholine receptor ligand of the formula II is selected from:

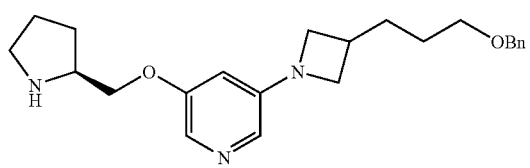 [SMILES: c1ccc(COCCCC2CN(c3cncc(OC[C@@H]4CCCN4)c3)C2)cc1]

3-[3-(3-(benzyloxy)propyl)-1-azetidinyl]-5-[(2(S)-pyrrolidinyl)methoxy]pyridine

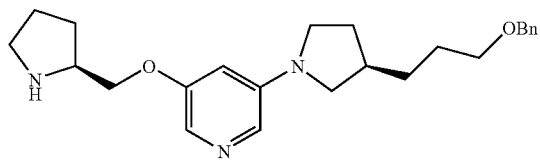 [SMILES: c1ccc(COCCC[C@@H]2CCN(c3cncc(OC[C@@H]4CCCN4)c3)C2)cc1]

3-[3(R)-[3-(benzyloxy)propyl]-1-pyrrolidinyl]-5-[(2(S)-pyrrolidinyl)methoxy]pyridine

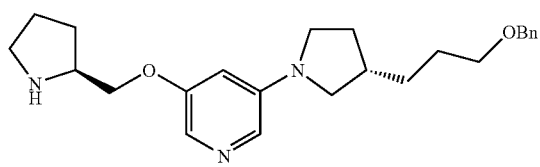 [SMILES: c1ccc(COCCC[C@H]2CCN(c3cncc(OC[C@@H]4CCCN4)c3)C2)cc1]

3-[3(S)-[3-(benzyloxy)propyl]-1-pyrrolidinyl]-5-[(2(S)-pyrrolidinyl)methoxy]pyridine

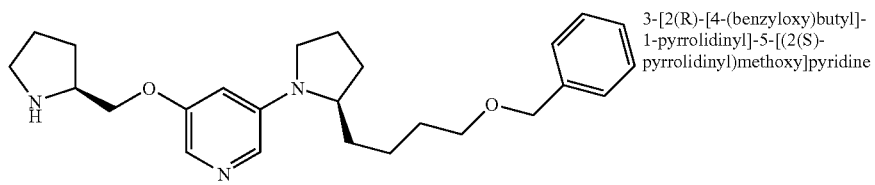

3-[2(R)-[4-(benzyloxy)butyl]-1-pyrrolidinyl]-5-[(2(S)-pyrrolidinyl)methoxy]pyridine

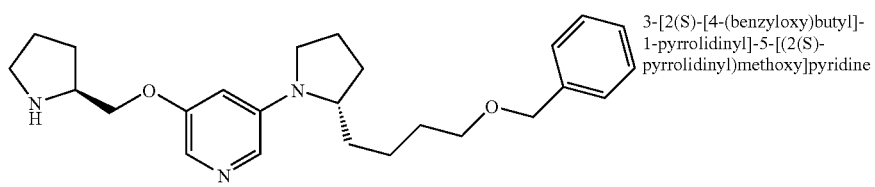

3-[2(S)-[4-(benzyloxy)butyl]-1-pyrrolidinyl]-5-[(2(S)-pyrrolidinyl)methoxy]pyridine In another embodiment, the pyridinyl nicotinic acetylcholine receptor ligand of the formula II is selected from:
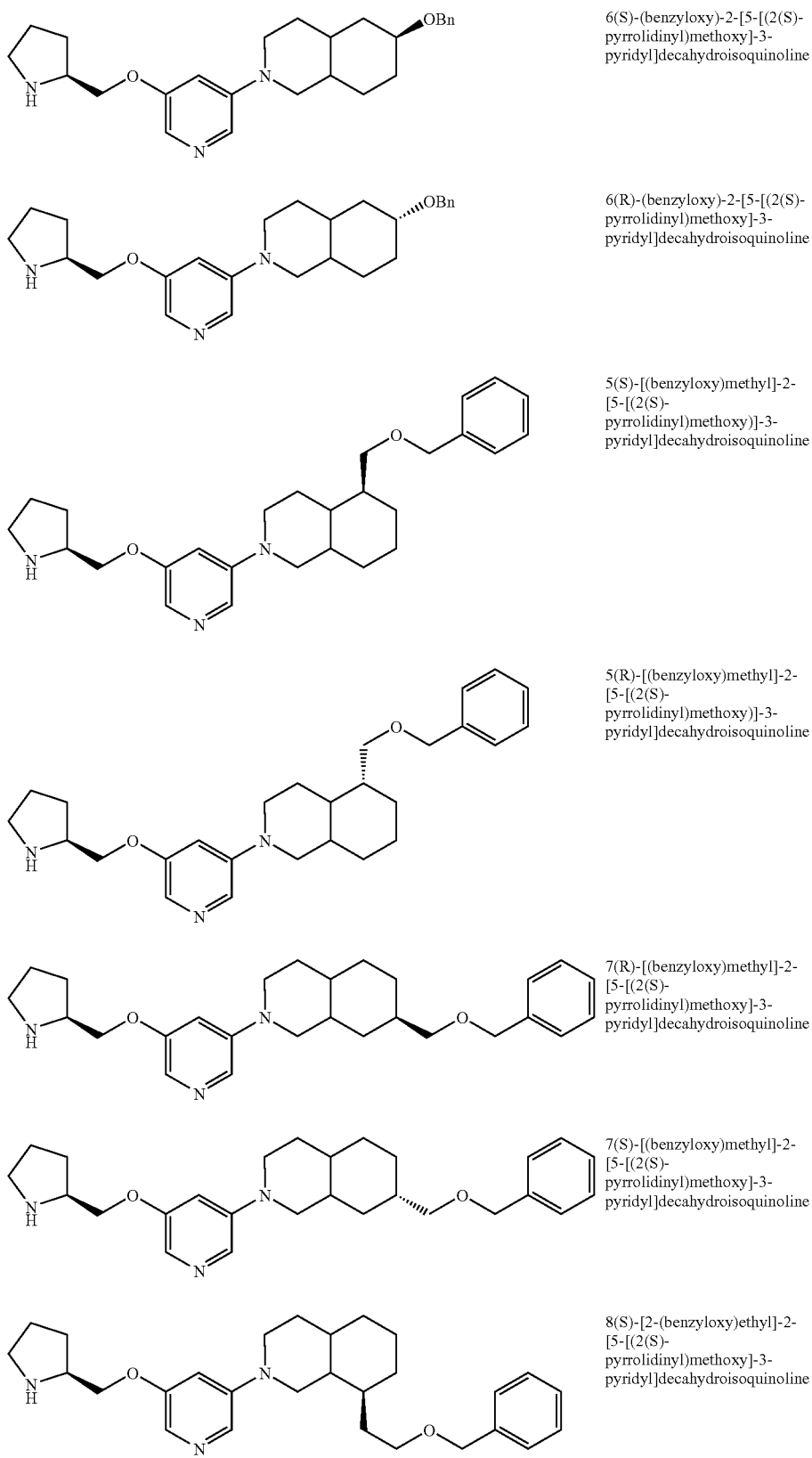

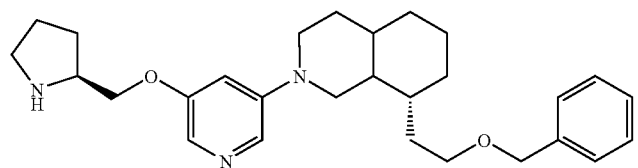 [SMILES: c1ccc(COCC[C@H]2CCCC3CCN(c4cncc(OC[C@@H]5CCCN5)c4)CC32)cc1]

8(R)-[2-(benzyloxy)ethyl]-2-[5-[(2(S)-pyrrolidinyl)methoxy]-3-pyridyl]decahydroisoquinoline

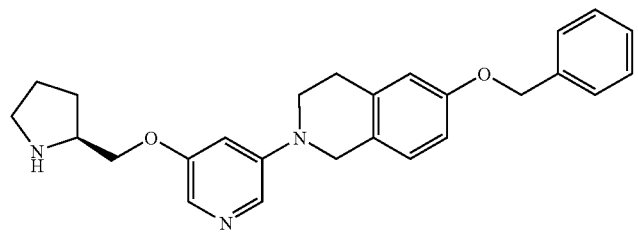 [SMILES: c1ccc(COc2ccc3c(c2)CCN(c2cncc(OC[C@@H]4CCCN4)c2)C3)cc1]

6-(benzyloxy)-1,2,3,4-tetrahydro-2-[5-[(2(S)-pyrrolidinyl)methoxy]-3-pyridyl]isoquinoline

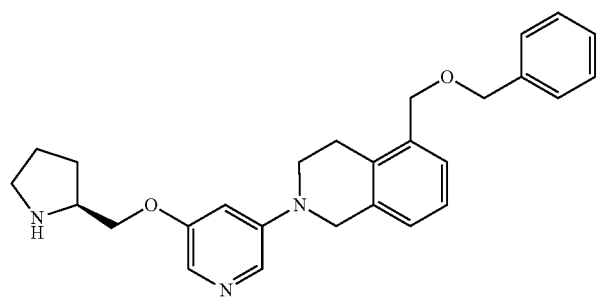 [SMILES: c1ccc(COCc2cccc3c2CCN(c2cncc(OC[C@@H]4CCCN4)c2)C3)cc1]

5-[(benzyloxy)methyl]-1,2,3,4-tetrahydro-2-[5-[(2(S)-pyrrolidinyl)methoxy]-3-pyridyl]isoquinoline

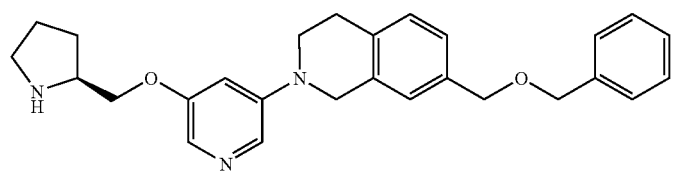 [SMILES: c1ccc(COCc2ccc3c(c2)CN(c2cncc(OC[C@@H]4CCCN4)c2)CC3)cc1]

7-[(benzyloxy)methyl]-1,2,3,4-tetrahydro-2-[5-[(2(S)-pyrrolidinyl)methoxy]-3-pyridyl]isoquinoline

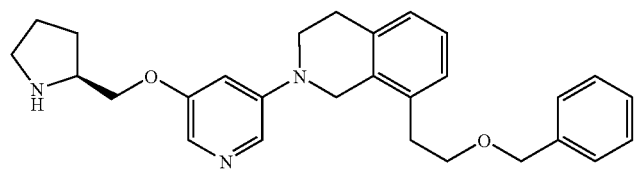 [SMILES: c1ccc(COCCc2cccc3c2CN(c2cncc(OC[C@@H]4CCCN4)c2)CC3)cc1]

8-[2-(benzyloxy)ethyl]-1,2,3,4-tetrahydro-2-[5-[(2(S)-pyrrolidinyl)methoxy]-3-pyridyl]isoquinoline

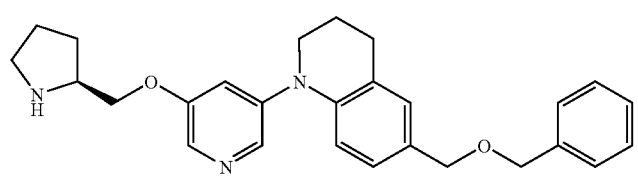 [SMILES: c1ccc(COCc2ccc3c(c2)CCCN3c2cncc(OC[C@@H]3CCCN3)c2)cc1]

6-[(benzyloxy)methyl]-1,2,3,4-tetrahydro-1-[5-[(2(S)-pyrrolidinyl)methoxy]-3-pyridyl]quinoline

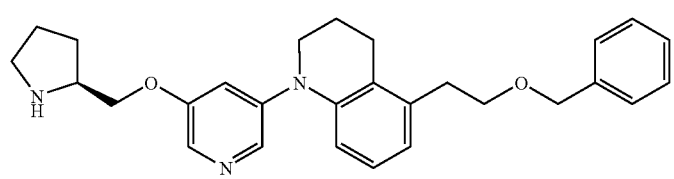 [SMILES: c1ccc(COCCc2cccc3c2CCCN3c2cncc(OC[C@@H]3CCCN3)c2)cc1]

5-[2-(benzyloxy)ethyl]-1,2,3,4-tetrahydro-1-[5-[(2(S)-pyrrolidinyl)methoxy]-3-pyridyl]quinoline

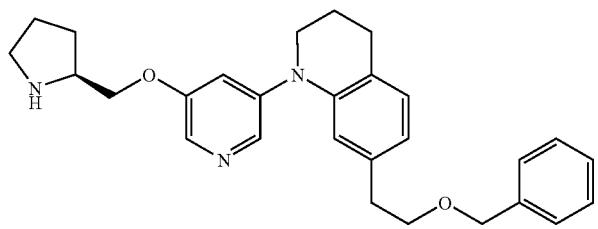 [SMILES: c1ccc(COCCc2ccc3c(c2)N(c2cncc(OC[C@@H]4CCCN4)c2)CCC3)cc1]

7-[2-(benzyloxy)ethyl]-1,2,3,4-tetrahydro-1-[5-[(2(S)-pyrrolidinyl)methoxy]-3-pyridyl]quinoline

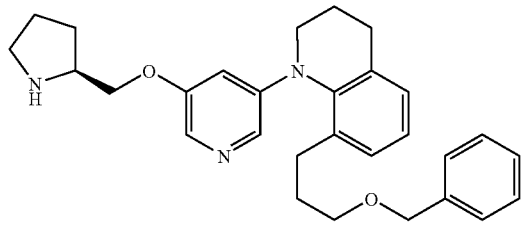 [SMILES: c1ccc(COCCCc2cccc3c2N(c2cncc(OC[C@@H]4CCCN4)c2)CCC3)cc1]

8-[3-(benzyloxy)propyl]-1,2,3,4-tetrahydro-1-[5-[(2(S)-pyrrolidinyl)methoxy]-3-pyridyl]quinoline In another embodiment, the pyridinyl nicotinic acetylcholine receptor ligand of the formula II is selected from:

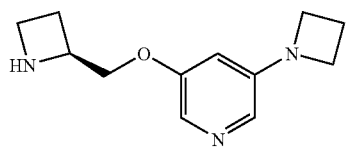 [SMILES: c1ncc(N2CCC2)cc1OC[C@@H]1CCN1]

3-(1-azetidinyl)-5-[(2(S)-azetidinyl)methoxy]pyridine

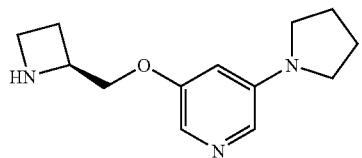 [SMILES: c1ncc(N2CCCC2)cc1OC[C@@H]1CCN1]

5-[(2(S)-azetidinyl)methoxy]-3-(1-pyrrolidinyl)pyridine

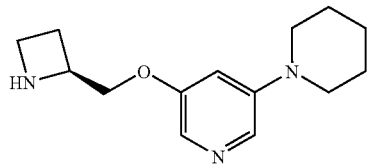 [SMILES: c1ncc(N2CCCCC2)cc1OC[C@@H]1CCN1]

5-[(2(S)-azetidinyl)methoxy]-3-(1-piperidinyl)pyridine

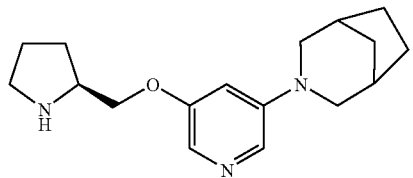 [SMILES: c1ncc(N2CC3CCC(C3)C2)cc1OC[C@@H]1CCCN1]

3-[5-[(2(S)-pyrrolidinyl)methoxy]-3-pyridyl]-3-azabicyclo[3.2.1]octane

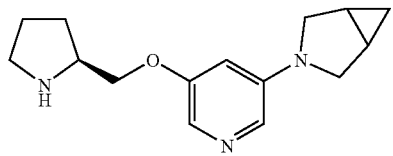 [SMILES: c1ncc(N2CC3CC3C2)cc1OC[C@@H]1CCCN1]

3-[5-[(2(S)-pyrrolidinyl)methoxy]-3-pyridyl]-3-azabicyclo[3.1.0]hexane

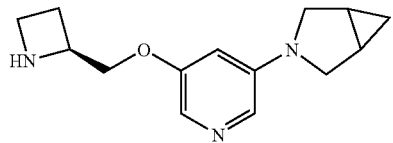 [SMILES: c1ncc(N2CC3CC3C2)cc1OC[C@@H]1CCN1]

3-[5-[(2(S)-azetidinyl)methoxy]-3-pyridyl]-3-azabicyclo[3.1.0]hexane

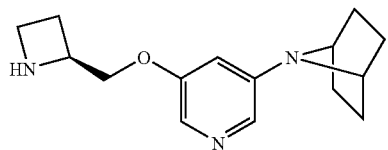 [SMILES: c1ncc(N2C3CCC2CC3)cc1OC[C@@H]1CCN1]

3-[5-[(2(S)-azetidinyl)methoxy]-3-pyridyl]-7-azabicyclo[2.2.1]heptane

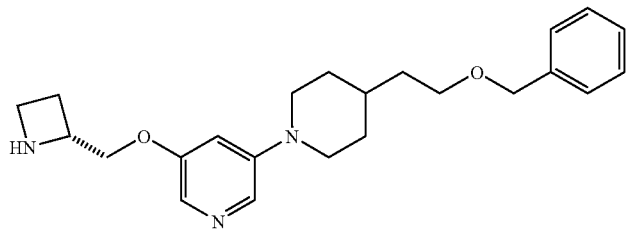

3-[(2(R)-azetidinyl)methoxy]-5-[4-[2-(benzyloxy)ethyl]-1-piperidinyl]pyridine

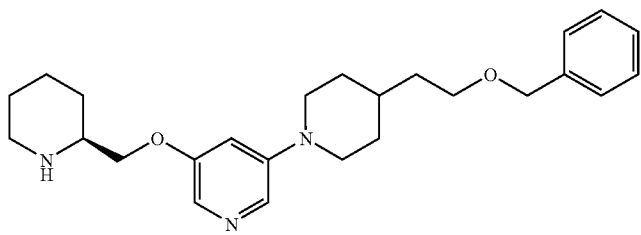 [SMILES: c1ccc(COCCC2CCN(c3cncc(OC[C@@H]4CCCCN4)c3)CC2)cc1]

3-[4-[2-(benzyloxy)ethyl]-1-piperidinyl]-5-[(2(S)-piperidinyl)methoxy]pyridine

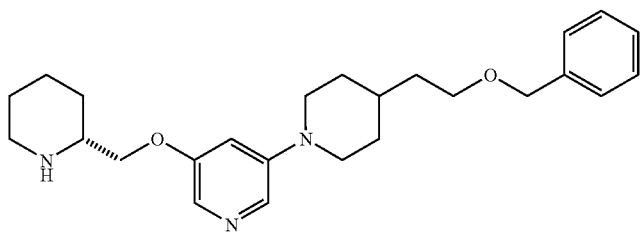

3-[4-[2-(benzyloxy)ethyl]-1-piperidinyl]-5-[(2(R)-piperidinyl)methoxy]pyridine

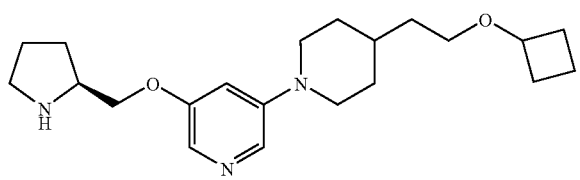 [SMILES: c1ncc(N2CCC(CCOC3CCC3)CC2)cc1OC[C@@H]1CCCN1]

3-[4-[2-(cyclobutoxy)ethyl]-1-piperidinyl]-5-[(2(S)-pyrrolidinyl)methoxy]pyridine

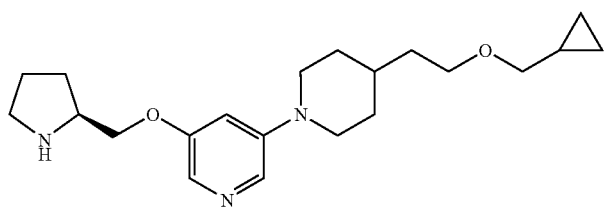 [SMILES: c1ncc(N2CCC(CCOCC3CC3)CC2)cc1OC[C@@H]1CCCN1]

3-[4-[2-(cyclopropylmethoxy)ethyl]-1-piperidinyl]-5-[(2(S)-pyrrolidinyl)methoxy]pyridine

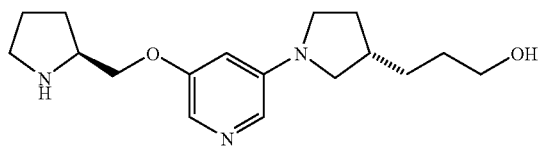 [SMILES: OCCC[C@H]1CCN(c2cncc(OC[C@@H]3CCCN3)c2)C1]

3-[1-[5-[(2(S)-pyrrolidinyl)methoxy]-3-pyridyl]-3(S)-pyrrolidinyl]-1-propanol

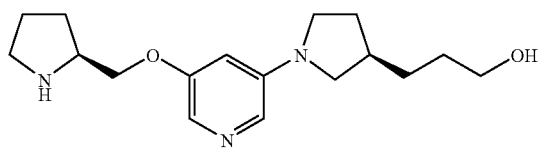 [SMILES: OCCC[C@@H]1CCN(c2cncc(OC[C@@H]3CCCN3)c2)C1]

3-[1-[5-[(2(S)-pyrrolidinyl)methoxy]-3-pyridyl]-3(R)-pyrrolidinyl]-1-propanol

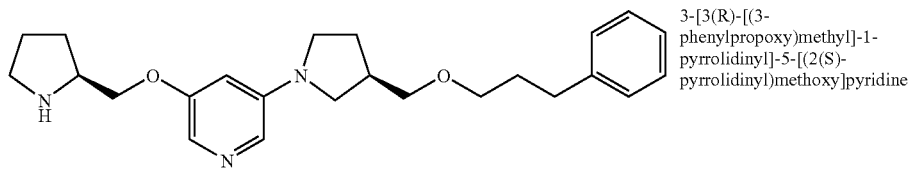

3-[3(R)-[(3-phenylpropoxy)methyl]-1-pyrrolidinyl]-5-[(2(S)-pyrrolidinyl)methoxy]pyridine

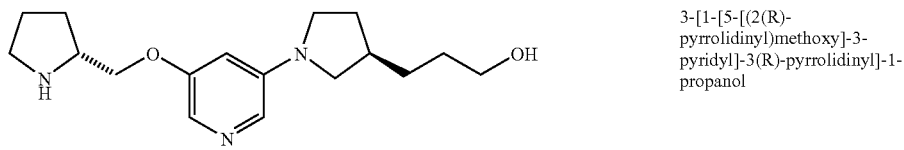

3-[1-[5-[(2(R)-pyrrolidinyl)methoxy]-3-pyridyl]-3(R)-pyrrolidinyl]-1-propanol

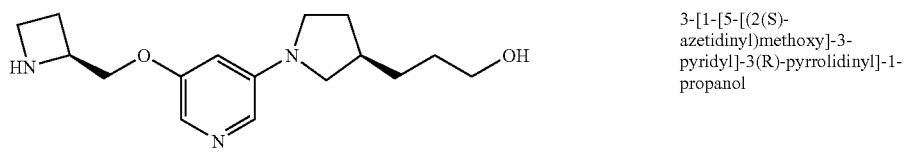

3-[1-[5-[(2(S)-azetidinyl)methoxy]-3-pyridyl]-3(R)-pyrrolidinyl]-1-propanol

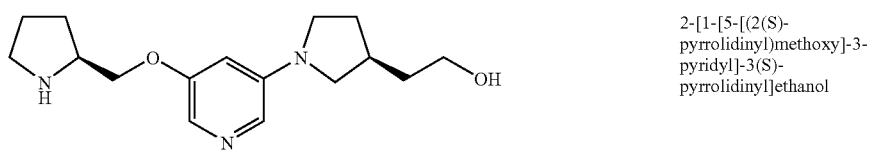

2-[1-[5-[(2(S)-pyrrolidinyl)methoxy]-3-pyridyl]-3(S)-pyrrolidinyl]ethanol

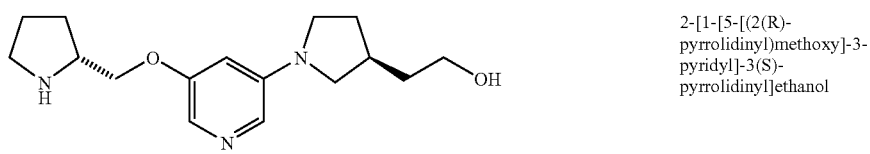

2-[1-[5-[(2(R)-pyrrolidinyl)methoxy]-3-pyridyl]-3(S)-pyrrolidinyl]ethanol

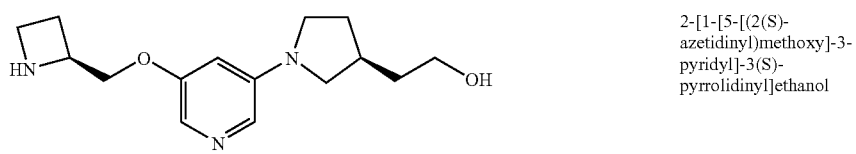

2-[1-[5-[(2(S)-azetidinyl)methoxy]-3-pyridyl]-3(S)-pyrrolidinyl]ethanol

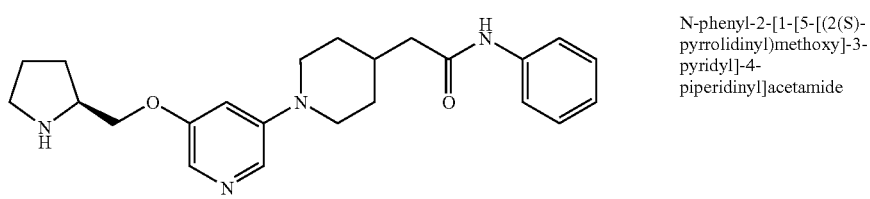

N-phenyl-2-[1-[5-[(2(S)-pyrrolidinyl)methoxy]-3-pyridyl]-4-piperidinyl]acetamide

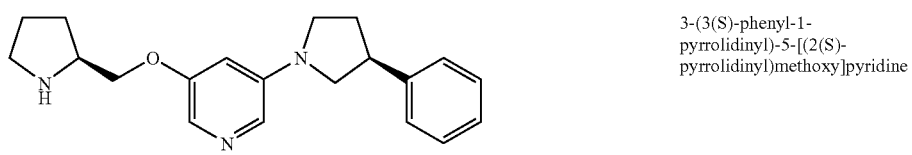

3-(3(S)-phenyl-1-pyrrolidinyl)-5-[(2(S)-pyrrolidinyl)methoxy]pyridine

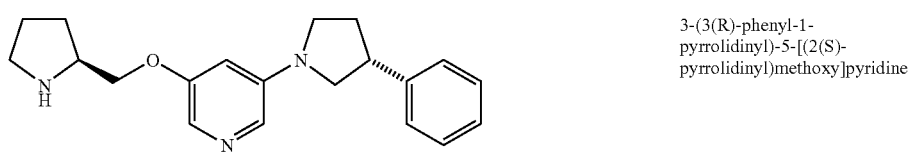

3-(3(R)-phenyl-1-pyrrolidinyl)-5-[(2(S)-pyrrolidinyl)methoxy]pyridine

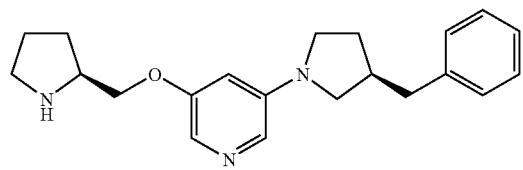 [SMILES: c1ccc(C[C@@H]2CCN(c3cncc(OC[C@@H]4CCCN4)c3)C2)cc1]

3-(3(R)-benzyl-1-pyrrolidinyl)-5-[(2(S)-pyrrolidinyl)methoxy]pyridine

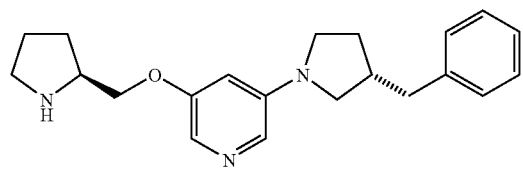 [SMILES: c1ccc(C[C@H]2CCN(c3cncc(OC[C@@H]4CCCN4)c3)C2)cc1]

3-(3(S)-benzyl-1-pyrrolidinyl)-5-[(2(S)-pyrrolidinyl)methoxy]pyridine

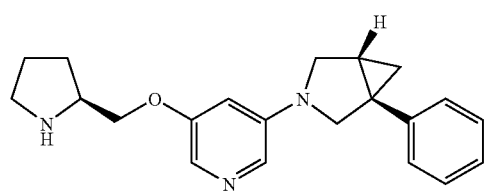 [SMILES: c1ccc([C@]23C[C@H]2CN(c2cncc(OC[C@@H]4CCCN4)c2)C3)cc1]

(1S,5R)-1-phenyl-3-[5-[(2(S)-pyrrolidinyl)methoxy]-3-pyridyl]-3-azabicyclo[3.1.0]hexane

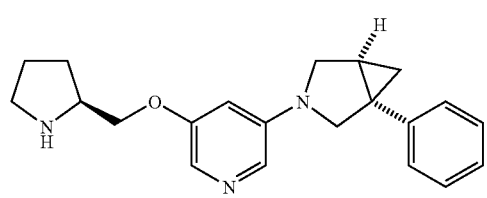 [SMILES: c1ccc([C@@]23C[C@@H]2CN(c2cncc(OC[C@@H]4CCCN4)c2)C3)cc1]

(1R,5S)-1-phenyl-3-[5-[(2(S)-pyrrolidinyl)methoxy]-3-pyridyl]-3-azabicyclo[3.1.0]hexane

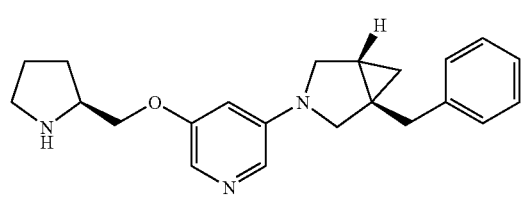 [SMILES: c1ccc(C[C@]23C[C@H]2CN(c2cncc(OC[C@@H]4CCCN4)c2)C3)cc1]

(1R,5R)-1-phenyl-3-[5-[(2(S)-pyrrolidinyl)methoxy]-3-pyridyl]-3-azabicyclo[3.1.0]hexane

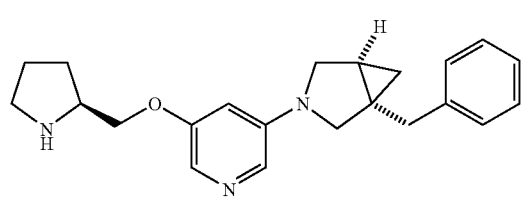 [SMILES: c1ccc(C[C@@]23C[C@@H]2CN(c2cncc(OC[C@@H]4CCCN4)c2)C3)cc1]

(1S,5S)-1-phenyl-3-[5-[(2(S)-pyrrolidinyl)methoxy]-3-pyridyl]-3-azabicyclo[3.1.0]hexane

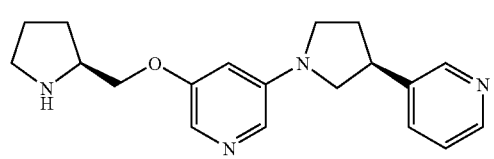 [SMILES: c1cncc([C@@H]2CCN(c3cncc(OC[C@@H]4CCCN4)c3)C2)c1]

3-[3(S)-(3-pyridyl)-1-pyrrolidinyl]-5-[(2(S)-pyrrolidinyl)methoxy]pyridine

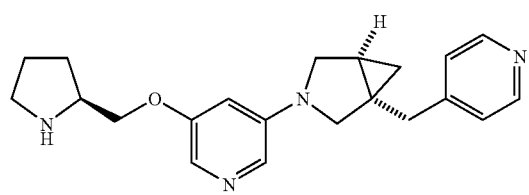 [SMILES: c1cc(C[C@@]23C[C@@H]2CN(c2cncc(OC[C@@H]4CCCN4)c2)C3)ccn1]

(1S,5S)-1-[(4-pyridyl)methyl]-3-[5-[(2(S)-pyrrolidinyl)methoxy]-3-pyridyl]-3-azabicyclo[3.1.0]hexane

| | |
|---|---|
| 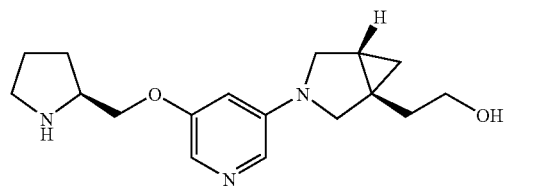 [SMILES: OCC[C@]12C[C@H]1CN(c1cncc(OC[C@@H]3CCCN3)c1)C2] | 2-[(1R,5R)-3-[5-[(2(S)-pyrrolidinyl)methoxy]-3-pyridyl]-3-azabicyclo[3.1.0]hexan-1-yl]ethanol |
| 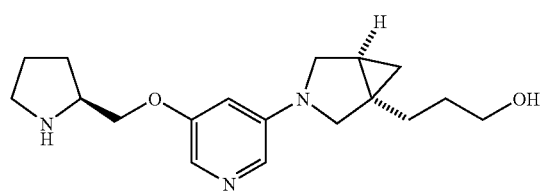 [SMILES: OCCC[C@@]12C[C@@H]1CN(c1cncc(OC[C@@H]3CCCN3)c1)C2] | 3-[(1R,5S)-3-[5-[(2(S)-pyrrolidinyl)methoxy]-3-pyridyl]-3-azabicyclo[3.1.0]hexan-1-yl]ethanol |
| 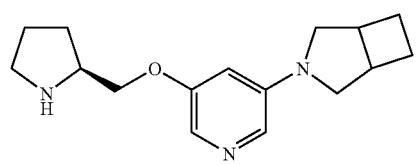 [SMILES: c1ncc(N2CC3CCC3C2)cc1OC[C@@H]1CCCN1] | 3-[5-[(2(S)-pyrrolidinyl)methoxy]-3-pyridyl]-3-azabicyclo[3.2.0]heptane |
| 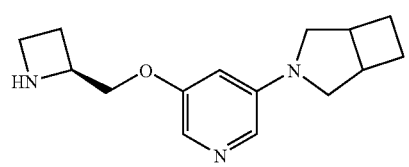 [SMILES: c1ncc(N2CC3CCC3C2)cc1OC[C@@H]1CCN1] | 3-[5-[(2(S)-azetidinyl)methoxy]-3-pyridyl]-3-azabicyclo[3.2.0]heptane |
| 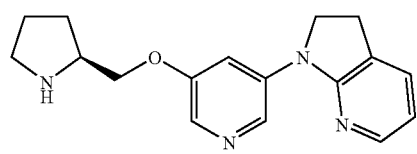 [SMILES: c1cnc2c(c1)CCN2c1cncc(OC[C@@H]2CCCN2)c1] | 1-[5-[(2(S)-pyrrolidinyl)methoxy]-3-pyridyl]-2,3-dihydro-1H-pyrrolo[2,3-b]pyridine |
| 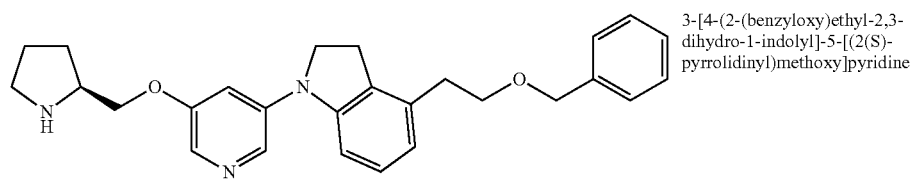 | 3-[4-(2-(benzyloxy)ethyl-2,3-dihydro-1-indolyl]-5-[(2(S)-pyrrolidinyl)methoxy]pyridine |

Nicotinic Acetylcholine Receptor Ligands of the Formula III

In another embodiment, the invention encompasses pyridinyl nicotinic acetylcholine receptor ligands of the formula III:

(III)

and pharmaceutically acceptable derivatives thereof, wherein all variables are as defined above for the pyridinyl nicotinic acetylcholine receptor ligands of the formula III.

In one embodiment, $R^{iv}$ is hydrogen.
In one embodiment, $R^{iv}$ is $C_1$-$C_6$ straight chain alkyl.
In another embodiment, $R^{iv}$ is $C_3$-$C_6$ branched chain alkyl.
In another embodiment, $R^{iv}$ is $C_3$-$C_6$ cycloalkyl.
In another embodiment, $R^{iv}$ is an acyl group having the formula:

wherein $R^i$ is $C_1$-$C_6$ straight chain alkyl.
In another embodiment, $R^{iv}$ is an acyl group as shown above and $R^i$ is $C_3$-$C_6$ branched chain alkyl.
In another embodiment, $R^{iv}$ is an acyl group as shown above and $R^i$ is $C_3$-$C_6$ cycloalkyl.
In one embodiment, $R_1$ is H.
In another embodiment, $R_1$ is $C_1$-$C_6$ straight chain alkyl.
In another embodiment, $R_1$ is $C_3$-$C_6$ branched chain alkyl.
In another embodiment, $R_1$ is allyl.
In another embodiment, $R_1$ is $C_3$-$C_6$ cycloalkyl.
In another embodiment, $R_2$ is H.

In another embodiment, $R_3$ is H.
In another embodiment, $R_4$ is H.
In another embodiment, $R_2$, $R_3$ and $R_4$ are each H.
In another embodiment, m is 1.
In another embodiment, m is 2.
In another embodiment, m is 3.
In another embodiment, n is 1.
In another embodiment, n is 2.
In another embodiment, p is 0.
In another embodiment, p is 1.
In another embodiment, p is 2.
In another embodiment, n is 1 and p is 0.
In one embodiment, Y is —$CH_2$— and Z is $C_3$-$C_6$ cycloalkyl.
In another embodiment, Y is —$CH_2$— and Z is a $C_4$-$C_6$ partially unsaturated carbocycle.
In another embodiment, Y is —$CH_2CH_2$— and Z is $C_3$-$C_6$ cycloalkyl.
In another embodiment, Y is —$CH_2CH_2$— and Z is a $C_4$-$C_6$ partially unsaturated carbocycle.
In another embodiment, Y is —$CH_2CH_2CH_2$— and Z is $C_3$-$C_6$ cycloalkyl.
In another embodiment, Y is —$CH_2CH_2CH_2$— and Z is a $C_4$-$C_6$ partially unsaturated carbocycle.
In another embodiment, Y is —$(CH_2)_4$— and Z is $C_3$-$C_6$ cycloalkyl.
In another embodiment, Y is —$(CH_2)_4$— and Z is a $C_4$-$C_6$ partially unsaturated carbocycle.
In another embodiment, Y is —$(CH_2)_5$— and Z is $C_3$-$C_6$ cycloalkyl.
In another embodiment, Y is —$(CH_2)_5$— and Z is a $C_4$-$C_6$ partially unsaturated carbocycle.
In another embodiment, Y is unsubstituted —$(CH_2)_q$— and q is an integer ranging from 1 to 5.
In another embodiment, Y is —$(CH_2)_q$—, q is an integer ranging from 1 to 5, and Y is substituted with one or two groups independently selected from methyl, ethyl, propyl, isopropyl, and cyclopropyl.
In another embodiment, m is 1, Y is a bond and Z is $C_3$-$C_6$ cycloalkyl.
In another embodiment, m is 1, Y is a bond and Z is a $C_4$-$C_6$ partially unsaturated carbocycle.
In another embodiment, m is 2, Y is a bond and Z is $C_3$-$C_6$ cycloalkyl.
In another embodiment, m is 2, Y is a bond and Z is a $C_4$-$C_6$ partially unsaturated carbocycle.
In another embodiment, m is 3, Y is a bond and Z is $C_3$-$C_6$ cycloalkyl.
In another embodiment, m is 3, Y is a bond and Z is a $C_4$-$C_6$ partially unsaturated carbocycle.
In another embodiment, m is 1, 2 or 3, Z is $C_3$-$C_6$ cycloalkyl or a $C_4$-$C_6$ partially unsaturated carbocycle, and if Z is a six-membered ring, $R_5$ is in the meta position on said ring with respect to Y.
In another embodiment, m is 1, 2 or 3, Z is $C_3$-$C_6$ cycloalkyl or a $C_4$-$C_6$ partially unsaturated carbocycle, and if Z is a six-membered ring, $R_5$ is in the para position on said ring with respect to Y.
In another embodiment, m is 1, 2 or 3, Z is $C_3$-$C_6$ cycloalkyl or a $C_4$-$C_6$ partially unsaturated carbocycle, and if Z is a six-membered ring, $R_5$ is in the ortho position on said ring with respect to Y.
In another embodiment, $R_5$ is $C_1$-$C_6$ hydroxyalkyl.
In another embodiment, $R_5$ is arylalkoxy in which the alkoxy portion contains from 1 to 6 carbon atoms.
In another embodiment, $R_5$ is aryl.
In another embodiment, $R_5$ is biaryl.

In another embodiment, $R_5$ is heteroarylalkyl in which the alkyl portion contains from 1 to 6 carbon atoms.
In another embodiment, $R_5$ is —$(CH_2)_{1-6}$—O—$(CH_2)_{0-6}$-aryl.
In another embodiment, $R_5$ is —$(CH_2)_{1-6}$—O—$(CH_2)_{0-6}$-heteroaryl.
In another embodiment, $R_5$ is —$(CH_2)_{0-6}$—O—$(CH_2)_{0-6}$—$C_3$-$C_6$ cycloalkyl.
In another embodiment, $R_5$ is heteroaryl.
In another embodiment, $R_5$ is —$(CH_2)_r NR^v R^{vi}$, wherein one of $R^v$ and $R^{vi}$ is hydrogen, $C_1$-$C_6$ straight chain alkyl, $C_3$-$C_6$ branched chain alkyl or $C_3$-$C_6$ cycloalkyl and the other of $R^v$ and $R^{vi}$ is —$(CO)R^{vii}$ or —$SO_2 R^{vii}$, and r and $R^{vii}$ are as described above for the pyridinyl nicotinic acetylcholine receptor ligands of the formula III.
In another embodiment, $R_5$ is —$(CH_2)_r C(O)NR^v R^{vi}$, and r, $R^v$ and $R^{vi}$ are as described above for the pyridinyl nicotinic acetylcholine receptor ligands of the formula III.
In another embodiment, $R_5$ is —$(CH_2)_r C(O)OR^{ix}$, and r and $R^{ix}$ have the same meanings as set forth above for the compounds of formula III.
In another embodiment, $R_5$ is —$(CH_2)_r SR^{viii}$, wherein $R^{viii}$ is hydrogen or —$C(O)R^x$, and r and $R^x$ are as defined above for the pyridinyl nicotinic acetylcholine receptor ligands of the formula III.
In another embodiment, $R_5$ is —$(CH_2)_r SO_2 R^{ix}$, wherein r is an integer ranging from 0 to 5 and $R^{ix}$ is as defined above for the compounds of formula III.
In another embodiment, $R_5$ is —$(CH_2)_r SOR^{ix}$, wherein r is an integer ranging from 0 to 5 and $R^{ix}$ is as defined above for the compounds of formula III.
In another embodiment, the invention encompasses compounds of formula III-1:

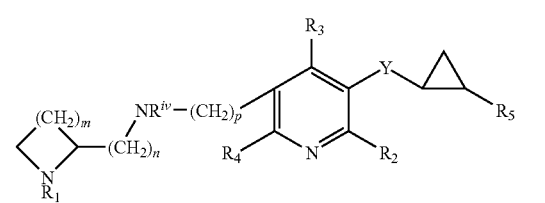

(III-1)

and pharmaceutically acceptable derivates thereof, wherein $R^{iv}$ is hydrogen, and all other variables have the same meanings as described above for the compounds of formula III.

In another embodiment, the invention encompasses compounds of formula III-1, and pharmaceutically acceptable derivatives thereof, wherein $R^{iv}$ is $C_1$-$C_6$ straight chain alkyl or $C_3$-$C_6$ branched chain alkyl, and all other variables have the same meanings as described above for the compounds of formula III.

In another embodiment, the invention encompasses compounds of formula III-1 and pharmaceutically acceptable derivates thereof, wherein $R^{iv}$ is $C_3$-$C_6$ cycloalkyl, and all other variables have the same meanings as described above for the compounds of formula III.

In another embodiment, the invention encompasses compounds of formula III-1 and pharmaceutically acceptable derivatives thereof, wherein $R^{iv}$ is an acyl group having the formula:

$R^i$ is $C_1$-$C_6$ straight chain alkyl, and all other variables have the same meanings as described above for the compounds of formula III.

Nicotinic Acetylcholine Receptor Ligands of the Formula IV

In another embodiment, the invention encompasses pyridinyl nicotinic acetylcholine receptor ligands of the formula IV:

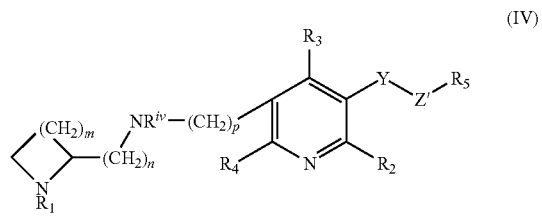

and pharmaceutically acceptable derivatives thereof, wherein all variables have the same meanings as defined above for the pyridinyl nicotinic acetylcholine receptor ligands of the formula IV.

In one embodiment, $R^{iv}$ is $C_1$-$C_6$ straight chain alkyl.
In another embodiment, $R^{iv}$ is $C_3$-$C_6$ branched chain alkyl.
In another embodiment, $R^{iv}$ is $C_3$-$C_6$ cycloalkyl.
In another embodiment, $R^{iv}$ is an acyl group having the formula:

wherein $R^i$ is $C_1$-$C_6$ straight chain alkyl.
In another embodiment, $R^{iv}$ is an acyl group as shown above and $R^i$ is $C_3$-$C_6$ branched chain alkyl.
In another embodiment, $R^{iv}$ is an acyl group as shown above and $R^i$ is $C_3$-$C_6$ cycloalkyl.
In one embodiment, $R_1$ is H.
In another embodiment, $R_1$ is $C_1$-$C_6$ straight chain alkyl.
In another embodiment, $R_1$ is $C_3$-$C_6$ branched chain alkyl.
In another embodiment, $R_1$ is allyl.
In another embodiment, $R_1$ is $C_3$-$C_6$ cycloalkyl.
In another embodiment, $R_2$ is H.
In another embodiment, $R_3$ is H.
In another embodiment, $R_4$ is H.
In another embodiment, $R_2$, $R_3$ and $R_4$ are each H.
In another embodiment, m is 1.
In another embodiment, m is 2.
In another embodiment, m is 3.
In another embodiment, n is 1.
In another embodiment, n is 2.
In another embodiment, p is 0.
In another embodiment, p is 1.
In another embodiment, p is 2.
In another embodiment, n is 1 and p is 0.

In another embodiment, Y is —$CH_2$— and Z' is a four- to six-membered saturated heterocycle.
In another embodiment, Y is —$CH_2$— and Z' is a five- or six-membered partially-unsaturated heterocycle.
In another embodiment, Y is —$CH_2CH_2$— and Z' is a four- to six-membered saturated heterocycle.
In another embodiment, Y is —$CH_2CH_2$— and Z' is a five- or six-membered partially-unsaturated heterocycle.
In another embodiment, Y is —$CH_2CH_2CH_2$— and Z' is a four- to six-membered saturated heterocycle.
In another embodiment, Y is —$CH_2CH_2CH_2$— and Z' is a five- or six-membered partially-unsaturated heterocycle.
In another embodiment, Y is —$(CH_2)_4$— and Z' is a four- to six-membered saturated heterocycle.
In another embodiment, Y is —$(CH_2)_4$— and Z' is a five- or six-membered partially-unsaturated heterocycle.
In another embodiment, Y is —$(CH_2)_5$— and Z' is a four- to six-membered saturated heterocycle.
In another embodiment, Y is —$(CH_2)_5$— and Z' is a five- or six-membered partially-unsaturated heterocycle.
In another embodiment, Y is unsubstituted —$(CH_2)_q$— and q is an integer ranging from 1 to 5.
In another embodiment, Y is —$(CH_2)_q$—, q is an integer ranging from 1 to 5, and Y is substituted with one or two groups independently selected from methyl, ethyl, propyl, isopropyl, and cyclopropyl.
In another embodiment, m is 1, Y is a bond and Z' is a four- to six-membered saturated heterocycle.
In another embodiment, m is 1, Y is a bond and Z' is a five- or six-membered partially-unsaturated heterocycle.
In another embodiment, m is 1, Y is a bond and Z' is a saturated azabicycle and wherein said saturated azabicycle is linked through its nitrogen atom to the pyridine ring.
In another embodiment of formula II, m is 1 or 2, Y is a bond, n is 1, p is 0, $R_1$, $R_2$, $R_3$, $R_4$, and $R_5$ are each hydrogen and Z' is a saturated azabicycle having 4 to 8 ring carbon atoms and one carbon to carbon bridge with 0-2 carbon atoms in the bridge and wherein said saturated azabicycle is linked through its nitrogen atom to the pyridine ring.
In another embodiment, m is 2, Y is a bond and Z' is a four- to six-membered saturated heterocycle.
In another embodiment, m is 2, Y is a bond and Z' is a five- or six-membered partially-unsaturated heterocycle.
In another embodiment, m is 3, Y is a bond and Z' is a four- to six-membered saturated heterocycle.
In another embodiment, m is 3, Y is a bond and Z' is a five- or six-membered partially-unsaturated heterocycle.
In another embodiment, m is 1, 2 or 3, Z' is a four- to six-membered saturated heterocycle or a five- or six-membered partially-unsaturated heterocycle having at least 3 carbon atoms and if Z' is a six-membered ring, $R_5$ is in the meta position on said ring with respect to Y.
In another embodiment, m is 1, 2 or 3, Z' is a saturated four- to six-membered heterocycle or a five- or six-membered partially-unsaturated heterocycle having at least carbon atoms and if Z' is a six-membered ring, $R_5$ is the para position on said ring with respect to Y.
In another embodiment, m is 1, 2 or 3, Z' is a saturated four- to six-membered heterocycle or a five- or six-membered partially-unsaturated heterocycle having at least 3 carbon atoms and if Z' is a six-membered ring, $R_5$ is the ortho position on said ring with respect to Y.
In another embodiment, $R_5$ is $C_1$-$C_6$ hydroxyalkyl.
In another embodiment, $R_5$ is alkoxyalkyl with one or two hydroxyl substitutents in which the alkoxy and alkyl portions each independently contain from 1 to 6 carbon atoms.

In another embodiment, $R_5$ is hydroxyalkoxyalkyl in which the alkoxy and alkyl portions each independently contain from 1 to 6 carbon atoms.

In another embodiment, $R_5$ is arylalkoxy in which the alkoxy portion contains from 1 to 6 carbon atoms.

In another embodiment, $R_5$ is aryl.

In another embodiment, $R_5$ is biaryl.

In another embodiment, $R_5$ is heteroarylalkyl in which the alkyl portion contains from 1 to 6 carbon atoms.

In another embodiment, $R_5$ is —(CH$_2$)$_{1\text{-}6}$—O—(CH$_2$)$_{0\text{-}6}$-aryl.

In another embodiment, $R_5$ is —(CH$_2$)$_{1\text{-}6}$—O—(CH$_2$)$_{0\text{-}6}$-heteroaryl.

In another embodiment, $R_5$ is —(CH$_2$)$_{0\text{-}6}$—O—(CH$_2$)$_{0\text{-}6}$—C$_3$-C$_6$ cycloalkyl.

In another embodiment, $R_5$ is heteroaryl.

In another embodiment, $R_5$ is —(CH$_2$)$_r$NR$^v$R$^{vi}$, wherein one of R$^v$ and R$^{vi}$ is hydrogen, C$_1$-C$_6$ straight chain alkyl, C$_3$-C$_6$ branched chain alkyl or C$_3$-C$_6$ cycloalkyl and the other of R$^v$ and R$^{vi}$ is —(CO)R$^{vii}$ or —SO$_2$R$^{vi}$, and r and R$^{vii}$ are as described above for the pyridinyl nicotinic acetylcholine receptor ligands of the formula IV.

In another embodiment, $R_5$ is —(CH$_2$)$_r$C(O)NR$^v$R$^{vi}$, and r, R$^v$ and R$^{vi}$ are as described above for the pyridinyl nicotinic acetylcholine receptor ligands of the formula IV.

In another embodiment, $R_5$ is —(CH$_2$)$_r$C(O)OR$^{ix}$, and r and R$^{ix}$ have the same meanings as set forth above for the compounds of formula IV.

In another embodiment, $R_5$ is —(CH$_2$)$_r$SR$^{viii}$, wherein R$^{viii}$ is hydrogen or —C(O)R$^x$, and r and R$^x$ are as defined above for the pyridinyl nicotinic acetylcholine receptor ligands of the formula IV.

In another embodiment, $R_5$ is —(CH$_2$)$_r$SO$_2$R$^{ix}$, wherein r is an integer ranging from 0 to 5 and R$^{ix}$ is as defined above for the compounds of formula IV.

In another embodiment, $R_5$ is —(CH$_2$)$_r$SOR$^{ix}$, wherein r is an integer ranging from 0 to 5 and R$^{ix}$ is as defined above for the compounds of formula IV.

Nicotinic Acetylcholine Receptor Ligands of the Formula V

As stated above, the invention encompasses pyridinyl nicotinic acetylcholine receptor ligands of the formula V:

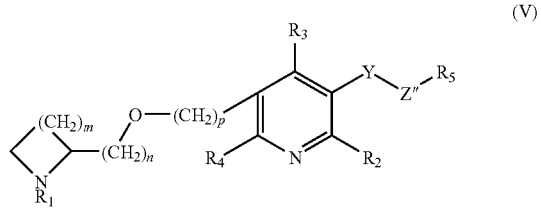

(V)

and pharmaceutically acceptable derivatives thereof, wherein all variables are as defined above for the pyridinyl nicotinic acetylcholine receptor ligands of the formula V.

In another embodiment, the invention encompasses the compounds of formula V, wherein all variables have the same meanings as described above for the compounds of formula V, and with the proviso that when Z" is an aryl group, m is 2 and Y is a bond, $R_5$ is not phenylalkyl in which the alkyl portion contains from 1 to 6 carbon atoms; —(CH$_2$)$_r$NR$^v$R$^{vi}$ when R$^v$ and R$^{vi}$ are each independently hydrogen, C$_1$-C$_6$ straight chain alkyl, C$_3$-C$_6$ branched chain alkyl or C$_3$-C$_6$ cycloalkyl; —(CH$_2$)$_r$SR$^{viii}$ when R$^{viii}$ is C$_1$-C$_6$ straight chain alkyl, C$_3$-C$_6$ branched chain alkyl, or C$_3$-C$_6$ cycloalkyl; —(CH$_2$)$_r$SO$_2$R$^{ix}$, —(CH$_2$)$_r$SOR$^{ix}$ or —(CH$_2$)$_r$C(O)OR$^{ix}$ when R$^{ix}$ is C$_1$-C$_6$ straight chain alkyl, C$_3$-C$_6$ branched chain alkyl or C$_3$-C$_6$ cycloalkyl; and with the proviso that when Z" is an aryl group, m is 1 or 3 and Y is a bond, $R_5$ is not —(CH$_2$)$_r$NR$^v$R$^{vi}$ when either R$^v$ and R$^{vi}$ are hydrogen, or when one of R$^v$ and R$^{vi}$ is hydrogen and the other of R$^v$ and R$^{vi}$ is C$_1$-C$_6$ straight chain alkyl, C$_3$-C$_6$ branched chain alkyl or C$_3$-C$_6$ cycloalkyl.

In one embodiment $R_1$ is H.

In another embodiment, $R_1$ is C$_1$-C$_6$ straight chain alkyl.

In another embodiment, $R_1$ is allyl.

In another embodiment, $R_1$ is C$_3$-C$_6$ cycloalkyl.

In another embodiment, $R_2$ is H.

In another embodiment, $R_3$ is H.

In another embodiment, $R_4$ is H.

In another embodiment, $R_2$, $R_3$ and $R_4$ are each H.

In another embodiment, one of $R_2$, $R_3$ and $R_4$ is methyl.

In another embodiment, m is 1.

In another embodiment, m is 2.

In another embodiment, m is 3.

In another embodiment, n is 1.

In another embodiment, n is 2.

In another embodiment, p is 0.

In another embodiment, p is 1.

In another embodiment, p is 2.

In another embodiment, n is 1 and p is 0.

In another embodiment, $R_5$ is alkoxyalkyl with one or two hydroxyl substituents in which the alkoxy and alkyl portions each independently contain from 1 to 6 carbon atoms.

In another embodiment, $R_5$ is hydroxyalkoxyalkyl in which the alkoxy and alkyl portions each independently contain from 1 to 6 carbon atoms.

In another embodiment, $R_5$ is C$_1$-C$_6$ hydroxyalkyl.

In another embodiment, $R_5$ is arylalkyl in which the alkyl portion contains from 1 to 6 carbon atoms.

In another embodiment, $R_5$ is arylalkoxy in which the alkoxy portion contains from 1 to 6 carbon atoms.

In another embodiment, $R_5$ is aryl.

In another embodiment, $R_5$ is biaryl.

In another embodiment, $R_5$ is heteroarylalkyl in which the alkyl portion contains from 1 to 6 carbon atoms.

In another embodiment, $R_5$ is —(CH$_2$)$_{1\text{-}6}$—O—(CH$_2$)$_{0\text{-}6}$-aryl.

In another embodiment, $R_5$ is —(CH$_2$)$_{1\text{-}6}$—O—(CH$_2$)$_{0\text{-}6}$-heteroaryl.

In another embodiment, $R_5$ is —(CH$_2$)$_{1\text{-}6}$—O—(CH$_2$)$_{0\text{-}6}$—C$_3$-C$_6$ cycloalkyl.

In another embodiment, $R_5$ is heteroaryl.

In another embodiment, $R_5$ is —(CH$_2$)$_r$NR$^v$R$^{vi}$, wherein r is an integer ranging from 0 to 5 and R$^v$ and R$^{vi}$ are each independently C$_1$-C$_6$ straight chain alkyl, C$_3$-C$_6$ branched chain alkyl; C$_3$-C$_6$ cycloalkyl; —(CO)R$^{vii}$; or —SO$_2$R$^{vii}$, and R$^{vii}$ has the meaning described above for the pyridinyl nicotinic acetylcholine receptor ligands of the formula V.

In another embodiment $R_5$ is —(CH$_2$)$_r$NR$^v$R$^{vi}$, wherein r is an integer ranging from 1 to 5.

In another embodiment, $R_5$ is —(CH$_2$)$_r$C(O)NR$^v$R$^{vi}$, wherein r, R$^v$ and R$^{vi}$ are as defined above for the pyridinyl nicotinic acetylcholine receptor ligands of the formula V.

In another embodiment, $R_5$ is —(CH$_2$)$_r$C(O)OR$^{ix}$, and r and R$^{ix}$ have the same meanings as set forth above for the compounds of formula V.

In another embodiment, $R_5$ is —(CH$_2$)$_r$SR$^{viii}$, wherein r and R$^{viii}$ are as defined above for the pyridinyl nicotinic acetylcholine receptor ligands of the formula V.

In another embodiment, $R_5$ is —$(CH_2)_rSO_2R^{ix}$, wherein r and $R^{ix}$ are as defined above for the pyridinyl nicotinic acetylcholine receptor ligands of the formula V.

In another embodiment, $R_5$ is —$(CH_2)_rSOR^{ix}$, wherein r and $R^{ix}$ are as defined above for the pyridinyl nicotinic acetylcholine receptor ligands of the formula V.

In another embodiment, Z" is phenyl and $R_5$ is in the meta position on said phenyl ring in relation to the pyridine ring.

In another embodiment, Y is a bond and Z" is an aryl group.

In another embodiment, Y is a bond and Z" is a phenyl group.

In another embodiment, Y is a bond, Z" is a phenyl group, and $R_5$ is in the para position on said ring with respect to the pyridine ring.

In another embodiment, Y is a bond, Z" is a phenyl group and $R_5$ is in the meta position on said ring with respect to the pyridine ring.

In another embodiment, Y is a bond, Z" is a phenyl group, and $R_5$ is in the ortho position on said ring with respect to the pyridine ring.

In another embodiment, Y is a bond, Z" is a phenyl group and $R_5$ is $C_1$-$C_6$ hydroxyalkyl.

In another embodiment, Y is —$CH_2$— and Z" is an aryl group.

In another embodiment, Y is —$CH_2CH_2$— and Z" is an aryl group.

In another embodiment, Y is —$CH_2$—, Z" is a phenyl group and $R_5$ is $C_1$-$C_6$ alkoxy that is in the meta position on said ring with repect to Y.

In another embodiment, Y is —$CH_2CH_2$—, Z" is phenyl and $R_5$ is $C_1$-$C_6$ alkoxy that is in the meta position on said ring with respect to Y.

In another embodiment, Y is —$CH_2CH_2CH_2$— and Z" is an aryl group.

In another embodiment, Y is —$(CH_2)_4$— and Z" is an aryl group.

In another embodiment, Y is —$(CH_2)_5$— and Z" is an aryl group.

In another embodiment, Y is unsubstituted —$(CH_2)_q$— and q is an integer ranging from 1 to 5.

In another embodiment, Y is —$(CH_2)_q$—, q is an integer ranging from 1 to 5, and Y is substituted with one or two groups independently selected from methyl, ethyl, propyl, isopropyl, and cyclopropyl.

In another embodiment, Y is —$(CH_2)_q$—, q is an integer ranging from 1 to 5, Z" is a phenyl group, and $R_5$ is —$(CH_2)_r$NR$^v$R$^{vi}$, wherein one of R$^v$ and R$^{vi}$ is hydrogen and the other is —$SO_2R^{vii}$, and R$^{vii}$ is $C_1$-$C_6$ straight chain alkyl or aryl, wherein $R_5$ is in the meta position on said ring with respect to Y.

In another embodiment, Y is —$(CH_2)_q$—, q is an integer ranging from 1 to 5, Z" is a phenyl group, $R_5$ is —$(CH_2)_r$NR$^v$R$^{vi}$, R$^v$ and R$^{vi}$ are each independently hydrogen, $C_1$-$C_6$ straight chain alkyl, $C_3$-$C_6$ branched chain alkyl, wherein $R_5$ is in the para position with respect to Y, and r is an integer ranging from 0 to 5.

In another embodiment, Z" is phenyl that is substituted with one or two substituents selected from $C_1$-$C_6$ straight chain alkyl; $C_3$-$C_6$ branched chain alkyl; $C_1$-$C_6$ fluoroalkyl; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —$NH_2$; $C_1$-$C_6$ alkylthio; $CF_3$; $C_1$-$C_6$ monoalkylamino; $C_1$-$C_6$ dialkylamino; carboxyl; and $C_2$-$C_6$ alkoxycarbonyl.

In another embodiment, Y is —$(CH_2)_q$—, q is an integer ranging from 1 to 5, Z" is phenyl and $R_5$ is —$(CH_2)_r$NR$^v$R$^{vi}$, wherein one of R$^v$ and R$^{vi}$ is hydrogen, and the other is $C_1$-$C_6$ straight chain alkyl, and R$^v$ and R$^{vi}$ are taken together to form a 4- to 7-membered ring, and wherein $R_5$ is in the meta position on said ring with respect to Y.

In another embodiment, Y is —$(CH_2)_q$—, q is an integer ranging from 1 to 5, Z" is phenyl and $R_5$ is —$(CH_2)_r$NR$^v$R$^{vi}$, wherein one of R$^v$ and R$^{vi}$ is hydrogen, and the other is $C_1$-$C_6$ straight chain alkyl, and R$^v$ and R$^{vi}$ are taken together to form a 4- to 7-membered ring, and wherein $R_5$ is in the ortho position on said ring with respect to Y.

In another embodiment, the invention encompasses compounds of formula V-1:

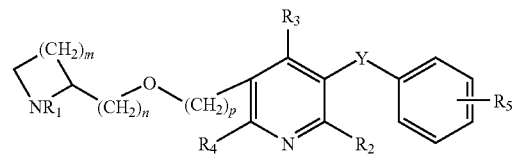

(V-1)

and pharmaceutically acceptable derivatives thereof, wherein $R_5$ is $C_1$-$C_6$ hydroxyalkyl and all other variables have the same meanings as set forth above for the compounds of formula V.

In another embodiment, the invention encompasses compounds of formula V-1, and pharmaceutically acceptable derivatives thereof, wherein all variables have the meanings as set forth above for the compounds of formula IXI, and with the proviso that when m is 2 and Y is a bond, $R_5$ is not phenylalkyl in which the alkyl portion contains from 1 to 6 carbon atoms; —$(CH_2)_r$NR$^v$R$^{vi}$ when R$^v$ and R$^{vi}$ are each independently hydrogen, $C_1$-$C_6$ straight chain alkyl, $C_3$-$C_6$ branched chain alkyl or $C_3$-$C_6$ cycloalkyl; —$(CH_2)_r$SR$^{viii}$ when R$^{viii}$ is $C_1$-$C_6$ straight chain alkyl, $C_3$-$C_6$ branched chain alkyl, or $C_3$-$C_6$ cycloalkyl; —$(CH_2)_r$SO$_2$R$^{ix}$, —$(CH_2)_r$SOR$^{ix}$ or —$(CH_2)_r$C(O)OR$^{ix}$ when R$^{ix}$ is $C_1$-$C_6$ straight chain alkyl, $C_3$-$C_6$ branched chain alkyl or $C_3$-$C_6$ cycloalkyl; and with the proviso that when m is 1 or 3 and Y is a bond, $R_5$ is not —$(CH_2)_r$NR$^v$R$^{vi}$ when both R$^v$ and R$^{vi}$ are hydrogen, or when one of R$^v$ and R$^{vi}$ is hydrogen and the other of R$^v$ and R$^{vi}$ is $C_1$-$C_6$ straight chain alkyl, $C_3$-$C_6$ branched chain alkyl or $C_3$-$C_6$ cycloalkyl.

In another embodiment, the invention encompasses the compounds of formula V-1, wherein $R_5$ is in the meta position on the phenyl group with respect to Y.

In another embodiment, the invention encompasses the compounds of formula V-1, wherein $R_5$ is in the para position on the phenyl group with respect to Y.

In another embodiment of formula V, m is 1, Y is a bond, n is 1, p is 0, $R_1$, $R_2$, $R_3$, and $R_4$ are each hydrogen and Z" is aryl.

In another embodiment of formula V, m is 1, Y is a bond, n is 1, p is 0, $R_1$, $R_2$, $R_3$, and $R_4$ are each hydrogen and Z" is phenyl.

In another embodiment of formula V, m is 1, Y is a bond, n is 1, p is 0, $R_1$, $R_2$, $R_3$, and $R_4$ are each hydrogen, Z" is phenyl and $R_5$ is selected from the group consisting of $C_1$-$C_6$ hydroxyalkyl, hydroxyalkoxyalkyl in which the alkoxy and alkyl portions each independently contain from 1 to 6 carbon atoms, arylalkoxy in which the alkoxy portion has from 1 to 6 carbon atoms, —$(CH_2)_{1-6}$—O—$(CH_2)_{0-6}$-aryl and —$(CH_2)_{1-6}$—O—$(CH_2)_{0-6}$-heteroaryl and wherein $R_5$ is on the Z" phenyl ring in the meta position with respect to the pyridine ring.

In another embodiment of formula V, m is 1, Y is a bond, n is 1, p is 0, $R_1$, $R_2$, $R_3$, and $R_4$ are each hydrogen, Z" is phenyl and $R_5$ is hydroxyalkoxyalkyl in which the alkoxy and alkyl portions each independently contain from 1 to 6 carbon atoms and wherein said $R_5$ is on the phenyl ring in the meta position with respect to the pyridine ring.

In another embodiment of formula V, m is 1, Y is a bond, n is 1, p is 0, $R_1$, $R_2$, $R_3$, and $R_4$ are each hydrogen, Z" is phenyl and $R_5$ is $C_1$-$C_6$ hydroxyalkyl and wherein said $R_5$ is on the Z" phenyl ring in the meta position with respect to the pyridine ring.

In another embodiment of formula V, m is 1, Y is a bond, n is 1, p is 0, $R_1$, $R_2$, $R_3$, and $R_4$ are each hydrogen, Z" is phenyl and $R_5$ is arylalkoxy in which the alkoxy portion has from 1 to 6 carbon atoms and wherein $R_5$ is on the phenyl ring in the meta position with respect to the pyridine ring.

In another embodiment of formula V, m is 1, Y is a bond, n is 1, p is 0, $R_1$, $R_2$, $R_3$, and $R_4$ are each hydrogen, Z" is phenyl and $R_5$ is —$(CH_2)_{1-6}$—O—$(CH_2)_{0-6}$-aryl and wherein $R_5$ is on the Z" phenyl ring in the meta position with respect to the pyridine ring and wherein said $R_5$ is optionally substituted by the optional substituents defined in formula I.

In another embodiment of formula V, m is 1, Y is a bond, n is 1, p is 0, $R_1$, $R_2$, $R_3$, and $R_4$ are each hydrogen, Z" is phenyl and $R_5$ is —$(CH_2)_{1-6}$—O—$(CH_2)_{0-6}$-heteroaryl and wherein $R_5$ is on the Z" phenyl ring in the meta position with respect to the pyridine ring and wherein said $R_5$ is optionally substituted defined in formula I.

In another embodiment, the invention encompasses the compounds of formula V-2:

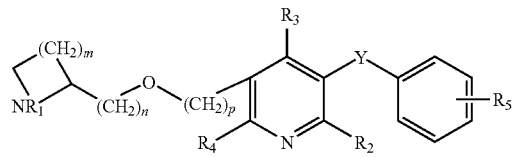

(V-2)

and pharmaceutically acceptable derivatives thereof, wherein $R_5$ is selected from arylalkyl in which the alkyl portion contains from 1 to 6 carbon atoms; arylalkoxy in which the alkoxy portion contains from 1 to 6 carbon atoms; aryl, biaryl, heteroarylalkyl in which the alkyl portion contains from 1 to 6 carbon atoms; heteroaryl; —$(CH_2)_{1-6}$—O—$(CH_2)_{0-6}$-aryl; —$(CH_2)_{1-6}$—O—$(CH_2)_{0-6}$-heteroaryl; —$(CH_2)_rC(O)NR'R^{vi}$; —$(CH_2)_rC(O)OR^{ix}$; —$(CH_2)_rSR^{viii}$; —$(CH_2)_rSO_2R^{ix}$ or —$(CH_2)_rSOR^{ix}$, and all other variables have the same meanings as set forth above for the compounds of formula V.

In some embodiments, the compound of formula V is selected from:

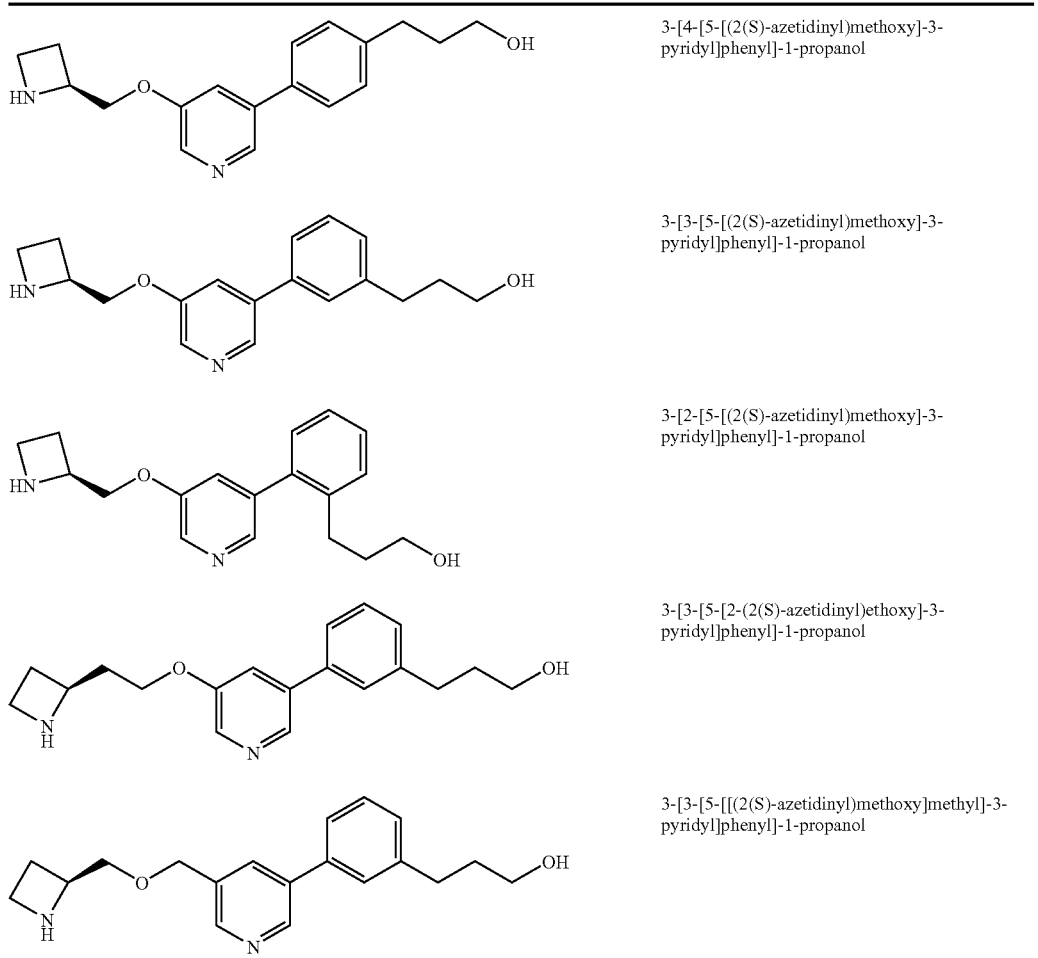

3-[4-[5-[(2(S)-azetidinyl)methoxy]-3-pyridyl]phenyl]-1-propanol

3-[3-[5-[(2(S)-azetidinyl)methoxy]-3-pyridyl]phenyl]-1-propanol

3-[2-[5-[(2(S)-azetidinyl)methoxy]-3-pyridyl]phenyl]-1-propanol

3-[3-[5-[2-(2(S)-azetidinyl)ethoxy]-3-pyridyl]phenyl]-1-propanol

3-[3-[5-[[(2(S)-azetidinyl)methoxy]methyl]-3-pyridyl]phenyl]-1-propanol

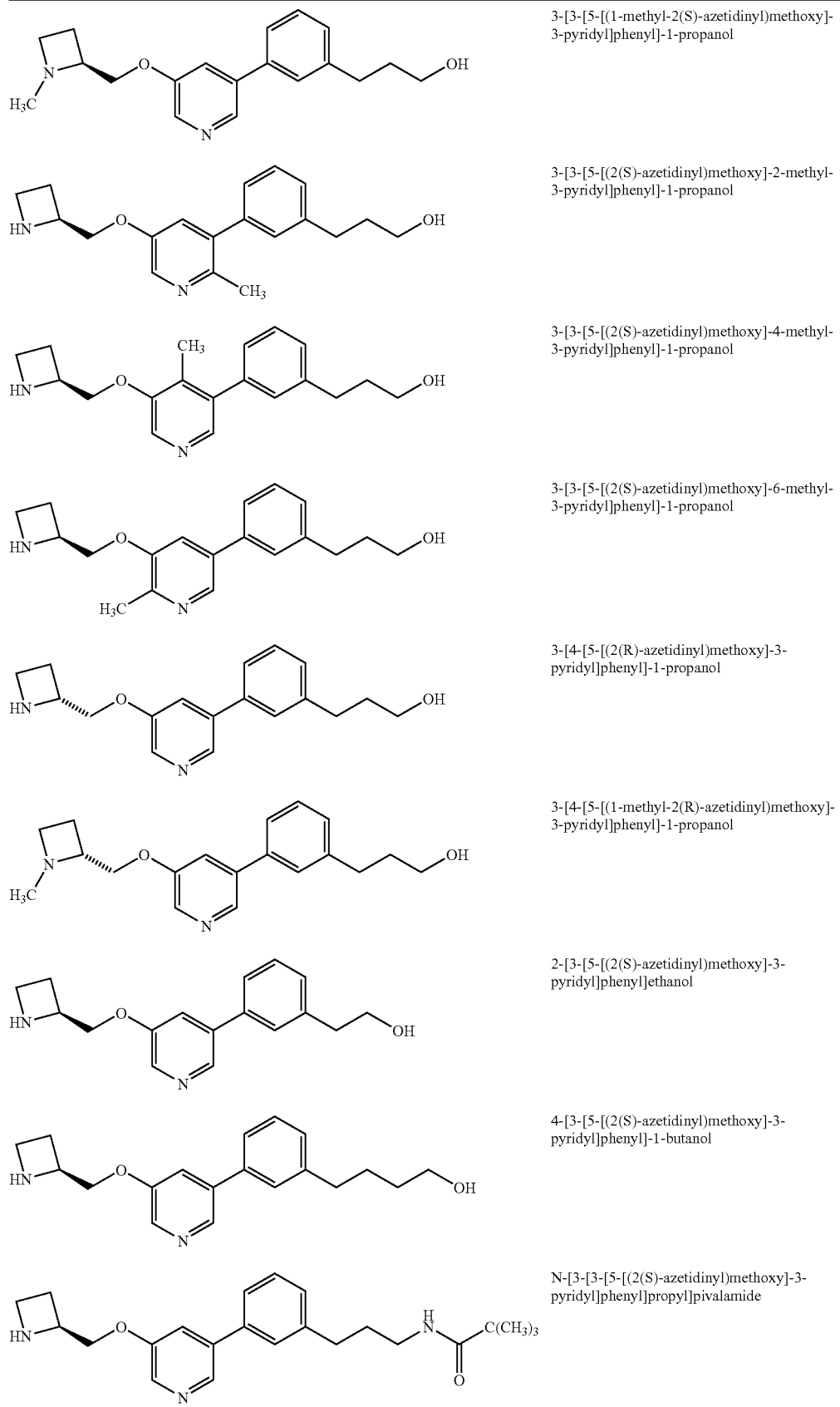

| | |
|---|---|
| | 3-[3-[5-[(1-methyl-2(S)-azetidinyl)methoxy]-3-pyridyl]phenyl]-1-propanol |
| | 3-[3-[5-[(2(S)-azetidinyl)methoxy]-2-methyl-3-pyridyl]phenyl]-1-propanol |
| | 3-[3-[5-[(2(S)-azetidinyl)methoxy]-4-methyl-3-pyridyl]phenyl]-1-propanol |
| | 3-[3-[5-[(2(S)-azetidinyl)methoxy]-6-methyl-3-pyridyl]phenyl]-1-propanol |
| | 3-[4-[5-[(2(R)-azetidinyl)methoxy]-3-pyridyl]phenyl]-1-propanol |
| | 3-[4-[5-[(1-methyl-2(R)-azetidinyl)methoxy]-3-pyridyl]phenyl]-1-propanol |
| | 2-[3-[5-[(2(S)-azetidinyl)methoxy]-3-pyridyl]phenyl]ethanol |
| | 4-[3-[5-[(2(S)-azetidinyl)methoxy]-3-pyridyl]phenyl]-1-butanol |
| | N-[3-[3-[5-[(2(S)-azetidinyl)methoxy]-3-pyridyl]phenyl]propyl]pivalamide |

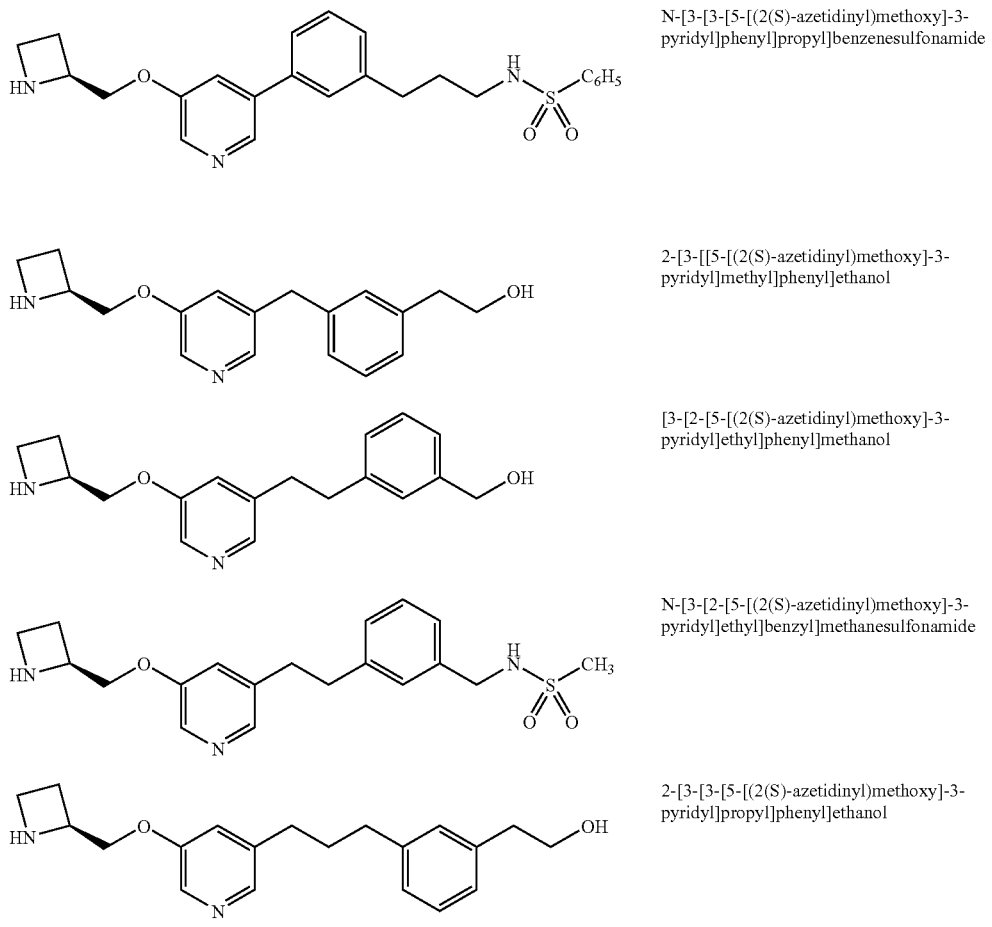

N-[3-[3-[5-[(2(S)-azetidinyl)methoxy]-3-pyridyl]phenyl]propyl]benzenesulfonamide 2-[3-[[5-[(2(S)-azetidinyl)methoxy]-3-pyridyl]methyl]phenyl]ethanol

[3-[2-[5-[(2(S)-azetidinyl)methoxy]-3-pyridyl]ethyl]phenyl]methanol

N-[3-[2-[5-[(2(S)-azetidinyl)methoxy]-3-pyridyl]ethyl]benzyl]methanesulfonamide

2-[3-[3-[5-[(2(S)-azetidinyl)methoxy]-3-pyridyl]propyl]phenyl]ethanol

In other embodiments, the compound of formula V is selected from:

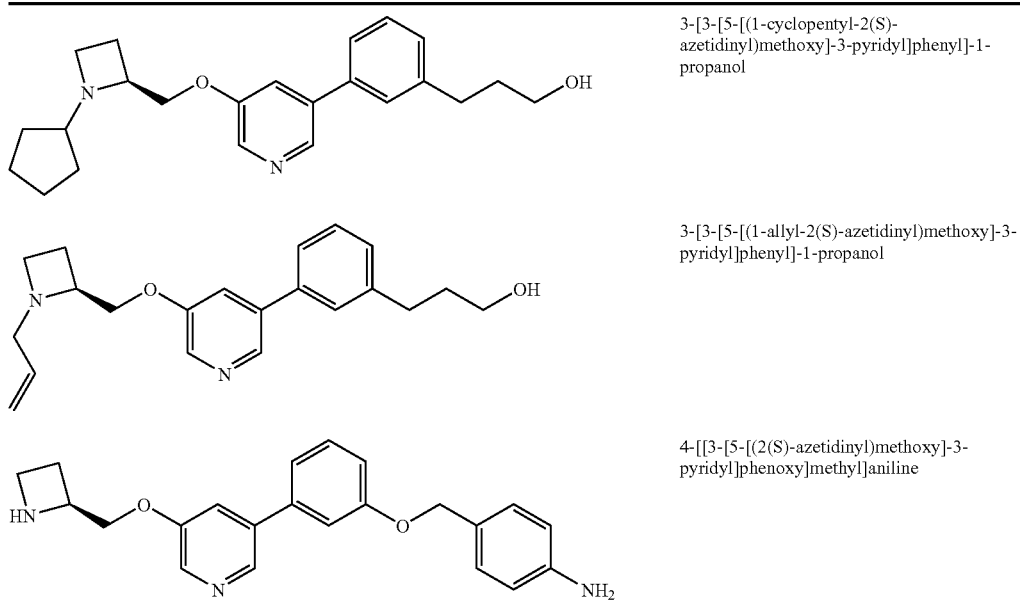

3-[3-[5-[(1-cyclopentyl-2(S)-azetidinyl)methoxy]-3-pyridyl]phenyl]-1-propanol

3-[3-[5-[(1-allyl-2(S)-azetidinyl)methoxy]-3-pyridyl]phenyl]-1-propanol

4-[[3-[5-[(2(S)-azetidinyl)methoxy]-3-pyridyl]phenoxy]methyl]aniline

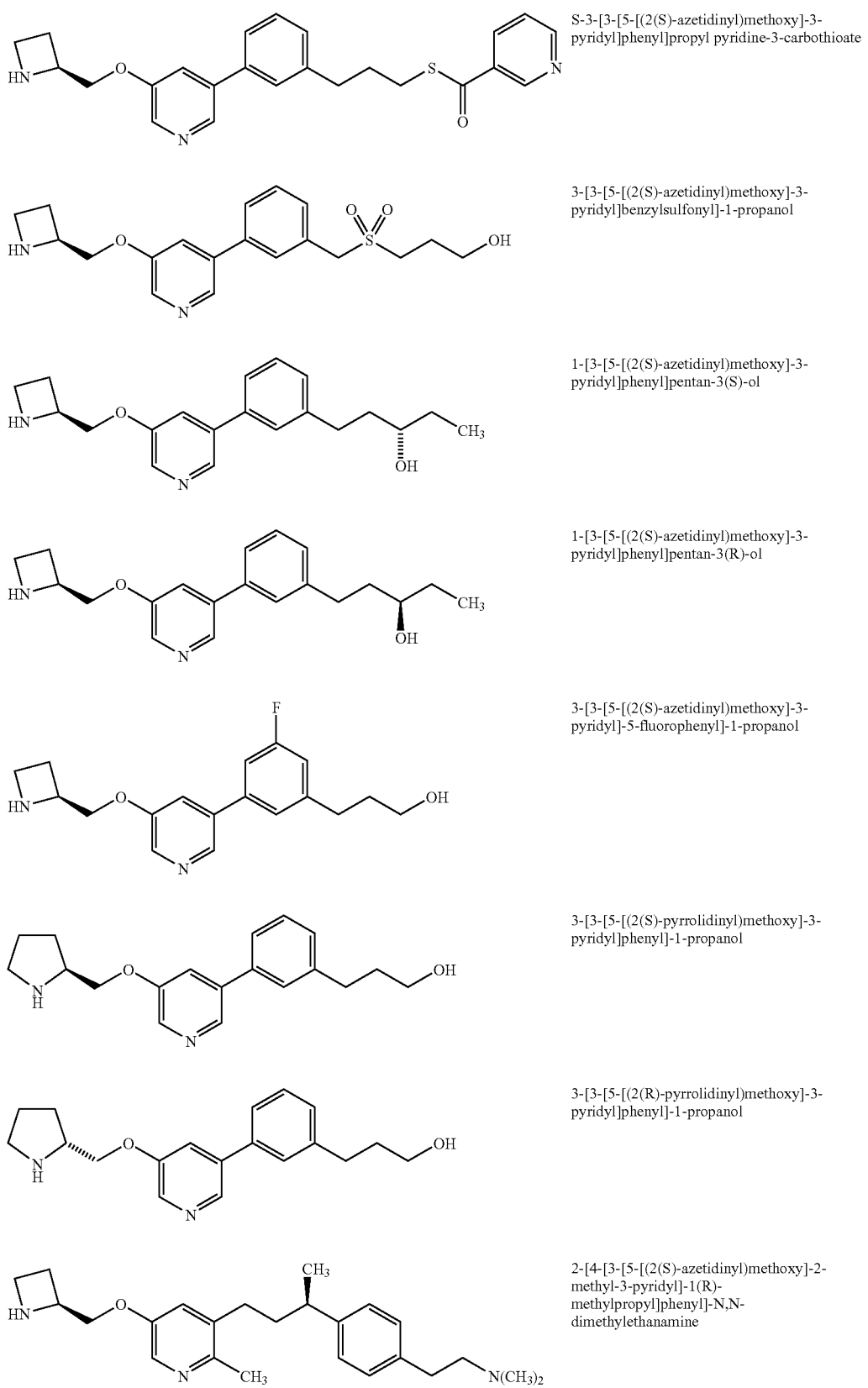

S-3-[3-[5-[(2(S)-azetidinyl)methoxy]-3-pyridyl]phenyl]propyl pyridine-3-carbothioate 3-[3-[5-[(2(S)-azetidinyl)methoxy]-3-pyridyl]benzylsulfonyl]-1-propanol 1-[3-[5-[(2(S)-azetidinyl)methoxy]-3-pyridyl]phenyl]pentan-3(S)-ol 1-[3-[5-[(2(S)-azetidinyl)methoxy]-3-pyridyl]phenyl]pentan-3(R)-ol 3-[3-[5-[(2(S)-azetidinyl)methoxy]-3-pyridyl]-5-fluorophenyl]-1-propanol 3-[3-[5-[(2(S)-pyrrolidinyl)methoxy]-3-pyridyl]phenyl]-1-propanol 3-[3-[5-[(2(R)-pyrrolidinyl)methoxy]-3-pyridyl]phenyl]-1-propanol 2-[4-[3-[5-[(2(S)-azetidinyl)methoxy]-2-methyl-3-pyridyl]-1(R)-methylpropyl]phenyl]-N,N-dimethylethanamine In another embodiment, the pyridinyl nicotinic acetylcholine receptor ligand of the formula V is selected from:

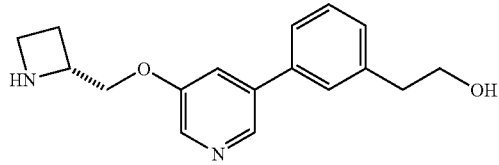

2-[3-[5-[(2(R)-azetidinyl)methoxy]-3-pyridyl]phenyl]ethanol

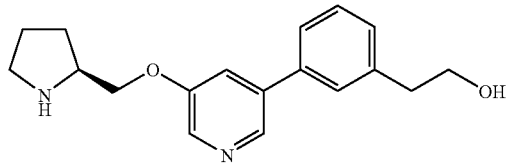 [SMILES: OCCc1cccc(-c2cncc(OC[C@@H]3CCCN3)c2)c1]

2-[3-[5-[(2(S)-pyrrolidinyl)methoxy]-3-pyridyl]phenyl]ethanol

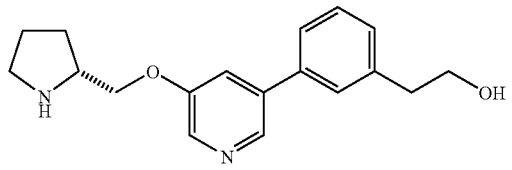

2-[3-[5-[(2(R)-pyrrolidinyl)methoxy]-3-pyridyl]phenyl]ethanol

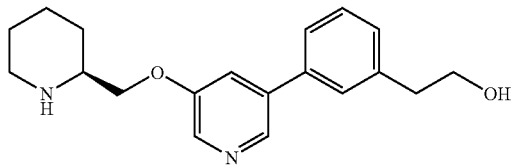 [SMILES: OCCc1cccc(-c2cncc(OC[C@@H]3CCCCN3)c2)c1]

2-[3-[5-[(2(S)-piperidinyl)methoxy]-3-pyridyl]phenyl]ethanol

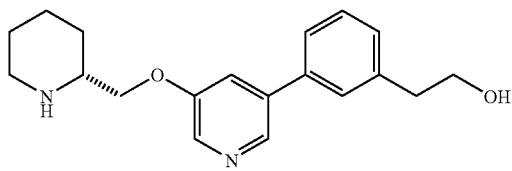

2-[3-[5-[(2(R)-piperidinyl)methoxy]-3-pyridyl]phenyl]ethanol

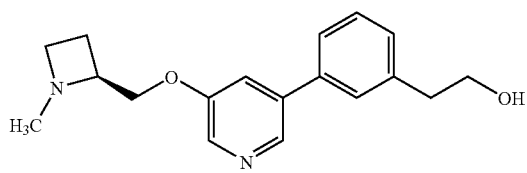 [SMILES: CN1CC[C@H]1COc1cncc(-c2cccc(CCO)c2)c1]

2-[3-[5-[(1-methyl-2(S)-azetidinyl)methoxy]-3-pyridyl]phenyl]ethanol

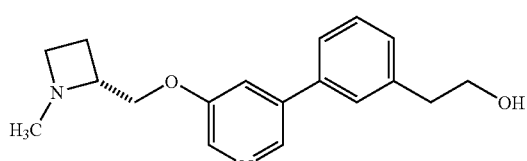

2-[3-[5-[(1-methyl-2(R)-azetidinyl)methoxy]-3-pyridyl]phenyl]ethanol

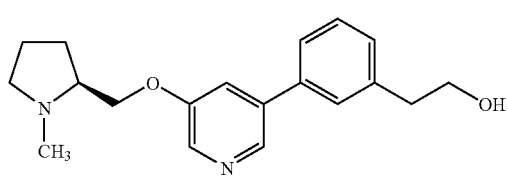 [SMILES: CN1CCC[C@H]1COc1cncc(-c2cccc(CCO)c2)c1]

2-[3-[5-[(1-methyl-2(S)-pyrrolidinyl)methoxy]-3-pyridyl]phenyl]ethanol

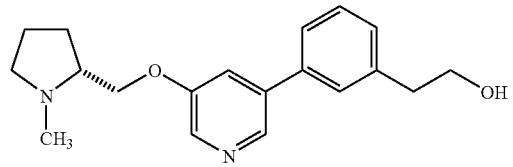
2-[3-[5-[(1-methyl-2(R)-pyrrolidinyl)methoxy]-3-pyridyl]phenyl]ethanol

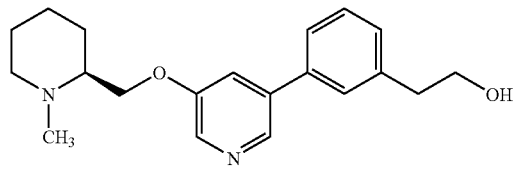 [SMILES: CN1CCCC[C@H]1COc1cncc(-c2cccc(CCO)c2)c1]
2-[3-[5-[(1-methyl-2(S)-piperidinyl)methoxy]-3-pyridyl]phenyl]ethanol

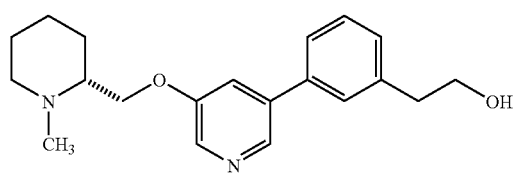
2-[3-[5-[(1-methyl-2(R)-piperidinyl)methoxy]-3-pyridyl]phenyl]ethanol

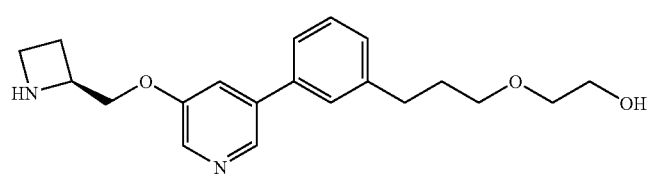 [SMILES: OCCOCCCc1cccc(-c2cncc(OC[C@@H]3CCN3)c2)c1]
2-[3-[3-[5-[(2(S)-azetidinyl)methoxy]-3-pyridyl]phenyl]propoxy]ethanol

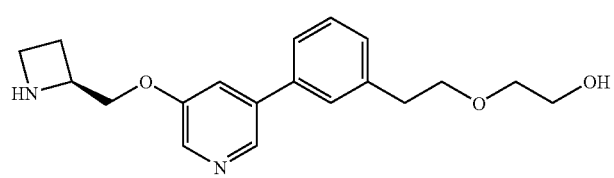 [SMILES: OCCOCCc1cccc(-c2cncc(OC[C@@H]3CCN3)c2)c1]
2-[2-[3-[5-[(2(S)-azetidinyl)methoxy]-3-pyridyl]phenyl]ethoxy]ethanol

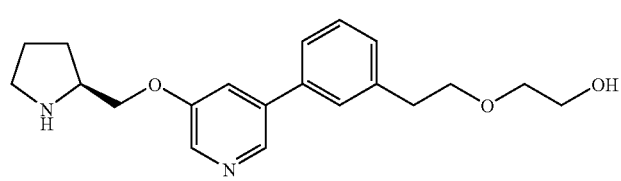 [SMILES: OCCOCCc1cccc(-c2cncc(OC[C@@H]3CCCN3)c2)c1]
2-[2-[3-[5-[(2(S)-pyrrolidinyl)methoxy]-3-pyridyl]phenyl]ethoxy]ethanol

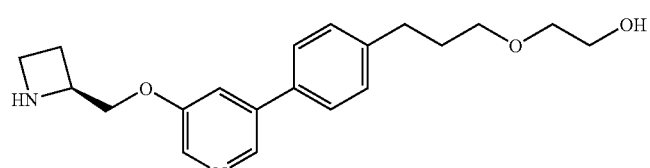
2-[3-[4-[5-[(2(S)-azetidinyl)methoxy]-3-pyridyl]phenyl]propoxy]ethanol

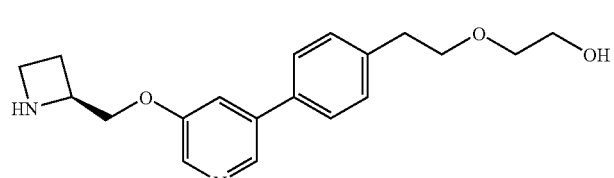
2-[2-[4-[5-[(2(S)-azetidinyl)methoxy]-3-pyridyl]phenyl]ethoxy]ethanol

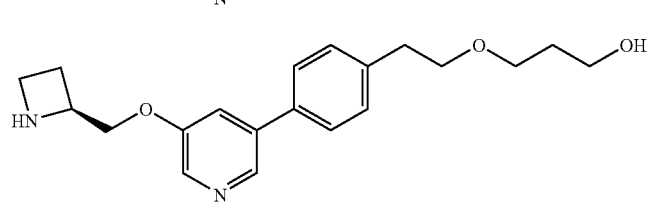
3-[2-[4-[5-[(2(S)-azetidinyl)methoxy]-3-pyridyl]phenyl]ethoxy]-1-propanol

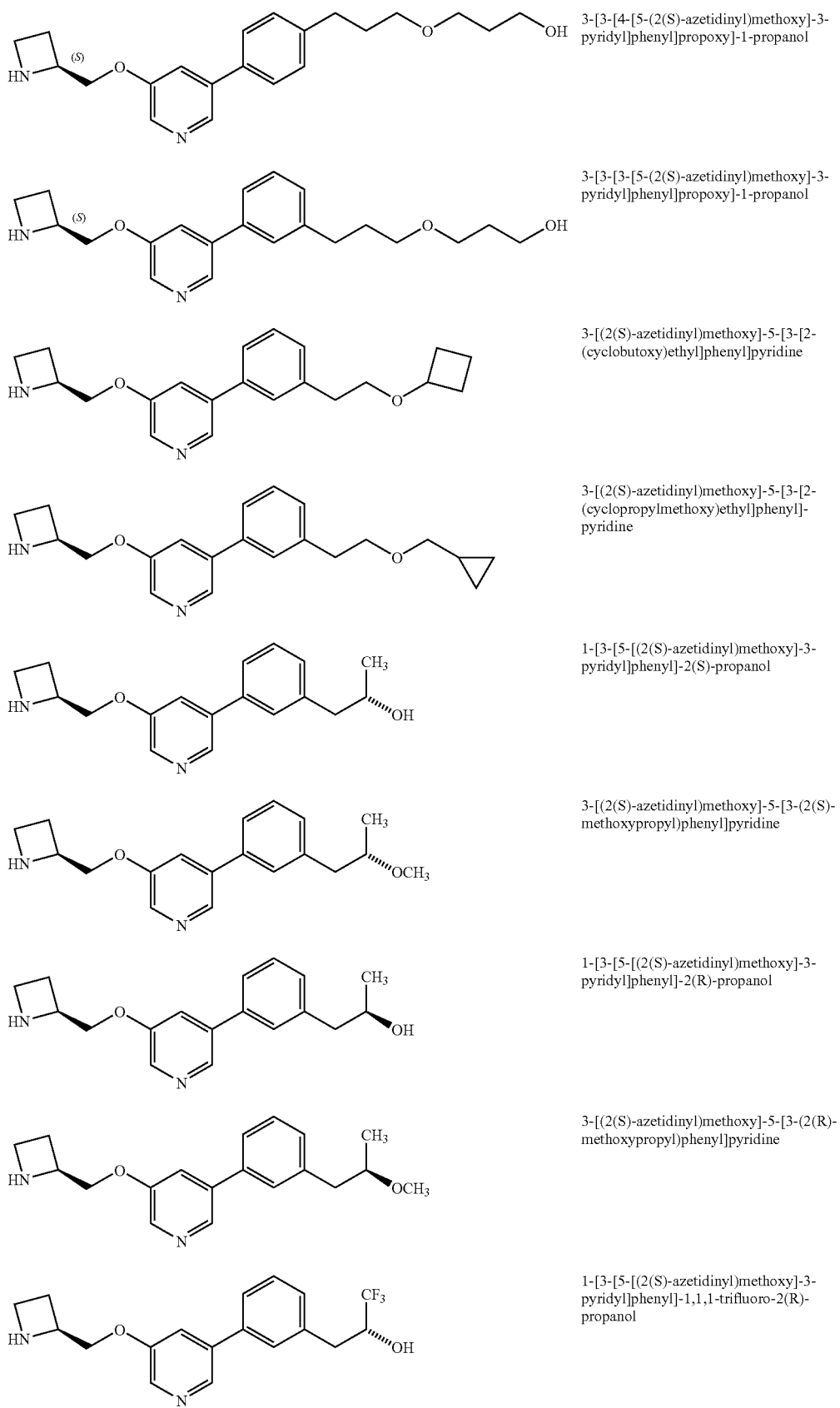

3-[3-[4-[5-(2(S)-azetidinyl)methoxy]-3-pyridyl]phenyl]propoxy]-1-propanol

3-[3-[3-[5-(2(S)-azetidinyl)methoxy]-3-pyridyl]phenyl]propoxy]-1-propanol

3-[(2(S)-azetidinyl)methoxy]-5-[3-[2-(cyclobutoxy)ethyl]phenyl]pyridine

3-[(2(S)-azetidinyl)methoxy]-5-[3-[2-(cyclopropylmethoxy)ethyl]phenyl]-pyridine

1-[3-[5-[(2(S)-azetidinyl)methoxy]-3-pyridyl]phenyl]-2(S)-propanol

3-[(2(S)-azetidinyl)methoxy]-5-[3-(2(S)-methoxypropyl)phenyl]pyridine

1-[3-[5-[(2(S)-azetidinyl)methoxy]-3-pyridyl]phenyl]-2(R)-propanol

3-[(2(S)-azetidinyl)methoxy]-5-[3-(2(R)-methoxypropyl)phenyl]pyridine

1-[3-[5-[(2(S)-azetidinyl)methoxy]-3-pyridyl]phenyl]-1,1-trifluoro-2(R)-propanol -continued

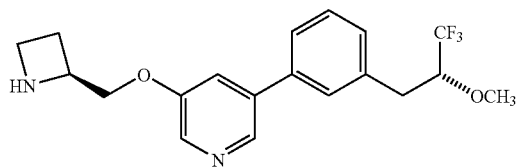 [SMILES: CO[C@H](Cc1cccc(-c2cncc(OC[C@@H]3CCN3)c2)c1)C(F)(F)F]
3-[(2(S)-azetidinyl)methoxy]-5-[3-(1,1,1-trifluoro-2(R)-methoxypropyl)phenyl]pyridine

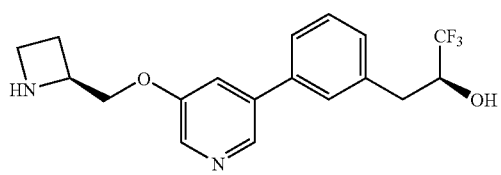 [SMILES: O[C@@H](Cc1cccc(-c2cncc(OC[C@@H]3CCN3)c2)c1)C(F)(F)F]
1-[3-[5-[(2(S)-azetidinyl)methoxy]-3-pyridyl]phenyl]-1,1,1-trifluoro-2(S)-propanol

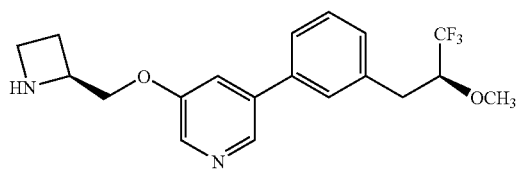 [SMILES: CO[C@@H](Cc1cccc(-c2cncc(OC[C@@H]3CCN3)c2)c1)C(F)(F)F]
3-[(2(S)-azetidinyl)methoxy]-5-[3-(1,1,1-trifluoro-2(S)-methoxypropyl)phenyl]pyridine

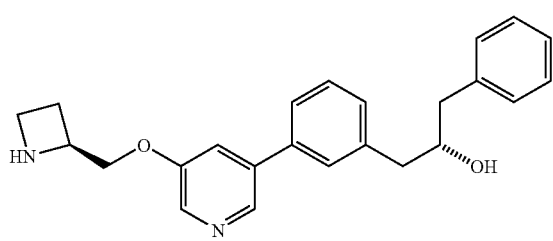 [SMILES: O[C@@H](Cc1ccccc1)Cc1cccc(-c2cncc(OC[C@@H]3CCN3)c2)c1]
1-[3-[5-[(2(S)-azetidinyl)methoxy]-3-pyridyl]phenyl]-3-phenyl-2(S)-propanol

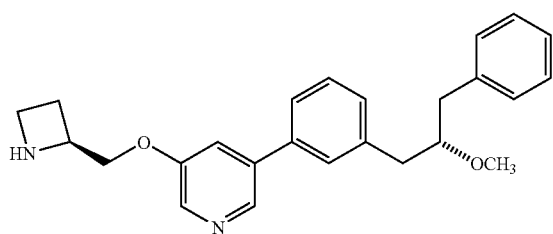 [SMILES: CO[C@@H](Cc1ccccc1)Cc1cccc(-c2cncc(OC[C@@H]3CCN3)c2)c1]
3-[(2(S)-azetidinyl)methoxy]-5-[3-(2(S)-methoxy-3-phenylpropyl)phenyl]pyridine

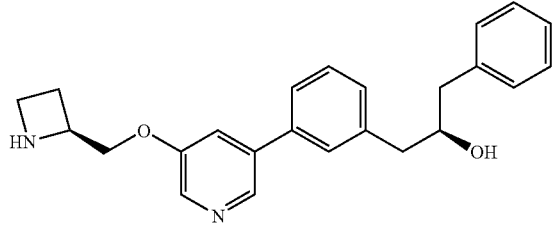 [SMILES: O[C@H](Cc1ccccc1)Cc1cccc(-c2cncc(OC[C@@H]3CCN3)c2)c1]
1-[3-[5-[(2(S)-azetidinyl)methoxy]-3-pyridyl]phenyl]-3-phenyl-2(R)-propanol

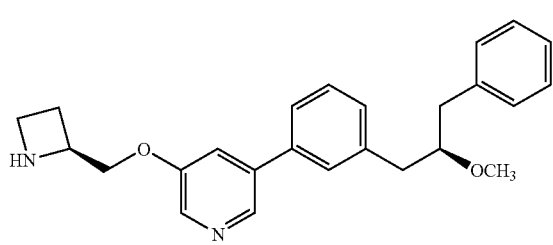 [SMILES: CO[C@H](Cc1ccccc1)Cc1cccc(-c2cncc(OC[C@@H]3CCN3)c2)c1]
3-[(2(S)-azetidinyl)methoxy]-5-[3-(2(R)-methoxy-3-phenylpropyl)phenyl]pyridine

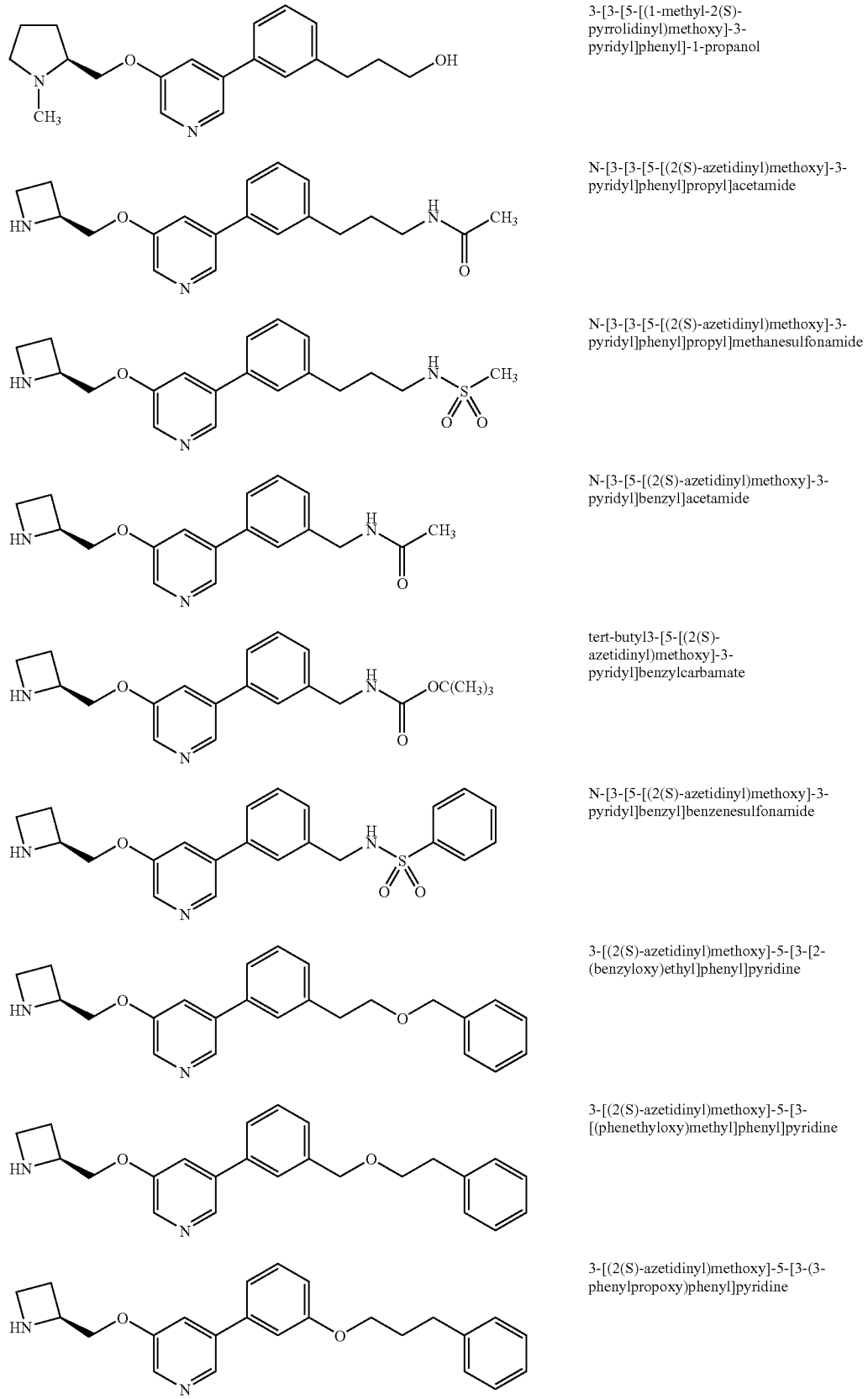

| | |
|---|---|
| | 3-[3-[5-[(1-methyl-2(S)-pyrrolidinyl)methoxy]-3-pyridyl]phenyl]-1-propanol |
| | N-[3-[3-[5-[(2(S)-azetidinyl)methoxy]-3-pyridyl]phenyl]propyl]acetamide |
| | N-[3-[3-[5-[(2(S)-azetidinyl)methoxy]-3-pyridyl]phenyl]propyl]methanesulfonamide |
| | N-[3-[5-[(2(S)-azetidinyl)methoxy]-3-pyridyl]benzyl]acetamide |
| | tert-butyl3-[5-[(2(S)-azetidinyl)methoxy]-3-pyridyl]benzylcarbamate |
| | N-[3-[5-[(2(S)-azetidinyl)methoxy]-3-pyridyl]benzyl]benzenesulfonamide |
| | 3-[(2(S)-azetidinyl)methoxy]-5-[3-[2-(benzyloxy)ethyl]phenyl]pyridine |
| | 3-[(2(S)-azetidinyl)methoxy]-5-[3-[(phenethyloxy)methyl]phenyl]pyridine |
| | 3-[(2(S)-azetidinyl)methoxy]-5-[3-(3-phenylpropoxy)phenyl]pyridine |

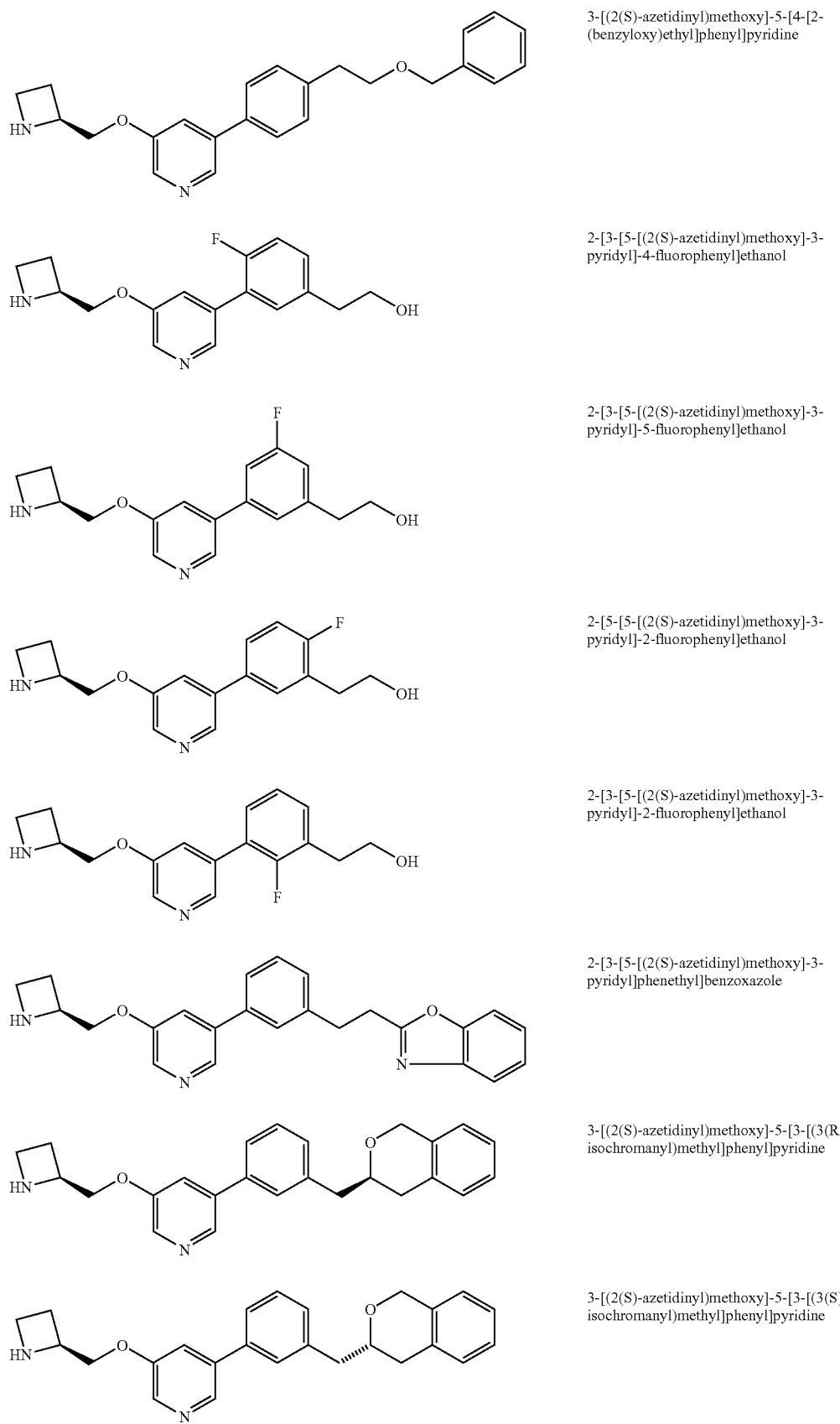

3-[(2(S)-azetidinyl)methoxy]-5-[4-[2-(benzyloxy)ethyl]phenyl]pyridine

2-[3-[5-[(2(S)-azetidinyl)methoxy]-3-pyridyl]-4-fluorophenyl]ethanol

2-[3-[5-[(2(S)-azetidinyl)methoxy]-3-pyridyl]-5-fluorophenyl]ethanol

2-[5-[5-[(2(S)-azetidinyl)methoxy]-3-pyridyl]-2-fluorophenyl]ethanol

2-[3-[5-[(2(S)-azetidinyl)methoxy]-3-pyridyl]-2-fluorophenyl]ethanol

2-[3-[5-[(2(S)-azetidinyl)methoxy]-3-pyridyl]phenethyl]benzoxazole

3-[(2(S)-azetidinyl)methoxy]-5-[3-[(3(R)-isochromanyl)methyl]phenyl]pyridine

3-[(2(S)-azetidinyl)methoxy]-5-[3-[(3(S)-isochromanyl)methyl]phenyl]pyridine

-continued

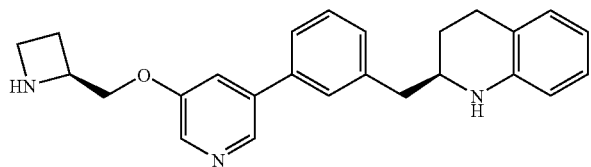 [SMILES: c1cc(C[C@H]2CCc3ccccc3N2)cc(-c2cncc(OC[C@@H]3CCN3)c2)c1]
2(R)-[3-[5-[(2(S)-azetidinyl)methoxy]-3-pyridyl]benzyl]-1,2,3,4-tetrahydroquinoline

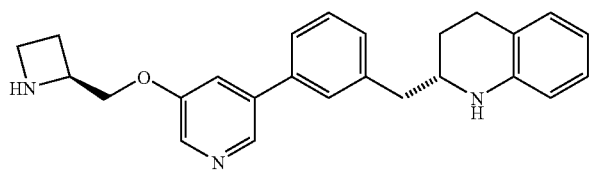
2(S)-[3-[5-[(2(S)-azetidinyl)methoxy]-3-pyridyl]benzyl]-1,2,3,4-tetrahydroquinoline

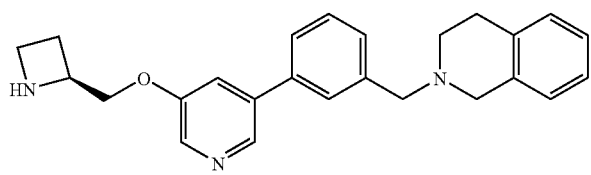 [SMILES: c1cc(CN2CCc3ccccc3C2)cc(-c2cncc(OC[C@@H]3CCN3)c2)c1]
2-[3-[5-[(2(S)-azetidinyl)methoxy]-3-pyridyl]benzyl]-1,2,3,4-tetrahydroisoquinoline

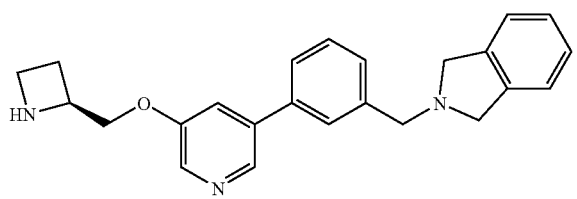 [SMILES: c1cc(CN2Cc3ccccc3C2)cc(-c2cncc(OC[C@@H]3CCN3)c2)c1]
2-[3-[5-[(2(S)-azetidinyl)methoxy]-3-pyridyl]benzyl]isoindoline

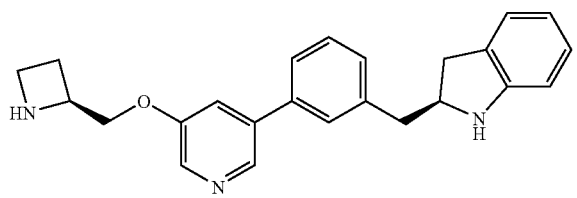 [SMILES: c1cc(C[C@H]2Cc3ccccc3N2)cc(-c2cncc(OC[C@@H]3CCN3)c2)c1]
2(S)-[3-[5-[(2(S)-azetidinyl)methoxy]-3-pyridyl]benzyl]indoline

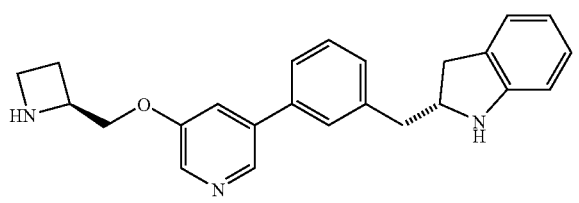
2(R)-[3-[5-[(2(S)-azetidinyl)methoxy]-3-pyridyl]benzyl]indoline

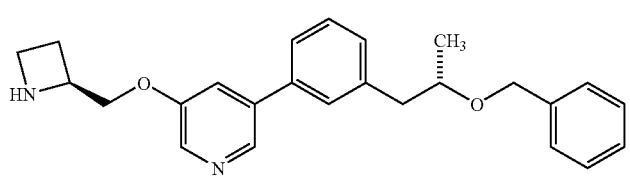 [SMILES: C[C@@H](Cc1cccc(-c2cncc(OC[C@@H]3CCN3)c2)c1)OCc1ccccc1]
3-[(2(S)-azetidinyl)methoxy]-5-[3-[2(S)-(benzyloxy)propyl]phenyl]pyridine

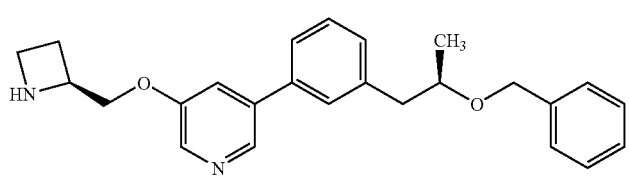 [SMILES: C[C@H](Cc1cccc(-c2cncc(OC[C@@H]3CCN3)c2)c1)OCc1ccccc1]
3-[(2(S)-azetidinyl)methoxy]-5-[3-[2(R)-(benzyloxy)propyl]phenyl]pyridine -continued

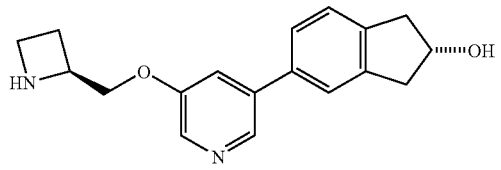 [SMILES: O[C@H]1Cc2ccc(-c3cncc(OC[C@@H]4CCN4)c3)cc2C1]
5-[5-[(2(S)-azetidinyl)methoxy]-3-pyridyl]-2,3-dihydro-1H-inden-2(S)-ol

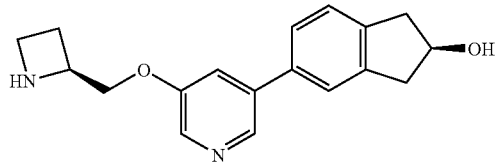 [SMILES: O[C@@H]1Cc2ccc(-c3cncc(OC[C@@H]4CCN4)c3)cc2C1]
5-[5-[(2(S)-azetidinyl)methoxy]-3-pyridyl]-2,3-dihydro-1H-inden-2(R)-ol

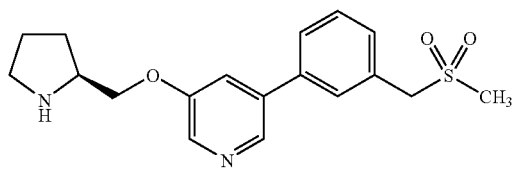 [SMILES: CS(=O)(=O)Cc1cccc(-c2cncc(OC[C@@H]3CCCN3)c2)c1]
3-[3-(methylsulfonylmethyl)phenyl]-5-[(2(S)-pyrrolidinyl)methoxy]pyridine

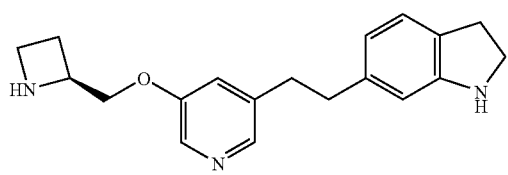 [SMILES: c1cc2c(cc1CCc1cncc(OC[C@@H]3CCN3)c1)NCC2]
6-[2-[5-[(2(S)-azetidinyl)methoxy]-3-pyridyl]ethyl]indoline

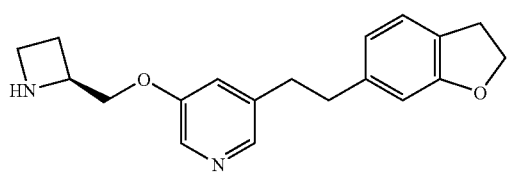 [SMILES: c1cc2c(cc1CCc1cncc(OC[C@@H]3CCN3)c1)OCC2]
3-[(2(S)-azetidinyl)methoxy]-5-[2-(2,3-dihydro-5-benzofuranyl)ethyl]pyridine

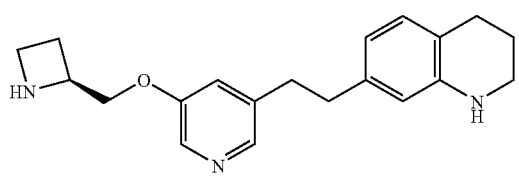 [SMILES: c1cc2c(cc1CCc1cncc(OC[C@@H]3CCN3)c1)NCCC2]
7-[2-[5-[(2(S)-azetidinyl)methoxy]-3-pyridyl]ethyl]-1,2,3,4-tetrahydroquinoline

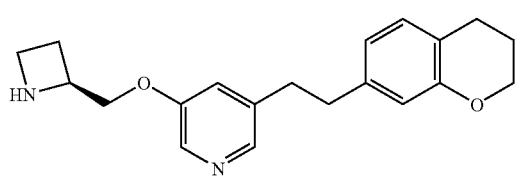 [SMILES: c1cc2c(cc1CCc1cncc(OC[C@@H]3CCN3)c1)OCCC2]
3-[(2(S)-azetidinyl)methoxy]-5-[2-(7-chromanyl)ethyl]pyridine

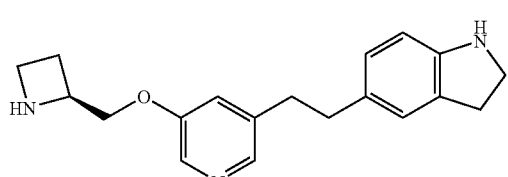
5-[2-[5-[(2(S)-azetidinyl)methoxy]-3-pyridyl]ethyl]indoline

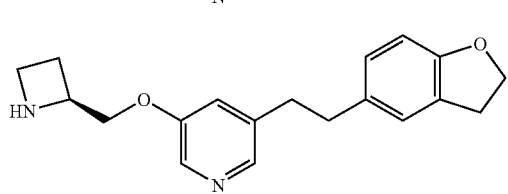
3-[(2(S)-azetidinyl)methoxy]-5-[2-(2,3-dihydro-5-benzofuranyl)ethyl]pyridine -continued

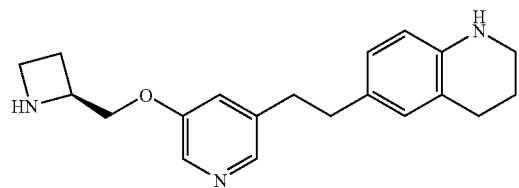 [SMILES: c1cc2c(cc1CCc1cncc(OC[C@@H]3CCN3)c1)CCCN2]

6-[2-[5-[(2(S)-azetidinyl)methoxy]-3-pyridyl]ethyl]-1,2,3,4-tetrahydroquinoline

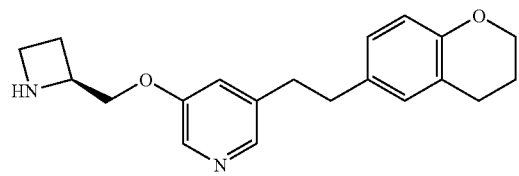 [SMILES: c1cc2c(cc1CCc1cncc(OC[C@@H]3CCN3)c1)CCCO2]

3-[(2(S)-azetidinyl)methoxy]-5-[2-(7-chromanyl)ethyl]pyridine

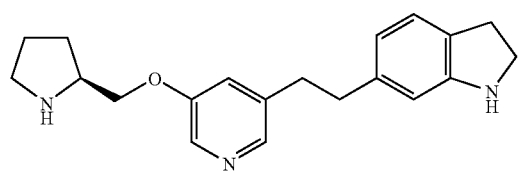 [SMILES: c1cc2c(cc1CCc1cncc(OC[C@@H]3CCCN3)c1)NCC2]

6-[2-[5-[(2(S)-pyrrolidinyl)methoxy]-3-pyridyl]ethyl]indoline

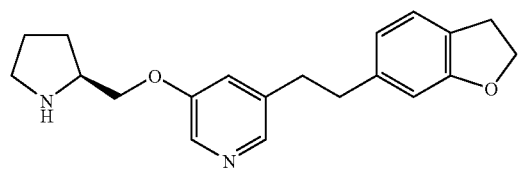 [SMILES: c1cc2c(cc1CCc1cncc(OC[C@@H]3CCCN3)c1)OCC2]

3-[2-(2,3-dihydro-6-benzofuranyl)ethyl]-5-[(2(S)-pyrrolidinyl)methoxy]pyridine

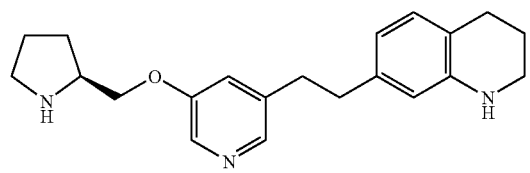 [SMILES: c1cc2c(cc1CCc1cncc(OC[C@@H]3CCCN3)c1)NCCC2]

7-[2-[5-[(2(S)-pyrrolidinyl)methoxy]-3-pyridyl]ethyl]-1,2,3,4-tetrahydroquinoline

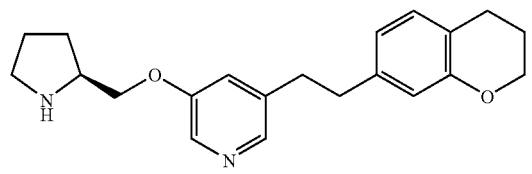 [SMILES: c1cc2c(cc1CCc1cncc(OC[C@@H]3CCCN3)c1)OCCC2]

3-[2-(7-chromanyl)ethyl]-5-[(2(S)-pyrrolidinyl)methoxy]pyridine

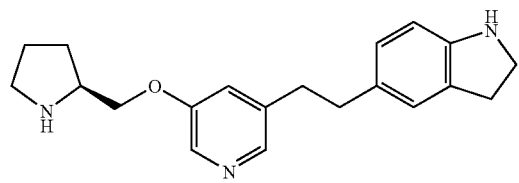 [SMILES: c1cc2c(cc1CCc1cncc(OC[C@@H]3CCCN3)c1)CCN2]

5-[2-[5-[(2(S)-pyrrolidinyl)methoxy]-3-pyridyl]ethyl]indoline

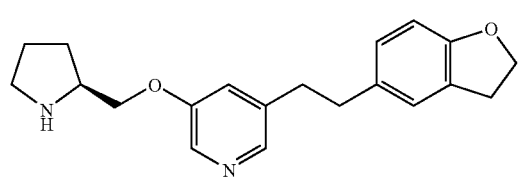 [SMILES: c1cc2c(cc1CCc1cncc(OC[C@@H]3CCCN3)c1)CCO2]

3-[2-(2,3-dihydro-5-benzofuranyl)ethyl]-5-[(2(S)-pyrrolidinyl)methoxy]pyridine

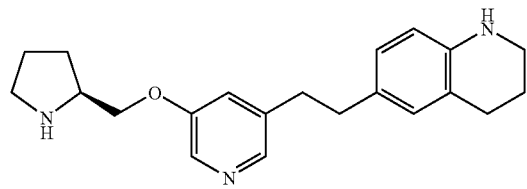 [SMILES: c1cc2c(cc1CCc1cncc(OC[C@@H]3CCCN3)c1)CCCN2]

6-[2-[5-[(2(S)-pyrrolidinyl)methoxy]-3-pyridyl]ethyl]-1,2,3,4-tetrahydroquinoline

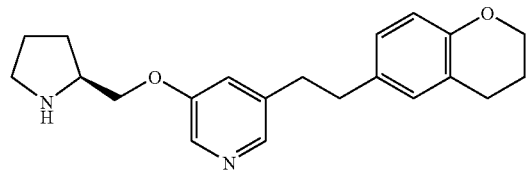 [SMILES: c1cc2c(cc1CCc1cncc(OC[C@@H]3CCCN3)c1)CCCO2]

3-[2-(6-chromanyl)ethyl]-5-[(2(S)-pyrrolidinyl)methoxy]pyridine

Nicotinic Acetylcholine Receptor Ligands of the Formula VI

As stated above, the invention encompasses pyridinyl nicotinic acetylcholine receptor ligands of the formula VI:

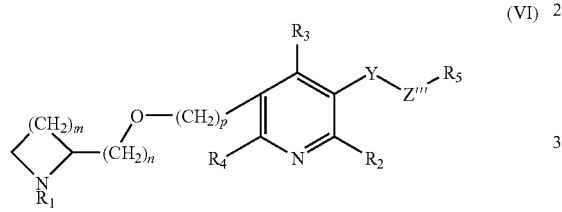

(VI)

and pharmaceutically acceptable derivatives thereof, wherein all variables have the same meanings as defined above for the pyridinyl nicotinic acetylcholine receptor ligands of the formula VI.

In some embodiments, the invention encompasses the compounds of formula VI, and pharmaceutically acceptable derivatives thereof, wherein all variables have the same meanings as set forth above for the compounds of formula VI, and with the proviso that when $Z'''$ is a heteroaryl group, m is 2 and Y is a bond, $R_5$ is not phenylalkyl in which the alkyl portion contains from 1 to 6 carbon atoms; $—(CH_2)_rNR^vR^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl; $—(CH_2)_rSR^{viii}$ when $R^{viii}$ is $C_1$-$C_6$ straight chain alkyl, $C_3$-$C_6$ branched chain alkyl or $C_3$-$C_6$ cycloalkyl; $—(CH_2)_rSO_2R^{ix}$, $—(CH_2)_rSOR^{ix}$ or $—(CH_2)_rC(O)OR^{ix}$ when $R^{ix}$ is $C_1$-$C_6$ straight chain alkyl, $C_3$-$C_6$ branched chain alkyl, or $C_3$-$C_6$ cycloalkyl; with the proviso that when $Z'''$ is pyridine, m is 2, and Y is a bond, $R_5$ is not $—CH_2OH$; and with the proviso that $Z'''$ is a heteroaryl group, when m is 1 or 3 and Y is a bond, $R_5$ is not $—(CH_2)_rNR^vR^{vi}$ when both $R^v$ and $R^{vi}$ are hydrogen, or when one of $R^v$ and $R^{vi}$ is hydrogen and the other of $R^v$ and $R^{vi}$ is $C_1$-$C_6$ straight chain alkyl, $C_3$-$C_6$ branched chain alkyl or $C_3$-$C_6$ cycloalkyl.

In one embodiment $R_1$ is H.
In another embodiment, $R_1$ is $C_1$-$C_6$ straight chain alkyl.
In another embodiment, $R_1$ is allyl.
In another embodiment, $R_1$ is $C_3$-$C_6$ cycloalkyl.
In another embodiment, $R_2$ is H.
In another embodiment, $R_3$ is H.
In another embodiment, $R_4$ is H.
In another embodiment, $R_2$, $R_3$ and $R_4$ are each H.
In another embodiment, one of $R_2$, $R_3$ and $R_4$ is methyl.
In another embodiment, m is 1.
In another embodiment, m is 2.
In another embodiment, m is 3.
In another embodiment, n is 1.
In another embodiment, n is 2.
In another embodiment, p is 0.
In another embodiment, p is 1.
In another embodiment, p is 2.
In another embodiment, n is 1 and p is 0.
In another embodiment, $R_5$ is alkoxyalkyl with one or two hydroxyl substitutents and in which the alkoxy and alkyl portions each independently contain from 1 to 6 carbon atoms.

In another embodiment, $R_5$ is hydroxyalkoxyalkyl in which the alkoxy and alkyl portions each independently contain from 1 to 6 carbon atoms.

In another embodiment, $R_5$ is $C_1$-$C_6$ hydroxyalkyl.
In another embodiment, $R_5$ is arylalkyl in which the alkyl portion contains from 1 to 6 carbon atoms.
In another embodiment, $R_5$ is arylalkoxy in which the alkoxy portion contains from 1 to 6 carbon atoms.
In another embodiment, $R_5$ is aryl.
In another embodiment, $R_5$ is biaryl.
In another embodiment, $R_5$ is heteroarylalkyl in which the alkyl portion contains from 1 to 6 carbon atoms.
In another embodiment, $R_5$ is $—(CH_2)_{1-6}—O—(CH_2)_{0-6}$-aryl.
In another embodiment, $R_5$ is $—(CH_2)_{1-6}—O—(CH_2)_{0-6}$-heteroaryl.
In another embodiment, $R_5$ is $—(CH_2)_{0-6}—O—(CH_2)_{0-6}$—$C_3$-$C_6$ cycloalkyl.
In another embodiment, $R_5$ is heteroaryl.
In another embodiment, $R_5$ is $—(CH_2)_rNR^vR^{vi}$, wherein r is an integer ranging from 0 to 5 and $R^v$ and $r^{vi}$ are each independently $C_1$-$C_6$ straight chain alkyl, $C_3$-$C_6$ branched chain alkyl; $C_3$-$C_6$ cycloalkyl; $—(CO)R^{vii}$; or $—SO_2R^{vii}$, and $R^{vii}$ has the meaning described above for the pyridinyl nicotinic acetylcholine receptor ligands of the formula VI.

In another embodiment $R_5$ is $—(CH_2)_rNR^vR^{vi}$, wherein r is an integer ranging from 1 to 5.

In another embodiment, $R_5$ is $—(CH_2)_rC(O)NR^vR^{vi}$, wherein r, $R^v$ and $R^{vi}$ are as defined above for the pyridinyl nicotinic acetylcholine receptor ligands of the formula VI.

In another embodiment, $R_5$ is $—(CH_2)_rC(O)OR^{ix}$, and r and $R^{ix}$ have the same meanings as set forth above for the compounds of formula VI.

In another embodiment, $R_5$ is $-(CH_2)_rSR^{viii}$, wherein r and $R^{viii}$ are as defined above for the pyridinyl nicotinic acetylcholine receptor ligands of the formula VI.

In another embodiment, $R_5$ is $-(CH_2)_rSO_2R^{ix}$, wherein r and $R^{ix}$ are as defined above for the pyridinyl nicotinic acetylcholine receptor ligands of the formula VI.

In another embodiment, $R_5$ is $-(CH_2)_rSOR^{ix}$, wherein r and $R^{ix}$ are as defined above for the pyridinyl nicotinic acetylcholine receptor ligands of the formula VI.

In another embodiment, Y is a bond.

In another embodiment, $R_5$ is in the para position with respect to Y.

In another embodiment, $R_5$ is in the meta position with respect to Y.

In another embodiment, $R_5$ is in the ortho position with respect to Y.

In another embodiment, Z''' is a 2,5-disubstituted pyridinyl group.

In another embodiment, Z''' is a 2,4-disubstituted pyridinyl group.

In another embodiment, Z''' is a 3,7-disubstituted 1H-indolyl group.

In another embodiment, Z''' is a 2,5-disubstituted thienyl group.

In another embodiment, Z''' is a 3,5-disubstituted isoxazolyl group.

In another embodiment, Y is $-CH_2-$ and Z''' is a heteroaryl group.

In another embodiment, Y is $-CH_2CH_2-$ and Z''' is a heteroaryl group.

In another embodiment, Y is $-CH_2CH_2CH_2-$ and Z''' is a heteroaryl group.

In another embodiment, Y is $-(CH_2)_4-$ and Z''' is a heteroaryl group.

In another embodiment, Y is $-(CH_2)_5-$ and Z''' is a heteroaryl group.

In another embodiment, Y is unsubstituted $-(CH_2)_q-$ and q is an integer ranging from 1 to 5.

In another embodiment, Y is $-(CH_2)_q-$, q is an integer ranging from 1 to 5, and Y is substituted with one or two groups independently selected from methyl, ethyl, propyl, isopropyl, and cyclopropyl.

In another embodiment, Y is $-(CH_2)_q-$, q is an integer ranging from 1 to 5, Z''' is a pyridinyl group, and $R_5$ is $C_1-C_6$ hydroxyalkyl, wherein $R_5$ is in the para position on said Z''' group with respect to Y.

In another embodiment, Y is $-(CH_2)_q-$, q is an integer ranging from 1 to 5, Z''' is a 1H-indol-3-yl group, and $R_5$ is $-(CH_2)_rNR^vR^{vi}$, $R^v$ and $R^{vi}$ are each independently hydrogen, $C_1-C_6$ straight chain alkyl, $C_3-C_6$ branched chain alkyl.

In another embodiment, Y is a bond, Z''' is a pyridinyl group, and $R_5-(CH_2)_rC(O)NR^vR^{vi}$, wherein r is an integer ranging between 0 and 5, and $R^v$ and $R^{vi}$ are each independently $C_1-C_6$ straight chain alkyl.

In another embodiment, Y is a bond, Z''' is a thienyl group, and $R_5$ is 2-(methoxycarbonyl)ethyl.

In another embodiment, Y is a bond, Z''' is an isoxazolyl group, and $R_5$ is $C_1-C_6$ hydroxyalkyl.

In one embodiment, the invention encompasses compounds of formula VI-1:

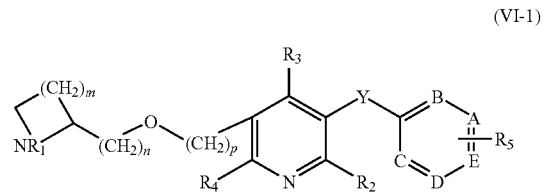

(VI-1)

and pharmaceutically acceptable derivatives thereof, wherein one or two of A, B, C, D and E is nitrogen and the other members of the cyclic aromatic ring are carbon atoms, $R_5$ is bound to a carbon atom, and all other variables have the same meanings as set forth above for the compounds of formula VI.

In another embodiment, the invention encompasses compounds of formula VI-1, wherein one or two of A, B, C, D and E is nitrogen, $R_5$ is bound to a carbon atom, and all other variables have the same meanings as set forth above for the compounds of formula VI, and with the proviso that when m is 2 and Y is a bond, $R_5$ is not phenylalkyl in which the alkyl portion contains from 1 to 6 carbon atoms; $-(CH_2)_rNR^vR^{vi}$ when $R^v$ and $R^{vi}$ are each independently hydrogen, $C_1-C_6$ straight chain alkyl, $C_3-C_6$ branched chain alkyl or $C_3-C_6$ cycloalkyl; $-(CH_2)_rSR^{viii}$ when $R^{viii}$ is $C_1-C_6$ straight chain alkyl, $C_3-C_6$ branched chain alkyl or $C_3-C_6$ cycloalkyl; $-(CH_2)_rSO_2R^{ix}$, $-(CH_2)_rSOR^{ix}$ or $-(CH_2)_rC(O)OR^{ix}$ when $R^{ix}$ is $C_1-C_6$ straight chain alkyl, $C_3-C_6$ branched chain alkyl, or $C_3-C_6$ cycloalkyl; with the proviso that when m is 2, Y is a bond and Z''' is pyridine, $R_5$ is not $-CH_2OH$; and with the proviso that when m is 1 or 3 and Y is a bond, $R_5$ is not $-(CH_2)_rNR^vR^{vi}$ when both $R^v$ and $R^{vi}$ are hydrogen, or when one of $R^v$ and $R^{vi}$ is hydrogen and the other of $R^v$ and $R^{vi}$ is $C_1-C_6$ straight chain alkyl, $C_3-C_6$ branched chain alkyl or $C_3-C_6$ cycloalkyl.

In another embodiment, the invention encompasses compounds of formula VI-1 wherein A is N, B, C, D and E are each carbon, $R_5$ is bound to the carbon atom at position E, and all other variables have the same meanings as set forth above for the compounds of formula VI.

In other embodiments, the invention emcompasses compounds of formula VI-1 wherein m is 1, $R_5$ is $C_1-C_6$ hydroxyalkyl and is bound to a carbon atom, and all other variables have the same meanings as set forth above for the compounds of formula VI.

In still other embodiments, the invention encompasses compounds of formula VI-1 wherein Y is $-(CH_2)_q$ and q is an integer ranging from 1 to 5, $R_5$ is $C_1-C_6$ hydroxyalkyl and is bound to a carbon atom, and all other variables have the same meanings as set forth above for the compounds of formula VI.

In other embodiments, the invention encompasses compounds of formula VI-1 wherein Z''' is:

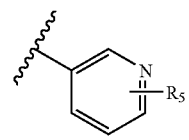

m is 1, $R_5$ is $C_1-C_6$ hydroxyalkyl, and all other variables have the same meanings as set forth above for the compounds of formula VI.

In other embodiments, the invention encompasses compounds of formula VI-1 wherein Z''' is:

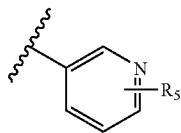

m is 1, Y is —(CH$_2$)$_q$ and q is an integer ranging from 1 to 5, R$_5$ is C$_1$-C$_6$ hydroxyalkyl and is bound to a carbon atom, and all other variables have the same meanings as set forth above for the compounds of formula VI.

In another embodiment, the invention encompasses compounds of formula VI-2:

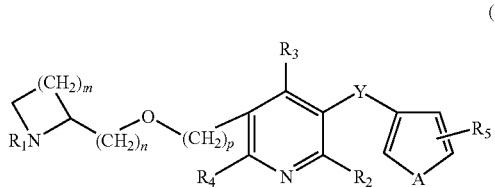

(VI-2)

and pharmaceutically acceptable derivatives thereof, wherein A is O or S, and all other variables have the same meanings as set forth above for the compounds of formula VI.

In other embodiments, the invention encompasses compounds of formula VI-2, and pharmaceutically acceptable derivatives thereof, wherein A is O or S, and all other variables have the same meanings as set forth above for the compounds of formula X, and with the proviso that when m is 2 and Y is a bond, R$_5$ is not phenylalkyl in which the alkyl portion contains from 1 to 6 carbon atoms; —(CH$_2$)$_r$NR$^v$R$^{vi}$ when R$^v$ and R$^{vi}$ are each independently hydrogen, C$_1$-C$_6$ straight chain alkyl, C$_3$-C$_6$ branched chain alkyl or C$_3$-C$_6$ cycloalkyl; —(CH$_2$)$_r$SR$^{viii}$ when R$^{viii}$ is C$_1$-C$_6$ straight chain alkyl, C$_3$-C$_6$ branched chain alkyl or C$_3$-C$_6$ cycloalkyl; —(CH$_2$)$_r$SO$_2$R$^{ix}$, —(CH$_2$)$_r$SOR$^{ix}$ or —(CH$_2$)$_r$C(O)OR$^{ix}$ when R$^{ix}$ is C$_1$-C$_6$ straight chain alkyl, C$_3$-C$_6$ branched chain alkyl, or C$_3$-C$_6$ cycloalkyl; and with the proviso that when m is 1 or 3 and Y is a bond, R$_5$ is not —(CH$_2$)$_r$NR$^v$R$^{vi}$ when both R$^v$ and R$^{vi}$ are hydrogen, or when one of R$^v$ and R$^{vi}$ is hydrogen and the other of R$^v$ and R$^{vi}$ is C$_1$-C$_6$ straight chain alkyl, C$_3$-C$_6$ branched chain alkyl or C$_3$-C$_6$ cycloalkyl.

In another embodiment, the invention encompasses compounds of formula VI-3:

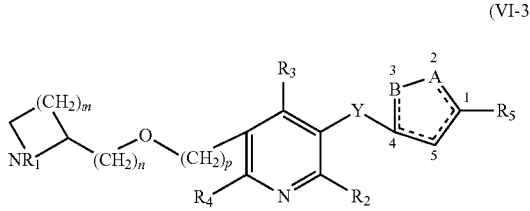

(VI-3)

and pharmaceutically acceptable derivatives thereof, wherein one of A and B is oxygen and the other is nitrogen, wherein if A is oxygen and B is nitrogen, then there is a double bond between carbon atoms 1 and 5 and between carbon atom 4 and B, and wherein if B is oxygen and A is nitrogen, then there is a double bond between carbon atom 1 and A, and between carbon atoms 4 and 5, and wherein all other variables have the same meanings as set forth above for the compounds of formula VI.

In another embodiment, the invention encompasses compounds of formula VI-3, and pharmaceutically acceptable derivatives thereof, wherein one of A and B is oxygen and the other is nitrogen, wherein if A is oxygen and B is nitrogen, then there is a double bond between carbon atoms 1 and 5 and between carbon atom 4 and B, and wherein if B is oxygen and A is nitrogen, then there is a double bond between carbon atom 1 and A, and between carbon atoms 4 and 5, and wherein all other variables have the same meanings as set forth above for the compounds of formula X, and with the proviso that when m is 2 and Y is a bond, R$_5$ is not phenylalkyl in which the alkyl portion contains from 1 to 6 carbon atoms; —(CH$_2$)$_r$NR$^v$R$^{vi}$ when R$^v$ and R$^{vi}$ are each independently hydrogen, C$_1$-C$_6$ straight chain alkyl, C$_3$-C$_6$ branched chain alkyl or C$_3$-C$_6$ cycloalkyl; —(CH$_2$)$_r$SR$^{viii}$ when R$^{viii}$ is C$_1$-C$_6$ straight chain alkyl, C$_3$-C$_6$ branched chain alkyl or C$_3$-C$_6$ cycloalkyl; —(CH$_2$)$_r$SO$_2$R$^{ix}$, —(CH$_2$)$_r$SOR$^{ix}$ or —(CH$_2$)$_r$C(O)OR$^{ix}$ when R$^{ix}$ is C$_1$-C$_6$ straight chain alkyl, C$_3$-C$_6$ branched chain alkyl, or C$_3$-C$_6$ cycloalkyl; and with the proviso that when m is 1 or 3 and Y is a bond, R$_5$ is not —(CH$_2$)$_r$NR$^v$R$^{vi}$ when both R$^v$ and R$^{vi}$ are hydrogen, or when one of R$^v$ and R$^{vi}$ is hydrogen and the other of R$^v$ and R$^{vi}$ is C$_1$-C$_6$ straight chain alkyl, C$_3$-C$_6$ branched chain alkyl or C$_3$-C$_6$ cycloalkyl.

In another embodiment, the invention encompasses compounds of formula VI-4:

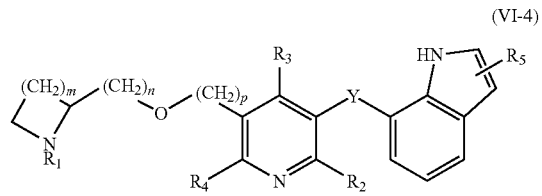

(VI-4)

and pharmaceutically acceptable derivatives thereof, wherein all variables have the same meanings as set forth above for the compounds of formula VI.

In another embodiment, the invention encompasses compounds of formula VI-4, wherein all variables have the same meanings as set forth above for the compounds of formula VI, and with the proviso that when m is 2 and Y is a bond, R$_5$ is not phenylalkyl in which the alkyl portion contains from 1 to 6 carbon atoms; —(CH$_2$)$_r$NR$^v$R$^{vi}$ when R$^v$ and R$^{vi}$ are each independently hydrogen, C$_1$-C$_6$ straight chain alkyl, C$_3$-C$_6$ branched chain alkyl or C$_3$-C$_6$ cycloalkyl; —(CH$_2$)$_r$SR$^{viii}$ when R$^{viii}$ is C$_1$-C$_6$ straight chain alkyl, C$_3$-C$_6$ branched chain alkyl or C$_3$-C$_6$ cycloalkyl; —(CH$_2$)$_r$SO$_2$R$^{ix}$, —(CH$_2$)$_r$SOR$^{ix}$ or —(CH$_2$)$_r$C(O)OR$^{ix}$ when R$^{ix}$ is C$_1$-C$_6$ straight chain alkyl, C$_3$-C$_6$ branched chain alkyl, or C$_3$-C$_6$ cycloalkyl; and with the proviso that when m is 1 or 3 and Y is a bond, R$_5$ is not —(CH$_2$)$_r$NR$^v$R$^{vi}$ when both R$^v$ and R$^{vi}$ are hydrogen, or when one of R$^v$ and R$^{vi}$ is hydrogen and the other of R$^v$ and R$^{vi}$ is C$_1$-C$_6$ straight chain alkyl, C$_3$-C$_6$ branched chain alkyl or C$_3$-C$_6$ cycloalkyl.

In another embodiment, the compound of formula VI is selected from:

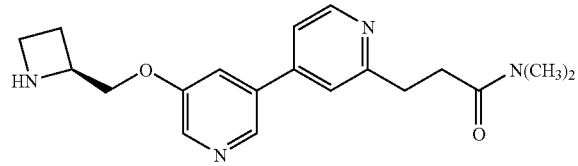 [SMILES: CN(C)C(=O)CCc1cc(-c2cncc(OC[C@@H]3CCN3)c2)ccn1]

3-[5-[(2(S)-azetidinyl)methoxy]-3,4'-bipyridin-2'-yl]-N,N-dimethylpropionamide

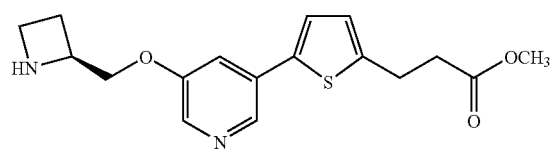 [SMILES: COC(=O)CCc1ccc(-c2cncc(OC[C@@H]3CCN3)c2)s1]

methyl 3-[5-[5-[(2(S)-azetidinyl)methoxy]-3-pyridyl]-2-thienyl]propionate

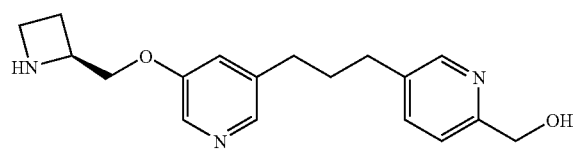 [SMILES: OCc1ccc(CCCc2cncc(OC[C@@H]3CCN3)c2)cn1]

[5-[3-[5-[(2(S)-azetidinyl)methoxy]-3-pyridyl]propyl]-2-pyridyl]methanol

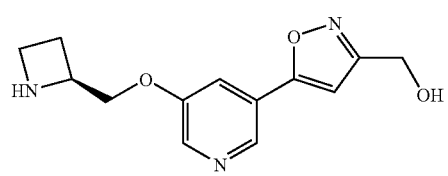 [SMILES: OCc1cc(-c2cncc(OC[C@@H]3CCN3)c2)on1]

[5-[5-[(2(S)-azetidinyl)methoxy]-3-pyridyl]-3-isoxazolyl]methanol

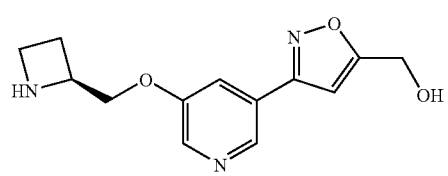 [SMILES: OCc1cc(-c2cncc(OC[C@@H]3CCN3)c2)no1]

[3-[5-[(2(S)-azetidinyl)methoxy]-3-pyridyl]-5-isoxazolyl]methanol

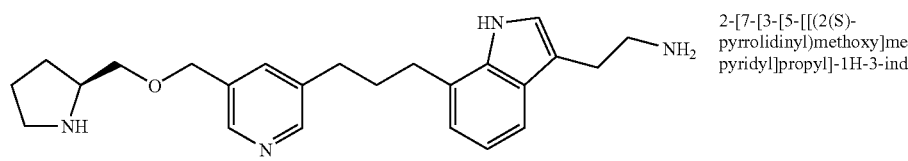

2-[7-[3-[5-[[(2(S)-pyrrolidinyl)methoxy]methyl]-3-pyridyl]propyl]-1H-3-indolyl]ethanamine

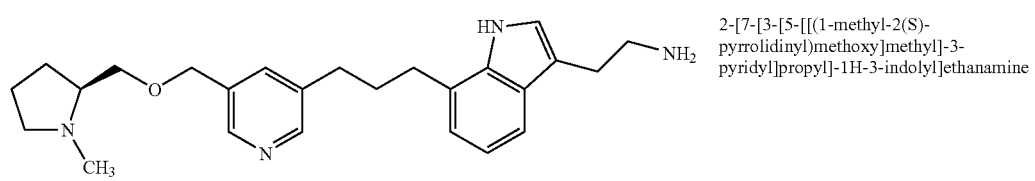

2-[7-[3-[5-[[(1-methyl-2(S)-pyrrolidinyl)methoxy]methyl]-3-pyridyl]propyl]-1H-3-indolyl]ethanamine In another embodiment, the compound of formula VI is selected from:

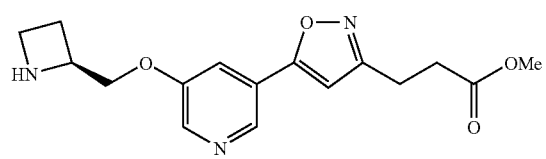 [SMILES: COC(=O)CCc1cc(-c2cncc(OC[C@@H]3CCN3)c2)on1]

methyl 3-[5-[5-[2(S)-azetidinyl)methoxy]-3-pyridyl]-3-isoxazolyl]propionate

-continued

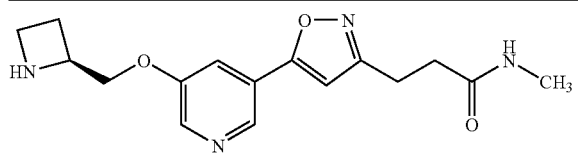
3-[5-[5-[2(S)-azetidinyl)methoxy]-3-pyridyl]-3-isoxazolyl]-N-methylpropionamide

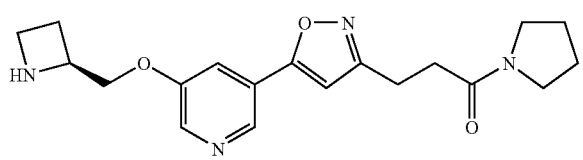 [SMILES: O=C(CCc1cc(-c2cncc(OC[C@@H]3CCN3)c2)on1)N1CCCC1]
3-[5-[5-[2(S)-azetidinyl)methoxy]-3-pyridyl]-3-isoxazolyl]-1-(1-pyrrolidinyl)-1-propanone

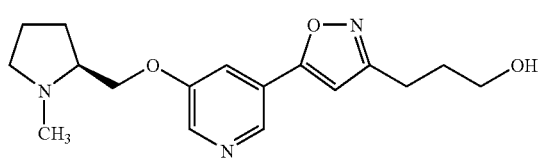 [SMILES: CN1CCC[C@H]1COc1cncc(-c2cc(CCCO)no2)c1]
3-[5-[5-[1-methyl-2(S)-pyrrolidinyl)methoxy]-3-pyridyl]-3-isoxazolyl]-1-propanol

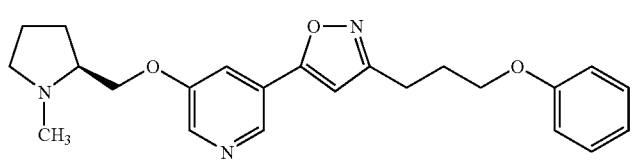 [SMILES: CN1CCC[C@H]1COc1cncc(-c2cc(CCCOc3ccccc3)no2)c1]
3-[(1-methyl-2(S)-pyrrolidinyl)methoxy]-5-[3-(3-phenoxypropyl)-5-isoxazolyl]pyridine

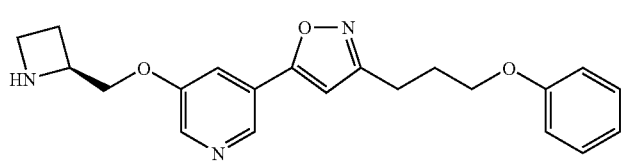 [SMILES: c1ccc(OCCCc2cc(-c3cncc(OC[C@@H]4CCN4)c3)on2)cc1]
3-[2(S)-azetidinyl)methoxy]-5-[3-(3-phenoxypropyl)-5-isoxazolyl]pyridine

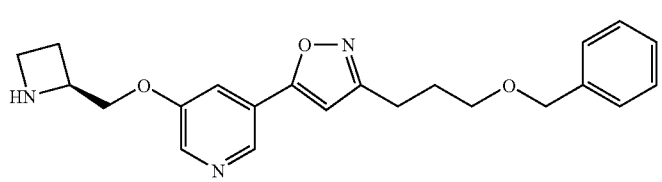 [SMILES: c1ccc(COCCCc2cc(-c3cncc(OC[C@@H]4CCN4)c3)on2)cc1]
3-[2(S)-azetidinyl)methoxy]-5-[3-(3-benzyloxypropyl)-5-isoxazolyl]pyridine

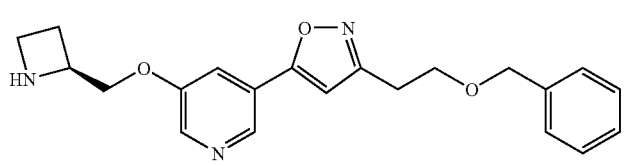 [SMILES: c1ccc(COCCc2cc(-c3cncc(OC[C@@H]4CCN4)c3)on2)cc1]
3-[2(S)-azetidinyl)methoxy]-5-[3-(2-benzyloxyethyl)-5-isoxazolyl]pyridine

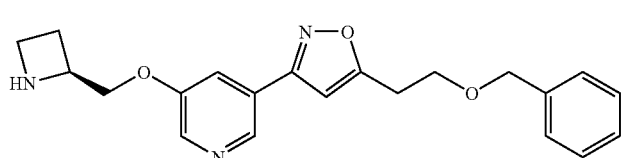
3-[2(S)-azetidinyl)methoxy]-5-[5-(2-benzyloxyethyl)-3-isoxazolyl]pyridine

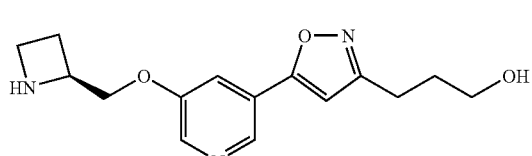
3-[5-[5-[2(S)-azetidinyl)methoxy]-3-pyridyl]-3-isoxazolyl]-1-propanol

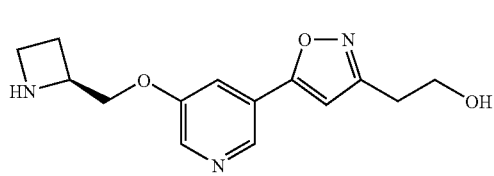 [SMILES: OCCc1cc(-c2cncc(OC[C@@H]3CCN3)c2)on1]
2-[5-[5-[2(S)-azetidinyl)methoxy]-3-pyridyl]-3-isoxazolyl]ethanol

-continued

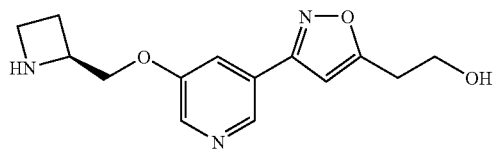 [SMILES: OCCc1cc(-c2cncc(OC[C@@H]3CCN3)c2)no1]
2-[3-[5-[2(S)-azetidinyl)methoxy]-3-pyridyl]-5-isoxazolyl]ethanol

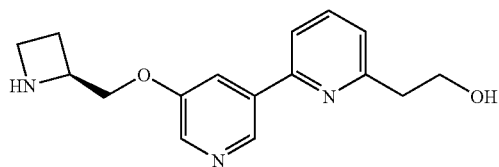 [SMILES: OCCc1cccc(-c2cncc(OC[C@@H]3CCN3)c2)n1]
2-[5'-[2(S)-azetidinyl)methoxy]-2,3'-bipyridin-6-yl]ethanol

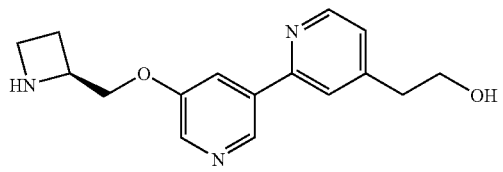 [SMILES: OCCc1ccnc(-c2cncc(OC[C@@H]3CCN3)c2)c1]
2-[5'-[2(S)-azetidinyl)methoxy]-2,3'-bipyridin-4-yl]ethanol

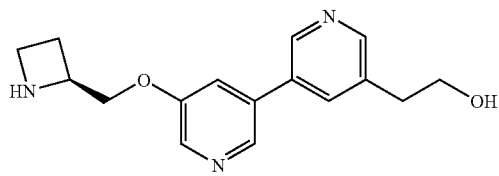 [SMILES: OCCc1cncc(-c2cncc(OC[C@@H]3CCN3)c2)c1]
2-[5'-[2(S)-azetidinyl)methoxy]-3,3'-bipyridin-5-yl]ethanol

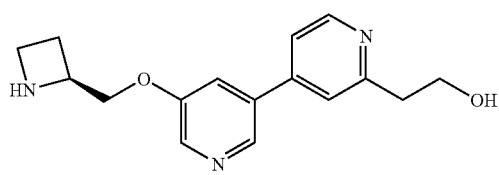 [SMILES: OCCc1cc(-c2cncc(OC[C@@H]3CCN3)c2)ccn1]
2-[5-[2(S)-azetidinyl)methoxy]-3,4'-bipyridin-2'-yl]ethanol

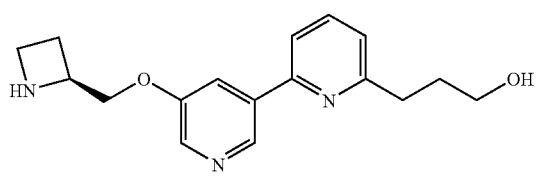 [SMILES: OCCCc1cccc(-c2cncc(OC[C@@H]3CCN3)c2)n1]
3-[5'-[2(S)-azetidinyl)methoxy]-2,3'-bipyridin-6-yl]-1-propanol

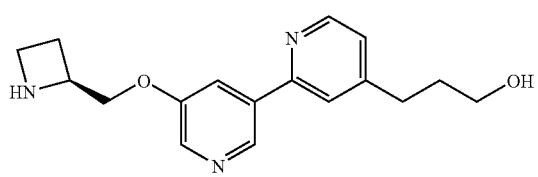 [SMILES: OCCCc1ccnc(-c2cncc(OC[C@@H]3CCN3)c2)c1]
3-[5'-[2(S)-azetidinyl)methoxy]-2,3'-bipyridin-4-yl]-1-propanol

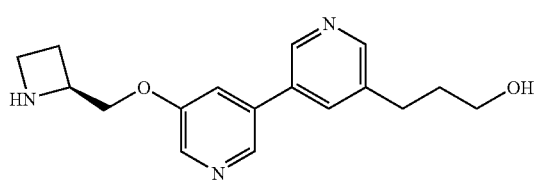 [SMILES: OCCCc1cncc(-c2cncc(OC[C@@H]3CCN3)c2)c1]
3-[5'-[2(S)-azetidinyl)methoxy]-3,3'-bipyridin-5-yl]-1-propanol

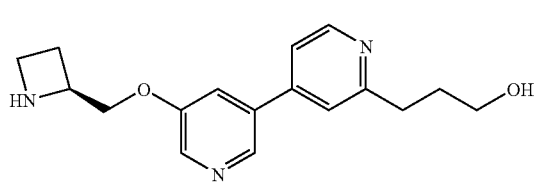 [SMILES: OCCCc1cc(-c2cncc(OC[C@@H]3CCN3)c2)ccn1]
3-[5-[2(S)-azetidinyl)methoxy]-3,4'-bipyridin-2'-yl]-1-propanol

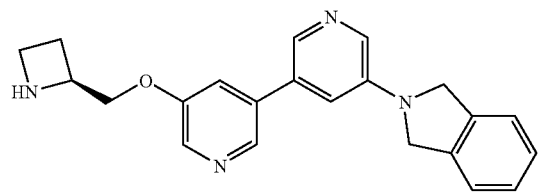 [SMILES: c1ccc2c(c1)CN(c1cncc(-c3cncc(OC[C@@H]4CCN4)c3)c1)C2]
2-[5'-[2(S)-azetidinyl)methoxy]-3,3'-bipyridin-5-yl]isoindoline
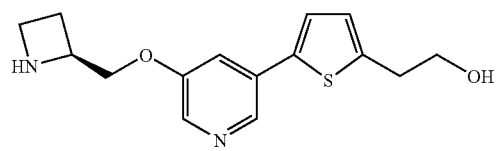 [SMILES: OCCc1ccc(-c2cncc(OC[C@@H]3CCN3)c2)s1]
2-[5-[5-[2(S)-azetidinyl)methoxy]-3-pyridyl]-2-thienyl]ethanol
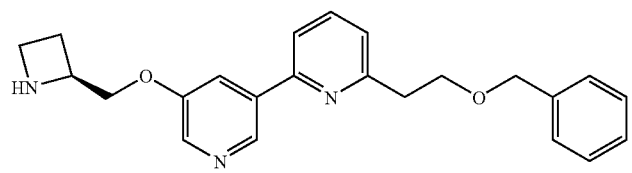 [SMILES: c1ccc(COCCc2cccc(-c3cncc(OC[C@@H]4CCN4)c3)n2)cc1]
5'-[2(S)-azetidinyl)methoxy]-6-[2-(benzyloxy)ethyl]-2,3'-bipyridine
5'-[2(S)-azetidinyl)methoxy]-4-[2-(benzyloxy)ethyl]-2,3'-bipyridine
5'-[2(S)-azetidinyl)methoxy]-5-[2-(benzyloxy)ethyl]-3,3'-bipyridine
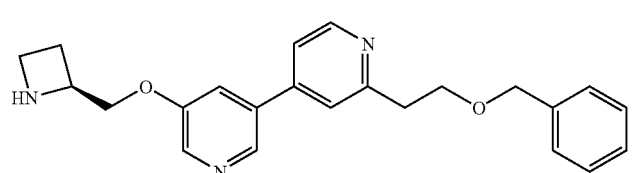
5-[2(S)-azetidinyl)methoxy]-2'-[2-(benzyloxy)ethyl]-3,4'-bipyridine
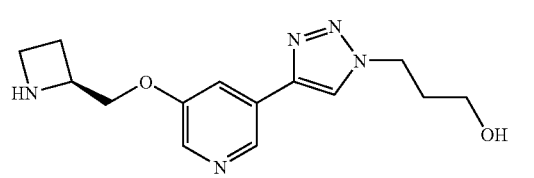 [SMILES: OCCCn1cc(-c2cncc(OC[C@@H]3CCN3)c2)nn1]
3-[4-[5-[(2(S)-azetidinyl)methoxy]-3-pyridyl]-1,2,3-triazol-1-yl]-1-propanol Nicotinic Acetylcholine Receptor Ligands of the Formula VII In another embodiment, the invention encompasses pyridinyl nicotinic acetylcholine receptor ligands of the formula VII:

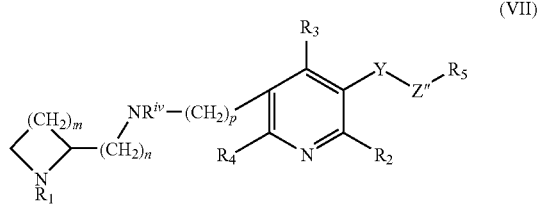

and pharmaceutically acceptable derivatives thereof, wherein all variables are as defined above for the pyridinyl nicotinic acetylcholine receptor ligands of the formula VII.

In one embodiment, $R^{iv}$ is hydrogen.
In another embodiment, $R^{iv}$ is $C_1$-$C_6$ straight chain alkyl.
In another embodiment, $R^{iv}$ is $C_3$-$C_6$ branched chain alkyl.
In another embodiment $R^{iv}$ is $C_3$-$C_6$ cycloalkyl.
In another embodiment, $R^{iv}$ is an acyl group having the formula:

wherein $R^i$ is $C_1$-$C_6$ straight chain alkyl.

In another embodiment, $R^{iv}$ is an acyl group as shown above and $R^i$ is $C_3$-$C_6$ branched chain alkyl.

In another embodiment, $R^{iv}$ is an acyl group as shown above and $R^i$ is $C_3$-$C_6$ cycloalkyl.

In one embodiment $R_1$ is H.
In another embodiment, $R_1$ is $C_1$-$C_6$ straight chain alkyl.
In another embodiment, $R_1$ is allyl.
In another embodiment, $R_1$ is $C_3$-$C_6$ cycloalkyl.
In another embodiment, $R_2$ is H.
In another embodiment, $R_3$ is H.
In another embodiment, $R_4$ is H.
In another embodiment, $R_2$, $R_3$ and $R_4$ are each H.
In another embodiment, m is 1.
In another embodiment, m is 2.
In another embodiment, m is 3.
In another embodiment, n is 1.
In another embodiment, n is 2.
In another embodiment, p is 0.
In another embodiment, p is 1.
In another embodiment, p is 2.
In another embodiment, n is 1 and p is 0.
In another embodiment, $R_5$ is —$(CH_2)_r$C(O)NR'$R^{vi}$, wherein r, $R^v$ and $R^{vi}$ are as defined above for the pyridinyl nicotinic acetylcholine receptor ligands of the formula VII.

In another embodiment, $R_5$ is —$(CH_2)_r$C(O)O$R^{ix}$, and r and $R^{ix}$ have the same meanings as set forth above for the compounds of formula VII.

In another embodiment, $R_5$ is —$(CH_2)_r$S$R^{viii}$, wherein r and $R^{viii}$ are as defined above for the pyridinyl nicotinic acetylcholine receptor ligands of the formula VII.

In another embodiment, $R_5$ is —$(CH_2)_r$SO$_2R^{ix}$, wherein r and $R^{ix}$ are as defined above for the pyridinyl nicotinic acetylcholine receptor ligands of the formula VII.

In another embodiment, $R_5$ is —$(CH_2)_r$SO$R^{ix}$, wherein r and $R^{ix}$ are as defined above for the pyridinyl nicotinic acetylcholine receptor ligands of the formula VII.

In another embodiment, $R_5$ is $C_1$-$C_6$ straight chain alkyl or $C_3$-$C_6$ branched chain alkyl.

In another embodiment, $R_5$ is $C_1$-$C_6$ hydroxyalkyl.

In another embodiment $R_5$ is alkoxyalkyl wherein the alkyl and alkoxy portions independently contain from 1 to 6 carbon atoms.

In another embodiment, $R_5$ is $C_1$-$C_6$ fluoroalkyl.

In another embodiment, $R_5$ is arylalkyl in which the alkyl portion contains from 1 to 6 carbon atoms.

In another embodiment, $R_5$ is arylalkoxy in which the alkoxy portion contains from 1 to 6 carbon atoms.

In another embodiment, $R_5$ is aryl.

In another embodiment, $R_5$ is heteroaryl.

In another embodiment, $R_5$ is heteroarylalkyl in which the alkyl portion contains from 1 to 6 carbon atoms.

In another embodiment, $R_5$ is —$(CH_2)_{1-6}$—O—$(CH_2)_{0-6}$-aryl.

In another embodiment, $R_5$ is —$(CH_2)_{0-6}$—O—$(CH_2)_{0-6}$—$C_3$-$C_6$ cycloalkyl.

In another embodiment $R_5$ is —$(CH_2)_{1-6}$—O—$(CH_2)_{0-6}$-heteroaryl.

In another embodiment, Y is a bond and Z' is an aryl group.

In another embodiment, Y is a bond and Z' is a phenyl group.

In another embodiment, Z" is a phenyl group, and $R_5$ is in the para position on said ring with respect to Y.

In another embodiment, Z" is a phenyl group and $R_5$ is in the meta position on said ring with respect to Y.

In another embodiment, Z" is a phenyl group, and $R_5$ is in the ortho position on said ring with respect to Y.

In another embodiment, Y is —$CH_2$— and Z" is an aryl group.

In another embodiment, Y is —$CH_2CH_2$— and Z" is an aryl group.

In another embodiment, Y is —$CH_2CH_2$—, Z" is phenyl and $R_5$ is $C_1$-$C_6$ alkoxy.

In another embodiment, Y is —$CH_2CH_2CH_2$— and Z" is an aryl group.

In another embodiment, Y is —$(CH_2)_4$— and Z" is an aryl group.

In another embodiment, Y is —$(CH_2)_5$— and Z" is an aryl group.

In another embodiment, Y is unsubstituted —$(CH_2)_q$— and q is an integer ranging from 1 to 5.

In another embodiment, Y is —$(CH_2)_q$—, q is an integer ranging from 1 to 5, and Y is substituted with one or two groups independently selected from methyl, ethyl, propyl, isopropyl, and cyclopropyl.

In another embodiment, Y is a bond or —$CH_2$—, Z" is phenyl and $R_5$ is $C_1$-$C_6$ alkoxy, wherein $R_5$ is in the meta position on said ring with respect to the pyridine ring.

In another embodiment, Y is a bond, Z" is phenyl and $R_5$ is —$(CH_2)_r$NR'$R^{vi}$ wherein one of $R^v$ and $R^{vi}$ is hydrogen, and the other is —(CO)$R^{vii}$, $R^v$ and $R^{vi}$ are taken together to form a 4- to 7-membered ring and $R^{vii}$ is as described above for the compounds of formula VII, wherein $R_5$ is in the meta position on said ring with respect to the pyridine ring.

In another embodiment, the invention encompasses compounds of formula VII-1:

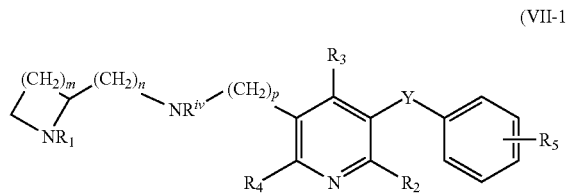
(VII-1)

and pharmaceutically acceptable derivatives thereof, wherein all variables have the same meanings as set forth above for the compounds of formula VII.

In another embodiment, the invention encompasses compounds of formula VII-1, wherein $R_5$ is in the meta position on the phenyl ring with respect to Y.

In another embodiment, the invention encompasses compounds of formula VII-1, wherein $R_5$ is in the para position on the phenyl ring with respect to Y.

In another embodiment, the compound of formula VII is selected from:

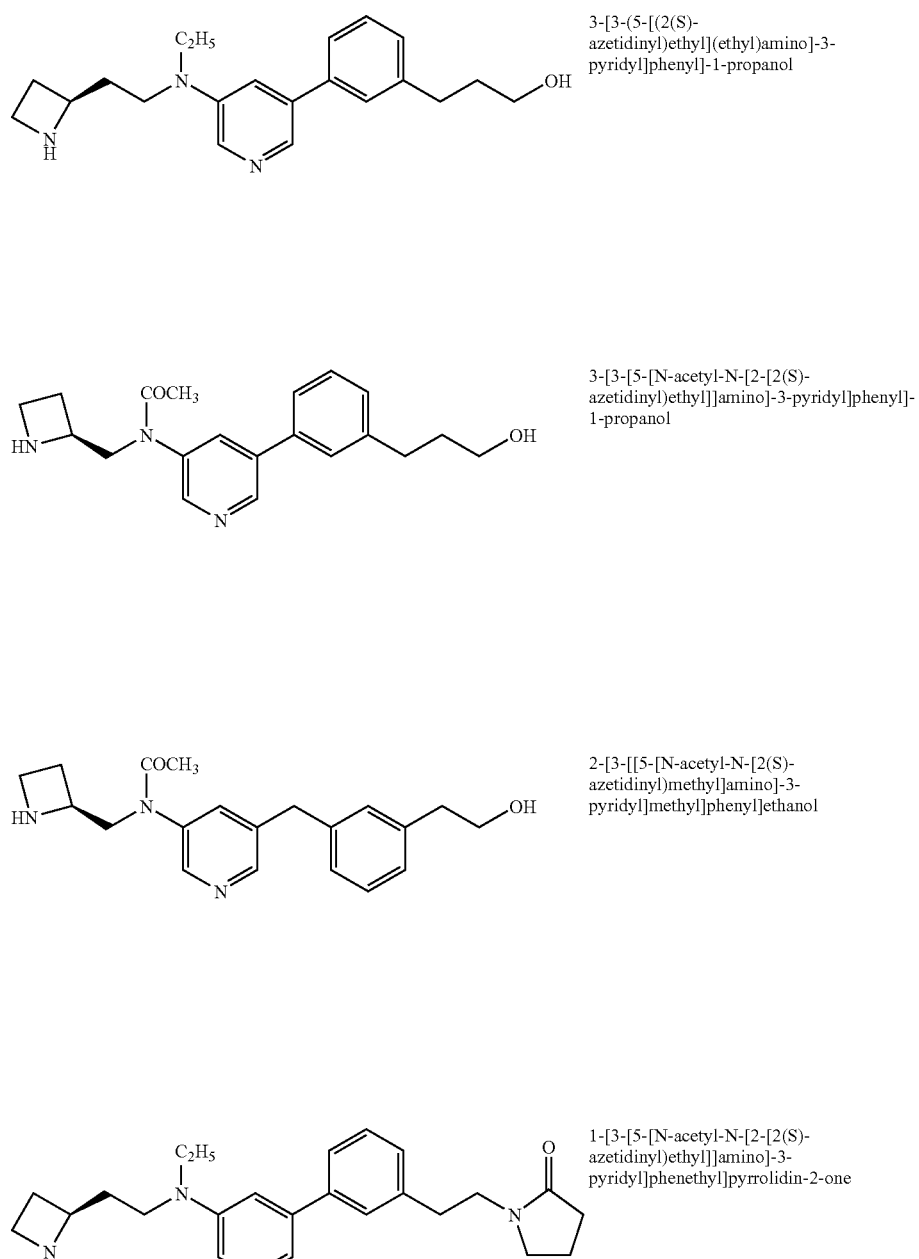

3-[3-(5-[(2(S)-azetidinyl)ethyl](ethyl)amino]-3-pyridyl]phenyl]-1-propanol

3-[3-[5-[N-acetyl-N-[2-[2(S)-azetidinyl)ethyl]]amino]-3-pyridyl]phenyl]-1-propanol 2-[3-[[5-[N-acetyl-N-[2(S)-azetidinyl)methyl]amino]-3-pyridyl]methyl]phenyl]ethanol 1-[3-[5-[N-acetyl-N-[2-[2(S)-azetidinyl)ethyl]]amino]-3-pyridyl]phenethyl]pyrrolidin-2-one Nicotinic Acetylcholine Receptor Ligands of the Formula VIII In another embodiment, the invention encompasses pyridinyl nicotinic acetylcholine receptor ligands of the formula VIII:

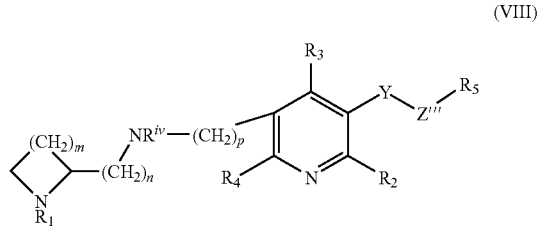

(VIII)

and pharmaceutically acceptable derivatives thereof, wherein all variables are as defined above for the pyridinyl nicotinic acetylcholine receptor ligands of the formula VIII.

In one embodiment, $R^{iv}$ is hydrogen.
In another embodiment, $R^{iv}$ is $C_1$-$C_6$ straight chain alkyl.
In another embodiment, $R^{iv}$ is $C_3$-$C_6$ branched chain alkyl.
In another embodiment $R^{iv}$ is $C_3$-$C_6$ cycloalkyl.
In another embodiment, $R^{iv}$ is an acyl group having the formula:

wherein $R^i$ is $C_1$-$C_6$ straight chain alkyl.
In another embodiment, $R^{iv}$ is an acyl group as shown above and $R^i$ is $C_3$-$C_6$ branched chain alkyl.
In another embodiment, $R^{iv}$ is an acyl group as shown above and $R^i$ is $C_3$-$C_6$ cycloalkyl.
In one embodiment $R_1$ is H.
In another embodiment, $R_1$ is $C_1$-$C_6$ straight chain alkyl.
In another embodiment, $R_1$ is allyl.
In another embodiment, $R_1$ is $C_3$-$C_6$ cycloalkyl.
In another embodiment, $R_2$ is H.
In another embodiment, $R_3$ is H.
In another embodiment, $R_4$ is H.
In another embodiment, $R_2$, $R_3$ and $R_4$ are each H.
In another embodiment, m is 1.
In another embodiment, m is 2.
In another embodiment, m is 3.
In another embodiment, n is 1.
In another embodiment, n is 2.
In another embodiment, p is 0.
In another embodiment, p is 1.
In another embodiment, p is 2.
In another embodiment, n is 1 and p is 0.
In another embodiment, $R_5$ is —$(CH_2)_rC(O)NR^vR^{vi}$, wherein r, $R^v$ and $R^{vi}$ are as defined above for the pyridinyl nicotinic acetylcholine receptor ligands of the formula VIII.
In another embodiment, $R_5$ is —$(CH_2)_rC(O)OR^{ix}$, and r and $R^{ix}$ have the same meanings as set forth above for the compounds of formula VIII.
In another embodiment, $R_5$ is —$(CH_2)_rSR^{viii}$, wherein r and $R^{viii}$ are as defined above for the pyridinyl nicotinic acetylcholine receptor ligands of the formula VIII.

In another embodiment, $R_5$ is —$(CH_2)_rSO_2R^{ix}$, wherein r and $R^{ix}$ are as defined above for the pyridinyl nicotinic acetylcholine receptor ligands of the formula VIII.

In another embodiment, $R_5$ is —$(CH_2)_rSOR^{ix}$, wherein r and $R^{ix}$ are as defined above for the pyridinyl nicotinic acetylcholine receptor ligands of the formula VIII.

In another embodiment, $R_5$ is $C_1$-$C_6$ straight chain alkyl or $C_3$-$C_6$ branched chain alkyl.

In another embodiment, $R_5$ is $C_1$-$C_6$ hydroxyalkyl.

In another embodiment $R_5$ is alkoxyalkyl wherein the alkyl and alkoxy portions independently contain from 1 to 6 carbon atoms.

In another embodiment, $R_5$ is $C_1$-$C_6$ fluoroalkyl.

In another embodiment, $R_5$ is arylalkyl in which the alkyl portion contains from 1 to 6 carbon atoms.

In another embodiment, $R_5$ is arylalkoxy in which the alkoxy portion contains from 1 to 6 carbon atoms.

In another embodiment, $R_5$ is aryl.

In another embodiment, $R_5$ is heteroaryl.

In another embodiment, $R_5$ is heteroarylalkyl in which the alkyl portion contains from 1 to 6 carbon atoms.

In another embodiment, $R_5$ is —$(CH_2)_{1-6}$—O—$(CH_2)_{0-6}$-aryl.

In another embodiment, $R_5$ is —$(CH_2)_{0-6}$—O—$(CH_2)_{0-6}$—$C_3$-$C_6$ cycloalkyl.

In another embodiment $R_5$ is —$(CH_2)_{1-6}$—O—$(CH_2)_{0-6}$-heteroaryl.

In another embodiment, Y is a bond and Z''' is a heteroaryl group.

In another embodiment, Z''' is a heteroaryl group and $R_5$ is in the para position on said ring with respect to Y.

In another embodiment, Z''' is a heteroaryl group and $R_5$ is in the meta position on said ring with respect Y.

In another embodiment, Z''' is a heteroaryl group and $R_5$ is in the ortho position with respect to Y.

In another embodiment, Y is —$CH_2$— and Z''' is a heteroaryl group.

In another embodiment, Y is —$CH_2CH_2$— and Z''' is a heteroaryl group.

In another embodiment, Y is —$CH_2CH_2CH_2$— and Z''' is a heteroaryl group.

In another embodiment, Y is —$(CH_2)_4$— and Z''' is a heteroaryl group.

In another embodiment, Y is —$(CH_2)_5$— and Z''' is a heteroaryl group.

In another embodiment, Y is unsubstituted —$(CH_2)_q$— and q is an integer ranging from 1 to 5.

In another embodiment, Y is —$(CH_2)_q$—, q is an integer ranging from 1 to 5, and Y is substituted with one or two groups independently selected from methyl, ethyl, propyl, isopropyl, and cyclopropyl.

Methods of Synthesis

Syntheses of compounds according to the invention can be accomplished by the reactions described below. In some embodiments, the present invention includes novel intermediates for the synthesis of nicotinic acetylcholine receptor ligands of the invention, some of which are shown below.

1. Synthesis of (1S,2S)-2-[5-[(2(S)-Azetidinyl)methoxy]-3-pyridyl]cyclopropylmethanol 1a. (1S,2S)-2-[5-(Benzyloxy)-3-pyridyl]cyclopropylmethanol via Racemate Resolution

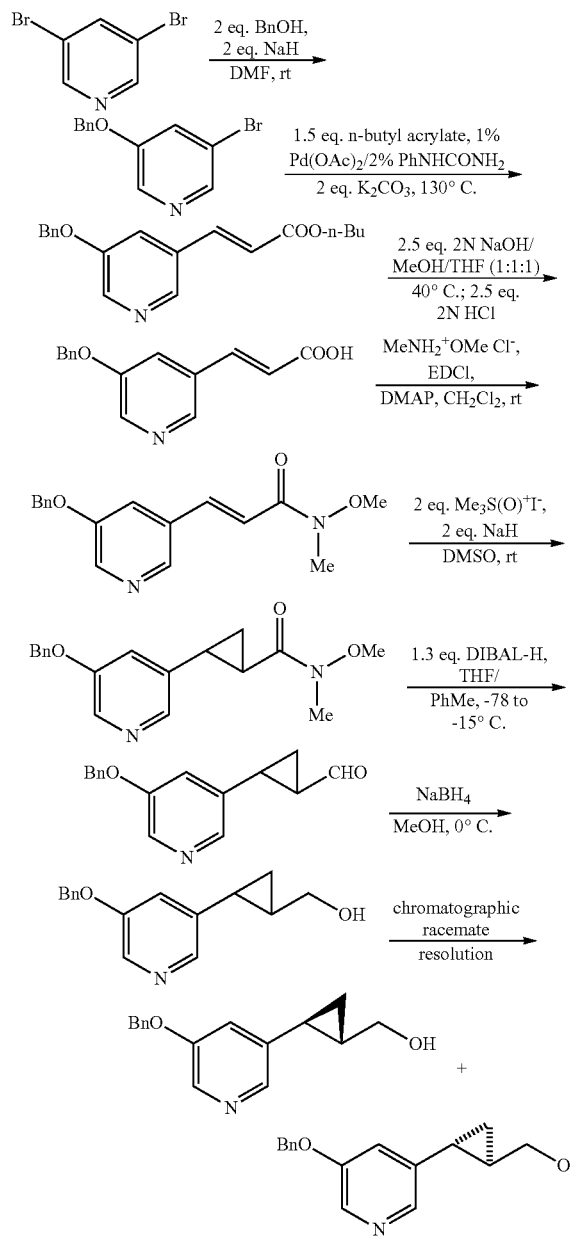

This synthetic sequence is depicted in Scheme 1a. 3-(Benzyloxy)-5-bromopyridine was prepared by a procedure reported in the literature (Zhu, G.-D. et al., *Bioorg. Med. Chem. Lett.* 2006, 16, 3150-3155) from 3,5-dibromopyridine. A recently reported variant of the Stille coupling reaction (Cui, X.; Zhou, Y.; Wang, N.; Liu, L.; Guo, Q.-X. *Tetrahedron Lett.* 2007, 48, 163-167) furnished the α,β-unsaturated ester, which was hydrolyzed to the free acid. For small-scale reactions, this acid could be transformed into its acid chloride hydrochloride, which was reacted with N,O-dimethylhydroxylamine hydrochloride in the presence of an excess of triethylamine to yield the α,β-unsaturated Weinreb amide. The need to control the exotherm during acid chloride formation at larger scale by cooling resulted in incomplete conversion of the poorly soluble acid into the poorly soluble acid chloride hydrochloride. It was in this case advantageous to couple acid and N,O-dimethylhydroxylamine hydrochloride by means of a standard peptide coupling reagent, the water-soluble carbodiimide EDCI. A large number of alternative amide forming/peptide coupling reagents are known in the literature, and it is likely that many of these are also of utility in this reaction.

The cyclopropanation of α,β-unsaturated esters with the Corey ylide [Me$_2$S(O)=CH$_2$, generated in situ from Me$_3$S(O)$^+$ I$^-$ and NaH) is a long-established reaction (Corey, E. J.; Chaykovsky, M. *J. Am. Chem. Soc.* 1965, 87, 1353-1364) but tends to give rather low yields (for example: Gooden, D. M. et al. *Bioorg. Med. Chem. Lett.* 2008, 18, 3047-3051). This was found to be the case when the reaction was applied to the α,β-unsaturated ester of Scheme 1a. On the other hand, α,β-unsaturated Weinreb amides have been shown to undergo this cyclopropanation efficiently (Toy, P. H. et al. *J. Org. Chem.* 1997, 62, 9114-9122). In accordance with this literature report, the above α,β-unsaturated Weinreb amide was transformed into the racemic cyclopropane in good yield. Sequential reduction with diisobutylaluminum hydride to the aldehyde and further with NaBH$_4$ to the primary alcohol proceeded efficiently. The enantiomers of this compound were resolved by HPLC on the chiral stationary phase, Chiralpak® AD (Chiral Technologies, Inc.) with methanol as the eluent.

1b. (1S,2S)-2-[5-(Benzyloxy)-3-pyridyl]cyclopropylmethanol via Asymmetric Simmons-Smith Cyclopropanation

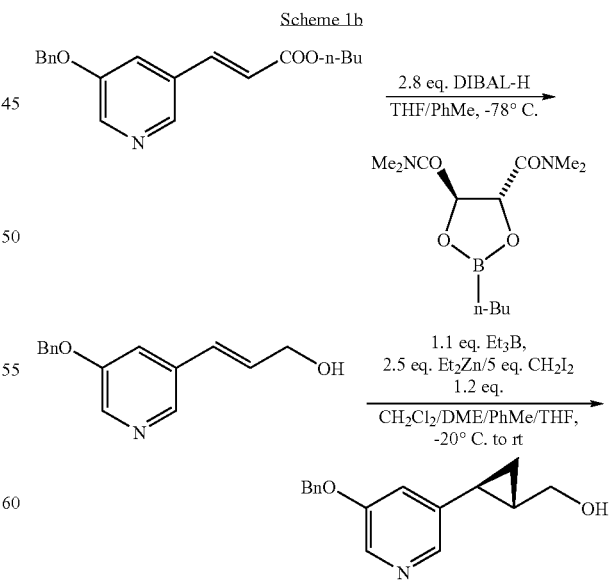

This approach (Charette, A. B.; Juteau, H.; Lebel, H.; Molinaro, C. *J. Am. Chem. Soc.* 1998, 120, 11943-11952) is inherently shorter than the one shown in Scheme 1a, but gave low yields and optical purities. Nevertheless, the completion of both sequences enabled the establishment of the absolute configuration of the individual enantiomers prepared by racemate resolution, since the generic stereochemical outcome of the asymmetric Simmons-Smith reaction is known. From the α,β-unsaturated ester of Scheme 1a, the allylic alcohol was synthesized via reduction with diisobutylaluminum hydride. While Charette's protocol usually furnishes good yields of cyclopropanes, the present case was complicated by the presence of the pyridine ring. In order to avoid this interference, triethylborane was added as a complexing agent for the pyridine nitrogen. The improvement in yield was, however, rather minor.

1c. Installation of the Azetidine Moiety and Deprotection

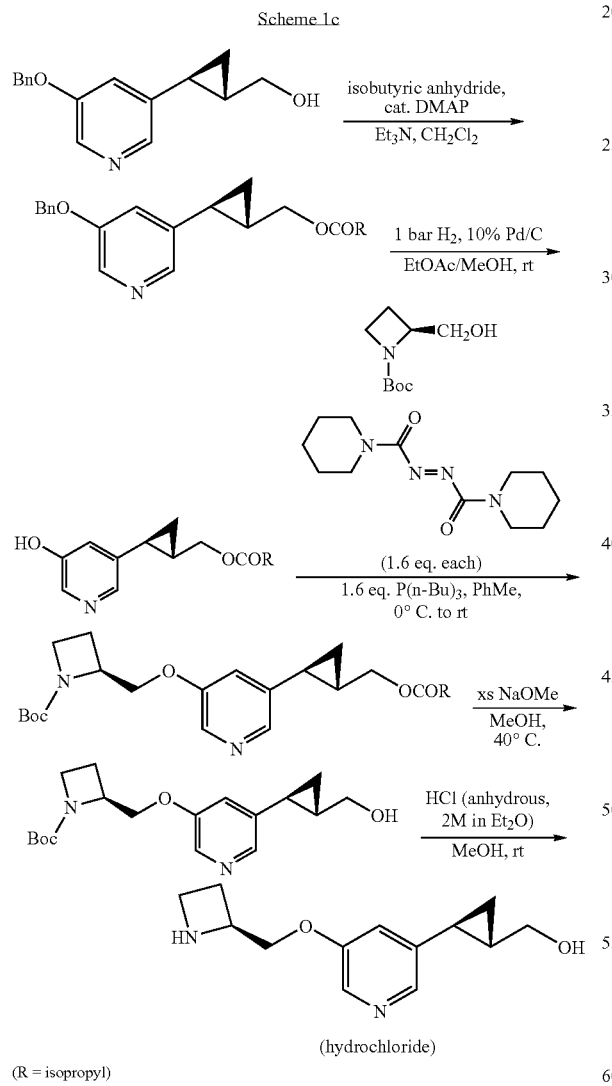

(R = isopropyl)

To prevent self-reactivity during the Mitsunobu reaction, the hydroxyl group of (1S,2S)-2-[5-(benzyloxy)-3-pyridyl]cyclopropylmethanol was acylated with isobutyric anhydride (alternatively with acetic anhydride), and then the phenolic hydroxyl deprotected by hydrogenolysis. Coupling of the hydroxypyridine intermediate with 1-(tert-butoxycarbonyl)-2(S)-azetidinylmethanol (Chu, W. et al. *J. Med. Chem.* 2005, 48, 7637-7647) was performed under modified Mitsunobu conditions (Tsunoda, T.; Yamamiya, Y.; Itô, S. 1,1'-(Azodicarbonyl)dipiperidine-tributylphosphine, a new reagent system for Mitsunobu reaction. *Tetrahedron Lett.* 1993, 34, 1639-1642) to yield the protected form of the final product. Initial removal of the isobutyrate with NaOMe, followed by acid treatment to cleave the Boc group furnished (1S,2S)-2-[5-[(2(S)-azetidinyl)methoxy]-3-pyridyl]cyclopropylmethanol as its hydrochloride.

2. Synthesis of (1R,2S)-2-[2-[5-[(2(S)-Azetidinyl)emthoxy]-3-pyridyl]cyclopropyl]ethanol

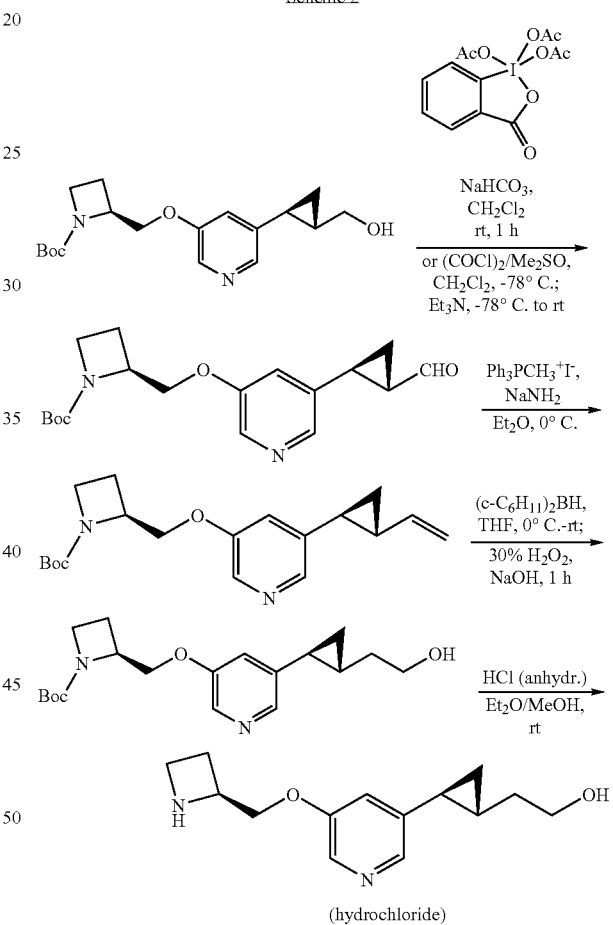

This compound was prepared according to Scheme 2. Dess-Martin oxidation (Dess, D. B.; Martin, J. C. *J. Org. Chem.* 1983, 48, 4155-4156; for the execution of this reaction in the presence of NaHCO$_3$, see, for example: Haidle, A. M.; Myers, A. G. *Proc. Natl. Acad. Sci. USA* 2004, 101, 12048-12053) or Swern oxidation of (1R,2S)-2-[5-[[1-(tert-butoxycarbonyl)-2(S)-azetidinyl]methoxy]-3-pyridyl]cyclopropylmethanol yielded the aldehyde, which was chain-extended to the vinylcyclopropane using a Wittig reaction. Hydroboration of the vinylcyclopropane with dicyclohexylborane (Zweifel, G.; Ayyangar, N. R.; Brown, H. C. *J. Am. Chem. Soc.* 1963, 85, 2072-2075) followed by oxidative workup resulted in the homologated alcohol, which upon acidic deprotection led to the desired product.

3. Synthesis of 3-[(2(S)-Azetidinyl)methoxy]-5-[(1S,2R)-2-(2-fluoroethyl)cyclopropyl]pyridine

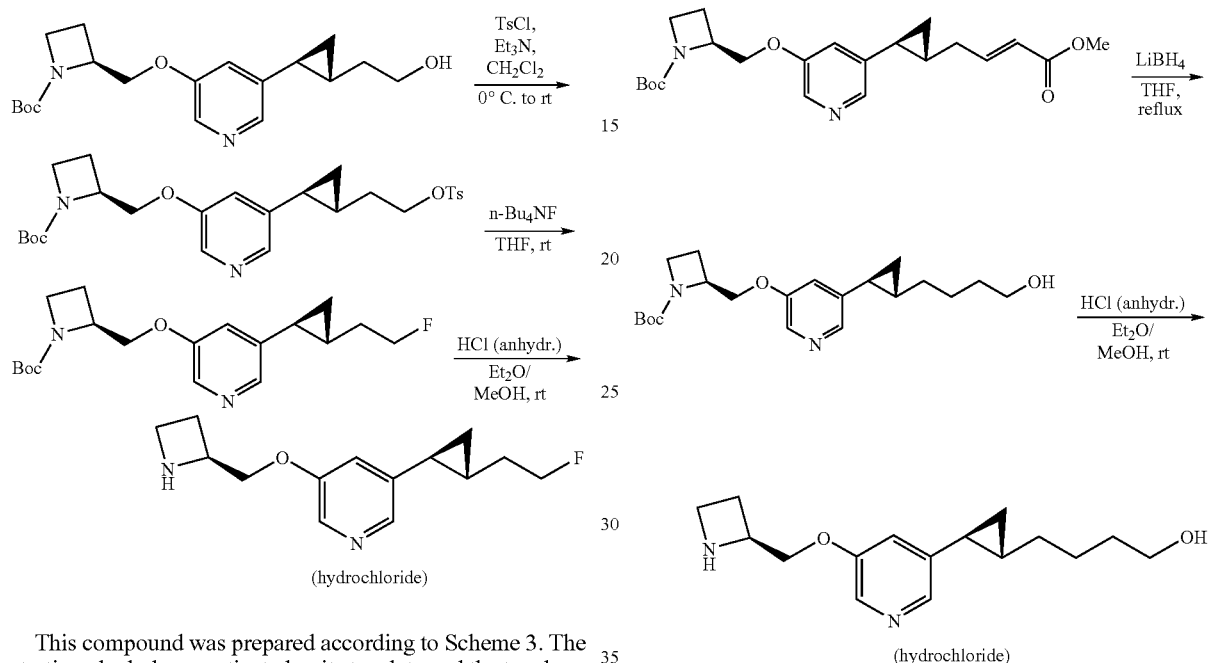

Scheme 3

This compound was prepared according to Scheme 3. The starting alcohol was activated as its tosylate and the tosyloxy group substituted by fluoride anion. Acidic deprotection of the resulting fluoride yielded the target compound.

4. Synthesis of 4-[(1S,2S)-2-[5-[(2(S)-Azetidinyl)methoxy]-3-pyridyl]cyclopropyl]-1-butanol

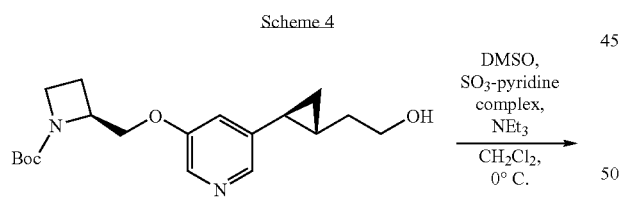

Scheme 4

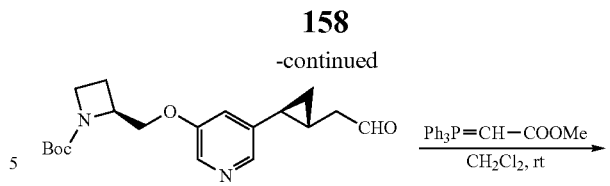
-continued

This compound was prepared according to Scheme 4. Chain extension of the starting alcohol by two carbon atoms was achieved in three steps. First, oxidation of with activated dimethylsulfoxide led to the aldehyde. Next, a Wittig reaction with Ph$_3$P=CHCOOMe introduced the requisite two carbon atoms. Lastly, the C=C double bond and the ester function were reduced simultaneously with lithium borohydride. Acidic deprotection of the protected, homologated alcohol yielded the target compound.

5. Synthesis of 3-[(2(S)-Azetidinyl)methoxy]-5-((1R,2R)-2-ethylcyclopropyl)pyridine

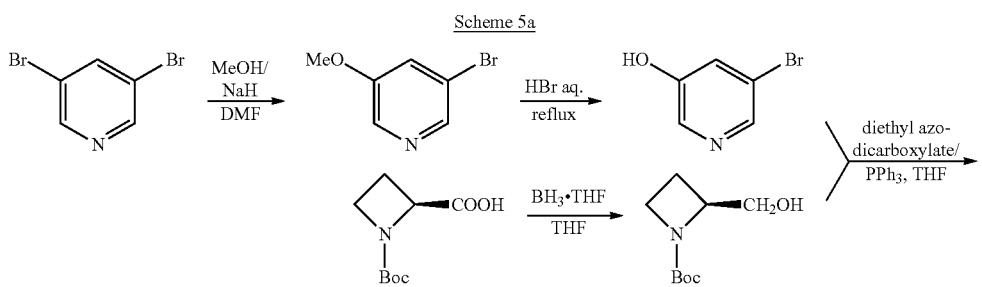

Scheme 5a

-continued
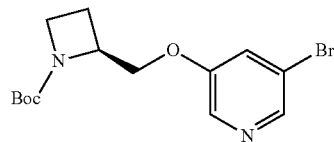
Scheme 5b
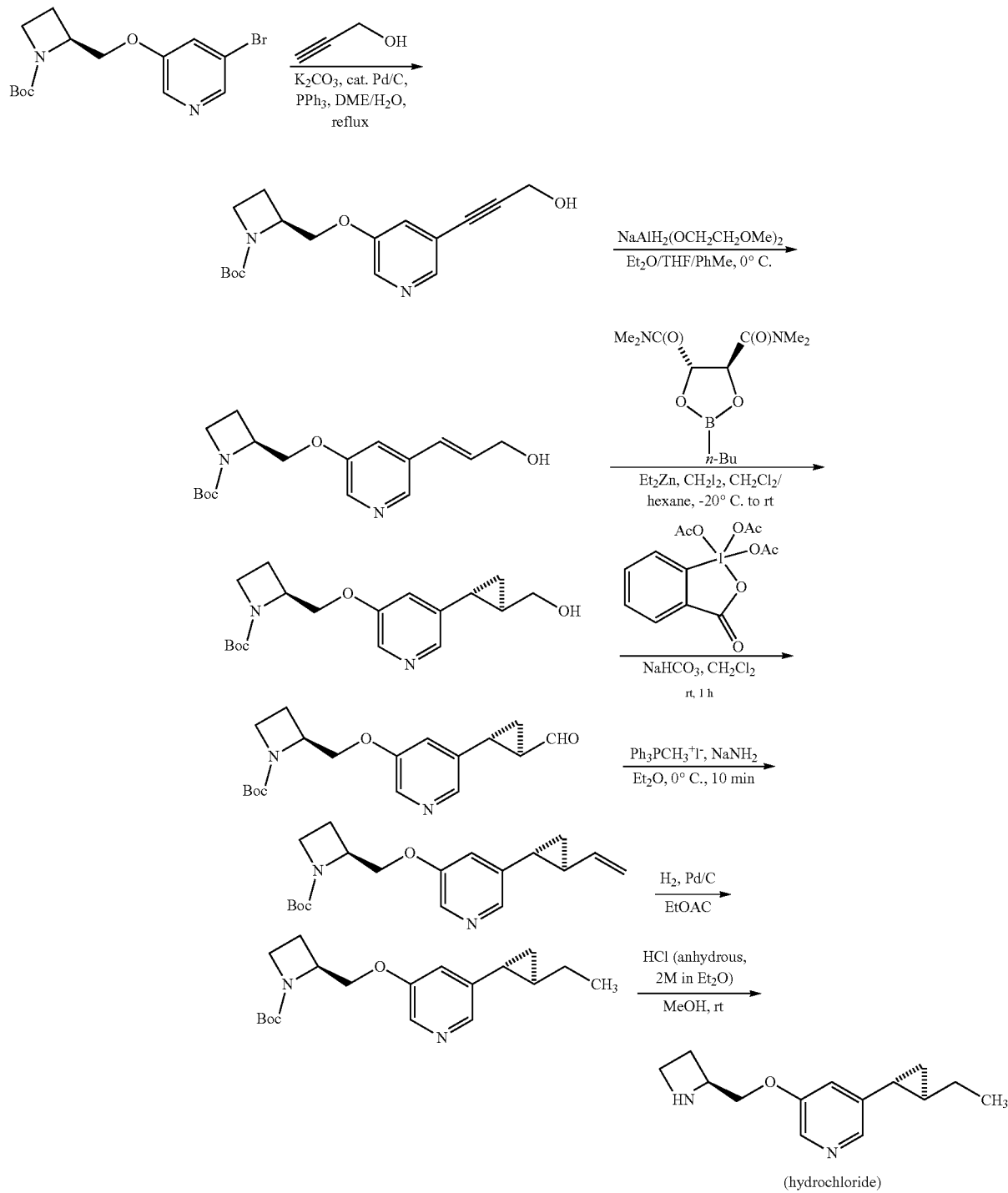

This compound may be prepared according to Schemes 5a and 5b. The starting material, 3-bromo-5-[[1-(tert-butoxycarbonyl)-2(S)-azetidinyl]methoxy]pyridine, is obtained as shown in Scheme 5a and as reported in U.S. Pat. No. 5,629,325 (May 13, 1997; col. 22 and 52). The starting material is coupled under modified Sonogashira conditions (López-Deber, M. P.; Castedo, L.; Granja, J. R. *Org. Lett.* 2001, 3, 2823-2826) with propargyl alcohol to yield the substituted alcohol. Reduction of the triple bond in this intermediate to a trans-double bond is effected by hydroalumination (Jones, T. K.; Denmark, S. E. *Org. Syn., Coll. Vol.* 7, p. 524-527 (1990)). The resulting allylic alcohol undergoes asymmetric cyclopropanation, albeit in low yield, using Charette's original procedure (without the addition of DME; Charette, A. B.; Juteau, H. *J. Am. Chem. Soc.* 1994, 116, 2651-2652). This cyclopropanated alcohol is oxidized to aldehyde with the Dess-Martin periodinane (for the execution of this reaction in the presence of NaHCO$_3$, see, for example: Haidle, A. M.; Myers, A. G. *Proc. Natl. Acad. Sci. USA* 2004, 101, 12048-12053). Alternatively, the Swern protocol is utilized (literature example for the preparation of a substituted cyclopropanecarboxaldehyde in this manner: Shuto, S.; Takada, H.; Mochizuki, D.; Tsujita, R.; Hase, Y.; Ono, S.; Shibuya, N.; Matsuda, A. *J. Med. Chem.* 1996, 38, 2964-2968). The aldehyde is subsequently subjected to a Wittig reaction to yield a vinylcyclopropane. These two steps correspond to the first two steps in Scheme 2. Catalytic hydrogenation and deprotection of the vinylcyclopropane produce the target compound. A better-yielding route to the cyclopropanated alcohol intermediate proceeds via (1S,2S)-2-[5-(benzyloxy)-3-pyridyl]cyclopropylmethanol prepared according to Scheme 1a, which is processed in the same manner as shown for its enantiomer in Scheme 1c.

6. Synthesis of 2-[(1S,2R)-2-[5-[(2(S)-Azetidinyl)methoxy]-3-pyridyl]cyclopropyl]ethanol

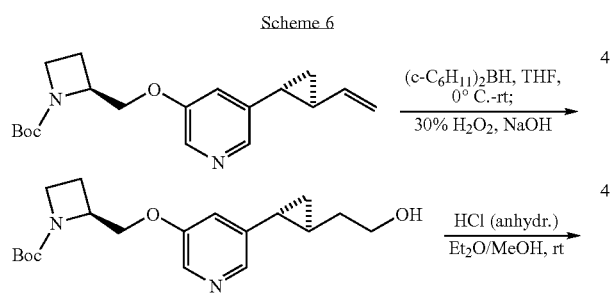

This compound was prepared according to Scheme 6. This sequence corresponds to the final two steps in Scheme 2 for the synthesis of the diastereomer having the opposite configuration at its two asymmetric cyclopropane carbon atoms.

7. Synthesis of 3-[(2(S)-Azetidinyl)methoxy]-5-[(1R,2S)-2-(2-fluoroethyl)cyclopropyl]pyridine

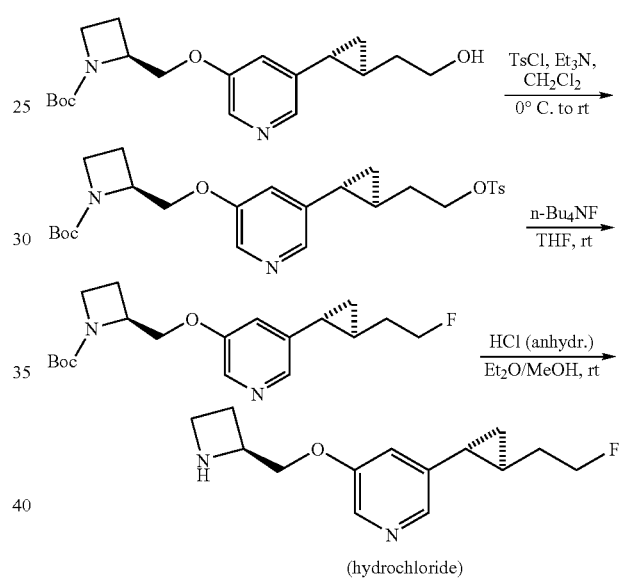

This compound was prepared according to Scheme 7. The individual steps are analogous to those shown in Scheme 3.

8. Synthesis of 2(S)-[[5-((1R,2S)-2-Azetidinylmethoxy)-3-pyridyl]methyl]cyclopropylmethanol

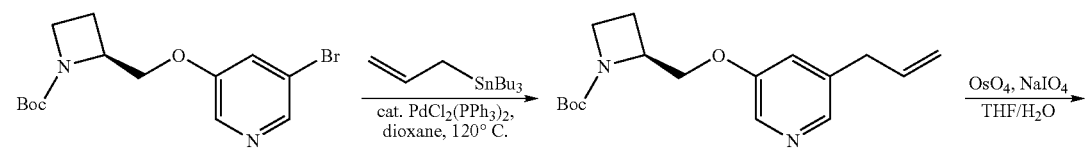

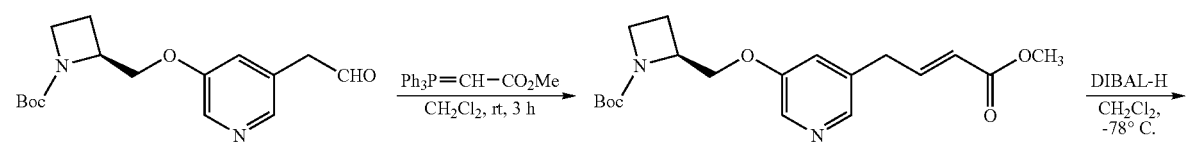

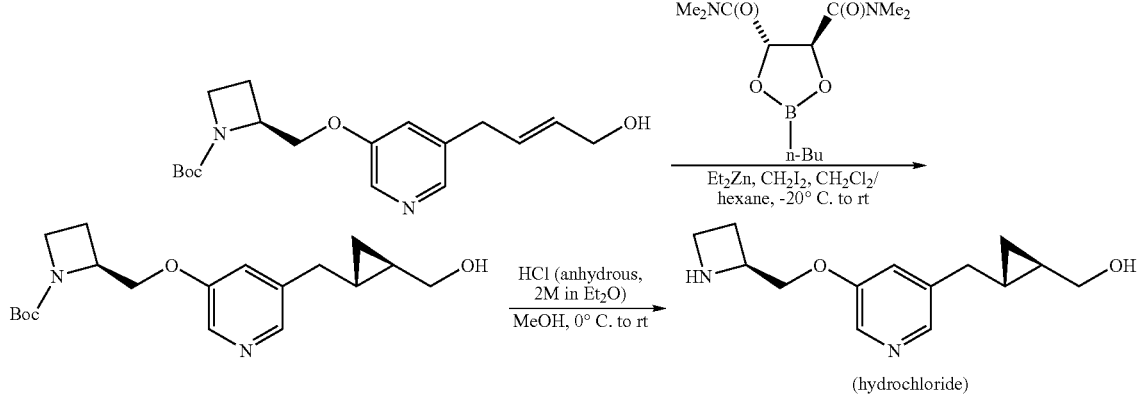

This compound may be prepared according to Scheme 8. Standard Stille coupling of 3-bromo-5-[[1-(tert-butoxycarbonyl)-2(S)-azetidinyl]methoxy]pyridine (Scheme 5a) with allyltributylstannane yields an allylpyridine. Lemieux-Johnson oxidation (Pappo, R.; Allen, D. S. Jr.; Lemieux, R. U.; Johnson, W. S. *J. Org. Chem.* 1956, 21, 478-479) of this olefin leads to an aldehyde, from which an α,β-unsaturated ester results by Wittig reaction. Reduction of this ester to the allylic alcohol is effected by diisobutylaluminum hydride, and asymmetric cyclopropanation as in preceding schemes then furnishes the cyclopropane. Deprotection of this intermediate with acid produces the title compound.

9. Synthesis of (1S,2R)-2-[[5-[(2(S)-Azetidinyl)methoxy]3-pyridyl]methyl]cyclopropylmethanol Scheme 9

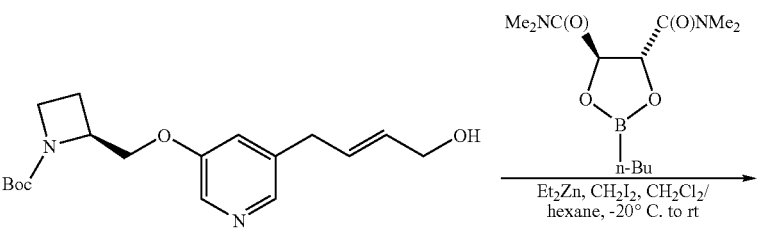

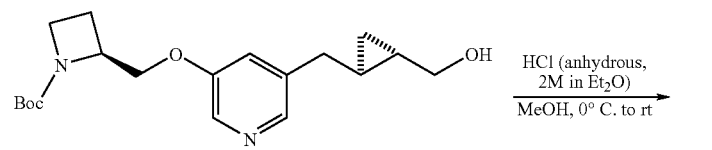

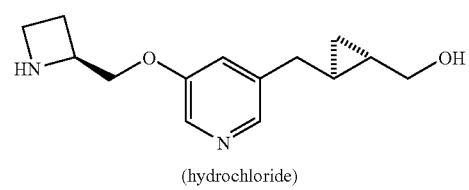

(hydrochloride)

This compound is made according to Scheme 9 by a procedure that is very similar to that detailed in Example 8, with the exception that butylboronic acid N,N,N',N'-tetramethyl-D(+)-tartaric acid diamide ester ((R,R)-configuration) is used in place of its (S,S)-enantiomer.

10. Synthesis of 3-[3-[5-[(2(S)-Azetidinyl)methoxy]-3-pyridyl]phenyl]-1-propanol and 3-[4-[5-[(2(S)-Azetidinyl)methoxy]-3-pyridyl]phenyl]-1-propanol The requisite 3-(iodophenyl)-1-propanols were prepared according to Scheme 10a.

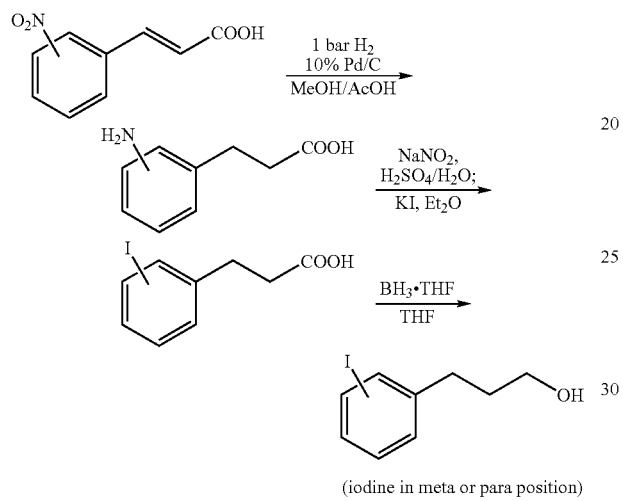

(iodine in meta or para position)

3-(3-Aminophenyl)propionic acid and 3-(4-aminophenyl)propionic acid were prepared from the appropriate regioisomers of nitrophenylcinnamic acid following the procedure of Carnazzi et al. (*J. Med. Chem.* 1994, 37, 1841-1849), with the modification that hydrogen was admitted to the reaction mixture via a balloon. The compounds were subsequently transformed into 3-(3-iodophenyl)-1-propanol and 3-(4-iodophenyl)-1-propanol through a sequence of diazotization/iodination and carboxyl reduction with borane as described by Xin et al. (U.S. Patent Publication No. 2004/0167188 A1, Aug. 26, 2004, p. 21) for the meta isomer.

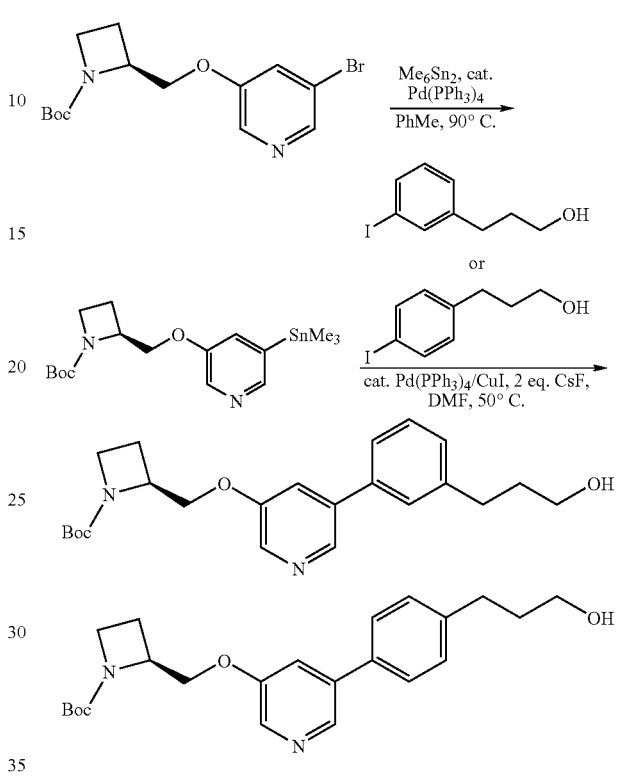

The N-Boc protected precursors of the title compounds were prepared according to Scheme 10b. Stille coupling of 3-bromo-5-[[1-(tert-butoxycarbonyl)-2(S)-azetidinyl]methoxy]pyridine (Scheme 5a) with hexamethyldistannane resulted in the pyridylstannane, from which the biaryls and were obtained via a second Stille coupling reaction with the iodophenylpropanols of Scheme 10a.

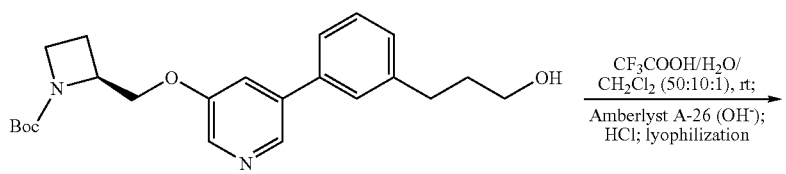

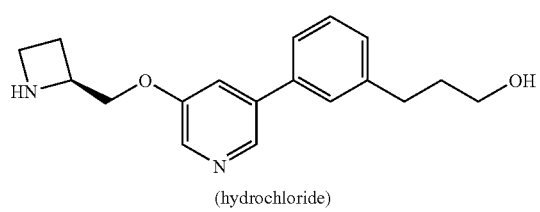

(hydrochloride)

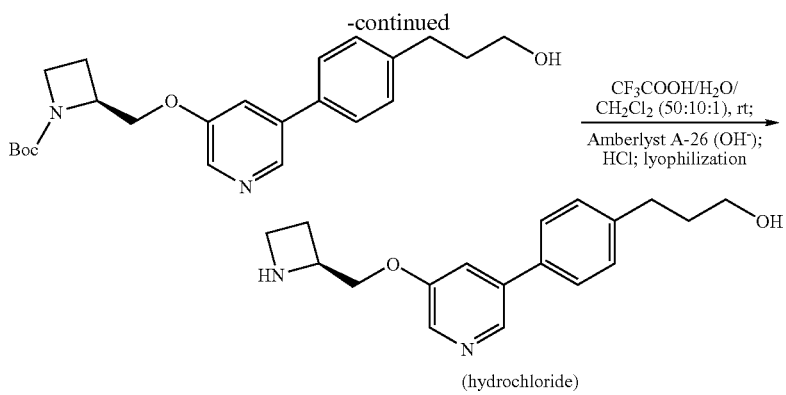
(hydrochloride)

The title compounds were prepared from their N-Boc-protected precursors by deprotection with trifluoroacetic acid as shown in Scheme 10c. To transform the initially obtained trifluoroacetates into the hydrochlorides, the free bases were prepared via ion exchange and then neutralized with HCl.

11. Synthesis of 3-[3-[5-[(2(S)-Azetidinyl)methoxy]-3-pyridyl]-5-fluorophenyl]-1-propanol Scheme 11

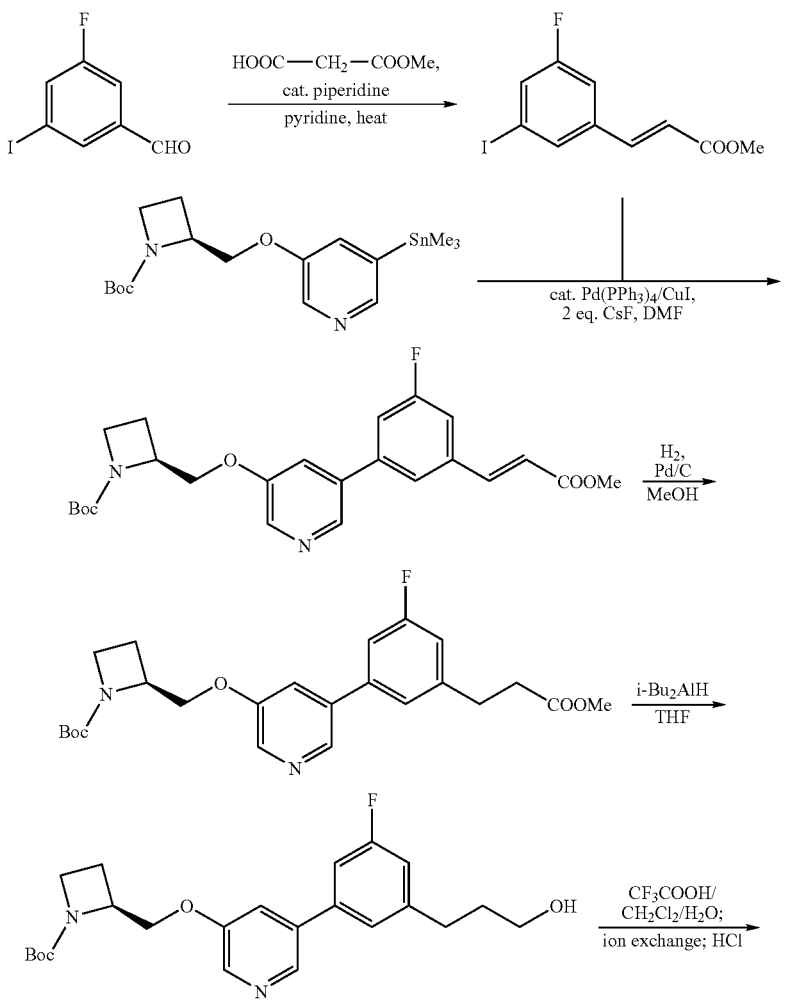

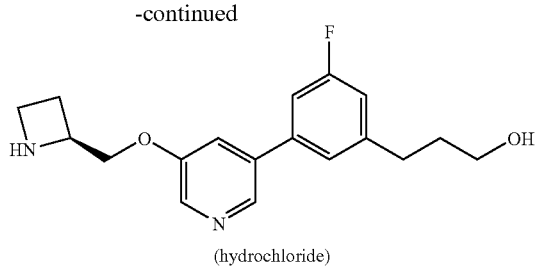

(hydrochloride)

3-[3-[5-[(2(S)-Azetidinyl)methoxy]-3-pyridyl]-5-fluorophenyl]-1-propanol is prepared according to Scheme 11. Commercially available 3-fluoro-5-iodobenzaldehyde is chain-extended to the cinnamate by Knoevenagel condensation with monomethyl malonate (Yang, Z. et al., *J. Org. Chem.* 1992, 57, 7248-7257). Alternatively, the Wadsworth-Emmons reaction may be used. Stille coupling with 3-[[1-(tert-butoxycarbonyl)-2(S)-azetidinyl]methoxy]-5-(trimethylstannyl)pyridine establishes the biaryl motif. The side chain is then modified by catalytic hydrogenation of the olefinic double bond followed by ester reduction. Finally, deprotection is effected by acid treatment (as shown, or directly with HCl).

12. Synthesis of 3-[2-[5-[(2(S)-azetidinyl)methoxy]-3-pyridyl]ethyl]phenylmethanol and N-[3-[2-[5-[(2(S)-azetidinyl)methoxy]-3-pyridyl]ethyl]phenylmethyl]methanesulfonamide Scheme 12

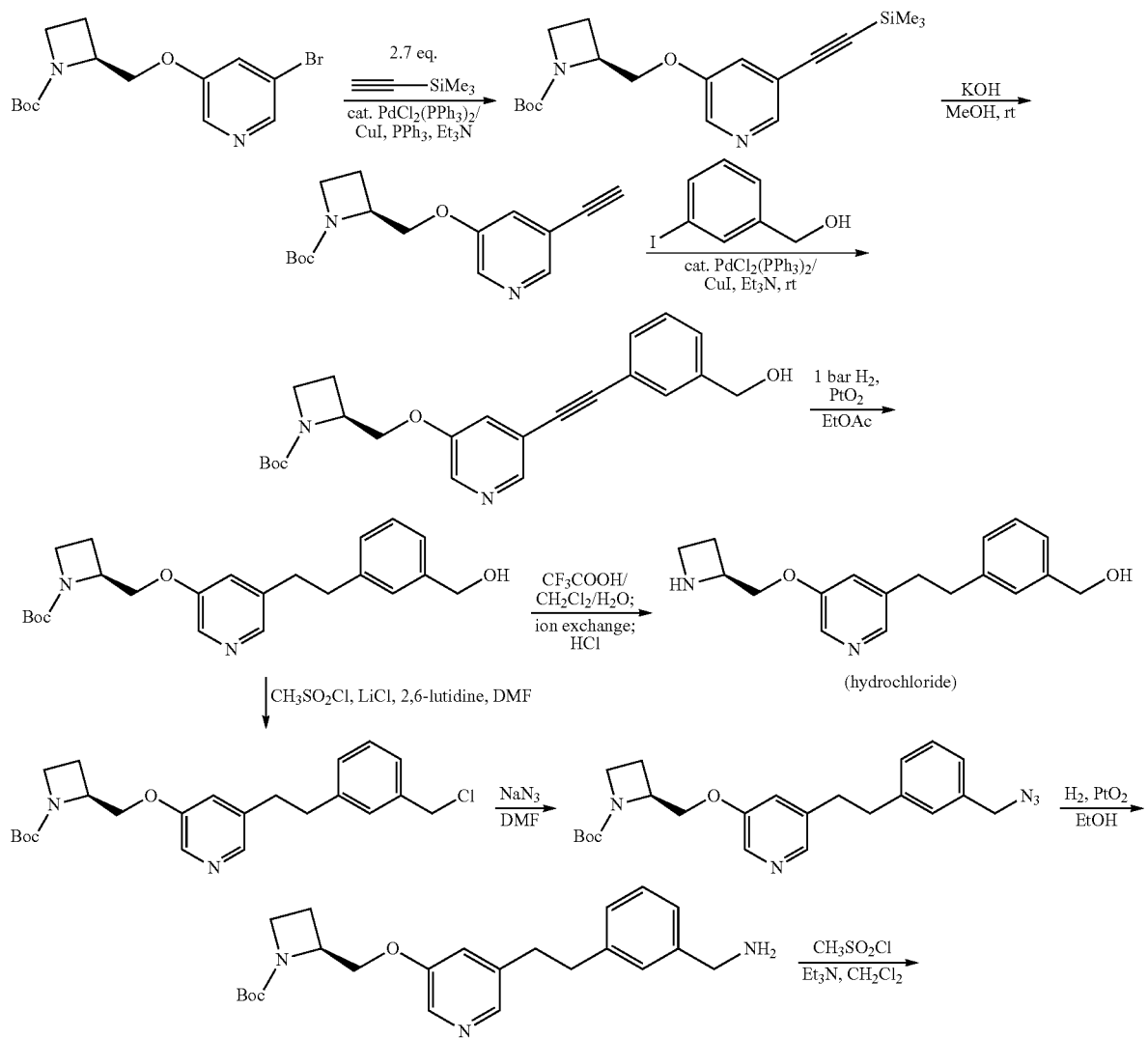

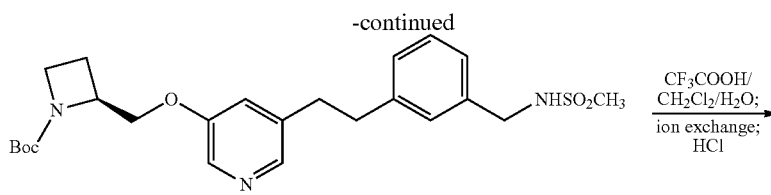

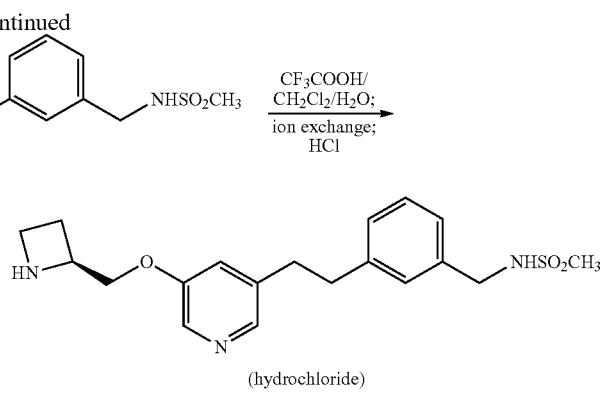

(hydrochloride)

These compounds, as well as cognate sulfonamides and carboxamides, are prepared as depicted in Scheme 12. A first Sonogashira coupling of 3-bromo-5-[[1-(tert-butoxycarbonyl)-2(S)-azetidinyl]methoxy]pyridine under standard conditions with trimethylsilylacetylene affords a pyridylalkyne, which is desilylated by treatment with KOH in methanol. Alternatively, tetra-n-butylammonium fluoride can be used. This step is followed by a second Sonogashira coupling with m-iodobenzyl alcohol (in an analogous fashion, the ortho and para isomer, as well as higher homologues of any of the regioisomers, and also the three iodophenols, can be employed). The triple bond is saturated by catalytic hydrogenation; $PtO_2$ is chosen as the catalyst to avoid hydrogenolysis of the benzylic C—O bond.

Amine deprotection is accomplished by treatment with trifluoroacetic acid, and the free amine is isolated by evaporation of the reaction mixture and ion exchange. Addition of HCl results in the hydrochloride.

To synthesize the analogous reverse amides or sulfonamides (illustrated by the example of the N-(methanesulfonyl) derivative), the OH group in the intermediate, [3-[2-[5-[[1-(tert-butoxycarbonyl)-2(S)-azetidinyl]methoxy]-3-pyridyl]ethyl]phenyl]methanol, is first replaced by an amino group. As one of a number of possible methods, the benzylic chloride is generated in a one-pot reaction via the mesylate (see, for example: Smith, A. B. III; Wan, Z. J. Org. Chem. 2000, 65, 3738). Chloride is then displaced by azide in DMF or another dipolar-aprotic solvent, and the azide function reduced to amine, e.g., by catalytic hydrogenation. Alternatively, the benzylic chloride may be reacted with other N nucleophiles, such as potassium phthalimide, in which case the amine is obtained by treatment with hydrazine. It is also possible to directly treat [3-[2-[5-[[1-(tert-butoxycarbonyl)-2(S)-azetidinyl]methoxy]-3-pyridyl]ethyl]phenyl]methanol with a free acidic nitrogen compound, such as $HN_3$, phthalimide, or tetrachlorophthalimide (Jia, Z. J. et al., Synlett 1999, 565-566) under Mitsunobu conditions (e. g., $EtOOCN=NCOOEt/PPh_3$) to obtain the amine precursors. In the case of the tetrachlorophthalimide derivative, the amine is obtained under milder conditions ($N_2H_4$ or ethylenediamine) than those needed for the cleavage of the unsubstituted phthalimide. The amine is then reacted with an appropriate electrophile, in this case, methanesulfonyl chloride.

Similarly, other electrophiles such as benzenesulfonyl chloride, acetic anhydride, pivaloyl chloride, benzoyl chloride, or nicotinoyl chloride, can be employed to synthesize the respective analogs. To complete the synthesis of the title compound, the N-Boc-precursor is deprotected as described above, or directly by treatment with anhydrous HCl in a suitable organic solvent (e. g., diethyl ether, dioxane, ethyl acetate, methanol, ethanol, or mixtures thereof).

13. Synthesis of 5-[5-(2(S)-Azetidinylmethoxy)-3-pyridyl]-3-isoxazolylmethanol (97)

Scheme 13

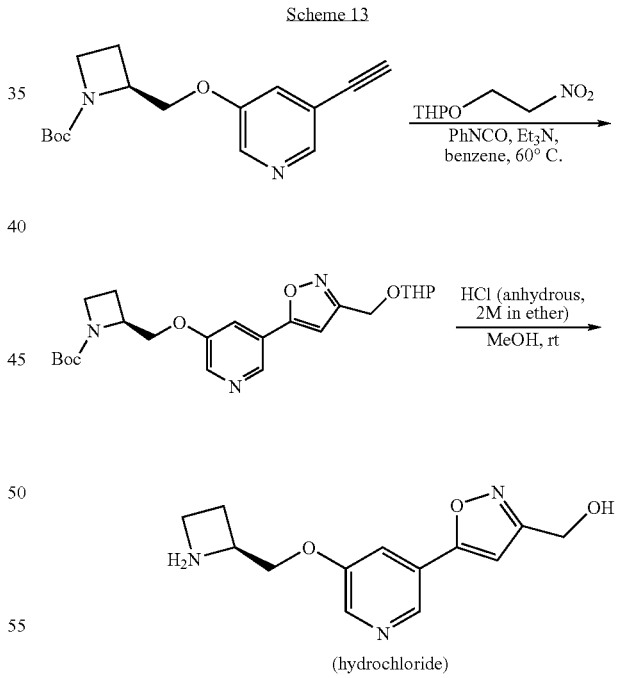

(hydrochloride)

The title compound was synthesized as outlined in Scheme 13. From the pyridylacetylene starting material, the N-Boc-protected precursor was prepared through 1,3-dipolar cycloaddition to a nitrile oxide generated from 1-nitro-2-(tetrahydro-2H-pyran-2-yloxy)ethane under Mukaiyama's conditions (Mukaiyama, T.; Hoshino, T. J. Am. Chem. Soc. 1960, 82, 5339-5342). Standard acidic deprotection simultaneously cleaved the Boc and tetrahydropyranyl (THP) protecting groups to arrive at the title compound.

14. Synthesis of 3-[[(2R,5S)-5-[2-[5-[(2(S)-Azetidinyl)methoxy]-3-pyridyl]ethyl]-2-tetrahydrofuranyl]methyl]pyridine

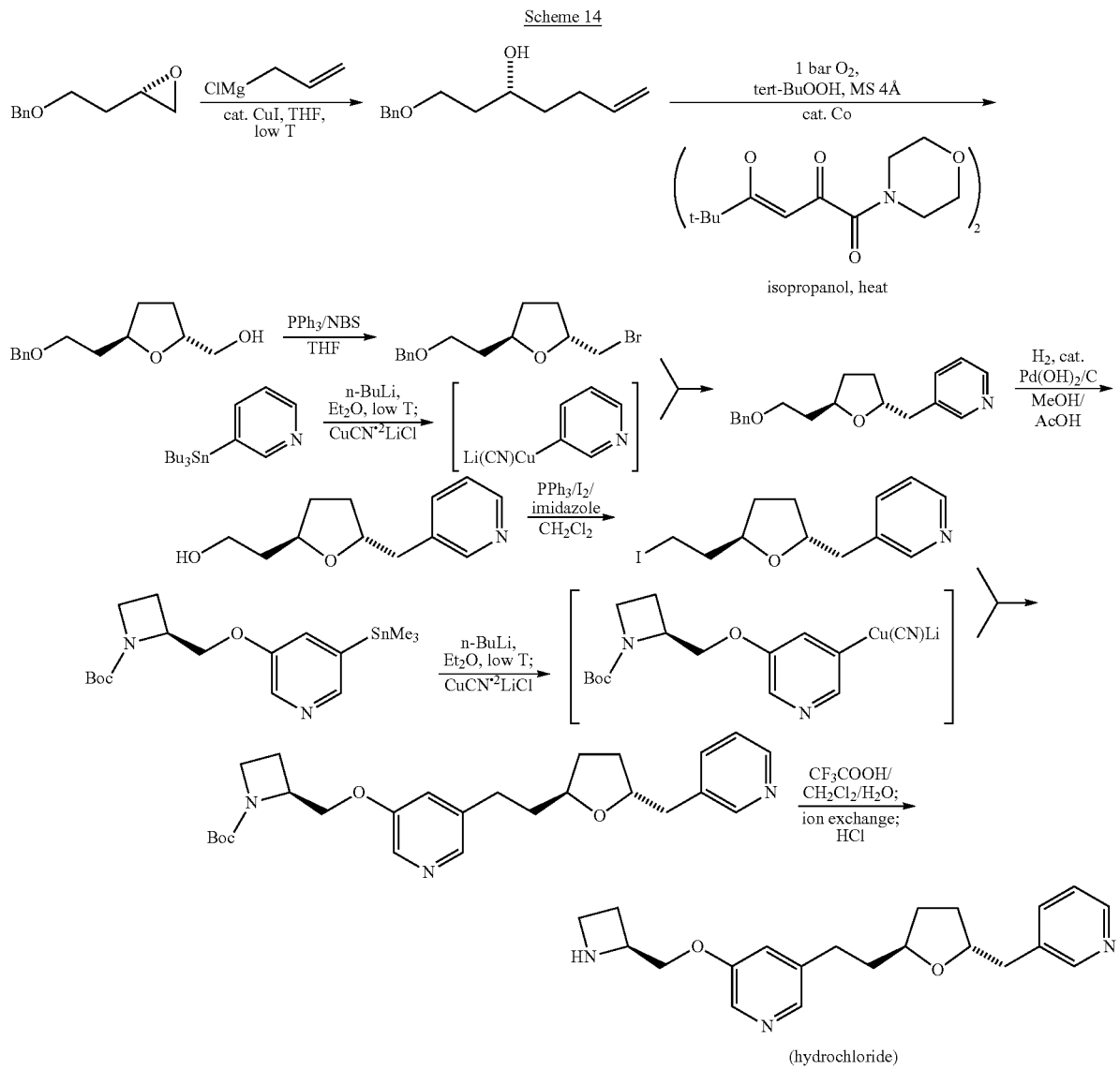

A synthesis of the title compound is depicted in Scheme 14. The synthesis starts from (S)-2-[2-(benzyloxy)ethyl]oxirane (Mulzer, J.; de Lasalle, P. *J. Chem. Res. (S)* 1983, 10). The opposite enantiomer is also available (Liu, C.; Coward, J. K. *J. Org. Chem.* 1991, 56, 2262-2264; Frick, J. A. et al., *Synthesis* 1992, 621-623), permitting the synthesis of the diastereoisomer of the title compound with opposite absolute configuration at the 2,5-positions of the tetrahydrofuran ring. Copper-catalyzed ring-opening of the oxirane with allylmagnesium chloride (Linstrumelle, G.; Lorne, R.; Dang, H. P. *Tetrahedron Lett.* 1978, 19, 4069-4072) results in an unsaturated alcohol, which is cyclized to a tetrahydrofuran using an oxidative process (Inoki, S.; Mukaiyama, T. *Chem. Lett.* 1990, 67). The hydroxyl group is replaced with bromine, and the resulting bromide is coupled with a cuprate derived from 3-(tributylstannyl)pyridine by transmetalation first with butyllithium (transmetalation of organostannanes with BuLi: Gilman, H.; Moore, F. W.; Jones, R. G. *J. Am. Chem. Soc.* 1941, 63, 2482), then with the CuCN.2LiCl complex (for the preparation of this soluble reagent and its use in the transmetalation of organolithium to organocopper reagents, see, for example: Lipshutz, B. H. et al. *J. Am. Chem. Soc.* 1990, 112, 4404-4410; reaction of cyanocuprates with halides: Hamon, L.; Levisalles, J. *J. Organometal. Chem.* 1983, 251, 133-138). The coupling product is debenzylated to form an alcohol, which is then transformed into the corresponding iodide. 3-[[1-(tert-Butoxycarbonyl)-2(S)-azetidinyl]methoxy]-5-(trimethylstannyl)pyridine is transmetalated to an organocopper reagent using the same method as described above, which is then coupled with the iodide to form the protected precursor of the title compound. Deprotection is performed by acid treatment.

15. Synthesis of [trans-4-[[3-[(2(S)-Pyrrolidinyl)methoxy]-5-pyridyl]methyl]cyclohexyl]methanol

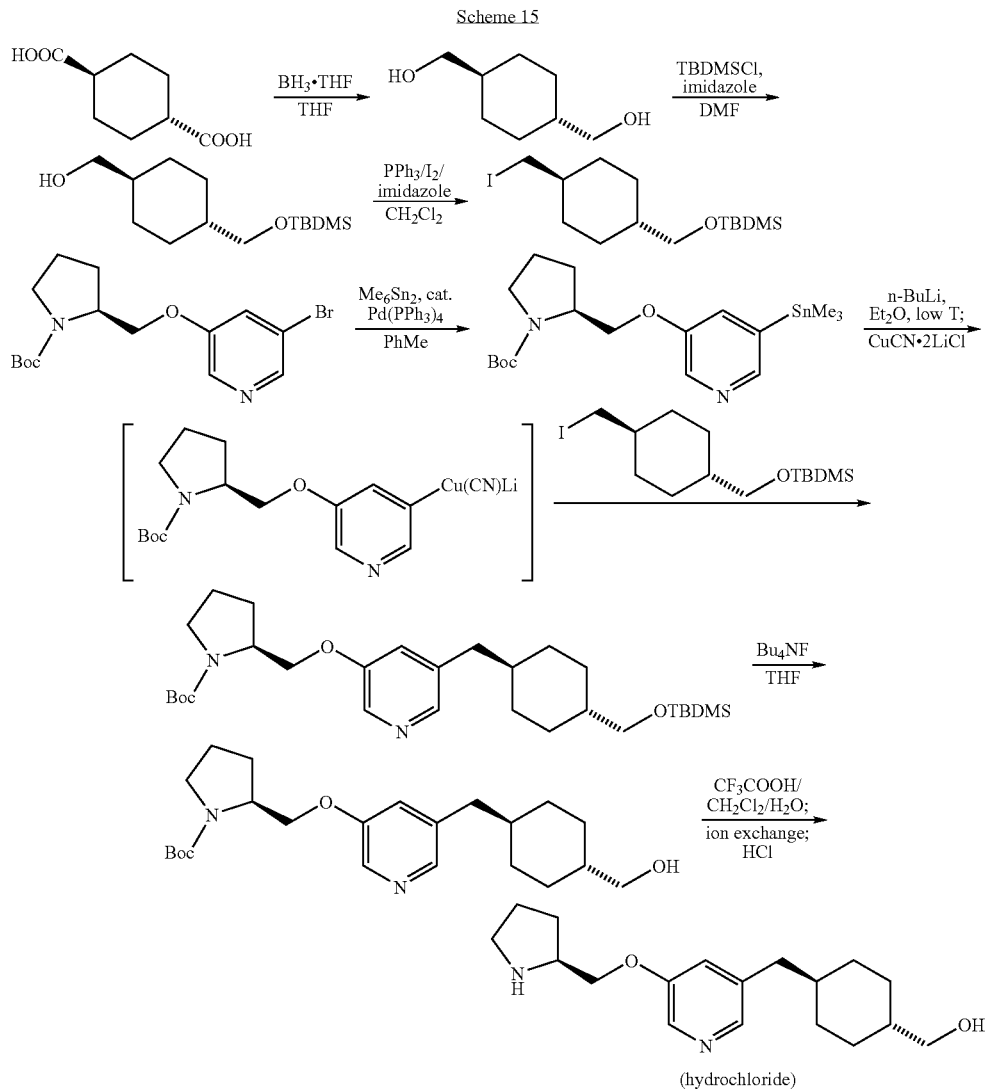

This compound is synthesized according to Scheme 15. The protected precursor results from a cross-coupling reaction between an iodide and a cuprate reagent. The iodide is derived by a sequence of routine reactions from commercially available trans-cyclohexane-1,4-dicarboxylic acid. The cuprate reagent is derived by halogen-metal exchange and transmetalation from 3-bromo-5-[[1-(tert-butoxycarbonyl)-2(S)-pyrrolidinyl]methoxy]pyridine, which is obtained (Lin, N.-H. et al., U.S. Pat. No. 5,629,325, May 13, 1997) through a Mitsunobu reaction in the same manner as its azetidine homologue (see Scheme 5a). Alcohol and amine deprotection lead to the target compound.

16. Synthesis of 2-[trans-4-[[3-[(2(S)-Pyrrolidinyl)methoxy]-5-pyridyl]methyl]cyclohexyl]ethanethiol m-Fluorobenzoate Scheme 16

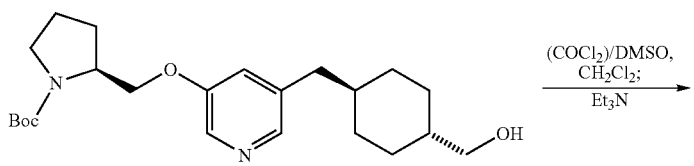

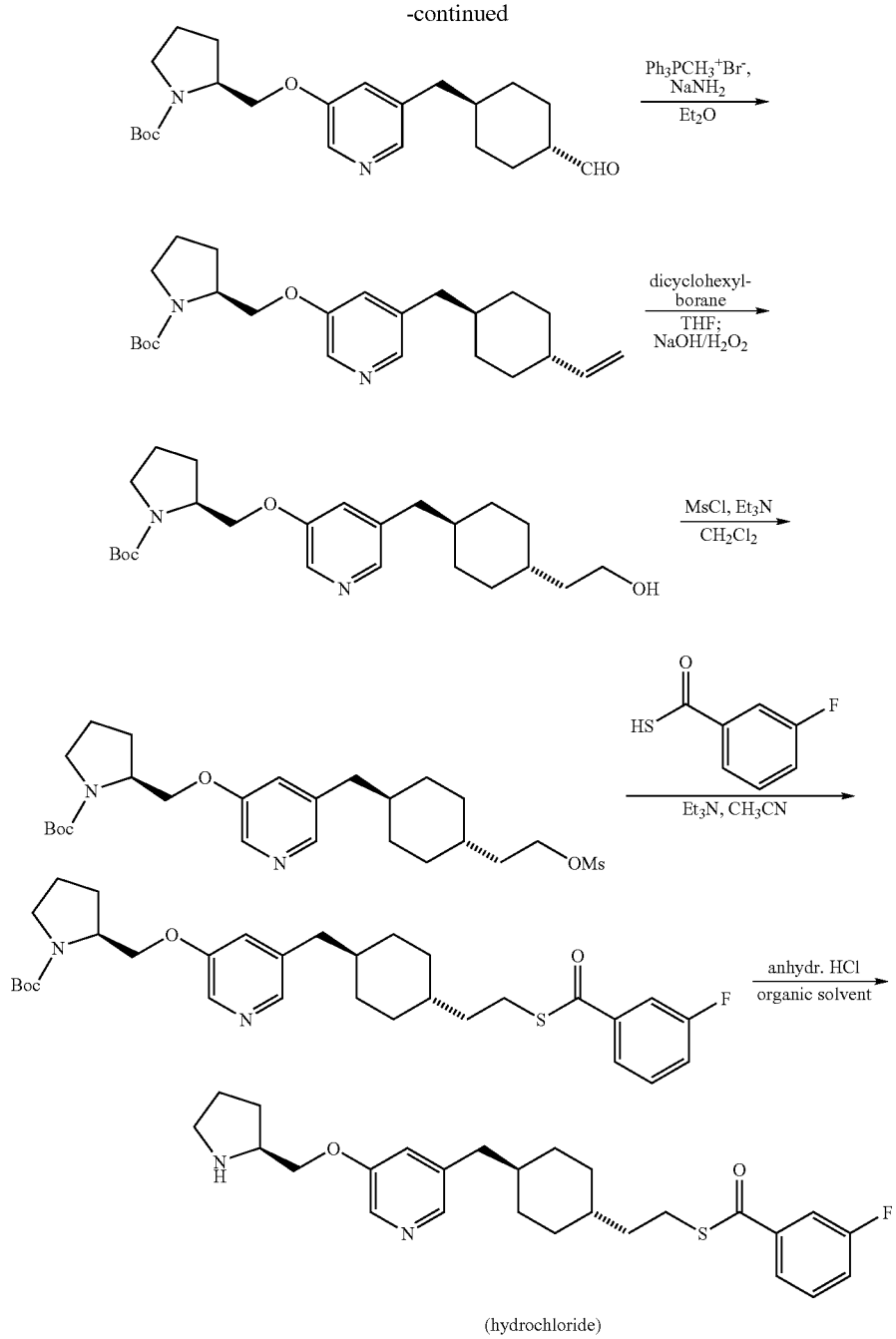

(hydrochloride)

Thiol ester analogs are prepared as shown in Scheme 16. While the depicted starting material, [trans-4-[[5-[(2(S)-pyrrolidinyl)methoxy]-3-pyridyl]methyl]cyclohexyl]methanol itself is also useful in the preparation of such compounds, the scheme shows the preparation of their next-higher homologs. The method of homologation is the same as that shown in Scheme 2 (Swern oxidation being depicted rather than Dess-Martin oxidation, which is also applicable). Introduction of the thiol ester function is effected by nucleophilic substitution performed on a derivative of the homologated alcohol, such as its mesylate (other derivatives such as the bromide, iodide, or other sulfonates also may be employed in this step), by the anion of the appropriate thiocarboxylic acid, which in the depicted case is m-fluorobenzenethioic acid. Thiocarboxylic acids can be synthesized from carboxylic acids using a variety of methods, such as treatment with $P_4S_{10}$ in the presence of a catalytic amount of $Ph_3SbO$ (Nomura, R.; Miyazaki, S.-I.; Nakano, T.; Matsuda, H. Chem. Ber. 1990, 123, 2081-2082) or by initial formation of an imidazolide with carbonyldiimidazole, followed by reaction of this intermediate with $H_2S$ (McKervey, M. A.; O'Sullivan, M. B.; Myers, P. L.; Green, R. H. J. Chem. Soc., Chem. Commun. 1993, 94-96).

An alternative route from the vinylcyclohexane intermediate to the N-Boc-precursor of the final product is provided by the direct addition of m-fluorobenzenethioic acid to the olefinic double bond under free-radical conditions [cat. dibenzoyl peroxide or azobis(isobutyronitrile), heat or irradiation; for example, Motesharei, K.; Myles, D. C. J. Am. Chem. Soc. 1994, 116, 7413-7414].

17. Synthesis of 2-[3-[[5-[N-Acetyl-N-[(2(S)-azetidinyl)methyl]amino]-3-pyridyl]methyl]phenyl]ethanol
Scheme 17
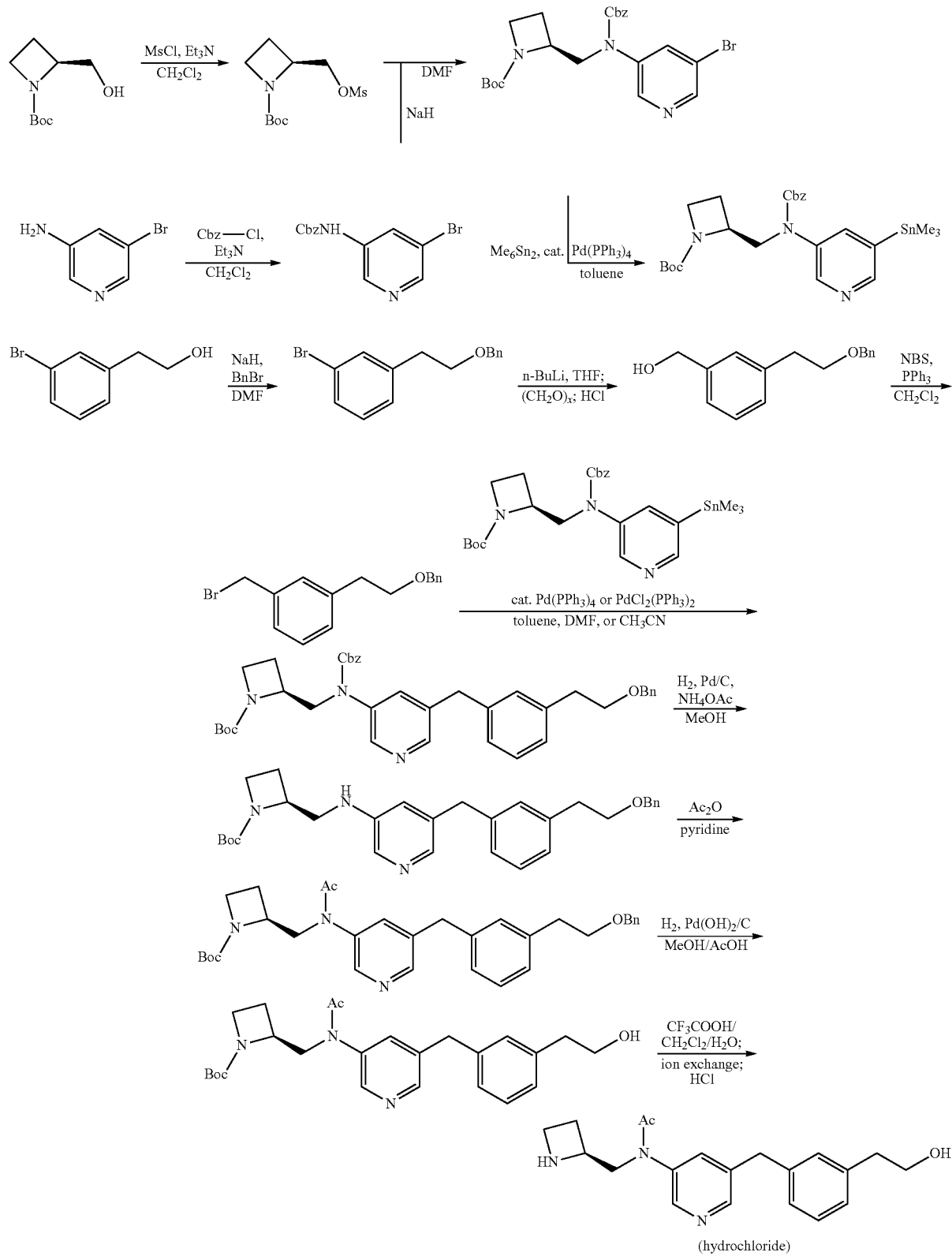

This compound is synthesized as shown in Scheme 17. The amino group of commercially available 3-amino-5-bromopyridine is protected with a benzyloxycarbonyl (Cbz) group. The resulting intermediate is deprotonated and alkylated with the mesylate derived from N-(tert-butoxycarbonyl)-2(S)-azetidinylmethanol. From the product thus obtained, the pyridylstannane is prepared by Stille coupling with Me$_6$Sn$_2$.

Commercially available m-bromophenethyl alcohol is O-benzylated and the derived aryllithium reacted with paraformaldehyde or 1,3,5-trioxane to produce the substituted benzyl alcohol, from which the bromide is prepared.

The building blocks obtained in the preceding two paragraphs are combined through another Stille coupling reaction. In the following step, selective hydrogenolysis of the Cbz protecting group without affecting the benzyl ether occurs in presence of NH$_4$OAc (Sajiki, H. *Tetrahedron Lett.* 1995, 36, 3465-3468). At this point, alkyl, acyl, or sulfonyl groups can be placed on the linker nitrogen by reaction with appropriate electrophiles. For example, reaction with acetic anhydride yields an acetamide. The O-benzyl group is then removed by hydrogenolysis under mildly acidic conditions, and eventually the N-Boc group removed to arrive at the target compound.

18. Synthesis of 2-[7-[3-[5-[[1-Methyl-(2(S)-pyrrolidinyl)methoxy]methyl]-3-pyridyl]propyl]-3-indolyl]ethanamine and 2-[7-[3-[5-[[(2(S)-Pyrrolidinyl)methoxy]methyl]-3-pyridyl]propyl]-3-indolyl]ethanamine

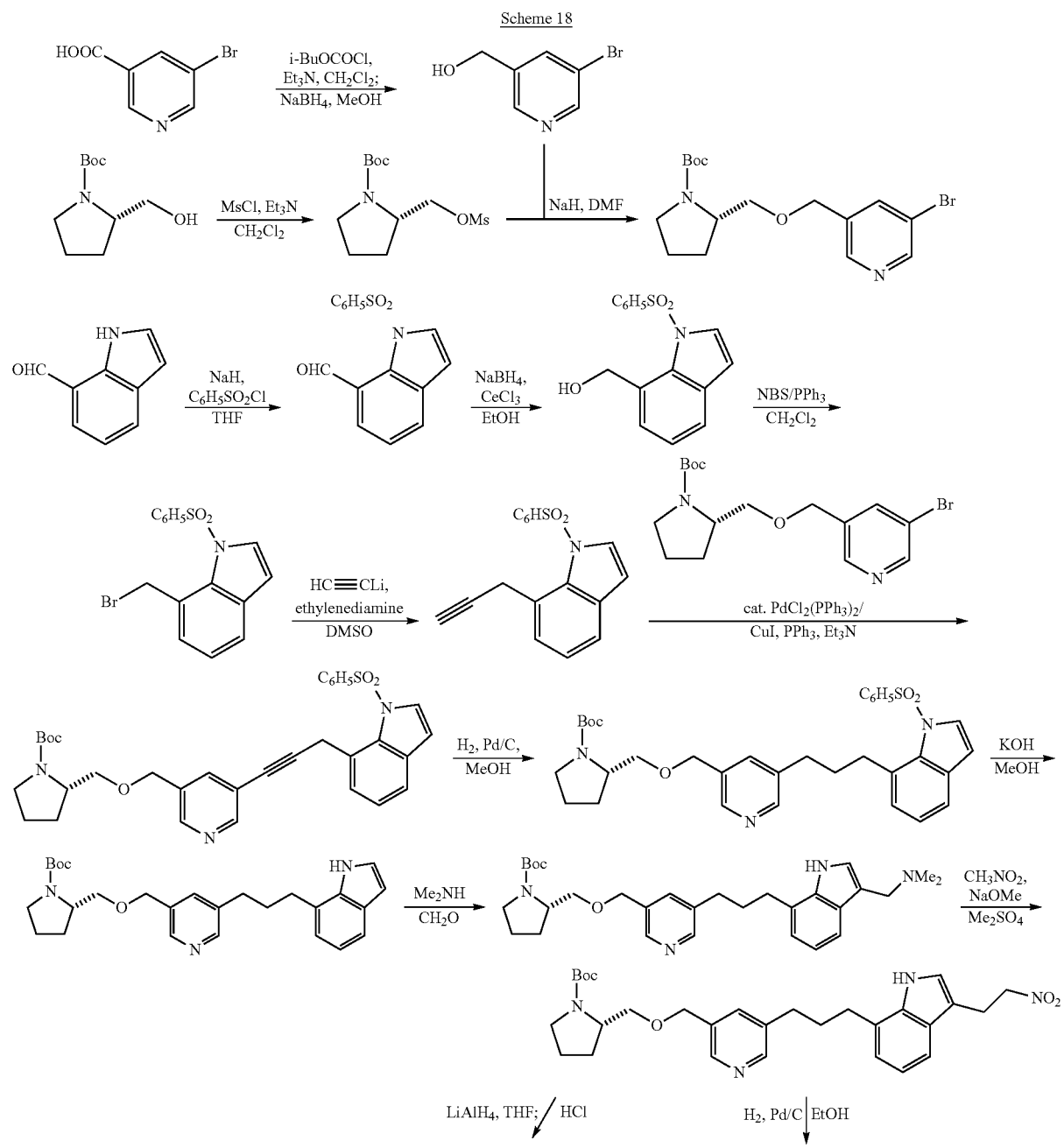

Scheme 18

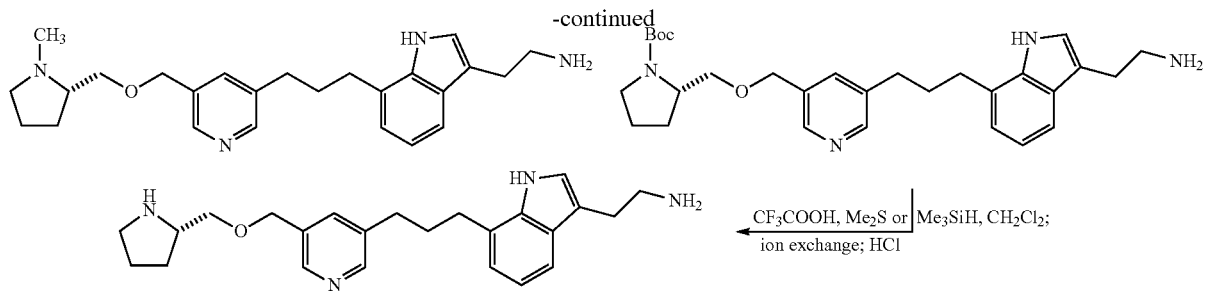

The synthesis of target compounds containing a $CH_2OCH_2$ linker between the saturated heterocycle and the pyridine ring is shown in Scheme 18. The required pyridine building block, 3-bromo-5-[[1-[(tert-butoxycarbonyl)-2(S)-pyrrolidinyl] methoxy]methyl]pyridine, is procured through a Williamson ether synthesis performed between the alcohol, 5-bromo-3-pyridylmethanol, and the alkylating agent, 1-(tert-butoxycarbonyl)-2(S)-pyrrolidinyl mesylate, both readily obtainable from commercially available starting materials. Commercially available indole-7-carboxaldehyde is transformed into the required indole building block by N-protection, aldehyde reduction, bromide formation, and reaction with the lithium acetylide-ethylenediamine complex (Smith, W. N.; Beumel, O. F., Jr. *Synthesis* 1974, 441). The pyridine and indole building blocks are joined through Sonogashira coupling, and the triple bond is hydrogenated to produce the precursor protected at both the pyrrolidine and indole nitrogens. The indole nitrogen is deprotected, and a side chain joined at C-3 of the indole ring by gramine formation and nucleophilic substitution with nitromethane (e. g., Hermkens, P. H. H. et al. *J. Org. Chem.* 1990, 55, 3998-4006). From the resulting 3-(2-nitroethyl)indole, either the N-methylated pyrrolidine or the N-unsubstituted pyrrolidine is obtainable by proper choice of conditions. Thus, treatment with $LiAlH_4$ results, after salt formation, in the N-methylated compound. On the other hand, the nitro group may be reduced instead by catalytic hydrogenation, and then the Boc group removed from the pyrrolidine with acid to produce the N-unsubstituted pyrrolidine. In this case, a carbocation scavenger ($Me_2S$ or $Et_3SiH$) is added to prevent attack of the tert-butyl cation formed in this step on the indole moiety.

19. Synthesis of 4'-[3-[5-[(2(S)-Azetidinyl)methoxy]-2-methyl-3-pyridyl]-1(R)-methylpropyl]-N,N-dimethylphenethylamine Scheme 19

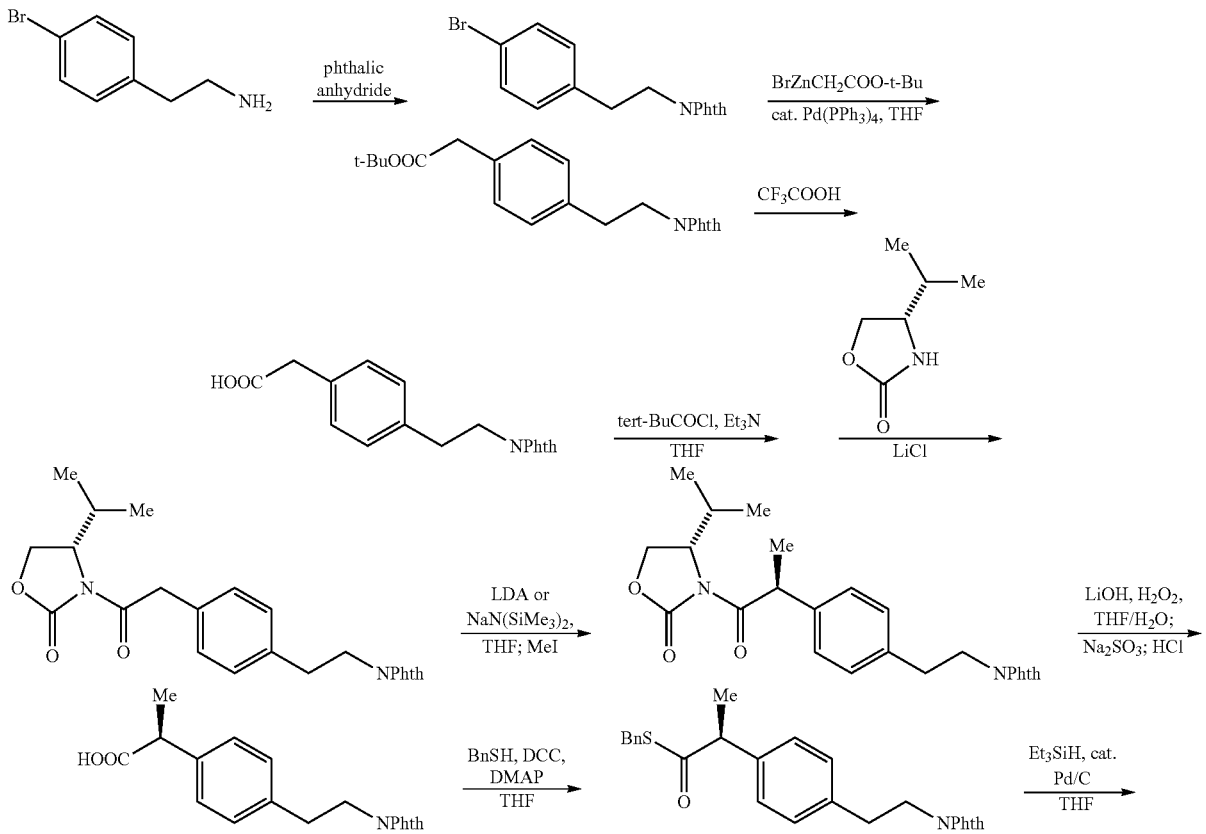

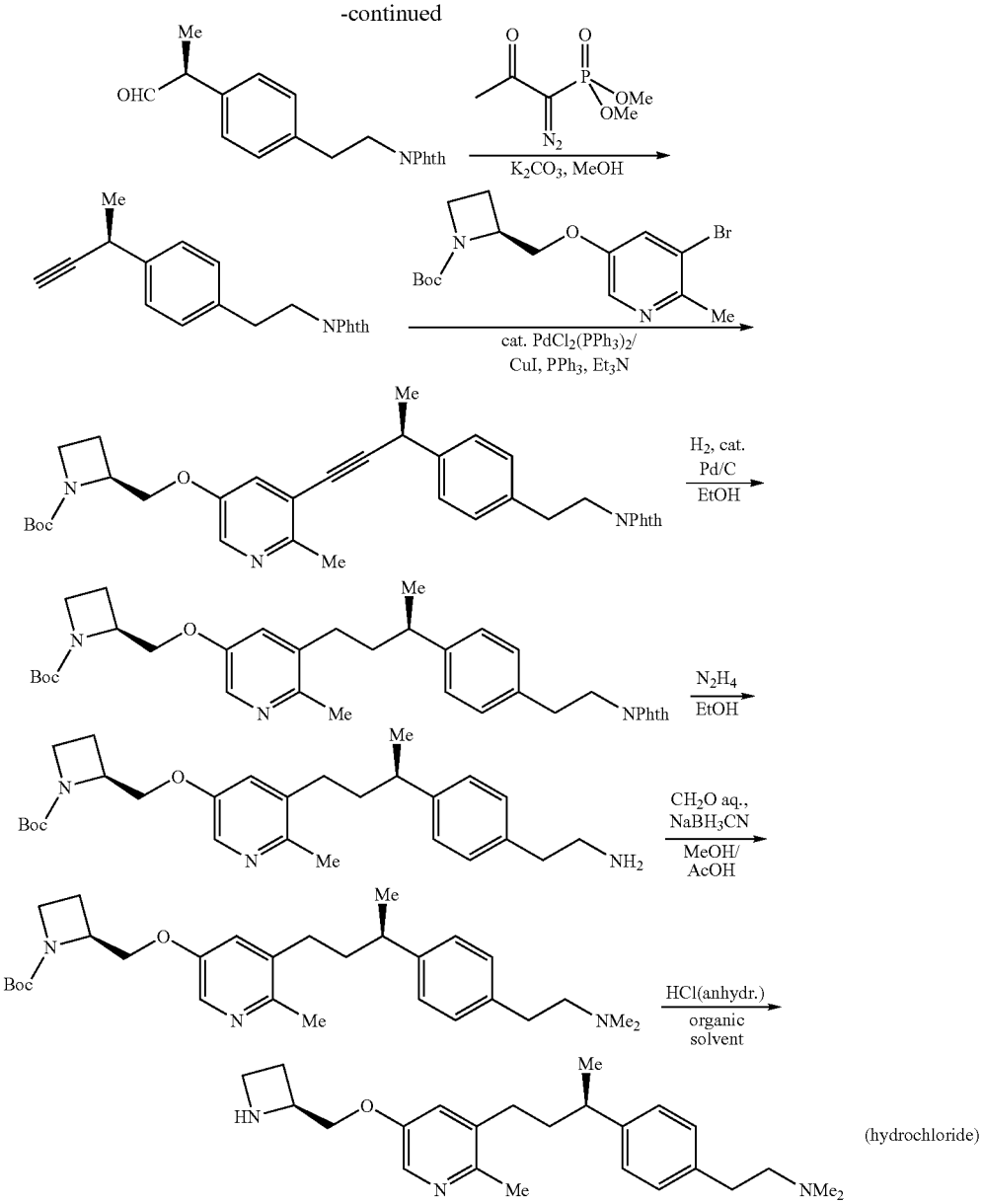

This compound is prepared as depicted in Scheme 19. Starting from commercially available p-bromophenethylamine, the amino group is protected as its phthaloyl derivative. This step is followed by a Pd-catalyzed coupling reaction of the bromoarene moiety with the Reformatsky reagent derived from tert-butyl bromoacetate (Bentz, E.; Moloney, M. G.; Westaway, S. M. *Tetrahedron Lett.* 2004, 45, 7395-7397). The tert-butyl ester is cleaved with trifluoroacetic acid, and the resulting carboxylic acid derivatized as its Evans imide by reaction of its mixed anhydride with pivalic acid with the depicted enantiomerically pure oxazolidinone in the presence of LiCl (Chakraborty, T. K.; Suresh, V. R. *Tetrahedron Lett.* 1998, 39, 7775-7778; Duan, M.; Paquette, L. A. *Angew. Chem., Int. Ed. Engl.* 2001, 113, 3632-3636). The requisite methyl group in the α-position to the carbonyl is introduced diastereoselectively by way of enolate alkylation (Evans, D. A.; Ennis, M. D.; Mathre, D. J. *J. Am. Chem. Soc.* 1982, 104, 1737-1739).

The resulting alkylation product is recrystallized to the desired level of diastereomeric purity. The chiral auxiliary is then removed by hydrolysis with alkaline $H_2O_2$ (see, for example: Sibi, M. P.; Lu, J.; Edwards, J. *J. Org. Chem.* 1997, 62, 5864-5872). The obtained carboxylic acid is activated as its thiol ester and then reduced to the aldehyde under neutral conditions with $Et_3SiH$ and a Pd catalyst (Fukuyama, T.; Lin, S. C.; Li, L. *J. Am. Chem. Soc.* 1990, 112, 7050-7051; Ho, P.-T.; Ngu, K.-Y. *J. Org. Chem.* 1993, 58, 2313-2316), a technique that has been demonstrated to proceed without racemization in the case of sensitive, protected α-aminoaldehydes.

Alternatively, the reduction of COOH to CHO can be executed in a single step with thexylmonochloroborane-dimethyl sulfide (Brown, H. C.; Nazer, B.; Cha, J. S.; Sikorski, J. A. *Org. Chem.* 1986, 51, 5264-5270; Brown, H. C.; Cha, J. S.; Yoon, N. M.; Nazer, B. *J. Org. Chem.* 1987, 52, 5400-5406). One-carbon chain-extension of the aldehyde to an acetylene is carried out with dimethyl 1-diazo-2-oxopropylphosphonate (the Bestmann-Ohira reagent). The second requisite building block, 3-bromo-5-[[1-(tert-butoxycarbonyl)-2(S)-azetidinyl]methoxy]-6-methylpyridine, is prepared according to a procedure known in the art (Holladay, M. W. et al., U.S. Pat. No. 6,133,253, Oct. 17, 2000), and joined to the acetylene by means of a Sonogashira coupling reaction. The triple bond is saturated by catalytic hydrogenation, the phthaloyl protecting group removed with hydrazine, and the primary amine reductively methylated before deprotection of the azetidine nitrogen leads to the target compound.

20. Synthesis of N-[2-[3-[5-[N-[2-(2(S)-Azetidinyl)ethyl]-N-ethyl]-3-pyridyl]phenyl]ethyl]-2-pyrrolidone

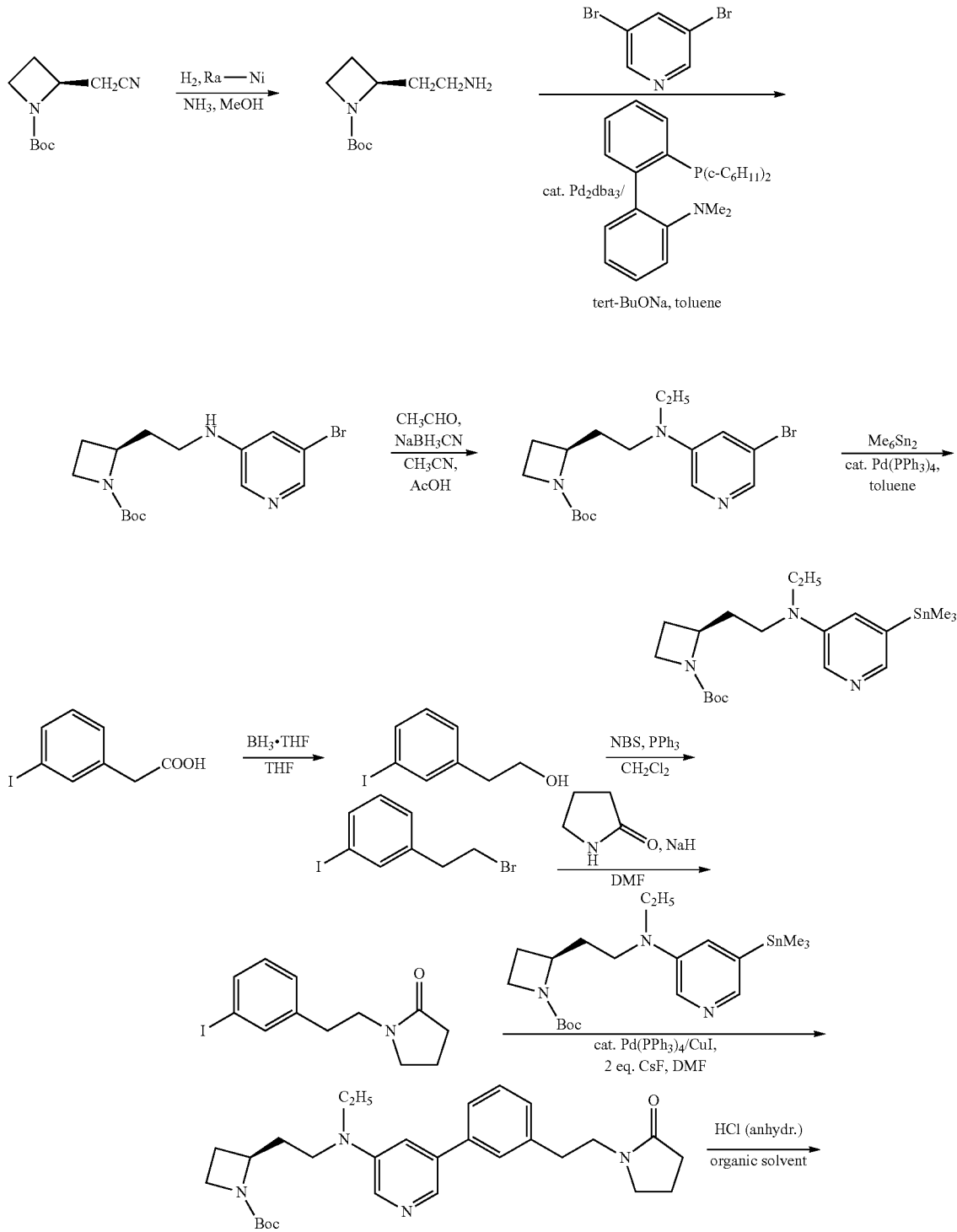

Scheme 20

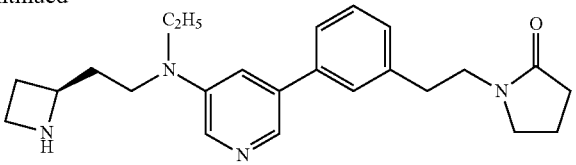

A synthesis of the title compound is set forth in Scheme 20. The requisite starting material, 1-(tert-butoxycarbonyl)-2(S)-azetidinylacetonitrile, is synthesized according to a procedure known in the art (Holladay, M. W. et al. WO 99/32480, Jul. 1, 1999, therein Example 555a [p. 344]). Catalytic hydrogenation of the cyano group yields the primary amine, which is N-arylated with 3,5-dibromopyridine by one of several known procedures (e. g., Wolfe, J. P. et al. *J. Am. Chem. Soc.* 1996, 118, 7215-7216; Driver, M. S.; Hartwig, J. F. *J. Am. Chem. Soc.* 1996, 118, 7217-7218; catalyst shown in the scheme: Old, D. W. et al. *J. Am. Chem. Soc.* 1998, 120, 9722-9723). The N-ethyl substituent is introduced into the arylation product by standard reductive amination, and Br is replaced with SnMe₃.

To assemble the "right-hand" side chain, m-iodophenylacetic acid is reduced to alcohol, OH is replaced with Br, and the bromide is reacted with the amide anion derived from 2-pyrrolidone. The two building blocks and are combined via Stille coupling, followed by removal of the Boc group to arrive at the target compound.

21. Synthesis of 3-[4-[5-[(2(S)-Azetidinyl)methoxy]-3-pyridyl]-1,2,3-triazol-1-yl]-1-propanol

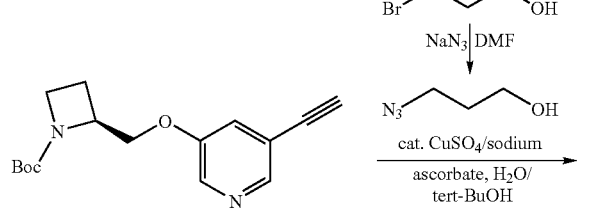

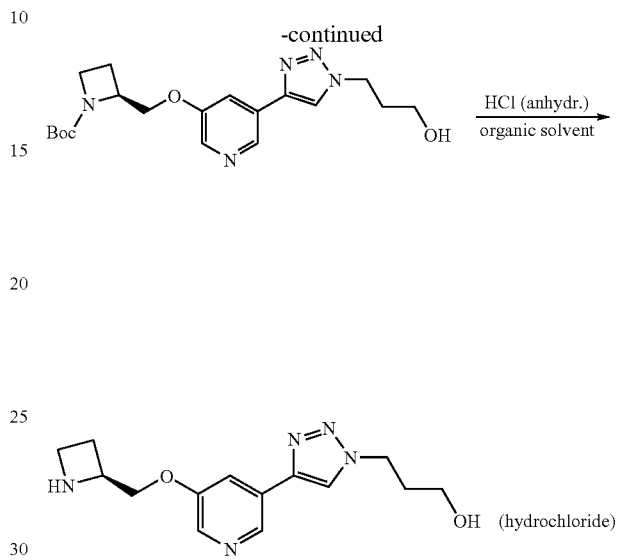

1,2,3-Triazole analogs (Scheme 21) are readily assembled from acetylenes and azides by Cu-catalyzed 1,3-dipolar cycloaddition (Rostovtsev, V. V.; Green, L. G.; Folkin, V. V.; Sharpless, K. B. *Angew. Chem., Int. Ed. Engl.* 2002, 41, 2596-2599; Tornøe, C. W.; Christensen, C.; Meldal, M. *J. Org. Chem.* 2002, 67, 3057-3062).

22. General Scheme for the Synthesis of Heteroaryl Analogs by Formation of the Pyridine-Heteroarene Bond via Stille or Suzuki Coupling

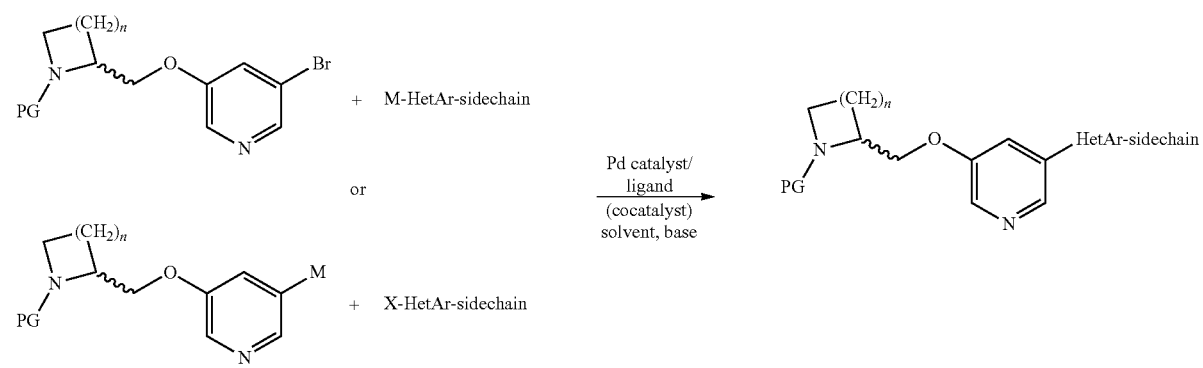

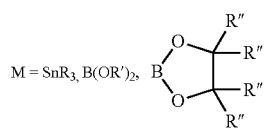

n = 1-3; R or S stereochemistry on the saturated heterocycle; PG = Boc, Cbz; R = Me, n-Bu; R' = H, Me, Et, i-Pr, n-Bu; R" = H, Me; X = Cl, Br, I, $OSO_2CF_3$ Regioselective bond formation between non-identical aromatic or heteroaromatic rings is most commonly effected by reaction of a halogen (or sulfonate) derivative of one (hetero-) aromatic moiety with an organometallic derivative of the second (hetero)-aromatic moiety. In many cases, those organometallic derivatives that are most stable or most readily available require for their successful conversion the addition to the reaction mixture of a catalytic amount of another metal compound (commonly a palladium salt or complex), and sometimes a third metal compound (cocatalyst), together with ligands (such as phosphines or heterocycles) that fine-tune the steric and/or electronic properties of the metal center (e. g., palladium) to which they bind, so as to produce favorable selectivities and reaction rates. Which of the two (hetero-)aromatics is employed in form of its halide or sulfonate and which in form of its organometallic derivative, is usually decided by consideration of synthetic accessibility. Among the most widely used organometallic derivatives for the present purpose are those of tin and boron, and their reactions with (hetero)-aryl halides and sulfonates form subsets of more general classes of carbon-carbon bond forming reactions known as the Stille and Suzuki coupling reactions, respectively. (Scheme 22; reviews: (a) Hassan, J.; Sévignon, M.; Gozzi, C.; Schulz, E.; Lemaire, M. Aryl-Aryl Bond Formation One Century after the Discovery of the Ullmann Reaction. Chem. Rev. 2002, 102, 1359-1469. (b) Miyaura, N. (Ed.) "Cross-Coupling Reactions—A Practical Guide". Springer Verlag, Berlin, 2002. (c) Kalinin, V. N. Carbon-Carbon Bond Formation in Heterocycles Using Ni- and Pd-Catalyzed Reactions. Synthesis 1992, 413-432. (d) Li, J. J.; Gribble, G. W. Palladium in Heterocyclic Chemistry. A Guide for the Synthetic Chemist. Pergamon, Amsterdam etc., 2000).

Therapeutic Uses

In accordance with the invention, pyridinyl nicotinic acetylcholine receptor ligands are administered to an animal in need of treatment or prevention of a condition.

In some embodiments, the pyridinyl nicotinic acetylcholine receptor ligands are administered to an animal in need of treatment or prevention of a condition selected from neurodegenerative disorders such as Alzheimer's disease and Parkinson's disease, age-related or disease-related cognitive impairment, dyskinesias, Tourette's syndrome, schizophrenia, attention-deficit hyperactivity disorder, depression, anxiety, mood disorders, pain, methamphetamine addiction and nicotine addiction.

In one embodiment, an effective amount of a pyridinyl nicotinic acetylcholine receptor ligand can be used to treat or prevent any condition treatable or preventable by desensitizing neuronal nAChR receptors.

In another embodiment, an effective amount of a pyridinyl nicotinic acetylcholine receptor ligand can be used to treat or prevent with fewer or reduced side effects any condition treatable or preventable by selectively desensitizing the α4β2 nAChR subtype.

In another embodiment, an effective amount of a pyridinyl nicotinic acetylcholine receptor ligand can be used to treat or prevent any condition treatable or preventable by activating neuronal nicotinic acetylcholine receptors.

In another embodiment, an effective amount of a pyridinyl nicotinic acetylcholine receptor ligand can be used to treat or prevent with fewer or reduced side effects any condition treatable or preventable by selectively activating the α4β2 nAChR subtype.

According to the invention, some of the pyridinyl nicotinic acetylcholine receptor ligands are agonists at neuronal nicotinic acetylcholine receptors, and some of the pyridinyl nicotinic acetylcholine receptor ligands are antagonists at neuronal nicotinic acetylcholine receptors. In another embodiment, pyridinyl nicotinic acetylcholine receptor ligands are agonists at the α4β2 nicotinic acetylcholine receptor subtype. In another embodiment, pyridinyl nicotinic acetylcholine receptor ligands are antagonists at the α4β2 nicotinic acetylcholine receptor subtype. In another embodiment, pyridinyl nicotinic acetylcholine receptor ligands desensitize a neuronal nicotinic acetylcholine receptor. In yet another embodiment, pyridinyl nicotinic acetylcholine receptor ligands desensitize the α4β2 nicotinic acetylcholine receptor subtype.

The invention also provides methods for inhibiting nAChR function in a cell, comprising contacting a cell capable of expressing the nAChR with an amount of a pyridinyl nicotinic acetylcholine receptor ligand effective to inhibit nAChR function in the cell. This method can be adapted for use in vitro as part of an assay to select compounds that may be useful for treating or preventing a condition in an animal. Alternatively, this method can be adapted for use in vivo, (i.e., in an animal such as a human) by contacting a cell in the animal with an effective amount of a pyridinyl nicotinic acetylcholine receptor ligand. In one embodiment, the method is useful for treating or preventing depression in an animal in need of such treatment or prevention. The invention also relates to methods for activating nAChR function in a cell, comprising contacting a cell capable of expressing the nAChR with an amount of a pyridinyl nicotinic acetylcholine receptor ligand effective to activate nAChR function in the cell. This method can be adapted for use in vitro as part of an assay to select compounds useful for treating or preventing a condition in an animal. Alternatively, the method can be adapted for use in vivo (i.e., in an animal such as a human), by contacting a cell in the animal with an effective amount of a pyridinyl nicotinic acetylcholine receptor ligand. In one embodiment, the method is useful for treating or preventing neurodegenerative disorders such as Alzheimer's disease and Parkinson's disease, age-related or disease-related cognitive impairment, dyskinesias, Tourette's syndrome, schizophrenia, attention-deficit hyperactivity disorder, depression, anxiety, mood disorders, pain, methamphetamine addiction and nicotine addiction in an animal in need of such treatment or prevention.

Examples of tissue comprising cells capable of expressing the nAChRs include but are not limited to brain, spinal cord, and the peripheral neurons. Methods for assaying cells that express nAChRs are known in the art; for example, see Eaton, J. B. et al. (2003) *Mol. Pharmacol.* 64:1283-1294; Peng, J. H. et al. (1999) *Brain Res.* 825:172-179; Gentry, C. L. et al. (2001) *J. Pharmacol. Exp. Ther.* 299:1038-1048; Houlihan L. M. et al. (2001) *J. Neurochem.* 78:1029-1043.

In some embodiments, the nicotinic acetylcholine receptor ligands of the invention are useful for modulating the activity of a nicotinic acetylcholine receptor. In certain embodiments, the nicotinic acetylcholine receptor ligands of formula I are useful for modulating the activity of a nicotinic acetylcholine receptor, wherein all variables are the same as defined above for the compounds of formula I, and with the proviso that when Y is a bond, $R_5$ is not —$(CH_2)_rNR'R^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl. In other embodiments, the nicotinic acetylcholine receptor ligands of formulas II-IV and VII-VIII, wherein all variables are as defined above for the compounds of formulas II-IV and VII-VIII, respectively, are useful for modulating the activity of a nicotinic acetylcholine receptor. In still other embodiments, the nicotinic acetylcholine receptor ligands of formula V are useful for modulating the activity of a nicotinic acetylcholine receptor, wherein all variables are as defined above for the compounds of formula V, and with the proviso that when Y is a bond, $R_5$ is not —$(CH_2)_rNR'R^{vi}$ when both $R^v$ and $R^{vi}$ are hydrogen, or when one of $R^v$ and $R^{vi}$ is hydrogen and the other of $R^v$ and $R^{vi}$ is $C_1$-$C_6$ straight chain alkyl, $C_3$-$C_6$ branched chain alkyl or $C_3$-$C_6$ cycloalkyl. In still other embodiments, the compounds of formula VI are useful for modulating the activity of a nicotinic acetylcholine receptor, wherein all variables are as defined above for the compounds of formula VI, and with the proviso that when Y is a bond and $Z'''$ is pyridine, $R_5$ is not —$CH_2OH$; or —$(CH_2)_rNR'R^{vi}$ when both $R^v$ and $R^{vi}$ are hydrogen, or when one of $R^v$ and $R^{vi}$ is hydrogen and the other of $R^v$ and $R^{vi}$ is $C_1$-$C_6$ straight chain alkyl, $C_3$-$C_6$ branched chain alkyl or $C_3$-$C_6$ cycloalkyl.

In various embodiments, the compounds of formulas I-VIII, wherein all variables are as defined above for the compounds of formulas I-VIII, respectively, are useful for treating depression.

In additional embodiments, the nicotinic acetylcholine receptor ligands of formulas I-IV and VII-VIII, wherein all variables are as defined above for the compounds of formulas I-IV and VI-VIII, respectively, are useful for treating or preventing a condition selected from Alzheimer's disease, Parkinson's disease, age-related cognitive impairment, disease-related cognitive impairment, dyskinesias, Tourette's syndrome, schizophrenia, attention-deficit hyperactivity disorder, depression, anxiety, mood disorders, pain, methamphetamine addiction and nicotine addiction. In various embodiments, the compounds of formula V are useful for treating or preventing a condition selected from Alzheimer's disease, Parkinson's disease, age-related cognitive impairment, disease-related cognitive impairment, dyskinesias, Tourette's syndrome, schizophrenia, attention-deficit hyperactivity disorder, depression, anxiety, mood disorders, pain, methamphetamine addiction and nicotine addiction, wherein all variables are the same as defined above for the compounds of formula V, and with the proviso that when Y is a bond, $R_5$ is not —$(CH_2)_rNR'R^{vi}$ when both $R^v$ and $R^{vi}$ are hydrogen, or one of $R^v$ and $R^{vi}$ is hydrogen and the other of $R^v$ and $R^{vi}$ is $C_1$-$C_6$ straight chain alkyl, $C_3$-$C_6$ branched chain alkyl or $C_3$-$C_6$ cycloalkyl. In other embodiments, the compounds of formula VI are useful for treating or preventing a condition selected from Alzheimer's disease, Parkinson's disease, age-related cognitive impairment, disease-related cognitive impairment, dyskinesias, Tourette's syndrome, schizophrenia, attention-deficit hyperactivity disorder, depression, anxiety, mood disorders, pain, methamphetamine addiction and nicotine addiction, wherein all variables are the same as defined above for the compounds of formula VI, and with the proviso that when Y is a bond and $Z'''$ is pyridine, $R_5$ is not —$CH_2OH$; or —$(CH_2)_rNR'R^{vi}$ when both $R^v$ and $R^{vi}$ are hydrogen, or when one of $R^v$ and $R^{vi}$ is hydrogen and the other of $R^v$ and $R^{vi}$ is $C_1$-$C_6$ straight chain alkyl, $C_3$-$C_6$ branched chain alkyl or $C_3$-$C_6$ cycloalkyl.

Therapeutic/Prophylactic Administration and Compositions of the Invention

Due to their activity, the pyridinyl nicotinic acetylcholine receptor ligands are advantageously useful in human and veterinary medicine. As described above, the pyridinyl nicotinic acetylcholine receptor ligands are useful for treating or preventing a condition in an animal in need thereof. The pyridinyl nicotinic acetylcholine receptor ligands of the invention can be administered to any animal requiring modulation of neuronal nicotinic acetylcholine receptors.

When administered to an animal, a pyridinyl nicotinic acetylcholine receptor ligand can be administered as a component of a composition that comprises a pharmaceutically acceptable carrier or excipient. The invention compositions, which comprise a pyridinyl nicotinic acetylcholine receptor ligand, can be administered orally. A pyridinyl nicotinic acetylcholine receptor ligand can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a pyridinyl nicotinic acetylcholine receptor ligand.

Methods of administration include, but are not limited to, intradermal, intramuscular, intraperitoneal, parenteral, intravenous, subcutaneous, intranasal, epidural, oral, sublingual, intracerebral, intravaginal, transdermal, rectal, by inhalation, or topical, particularly to the ears, nose, eyes, or skin. The method of administration is left to the discretion of the practitioner. In most instances, administration will result in the release of a pyridinyl nicotinic acetylcholine receptor ligand into the bloodstream.

In certain embodiments, it can be desirable to introduce a pyridinyl nicotinic acetylcholine receptor ligand into the central nervous system by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a pyridinyl nicotinic acetylcholine receptor ligand can be formulated as a suppository, with traditional binders and excipients such as triglycerides.

When a pyridinyl nicotinic acetylcholine receptor ligand of the invention is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A pyridinyl nicotinic acetylcholine receptor ligand of the invention can also be in the form of a powder for reconstitution as an injectable formulation.

In another embodiment, a pyridinyl nicotinic acetylcholine receptor ligand can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In yet another embodiment, a pyridinyl nicotinic acetylcholine receptor ligand can be delivered in a controlled-release system or sustained-release system (see, e.g., Goodson, "Dental Applications" (pp. 115-138) in *Medical Applications of Controlled Release, Vol. 2, Applications and Evaluation*, R. S. Langer and D. L. Wise eds., CRC Press (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N. Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a pyridinyl nicotinic acetylcholine receptor ligand, e.g., the spinal column or brain, thus requiring only a fraction of the systemic dose.

The invention compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a pyridinyl nicotinic acetylcholine receptor ligand is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

The invention compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the pyridinyl nicotinic acetylcholine receptor ligands are formulated in accordance with routine procedures as a composition adapted for oral administration to human beings. A pyridinyl nicotinic acetylcholine receptor ligand to be orally delivered can be in the form of tablets, capsules, gelcaps, caplets, lozenges, aqueous or oily solutions, suspensions, granules, powders, emulsions, syrups, or elixirs, for example. When a pyridinyl nicotinic acetylcholine receptor ligand is incorporated into oral tablets, such tablets can be compressed tablets, tablet triturates (e.g., powdered or crushed tablets), enteric-coated tablets, sugar-coated tablets, film-coated tablets, multiply compressed tablets or multiply layered tablets. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems*, (Lieberman, Rieger and Banker, eds.) published by Marcel Dekker, Inc.

When a pyridinyl nicotinic acetylcholine receptor ligand is to be injected parenterally, it can be, e.g., in the form of an isotonic sterile solution. Alternatively, when a pyridinyl nicotinic acetylcholine receptor ligand is to be inhaled, it can be formulated into a dry aerosol or can be formulated into an aqueous or partially aqueous solution.

An orally administered pyridinyl nicotinic acetylcholine receptor ligand can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the pyridinyl nicotinic acetylcholine receptor ligand can be formulated for intravenous administration. Typically, compositions for intravenous administration comprise sterile isotonic aqueous buffer. Where necessary, the compositions can also include a solubilizing agent. A pyridinyl nicotinic acetylcholine receptor ligand for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where a pyridinyl nicotinic acetylcholine receptor ligand is to be administered by infusion, it can be dispensed, for example, with an infusion bottle containing sterile pharmaceutical grade water or saline. Where a pyridinyl nicotinic acetylcholine receptor ligand is administered by injection, an ampule of sterile water for injection or saline can be provided so that the ingredients can be mixed prior to administration.

A pyridinyl nicotinic acetylcholine receptor ligand can be administered by controlled-release or sustained-release means or by delivery devices that are known to those in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydroxypropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a pyridinyl nicotinic acetylcholine receptor ligand to treat or prevent the condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the pyridinyl nicotinic acetylcholine receptor ligand, and can thus reduce the occurrence of adverse side effects.

Controlled- or sustained-release compositions can initially release an amount of a pyridinyl nicotinic acetylcholine receptor ligand that promptly produces the desired therapeutic or prophylactic effect, and gradually and continually release other amounts of the pyridinyl nicotinic acetylcholine receptor ligand to maintain this level of therapeutic or prophylactic effect over an extended period of time. To maintain a constant level of the pyridinyl nicotinic acetylcholine receptor ligand in the body, the pyridinyl nicotinic acetylcholine receptor ligand can be released from the dosage form at a rate that will replace the amount of pyridinyl nicotinic acetylcholine receptor ligand being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the pyridinyl nicotinic acetylcholine receptor ligand that is effective for the treatment or prevention of a condition can be determined by standard clinical techniques. In addition, in vitro and/or in vivo assays can optionally be employed to help identify optimal dosage ranges. The precise dose to be employed will also depend on, e.g., the route of administration and the seriousness of the condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a pyridinyl nicotinic acetylcholine receptor ligand, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 h until the condition is abated. In another embodiment, an effective dosage amount is administered about every 12 h until the condition is abated. In another embodiment, an effective dosage amount is administered about every 8 h until the condition is abated. In another embodiment, an effective dosage amount is administered about every 6 h until the condition is abated. In another embodiment, an effective dosage amount is administered about every 4 h until the condition is abated. The effective dosage amounts described herein refer to total amounts administered; that is, if more than one pyridinyl nicotinic acetylcholine receptor ligand is administered, the effective dosage amounts correspond to the total amount administered.

Where a cell capable of expressing the nicotinic acetylcholine receptor is contacted with a pyridinyl nicotinic acetylcholine receptor ligand in vitro, the amount effective for inhibiting or activating the nAChR function in a cell will typically range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the pyridinyl nicotinic acetylcholine receptor ligand will be from about 0.01 µL to about 1 mL. In another embodiment, the volume of solution or suspension will be about 200 µL.

The pyridinyl nicotinic acetylcholine receptor ligand will have a binding affinity ($K_i$) for the α4β2 nAChR subtype of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment or about 1 nM or less in another embodiment. The binding affinity $K_i$ can be measured in ways known to the art, e.g., by an assay utilizing membranes from recombinant SH-EP1 cells expressing the α4β2 nACh receptor subtype. See, e.g., Eaton J. B. et al. (2003) Mol. Phannacol. 64:1283-1294.

The pyridinyl nicotinic acetylcholine receptor ligand will have a $K_i$ for the α4β2 nAChR subtype that is at least 3-fold lower than the $K_i$ for any other nAChR subtype, including but not limited to the α2β4, the α3β2, the α3β4, the α4β4, and the α4β2* nAChR subtypes in one embodiment, at least 100-fold lower $K_i$ for the α4β2 nAChR subtype than the $K_i$ for any other nAChR subtype in another embodiment, or at least 1000-fold lower $K_i$ for the α4β2 nAChR subtype than the $K_i$ for any other nAChR subtype in yet another embodiment. In yet another embodiment, the pyridinyl nicotinic acetylcholine receptor ligand will have a $K_i$ for the α4β2 nAChR subtype that is at least 10,000-fold lower than the $K_i$ for any other nAChR subtype. In another embodiment, the pyridinyl nicotinic acetylcholine receptor ligand will have a $K_i$ for the α4β2 nAChR subtype that is at least 100,000-fold lower than the $K_i$ for any other nAChR subtype.

Typically, the pyridinyl nicotinic acetylcholine receptor ligand will have a $K_i$ (nM) of from about 1000 to about 0.1 for binding to the α4β2 nAChR subtype. In one embodiment, the pyridinyl nicotinic acetylcholine receptor ligand will have a $K_i$ (nM) of from about 1000 to 600. In another embodiment, the pyridinyl nicotinic acetylcholine receptor ligands of the invention will have a $K_i$ (nM) of from about 600 to about 300. In another embodiment, the pyridinyl nicotinic acetylcholine receptor ligands of the invention will have a $K_i$ (nM) of from about 300 to about 100. In another embodiment, the pyridinyl nicotinic acetylcholine receptor ligands of the invention will have a $K_i$ (nM) of from about 100 to about 35. In another embodiment, the pyridinyl nicotinic acetylcholine receptor ligands of the invention will have a $K_i$ (nM) of from about 35 to about 20. In another embodiment, the pyridinyl nicotinic acetylcholine receptor ligands of the invention will have a $K_i$ (nM) of from about 20 to about 15. In another embodiment, the pyridinyl nicotinic acetylcholine receptor ligands of the invention will have a $K_i$ (nM) of from about 15 to about 10. In another embodiment, the pyridinyl nicotinic acetylcholine receptor ligands of the invention will have a $K_i$ (nM) of from about 10 to about 4. In another embodiment, the pyridinyl nicotinic acetylcholine receptor ligands of the invention will have a $K_i$ (nM) of from about 4 to about 1. In another embodiment, the pyridinyl nicotinic acetylcholine receptor ligands of the invention will have a $K_i$ (nM) of from about 1 to about 0.4. In another embodiment, the pyridinyl nicotinic acetylcholine receptor ligands of the invention will have a $K_i$ (nM) of from about 0.4 to about 0.1 or less.

In some embodiments, the nicotinic acetylcholine receptor ligands of the invention are partial agonists of nicotinic acetylcholine receptors, and do not elicit as large a functional response at the receptors as a full agonist, such as nicotine. In other embodiments, the nicotinic acetylcholine receptor ligands of the invention are partial agonists that are selective for the α4β2 receptor subtype.

Where a cell capable of expressing nicotinic acetylcholine receptors is contacted with a pyridinyl nicotinic acetylcholine receptor ligand in vitro, the amount effective for inhibiting or activating the α4β2 nAChR subtype function in a cell will typically range from about $1\times10^{-12}$ mol/L to about 0.1 mol/L, in one embodiment, from about $1\times10^{-9}$ mol/L to about 0.01 mol/L, and in another embodiment, from about $1\times10^{-6}$ mol/L to about 0.001 mol/L of a pyridinyl nicotinic acetylcholine receptor ligand in a solution or suspension of a pharmaceutically acceptable carrier or excipient. In one embodiment, the volume of solution or suspension comprising the pyridinyl nicotinic acetylcholine receptor ligand will be from about 0.01 μL to about 1 mL. In another embodiment, the volume of solution or suspension will be about 100 μL to 200 μL.

The pyridinyl nicotinic acetylcholine receptor ligands will have a binding affinity ($K_i$) for the human α4β2 nAChR subtype of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment.

The pyridinyl nicotinic acetylcholine receptor ligands can be assayed in vitro or in vivo for the desired therapeutic or prophylactic activity prior to use in humans. Animal model systems can be used to demonstrate safety and efficacy.

The invention methods for treating or preventing a condition in an animal in need thereof can further comprise co-administering to the animal being administered a pyridinyl nicotinic acetylcholine receptor ligand (i.e., a first therapeutic agent) a second therapeutic agent. In one embodiment, the second therapeutic agent is administered in an effective amount.

An effective amount of the second therapeutic agent will be known to the art depending on the agent. However, it is well within the skilled artisan's purview to determine the second therapeutic agent's optimal effective-amount range. In one embodiment of the invention, where a second therapeutic agent is administered to an animal for treatment of a condition (e.g., depression), the minimal effective amount of the pyridinyl nicotinic acetylcholine receptor ligand will be less than its minimal effective amount would be where the second therapeutic agent is not administered. In this embodiment, the pyridinyl nicotinic acetylcholine receptor ligand and the second therapeutic agent can act synergistically to treat or prevent a condition.

The second therapeutic agent can be, but is not limited to, an agent for treating or preventing pain, an agent for treating or preventing anxiety, an agent for treating or preventing a memory disorder, an agent for treating or preventing nicotine addiction, an agent for treating or preventing Parkinson's disease and parkinsonism, an agent for treating or preventing psychosis associated with schizophrenia, an agent for treating or preventing a cognitive disorder, an agent for treating or preventing dyskinesias, an agent for treating or preventing depression or a mood disorder, an agent for treating or preventing Alzheimer's disease, an agent for treating or preventing Tourette's syndrome, an agent for treating or preventing pain, an agent for treating or preventing attention-deficit hyperactivity disorder, or any mixture thereof.

Examples of useful agents for treating or preventing pain include, but are not limited to, opioid agonists such as alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

Other agents useful for treating or preventing pain include non-opioid analgesics such as non-steroidal anti-inflammatory agents, e.g., aspirin and other salicylic acid derivatives, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof.

Still other agents useful for treating or preventing pain include Cox-II inhibitors and 5-lipoxygenase inhibitors. Cox-II inhibitors include, but are not limited to, celecoxib, flosulide, meloxicam, rofecoxib, nabumetone, nimesulide, etoricoxib, valdecoxib, and parecoxib.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing depression or a mood disorder include, but are not limited to, amytriptyline, amoxapine, clomipramine, desipramine, doxepin, imipramine, maprotiline, nortriptyline, protriptyline, trimipramine, citalopram, fluoxetine, fluvoxamine, paroxetine, sertraline, phenelzine, tranylcypromine, bupropion, mirtazapine, nefazodone, trazodone, venlafaxine or any mixtures thereof.

Examples of useful therapeutic agents for treating or preventing psychosis associated with schizophrenia include, but are not limited to, chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, ziprasidone, or any mixtures thereof.

Examples of useful therapeutic agents for treating or preventing nicotine addiction include, but are not limited to, bupropion, varenicline, nicotine gum, nicotine lozenges, nicotine patches, nicotine inhaler, nicotine nasal spray or any mixtures thereof.

Examples of useful therapeutic agents for treating or preventing methamphetamine addiction include, but are not limited to, chlorpromazine and haloperidol.

Examples of useful therapeutic agents for treating or preventing dyskinesias include, but are not limited to, a benzodiazepine, an opioid, reserpine, propranolol or mixtures thereof.

Examples of useful therapeutic agents for treating or preventing Parkinson's Disease or parkinsonism, but are not limited to, levodopa-carbidopa, amantadine, dopamine agonists such as pramipexole, ropinerole, rotigotine, and apomorphine, monoamine oxidase inhibitors such as rasagiline and selegiline, entacapone, tolcapone, benztropine, trihexyphenidyl, propranolol or mixtures thereof.

Examples of useful therapeutic agents for treating or preventing Alzheimer's disease include, but are not limited to, donepezil, galantamine, rivastigmine, tacrine or mixtures thereof.

Examples of useful therapeutic agents for treating or preventing attention-deficit hyperactivity disorder include, but are not limited to, methylphenidate, dextroamphetamine, methamphetamine, lisdexamphetamine dimesylate, clonidine, antianxiety agents or mixtures thereof.

Examples of useful therapeutic agents for treating or preventing Tourette's syndrome include, but are not limited to, clonidine, guanfacine, clonazepam, diazepam, haloperidol, olanzapine, pimozide, risperidone, or mixtures thereof.

Examples of useful therapeutic agents for treating or preventing pain, anxiety, a memory disorder, nicotine addiction, methamphetamine addiction, pain, Parkinson's disease and parkinsonism, psychosis associated with schizophrenia, a cognitive disorder, dyskinesias, depression, anxiety, a mood disorder, Alzheimer's disease, and Tourette's syndrome include those that are known in the art and can be selected by those skilled in the art.

A pyridinyl nicotinic acetylcholine receptor ligand and the second therapeutic agent combined can act either additively or synergistically to treat the same condition, or they may act independently of each other such that the pyridinyl nicotinic acetylcholine receptor ligand treats or prevents a first condition and the second therapeutic agent treats or prevents a second condition. In one embodiment, a pyridinyl nicotinic acetylcholine receptor ligand is administered concurrently with a second therapeutic agent as a single composition comprising an effective amount of a pyridinyl nicotinic acetylcholine receptor ligand and an effective amount of the second therapeutic agent. Alternatively, a composition comprising an effective amount of a pyridinyl nicotinic acetylcholine receptor ligand and a second composition comprising an effective amount of the second therapeutic agent are concurrently administered. In another embodiment, an effective amount of a pyridinyl nicotinic acetylcholine receptor ligand is administered prior or subsequent to administration of an effective amount of the second therapeutic agent. In this embodiment, the pyridinyl nicotinic acetylcholine receptor ligand is administered while the second therapeutic agent exerts its therapeutic effect, or the second therapeutic agent is administered while the pyridinyl nicotinic acetylcholine receptor ligand exerts its therapeutic effect for treating or preventing a condition.

A composition of the invention is prepared by a method comprising admixing a pyridinyl nicotinic acetylcholine receptor ligand or a pharmaceutically acceptable derivative thereof with a pharmaceutically acceptable carrier or excipient. Admixing can be accomplished using methods known for admixing a compound (or derivative) and a pharmaceutically acceptable carrier or excipient. In one embodiment, the pyridinyl nicotinic acetylcholine receptor ligand is present in the composition in an effective amount.

Kits

The invention further provides kits that can simplify the handling and administration of a pyridinyl nicotinic acetylcholine receptor ligand to an animal.

A typical kit of the invention comprises a unit dosage form of a pyridinyl nicotinic acetylcholine receptor ligand. In one embodiment, the unit dosage form comprises a first container, which can be sterile, containing an effective amount of a pyridinyl nicotinic acetylcholine receptor ligand and a pharmaceutically acceptable carrier or excipient. The kit can further comprise a label or printed instructions instructing the use of the pyridinyl nicotinic acetylcholine receptor ligand to treat or prevent a condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a pyridinyl nicotinic acetylcholine receptor ligand, an effective amount of a second therapeutic agent and a pharmaceutically acceptable carrier or excipient. Examples of second therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

EXAMPLES

General Chemistry Methods

All starting materials, solvents, and reagents were used as obtained from commercial sources unless otherwise indicated. Oil pump vacuum was generated with pumps rated for a final vacuum of at least 0.01 torr, but because of imperfect sealing and the substantial length of vacuum tubing between the pump and the evacuated apparatus is estimated to have been in the range of 0.1 to 1 torr. For reactions that were performed under a controlled atmosphere, if not described otherwise in the example, the atmosphere was exchanged by repeated evacuation and admission of the required gas at the beginning of the procedure. Where details are not mentioned, drying of solutions over a solid desiccant entails (1) addition of an effective amount of the drying agent to the solution, (2) agitation by stirring or swirling for several minutes, or until the solution appears clear, (3) filtration from the drying agent over a paper filter, cotton plug, or with gentle suction over a glass frit preferably covered with a thin layer of celite, and (4) rinsing of the filter residue with one or several small volumes of solvent. $^1$H and $^{13}$C NMR spectra were recorded on a variety of instruments at the indicated operating frequencies. $^1$H chemical shifts are reported in ppm downfield from tetramethylsilane (TMS). TMS was contained in low concentration in the deuterated solvent as the internal standard if so indicated, or otherwise the deuterium frequency of the solvent peak was used as a reference. $^{13}$C chemical shifts are referenced to CDCl$_3$ (central peak, δ=77.00 ppm) as the internal standard. Mass spectra were measured in positive mode electrospray ionization (ESI) or in electron impact ionization mode (EI; 70 eV, direct inlet).

Example 1

Synthesis of (1S,2S)-2-[5-[(2(S)-Azetidinyl)methoxy]-3-pyridyl]cyclopropylmethanol This compound was prepared according to Schemes 1a and 1c. An alternative route to its protected precursor is provided in Scheme 1b. Each step is described under the appropriate sub-headings below.

3-(Benzyloxy)-5-bromopyridine (Zhu. G.-D. et al., *Bioorg. Med. Chem. Lett.* 2006, 16, 3150-3155)

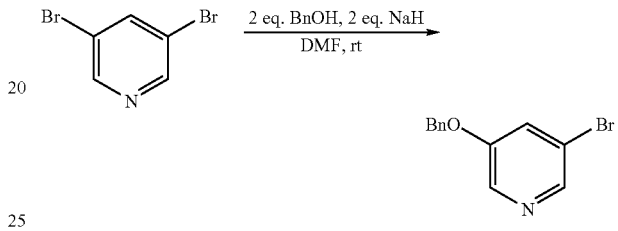

A 500 mL three-necked flask was charged with sodium hydride (60% dispersion in oil; 9.6 g, 240 mmol, 2.0 equiv.) and fitted out with stir bar, dropping funnel, N$_2$ balloon, and septa. The sodium hydride was washed with hexane (2×150 mL), then anhydrous DMF (110 mL) was added. With stirring and intermittent ice cooling, benzyl alcohol (25 mL, 240 mmol, 2.0 equiv.) was added dropwise within 105 min. The temperature was kept high enough to permit efficient stirring and prevent excessive frothing. After the addition was finished, the dropping funnel was rinsed with anhydrous DMF. Stirring was continued at room temperature for 20 min. The flask was briefly opened to add 3,5-dibromopyridine (28.4 g, 120 mmol) all at once. The atmosphere was again replaced with N$_2$, and the reaction mixture was stirred at room temperature for 15 h. A thin layer chromatogram (small aliquot quenched into EtOAc/H$_2$O; silica gel, EtOAc/hexane 15:85) taken shortly before the end of this period demonstrated the near-absence of starting material (R$_f$ 0.6) and the formation of a product (R$_f$ 0.25); benzyl alcohol was detected at R$_f$ 0.15. The bulk of DMF was distilled in an oil pump vacuum at a bath temperature of 40° C. into a receiver cooled with acetone/dry ice. Initial foaming was due to the evaporation of residual hexane. The receiver was subsequently changed to maintain a high vacuum. The residue was taken up in diethyl ether (300 mL) and the resulting suspension poured into ice water (300 mL). The phases were separated, and the aqueous phase was twice extracted with ether (100 mL each). The combined organic phases were washed with brine (100 mL) and dried over MgSO$_4$ (15 g). Evaporation furnished an orange-colored liquid together with a colorless solid. After transfer into a 200 mL flask, benzyl alcohol was distilled off in an oil pump vacuum into a −78° C. receiver. The product began to crystallize after partial cooling, whereon methanol (60 mL) was added. Crystallization was initially allowed to proceed at room temperature, then in the freezer overnight.

The product was isolated by suction filtration, washed with two portions of freezer-chilled methanol (20 mL each), and dried (40° C./oil pump) to obtain 23.2 g (73%) of light-tan crystals (mp 67-68.5° C.). The mother liquor was concentrated to a few mL, diluted with methanol (15 mL), seeded, and placed in the freezer. Isolation as above gave 1.7 g of a solid which upon TLC examination revealed contamination with polar material. The second mother liquor still contained substantial amounts of benzyl alcohol, which was removed by evaporation into a 50 mL flask and bulb-to-bulb distillation at 80° C. in an oil pump vacuum until by visual appearance no further distillate was formed. The dark residue (2.7 g) together with the impure second crystal fraction was taken up in $CH_2Cl_2$ (3 mL) and chromatographed on silica gel (25×3.8 cm, EtOAc/hexane 1:9) to yield, after evaporation and drying, another 2.4 g (8%) of the product 2. $^1$H NMR ($CDCl_3$, 300 MHz) δ 8.33 (narrow m, 2H), 7.50-7.32 (m, 6H), 5.11 (s, 2H).

trans-3-[5-(Benzyloxy)-3-pyridyl]acrylic acid n-Butyl Ester (reaction conditions, with 3-bromopyridine as example: Cui, X.; Zhou, Y.; Wang, N.; Liu, L.; Guo, Q.-X. *Tetrahedron Lett.* 2007, 48, 163-167)

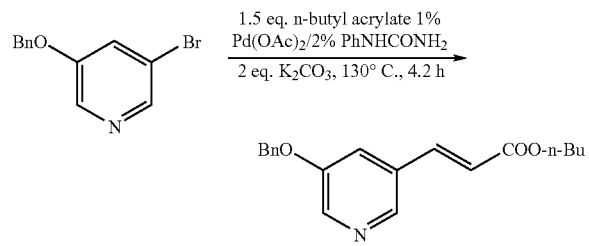

A 500 mL round-bottom flask with stir bar was charged with 3-(benzyloxy)-5-bromopyridine (23.2 g, 87.8 mmol), palladium(II) acetate (198 mg, 0.88 mmol, 0.01 equiv.), phenylurea (240 mg, 1.76 mmol, 0.02 equiv.), finely ground potassium carbonate (24.3 g, 176 mmol, 2 equiv.), and anhydrous DMF (160 mL). n-Butyl acrylate (18.9 mL, 132 mmol, 1.5 equiv.) was added. The flask was fitted with a reflux condenser and $N_2$ balloon and, after exchange of the atmosphere, placed in an oil bath and heated at 130° C. for 250 min. The initially orange-colored reaction mixture soon turned black. After cooling, volatiles were distilled off in an oil pump vacuum at a bath temperature of 40° C. into a receiver cooled with acetone/dry ice. The residue was taken up in EtOAc (100 mL) and filtered over a 1 cm layer of celite in a coarse frit. The filtration residue was washed with two portions of EtOAc (50 mL each). After evaporation, the residue was taken up in the eluent (10 mL) and chromatographed on silica gel (23×5 cm, EtOAc/hexane 2:3). Impure early and late fractions were combined, evaporated, and again chromatographed on silica gel (24×2.5 cm, EtOAc/hexane 1:2). All pure fractions were combined, evaporated, and dried (40° C./oil pump) to obtain 27.5 g (100.5%, apparently traces of solvent) of the product as a tan solid.

A sample was recrystallized from a small volume of methanol (gentle warming, then freezer) to yield colorless crystals. Mp 57.5-58.5° C. $^1$H NMR ($CDCl_3$, 300 MHz) δ 8.40 (s, 2H), 7.66 (d, 1H, J=16.2 Hz), 7.48-7.33 (m, 6H), 6.50 (d, 1H, J=16.2 Hz), 5.17 (s, 2H), 4.25 (t, 2H, J=6.7 Hz), 1.73 (m, 2H), 1.46 (sextuplet, 2H, J=7.4 Hz), 0.97 (t, 3H, J=7.1 Hz). MS (EI) m/z 311 ($M^+$, 5.2%), 238 ($M^+$-OBu, 1.1%), 91 (100%).

trans-3-[5-(Benzyloxy)-3-pyridyl]acrylic Acid

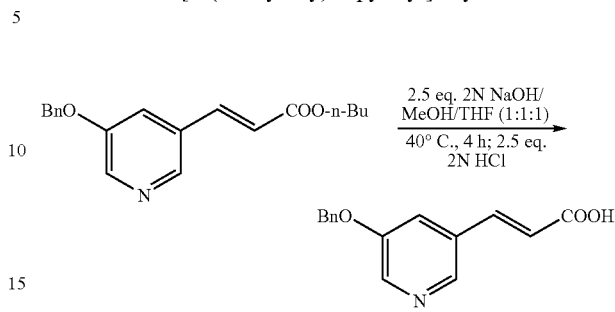

Trans-3-[5-(benzyloxy)-3-pyridyl]acrylic acid n-butyl ester (27.3 g, 87.7 mmol) was dissolved in THF (110 mL) and methanol (110 mL) in a 1 L round-bottom flask with stir bar. To this solution was added approx. 2N aqueous NaOH (110 mL, approx. 220 mmol, 2.5 equiv.). The homogeneous solution was warmed to 40° C. for 4 h while the flask was loosely stoppered. At this point, TLC (silica gel, EtOAc/hexane 3:7) showed the presence of baseline material only. After cooling to room temperature, approx. 2N aqueous HCl (114 mL, approx. 220 mmol, 2.5 equiv.) was added.[1] The resulting pH (by indicator paper) was 5-6.

[1] Before use, the base and acid were titrated against each other to ensure accurate neutralization. 1.00 mL of NaOH was found to be equivalent to 1.035 mL of HCl, which corresponds to the above volume ratio.

The resulting warm solution, upon cooling to room temperature, deposited the product as a crystalline solid. Crystallization was completed by storage in an ice bath for 2 h. The light-tan solid was isolated by suction filtration over a C frit, washed with methanol/$H_2O$ 1:1 (30 mL) and water (30 mL), and dried (70° C./oil pump) to furnish 20.2 g (90%) of the carboxylic acid. The compound sintered from 132° C. on and then melted at 140° C. MS (EI) m/z 255 ($M^+$, 3.3%), 91 (100%). $^1$H NMR ($CDCl_3$, 300 MHz) δ 8.45 (narrow m, 2H), 7.76 (d, 1H, J=16.5 Hz), 7.50-7.33 (m, 6H), 6.55 (d, 1H, J=16.2 Hz), 5.19 (s, 2H). MS (EI) m/z 255 ($M^+$, 3.3%), 91 (100%).

Upon concentration to 270 mL, the mother liquor deposited an additional, darker-colored solid which adhered to the wall of the flask. The liquid phase was decanted and the solid washed by decantation with two portions of water (20 mL each). The solid was then recrystallized from a boiling mixture of water (50 mL) and ethanol (30 mL). After filtration (some loss due to premature crystallization), the solution was placed in an ice bath. The second crystal crop was isolated by suction filtration, washed with ethanol/water 1:2 (6 mL), and dried as above. Thus was obtained an additional 1.3 g (6%) of the carboxylic acid as a tan solid.

trans-3-[5-(Benzyloxy)-3-pyridyl]-N-methoxy-N-methylacrylamide via amide Formation with a Coupling Reagent

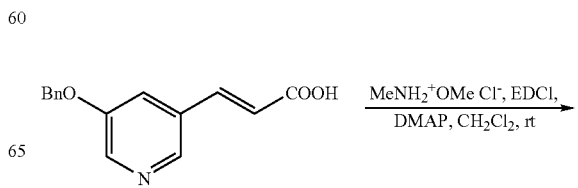

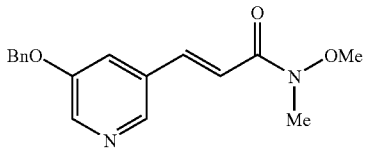

A solution of trans-3-[5-(benzyloxy)-3-pyridyl]acrylic acid (36.0 g, 141 mmol), N,O-dimethylhydroxylamine hydrochloride (17.9 g, 183 mmol, 1.3 equiv.), 4-(dimethylamino)pyridine (DMAP; 17.2 g, 141 mmol, 1.0 equiv.) and N-ethyl-N'-[3-(dimethylamino)propyl]carbodiimide hydrochloride (EDCI, 27.0 g, 141 mmol, 1.0 equiv.) in $CH_2Cl_2$ (700 mL) was stirred for 2 h at room temperature under $N_2$. The solution was washed with hydrochloric acid (pH 2) until the pH of the aqueous layer was acidic. The organic layer was dried over $Na_2SO_4$. After filtration and concentration, the residue was purified by CC on silica gel with EtOAc/petroleum ether 1:10-1:5. This resulted in 36.0 g (86%) of the amide as a yellowish solid; mp 87-90° C. $^1$H NMR ($CDCl_3$, 300 MHz) δ 8.43 (s, 1H), 8.38 (d, 1H, J=3.0 Hz), 7.70 (d, 1H, J=15.6 Hz), 7.49-7.32 (m, 6H), 7.08 (d, 1H, J=15.9 Hz), 5.17 (s, 2H), 3.79 (s, 3H), 3.33 (s, 3H). MS (EI) m/z 298 ($M^+$, 0.4%), 268 ($M^+$-$CH_2O$, 0.6%), 238 [$M^+$-N(Me)OMe, 17%], 91 (100%); LC-MS (ESI) m/z 299 ($M+H^+$).

trans-3-[5-(Benzyloxy)-3-pyridyl]-N-methoxy-N-methylacrylamide via the acid chloride

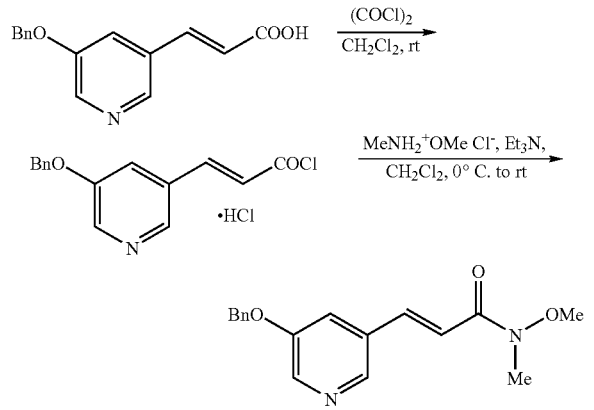

For small-scale preparations, the following method can also be used: Oxalyl chloride (0.20 mL, 2.3 mmol, 2.0 equiv.) was added all at once to a suspension of trans-3-[5-(benzyloxy)-3pyridyl]acrylic acid (302 mg, 1.18 mmol) in anhydrous $CH_2Cl_2$ (3 mL) in a 100 mL round bottom flask with stir bar and drierite tube. An exotherm and immediate gas evolution ensued. The carboxylic acid initially dissolved, then a new precipitate appeared. After the mixture had been stirred at room temperature for 13 min, volatiles were evaporated. The residual acid chloride hydrochloride was evaporated with toluene (10 mL; in order to remove residual oxalyl chloride) and then briefly dried (35° C./14 torr).

In the meantime, triethylamine (0.82 mL, 5.9 mmol, 5.0 equiv.) was added at room temperature to a suspension of N,O-dimethylhydroxylamine hydrochloride (230 mg, 2.36 mmol, 2.0 equiv.) in $CH_2Cl_2$ (5 mL). After stirring at room temperature for 10 min, the suspension was cooled in an ice bath with exclusion of moisture (drierite tube). The above solid acid chloride hydrochloride was added portionwise in 17 min. After each addition, a yellow to orange color appeared or intensified and then gradually but incompletely faded. The mixture was stirred in the ice bath for 10 min and then (to avoid mechanical losses) poured back into the 100 mL flask to which residual acid chloride hydrochloride adhered. Stirring was continued at room temperature. After 70 min, TLC analysis (silica gel, EtOAc) showed a major spot ($R_f$ 0.35) together with a nonpolar and a polar byproduct and baseline material. After 85 min, water (10 mL) was added, and the phases were separated.

The aqueous phase was extracted with two portions of EtOAc (10 mL each). Without drying, the combined organic phases were evaporated, and the residue was chromatographed on silica gel (24×2.5 cm, ethyl acetate/hexane 85:15). The product eluted very broadly, requiring approx. 900 mL of eluent. Evaporation of appropriate fractions and drying of the residue (40° C./oil pump) delivered 270 mg (76%) of the title compound as a slightly colored syrup.

(±)-trans-2-[5-(Benzyloxy)-3-pyridyl]-N-methoxy-N-methylcyclopropanecarboxamide (general method: Toy, P. H.; Dhanabalasingam, B.; Newcomb, M.; Hanna, I. H.; Hollenberg, P. F. *J. Org. Chem.* 1997, 62, 9114-9122.[2])

[2] The good yields obtained by the authors with Weinreb amides contrast favorably with lower yields reported by others for esters, e. g., for 3-(3-pyridyl) acrylic acid methyl ester (34%): Gooden, D. M.; Schmidt, D. M. Z.; Pollock, J. A.; Kabadi, A. M.; McCafferty, D. G. *Bioorg. Med. Chem. Lett.* 2008, 18, 3047-3051. In our hands, 3-[5-(benzyloxy)-3-pyridyl]acrylic acid n-butyl ester gave a poor yield of the cyclopropanation product.

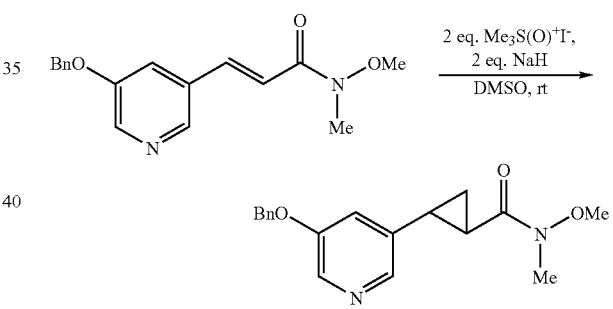

In a 500 mL three-necked flask with magnetic stirrer, septa, and a room temperature water bath, was placed trimethylsulfoxonium iodide (19.9 g, 90.5 mmol, 2.0 equiv.) in anhydrous DMSO (80 mL). Most of the air was displaced from the flask by introduction of nitrogen from a tube into one opened neck. The open neck was re-stoppered with a septum on which a $N_2$ balloon was placed through a needle. IMPORTANT PRECAUTION: To prevent any spilled NaH from falling into water, the water bath was covered tightly with aluminum foil. Sodium hydride (60% dispersion in oil; 3.6 g, 90.5 mmol, 2.0 equiv.) was added in portions over a period of 25 min to the flask through a temporarily opened neck. After the addition was finished, stirring was continued until $H_2$ evolution became slow. Two septa were removed from the flask, and one neck was fitted with a dropping funnel containing trans-3-[5-(benzyloxy)-3-pyridyl]-N-methoxy-N-methylacrylamide (13.5 g, 45.3 mmol) in anhydrous DMSO (40 mL; starting material needs gentle warming to dissolve completely), which was stoppered with a septum. The second open neck was attached to a $N_2$ balloon by way of a three-way stopcock, and the atmosphere was exchanged. The water bath was removed. Stirring at room temperature for 60 min led to a milky suspension. The solution of the starting material was added dropwise in 30 min (insignificant exotherm). After 2 h at room temperature, a small aliquot was quenched into ether/dilute brine for TLC analysis (silica gel, EtOAc). Besides oil moving with the solvent front, a single spot was detected ($R_f$ 0.28; starting material: $R_f$ 0.33). After 2.5 h, the reaction mixture was poured into saturated aqueous $NH_4Cl$ solution (500 mL), causing an exotherm, and enough ice was added to return the mixture to room temperature. The product was extracted into ether (3 portions of 200 mL each). The combined organic phases were concentrated to approx. 200 mL and washed with brine (50 mL). Evaporation yielded 16.5 g of two liquid phases (the oil from NaH forming the smaller, second phase). TLC on silica gel with $CH_2Cl_2$/MeOH 95:5 showed the product at $R_f$ approx. 0.45, the oil from NaH at the solvent front, and traces of polar impurities. This residue was chromatographed on silica gel (24×5 cm, $CH_2Cl_2$/MeOH 97:3 to remove the oil, then 95:5). The later fractions contained a polar contaminant, but HPLC analysis indicated that its amount was too low for concern. The product-containing fractions were pooled, evaporated, and dried (50° C./oil pump) to yield 13.1 g (93%) of the cyclopropane as a yellowish syrup. $^1H$ NMR (300 MHz, $CDCl_3$) δ 8.25 (br s, 1H), 8.11 (s, 1H), 7.48-7.32 (m, 5H), 6.99 (narrow m, 1H), 5.13 (s, 2H), 3.71 (s, 3H), 3.26 (s, 3H), 2.55-2.38 (m, 2H), 1.68 (m, 1H), 1.31 (m, 1H). MS (EI) m/z 312 ($M^+$, 0.6%), 281 ($M^+$-$OCH_3$, 1.6%), 252 [$M^+$-N(Me)OMe, 4.4%], 221 (3.8%), 91 (100%).

(±)-trans-2-[5-(Benzyloxy)-3-pyridyl]cyclopropyl-methanol

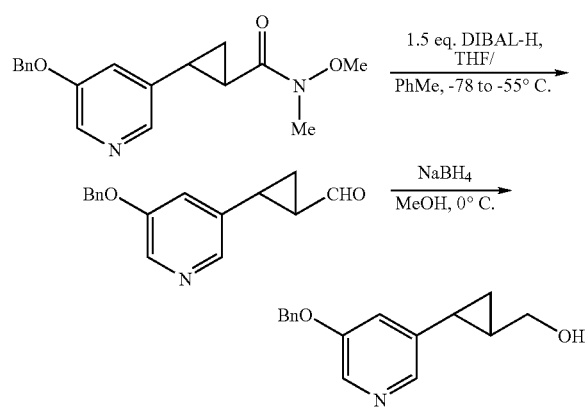

A 500 mL flask equipped with two-neck adapter, stir bar, $N_2$ balloon, and septum was charged with a solution of (±)-trans-2-[5-(benzyloxy)-3-pyridyl]-N-methoxy-N-methylcyclopropanecarboxamide (13.1 g, 41.9 mmol) in THF (150 mL, anhydrous from septum bottle). Diisobutylaluminum hydride (1.0M in toluene, 63 mL, 1.5 equiv.) was added dropwise from a syringe in 35 min at −78° C. (acetone/$CO_2$ bath). The mixture was stirred at −78° C. for 50 min, then the cold bath was allowed to thaw. At a total of 60 min after the end of the addition, a small aliquot was quenched into EtOAc/saturated potassium sodium tartrate solution and analyzed by TLC (silica gel, EtOAc/hexane 3:1). Besides a strong baseline spot, the product appeared at $R_f$ 0.4, with no starting material ($R_f$ 0.2) remaining. After a total of 90 min (−55° C., yellow solution), the cold bath was removed, and saturated potassium sodium tartrate solution (100 mL) was added. The mixture was stirred vigorously without temperature control for 75 min (gentle exotherm, disappearance of color). The phases were separated, and the organic phase was twice extracted with EtOAc (100 mL each). The combined organic phases were washed with brine (100 mL) and dried over $Na_2SO_4$ (30 g). The drying agent was filtered off with suction, the filtrate was evaporated (bath 30° C.), and the residue was evaporated with toluene (30 mL) to leave a slightly turbid yellow oil.

The residue contained in a 1 L round-bottom flask with magnetic stirrer was taken up in methanol (200 mL). The moisture-protected (balloon) solution was placed in an ice bath, and $NaBH_4$ (4.75 g, 126 mmol, 3.0 equiv.) was added portionwise in 15 min. Some gas evolution occurred, and the yellow color faded. The reaction mixture was stirred in the ice bath. After 20 min, TLC analysis (silica gel, EtOAc) revealed the presence of a polar product ($R_f$ 0.25) besides a weak nonpolar spot ($R_f$ 0.7) and a mere trace of unreacted aldehyde. After a total of 40 min, the mixture was concentrated (bath 35° C.) to a small volume (foaming!), and the residue was taken up in cold water (100 mL) and extracted (CAUTION, some gas evolution) three times with EtOAc (50 mL each). The combined organic phases were washed with brine (50 mL) and evaporated without drying. The residue was subjected to CC on silica gel (26×5 cm, EtOAc/hexane 2:1 until appearance of the alcohol, then EtOAc/EtOH 10:1 for the product). The product-containing fractions were evaporated and dried on the rotary evaporator at 50° C./oil pump to furnish 10.1 g (94%) of a yellowish syrup. MS (EI) m/z 255 ($M^+$, 6.1%), 91 (100%).

Further purification can be achieved by preparative HPLC. The pre-purified alcohol (150 mg) was taken up in DMSO (1 mL), and the solution was filtered over a cotton plug. This solution was injected in two approximately equal portions onto a preparative HPLC column (Supelco Discovery $C_{18}$, 250×21.2 mm, 5 μm particle size) which was operated at a flow of 12.5 mL/min with UV detection at 270 nm. Elution was isocratic for 8 min with 20% $CH_3CN$/$H_2O$ followed by a gradient leading to 100% $CH_3CN$ in another 40 min. The alcohol eluted at $t_R$ 26.5-27.4 min. Its solution was partially evaporated to remove $CH_3CN$, and the alcohol then extracted into three portions of $CH_2Cl_2$ (10 and 2×5 mL). The combined organic phases were dried over $MgSO_4$ and evaporated. The material gradually solidified after standing in a freezer overnight. After drying (40° C./oil pump) there was obtained 128 mg of colorless crystals. Mp 67-69° C. $^1H$ NMR ($CDCl_3$, TMS, 400 MHz) δ 8.16 (d, 1H, J=2.8 Hz), 8.03 (d, 1H, J=1.8 Hz), 7.44-7.32 (m, 5H), 6.88 (m, 1H), 5.08 (s, 2H), 3.67, 3.61 (ABq, 2H, J=11.4 Hz, low-field part d with J=6.0 Hz, high-field part d with J=6.9 Hz), 1.89 (br, 1H, OH), 1.81 (m, 1H), 1.45 (m, 1H), 1.02-0.93 (m, 2H).

(1S,2S)-2-[5-(Benzyloxy)-3-pyridyl]cyclopropyl-methanol and (1R,2R)-2-[5-(Benzyloxy)-3-pyridyl] cyclopropylmethanol The above racemate was resolved by preparative HPLC on the chiral stationary phase, Chiralpak® AD (Chiral Technologies, Inc.). For analytical separations, the column dimensions were 250×4.6 mm, the mobile phase methanol, and the flow rate 1 mL/min. The resulting chromatogram exhibited a separation factor of 2.4 and better than baseline resolution. The retention times of the individual enantiomers were 7.7 and 14.3 min, respectively. On a preparative scale, the separation of 9.0 g of racemate yielded 4.5 g each of the enantiomers with at least 99.8% enantiomeric excess. The (S,S)-enantiomer eluted first; $[α]_D$ −69.3, $[α]_{546}$ −83.4 (c 7.6 g/L, EtOAc).

Alternatively, supercritical fluid chromatography (SFC) resolution of 24.0 g of racemate on Chiralpak AD-H at 40° C. with methanol/$CO_2$ 2:3 gave 12.1 g of the first-eluting enantiomer of 100% enantiomeric excess and 10.3 g of the second-eluting enantiomer of 99.5% enantiomeric excess. The (S,S)-enantiomer eluted as the second peak under these conditions; $[\alpha]_D$ −71.1, $[\alpha]_{546}$ −85.5 (c 8.65 g/L, EtOAc).

The absolute configuration of the levorotatory enantiomer was established as the required (S,S)-configuration by its independent synthesis through enantioselective cyclopropanation employing the Charette protocol (Charette, A. B.; Juteau, H.; Lebel, H.; Molinaro, C. Enantioselective Cyclopropanation of Allylic Alcohols with Dioxaborolane Ligands: Scope and Synthetic Applications. *J. Am. Chem. Soc.* 1998, 120, 11943-11952), for which the stereochemical outcome is well-precedented. The chemical yield and enantiomeric purity were, however, inadequate to procure sufficient amounts of pure material on this route.

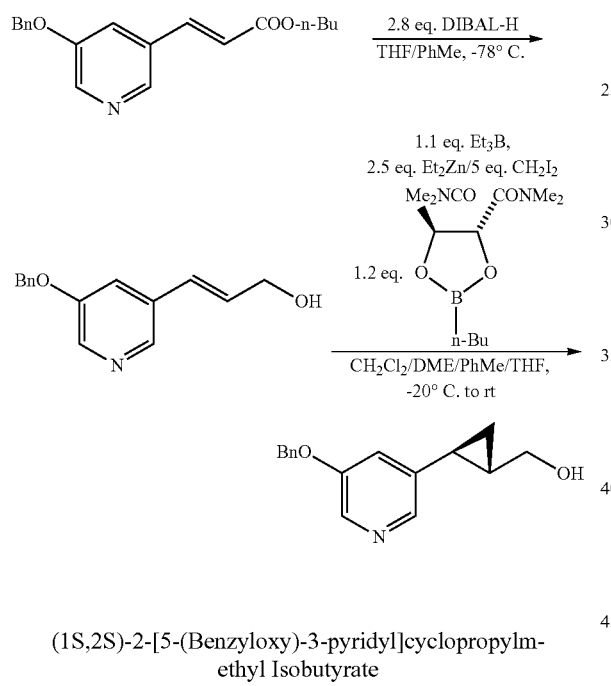

(1S,2S)-2-[5-(Benzyloxy)-3-pyridyl]cyclopropylmethyl Isobutyrate

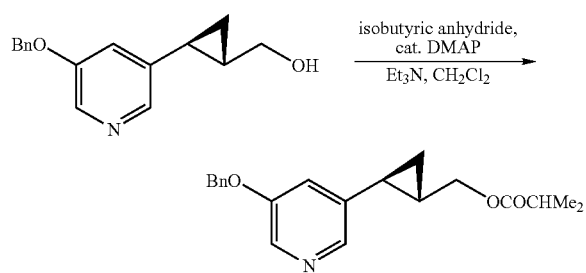

In a 250 mL round-bottom flask with stir bar, septum, and balloon (for pressure equalization and exclusion of moisture), (1S,2S)-2-[5-(benzyloxy)-3-pyridyl]cyclopropylmethanol (prepared by chromatographic racemate resolution; 2.03 g, 7.91 mmol) and 4-(dimethylamino)pyridine (DMAP; 97 mg, 0.79 mmol, 0.1 equiv.) were dissolved in anhydrous $CH_2Cl_2$ (38 mL). Anhydrous triethylamine (4.4 mL, 32 mmol, 4.0 equiv.) was added. The solution was cooled in an ice bath before isobutyric anhydride (2.6 mL, 15.8 mmol, 2.0 equiv.) was added dropwise in 20 min. The reaction mixture was then stirred at 0° C. After 85 min, TLC analysis (silica gel, EtOAc; $R_f$ 0.7; starting material, $R_f$ 0.15) indicated completion of the reaction. After 100 min, methanol (1.0 mL) was added dropwise in 4 min. The mixture was stirred at 0° C. for 15 min and at room temperature for 30 min. Water (50 mL) was added. The phases were separated, and the aqueous phase was extracted with 3 portions of EtOAc (25 mL each). The combined organic phases were washed with brine (25 mL) and evaporated, and the residue was chromatographed on silica gel (22×3.8 cm, EtOAc/hexane 3:2). The product-containing fractions were evaporated and the residue dried (50° C./oil pump) to yield 2.40 g (93%) of the ester as an oil. $^1$H NMR ($CDCl_3$, 500 MHz) δ 8.21 (d, 1H, J=2.6 Hz), 8.08 (s, 1H), 8.47-8.35 (m, 5H), 5.11 (s, 2H), 4.15, 4.05 (ABq, 2H, J=11.5 Hz, low-field part d with J=6.5 Hz, high-field part d with J=7.5 Hz), 2.59 (septuplet, 1H, J=7.0 Hz), 1.91 (m, 1H), 1.50 (m, 1H), 1.20 (d, 6H, J=7.0 Hz), 1.07-1.02 (m, 2H). MS (EI) m/z 325 ($M^+$, 2.8%), 91 (100%), 65 (7.5%), 43 (16%).

(1S,2S)-2-(5-Hydroxy-3-pyridyl)cyclopropylmethyl Isobutyrate

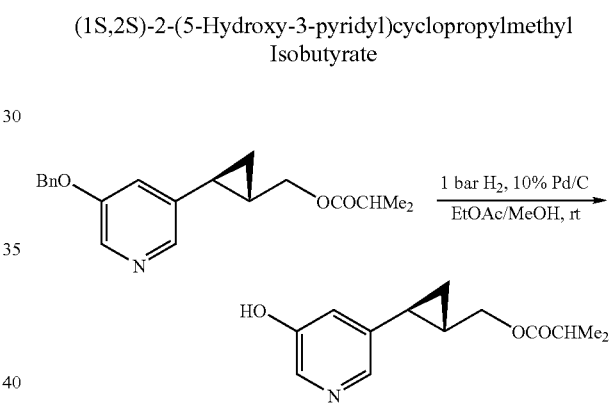

In a 500 mL three-necked flask with stir bar and two septa was placed a solution of (1S,2S)-2-[5-(benzyloxy)-3-pyridyl]cyclopropylmethyl isobutyrate (2.39 g, 7.34 mmol) in EtOAc (40 mL) and methanol (80 mL), as well as 10% Pd/C (160 mg, containing 50% water; Alfa Aesar #38305). A $H_2$ balloon was connected to the central neck through a three-way stopcock, the reaction mixture was cooled in an ice bath, and the atmosphere was exchanged. After 35 min, no reaction had taken place. The reaction was continued at room temperature. After 1 h at rt, TLC on silica gel (EtOAc; $R_f$ 0.35 with tail) indicated completion of the reaction. The atmosphere was replaced with $N_2$ before opening the flask, the reaction mixture was filtered from the catalyst over a compacted cotton plug in the stem of a funnel, and the filtrate was evaporated and dried (40° C./oil pump) to furnish 1.78 g (nominally 103%, evidently containing MeOH) of the hydroxypyridine as a nearly colorless glass. This product was evaporated with toluene (20 mL) to remove MeOH, and directly used in the subsequent Mitsunobu reaction. MS (EI) m/z 235 ($M^+$, 6.4%), 147 (13%), 146 (58%), 124 (19%), 71 (17%), 43 (100%).

(1S,2S)-2-[5-[[1-(tert-Butoxycarbonyl)-(2S)-azetidinyl]methoxy]-3-pyridyl]cyclopropylmethyl Isobutyrate

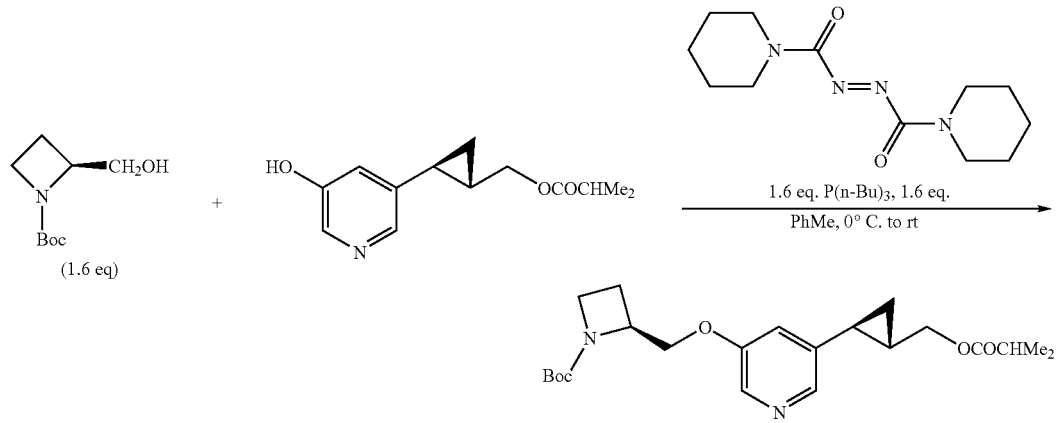

In a 50 mL side-arm flask with stir bar, septum, and Ar balloon, tri-n-butylphosphine (2.89 mL, 11.7 mmol, 1.6 equiv.) was added dropwise in 25 min to a solution of N,N'-azodicarbonyldipiperidine (2.95 g, 11.7 mmol, 1.6 equiv.) in anhydrous toluene (25 mL). Stirring was continued at room temperature for 35 min to result in a light-orange solution of the Mitsunobu reagent. In the meantime, crude (1S,2S)-2-(5-hydroxy-3-pyridyl)cyclopropylmethyl isobutyrate (1.78 g as weighed after the initial evaporation, no more than 7.34 mmol due to residual solvent content) and 1-(tert-butoxycarbonyl)-(2S)-azetidinylmethanol (2.20 g, 11.7 mmol, 1.6 equiv.) were placed in a 300 mL round-bottom flask equipped with two-neck adapter, septum, and an Ar balloon. The starting materials were dissolved in anhydrous toluene (25 mL), and the solution was cooled in an ice bath. The Mitsunobu reagent was taken up in a syringe and added dropwise in 40 min. A precipitate began to form after addition of approx. one third of the reagent, and the mixture turned highly viscous. Stirring of the mixture at 0° C. for 80 min resulted in little conversion, whereon the reaction was allowed to proceed at room temperature for 6 h. Shortly before termination of the reaction, a TLC was taken (silica gel, EtOAc/hexane 3:1). The product was observed at $R_f$ 0.42 (UV- and KMnO$_4$-active) preceded by residual N-(tert-butoxycarbonyl)-(2S)-azetidinylmethanol ($R_f$ 0.48, UV-inactive, slowly staining with KMnO$_4$ on heating). Byproducts derived from the Mitsunobu reagent stayed near the baseline.

The reaction mixture was diluted with toluene (20 mL), and air was bubbled through for 100 min (to oxidize any potentially remaining tributylphosphine to the polar phosphine oxide). Then the mixture was evaporated and the residue chromatographed on silica gel (43×7.5 cm, EtOAc/hexane 35:65). A total volume of approx. 16 L (including the amount used to fill the column) was required to completely elute the excess of N-(tert-butoxycarbonyl)-(2S)-azetidinylmethanol. The product was subsequently eluted with EtOAc/hexane 3:2. Evaporation and drying (50° C./oil pump) yielded 2.83 g (95% over both the hydrogenolysis and Mitsunobu steps) of a yellowish syrup. $[\alpha]_D$ –106.5, $[\alpha]_{546}$ –127 (c 11.7 g/L, EtOAc). $^1$H NMR (CDCl$_3$, 500 MHz) δ 8.16 (d, 1H, J=2.7 Hz), 8.07 (s, 1H), 6.88 (d, 1H, J=1.9 Hz), 4.53 (m, 1H), 4.32 (m, 1H), 4.17-4.11 (m, 2H, including the low-field part of an ABq), 4.06 (high-field part of an ABq, 1H, J=11.5 Hz, d with J=7.4 Hz), 3.94-3.89 (m, 2H), 2.60 (septuplet, 1H, J=7.0 Hz), 2.41-2.34 (m, 1H), 2.34-2.27 (m, 1H), 1.91 (dt, 1H, J=7.0 Hz (t), 4.5 Hz (d)), 1.57-1.47 (m, 1H), 1.44 (s, 9H), 1.202 (d, 3H, J=7.0 Hz), 1.200 (d, 3H, J=7.0 Hz), 1.06 (t, 2H, J=7.1 Hz). MS (EI) m/z 404 (M$^+$, 2.5%), 261 (5.5%), 248 (11%), 236 (5.4%), 160 (8.3%), 156 (5.1%), 148 (5.7%), 146 (7.0%), 130 (4.9%), 114 (8.5%), 113 (12%), 100 (30%), 70 (11%), 57 (100%), 56 (83%), 43 (50%), 41 (47%).

(1S,2S)-2-[5-[[1-(tert-Butoxycarbonyl)-(2S)-azetidinyl]methoxy]-3-pyridyl]cyclopropylmethanol

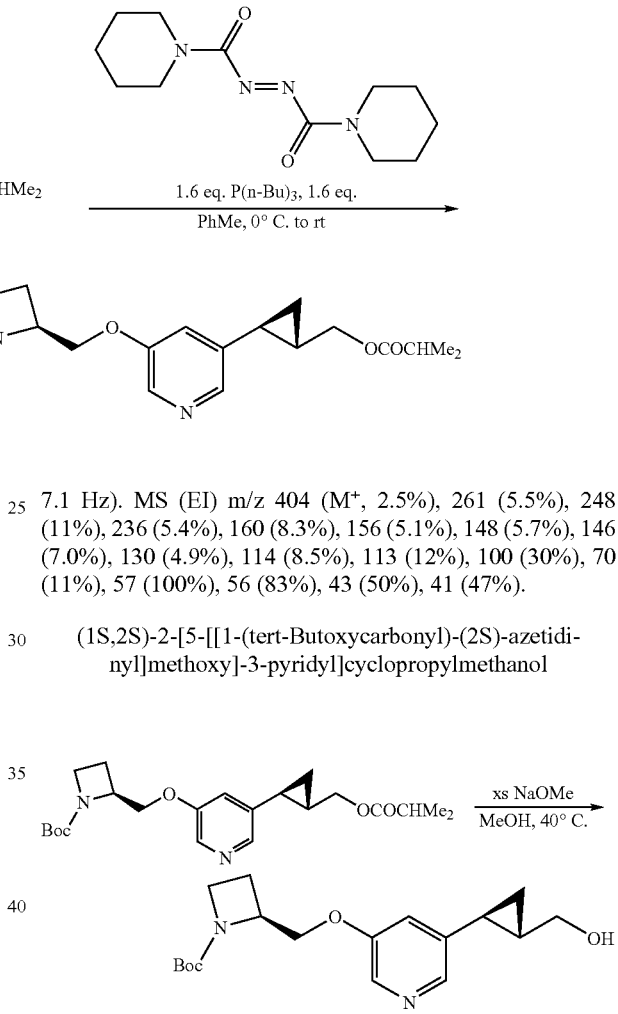

To a solution of (1S,2S)-2-[5-[[1-(tert-butoxycarbonyl)-(2S)-azetidinyl]methoxy]-3-pyridyl]cyclopropylmethyl isobutyrate (2.82 g, 6.97 mmol) in anhydrous methanol (35 mL) in a 250 mL round-bottom flask with magnetic stirrer was added a 25-30 wt % solution of sodium methoxide in methanol (0.4 mL; d 0.97 kg/L according to supplier, which makes approx. 2 mmol). The flask was fitted with an Ar balloon, the atmosphere was exchanged, and the reaction mixture was kept at 40° C. for 6 h. The reaction mixture was evaporated and the residue directly filtered over silica gel (24×3.8 cm, CH$_2$Cl$_2$/MeOH 93:7, then 9:1). Evaporation and drying (50° C./oil pump) gave 2.29 g (98%) of a slightly yellowish glass. $^1$H NMR (CDCl$_3$, TMS, 400 MHz) δ 8.13 (d, 1H, J=2.8 Hz), 8.04 (narrow m, 1H), 6.89 (m, 1H), 4.50 (m, 1H), 4.29 (m, 1H), 4.12 (m, 1H; the main structure of this signal is a dd with J=2.8 and 10.1 Hz, accompanied by minor peaks that may result from the presence of a second rotamer), 3.93-3.85 (m, 2H), 3.68, 3.62 (ABq, 2H, J=11.4 Hz, low-field part d with J=6.4 Hz, high-field part d with J=6.9 Hz), 2.40-2.22 (m, 2H), 1.83 (m, 1H), 1.70 (very br, 1H, OH), 1.48 (m, 1H), 1.42 (s, 9H), 1.03-0.97 (m, 2H). MS (EI) m/z 334 (M$^+$, 1.0%), 278 (M+-C4H8, 2.4%), 237 (10%), 178 (19%), 100 (21%), 57 (100%), 56 (76%), 41 (44%).

The sequence esterification—hydrogenolysis—Mitsunobu reaction—ester hydrolysis has also been performed using the acetate in place of the isobutyrate ester (see scheme below).

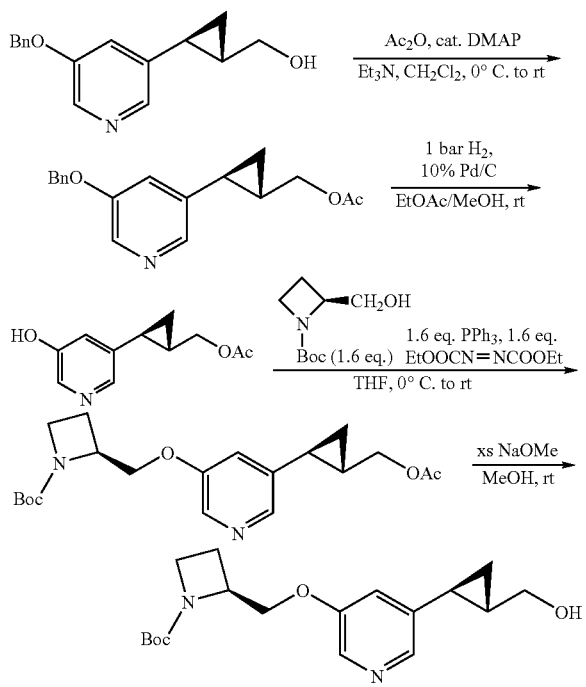

In this case, acetic anhydride was substituted for isobutyric anhydride. The Mitsunobu reaction was executed in 61% yield using the less reactive, traditional Mitsunobu reagent, diethyl azodicarboxylate/triphenylphosphine, extending the reaction period to 92.5 h at room temperature. The final hydrolysis of the acetate ester proceeded smoothly at room temperature.

(1S,2S)-2-[5-[(2(S)-Azetidinyl)methoxy]-3-pyridyl]cyclopropylmethanol Hydrochloride

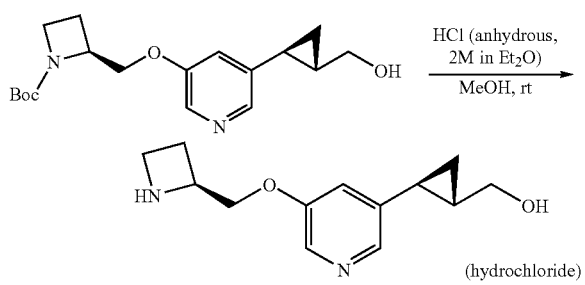

2M anhydrous HCl/ether (2.0 mL) was added to a stirred solution of (1S,2S)-2-[5-[[1-(tert-butoxycarbonyl)-(2S)-azetidinyl]methoxy]-3-pyridyl]cyclopropylmethanol (200 mg, 0.59 mmol) in dry MeOH (2.0 mL) at 0° C. The resulting mixture was stirred at room temperature for 12 h, concentrated, and purified by HPLC to give the title compound as its hydrochloride (106 mg). $^1$H NMR (CD$_3$OD, 300 MHz) δ 8.36 (s, 1H), 8.28 (s, 1H), 7.70 (s, 1H), 4.98-4.92 (m, 1H), 4.52-4.47 (m, 2H), 4.16-4.02 (m, 2H), 3.76-3.68 (m, 1H), 3.53-3.45 (m, 1H), 3.33-3.29 (m, 2H), 2.10-2.02 (m, 1H), 1.64-1.49 (m, 1H), 1.17 (t, 1H, J=7.2 Hz); MS (ESI) m/z 257 (M+Na+).

Example 2

Synthesis of 2-[(1R,2S)-2-[5-[(2(S)-Azetidinyl)methoxy]-3-pyridyl]cyclopropyl]ethanol This compound was prepared according to Scheme 2.

3-[[1-(tert-Butoxycarbonyl)-2(S)-azetidinyl]methoxy]-5-((1S,2R)-2-vinylcyclopropyl)pyridine

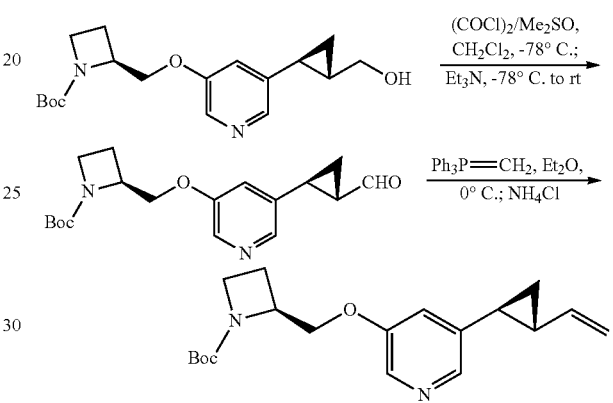

To a sample (9.35 g, 22.4 mmol, 5.0 equiv.) of methyltriphenylphosphonium bromide/NaNH$_2$ mixture (Sigma-Aldrich; 2.4 mmol of phosphonium salt/g) in a 250 mL three-necked flask equipped with magnetic stirrer, 2 septa, and an Ar balloon was added at room temperature all at once diethyl ether (freshly distilled from Na/benzophenone; 110 mL). Upon stirring for 4 h at room temperature, the liquid phase gradually turned and eventually remained yellow from the Wittig reagent that was formed. The residual solid was then allowed to settle, and as much of the solution (101 mL) as possible without disturbing the solid was transferred with a syringe into a 250 mL three-necked flask fitted with a magnetic stirrer, two septa, and an Ar balloon. The solution was cooled in an ice bath.

In the meantime, a 100 mL three-necked flask with magnetic stirrer, two septa, and an Ar balloon was charged with anhydrous CH$_2$Cl$_2$ (40 mL) and oxalyl chloride (0.64 mL, 7.6 mmol, 1.7 equiv.). The flask was immersed in an acetone/CO$_2$ bath, and the solution was stirred. A solution of anhydrous DMSO (9.0 mmol, 2.0 equiv.) in anhydrous CH$_2$Cl$_2$ (4 mL) was added dropwise in 6 min. The Swern reagent solution was stirred at approx. −70° C. for another 13 min. A solution of (1S,2S)-2-[5-[[1-(tert-butoxycarbonyl)-(2S)-azetidinyl]methoxy]-3-pyridyl]cyclopropylmethanol (1.50 g, 4.49 mmol) in anhydrous CH$_2$Cl$_2$ (12 mL) was added in 24 min. Stirring at approx. −70° C. was continued for another 32 min. Anhydrous triethylamine (3.8 mL, 27 mmol, 6.0 equiv.) was added dropwise in 11 min. The reaction mixture was stirred for another 8 min at approx. −70° C. and then allowed to warm in the thawing cold bath to +4° C. within 105 min. The initially colorless solution turned pinkish and deposited a small quantity of precipitate. The mixture was subsequently stirred at room temperature for 25 min, then washed with two 40 mL portions of water, each time back-extracting with CH$_2$Cl$_2$ (10 mL). The combined organic phases, without drying, were evaporated, and the residue was rapidly filtered over silica gel (15×3.8 cm; 400 mL ether, then 1.4 L of EtOAc/hexane 4:1) to remove baseline impurities (R$_f$ of product: 0.18 with EtOAc/hexane 3:1). Evaporation at 30° C. and brief drying in an oil pump vacuum at the same temperature furnished 1.46 g of the intermediate aldehyde as a yellowish syrup.

The aldehyde was dissolved in anhydrous ether (20 mL) and this solution added dropwise in 11 min to the ice-cooled solution/suspension of the above-prepared Wittig reagent (some of which had precipitated at the low temperature but gradually dissolved as the reaction progressed). The solution, which turned from yellow to orange, was stirred at 0° C. for 20 min. TLC analysis (as above) after 11 min demonstrated the replacement of the rapidly KMnO$_4$-reactive aldehyde with the also fast-staining olefin (R$_f$ 0.45) and two slow-staining byproducts, triphenylphosphine oxide (R$_f$ 0.2) and methyldiphenylphosphine oxide (R$_f$ 0.05). The reaction was quenched by addition of saturated aqueous NH$_4$Cl solution (40 mL). The phases were separated and the aqueous phase extracted with ether (20 mL). The combined organic phases were washed with saturated aqueous NH$_4$Cl solution (20 mL), and the aqueous phase back-extracted with ether (20 mL). The combined organic phases were finally washed with brine (20 mL) and, without drying, evaporated. The residual orange-colored syrup was chromatographed on SiO$_2$ (17×5 cm, EtOAc/hexane 2:3 up to the beginning elution of the olefin, then 1:1). The separation of the olefin from POPh$_3$ was just sufficient. Evaporation and drying (30° C./oil pump) yielded 1.31 g (88%) of the olefin as a yellowish syrup. $^1$H NMR (CDCl$_3$, 500 MHz) δ 8.16 (d, 1H, J=2.6 Hz), 8.07 (s, 1H), 6.88 (s, 1H), 5.59-5.51 (m, 1H), 5.16 (d, 1H, J=17.0 Hz), 5.00 (d, 1H, J=10.3 Hz), 4.53 (m, 1H), 4.32 (m, 1H), 4.14 (dd, 1H, J=2.8, 9.9 Hz), 3.92 (m, 2H), 2.42-2.25 (m, 2H), 1.93 (m, 1H), 1.74 (m, 1H), 1.44 (s, 9H), 1.26-1.16 (m, 2H). MS (EI) m/z 330 (M$^+$, 0.1%), 274 (M$^+$-C$_4$H$_8$, 4.7%), 174 (12%), 100 (12%), 70 (9.3%), 57 (100%), 56 (63%).

The oxidation of the alcohol to the aldehyde can alternatively also be performed using 1,1,1-Tris(acetoxy)-1,1-dihydro-1,2-benziodoxol-3(1H)-one (the Dess-Martin periodinane).

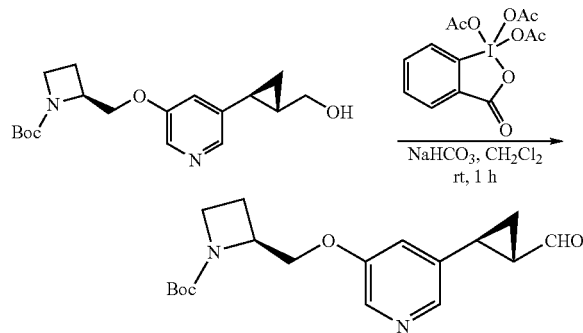

A solution of (1S,2S)-2-[5-[[1-(tert-butoxycarbonyl)-(2S)-azetidinyl]methoxy]-3-pyridyl]cyclopropylmethanol (3.00 g, 8.97 mmol) in CH$_2$Cl$_2$ (25 mL) was treated with 3 equiv. of NaHCO$_3$ followed by Dess-Martin periodinane (7.60 g, 18.0 mmol, 2.0 equiv.). The solution was stirred for 2 h at room temperature. Saturated aqueous Na$_2$SO$_3$ (5 mL) and NaHCO$_3$ (5 mL) were then added, and the biphasic mixture was stirred for 15 min and extracted with EtOAc (2×100 mL). The organic phase was washed with brine (50 mL), dried (Na$_2$SO$_4$), and concentrated in vacuo. The resulting aldehyde was purified by CC and directly used in the next reaction.

2-[(1R,2S)-2-[5-[[1-(tert-Butoxycarbonyl)-(2S)-azetidinyl]methoxy]-3-pyridyl]cyclopropyl]ethanol

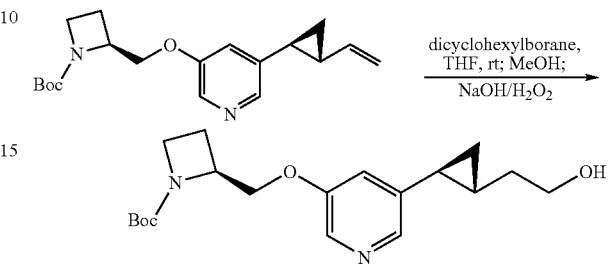

In a 250 mL three-necked flask equipped with magnetic stirrer, 2 septa, and an Ar balloon, cyclohexene (2.80 mL, 27.6 mmol, 7.0 equiv.) was added at room temperature in 10 min to borane-dimethylsulfide complex (1.38 mL, 13.8 mmol, 3.5 equiv.) in tetrahydrofuran (15 mL, freshly distilled over Na/benzophenone). A mild exotherm occured upon the initial addition, followed by a slightly stronger exotherm as dicyclohexylborane crystallized. The reagent solution was stirred at room temperature for 80 min and then cooled with an ice bath. A solution of 3-[[1-(tert-butoxycarbonyl)-2(S)-azetidinyl]methoxy]-5-((1S,2R)-2-vinylcyclopropyl)pyridine (1.30 g, 3.93 mmol) in anhydrous THF (12 mL) was added in 25 min. The mixture was stirred at room temperature for 250 min, after which time it formed a turbid, colorless solution. Methanol (0.16 mL, 3.9 mmol, 1.0 equiv.) was added dropwise in 5 min (caution, H$_2$ evolution), whereafter the mixture was stirred at room temperature for 5 min. Aqueous NaOH (3N, 11.7 mL, 35 mmol, 9 equiv.) was added (dropwise initially until additional H$_2$ evolution subsided). Aqueous hydrogen peroxide (35%, 7.1 mL diluted with 0.9 mL of water, 83 mmol, 21 equiv.) was added very cautiously and dropwise in 22 min. A vigorous exotherm was noted during the addition of approx. the first half of the peroxide. After completion of the addition, the mixture was placed in an oil bath which was heated to 55° C. in 25 min and kept at this temperature for another 60 min. The mixture was cooled to room temperature and at this point consisted of two colorless phases. The aqueous phase, but not the organic phase, gave a strong reaction for peroxides with KI/starch paper after the paper was exposed to HCl fumes. The phases were separated, the aqueous phase was extracted with five portions of EtOAc (25 mL each), and the combined organic phases were twice washed with brine (25 mL each). They gave at this point a negative reaction with KI/starch paper and were evaporated. TLC (SiO$_2$, CH$_2$Cl$_2$/MeOH 95:5) showed spots at R$_f$ 0.5, 0.4 (cyclohexanol), and 0.08 (product). The residue was chromatographed on SiO$_2$ (25×5 cm, CH$_2$Cl$_2$/MeOH 96:4 until all cyclohexanol was eluted, 93:7 to the appearance of the product, and finally 90:10). Evaporation of the product-containing fractions yielded 1.28 g of a yellowish glass. This material was taken up in DMSO (3 mL), and the solution was filtered over a cotton plug. Preparative HPLC was performed in 10 portions (Supelco Discovery C$_{18}$ column, 250×21.2 mm, 5 μm particle size; UV detection at 270 nm; flow 12.5 mL/min; 0-8 min, 20% CH$_3$CN in water, then gradient from 20 to 100% of CH$_3$CN in water within another 40 min; runs aborted after elution of major peak and column washed with CH₃CN; $t_R$ 25.5-27.4 min). The combined product-containing eluate was partially evaporated to remove CH₃CN, and the product was extracted from the residue with CH₂Cl₂ (20+3×10 mL). The solution was dried over MgSO₄ and evaporated, and the residue was dried (50° C./oil pump) to yield 1.21 g (88%) of a colorless glass. [α]$_D$–107, [α]$_{546}$–128 (c 9.25 g/L, EtOAc). ¹H NMR (CDCl₃, 500 MHz) δ 8.13 (d, 1H, J=2.6 Hz), 8.04 (s, 1H), 6.87 (s, 1H), 4.52 (br m, 1H), 4.31 (br, 1H), 4.14 (dd, 1H, J=2.8, 10.0 Hz), 3.94-3.88 (m, 2H), 3.83-3.77 (m, 2H), 2.41-2.33 (m, 1H), 2.33-2.25 (m, 1H) 1.80 (br m, 1H), 1.75-1.64 (m, 3H), 1.43 (s, 9H), 1.17 (m, 1H), 0.98 (dt, 1H, J(d)=8.5 Hz, J(t)=5.0 Hz), 0.91 (dt, 1H, J(d)=8.5 Hz, J(t)=5.4 Hz). MS (EI) m/z 348 (M⁺, 0.4%), 292 (3.5%), 192 (14%), 100 (14%), 70 (11%), 56 (64%), 41 (61%).

2-[(1R,2S)-2-[5-[(2(S)-Azetidinyl)methoxy]-3-pyridyl]cyclopropyl]ethanol Hydrochloride from 2-[(1R,2S)-2-[5-[[1-(tert-Butoxycarbonyl)-(2S)-azetidinyl]methoxy]-3-pyridyl]cyclopropyl]ethanol by Deprotection with HCl

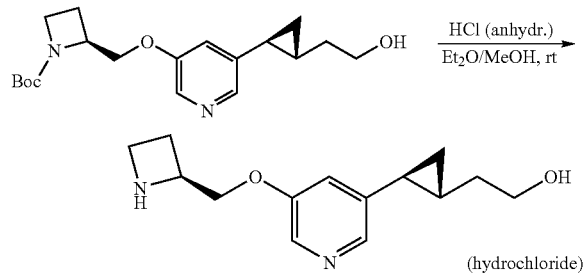

2M HCl (anhydrous)/ether (2.0 mL) was added to a stirred solution of 2-[(1R,2S)-2-[5-[[1-(tert-butoxycarbonyl)-(2S)-azetidinyl]methoxy]-3-pyridyl]cyclopropyl]ethanol (200 mg, 575 µmol) in dry MeOH (2.0 mL) at 0° C. The resulting mixture was stirred at room temperature for 12 h. The above solution was concentrated and purified by HPLC to give the title compound (115 mg). ¹H NMR (CD₃OD, 400 MHz) δ 8.60 (s, 1H), 8.45 (s, 1H), 8.07 (s, 1H), 5.02-4.98 (m, 1H), 4.73-4.66 (m, 2H), 4.21-4.01 (m, 2H), 3.71 (t, 2H, J=6.4 Hz), 2.81-2.57 (m, 2H), 2.12-1.84 (m, 1H), 1.79-1.72 (m, 2H), 1.55-1.49 (m, 1H), 1.40-1.33 (m, 1H), 1.24-1.19 (m, 2H). MS (ESI) m/z 271 (M+Na⁺).

2-[(1R,2S)-2-[5-[((2S)-Azetidinyl)methoxy]-3-pyridyl]cyclopropyl]ethanol from 2-[(1R,2S)-2-[5-[[1-(tert-Butoxycarbonyl)-(2S)-azetidinyl]methoxy]-3-pyridyl]cyclopropyl]ethanol by Deprotection with Trifluoroacetic Acid

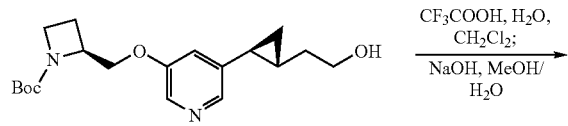

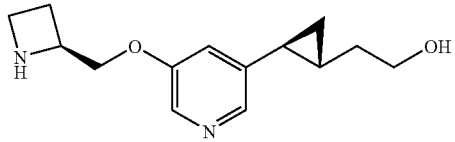

In a 15 mL round-bottom flask, a mixture of trifluoroacetic acid (0.8 mL) and water (0.08 mL) was added to a solution of the starting material (152.5 mg, 438 µmol) in CH₂Cl₂ (4 mL). The flask was loosely stoppered, and the mixture was stirred magnetically for 24 h. At this point, TLC of an evaporated small sample (SiO₂ fumigated with NH₃; CH₂Cl₂/MeOH/conc. aq. NH₃ 17:2.7:0.3; UV detection) indicated complete conversion of the starting material ($R_f$ 0.6) to the amine ($R_f$ 0.2). The mixture was evaporated (30° C./14 torr) and lyophilized from water (20 mL) to obtain a colorless glass (288 mg). Analysis by HPLC (Supelco Discovery C₁₈, 250×3 mm with guard column, 5 µm particle size; UV detection at 270 nm; flow 0.5 mL/min; gradient from 8 to 25% CH₃CN in water [both containing 0.1 vol % CF₃COOH] within 10 min, from 25 to 100% in another 10 min, then 15 min CH₃CN) showed peaks at $t_R$ 6.1 min (75.1%, the desired product), 15.5 min (0.7%) and 21.5 min (23.7%, likely the O-trifluoroacetyl derivative).

To cleave the putative trifluoroacetyl derivative back to the amine, the crude TFA salt was dissolved in MeOH (5 mL), and 2N aqueous NaOH (1.14 mL) was added. The solution (strongly basic reaction verified with pH paper) was stirred at room temperature for 2 h, then evaporated. The residue was directly chromatographed on SiO₂ (14×1.8 cm, CH₂Cl₂/MeOH/conc. aq. NH₃ 16:3.5:0.5), and the product-containing eluate was evaporated, evaporated with 5 mL of CH₂Cl₂, and dried (35° C./oil pump) to obtain 109 mg (100%) of the free amine as a colorless glass. Its purity by HPLC (ACE 5 AQ, 250×3 mm; UV detection at 270 nm; flow 0.5 mL/min; gradient from 1 to 10% CH₃CN in water [both containing 0.1 vol % CF₃COOH] within 10 min, from 10 to 30% in the next 10 min, from 30 to 100% in another 10 min, then 5 min CH₃CN) was 96.3% ($t_R$ 18.1 min). The major impurity eluted at 23.1 min (1.4%). [α]$_D$–77.0, [α]$_{546}$–92.9 (c 7.9 g/L, MeOH). MS (EI) m/z 248 (M⁺, 0.7%), 193 (41%), 192 (73%), 163 (13%), 70 (9.2%), 56 (100%). The impurity eluting at 23.1 min could be removed by way of the N-Cbz derivative.

2-[(1R,2S)-2-[5-[[1-(Benzyloxycarbonyl)-(2S)-azetidinyl]methoxy]-3-pyridyl]cyclopropyl]ethanol

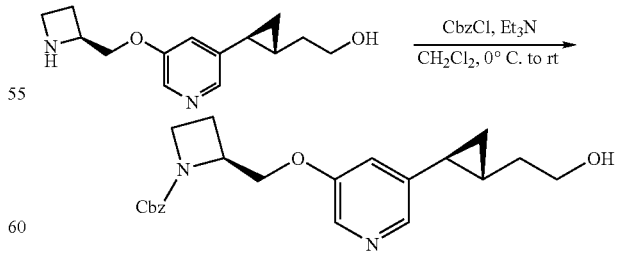

In a 25 mL round-bottom flask with magnetic stirrer, septum, balloon (for exclusion of moisture) and ice bath was placed a solution of 2-[(1R,2S)-2-[5-[((2S)-azetidinyl)methoxy]-3-pyridyl]cyclopropyl]ethanol (109 mg, 439 µmol) and triethylamine (83 µL, 0.60 mmol, 3.5 equiv.) in CH₂Cl₂ (1 mL). Benzyl chloroformate (78 μL, 0.55 mmol, 1.25 equiv.) was added dropwise in 10 min. The reaction mixture was stirred for 4 h in the thawing bath and at room temperature for 5 h before direct CC on SiO$_2$ (26×1.3 cm, CH$_2$Cl$_2$/MeOH 19:1). A nonpolar forerun (BnOH) was just sufficiently separated. The product-containing fractions were evaporated, and the residue was dried (50° C./oil pump) to yield 133 mg (79% from the N-Boc precursor) of a colorless glass. The compound slowly solidified on standing; mp 65-66° C. [α]$_D$–108, [α]$_{546}$–129 (c 9.25 g/L, EtOAc). $^1$H NMR (CDCl$_3$, 500 MHz) δ 8.11 (br, 1H), 8.06 (s, 1H), 7.35-7.28 (m, 5H), 6.83 (br, 1H), 5.12, 5.09 (ABq, 2H, J=12.4 Hz), 4.62 (br, 1H), 4.37 (very br, 1H), 4.13 (br, 1H), 4.06-3.97 (m, 2H), 3.80 (br, 2H), 2.47-2.39 (m, 1H), 2.37 (br, 1H), 1.78-1.65 (m, 2H), 1.63 (s, OH and H$_2$O), 1.57 (br, 1H), 1.17 (br m, 1H), 0.97 (m, 1H), 0.92 (m, 1H). MS (EI) m/z 382 (M$^+$, 1.8%), 351 (0.9%), 337 (3.0%), 91 (100%).

2-[(1R,2S)-2-[5-[((2S)-Azetidinyl)methoxy]-3-pyridyl]cyclopropyl]ethanol from 2-[(1R,2S)-2-[5-[[1-(Benzyloxycarbonyl)-(2S)-azetidinyl]methoxy]-3-pyridyl]cyclopropyl]ethanol

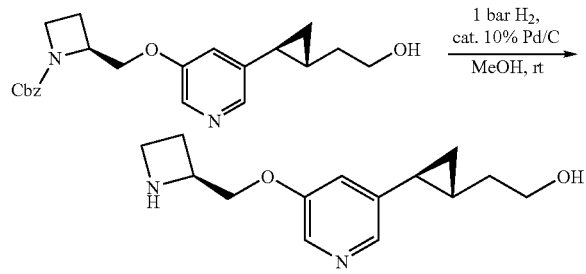

In a 50 mL round-bottom flask with magnetic stirrer and H$_2$ balloon, 2-[(1R,2S)-2-[5-[[1-(benzyloxycarbonyl)-(2S)-azetidinyl]methoxy]-3-pyridyl]cyclopropyl]ethanol (128 mg, 335 μmol) in MeOH (3 mL) was stirred with 10% Pd/C (23 mg; Alfa Aesar #38305, water content 50%) at room temperature for 2 h. H$_2$ was replaced with Ar, and the catalyst was filtered off over a cotton plug and rinsed with MeOH (1 mL). The solution was evaporated to yield 80 mg (96%) of a colorless film. $^1$H NMR (CDCl$_3$, 500 MHz) δ 8.10 (s, 1H), 8.04 (narrow m, 1H), 6.83 (d, 1H, J=2.2 Hz), 4.28 (m, 1H), 4.05, 4.01 (ABq, 2H, J=9.5 Hz, low-field part d with J=6.5 Hz, high-field part d with J=4.6 Hz), 3.79 (t, 2H, J=6.4 Hz), 3.73 (q, 1H, J=8.0 Hz), 3.48 (m, 1H), 2.41 (m, 1H), 2.29 (m, 1H), 1.86 (br, NH, OH, and H$_2$O), 1.75-1.64 (m, 3H), 1.16 (m, 1H), 0.97 (dt, 1H, J=8.5 Hz (d), 5.0 Hz (t)), 0.91 (dt, 1H, J=8.5 Hz (d), 5.4 Hz (t)).

2-[(1R,2S)-2-[5-[((2S)-Azetidinyl)methoxy]-3-pyridyl]cyclopropyl]ethanol Hydrochloride from the Free Base

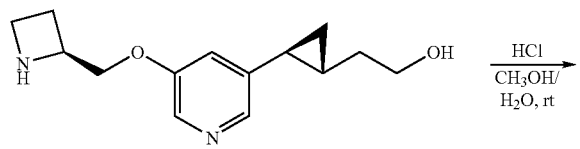

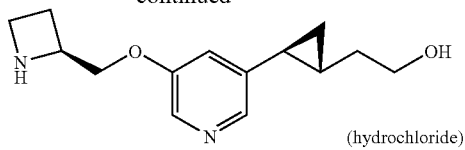

2-[(1R,2S)-2-[5-[((2S)-Azetidinyl)methoxy]-3-pyridyl]cyclopropyl]ethanol (76 mg, 306 μmol) was dissolved in MeOH (0.2 mL) Aqueous hydrochloric acid (1.00M, 0.61 mL, 2 equiv.) was added. The solution was filtered from a slight turbidity over a cotton plug, then diluted with water (3 mL) and lyophilized to yield 100 mg of the hydrochloride as a colorless foam. $^1$H NMR (CD$_3$OD, 500 MHz) δ 8.54 (s, 1H), 8.41 (s, 1H), 8.02 (s, 1H), 4.68, 4.59 (ABq, 2H, J=11.2 Hz, low-field part d with J=6.0 Hz, high-field part d with J=3.0 Hz), 4.20-4.10 (m, 2H), 3.72 (t, 2H, J=6.4 Hz), 2.78-2.67 (m, 2H), 2.07 (dt, 1H, J=8.4 Hz (d), 4.8 Hz (t)), 1.78-1.64 (m, 2H), 1.52-1.45 (m, 1H), 1.31 (dt, 1H, J=8.8 Hz (d), 5.1 Hz (t)), 1.18 (dt, 1H, J=8.5 Hz (d), 5.7 Hz (t)); 1H coinciding with CD$_3$OH peak at 4.96. $^{13}$C NMR (CD$_3$OD, 125 MHz) δ 156.7, 147.0, 132.4, 128.2, 126.4, 68.1, 61.0, 58.7, 43.4, 36.4, 22.9, 20.3, 20.0, 16.8. Anal. Calcd. for C$_{14}$H$_{20}$N$_2$O$_2$.2.15HCl: C, 51.74; H, 6.83; N, 8.57; Cl, 23.33. Found: C, 51.74; H, 7.23; N, 8.41; Cl, 23.80.

Example 3

Synthesis of 3-[(2(S)-Azetidinyl)methoxy]-5-[(1S, 2R)-2-(2-fluoroethyl)cyclopropyl]pyridine This compound was prepared according to Scheme 3.

3-[[1-(tert-Butoxycarbonyl)-2(S)-azetidinyl]methoxy]-5-[(1S,2R)-2-(2-fluoroethyl)cyclopropyl]pyridine

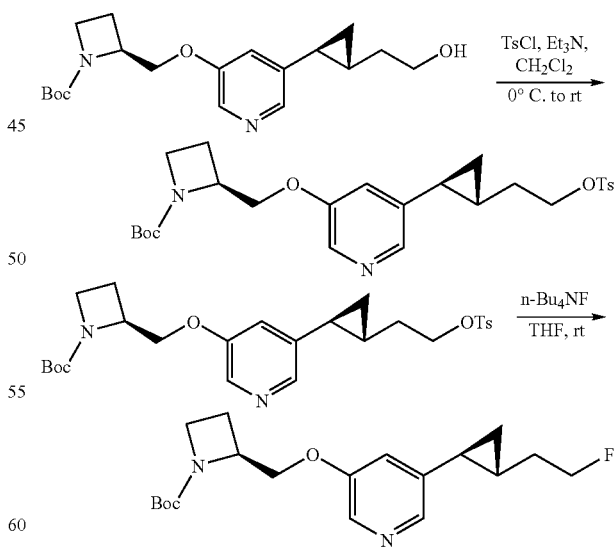

4-(Dimethylamino)pyridine (DMAP; 14 mg, 0.11 mmol, 0.02 equiv.), Et$_3$N (0.24 mL, 1.7 mmol, 3.0 equiv.), and p-toluenesulfonyl chloride (164 mg, 0.86 mmol, 1.5 equiv.) were added to a stirred solution of 2-[(1R,2S)-2-[5-[[1-(tert-butoxycarbonyl)-(2S)-azetidinyl]methoxy]-3-pyridyl]cyclopropyl]ethanol (200 mg, 574 μmol) in dry CH$_2$Cl$_2$ (5 mL) at 0° C. The reaction mixture was stirred at room temperature overnight, then diluted with CH$_2$Cl$_2$ (50 mL). The organic phase was washed with aqueous NaHCO$_3$ and brine, dried over Na$_2$SO$_4$, and concentrated in vacuo. 2-[(1R,2S)-2-[5-[(2 (S)-Azetidinyl)methoxy]-3-pyridyl]cyclopropyl]ethyl p-toluenesulfonate (R$_f$=0.4, 50% EtOAc in petroleum ether) was obtained by CC (237 mg, 82%) and was directly used for the next reaction.

A mixture of this p-toluenesulfonate (237 mg, 470 μmol) and 5 mL of 1.0 M solution of tetra-n-butylammonium fluoride in THF was stirred at room temperature for 10 h. The reaction mixture was concentrated. The residue was purified by CC (SiO$_2$, 50-60% EtOAc in hexane as the eluent) to give 3-[[1-(tert-butoxycarbonyl)-2(S)-azetidinyl]methoxy]-5-[(1S,2R)-2-(2-fluoroethyl)cyclopropyl]pyridine as a viscous oil (160 mg, 97%). $^1$H NMR (CDCl$_3$, 400 MHz) δ 8.12 (s, 1H), 8.04 (s, 1H), 6.88 (s, 1H), 4.81-4.62 (m, 3H), 4.34-4.26 (m, 1H), 4.13 (dd, 1H, J=10.1, 2.7 Hz), 3.89 (t, 2H, J=7.8 Hz), 2.38-2.22 (m, 2H), 1.77-1.68 (m, 3H), 1.41 (s, 9H), 1.14-0.95 (m, 1H), 0.94-0.84 (m, 2H). MS (ESI) m/z 351 (M+H$^+$).

3-[(2(S)-Azetidinyl)methoxy]-5-[(1S,2R)-2-(2-fluoroethyl)cyclopropyl]pyridine Hydrochloride

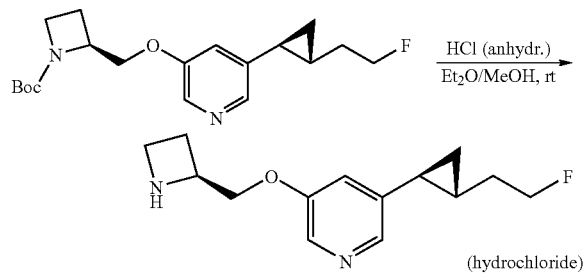

2M HCl (anhydrous)/ether (2.0 mL) was added to a stirred solution of 3-[[1-(tert-butoxycarbonyl)-2(S)-azetidinyl]methoxy]-5-[(1S,2R)-2-(2-fluoroethyl)cyclopropyl]pyridine (160 mg, 0.45 mmol) in dry MeOH (2.0 mL) at 0° C. The mixture was stirred at room temperature for 12 h. The above solution was concentrated and purified by HPLC to give the title compound (97 mg). $^1$H NMR (CD$_3$OD, 400 MHz) δ 8.38 (s, 1H), 8.28 (s, 1H), 7.71 (s, 1H), 4.92-4.86 (m, 1H), 4.61-4.48 (m, 4H), 4.18-4.04 (m, 2H), 2.75-2.61 (m, 2H), 2.03-1.97 (m, 1H), 1.91-1.77 (m, 2H), 1.46-1.35 (m, 1H), 1.25-1.19 (m, 1H), 1.16-1.09 (m, 1H). MS (ESI) m/z 273 (M+Na$^+$).

Example 4

Synthesis of 4-[(1S,2S)-2-[5-[(2(S)-Azetidinyl)methoxy]-3-pyridyl]cyclopropyl]-1-butanol This compound was prepared according to Scheme 4.

4-[(1S,2S)-2-[5-[[1-(tert-Butoxycarbonyl)-2(S)-azetidinyl]methoxy]-3-pyridyl]cyclopropyl]-2-trans-butenoic Acid Methyl Ester

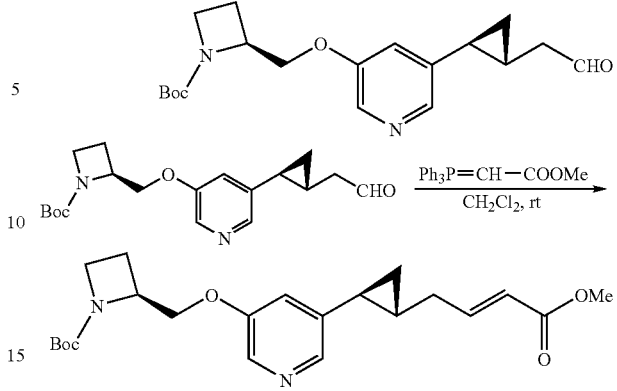

DMSO (2.0 mL), Et$_3$N (0.54 mL, 3.9 mmol, 5.0 equiv.), and finally portionwise SO$_3$-pyridine complex (617 mg, 3.87 mmol, 5.0 equiv.) were added with stirring to a solution of 2-[(1R,2S)-2-[5-[[1-(tert-butoxycarbonyl)-(2S)-azetidinyl]methoxy]-3-pyridyl]cyclopropyl]ethanol (270 mg, 0.77 mmol) in dry CH$_2$Cl$_2$ (1.6 mL) at 0° C. under N$_2$. After 60 min of stirring at 0° C., the reaction was quenched with saturated aqueous NH$_4$Cl (50 mL), and the mixture was extracted with EtOAc (2×50 mL). The combined organic extracts were washed with saturated aqueous NH$_4$Cl (30 mL), water (30 mL), and brine (30 mL), dried (Na$_2$SO$_4$), and concentrated in vacuo. The resulting aldehyde (R$_f$=0.4, 50% EtOAc in petroleum ether) was obtained by CC in a yield of 255 mg (95%), and was directly used for the next reaction.

Methyl (triphenylphosphoranylidene)acetate (492 mg, 1.47 mmol, 2.0 equiv.) was added to a solution of the aldehyde (255 mg, 0.73 mmol) in dry CH$_2$Cl$_2$ (10 mL), and the mixture was stirred at room temperature for 8 h. It was then concentrated in vacuo. Purification by CC (SiO$_2$, 40% EtOAc in petroleum ether as the eluent) furnished 4-[(1S,2S)-2-[5-[[1-(tert-butoxycarbonyl)-2(S)-azetidinyl]methoxy]-3-pyridyl]cyclopropyl]-2-trans-butenoic acid methyl ester (264 mg, 89%) as a colorless liquid. $^1$H NMR (CDCl$_3$, 400 MHz) δ 8.13 (s, 1H), 8.02 (s, 1H), 7.06-7.02 (m, 1H), 6.83 (s, 1H), 5.91 (d, 1H, J=16.0 Hz), 4.54-4.46 (m, 1H), 4.32-4.24 (m, 1H), 4.12 (dd, J=9.8, 2.9 Hz), 3.86 (t, J=6.9 Hz), 3.71 (s, 3H), 2.35-2.19 (m, 4H), 1.71-1.64 (m, 1H), 1.42 (s, 9H), 1.22-1.11 (m, 1H), 1.02-0.96 (m, 1H), 0.94-0.82 (m, 1H). MS (ESI) m/z 403 (M+H$^+$).

4-[(1S,2S)-2-[5-[[1-(tert-Butoxycarbonyl)-2(S)-azetidinyl]methoxy]-3-pyridyl]cyclopropyl]-1-butanol

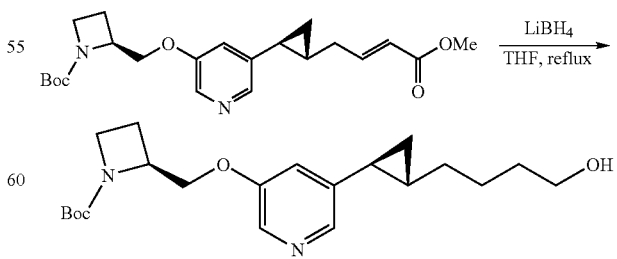

LiCl (138 mg, 3.27 mmol, 5.0 equiv.) was added to a stirred solution of NaBH$_4$ (124 mg, 3.27 mol, 5.0 equiv.) in dry EtOH (10 mL) at 0° C., and the mixture was stirred at that tempera-

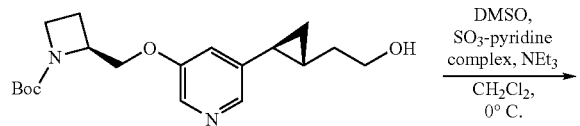

ture for 10 min. Then 4-[(1S,2S)-2-[5-[[1-(tert-butoxycarbonyl)-2(S)-azetidinyl]methoxy]-3-pyridyl]cyclopropyl]-2-trans-butenoic acid methyl ester (263 mg, 653 μmol) dissolved in THF (10 mL) was cannulated into the reaction mixture, which was subsequently refluxed for 24 h. The reaction was then quenched cautiously with saturated aqueous NH$_4$Cl solution (10 mL), and the mixture was extracted with EtOAc (2×100 mL). The organic extracts were washed with water (50 mL) and brine (50 mL) and dried over Na$_2$SO$_4$. After concentration in vacuo, the crude product was purified by CC (SiO$_2$, 3-4% MeOH in CH$_2$Cl$_2$ as the eluent) to provide 4-[(1S,2S)-2-[5-[[1-(tert-butoxycarbonyl)-2(S)-azetidinyl]methoxy]-3-pyridyl]cyclopropyl]-1-butanol (207 mg, 84%) as a colorless oil. $^1$H NMR (CDCl$_3$, 300 MHz) δ 8.10 (s, 1H), 8.01 (s, 1H), 6.84 (s, 1H), 4.56-4.43 (m, 1H), 4.37-4.23 (m, 1H), 4.11 (dd, 1H, J=9.8, 3.01 Hz), 3.89 (t, 2H, J=7.3 Hz), 3.66 (t, 2H, J=6.4 Hz), 2.43-2.19 (m, 1H), 1.69-1.45 (m, 7H), 1.41 (s, 9H), 1.12-0.98 (m, 1H), 0.97-0.87 (m, 1H), 0.86-0.76 (m, 1H). MS (ESI) m/z 376 (M$^+$).

4-[(1S,2S)-2-[5-[(2(S)-Azetidinyl)methoxy]-3-pyridyl]cyclopropyl]-1-butanol Hydrochloride

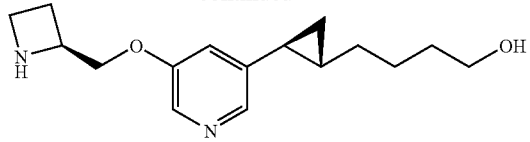

2M anhydrous HCl/ether (2.0 mL) was added to a stirred solution of 4-[(1S,2S)-2-[5-[[1-(tert-butoxycarbonyl)-2(S)-azetidinyl]methoxy]-3-pyridyl]cyclopropyl]-1-butanol (200 mg, 0.53 mmol) in dry MeOH (2.0 mL) at 0° C. The mixture was stirred at room temperature for 12 h. The above solution was concentrated in vacuo and purified by HPLC to obtain 4-[(1S,2S)-2-[5-[(2(S)-azetidinyl)methoxy]-3-pyridyl]cyclopropyl]-1-butanol hydrochloride (128 mg). $^1$H NMR (CD$_3$OD, 300 MHz) δ 8.25 (br s, 2H), 7.51 (s, 1H), 5.02-4.93 (m, 2H), 4.55-4.38 (m, 2H), 4.21-4.00 (m, 2H), 3.56 (t, 2H, J=6.2 Hz), 2.82-2.55 (m, 2H), 1.93-1.75 (m, 1H), 1.70-1.36 (m, 6H), 1.33-1.17 (m, 1H), 1.16-1.06 (m, 1H), 1.05-0.93 (m, 1H). MS (ESI) m/z 277 (M+H$^+$).

Example 5

Synthesis of 3-[(2(S)-Azetidinyl)methoxy]-5-((1R,2R)-2-ethylcyclopropyl)pyridine (1R,2R)-2-[5-[[1-(tert-Butoxycarbonyl)-(2S)-azetidinyl]methoxy]-3-pyridyl]cyclopropylmethanol

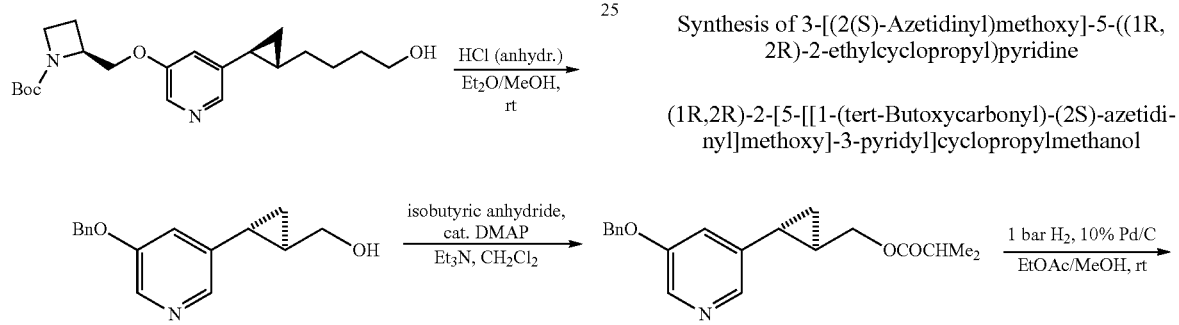

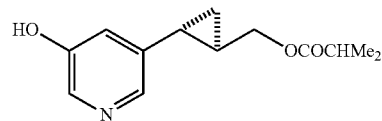

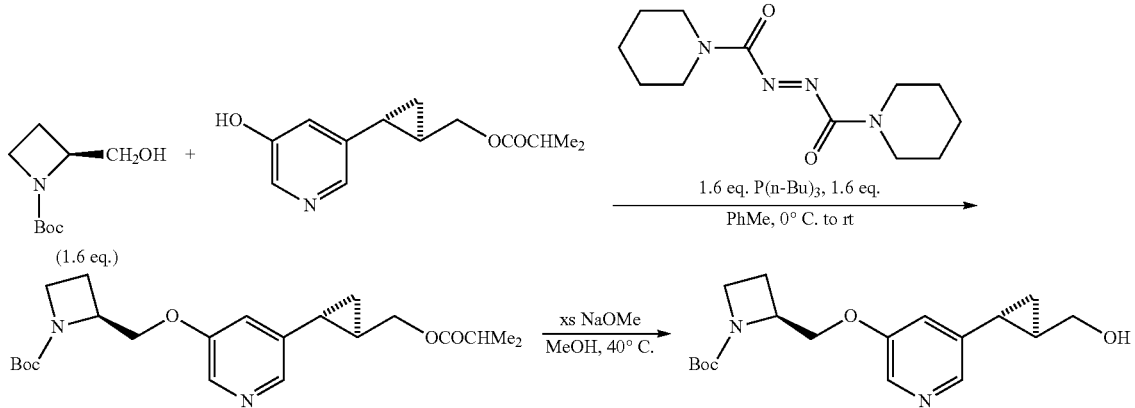

This compound is prepared from (1R,2R)-2-[5-(benzyloxy)-3-pyridyl]cyclopropylmethanol in the same manner as its diastereoisomer, (1S,2S)-2-[5-[[1-(tert-butoxycarbonyl)-(2S)-azetidinyl]methoxy]-3-pyridyl]cyclopropylmethanol, is prepared in Example 1 from (1S,2S)-2-[5-(benzyloxy)-3-pyridyl]cyclopropylmethanol.

3-[[1-(tert-Butoxycarbonyl)-2(S)-azetidinyl]-5-((1R,2S)-2-vinylcyclopropyl)pyridine

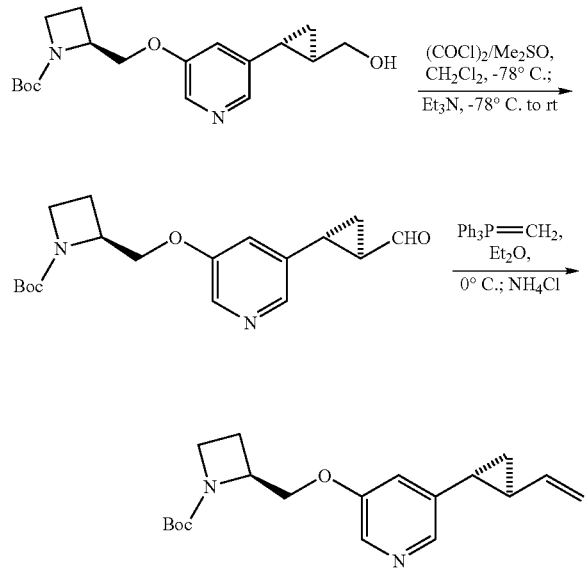

(1R,2R)-2-[5-[[1-(tert-Butoxycarbonyl)-(2S)-azetidinyl]methoxy]-3-pyridyl]cyclopropylmethanol is oxidized to the aldehyde and the aldehyde homologated to the title compound in the same manner as described in Example 2 for their diastereoisomers.

3-[1-(tert-Butoxycarbonyl)-2(S)-azetidinyl]methoxy]-5-((1R,2R)-2-ethylcyclopropyl)pyridine

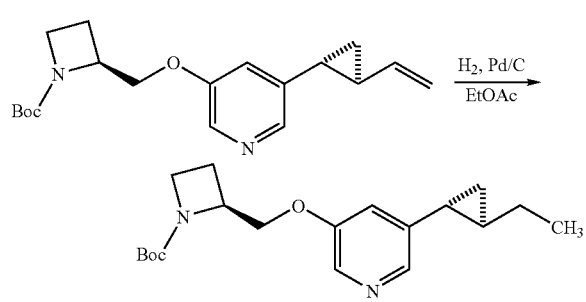

To solution of 3-[[1-(tert-butoxycarbonyl)-2(S)-azetidinyl]-5-(1R,2S)-2-vinylcyclopropyl)pyridine in ethyl acetate is added a catalytic amount of Pd/C. The atmosphere is replaced with hydrogen (balloon), and the reaction mixture is stirred at room temperature until TLC or HPLC demonstrates completion of the reaction. To remove the catalyst, the mixture is filtered over a pad of silica gel with ethyl acetate, and the eluate is evaporated to yield the title compound.

3-[(2(S)-Azetidinyl)methoxy]-5-((1R,2R)-2-ethylcyclopropyl)pyridine Hydrochloride

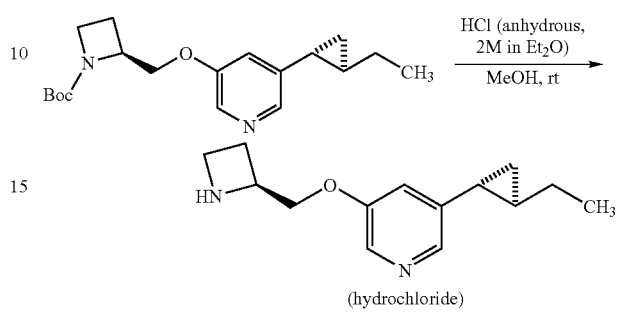

(hydrochloride)

To a solution of 3-[1-(tert-butoxycarbonyl)-2(S)-azetidinyl]methoxy]-5-((1R,2R)-2-ethylcyclopropyl)pyridine in MeOH is added an excess of a 2M solution of anhydrous HCl in diethyl ether. The reaction mixture is stirred at room temperature overnight, or until the reaction is complete, and the precipitate isolated by filtration. If a preciptitate fails to form, the mixture is evaporated to dryness and the residue triturated with ether until solidification occurs. The product is obtained as hydrochloride in the form of an amorphous solid.

Example 6

Synthesis of 2-[(1S,2R)-2-[5-[(2(S)-Azetidinyl)methoxy]-3-pyridyl]cyclopropyl]ethanol This compound was prepared according to Scheme 6.

2-[(1S,2R)-2-[5-[[1-(tert-Butoxycarbonyl)-2(S)-azetidinyl]methoxy]-3-pyridyl]cyclopropyl]ethanol

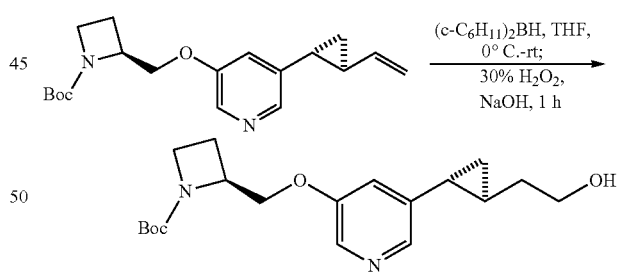

Dicyclohexylborane was freshly prepared by the addition of cyclohexene (3.65 mL, 36.0 mmol, 7.0 equiv.) to BH$_3$.SMe$_2$ (1.73 mL, 18.0 mmol, 3.5 equiv.) in dry THF (20 mL) at room temperature. 3-[[1-(tert-Butoxycarbonyl)-2(S)-azetidinyl]-5-((1R,2S)-2-vinylcyclopropyl)pyridine (1.70 g, 5.14 mmol) was added to the above-prepared reagent solution in THF (15 mL) at 0° C. under N$_2$. After stirring for 4 h at the same temperature, dry MeOH (0.21 mL, 5.2 mmol), NaOH (3 N aqueous solution, 15.4 mL, 46.3 mmol) and H$_2$O$_2$ (30% w/v, 12.2 mL, 108 mmol) were slowly added sequentially. Then, the reaction mixture was slowly warmed to 55° C. and maintained at that temperature for 1 hour, during which time the turbid solution became clear. The solution was cooled to room temperature and extracted with EtOAc (2×100 mL). The combined organic layers were washed with water and brine, dried over Na$_2$SO$_4$, and concentrated in vacuo. Purification by CC (SiO$_2$, 3-4% MeOH in CH$_2$Cl$_2$ as eluent) gave pure 2-[(1S,2R)-2-[5-[[1-(tert-butoxycarbonyl)-2(S)-azetidinyl]methoxy]-3-pyridyl]cyclopropyl]ethanol (1.70 g, 95%) as a clear oil. $^1$H NMR (CDCl$_3$, 400 MHz) δ 8.09 (s, 1H), 8.01 (s, 1H), 6.85 (s, 1H), 4.54-4.45 (m, 1H), 4.35-4.25 (m, 1H), 4.11 (dd, 1H, J=9.9, 2.7 Hz), 3.88 (t, 2H, J=8.1 Hz), 3.76 (t, 2H, J=6.5 Hz), 2.49-2.06 (m, 3H), 1.77-1.56 (m, 3H), 1.41 (s, 9H), 1.20-1.11 (m, 1H), 0.99-0.92 (m, 1H), 0.91-0.84 (m, 1H). MS (ESI) m/z 349 (M+H$^+$).

2-[(1S,2R)-2-[5-[(2(S)-Azetidinyl)methoxy]-3-pyridyl]cyclopropyl]ethanol Hydrochloride

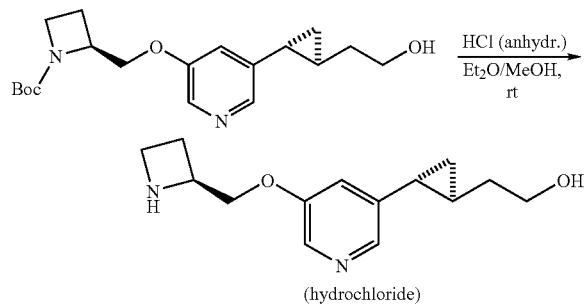

2M anhydrous HCl/ether (2.0 mL) was added to a stirred solution of 2-[(1S,2R)-2-[5-[[1-(tert-butoxycarbonyl)-2(S)-azetidinyl]methoxy]-3-pyridyl]cyclopropyl]ethanol (200 mg, 0.57 mmol) in dry MeOH (2.0 mL) at 0° C. The mixture was stirred at room temperature for 12 h and concentrated, and the residue was purified by HPLC to obtain pure 2-[(1S,2R)-2-[5-[(2(S)-azetidinyl)methoxy]-3-pyridyl]cyclopropyl]ethanol hydrochloride (115 mg). $^1$H NMR (CD$_3$OD, 400 MHz) δ 8.53 (s, 1H), 8.37 (s, 1H), 7.99 (s, 1H), 5.05-4.90 (m, 1H), 4.75-4.51 (m, 2H), 4.23-4.05 (m, 2H), 3.76-3.64 (m, 2H), 2.83-2.59 (m, 2H), 2.11-1.99 (m, 1H), 1.79-1.58 (m, 2H), 1.55-1.39 (m, 1H), 1.34-1.23 (m, 1H), 1.21-1.09 (m, 1H). MS m/z (ESI) 271 (M+Na$^+$).

Example 7

Synthesis of 3-[(2(S)-Azetidinyl)methoxy]-5-[(1R,2S)-2-(2-fluoroethyl)cyclopropyl]pyridine This compound was prepared according to Scheme 7.

3-[[1-(tert-Butoxycarbonyl)-2(S)-azetidinyl]methoxy]-5-[(1R,2S)-2-(2-fluoroethyl)cyclopropyl]pyridine

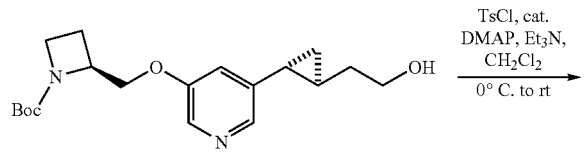

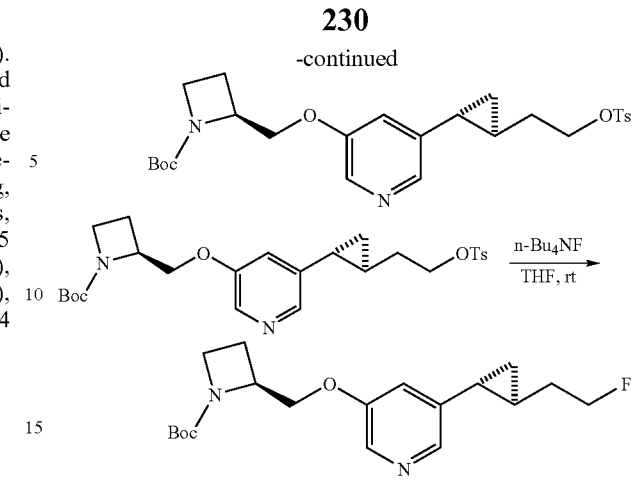

4-(Dimethylamino)pyridine (DMAP; 14 mg, 0.11 mmol, 0.2 equiv.), Et$_3$N (0.24 mL, 1.7 mmol, 3.0 equiv.), and p-toluenesulfonyl chloride (164 mg, 0.86 mmol, 1.5 equiv.) were added to a stirred solution of 2-[(1S,2R)-2-[5-[[1-(tert-butoxycarbonyl)-2(S)-azetidinyl]methoxy]-3-pyridyl]cyclopropyl]ethanol (200 mg, 0.57 mmol) in dry CH$_2$Cl$_2$ (5 mL) at 0° C. The reaction mixture was stirred at room temperature overnight, then diluted with CH$_2$Cl$_2$ (50 mL). The organic phase was washed with aqueous NaHCO$_3$ and brine, dried over Na$_2$SO$_4$, and concentrated. The residue was purified by CC (SiO$_2$, 60-70% EtOAc in hexane as the eluent) to give 2-[(1S,2R)-2-[5-[[1-(tert-butoxycarbonyl)-2(S)-azetidinyl]methoxy]-3-pyridyl]cyclopropyl]ethyl p-toluenesulfonate (175 mg, 82%), which was directly used for the next reaction.

A mixture of the p-toluenesulfonate (237 mg, 0.47 mmol) and 5 mL of 1.0 M solution of n-Bu$_4$NF in THF was stirred at room temperature for 10 h. The reaction mixture was concentrated in vacuo. The residue was purified by CC (SiO$_2$, 50-60% EtOAc in hexane eluent) to give 3-[[1-(tert-butoxycarbonyl)-2(S)-azetidinyl]methoxy]-5-[(1R,2S)-2-(2-fluoroethyl)cyclopropyl]pyridine as a viscous oil (160 mg, 97%). $^1$H NMR (CDCl$_3$, 400 MHz) δ 8.14 (s, 1H), 8.06 (s, 1H), 6.84 (s, 1H), 4.78-4.51 (m, 3H), 4.37-4.22 (m, 1H), 4.11 (dd, J=10.1, 2.7 Hz), 3.87 (t, 2H, J=7.6 Hz), 2.36-2.21 (m, 2H), 1.75-1.66 (m, 3H), 1.42 (s, 9H), 1.12-0.96 (m, 1H), 0.95-0.82 (m, 2H). MS (ESI) m/z 351 (M+H$^+$).

3-[(2(S)-Azetidinyl)methoxy]-5-[(1R,2S)-2-(2-fluoroethyl)cyclopropyl]pyridine Hydrochloride

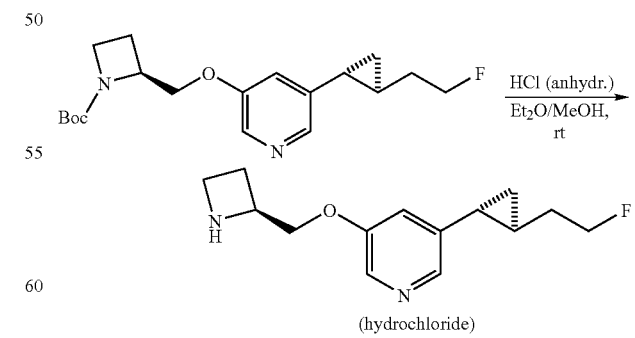

2M HCl (anhydrous) in ether (2.0 mL) was added to a stirred solution of 3-[[1-(tert-butoxycarbonyl)-2(S)-azetidinyl]methoxy]-5-[(1R,2S)-2-(2-fluoroethyl)cyclopropyl]pyridine (160 mg, 0.45 mmol) in dry MeOH (2.0 mL) at 0° C.

The mixture was stirred at room temperature for 12 h. The above solution was concentrated and purified by HPLC to obtain the title compound (97 mg). $^1$H NMR (CD$_3$OD, 400 MHz) δ 8.40 (br s, 1H), 8.29 (br s, 1H), 7.75 (s, 1H), 4.91-4.85 (m, 1H), 4.63-4.47 (m, 4H), 4.17-4.04 (m, 2H), 2.79-2.58 (m, 2H), 2.04-1.97 (m, 1H), 1.91-1.77 (m, 2H), 1.46-1.34 (m, 1H), 1.26-1.19 (m, 1H), 1.16-1.09 (m, 1H). MS (ESI) m/z 273 (M+Na$^+$).

Example 8

Synthesis of (1R,2S)-2-[[5-[(2(S)-Azetidinyl)methoxy]-3-pyridyl]methyl]cyclopropylmethanol This compound is prepared according to Scheme 8. The starting material, 3-bromo-5-[[1-(tert-butoxycarbonyl)-2(S)-azetidinyl]methoxy]pyridine, was obtained as shown in Scheme 5a and as reported in U.S. Pat. No. 5,629,325 (May 13, 1997; col. 22 and 52).

3-Allyl-5-[[(1-(tert-butoxycarbonyl)-2(S)-azetidinyl]methoxy]pyridine

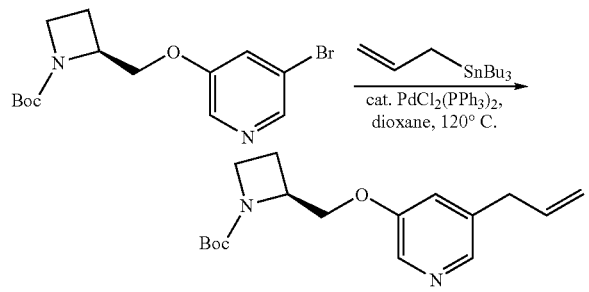

The cross coupling reaction between allyltributyltin (3.0 mL, 9.8 mmol, 1.7 equiv.) and 3-bromo-5-[[1-(tert-butoxycarbonyl)-2(S)-azetidinyl]methoxy]pyridine (2.0 g, 5.8 mmol) was carried out in dioxane for 1 h under reflux (120° C.) in the presence of a catalytic amount of Pd(PPh$_3$)$_2$Cl$_2$ as previously reported (in analogy to Marrière, E.; Rouden, J.; Tadino, V.; Lasne, M.-C. Org. Lett. 2000, 2, 1121-1124). After cooling and removing the solvent under vacuum, a saturated aqueous solution of KF was added, and the reaction mixture was stirred at room temperature for 5 h. After workup, the crude product was purified by CC (SiO$_2$, 25% EtOAc in hexane) to obtain the allylation product as a colorless oil (1.4 g, 80%). $^1$H NMR (CDCl$_3$, 400 MHz) δ 8.26 (s, 1H), 8.17 (s, 1H), 7.05 (s, 1H), 5.91 (m, 1H), 5.08 (m, 2H), 4.48 (m, 1H), 4.29 (m, 1H), 4.08 (dd, 8.1, 4.0 Hz, 1H), 3.87 (t, J=8.0 Hz, 2H), 3.33 (d, J=8.2 Hz, 2H), 2.32 (m, 2H), 1.39 (s, 9H); $^{13}$C NMR (CDCl$_3$, 100 MHz) δ 156.0, 154.9, 142.4, 135.9, 121.4, 116.7, 79.5, 68.5, 60.0, 46.9, 36.9, 28.2; MS (ESI) 305 (M+H$^+$).

4-[5-[1-(tert-Butoxycarbonyl)-2(S)-azetidinyl]-3-pyridyl]-trans-2-butenoic Acid Methyl Ester

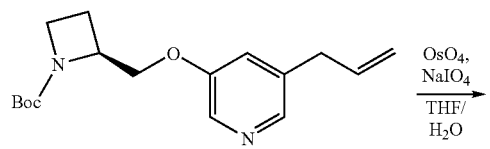

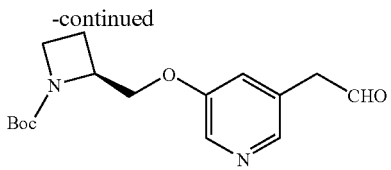

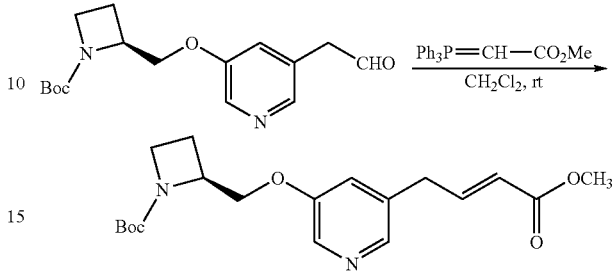

2,6-Lutidine (0.76 mL, 6.5 mmol, 2.0 equiv.), OsO$_4$ (16 mg, 0.06 mmol, 0.02 equiv.) and NaIO$_4$ (2.1 g, 9.6 mmol, 2.9 equiv.) were added to a stirred solution of 3-allyl-5-[[(1-(tert-butoxycarbonyl)-2(S)-azetidinyl]methoxy]pyridine (1.0 g, 3.3 mmol) in THF-water (20 mL, 3:1). The reaction mixture was stirred at 25° C. and monitored by TLC. After the reaction was complete, water and CH$_2$Cl$_2$ were added. The organic layer was separated, and the water layer was extracted three times with CH$_2$Cl$_2$. The combined organic layers were washed with brine and dried over Na$_2$SO$_4$. The solvents were removed, and the resulting [5-[[(1-(tert-butoxycarbonyl)-2(S)-azetidinyl]methoxy]-3-pyridyl]acetaldehyde was subjected to the next reaction without further purification.

Methyl (triphenylphosphoranylidene)acetate (0.78 g, 2.35 mmol, 1.2 equiv.) was added to a solution of the above aldehyde (600 mg, 1.96 mmol) in dry CH$_2$Cl$_2$ (10 mL), and the solution was stirred at room temperature for 8 h. It was then concentrated under vacuum. Purification by CC (SiO$_2$, 40% EtOAc in petroleum ether) furnished 4-[5-[1-(tert-butoxycarbonyl)-2(S)-azetidinyl]-3-pyridyl]-trans-2-butenoic acid methyl ester (0.56 g, 80%) as a colorless liquid. $^1$H NMR (CDCl$_3$, 400 MHz) δ 8.63 (s, 2H), 7.50 (d, J=16.1 Hz, 1H), 7.34 (s, 1H), 6.41 (d, J=16.2 Hz, 1H), 4.41 (m, 1H), 4.25 (m, 1H), 4.05 (dd, J=8.1, 4.0 Hz, 1H), 3.78 (t, J=8.2 Hz, 2H), 3.59 (s, 3H), 2.26 (m, 2H), 1.38 (s, 9H); $^{13}$C NMR (CDCl$_3$, 100 MHz) δ 166.4, 155.9, 155.0, 142.1, 140.7, 139.7, 130.4, 120.0, 118.3, 79.5, 68.6, 59.8, 51.6, 47.0, 29.4, 18.8; MS (ESI) 363 (M+H$^+$).

4-[5-[1-(tert-Butoxycarbonyl)-2(S)-azetidinyl]-3-pyridyl]-trans-2-butenol

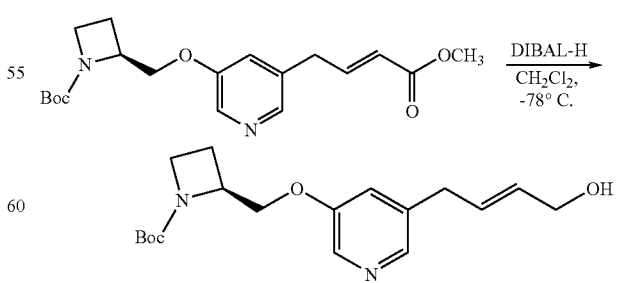

DIBAL-H (1.5M in toluene, 4.9 mL, 7.35 mmol, 2.7 equiv.) was added dropwise to a stirred solution of 4-[5-[1-(tert-butoxycarbonyl)-2(S)-azetidinyl]-3-pyridyl]-trans-2- butenoic acid methyl ester (1.00 g, 2.75 mmol) in dry CH$_2$Cl$_2$ at −78° C. The mixture was stirred at −78° C. for 3 hours before the reaction was quenched by adding methanol followed by saturated aqueous sodium potassium tartrate solution. The reaction mixture was then allowed to warm to room temperature where it was vigorously stirred for 1 h. The organic layer was separated, and the aqueous layer was extracted three times with CH$_2$Cl$_2$. The combined organic layers were washed with brine and dried over Na$_2$SO$_4$. Filtration and solvent removal afforded the crude product, which was purified by CC (SiO$_2$, 3% methanol in CH$_2$Cl$_2$) to give the title alcohol as a colorless oil. $^1$H NMR (CDCl$_3$, 400 MHz) δ 8.17 (s, 2H), 7.24 (s, 1H), 6.60 (d, J=18.2 Hz, 1H), 6.38 (m, 1H) 4.49 (m, 1H), 4.33 (m, 1H), 4.10 (dd, J=6.1, 3.2 Hz, 1H), 3.62 (t, J=6.1 Hz, 2H), 3.20 (1H, OH), 2.31 (m, 2H), 1.39 (s, 9H); $^{13}$C NMR (CDCl$_3$, 100 MHz) δ 156.4, 155.0, 155.0, 140.4, 136.3, 133.3, 125.5, 117.8, 79.5, 71.4, 68.4, 59.9, 46.9, 43.5, 28.3, 18.7; MS (ESI) 335 (M+H$^+$).

(1R,2S)-2-[[5-[[N-(tert-Butoxycarbonyl)-2(S)-azetidinyl]methoxy]-3-pyridyl]methyl]cyclopropylmethanol (CDCl$_3$, 300 MHz) δ 8.12 (br s, 2H), 7.14 (s, 1H), 4.72 (m, 1H), 4.53 (m, 1H), 4.18 (dd, J=6.1 Hz, 3.1 Hz), 3.91 (t, J=6.2 Hz, 2H), 3.67 (m, 2H), 2.31 (m, 2H), 1.93 (m, 2H), 1.43 (s, 9H), 1.27-0.72 (m, 2H); MS (ESI) 349 (M+H$^+$).

(1R,2S)-2-[[5-[(2(S)-Azetidinyl)methoxy]-3-pyridyl]methyl]cyclopropylmethanol Hydrochloride

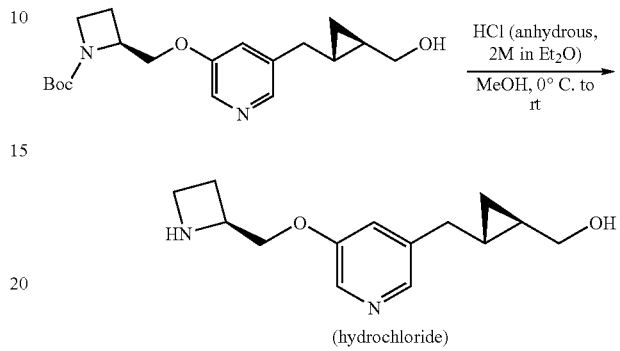

(hydrochloride)

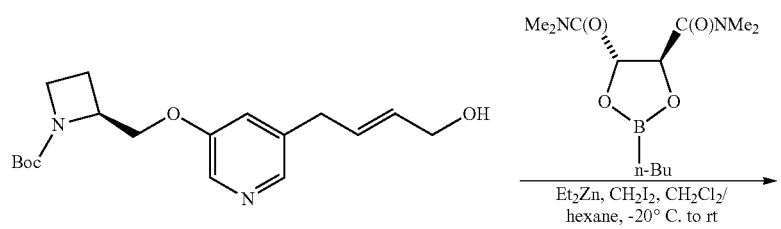

Anhydrous CH$_2$Cl$_2$ (150 mL) was added to a flame-dried 500 mL flask and then cooled to −20° C. Et$_2$Zn (5.9 mL, 1.0 M in hexanes, 5.9 mmol, 2.0 equiv.) was carefully added, followed by the slow addition of diiodomethane (0.96 mL, 12.0 mmol, 4.0 equiv.) in 20 mL of anhydrous CH$_2$Cl$_2$ over 30 min. The solution was stirred for 30 min. Then butylboronic acid N,N,N',N'-tetramethyl-L(−)-tartaric acid diamide ester (the S,S-enantiomer; 0.88 g, 3.28 mmol, 1.1 equiv.) in 30 mL of anhydrous CH$_2$Cl$_2$ was added over 10 min. After 10 min, 4-[5-[1-(tert-butoxycarbonyl)-2(S)-azetidinyl]-3-pyridyl]-trans-2-butenol (1.00 g, 2.99 mmol) was added in 50 mL of anhydrous CH$_2$Cl$_2$. The mixture was allowed to warm to room temperature and was stirred for 12 h. The reaction was then quenched with 20 mL of saturated aqueous NH$_4$Cl. The organic layer was separated, and the aqueous layer was extracted with 3×100 mL of CH$_2$Cl$_2$. The combined organic layers were washed with 100 mL of water, 100 mL of saturated aqueous NaHCO$_3$, and 100 mL of saturated aqueous NaCl, dried over Na$_2$SO$_4$, and concentrated under reduced pressure. Purification by CC (SiO$_2$, 3-4% MeOH in CH$_2$Cl$_2$) yielded the title compound as a clear oil in low yield. $^1$H NMR 2M anhydrous HCl in ether is added to a stirred solution of (1R,2S)-2-[[5-[[1-(tert-butoxycarbonyl)-2(S)-azetidinyl]methoxy]-3-pyridyl]methyl]cyclopropylmethanol in dry MeOH at 0° C. The mixture is stirred at room temperature overnight and the conversion of starting material confirmed by TLC. The above solution is concentrated and purified by HPLC to obtain the title compound.

Example 9

Synthesis of (1S,2R)-2-[[5-[(2(S)-Azetidinyl)methoxy]-3-pyridyl]methyl]cyclopropylmethanol This compound, an isomer of the compound of Example 8, is made according to Scheme 9 by a procedure that is very similar to that detailed in Example 8, with the exception that butylboronic acid N,N,N',N'-tetramethyl-D(+)-tartaric acid diamide ester (the R,R-enantiomer) is used in place of its S,S-enantiomer.

Example 10

Synthesis of 3-[(2(S)-Azetidinyl)methoxy]-5-[(1S,2R)-(2-methoxyethyl)cyclopropyl]pyridine (1S,2S)-2-[5-(Benzyloxy)-3-pyridyl]cyclopropanecarboxaldehyde

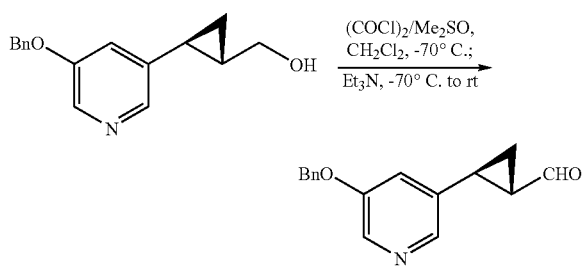

A solution of oxalyl chloride (2.8 mL, 33 mmol, 1.7 equiv.) in anhydrous $CH_2Cl_2$ (120 mL) was cooled to −70° C. under $N_2$. Then a solution of DMSO (3.0 g, 38 mmol, 1.95 equiv.) in anhydrous $CH_2Cl_2$ (30 mL) was added dropwise in 10 min. The Swern reagent solution was stirred at approx. −70° C. for another 15 min. A solution of (2S)-[5-(benzyloxy)-3-pyridyl]-(1S)-cyclopropylmethanol (5.00 g, 19.6 mmol) in anhydrous $CH_2Cl_2$ (40 mL) was added in 30 min, and stirring was continued at −70° C. for another 32 min. Anhydrous triethylamine (16.8 mL, 121 mmol, 6.1 equiv.) was added dropwise in 15 min. The solution was stirred for another 10 min at approx. −70° C. and then allowed to warm to 4° C. within 2 h. The reaction was quenched with water, the phases were separated, and the organic phase was extracted with EtOAc. The combined organic phases were washed with brine and dried over $Na_2SO_4$. After filtration and concentration, the residue was chromatographed on a silica gel column with EtOAc/petroleum ether (1:10-4:1) to give the aldehyde (4.0 g, 81%) as a yellow solid. LC-MS (ESI) m/z 254 (M+H$^+$).

3-(Benzyloxy)-5-[(1S,2S)-2-(2-methoxyvinyl)cyclopropyl]pyridine

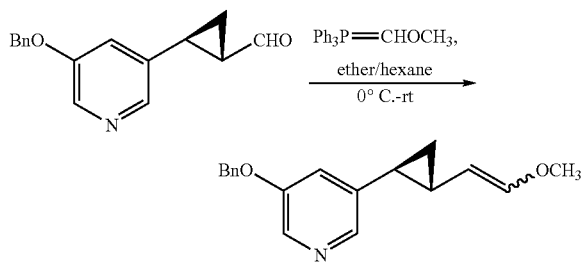

To a suspension of (methoxymethyl)triphenylphosphonium chloride (13.4 g, 39.1 mmol, 3.0 equiv.) in 200 mL of anhydrous ether was added n-butyllithium (2.5M in hexane, 15.6 mL, 39 mmol, 3.0 equiv.) at 0° C. under $N_2$. The liquid phase turned yellow and eventually brownish yellow from the Wittig reagent that was formed. To this solution was added a solution of (1S,2S)-2-[5-(benzyloxy)-3-pyridyl]cyclopropanecarboxaldehyde (3.3 g, 13 mmol) in anhydrous ether (50 mL) at 0° C. via syringe. The mixture was stirred for 2 h at room temperature. Then water was added, the phases were separated, and the aqueous phase was extracted with EtOAc (3×80 mL). The combined organic layers were washed with brine, dried over $Na_2SO_4$, and concentrated under reduced pressure. Purification of the crude product by CC on silica gel furnished the enol ether (2.0 g, 55%) as a yellow oil with a ratio of the E and Z olefin stereoisomers of approx. 2:1. $^1$H NMR (CDCl$_3$, 300 MHz) δ 8.22-8.17 (m, 1H), 8.12-8.05 (m, 1H), 7.48-7.32 (m, 5H), 6.91-6.86 (m, 1H), 6.45 (d, 1H of E isomer, J=12.6 Hz), 5.99 (d, 1H of Z isomer, J=6.3 Hz), 5.11 (s, 2H), 4.64 (dd, 1H of E isomer, J=12.6, 7.2 Hz), 4.06 (dd, 1H of Z isomer, J=9.1, 6.2 Hz), 3.64 (s, 1H of Z isomer), 3.54 (s, 1H of E isomer), 1.99 (m, 1H of Z isomer), 1.85 (m, 1H of Z isomer), 1.79 (m, 1H of E isomer), 1.56 (m, 1H of E isomer), 1.22-1.02 (m, 2H). LC-MS (ESI) m/z 282 (M+H$^+$).

3-(Benzyloxy)-5-[(1S,2R)-2-(2-methoxyethyl)cyclopropyl]pyridine

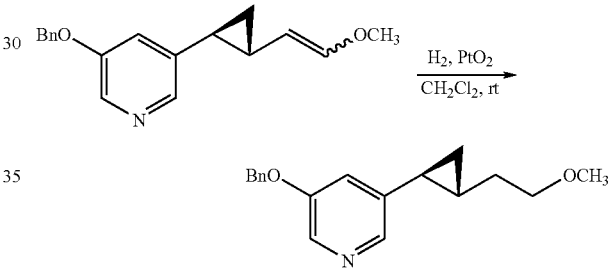

In a 100 mL round-bottom flask, PtO$_2$ (77 mg, 0.34 mmol, 0.05 equiv.) was added under $N_2$ at room temperature to a solution of 3-(benzyloxy)-5-[(1S,2S)-2-(2-methoxyvinyl)cyclopropyl]pyridine (1.90 g, 6.75 mmol) in $CH_2Cl_2$ (18 mL). A $H_2$ balloon was attached, and the atmosphere was exchanged three times. The reaction mixture was stirred at room temperature for 6 h, after which time TLC analysis indicated that the starting material had disappeared completely. The catalyst was filtered off and washed with $CH_2Cl_2$ (2×5 mL). The combined filtrates were concentrated in vacuo to yield crude 3-(benzyloxy)-5-[(1S,2R)-2-(2-methoxyethyl)cyclopropyl]pyridine (1.90 g) as a yellowish oil. LC-MS (ESI) m/z 284 (M+H$^+$).

3-Hydroxy-5-[(1S,2R)-2-(2-methoxyethyl)cyclopropyl]pyridine

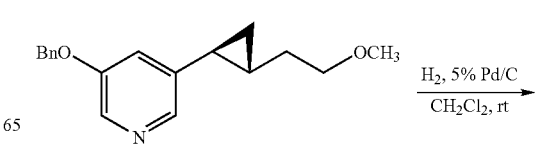

-continued

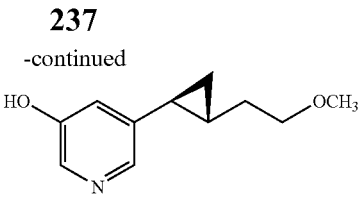

In a 100 mL round-bottom flask, 5% palladium on activated carbon (100 mg) was added under N₂ to a solution of 3-(benzyloxy)-5-[(1S,2R)-2-(2-methoxyethyl)cyclopropyl]pyridine (1.90 g, 6.75 mmol) in CH₂Cl₂ (18 mL). A H₂ balloon was attached, and the atmosphere was exchanged three times. The mixture was stirred at room temperature overnight. The catalyst was filtered off over a compacted cotton plug in the stem of a funnel and washed with CH₂Cl₂. The combined filtrates were concentrated in vacuo and dried (40° C./oil pump) to yield the crude hydroxypyridine (1.27 g) as a yellowish oil. ¹H NMR (CDCl₃, 300 MHz) δ 7.97 (br s, 1H), 7.81 (s, 1H), 7.19 (s, 1H), 6.81 (br s, 1H), 3.42 (t, 2H, J=6.3 Hz), 3.28 (s, 3H); high-field (δ<2) region obscured by aliphatic impurities. LC-MS (ESI) m/z 194 (M+H⁺).

1-(tert-Butoxycarbonyl)-2(S)-(4-toluenesulfonyloxy)azetidine

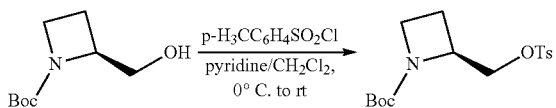 [SMILES: CC(C)(C)OC(=O)N1CC[C@H]1CO ; Cc1ccc(S(=O)(=O)OC[C@@H]2CCN2C(=O)OC(C)(C)C)cc1]

To a solution of [1-(tert-butoxycarbonyl)-2(S)-azetidinyl]methanol (3.74 g, 20 mmol) and pyridine (24 g, 300 mmol, 15 equiv.) in CH₂Cl₂ (20 mL) was added p-toluenesulfonyl chloride (5.72 g, 30 mmol, 1.5 equiv.) with ice cooling under N₂. The solution was stirred overnight at room temperature and diluted with water. After phase separation, the aqueous layer was extracted with EtOAc (3×100 mL). The combined organic layers were washed with saturated aqueous NH₄Cl solution and brine, dried over Na₂SO₄, and concentrated. The residue was loaded onto a silica gel column, which was eluted with EtOAc/petroleum ether 1:10 to give the tosylate (6.5 g, 96%) as a colorless oil. ¹H NMR (CDCl₃, 500 MHz) δ 7.82 (d, 2H, J=8.2 Hz), 7.37 (d, 1H, J=8.0 Hz), 4.35 (br s, 1H), 4.26 (br s, 1H), 4.15 (dd, 1H, J=10.2, 2.8 Hz), 3.84-3.77 (m, 2H), 2.46 (s, 3H), 2.30-2.23 (m, 1H), 2.17 (br s, 1H), 1.39 (s, 9H). LC-MS (ESI) m/z 364 (M+Na⁺).

3-[[1-(tert-Butoxycarbonyl)-2(S)-azetidinyl]methoxy]-5-[(1S,2R)-(2-methoxyethyl)cyclopropyl]pyridine

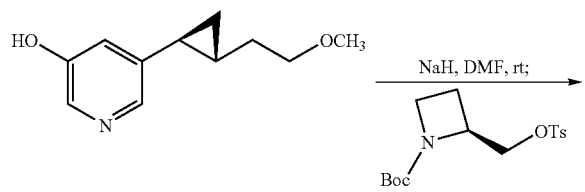

-continued

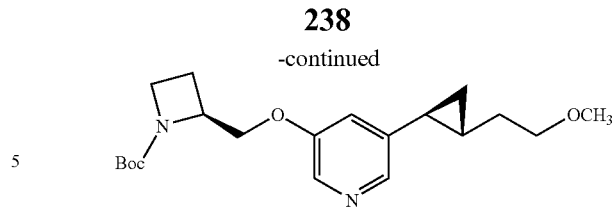

NaH (60% dispersion in mineral oil, 526 mg, 13.2 mmol, 2.0 equiv.) was added portionwise to a solution of 3-hydroxy-5-[(1S,2R)-2-(2-methoxyethyl)cyclopropyl]pyridine (1.27 g, 6.58 mmol) in anhydrous DMF (30 mL) at room temperature under N₂. After stirring for 1 h at room temperature, 1-(tert-butoxycarbonyl)-2(S)-(4-toluenesulfonyloxy)azetidine (2.69 g, 7.9 mmol, 1.2 equiv.) in 10 mL of DMF was added, and the resulting solution was stirred for 4 h at 80° C. under N₂. After cooling, the reaction was quenched with saturated aqueous NH₄Cl solution, and the mixture was extracted with EtOAc (3×80 mL). The combined organic layers were washed with brine and dried over Na₂SO₄. After filtration and concentration, the residue was chromatographed on a silica gel column with EtOAc/petroleum ether to give the product (1.81 g, 76%) as a colorless oil. LC-MS (ESI) m/z 363 (M+H⁺).

3-[(2(S)-Azetidinyl)methoxy]-5-[(1S,2R)-(2-methoxyethyl)cyclopropyl]pyridine

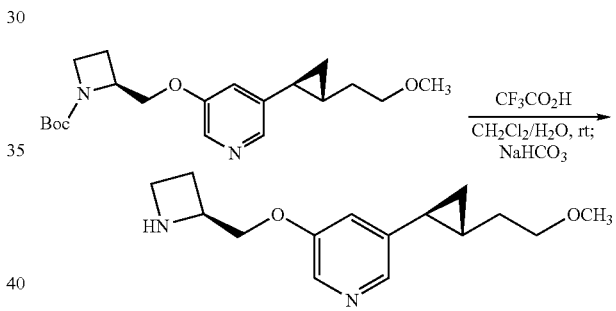

Trifluoroacetic acid (8 mL) was added to CH₂Cl₂ (40 mL) and water (0.8 mL) at 0° C. This mixture was added to 3-[[1-(tert-butoxycarbonyl)-2(S)-azetidinyl]methoxy]-5-[(1S,2R)-(2-methoxyethyl)cyclopropyl]pyridine (1.80 g, 5.0 mmol) at 0° C. under N₂. After stirring at room temperature for 3 h, TLC analysis indicated complete conversion. The solvent was removed, and the crude product (1.5 g) was purified by preparative HPLC (column: SunFire Prep C₁₈, 5 µm particle size, 150×19 mm; UV detection at UV 220 and 254 nm; flow 20 mL/min; mobile phase: A, water with 0.05% TFA; B, CH₃CN; 5-13% B in A in 5.5 min, 13-100% in 1.5 min). The product-containing eluate was partially evaporated under reduced pressure (bath 30° C.) to remove CH₃CN. The pH of the residual solution was adjusted to 8 with saturated aqueous NaHCO₃ solution, and the product was extracted into EtOAc (6×50 mL). The combined organic layers were washed with brine and dried over Na₂SO₄. After filtration and concentration, the free base (725 mg, 55%) was obtained as a colorless oil. ¹H NMR (CDCl₃, 500 MHz) δ 8.11 (narrow m, 1H), 8.06 (narrow m, 1H), 6.85 (narrow m, 1H), 4.41 (m, 1H), 4.13, 4.08 (ABq, 2H, J=9.7 Hz, low-field part d with J=6.1 Hz, high-field part d with J=4.4 Hz), 3.81 (q, 1H, J=8.2 Hz), 3.61 (dt, 1H, J=4.8 Hz (d), 8.5 Hz (t)), 3.50 (t, 2H, J=6.8 Hz), 3.38 (s, 3H), 2.65 (br, 1H, NH+H₂O), 2.47 (m, 1H), 2.37 (m, 1H), 1.77-1.62 (m, 3H), 1.16 (m, 1H), 0.96 (dt, 1H, J=8.5 Hz (d), 5.0 Hz (t), 0.89 (dt, 1H, J=8.5 Hz (d), 5.4 Hz (t)). MS (EI) m/z 263 (M+H$^+$, 0.9%), 262 (M$^+$, 0.8%), 207 (19%), 206 (39%), 177 (10%), 70 (11%), 56 (100%), 45 (40%), 41 (22%). LC-MS (ESI) m/z 263 (M+H$^+$).

3-[(2(S)-Azetidinyl)methoxy]-5-[(1S,2R)-(2-methoxyethyl)cyclopropyl]pyridine Hydrochloride

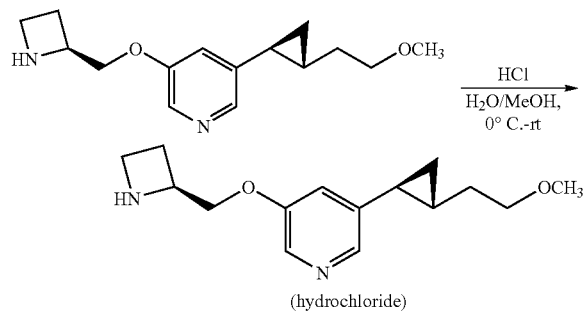

To a 25 mL round-bottom flask containing a solution of 3-[(2(S)-azetidinyl)methoxy]-5-[(1S,2R)-(2-methoxyethyl)cyclopropyl]pyridine (943 mg, 3.6 mmol) in 3 mL of CH$_3$OH was added 2.0M hydrochloric acid (10.8 mmol, 5.4 mL, 3.0 equiv.) at 0° C. under N$_2$. The solution was stirred for 3 h at room temperature and then lyophilized overnight. The residue was dissolved in 10 mL of deionized water and re-lyophilized. The lyophilization process was repeated four times to afford the hydrochloride (1.03 g) as a yellowish solid. $^1$H NMR (300 MHz, D$_2$O) δ 8.25 (br s, 1H), 8.14 (br s, 1H), 7.77 (t, 1H, J=2.1 Hz), 4.92-4.71 (m, 1H), 4.45 (d, 2H, J=4.2 Hz), 4.08-3.97 (m, 2H), 3.51 (t, 2H, J=6.6 Hz), 3.26 (s, 3H), 2.62 (q, 2H, J=8.4 Hz), 1.94-1.88 (m, 1H), 1.67-1.59 (m, 2H), 1.28-1.12 (m, 1H), 1.11-1.04 (m, 2H). $^1$H NMR (CD$_3$OD, 500 MHz) δ 8.23 (d, 1H, J=2.5 Hz), 8.13 (s, 1H), 7.72 (narrow m, 1H), 4.87 (m, 1H), 4.42 (d, 2H, J=4.1 Hz), 4.03 (m, 1H), 3.97 (m, 1H), 3.50 (t, 2H, J=6.4 Hz), 3.25 (s, 3H), 2.59 (q, 2H, J=8.5 Hz), 1.89 (dt, 1H, J=8.3 Hz (d), 4.8 Hz (t), 1.68-1.55 (m, 2H), 1.22 (m, 1H), 1.09-1.02 (m, 2H). LC-MS (ESI) m/z 263 (M+H$^+$).

Example 11

3-[(2(S)-Azetidinyl)methoxy]-5-[(1S,2S)-2-(phenoxymethyl)cyclopropyl]pyridine 3-(Benzyloxy)-5-[(1S,2S)-2-(phenoxymethyl)cyclopropyl]pyridine

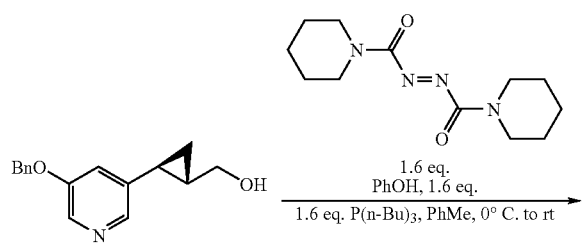

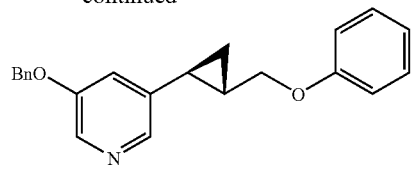

1,1'-(Azodicarbonyl)dipiperidine (316 mg, 1.25 mmol, 1.6 equiv.) was dissolved in 2 mL of toluene (dried with molecular sieve 3 Å) in a 10 mL round-bottom flask with a side neck. The flask was equipped with rubber septa and a magnetic stirrer. The atmosphere was exchanged with Ar (3 times), and the flask was cooled with an ice bath. Tributylphosphine (309 µL, 1.25 mmol, 1.6 equiv.) was added dropwise. The mixture was warmed to room temperature and stirred for 10 min. The colorless solution formed was then added dropwise (via syringe) to a solution of (1S,2S)-2-(5-benzyloxy-3-pyridyl)cyclopropylmethanol (200 mg, 0.78 mmol, 1 equiv.) and phenol (118 mg, 1.25 mmol, 1.6 equiv.) in a 25 mL round-bottom flask (equipped with a magnetic stirrer and an Ar balloon, and cooled with an ice bath). The resulting mixture was warmed to room temperature and stirred overnight. The reaction was quenched by addition of saturated NaHCO$_3$ solution (10 mL), and the mixture was extracted with EtOAc (3×20 mL). The combined organic phases were concentrated, and the residue was purified by CC on SiO$_2$ (25×2.5 cm, EtOAc/hexanes 2:1) to give the crude phenyl ether as a white solid (248 mg, 96%), which was used for next step without further purification. MS (EI) m/z 331 (M$^+$, 0.2%).

5-[(1S,2S)-2-(Phenoxymethyl)cyclopropyl]-3-pyridinol

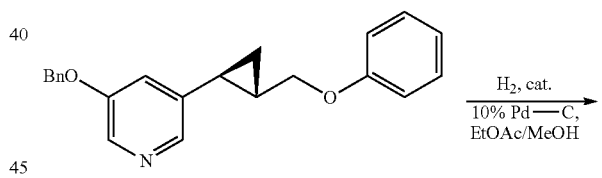

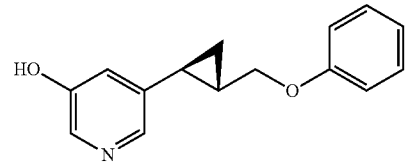

To a solution of 3-(benzyloxy)-5-[(1S,2S)-2-(phenoxymethyl)cyclopropyl]pyridine (248 mg, 0.75 mmol) in EtOAc (10 mL) and methanol (5 mL) was added 10% palladium on carbon (25 mg). The atmosphere was exchanged with H$_2$ (3 times), and the mixture was stirred under H$_2$ (balloon) for 2 h. The resulting mixture was filtered through a cotton plug, and the filtrate was concentrated. The residue was purified by CC on SiO$_2$ (38×1.0 cm, EtOAc/hexanes 7:3) to give the pyridinol as a colorless solid (151 mg, 83%). MS (EI) m/z 241 (M$^+$, 0.7%).

3-[[1-(tert-Butoxycarbonyl)-2(S)-azetidinyl]methoxy]-5-[(1S,2S)-2-(phenoxymethyl)cyclopropyl]pyridine

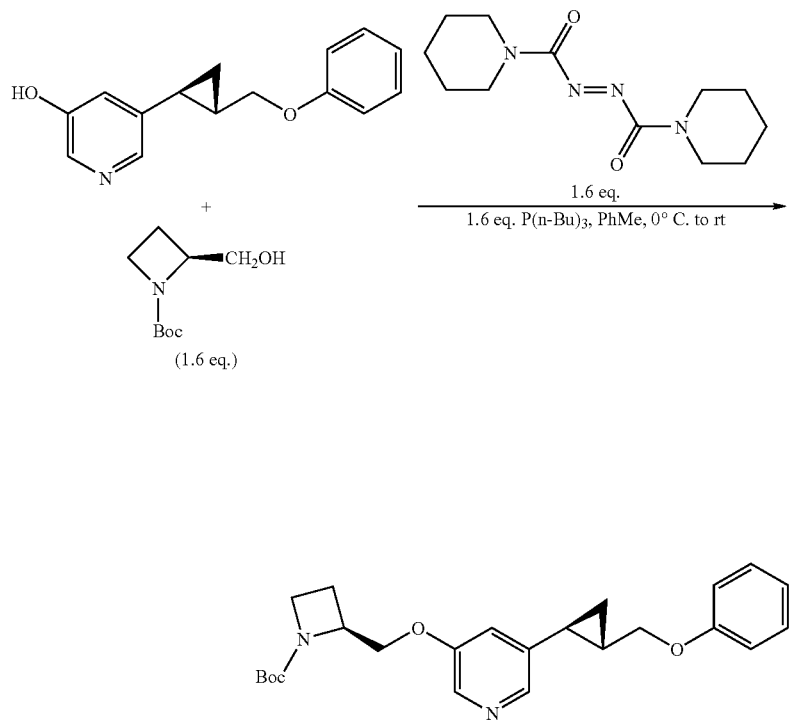

1,1'-(Azodicarbonyl)dipiperidine (253 mg, 1.00 mmol, 1.6 equiv.) was dissolved in 2 mL of toluene (dried with molecular sieve 3 Å) in a 10 mL round-bottom flask with a side neck. The flask was equipped with rubber septa and a magnetic stirrer. The atmosphere was exchanged with Ar (3 times), and the flask was cooled with an ice bath. Tributylphosphine (248 µL, 1.00 mmol, 1.6 equiv.) was added dropwise. The mixture was warmed to room temperature and was stirred for 10 min. The colorless solution formed was then transferred dropwise (via syringe) with ice cooling into a solution of 1-(tert-butoxycarbonyl)-2(R)-azetidinylmethanol (188 mg, 1.00 mmol, 1.6 equiv.) and 5-[(1S,2S)-2-(phenoxymethyl)cyclopropyl]-3-pyridinol (151 mg, 626 µmol) in a 25 mL round-bottom flask equipped with a magnetic stirrer and an Ar balloon. The resulting mixture was warmed to room temperature and stirred overnight. The reaction was quenched by addition of saturated NaHCO$_3$ solution (10 mL). The product was extracted into EtOAc (3×20 mL). The combined organic phases were dried over Na$_2$SO$_4$ and concentrated. The residue was purified by CC on SiO$_2$ (25×2.5 cm, EtOAc/hexanes 2:1) to give the crude product, which was further purified by preparative HPLC in two portions (Supelco Discovery C$_{18}$, 250×21.2 mm, 5 µm particle size, UV detection at 270 nm, flow rate 12.5 mL/min, gradient from 20% to 100% CH$_3$CN in water within 40 min, then 100% CH$_3$CN for 20 min; t$_R$ 29.1-31.1 min) to give the title compound as a yellowish oil (231 mg, 90%). MS (EI) m/z 410 (M$^+$, 0.1%).

3-[(2(S)-Azetidinyl)methoxy]-5-[(1S,2S)-2-(phenoxymethyl)cyclopropyl]pyridine Trifluoroacetate

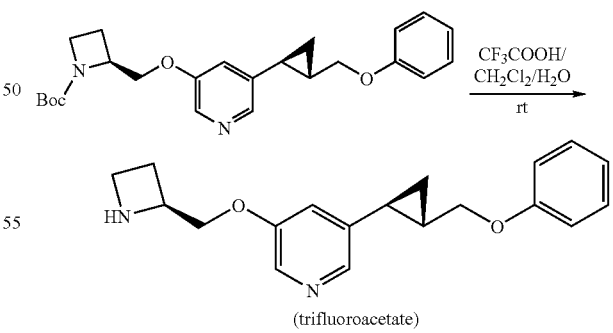

Trifluoroacetic acid (1.0 mL) and water (0.1 mL) were added to CH$_2$Cl$_2$ (5.0 mL). This mixture was added to 3-[[1-(tert-butoxycarbonyl)-2(S)-azetidinyl]methoxy]-5-[(1S,2S)-2-(phenoxymethyl)cyclopropyl]pyridine (230 mg, 0.56 mmol) in a 15 mL round-bottom flask with magnetic stirrer. The flask was capped with a glass stopper, and the reactants were stirred at room temperature for 3 h. The reaction mixture was concentrated with a rotary evaporator (bath up to 35° C.) and was further dried with an oil pump (35° C.). The residue was dissolved in water (5 mL), and the aqueous solution was lyophilized to give the trifluoroacetate (394 mg, 96%) as a colorless oil. $^1$H NMR (CD$_3$OD, 500 MHz) δ 8.50 (d, 1H, J=2.5 Hz), 8.40 (d, 1H, J=0.8 Hz), 7.95 (t, 1H, J=2.1 Hz), 7.32-7.25 (m, 2H), 6.98-6.90 (m, 3H), 4.95-4.90 (m, 1H), 4.62-4.51 (m, 2H), 4.21 (dd, 1H, J=10.3, 5.6 Hz), 4.18-4.07 (m, 2H), 3.97 (dd, 1H, J=10.3, 7.1 Hz), 2.78-2.64 (m, 2H), 2.31 (quint, 1H, J=4.6 Hz), 1.96-1.86 (m, 1H), 1.43-1.33 (m, 2H). MS (EI) m/z 310 (M$^+$ of free base, 0.7%). Anal. Calcd. for C$_{19}$H$_{22}$N$_2$O$_2$.3.52CF$_3$COOH.1.04H$_2$O (FW 730.5): C, 42.82; H, 3.81; N, 3.83; F, 27.46. Found: C, 42.64; H, 3.62; N, 3.72; F, 27.30.

Example 12

Synthesis of 3-[(2(S)-Azetidinyl)methoxy]-5-[(1S, 2S)-2-[(3-pyridyloxy)methyl]cyclopropyl]pyridine 3-(Benzyloxy)-5-[(1S,2S)-2-[(3-pyridyloxy)methyl]cyclopropyl]pyridine

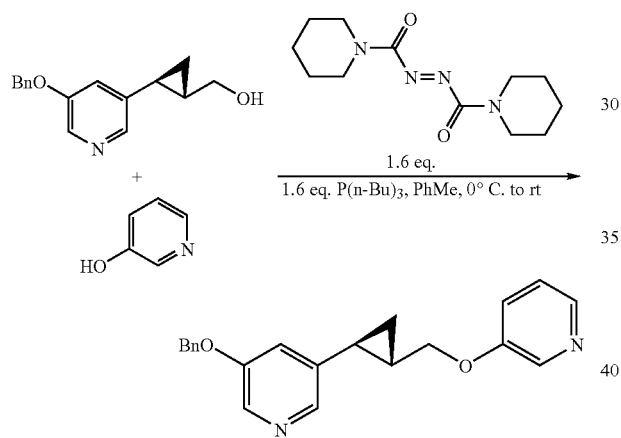

1,1'-(Azodicarbonyl)dipiperidine (237 mg, 0.94 mmol, 1.6 equiv.) was dissolved in 2 mL of toluene (dried with molecular sieve 3 Å) in a 10 mL round-bottom flask with a side neck. The flask was equipped with rubber septa and a magnetic stirrer. The atmosphere was exchanged with Ar (3 times), and the flask was cooled with an ice bath. Tri-n-butylphosphine (232 μL, 0.94 mmol, 1.6 equiv.) was added dropwise. The mixture was warmed to room temperature and stirred for 10 min. The resulting colorless solution was then added dropwise (via syringe) with ice cooling to a solution of (1S,2S)-2-[(5-(benzyloxy)-3-pyridyl]cyclopropylmethanol (50 mg, 0.59 mmol) and 3-hydroxypyridine (89 mg, 0.94 mmol, 1.6 equiv.) in a 25 mL round-bottom flask (equipped with a magnetic stirrer and an Ar balloon). The resulting mixture was warmed to room temperature and stirred for 6 h. Air was bubbled through the mixture with stirring for 1 h. Toluene was evaporated, and the residue was purified by CC on SiO$_2$ (15×1.0 cm, EtOAc) to give the crude product, which was contaminated with a by-product, 2,5-di-(1-piperidinyl)-1,3,4-oxadiazole. This material was further purified by preparative HPLC in two portions (Supelco Discovery C$_{18}$, 250×21.2 mm, 5 μm particle size, UV detection at 270 nm, flow rate 12.5 mL/min, gradient from 20% to 100% CH$_3$CN in water within 40 min, then 100% CH$_3$CN for 20 min; t$_R$ 22.7-24.0 min) to give a yellowish oil (125 mg, 64%). MS (EI) m/z 332 (M$^+$, 67%).

5-[(1S,2S)-2-[(3-Pyridyloxy)methyl]cyclopropyl]-3-pyridinol

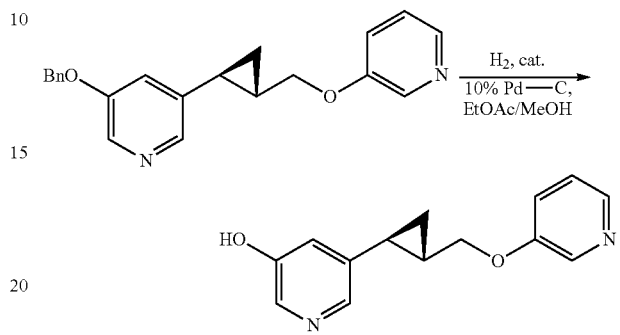

To a solution of 3-(benzyloxy)-5-[(1S,2S)-2-[(3-pyridyloxy)methyl]cyclopropyl]pyridine (125 mg, 376 μmol) in EtOAc (10 mL) and methanol (5 mL) was added 10% palladium on carbon (25 mg). The atmosphere was exchanged with H$_2$ (3 times), and the mixture was stirred under H$_2$ for 2 h. The resulting mixture was filtered through a cotton plug, and the filtrate was concentrated. The residue was evaporated with EtOAc (3×5 mL) to give the pyridinol as a light-yellow oil, which turned in to a colorless solid during storage (92 mg, quantitative). MS (EI) m/z 242 (M$^+$, 14%).

3-[[(S)-N-(tert-Butoxycarbonyl)-2-azetidinyl]methoxy]-5-[(1S,2S)-2-[(3-pyridyloxy)methyl]cyclopropyl]pyridine

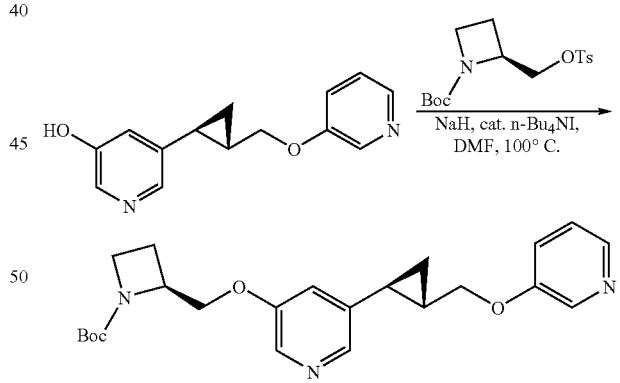

To a solution of 5-[(1S,2S)-2-[(3-pyridyloxy)methyl]cyclopropyl]-3-pyridinol (92 mg, 0.38 mmol) in anhydrous DMF (5 mL) in a 25 mL round-bottom flask was added NaH (60% dispersion in mineral oil, 23 mg, 0.57 mmol, 1.5 equiv.). The flask was equipped with a condenser, and the atmosphere was exchanged with Ar (3 times). The suspension was heated to 100° C. (oil bath) and stirred for 1 h. After cooling to room temperature, 1-(tert-butoxycarbonyl)-2(S)-[(4-toluenesulfonyloxy)methyl]azetidine (195 mg, 0.57 mmol, 1.5 equiv.) in dry DMF (2 mL) and tetra-n-butylammonium iodide (14 mg, 0.04 mmol, 0.1 equiv.) were added. The resulting mixture was again protected with Ar and stirred at 100° C. overnight. After the reaction mixture was cooled to room temperature, saturated NH$_4$Cl solution (15 mL) was added to quench excessive NaH. The product was extracted into EtOAc (3×15 mL). The combined organic phases were washed with brine (15 mL), dried over Na$_2$SO$_4$, and concentrated. The residue was purified by CC on SiO$_2$ (10×1.0 cm, EtOAc) to give the crude product, which was further purified by preparative HPLC in two portions (Supelco Discovery C$_{18}$, 250×21.2 mm, 5 μm particle size, UV detection at 270 nm, flow rate 12.5 mL/min, gradient from 20% to 100% CH$_3$CN in water within 40 min, then 100% CH$_3$CN for 20 min; $t_R$ 22.0-23.2 min) to give a yellowish oil (123 mg, 79%). $^1$H NMR (CDCl$_3$, 500 MHz) δ 8.35 (s, 1H), 8.26 (d, 1H, J=3.8 Hz), 8.18 (s, 1H), 8.10 (s, 1H), 7.29-7.22 (m, 2H), 6.95 (s, 1H), 4.53 (d, 1H, J=4.6 Hz), 4.33 (s, br, 1H), 4.15 (dd, 1H, J=10.0, 2.4 Hz), 4.10 (dd, 1H, J=9.9, 6.6 Hz), 4.03 (dd, 1H, J=9.8, 6.8 Hz), 3.92 (t, 2H, J=7.6 Hz), 2.39-2.28 (m, 2H), 2.02-1.97 (m, 1H), 1.67 (dd, 1H, J=12.6, 5.8 Hz), 1.44 (s, 9H), 1.19-1.13 (m, 2H).

3-[(2(S)-Azetidinyl)methoxy]-5-[(1S,2S)-2-[(3-pyridyloxy)methyl]cyclopropyl]pyridine Trifluoroacetate

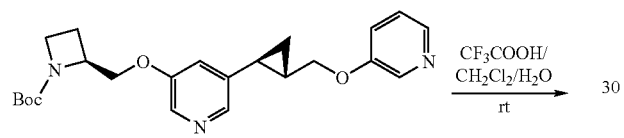

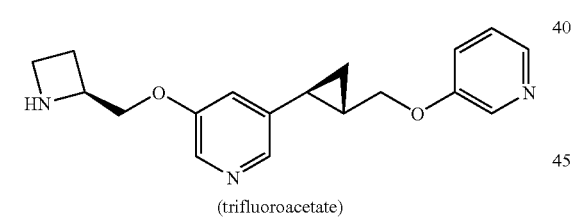

(trifluoroacetate)

Trifluoroacetic acid (0.7 mL) and water (0.07 mL) were added to CH$_2$Cl$_2$ (3.5 mL). This mixture was added to a sample of 3-[[(S)-1-(tert-butoxycarbonyl)-2-azetidinyl]methoxy]-5-[(1S,2S)-2-[(3-pyridyloxy)methyl]cyclopropyl]pyridine (115 mg, 279 μmol) in a 15 mL round-bottom flask with magnetic stirrer. The flask was capped with a glass stopper, and the reactants were stirred at room temperature for 2 h. The mixture was concentrated with a rotary evaporator (bath up to 35° C.) and further dried with an oil pump (35° C.). The residue was dissolved in water (2 mL), and the aqueous solution was lyophilized to give the trifluoroacetate as a yellow oil (247 mg, 93%). $^1$H NMR (CD$_3$OD, 500 MHz) δ 8.64 (d, 1H, J=2.6 Hz), 8.53 (d, 1H, J=2.3 Hz), 8.50 (d, 1H, J=5.4 Hz), 8.45 (s, 1H), 8.25-8.22 (m, 1H), 8.02 (dd, 1H, J=8.8, 5.6 Hz), 7.99 (d, 1H, J=2.0 Hz), 4.98-4.94 (m, 1H), 4.61 (dd, 1H, J=11.2, 5.8 Hz), 4.56 (dd, 1H, J=11.1, 3.0 Hz), 4.42 (dd, 1H, J=10.2, 6.2 Hz), 4.28 (dd, 1H, J=10.2, 7.2 Hz), 4.19-4.09 (m, 2H), 2.77-2.66 (m, 2H), 2.42-2.37 (m, 1H) 2.02 (dd, 1H, J=11.6 Hz, 6.4 Hz), 1.45 (t, 2H, J=7.3 Hz). Anal. Calcd. for C$_{18}$H$_{21}$N$_3$O$_2$.5.56CF$_3$COOH.0.60H$_2$O (FW 956): C, 36.58; H, 2.93; N, 4.39; F, 33.14. Found: C, 36.58; H, 2.98; N, 4.43; F, 33.19.

Example 13

Synthesis of 3-[(2(S)-Azetidinyl)methoxy]-5-[(1S, 2S)-2-(benzyloxymethyl)cyclopropyl]pyridine 3-(Benzyloxy)-5-[(1S,2S)-2-(benzyloxymethyl)cyclopropyl]pyridine

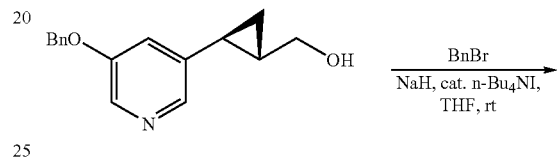

To a solution of (1S,2S)-2-[(5-(benzyloxy)-3-pyridyl]cyclopropylmethanol (150 mg, 0.59 mmol) in anhydrous THF (5 mL) in a 25 mL round-bottom flask was added NaH (60% dispersion in mineral oil, 36 mg, 0.89 mmol, 1.5 equiv.). The flask was equipped with a condenser, and the atmosphere was exchanged with Ar (3 times). The suspension was stirred at room temperature for 2 h. Benzyl bromide (131 mg, 0.77 mmol, 1.3 equiv.) and tetra-n-butylammonium iodide (23 mg, 60 μmol, 0.1 equiv.) in dry THF (2 mL) were added. The resulting mixture was again protected with Ar and was stirred at room temperature overnight. Saturated NH$_4$Cl solution (20 mL) was added to quench excessive NaH, and the product was extracted into EtOAc (3×20 mL). The combined organic phases were washed with brine (15 mL), dried over Na$_2$SO$_4$, and concentrated. The residue was purified by CC on SiO$_2$ (25×1.0 cm, EtOAc/hexanes 1:1) to give the crude benzyl ether as a light yellow oil (210 mg, quantitative). MS (EI) m/z 345 (M$^+$, 3.7%).

3-[[1-(tert-Butoxycarbonyl)-2(S)-azetidinyl]methoxy]-5-[(1S,2S)-2-(benzyloxymethyl)cyclopropyl]pyridine

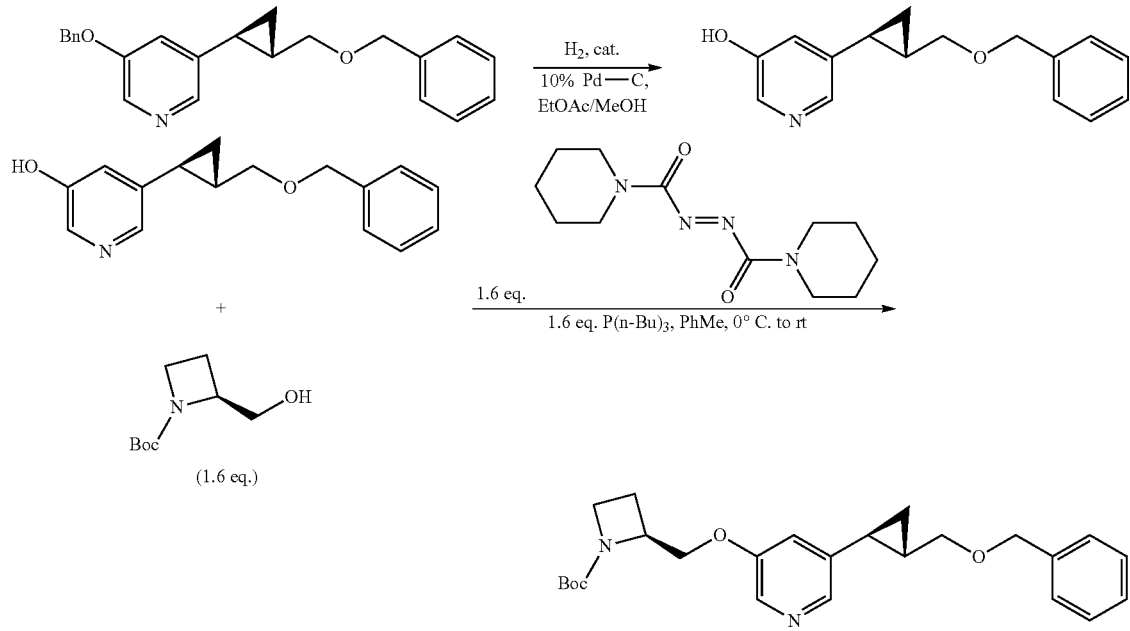

To a solution of 3-(benzyloxy)-5-[(1S,2S)-2-(benzyloxymethyl)cyclopropyl]pyridine (210 mg, 608 μmol) in EtOAc (10 mL) and methanol (5.0 mL) was added 10% palladium on carbon (42 mg). The atmosphere was exchanged with H₂ (3 times), and the mixture was stirred under H₂ for 4 h. The resulting mixture was filtered through a cotton plug, and the filtrate was concentrated and azeotroped with toluene (3×5 mL) to give 5-[(1S,2S)-2-(benzyloxymethyl)cyclopropyl]-3-pyridinol as a light-yellow oil (131 mg, 84%).

1,1'-(Azodicarbonyl)dipiperidine (207 mg, 0.82 mmol, 1.6 equiv.) was dissolved in 2.0 mL of toluene (dried with molecular sieve 3 Å) in a 10 mL round-bottom flask with a side neck. The flask was equipped with rubber septa and a magnetic stirrer. The atmosphere was exchanged with Ar (3 times), and the flask was cooled with an ice bath. Tributylphosphine (203 μL, 0.82 mmol, 1.6 equiv.) was added dropwise. The mixture was warmed to room temperature and stirred for 10 min. The resulting colorless solution was then added dropwise (via syringe) with ice cooling to a solution of 5-[(1S,2S)-2-(benzyloxymethyl)cyclopropyl]-3-pyridinol (131 mg, 0.51 mmol) and 1-(tert-butoxycarbonyl)-2(S)-azetidinylmethanol (154 mg, 0.82 mmol, 1.6 equiv.) in a 25 mL round-bottom flask (equipped with a magnetic stirrer and an Ar balloon). The resulting mixture was warmed to room temperature and stirred overnight. Air was bubbled through the mixture for 2 h. The solvent was evaporated, and the residue was purified by CC on SiO₂ (15×1.0 cm, EtOAc) to give the crude product, which was further purified by preparative HPLC (Supelco Discovery C₁₈, 250×21.2 mm, 5 μm particle size, UV detection at 270 nm, flow rate 12.5 mL/min, gradient from 20% to 100% CH₃CN in water within 40 min, then 100% CH₃CN for 20 min; $t_R$ 28.5-30.9 min) to give a colorless oil (170 mg, 79%). MS (EI) m/z 424 (M⁺, 0.5%).

3-[(2(S)-Azetidinyl)methoxy]-5-[(1S,2S)-2-(benzyloxymethyl)cyclopropyl]pyridine Trifluoroacetate

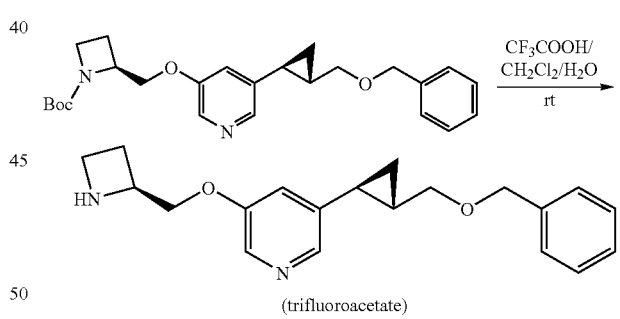

(trifluoroacetate)

Trifluoroacetic acid (0.80 mL) and water (0.08 mL) were added to CH₂Cl₂ (4.0 mL). This mixture was added to a sample of 3-[[1-(tert-butoxycarbonyl)-2(S)-azetidinyl]methoxy]-5-[(1S,2S)-2-(benzyloxymethyl)cyclopropyl]pyridine (170 mg, 400 μmol) in a 15 mL round-bottom flask with magnetic stirrer. The flask was capped with a glass stopper, and the reactants were stirred at room temperature overnight. The reaction mixture was concentrated with a rotary evaporator and further dried with an oil pump (bath up to 35° C.) to give the trifluoroacetate (294 mg, quantitative) as a colorless oil. ¹H NMR (CD₃OD, 500 MHz) δ 8.48 (d, 1H, J=2.4 Hz), 8.37 (s, 1H), 7.92 (t, 1H, J=2.0 Hz), 7.39-7.32 (m, 4H), 7.32-7.26 (m, 1H), 4.97-4.90 (m, 1H), 4.62-4.51 (m, 4H), 4.19-4.07 (m, 2H), 3.73 (dd, 1H, J=10.4, 5.6 Hz), 3.48 (dd, 1H, J=10.5, 7.2 Hz), 2.79-2.63 (m, 2H), 2.20-2.13 (m, 1H), 1.77-1.69 (m, 1H), 1.31-1.24 (m, 2H). Anal. Calcd. for C$_{20}$H$_{24}$N$_2$O$_2$.3.54CF$_3$COOH.0.18H$_2$O (FW 731.3): C, 44.48; H, 3.85; N, 3.83; F, 27.59. Found: C, 44.32; H, 3.66; N, 3.95; F, 27.41.

Example 14

Synthesis of 3-[(2(S)-Azetidinyl)methoxy]-5-[(1S,2S)-2-[(2-pyridinylmethoxy)methyl]cyclopropyl]pyridine 3-(Benzyloxy)-5-[(1S,2S)-2-[(2-pyridylmethoxy)methyl]cyclopropyl]pyridine

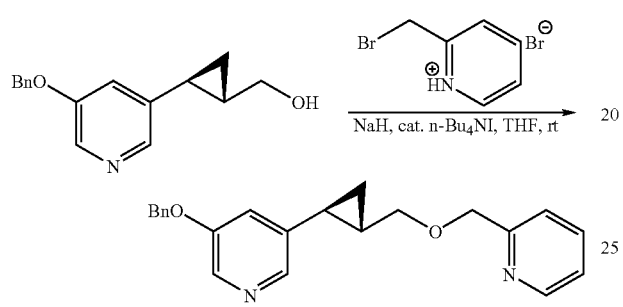

To a solution of (1S,2S)-2-[5-(benzyloxy)-3-pyridyl]cyclopropylmethanol (150 mg, 0.59 mmol) in anhydrous THF (5 mL) in a 25 mL round-bottom flask was added sodium hydride (60% dispersion in mineral oil, 57 mg, 1.41 mmol, 2.4 equiv.). The flask was equipped with a condenser, and the atmosphere was exchanged with Ar (3 times). The suspension was stirred at room temperature for 2 h. 2-(Bromomethyl)pyridine hydrobromide (178 mg, 0.70 mmol, 1.2 equiv.) and tetra-n-butylammonium iodide (23 mg, 60 µmol, 0.1 equiv.) in dry THF (2 mL) were added. The resulting mixture was again protected with Ar and was stirred at room temperature overnight. Saturated NH$_4$Cl solution (15 mL) was added to quench excessive sodium hydride, and the product was extracted into EtOAc (3×20 mL). The combined organic phases were washed with brine (15 mL), dried over Na$_2$SO$_4$, and concentrated. The residue was purified by CC on SiO$_2$ (25×1.0 cm, EtOAc) to give the crude product as a colorless oil (181 mg, 88%). MS (EI) m/z 346 (M$^+$, 6.8%).

5-[(1S,2S)-2-[(2-Pyridylmethoxy)methyl]cyclopropyl]-3-pyridinol

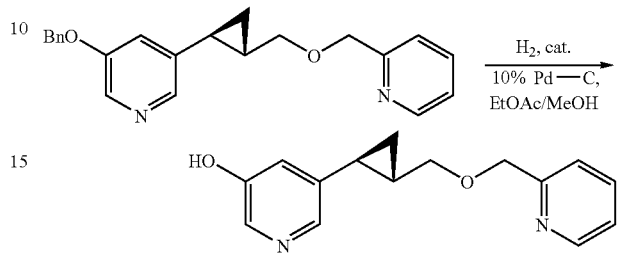

To a solution of 3-(benzyloxy)-5-[(1S,2S)-2-[(2-pyridylmethoxy)methyl]cyclopropyl]pyridine (181 mg, 522 µmol) in EtOAc (15 mL) and methanol (7.5 mL) was added 10% palladium on carbon (36 mg). The atmosphere was exchanged with H$_2$ (3 times), and the mixture was stirred under H$_2$ for 6 h. The resulting mixture was filtered through a cotton plug, and the filtrate was concentrated to give the pyridinol as a colorless oil (138 mg, quantitative). MS (EI) m/z 256 (M$^+$, 4.6%).

3-[[1-(tert-Butoxycarbonyl)-2(S)-azetidinyl]methoxy]-5-[(1S,2S)-2-[(2-pyridylmethoxy)methyl]cyclopropyl]pyridine

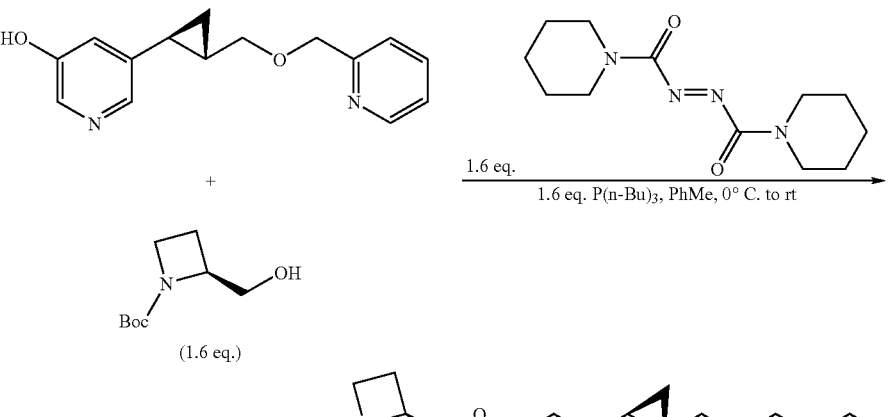

1,1'-(Azodicarbonyl)dipiperidine (218 mg, 0.86 mmol, 1.6 equiv.) was dissolved in 2.5 mL of toluene (dried with molecular sieve 3 Å) in a 10 mL round-bottom flask with a side neck. The flask was equipped with rubber septa and a magnetic stirrer. The atmosphere was exchanged with Ar (3 times), and the flask was cooled with an ice bath. Tributylphosphine (213 µL, 0.86 mmol, 1.6 equiv.) was added dropwise. The mixture was warmed to room temperature and stirred for 10 min. The colorless solution formed was then added dropwise (via syringe) with ice cooling to a solution of 5-[(1S,2S)-2-[(2-pyridylmethoxy)methyl]cyclopropyl]-3-pyridinol (138 mg, 0.54 mmol, evaporated three times with 5 mL of toluene each time) and 1-(tert-butoxycarbonyl)-2(S)-azetidinylmethanol (162 mg, 0.86 mmol, 1.6 equiv.) in a 25 mL round-bottom flask (equipped with a magnetic stirrer and an Ar balloon). The resulting mixture was warmed to room temperature and stirred overnight. Air was bubbled through the mixture for 3 h. The solvent was evaporated, and the residue was purified by CC on $SiO_2$ (10×1.0 cm, EtOAc) to give the crude product, which was further purified by preparative HPLC in 3 portions (Supelco Discovery $C_{18}$, 250×21.2 mm, 5 μm particle size, UV detection at 270 nm, flow rate 12.5 mL/min, gradient from 20% to 100% $CH_3CN$ in water within 40 min, then 100% $CH_3CN$ for 20 min; $t_R$ 21.9-23.1 min) to give the product as a colorless oil (161 mg, 70%). $[\alpha]_{546}$ −143; $[\alpha]_{589}$ −120 (c 8.55 g/L, EtOAc). $^1H$ NMR ($CDCl_3$, 500 MHz) δ 8.57 (d, 1H, J=4.9 Hz), 8.15 (d, 1H, J=2.7 Hz), 8.07 (s, 1H), 7.71 (td, 1H, J=7.7, 1.8 Hz), 7.48 (d, 1H, J=7.8 Hz), 7.21 (dd, 1H, J=7.0, 5.4 Hz), 6.88 (d, 1H, J=2.0 Hz), 4.70 (s, 2H), 4.56-4.49 (m, 1H), 4.31 (s, br, 1H), 4.13 (dd, 1H, J=9.9, 2.9 Hz), 3.95-3.88 (m, 2H), 3.65 (dd, 1H, J=10.5, 6.4 Hz), 3.60 (dd, 1H, J=10.4, 6.7 Hz), 2.42-2.33 (m, 1H), 2.33-2.24 (m, 1H), 1.87 (dt, 1H, J=8.0, 5.7 Hz), 1.58-1.50 (m, 1H), 1.43 (s, 9H), 1.08-1.01 (m, 2H). MS (EI) m/z 425 ($M^+$, 7.0%).

3-[(2(S)-Azetidinyl)methoxy]-5-[(1S,2S)-2-[(2-pyridylmethoxy)methyl]cyclopropyl]pyridine Trifluoroacetate

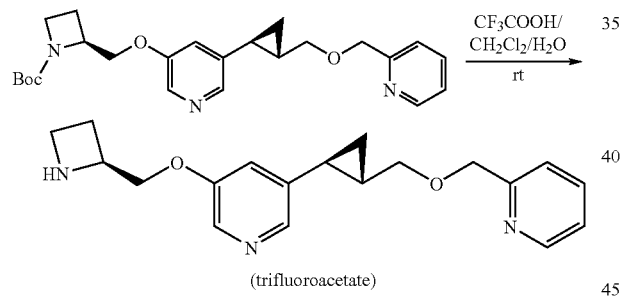

Trifluoroacetic acid (1.0 mL) and water (0.10 mL) were added to $CH_2Cl_2$ (5.0 mL). This mixture was added to 3-[[1-(tert-butoxycarbonyl)-2(S)-azetidinyl]methoxy]-5-[(1S,2S)-2-[(2-pyridylmethoxy)methyl]cyclopropyl]pyridine (152 mg, 357 μmol) in a 15 mL round-bottom flask with magnetic stirrer. The flask was capped with a glass stopper, and the reactants were stirred at room temperature overnight. The reaction mixture was concentrated with a rotary evaporator and further dried with an oil pump (bath up to 35° C.) to give the trifluoroacetate (328 mg, quantitative) as a colorless oil. $^1H$ NMR ($CD_3OD$, 500 MHz) δ 8.80 (d, 1H, J=5.7 Hz), 8.57 (t, 1H, J=7.9 Hz), 8.50 (d, 1H, J=1.1 Hz), 8.40 (s, 1H), 8.05 (d, 1H, J=8.1 Hz), 7.98 (t, 1H, J=6.6 Hz), 7.93 (s, 1H), 4.97-4.91 (m, 3H), 4.60 (dd, 1H, J=11.1, 5.5 Hz), 4.55 (dd, 1H, J=11.1, 2.8 Hz), 4.19-4.08 (m, 2H), 3.86 (dd, 1H, J=10.6, 6.1 Hz), 3.73 (dd, 1H, J=10.6, 7.0 Hz), 2.78-2.63 (m, 2H), 2.26 (dd, 1H, J=11.3, 6.8 Hz), 1.88-1.80 (m, 1H), 1.34 (t, 2H, J=7.1 Hz). MS (EI) m/z 325 ($M^+$ of free base, 0.4%). Anal. Calcd. for $C_{19}H_{23}N_3O_2 \cdot 4.89CF_3COOH \cdot 1.39H_2O$ (FW 908): C, 38.06; H, 3.40; N, 4.63; F, 30.70. Found: C, 37.78; H, 3.12; N, 4.37; F, 30.42.

Example 15

15a: Synthesis of 3-(3-Iodophenyl)-1-propanol and 3-(4-Iodophenyl)-1-propanol

These compounds were prepared according to Scheme 10a. Both isomers were subjected to a final purification by vacuum distillation.

15b: Synthesis of 3-[3-[5-[[1-(tert-Butoxycarbonyl)-2(S)-azetidinyl]methoxy]-3-pyridyl]phenyl]-1-propanol and 3-[4-[5-[[1-(tert-Butoxycarbonyl)-2(S)-azetidinyl]methoxy]-3-pyridyl]phenyl]-1-propanol These compounds were prepared according to Scheme 10b.

3-[[1-(tert-Butoxycarbonyl)-2(S)-azetidinyl]methoxy]-5-(trimethylstannyl)pyridine

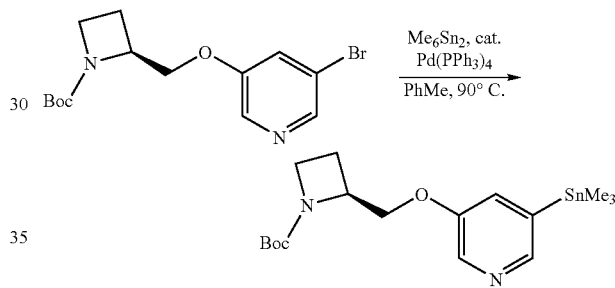

A solution of 3-bromo-5-[[1-(tert-butoxycarbonyl)-2(S)-azetidinyl]methoxy]pyridine (859 mg, 2.50 mmol) and tetrakis(triphenylphosphine)palladium(0) (87 mg, 75 μmol, 0.03 equiv.) in anhydrous toluene (8 mL) was purged with nitrogen in a 38 mL Chemglass pressure tube. Hexamethyldistannane (1.56 mL, 7.5 mmol, 3.0 equiv.) was added all at once, and the tube was capped and heated to 90° C. for 27 h. After cooling, the heterogeneous reaction mixture (solution and precipitate) was directly loaded onto a silica gel column (25×3.8 cm), and the product was rapidly eluted with EtOAc/hexane/triethylamine 25:70:5. The product-containing fractions were evaporated, and the residue was twice evaporated with acetonitrile (to remove residual triethylamine). Drying (40° C./14 torr) yielded 964 mg (90%) of the stannane as an oil which was suitable for subsequent reactions.

A small sample was purified by preparative HPLC (Supelco Discovery $C_{18}$, 250×10 mm with guard column, 5 μm particle size; UV detection at 270 nm; flow 2.5 mL/min; gradient from 20 to 100% acetonitrile in water within 40 min). The major peak (eluting broadly at $t_R$ approx. 32-35 min) was collected, and the solution was concentrated to a small volume with a rotary evaporator (bath up to 40° C.). The residue was twice evaporated with ethanol to remove residual water, and once more with acetonitrile. $^1H$ NMR ($C_6D_6$, TMS, 250 MHz) δ 8.56-8.50 (m, 2H; Sn satellites present but too broad to read coupling constants), 7.34 (dd, 1H, J=1.0, 3.0 Hz; Sn satellites present but too broad to read coupling constants), 4.15 (br, 2H), 3.81-3.53 (m, 3H), 1.88-1.72 (m, 1H), 1.72-1.56 (m, 1H), 1.40 (s, 9H), 0.14 (s, 9H, with Sn satellites, $J_{H-Sn}$=55.8 and 53.5 Hz, resp.). $^{13}$C NMR (C$_6$D$_6$, TMS, 62.5 MHz) δ 155.1, 155.5, 148.9 (with weak Sn satellites), 138.1 (br), 137.0 (two pyridine C not observed, probably coinciding with the intense C$_6$D$_6$ signal), 79.1, 68.8, 60.3, 47.4 (br), 28.5, 19.3, −9.9 (with Sn satellites, $J_{C-Sn}$=354 and 338 Hz, resp.). MS (EI) m/z 413/411/409 (M$^+$−CH$_3$, 4.4/3.3/1.9%), 357/355/353 (49/39/24%), 57 (100%), 56 (56%).

3-[3-[5-[[1-(tert-Butoxycarbonyl)-2(S)-azetidinyl]methoxy]-3-pyridyl]phenyl]-1-propanol

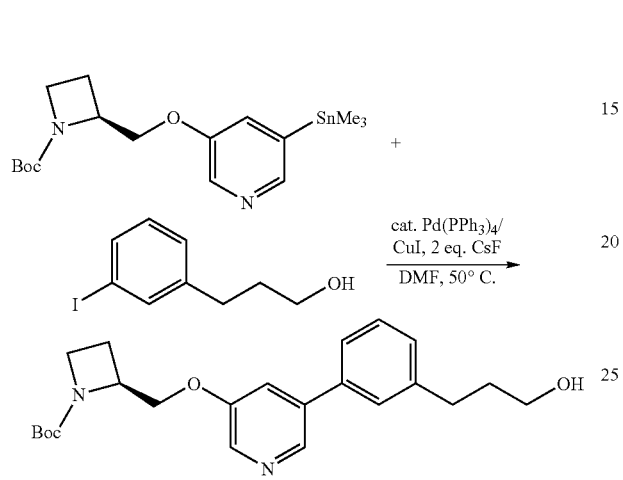

3-[[1-(tert-Butoxycarbonyl)-2(S)-azetidinyl]methoxy]-5-(trimethylstannyl)pyridine (310 mg, 726 µmol), 3-(3-iodophenyl)-1-propanol (190 mg, 726 µmol), and anhydrous DMF (2.5 mL) were placed in a 50 mL round bottom flask with magnetic stirrer. To this mixture were added rapidly CsF (221 mg, 1.45 mmol, 2.0 equiv.), CuI (14 mg, 73 µmol, 0.1 equiv.), and tetrakis(triphenylphosphine)palladium(0) (42 mg, 36 µmol, 0.05 equiv.). The flask was fitted with a three-way stopcock with nitrogen balloon, and the atmosphere was exchanged. The reaction mixture was heated at 50° C. for 250 min. After this period of time, the TLC of an evaporated aliquot (SiO$_2$, EtOAc) showed the absence of the aryl iodide and the formation of a new, polar spot. The bulk of solvent was pumped off at room temperature with an oil pump, and EtOAc was added to the residue, resulting in a solution and a precipitate. Both were loaded on a silica gel column (24×2.5 cm), which was eluted with EtOAc. Product-containing fractions were combined, evaporated, and evaporated with acetonitrile. The residue was taken up in acetonitrile and the solution was filtered from a small amount of wax over a cotton plug. The solution was again evaporated and the residue was taken up in DMSO (1 mL). Further purification was achieved by preparative HPLC in two portions on a Supelco Discovery C$_{18}$ column (250×21.2 mm, 5 µm particle size; UV detection at 270 nm; flow 12.5 mL/min; gradient from 20 to 100% of acetonitrile in water within 50 min). The coupling product eluted as the main peak at $t_R$ approx. 25-27 min. The eluate was partially evaporated to remove acetonitrile, and the product was extracted from the residue with CH$_2$Cl$_2$ (3×10 mL). After drying over MgSO$_4$, the combined organic phases were evaporated and dried (45° C./14 torr) to obtain 241 mg (83%) of the product as a glass. $^1$H NMR (CDCl$_3$, TMS, 250 MHz) δ 8.45 (d, 1H, J=1.7 Hz), 8.31 (d, 1H, J=2.7 Hz), 7.46-7.34 (m, 4H), 7.29-7.22 (m, 1H), 4.55 (m, 1H), 4.40 (m, 1H), 4.21 (dd, 1H, J=2.9, 10.0 Hz), 3.92 (m, 2H), 3.72 (t, 2H, J=6.4 Hz), 2.80 (m, 2H), 2.47-2.24 (m, 2H), 2.21 (s, 1H, OH), 2.02-1.88 (m, 2H), 1.40 (s, 9H). $^{13}$C NMR (CDCl$_3$, 62.5 MHz) δ 156.2, 155.2, 142.8, 140.8, 137.6, 137.5, 136.5 (br), 129.0, 128.4, 127.4, 124.8, 119.9, 79.7, 68.8, 61.9, 60.1, 47.1 (br), 34.2, 32.0, 28.3, 19.1. MS (EI) m/z 398 (M$^+$, 4.1%), 243 (17%), 242 (34%), 100 (29%), 57 (100%), 56 (95%).

3-[4-[5-[[1-(tert-Butoxycarbonyl)-2(S)-azetidinyl]methoxy]-3-pyridyl]phenyl]-1-propanol

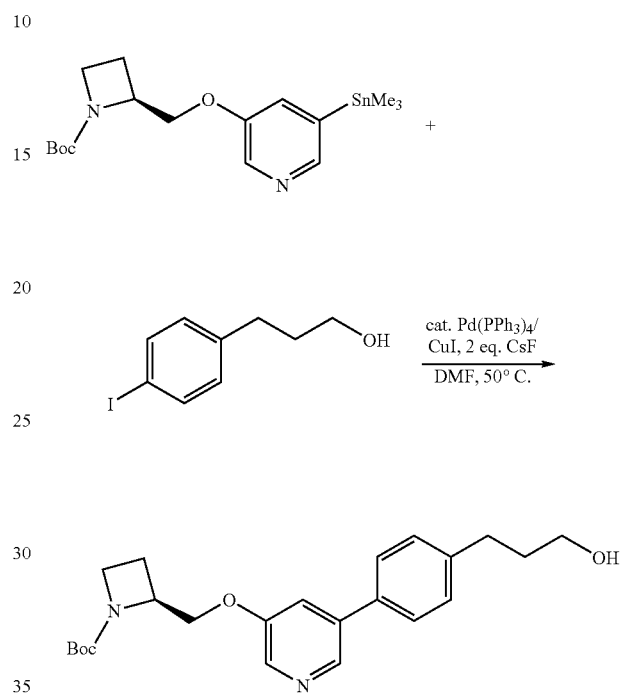

Starting from 344 mg (805 µmol) of 3-[[1-(tert-butoxycarbonyl)-2(S)-azetidinyl]methoxy]-5-(trimethylstannyl)pyridine and 211 mg (805 µmol) of 3-(4-iodophenyl)-1-propanol, the procedure outlined for the meta isomer was followed, resulting in 272 mg (85%) of the product, 3-[4-[5-[[1-(tert-butoxycarbonyl)-2(S)-azetidinyl]methoxy]-3-pyridyl]phenyl]-1-propanol, as a glass. $^1$H NMR (CDCl$_3$, TMS, 250 MHz) δ 8.45 (br s, 1H), 8.31 (br s, 1H), 7.51, 7.31 (AA'XX' multiplet, 4H, $J_{AX}$+$J_{AX'}$=8.2 Hz), 7.43 (m, 1H), 4.55 (m, 1H), 4.40 (m, 1H), 4.20 (dd, 1H, J=2.9, 10.0 Hz), 3.91 (m, 2H), 3.71 (m, 2H), 2.78 (m, 2H), 2.46-2.24 (m, 2H), approx. 2.2 (very br, 1H, OH), 2.00-1.86 (m, 2H), 1.41 (s, 9H). $^{13}$C NMR (CDCl$_3$, 62.5 MHz) δ 156.0, 155.0, 142.3, 140.3, 137.1, 135.9, 134.5, 128.9, 126.9, 119.5, 79.5, 68.4, 61.3, 59.9, 46.7 (br), 34.0, 31.5, 28.1, 18.8. MS (EI) m/z 398 (M$^+$, 4.4%), 243 (14%), 242 (30%), 100 (31%), 57 (100%), 56 (92%).

15c: Synthesis of 3-[3-[5-[(2(S)-Azetidinyl)methoxy]-3-pyridyl]phenyl]-1-propanol and 15d: 3-[4-[5-[(2(S)-Azetidinyl)methoxy)]-3-pyridyl]phenyl]-1-propanol These compounds were prepared, respectively, from 3-[3-[5-[[1-(tert-butoxycarbonyl)-2(S)-azetidinyl]methoxy]-3-pyridyl]phenyl]-1-propanol and 3-[4-[5-[[1-(tert-butoxycarbonyl)-2(S)-azetidinyl]methoxy]-3-pyridyl]phenyl]-1-propanol according to the procedure set forth in Scheme 10c.

3-[3-[5-[(2(S)-Azetidinyl)methoxy]-3-pyridyl]phenyl]-1-propanol Hydrochloride

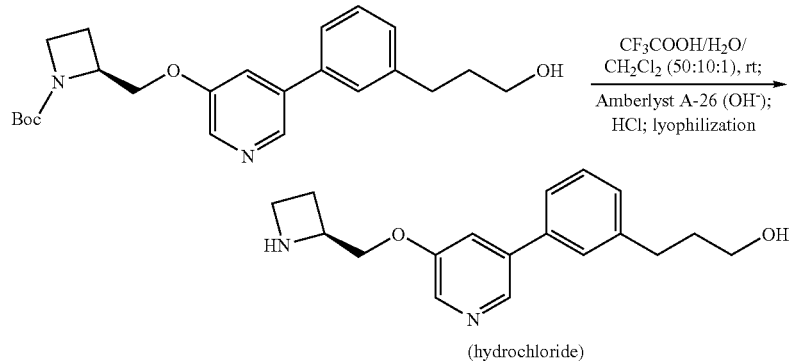

Trifluoroacetic acid (1.1 mL) was diluted with water (0.11 mL), then with CH$_2$Cl$_2$ (5.5 mL). A sample of 3-[3-[5-[[1-(tert-butoxycarbonyl)-2(S)-azetidinyl]methoxy]-3-pyridyl]phenyl]-1-propanol (240 mg, 602 μmol) was dissolved in this mixture, and the reactants were kept in a stoppered flask at room temperature for 23 h. The reaction mixture was then evaporated (35° C./14 torr). The crude material was dissolved in 1 mL of DMSO and was purified by preparative HPLC in two portions (Supelco Discovery C$_{18}$, 250×10 mm with guard column, 5 μm particle size; UV detection at 270 nm; flow 2.5 mL/min; gradient from 8 to 25% of acetonitrile in water within 20 min, then 25 to 100% in another 20 min; both solvents containing 0.1 vol % CF$_3$COOH). The major peak (eluting broadly at t$_R$ approx. 28-31 min) was collected, and the solution was concentrated to a small volume with a rotary evaporator (bath up to 40° C.). The residue was filtered over a column of Amberlyst A-26 ion exchange resin (20 g; OH$^-$ form, 0.95 equiv. OH$^-$/L), which had been set up in and washed with methanol. After elution with methanol, UV-active fractions were combined and evaporated, and the residue was dried (40° C./14 torr) to yield 104 mg (58%) of the free base. $^1$H NMR (CDCl$_3$, TMS, 250 MHz) δ 8.43 (br s, 1H), 8.28 (br s, 1H), 7.42-7.33 (m, 4H), 7.27-7.20 (m, 1H), 4.31 (br, 1H), 4.18-4.04 (m, 2H), 3.78-3.64 (m, 1H overlapping with t, 2H, J=6.4 Hz, at δ 3.70), 3.48 (br, 1H), 2.78 (m, 2H), 2.61 (br, 2H), 2.40 (br, 1H), 2.39-2.21 (m, 1H), 2.00-1.86 (m, 2H). $^{13}$C NMR (CDCl$_3$, 62.5 MHz) δ 155.1, 142.9, 140.7, 137.6, 137.4, 136.3, 129.0, 128.3, 127.3, 124.7, 119.8, 72.6, 61.7, 57.1, 44.1, 34.2, 32.1, 23.9. MS (EI) m/z 298 (M$^+$, 2.4%), 268 (2.6%), 243 (48%), 242 (71%), 56 (100%).

A smaller run starting from 43.8 mg (110 μmol) of 3-[3-[5-[[1-(tert-butoxycarbonyl)-2(S)-azetidinyl]methoxy]-3-pyridyl]phenyl]-1-propanol was processed similarly to yield 25.6 mg (78%) of the free base. Both batches were combined and dissolved in methanol (0.1 mL), and 2N aqueous HCl (0.65 mL, 3 equiv.) was added. Lyophilization resulted in 163 mg of the hydrochloride as a brittle foam. $^1$H NMR (D$_2$O, 250 MHz) δ 8.70 (d, 1H, J=1.2 Hz), 8.55 (d, 1H, J=2.5 Hz), 8.42 (dd, 1H, J=1.7, 2.2 Hz), 7.62-7.40 (m, 4H), 5.00 (m, 1H), 4.62 (d, 2H, J=4.0 Hz), 4.11 (m, 2H), 3.60 (t, 2H, J=6.5 Hz), 2.80-2.65 (m, 4H), 1.88 (m, 2H). Anal. Calcd. for C$_{18}$H$_{22}$N$_2$O$_2$.2.22HCl.1.04H$_2$O: C, 54.31; H, 6.66; N, 7.04; Cl, 19.77. Found: C, 54.36; H, 6.53; N, 7.00; Cl, 19.65.

3-[4-[5-[(2(S)-Azetidinyl)methoxy)]-3-pyridyl]phenyl]-1-propanol Hydrochloride

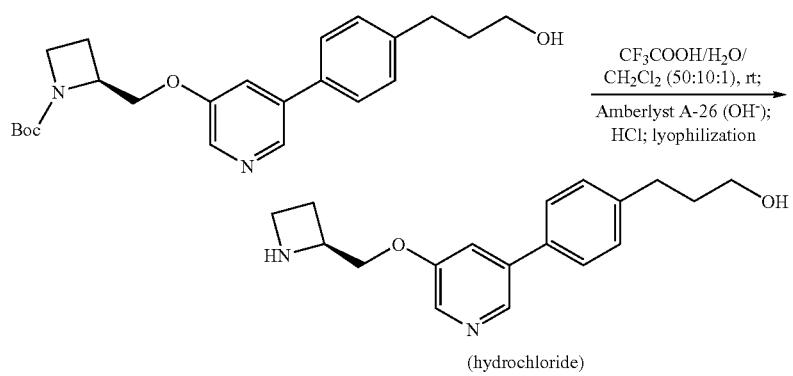

Trifluoroacetic acid (1.3 mL) was diluted with water (0.13 mL), then with CH$_2$Cl$_2$ (6.6 mL). A sample of 3-[4-[5-[[1-(tert-butoxycarbonyl)-2(S)-azetidinyl]methoxy]-3-pyridyl]phenyl]-1-propanol (240 mg, 602 μmol) was dissolved in this mixture. The reaction and purification were conducted as described for the meta isomer. Yield of the free base was 99.8 mg (46%); yield of the hydrochloride was 117 mg. Free base: $^1$H NMR (CDCl$_3$, TMS, 250 MHz) δ 8.43 (d, 1H, J=1.5 Hz), 8.28 (d, 1H, J=2.7 Hz), 7.49, 7.29 (AA'XX' multiplet, 4H, J$_{AX}$+J$_{AX'}$=8.1 Hz), 7.39 (m, 1H), 4.31 (m, 1H), 4.17-4.04 (m, 2H), 3.78-3.64 (m, 1H overlapping with t, 2H, J=6.4 Hz, at δ

3.70), 3.48 (m, 1H), 2.76 (m, 2H), 2.48-2.17 (m, 4H), 1.99-1.85 (m, 2H). $^{13}$C NMR (CDCl$_3$, 62.5 MHz) δ 155.0, 142.3, 140.3, 137.1, 135.8, 134.6, 128.9, 128.9, 119.4, 72.3, 61.1, 56.8, 43.9, 34.1, 31.6, 23.6. MS (EI) m/z 298 (M$^+$, 4.7%), 268 (3.6%), 243 (44%), 242 (72%), 56 (100%). Hydrochloride: $^1$H NMR (D$_2$O, 250 MHz) δ 8.71 (br s, 1H), 8.52 (m, 1H), 8.42 (m, 1H), 7.69, 7.47 (AA'XX' multiplet, 4H, J$_{AX}$+J$_{Ax'}$=8.1 Hz), 5.00 (m, 1H), 4.62 (d, 2H, J=4.0 Hz), 4.11 (m, 2H), 3.61 (t, 2H, J=6.5 Hz), 2.80-2.65 (m, 4H), 1.88 (m, 2H). Anal. Calcd. for C$_{18}$H$_{22}$N$_2$O$_2$.2.22HCl.1.00H$_2$O: C, 54.41; H, 6.65; N, 7.05; Cl, 19.81. Found: C, 54.50; H, 6.74; N, 6.95; Cl, 19.75.

Example 16

Synthesis of 3-[3-[5-[(2(S)-Azetidinyl)methoxy]-3-pyridyl]-5-fluorophenyl]-1-propanol This compound is synthesized according to Scheme 11.

3-Fluoro-5-iodocinnamic Acid Methyl Ester

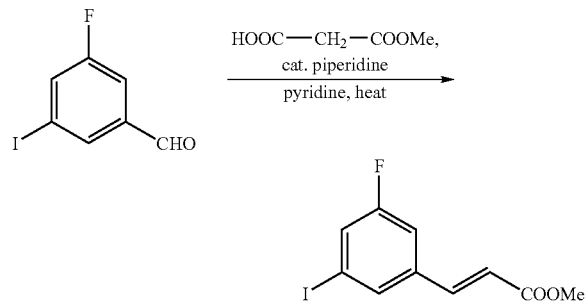

3-Fluoro-5-iodobenzaldehyde, monomethyl malonate, and a catalytic amount of pyrrolidine are heated in pyridine. After cooling, the solvent is distilled off in vacuo. 2N HCl and ethyl acetate are added to the residue, and the phases are separated. The organic layer is washed with brine and dried over Na$_2$SO$_4$. After evaporation, the residue is purified by CC on silica gel with EtOAc/hexane. Evaporation of appropriate fractions yields the title compound.

3-[5-[[1-(tert-Butoxycarbonyl)-2(S)-azetidinyl]methoxy]-3-pyridyl]-5-fluorocinnamic Acid Methyl Ester

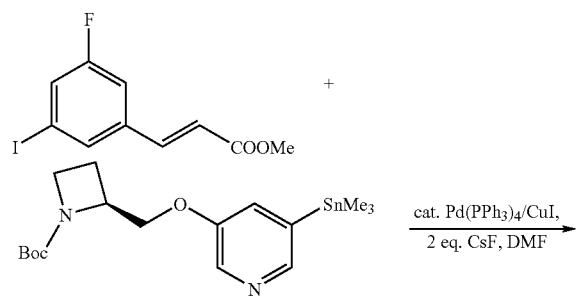

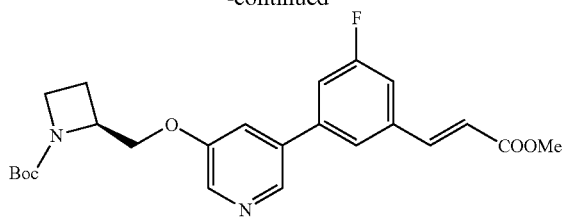

This compound is prepared by Stille coupling of 3-fluoro-5-iodocinnamic acid methyl ester and 3-[[1-(tert-butoxycarbonyl)-2(S)-azetidinyl]methoxy]-5-(trimethylstannyl)pyridine, using the same procedure as described above for the preparation of 3-[3-[5-[[1-(tert-butoxycarbonyl)-2(S)-azetidinyl]methoxy]-3-pyridyl]phenyl]-1-propanol.

3-[5-[[1-(tert-Butoxycarbonyl)-2(S)-azetidinyl]methoxy]-3-pyridyl]-5-fluoropropionic Acid Methyl Ester

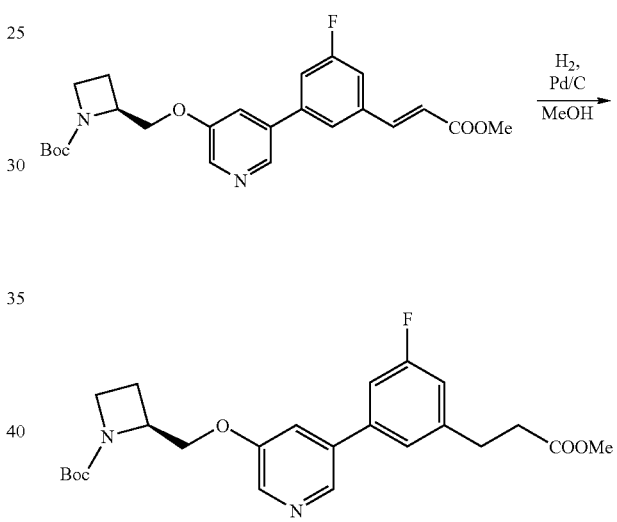

To a solution of 3-[5-[[1-(tert-butoxycarbonyl)-2(S)-azetidinyl]methoxy]-3-pyridyl]-5-fluorocinnamic acid methyl ester in methanol is added a catalytic amount of palladium on carbon. The mixture is stirred under 1 bar of H$_2$ (balloon) until the reaction is completed as monitored by TLC or HPLC. The solvent is evaporated, and the residue is filtered over silica gel using an EtOAc/hexane mixture. Evaporation of appropriate fractions yields the title compound.

3-[3-[5-[[1-(tert-Butoxycarbonyl)-2(S)-azetidinyl]methoxy]-3-pyridyl]-5-fluorophenyl]-1-propanol

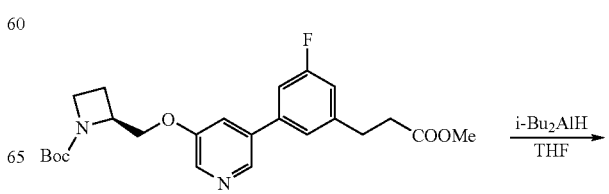

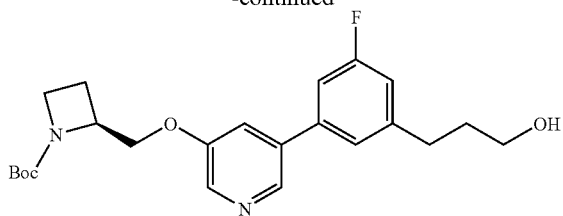

Diisobutylaluminum hydride (DIBAL-H; 1.0M solution in toluene, 2-3 equiv.) is added dropwise at −78° C. (acetone/CO₂ bath) to a solution of 3-[5-[[1-(tert-butoxycarbonyl)-2(S)-azetidinyl]methoxy]-3-pyridyl]-5-fluoropropionic acid methyl ester in anhydrous THF (same volume as DIBAL-H solution) in a three-necked flask equipped with a stir bar, N₂ balloon, septum, and glass stopper. The reaction is monitored by quenching small aliquots into EtOAc/saturated potassium sodium tartrate solution and TLC analysis on silica gel. After completion of the reaction, methanol (1 mL for each 22 mL of DIBAL-H solution) is added dropwise, resulting in H₂ evolution. The cold bath is removed, and saturated aqueous potassium sodium tartrate solution (twice the volume of the DIBAL-H solution) is added all at once. The mixture is stirred vigorously at room temperature for 1 h. The resulting solution or emulsion is extracted several times with EtOAc. The combined organic phases are washed with brine and evaporated. The residue is chromatographed on silica gel, and the product-containing fractions are evaporated to yield the title compound.

3-[3-[5-[(2(S)-Azetidinyl)methoxy]-3-pyridyl]-5-fluorophenyl]-1-propanol Hydrochloride

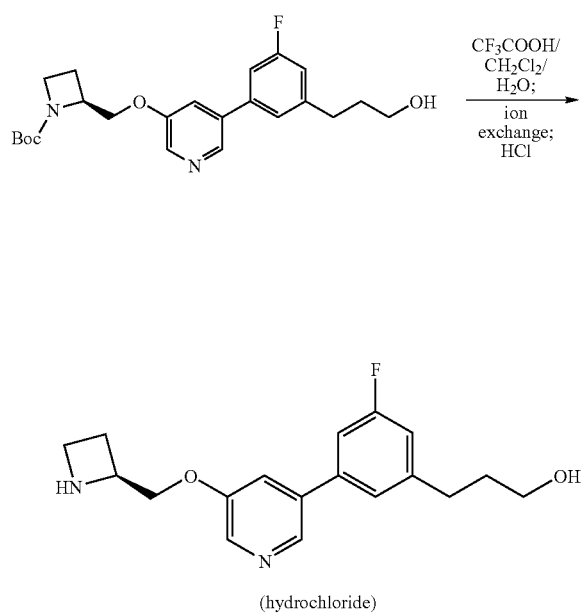

(hydrochloride)

This compound is obtained from its precursor, 3-[3-[5-[[1-(tert-butoxycarbonyl)-2(S)-azetidinyl]methoxy]-3-pyridyl]-5-fluorophenyl]-1-propanol by deprotection in an analogous manner as described in Scheme 10c for the preparation of 3-[3-[5-[(2(S)-azetidinyl)methoxy]-3-pyridyl]phenyl]-1-propanol hydrochloride and 3-[4-[5-[(2(S)-azetidinyl)methoxy)]-3-pyridyl]phenyl]-1-propanol hydrochloride.

Example 17

3-[2-[5-[(2(S)-Azetidinyl)methoxy]-3-pyridyl]phenyl]-1-propanol 3-(2-Bromophenyl)-1-propanol

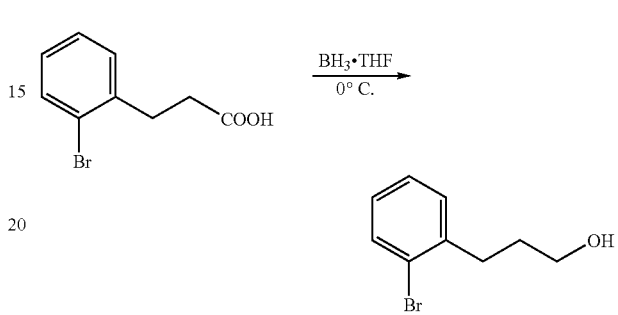

3-(2-Bromophenyl)propionic acid (1.15 g, 5.0 mmol) was placed in a 100 mL three-necked flask with magnetic stirrer. The atmosphere was exchanged with N₂ (3 times). With ice cooling, a solution of BH₃.THF in THF (1.0M, 7.0 mL, 1.4 equiv.) was added dropwise via syringe with stirring over a 15 min period (H₂ evolution). The resulting mixture was stirred in the ice bath for 1 h, and residual borane was quenched by cautious addition of water. The solvents were evaporated, and the residue was partitioned between ether (20 mL) and water (20 mL). The aqueous phase was extracted with ether (20 mL). The combined ether layers were washed with brine, dried over Na₂SO₄, and concentrated to give the alcohol as a clear oil (1.05 g, 98%). ¹H NMR (CDCl₃, 400 MHz) δ 7.53 (d, 1H, J=7.8 Hz), 7.26-7.22 (m, 2H), 7.09-7.03 (m, 1H), 3.71 (t, 2H, J=6.4 Hz), 2.87-2.82 (m, 2H), 1.94-1.86 (m, 2H), 1.36 (br s, 1H).

3-(2-Iodophenyl)-1-propanol

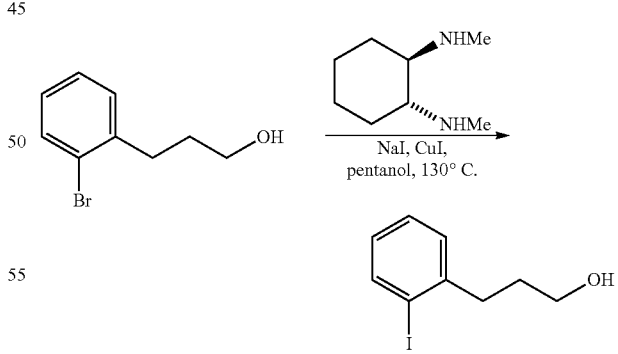

To a 10 mL resealable tube were added 3-(2-bromophenyl)-1-propanol (215 mg, 1.0 mmol) and CuI (9.6 mg, 0.05 mmol, 0.05 equiv.). The tube was sealed with a rubber septum and evacuated and recharged with N₂ three times. A solution of NaI (300 mg, 2.0 mmol, 2.0 equiv.) and trans-N,N'-dimethylcyclohexane-1,2-diamine (16 µL, 0.10 mmol, 0.1 equiv.) in n-pentanol (1 mL) was added. The septum was quickly removed under positive N₂ flow and replaced with a screw cap. The tube was heated in a 130° C. oil bath for 48 h. The reaction was quenched by addition of saturated aqueous ammonia (5 mL). The mixture was partitioned between water (20 mL) and dichloromethane (15 mL). The aqueous phase was extracted with dichloromethane (2×15 mL). The combined organic phases were dried with MgSO$_4$, concentrated, and further dried in an oil pump vacuum at 60° C. The residue was purified by CC on SiO$_2$ (25×1.0 cm, EtOAc/hexanes 1:1) to give the iodide as a pale oil (245 mg, 93%). This material exhibited a purity of 93.1% by HPLC; 5.7% of unreacted bromide was observed. $^1$H NMR (CDCl$_3$, 400 MHz) δ 7.82 (dd, 1H, J=7.8, 1.4 Hz), 7.27-7.22 (m, 2H), 6.89 (td, 1H, J=7.8, 1.8 Hz), 3.72 (q, 2H, J=6.0 Hz), 2.85-2.80 (m, 2H), 1.92-1.84 (m, 2H), 1.37-1.33 (m, 1H).

3-[2-[5-[[1-(tert-Butoxycarbonyl)-2(S)-azetidinyl]methoxy]-3-pyridyl]phenyl]-1-propanol

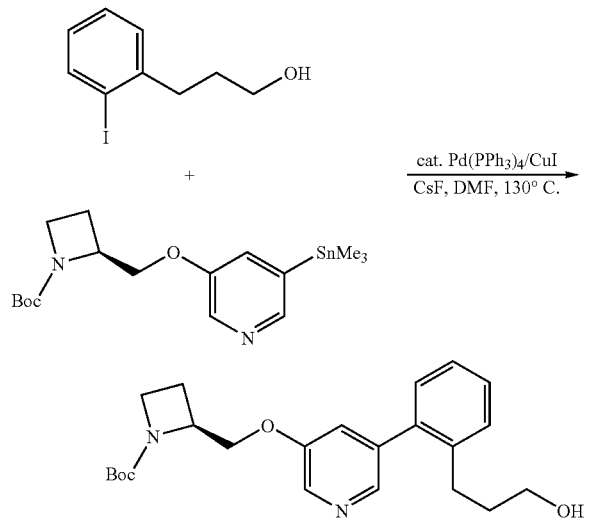

3-[[1-(tert-Butoxycarbonyl)-2(S)-azetidinyl]methoxy]-5-(trimethylstannyl)pyridine (214 mg, 0.50 mmol) and 3-(2-iodophenyl)-1-propanol (131 mg, 0.50 mmol) were dissolved in anhydrous DMF (2 mL) in a 10 mL round-bottom flask with a magnetic stirrer. CsF (152 mg, 1.0 mmol, 2.0 equiv.), CuI (9.5 mg, 50 µmol, 0.1 equiv.) and Pd(PPh$_3$)$_4$ (29 mg, 25 µmol, 0.05 equiv.) were added. The flask was equipped with a condenser, and the atmosphere was exchanged with N$_2$ (3 times). The mixture was stirred in a 130° C. oil bath for 26 h and cooled to room temperature. The solvent was evaporated (oil pump, 60° C.), and the residue was purified by CC on silica gel (28×1.0 cm, EtOAc) to give the crude product as a yellow oil. This material was further purified by preparative HPLC in two portions (Supelco Discovery C$_{18}$, 250×21.2 mm, 5 µm particle size, UV detection at 270 nm, flow rate 12.5 mL/min, gradient from 20% to 100% CH$_3$CN in water within 40 min, then 100% CH$_3$CN for 20 min; t$_R$ 23.4-24.5 min) to give, after evaporation, the product as a colorless glass (128 mg, 64%). [α]$_{546}$–51.3; [α]$_{589}$–43.3 (c 9.15 g/L, EtOAc). $^1$H NMR (CDCl$_3$, 400 MHz) δ 8.34 (d, 1H, J=2.8 Hz), 8.19 (d, 1H, J=1.4 Hz), 7.37-7.32 (m, 2H), 7.29-7.23 (m, 2H), 7.20 (d, 1H, J=7.3 Hz), 4.56-4.49 (m, 1H), 4.40 (dd, 1H, J=10.0, 4.6 Hz), 4.61 (dd, 1H, J=10.1, 2.7 Hz), 3.90 (t, 2H, J=7.8 Hz), 3.55 (q, 2H, J=5.5 Hz), 2.70-2.64 (m, 2H), 2.42-2.28 (m, 2H), 1.80-1.71 (m, 2H), 1.39 (s, 9H).

3-[2-[5-[(2(S)-Azetidinyl)methoxy]-3-pyridyl]phenyl]-1-propanol Trifluoroacetate

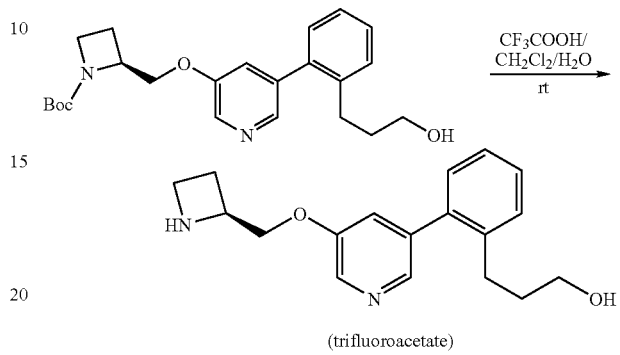

(trifluoroacetate)

A mixture of CF$_3$COOH, H$_2$O, and CH$_2$Cl$_2$ (10:1:50, 2.44 mL) was added to a 10 mL round-bottom flask containing 3-[2-[5-[[1-(tert-butoxycarbonyl)-2(S)-azetidinyl]methoxy]-3-pyridyl]phenyl]-1-propanol (99.5 mg, 0.25 mmol). The flask was capped with a glass stopper, and the reactants were stirred at room temperature for 14 h. The reaction mixture was concentrated with a rotary evaporator (bath up to 35° C.) and was further dried on an oil pump (35° C.). The residue was dissolved in water (1 mL), and the aqueous solution was lyophilized. The resulting oil was purified by preparative HPLC in two portions (Supelco Discovery C$_{18}$, 250×21.2 mm, 5 µm particle size, UV detection at 270 nm, flow rate 12.5 mL/min, gradient from 8% to 25% CH$_3$CN in water within 20 min, from 25% to 100% in another 20 min, then 100% CH$_3$CN for 20 min, both solvents containing 0.1 vol % CF$_3$COOH; t$_R$ 19.6-23.7 min). Partial evaporation to remove CH$_3$CN, followed by lyophilization, gave the product as a yellowish oil (121 mg, 82%). $^1$H NMR (CD$_3$OD, 500 MHz) δ 8.85 (s, 1H), 8.41 (s, 1H), 7.93 (s, 1H), 7.45 (d, 2H, J=4.6 Hz), 7.38-7.33 (m, 1H), 7.29 (d, 1H, J=7.6 Hz), 4.98-4.95 (m, 1H), 4.61-4.52 (m, 2H), 4.21-4.09 (m, 2H), 3.48 (t, 2H, J=6.2 Hz), 2.72 (t, 4H, J=6.2 Hz), 1.78-1.69 (m, 2H). Anal. Calcd. for C$_{18}$H$_{22}$N$_2$O$_2$.2.41CF$_3$COOH.1.04H$_2$O (FW 591.9): C, 46.30; H, 4.51; N, 4.73; F, 23.21. Found: C, 46.31; H, 4.40; N, 4.71; F 23.18.

Example 18

3-[3-[5-[(2(S)-Pyrrolidinyl)methoxy]-3-pyridyl]phenyl]-1-propanol

3-[[1-(tert-Butoxycarbonyl)-2(S)-pyrrolidinyl]methoxy]-5-(trimethylstannyl)pyridine

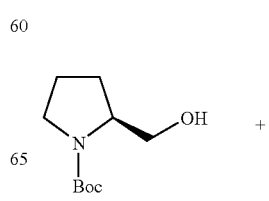

+

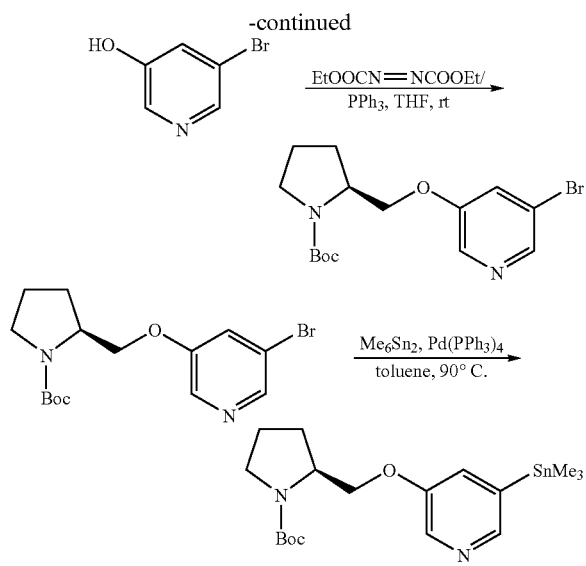

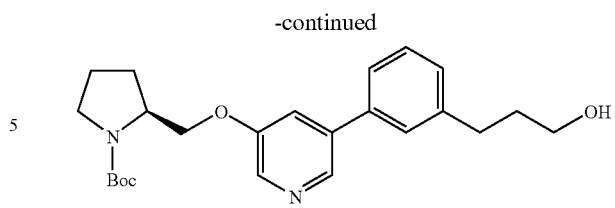

To a solution of [1-(tert-butoxycarbonyl)-2(S)-pyrrolidinyl]methanol (1.39 g, 6.9 mmol, 1.5 equiv.), 5-bromo-3-pyridinol (796 mg, 4.6 mmol) and Ph₃P (1.80 g, 6.9 mmol, 1.5 equiv.) in anhydrous THF (35 mL) was added diethyl azodicarboxylate (1.09 mL, 6.9 mmol, 1.5 equiv.) dropwise at 0° C. under Ar protection. After stirring at rt for 120 h, the solvent was removed under reduced pressure. The mixture was diluted with hexane/EtOAc 4:1, and the solution was washed with brine and dried over Na₂SO₄. After evaporation, the residue was purified by CC (SiO₂, hexane/EtOAc 4:1, then 1:1) to afford 3-bromo-5-[[1-(tert-butoxycarbonyl)-2(S)-pyrrolidinyl]methoxy]pyridine (1.41 g, 86%) as a pale yellow oil, which solidified upon storage at room temperature.

3-Bromo-5-[[1-(tert-butoxycarbonyl)-2(S)-pyrrolidinyl]methoxy]pyridine (893 mg, 2.50 mmol) and Pd(PPh₃)₄ (87 mg, 75 μmol, 0.03 equiv.) were dissolved in 8 mL of anhydrous toluene in a 38 mL Chemglass pressure tube. The mixture was purged with N₂ for 5 min. Hexamethyldistannane (1.56 mL, 7.50 mmol) was added quickly, and the tube was sealed and heated to 90° C. for 29 h. After cooling to room temperature, the mixture was purified by CC on SiO₂ (25×3.8 cm, EtOAc/hexanes/triethylamine 25:70:5) to give the stannylpyridine as an oil (1.04 g, 94%). ¹H NMR (CD₃OD, 400 MHz) δ 8.25-8.15 (m, 2H), 7.38 (br s, 1H), 4.22-4.08 (m, 2H), 4.01-3.79 (m, 1H), 3.41 (br s, 2H), 2.09-1.98 (m, 2H), 1.92-1.84 (m, 2H), 1.47 (s, 9H), 0.34 (s, 9H, with Sn satellites).

3-[3-[5-[[1-(tert-Butoxycarbonyl)-2(S)-pyrrolidinyl]methoxy]-3-pyridyl]phenyl]-1-propanol

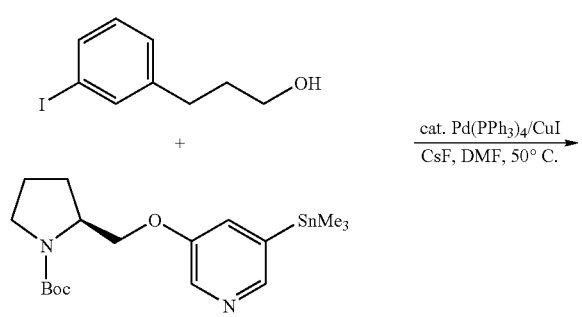

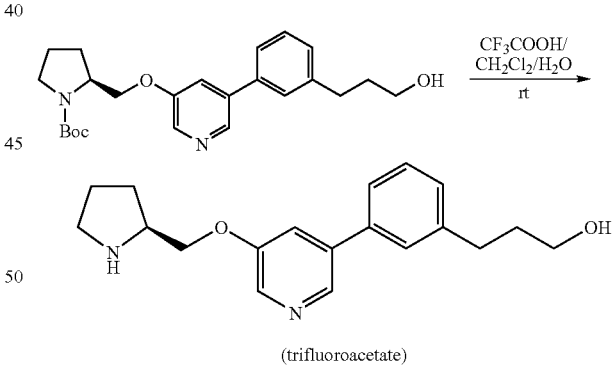

3-[[1-(tert-Butoxycarbonyl)-2(S)-pyrrolidinyl]methoxy]-5-(trimethylstannyl)pyridine (321 mg, 726 μmol) and 3-(3-iodophenyl)-1-propanol (190 mg, 726 μmol) were dissolved in anhydrous DMF (2.5 mL) in a 25 mL round-bottom flask equipped with magnetic stirrer and rubber septum. CsF (221 mg, 1.45 mmol, 2.0 equiv.), CuI (14 mg, 73 μmol, 0.1 equiv.) and Pd(PPh₃)₄ (42 mg, 36 μmol, 0.05 equiv.) were added to the solution. The flask was fitted with an N₂ balloon though a three-way stopcock, and the atmosphere was exchanged with N₂ (3 times). The mixture was stirred in 50° C. oil bath for 5 h, and DMF was evaporated (oil pump, 40° C.). The residue was purified by CC on SiO₂ (25×3.8 cm, EtOAc) to give the crude product, which was further purified by preparative HPLC in two portions (Supelco Discovery C₁₈, 250×21.2 mm, 5 μm particle size, UV detection at 270 nm, flow rate 12.5 mL/min, gradient from 20% to 100% CH₃CN in water within 40 min, then 100% CH₃CN for 20 min; t_R 30.7-32.2 min) to give a yellow oil (237 mg, 79%). [α]₅₄₆ −42.8; [α]₅₈₉ −36.0 (c 8.30 g/L, EtOAc). ¹H NMR (CDCl₃, 400 MHz) δ 8.44 (br s, 1H), 8.29 (d, 1H, J=1.8 Hz), 7.52-7.34 (m, 4H), 7.24 (br s, 1H), 4.32-4.10 (m, 2H), 4.08-3.89 (m, 1H), 3.72 (q, 2H, J=6.0 Hz), 3.52-3.30 (m, 2H), 2.12-1.86 (m, 2H), 1.92-1.84 (m, 6H), 1.46 (s, 9H).

3-[3-[5-[(2(S)-Pyrrolidinyl)methoxy]-3-pyridyl]phenyl]-1-propanol Trifluoroacetate A mixture of CF₃COOH, H₂O, and CH₂Cl₂ (10:1:50, 6.7 mL) was added to a 15 mL round-bottom flask containing 3-[3-[5-[[1-(tert-butoxycarbonyl)-2(S)-pyrrolidinyl]methoxy]-3-pyridyl]phenyl]-1-propanol (237 mg, 574 μmol). The flask was capped with a glass stopper, and the reactants were stirred at room temperature for 14 h. The reaction mixture was concentrated with a rotary evaporator (bath up to 35° C.) and was further dried with an oil pump (35° C.) to give the trifluoroacetate as a yellowish oil (387 mg, quantitative). ¹H NMR (CD₃OD, 400 MHz) δ 8.69 (br s, 1H), 8.49 (br s, 1H), 8.12 (d, 1H, J=9.2 Hz), 7.62-7.54 (m, 2H), 7.52-7.44 (m, 1H), 7.41-7.35 (d, 1H, J=7.8 Hz), 4.89-4.85 (m, 1H, overlapping with the CD$_3$OH peak), 4.61 (dd, 1H, J=10.5, 3.2 Hz), 4.45-4.39 (m 1H), 4.13 (qd, 2H, J=8.4, 3.7 Hz), 3.60 (t, 2H, J=6.4 Hz), 3.46-3.38 (m, 2H), 2.36-2.28 (m, 1H), 2.24-2.08 (m, 2H), 2.03-1.85 (m, 3H). Anal. Calcd. for C$_{19}$H$_{24}$N$_2$O$_2$.3.02CF$_3$COOH.0.57H$_2$O (FW 667.0): C, 45.09; H, 4.26; N, 4.20; F, 25.80. Found: C, 45.09; H, 4.15; N, 4.28; F 25.78.

Example 19

3-[3-[5-[(2(R)-Azetidinyl)methoxy]-3-pyridyl]phenyl]-1-propanol

[1-(tert-Butoxycarbonyl)-2(R)-azetidinyl]methanol was prepared as described in the literature (Lynch, J. K.; Holladay, M. W.; Ryther, K. B.; Bai, H.; Hsiao, C.-N.; Morton, H. E.; Dickman, D. A.; Arnold, W.; King, S. A. Efficient asymmetric synthesis of ABT-594; a potent, orally effective analgesic. *Tetrahedron: Asymmetry* 1998, 9, 2791-2794).

3-Bromo-5-[[1-(tert-butoxycarbonyl)-2(R)-azetidinyl]methoxy]pyridine

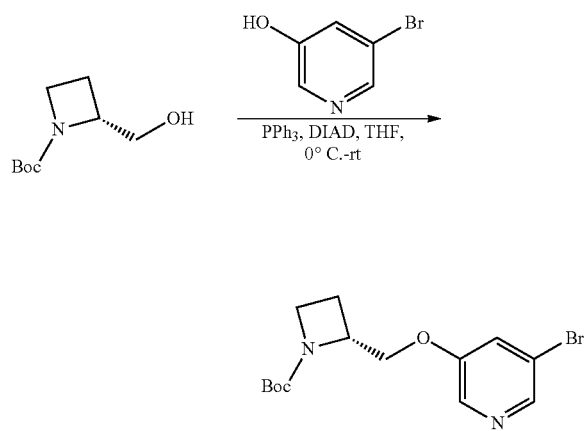

[1-(tert-Butoxycarbonyl)-2(R)-azetidinyl]methanol (1.42 g, 7.60 mmol) was dried by azeotropic evaporation with toluene (3×10 mL) in a 50 mL round-bottom flask. 3-Bromo-5-hydroxypyridine (1.32 g, 7.60 mmol) and triphenylphosphine (2.20 g, 8.40 mmol, 1.1 equiv.) were added. The flask was capped with a rubber septum, and the atmosphere was exchanged three times with N$_2$ (balloon). Anhydrous THF (25 mL) was added via syringe, and the mixture was stirred in an ice bath until all reagents were dissolved. Diisopropyl azodicarboxylate (DIAD, 1.76 mL, 8.40 mmol, 1.1 equiv.) was added dropwise in several portions over 30 min. The resulting mixture was stirred in the thawing ice bath overnight. After removal of the THF, the residue was purified by CC on SiO$_2$ (25×3.8 cm, EtOAc/hexanes 1:4 to 3:7) to give crude product. A $^1$H NMR spectrum showed that the material was a mixture with diisopropyl hydrazodicarboxylate (containing approx. 56% of the title compound by mass), which was used directly for the next step. $^1$H NMR (CDCl$_3$, 400 MHz; signals of the title compound only) δ 8.29 (d, 1H, J=1.8 Hz), 8.28 (d, 1H, J=2.7 Hz), 7.43 (t, 1H, J=2.3 Hz), 4.55-4.47 (m, 1H), 4.33 (br s, 1H), 4.13-4.09 (m, 1H), 3.93-3.85 (m, 2H), 2.40-2.20 (m, 2H), 1.43 (s, 9H).

3-[[1-(tert-Butoxycarbonyl)-2(R)-azetidinyl]methoxy]-5-(trimethylstannyl)pyridine

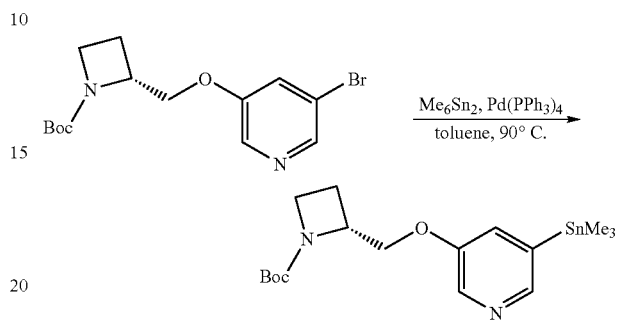

The mixture of 3-bromo-5-[[1-(tert-butoxycarbonyl)-2(R)-azetidinyl]methoxy]pyridine and diisopropyl hydrazodicarboxylate obtained in the preceding reaction (1.54 g, approx. 2.5 mmol) and Pd(PPh$_3$)$_4$ (87 mg, 75 μmol, 0.03 equiv.) were dissolved in 8 mL of anhydrous toluene in a 38 mL Chemglass pressure tube. The mixture was purged with N$_2$ for 5 min. Hexamethyldistannane (1.56 mL, 7.50 mmol, 3.0 equiv.) was added quickly, and the tube was sealed and heated to 90° C. for 26 h. After cooling to room temperature, the mixture was purified by CC on silica gel (25×3.8 cm, EtOAc/hexanes/triethylamine 25:70:5) to give the crude stannane, which still contained diisopropyl hydrazodicarboxylate. The crude product was purified by preparative HPLC in four portions (Supelco Discovery C$_{18}$, 250×21.2 mm, 5 μm particle size, UV detection at 270 nm, flow rate 12.5 mL/min, gradient from 20% to 100% CH$_3$CN in water within 40 min, then 100% CH$_3$CN for 20 min; column prewashed with 100 μL of pyridine while eluting with CH$_3$CN to prevent protodestannylation; t$_R$ 38.7-41.4 min) to give the pure stannane as a yellow oil (395 mg, 37%). $^1$H NMR (CDCl$_3$, 400 MHz) δ 8.27-8.19 (m, 2H), 7.32 (dd, 1H, J=3.2, 0.9 Hz), 4.57-4.48 (m, 1H), 4.36-4.39 (m, 1H), 4.15 (dd, 1H, J=9.6, 2.8 Hz), 3.96-3.85 (m, 2H), 2.41-2.25 (m, 2H), 1.42 (s, 9H), 0.34 (s, 9H, with Sn satellites).

3-[3-[5-[[1-(tert-Butoxycarbonyl)-2(R)-azetidinyl]methoxy]-3-pyridyl]phenyl]-1-propanol

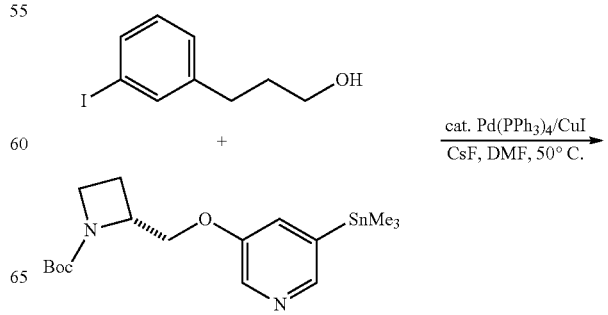

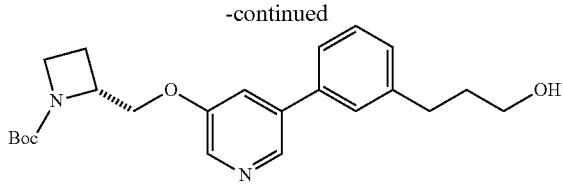

3-[[1-(tert-Butoxycarbonyl)-2(S)-azetidinyl]methoxy]-5-(trimethylstannyl)pyridine (289 mg, 677 μmol) and 3-(3-iodophenyl)-1-propanol (177 mg, 677 μmol) were dissolved in anhydrous DMF (2.5 mL) in a 15 mL round-bottom flask equipped with magnetic stirrer and rubber septum. CsF (206 mg, 1.35 mmol, 2.0 equiv.), CuI (13 mg, 68 μmol, 0.1 equiv.) and Pd(PPh$_3$)$_4$ (39 mg, 34 μmol, 0.05 equiv.) were added to the solution. The flask was fitted with an Ar balloon though a three-way stopcock, and the atmosphere was exchanged with Ar (3 times). The mixture was stirred in a 50° C. oil bath for 5 h, and the DMF was evaporated (oil pump, 40° C.). The residue was purified by CC on silica gel (25×3.8 cm, EtOAc) to give, after evaporation, the crude product, which was further purified by preparative HPLC in two portions (Supelco Discovery C$_{18}$, 250×21.2 mm, 5 μm particle size, UV detection at 270 nm, flow rate 12.5 mL/min, gradient from 20% to 100% CH$_3$CN in water within 40 min, then 100% CH$_3$CN for 20 min; t$_R$ 22.6-23.7 min) to give the pure product as a yellow oil (231 mg, 86%). [α]$_{546}$+53.4; [α]$_{589}$+44.9 (c 8.60 g/L, EtOAc). $^1$H NMR (CDCl$_3$, 400 MHz) δ 8.46 (s, 1H), 8.32 (s, 1H), 7.44-7.36 (m, 4H), 7.26-7.23 (m, 1H), 4.58-4.52 (m, 1H), 4.40 (br s, 1H), 4.22 (dd, 1H, J=10.1, 2.7 Hz), 3.96-3.87 (m, 2H), 3.72 (q, 2H, J=5.8 Hz), 2.80 (t, 2H, J=7.3 Hz), 2.43-2.26 (m, 2H), 1.99-1.91 (m, 2H), 1.52 (br s, 1H), 1.40 (s, 9H).

3-[3-[5-[(2(R)-Azetidinyl)methoxy]-3-pyridyl]phenyl]-1-propanol Trifluoroacetate

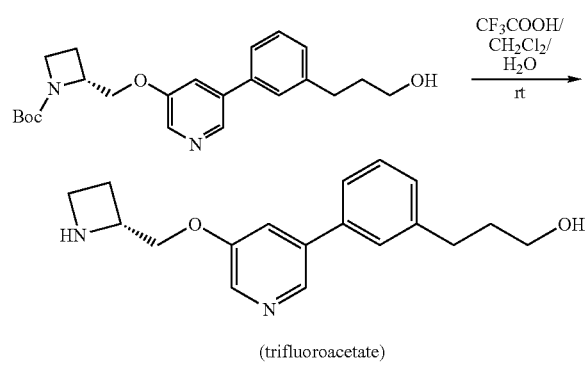

A mixture of CF$_3$COOH, H$_2$O, and CH$_2$Cl$_2$ (10:1:50, 6.7 mL) was added to a 15 mL round bottom flask containing 3-[3-[5-[[1-(tert-butoxycarbonyl)-2(R)-azetidinyl]methoxy]-3-pyridyl]phenyl]-1-propanol (225 mg, 565 μmol). The flask was capped with a glass stopper, and the reactants were stirred at room temperature for 14 h. The reaction mixture was concentrated with a rotary evaporator (bath up to 35° C.) and was further dried with an oil pump (35° C.). The residue was dissolved in water (1 mL) and lyophilized. The resulting yellowish oil was left standing with some exposure to air for 4 days to allow the TFA ester formed as a byproduct during the lyophilization to be hydrolyzed by atmospheric moisture. The trifluoroacetate was obtained in quantitative yield (356 mg). $^1$H NMR (CD$_3$OD, 400 MHz) δ 8.67 (br s, 1H), 8.51 (br s, 1H), 8.06 (s, 1H), 7.59 (s, 1H), 7.56 (d, 1H, J=7.8 Hz), 7.47 (t, 1H, J=7.6 Hz), 7.37 (d, 1H, J=7.3 Hz), 4.98-4.90 (m, 1H), 4.60-4.53 (m, 2H), 4.19-4.06 (m, 2H), 3.61 (t, 2H, J=6.2 Hz), 2.81 (t, 2H, J=7.8 Hz), 2.76-2.66 (m, 2H), 1.94-1.86 (m, 2H); MS (EI) m/z 298 (M$^+$ of free base, 1.0%). Anal. Calcd. for C$_{18}$H$_{22}$N$_2$O$_2$.2.81CF$_3$COOH.0.69H$_2$O (FW 631.2): C, 44.94; H, 4.18; N, 4.44; F, 25.37. Found: C, 44.95; H, 4.07; N, 4.44; F 25.37.

Example 20

3-[3-[5-[(1-Methyl-2(S)-azetidinyl)methoxy]-3-pyridyl]phenyl]-1-propanol Trifluoroacetate

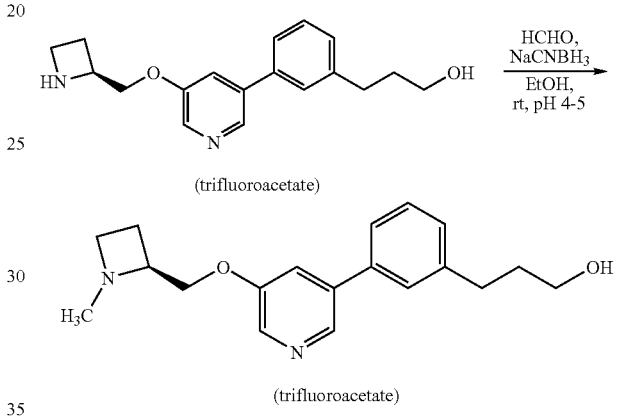

To a solution of 3-[2-[5-[(2(S)-azetidinyl)methoxy]-3-pyridyl]phenyl]-1-propanol trifluoroacetate (473 mg, containing water and an excess of CF$_3$COOH; 525 μmol) in ethanol (1.4 mL) in a 15 mL round-bottom flask was added formalin (37% formaldehyde in water, 0.21 mL, 7.6 mmol, 14.4 equiv.). A small amount of bromocresol green was added to the reaction mixture to monitor the pH, which was adjusted to 4-5 by addition of NaOAc. The mixture was stirred at room temperature for 30 min. Sodium cyanoborohydride (50 mg, 0.79 mmol, 1.5 equiv.) was added, whereon the pH increased. Small amounts of CF$_3$COOH were added over several hours to keep the pH between 4 and 5. The resulting mixture was stirred at room temperature for an additional 24 h. Solvents were evaporated, and the residue was purified by CC on silica gel (38×1.0 cm, CH$_2$Cl$_2$/methanol/saturated aqueous ammonia 20:1:0.1). The crude product was purified by preparative HPLC (Supelco Discovery C$_{18}$, 250×21.2 mm, 5 μm particle size, UV detection at 270 nm, flow rate 12.5 mL/min, gradient from 8% to 25% CH$_3$CN in water within 20 min, from 25% to 100% for another 20 min, then 100% CH$_3$CN for 20 min, both solvents containing 0.1 vol % CF$_3$COOH; t$_R$ 16.9-23.6 min) to give the methylation product as a trifluoroacetate (colorless oil, 218 mg, 62%). $^1$H NMR (CD$_3$OD, 500 MHz) δ 8.64 (s, 1H), 8.48 (s, 1H), 8.03 (d, 1H, J=2.1 Hz), 7.61 (s, 1H), 7.58 (d, 1H, J=7.6 Hz), 7.50-7.45 (m, 1H), 7.38 (d, 1H, J=7.3 Hz), 4.88-4.82 (m, 1H), 4.64 (dd, 1H, J=11.6, 3.1 Hz), 4.57 (dd, 1H, J=11.4, 6.2 Hz), 4.31 (td, 1H, J=9.8, 4.8 Hz), 4.05 (q, 1H, J=9.9 Hz), 3.63 (t, 2H, J=6.4 Hz), 3.06 (d, 3H, J=4.7 Hz), 2.82 (t, 2H, J=7.8 Hz), 2.75-2.60 (m, 2H), 1.96-1.88 (m, 2H); MS (EI) m/z 312 (M$^+$, 0.4%). Anal. Calcd. for $C_{19}H_{24}N_2O_2 \cdot 3.02CF_3COOH \cdot 0.56H_2O$ (FW 667) C, 45.10; H, 4.25; N, 4.20; F, 25.81. Found: C, 45.08; H, 4.35; N, 4.27; F, 25.85.

Example 21

3-[3-[5-[(1-Methyl-2(S)-pyrrolidinyl)methoxy]-3-pyridyl]phenyl]-1-propanol Trifluoroacetate

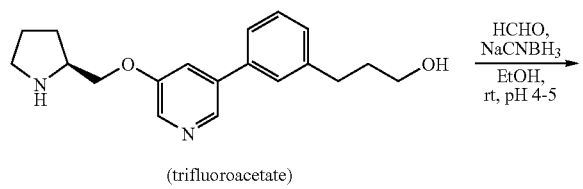

(trifluoroacetate)

To a solution of 3-[3-[5-[(2(S)-pyrrolidinyl)methoxy]-3-pyridyl]phenyl]-1-propanol trifluoroacetate ($C_{19}H_{24}N_2O_2 \cdot 3.02CF_3COOH \cdot 0.57H_2O$, 296 mg, 443 µmol) in ethanol (1.5 mL) in a 15 mL round bottom flask was added formalin (0.18 mL, 6.6 mmol, 15 equiv.). A small amount of bromocresol green was added to the reaction mixture to monitor the pH, which was adjusted to 4-5 by addition of NaOAc. The mixture was stirred at room temperature for 30 min. Sodium cyanoborohydride (42 mg, 0.67 mmol, 1.5 equiv.) was added, whereon the pH increased. Small amounts of $CF_3COOH$ were added over several hours to keep the pH between 4 and 5. The resulting mixture was stirred at room temperature for an additional 24 h. The solvents were evaporated, and the residue was purified by CC on silica gel (38×1.0 cm, $CH_2Cl_2$/methanol/saturated aqueous ammonia 20:1:0.1). The crude product was purified by preparative HPLC (Supelco Discovery $C_{18}$, 250×21.2 mm, 5 µm particle size, UV detection at 270 nm, flow rate 12.5 mL/min, gradient from 8% to 25% $CH_3CN$ in water within 20 min, from 25% to 100% for another 20 min, then 100% $CH_3CN$ for 20 min, both solvents containing 0.1 vol % $CF_3COOH$; $t_R$ 18.0-24.3 min) to give the methylation product as a trifluoroacetate (colorless oil, 131 mg, 44%). $^1$H NMR ($CD_3OD$, 500 MHz) δ 8.66 (s, 1H), 8.48 (s, 1H), 8.06 (d, 1H, J=1.9 Hz), 7.61 (s, 1H), 7.58 (d, 1H, J=7.8 Hz), 7.51-7.45 (m, 1H), 7.38 (d, 1H, J=7.8 Hz), 4.92-4.88 (m, 1H, overlapping with the $CD_3OH$ peak), 4.68 (dd, 1H, J=11.2, 3.0 Hz), 4.52 (dd, 1H, J=11.0, 6.8 Hz), 4.03-3.94 (m, 1H), 3.84-3.76 (m, 1H), 3.65-3.59 (m, 2H), 3.13 (d, 3H, J=3.7 Hz), 2.82 (t, 2H, J=7.8 Hz), 2.50-2.42 (m, 1H), 2.32-2.22 (m, 1H), 2.22-2.08 (m, 2H), 1.96-1.88 (m, 2H). Anal. Calcd. for $C_{20}H_{26}N_2O_2 \cdot 3.00CF_3COOH$ (FW 668.5) C, 46.71; H, 4.37; N, 4.19; F, 25.58. Found: C, 46.93; H, 4.49; N, 4.26; F, 25.83.

Example 22

N-(3-[3-[5-[(2(S)-Azetidinyl)methoxy]-3-pyridyl]phenyl]propyl]acetamide

N-[3-[3-[5-[[1-(tert-Butoxycarbonyl)-2(S)-azetidinyl]methoxy]-3-pyridyl]phenyl]propyl]-3,4,5,6-tetrachlorophthalimide

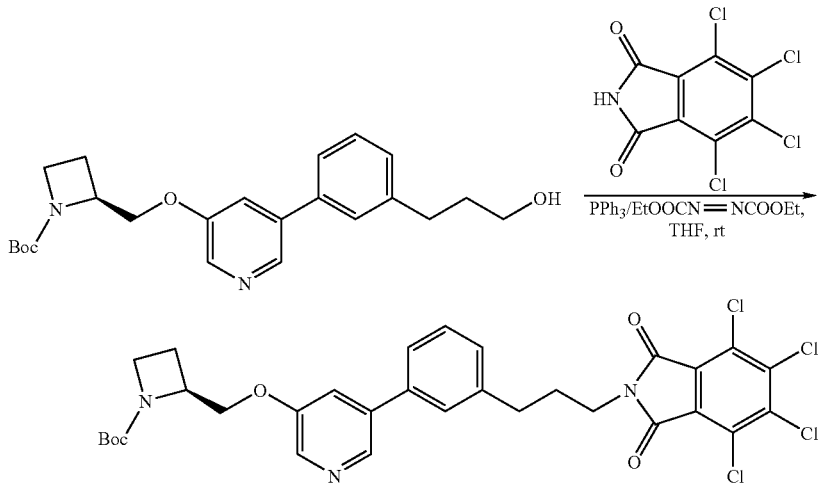

A 15 mL round-bottom flask equipped with magnetic stirrer, septum and $N_2$ balloon was charged with 3-[3-[5-[[1-(tert-butoxycarbonyl)-2(S)-azetidinyl]methoxy]-3-pyridyl]phenyl]-1-propanol (62.6 mg, 157 µmol), triphenylphosphine (54 mg, 0.20 mmol, 1.3 equiv.), tetrachlorophthalimide (58 mg, 0.20 mmol, 1.3 equiv.), and anhydrous tetrahydrofuran (1.0 mL; freshly distilled over Na/benzophenone). Neat diethyl azodicarboxylate (32 µL, 0.20 mmol, 1.3 equiv.) was added dropwise at room temperature within 4 min, whereon its color was discharged and most of the poorly soluble tetrachlorophthalimide went into solution. The reaction mixture was stirred at room temperature in the stoppered flask for 18.5 h. After 18 h, TLC analysis was performed to confirm complete conversion. On $SiO_2$ (EtOAc/hexane 55:45) the product moves with $R_f$ approx. 0.35, closely preceded by the byproduct, diethyl hydrazodicarboxylate. On alumina (Selecto alumina B, F-254, cat#11045; same eluent), its $R_f$ is approx. 0.6, well ahead of the byproducts. The reaction mixture was evaporated and the residue rapidly chromatographed on a column filled with 36 g of alumina (basic, activity Brockmann I, 58 Å pore size; Alfa Aesar cat#11503) which had previously been deactivated with 1.8 mL of water (final dimensions: 25×1.3 cm), eluting with EtOAc/hexane 1:2. The product-containing fractions were combined and evaporated, and the residue dried (50° C./oil pump) to furnish the product (84.3 mg, 81%) as a colorless film MS (EI) m/z 665/663 (M+, 0.6/0.4%, $^{35}Cl_3{}^{37}Cl/^{35}Cl_4$), 511/509/507 (3.6/6.8/5.5%, $^{35}Cl_2{}^{37}Cl_2/^{35}Cl_3{}^{37}Cl/^{35}Cl_4$), 100 (31%), 57 (100%), 56 (88%).

A 1.37 mmolar run, using a proportionally larger column for the chromatographic separation of the reaction mixture, yielded only 40% of the product. This is likely due to longer contact time of the product with the stationary phase, by which the tetrachlorophthalimide moiety appears to be hydrolyzed.

Benzyl 3-[3-[5-[[1-(tert-Butoxycarbonyl)-2(S)-azetidinyl]methoxy]-3-pyridyl]phenyl]propylcarbamate In a 50 mL round-bottom flask with magnetic stirrer, N-[3-[3-[5-[[1-(tert-butoxycarbonyl)-2(S)-azetidinyl]methoxy]-3-pyridyl]phenyl]propyl]-3,4,5,6-tetrachlorophthalimide (347 mg, 522 µmol) was dissolved in acetonitrile (2 mL), tetrahydrofuran (1 mL), and ethanol (1 mL). Ethylenediamine (157 µL, 2.35 mmol, 4.5 equiv.) was added. The flask was equipped with a reflux condenser, three-way stopcock, and Ar balloon, and the atmosphere was exchanged. The mixture was heated in an oil bath at 60° C. for 160 min. The resulting yellowish solution and fine, colorless precipitate were cooled to room temperature. TLC (SiO$_2$, CH$_2$Cl$_2$/MeOH/Et$_3$N 90:10:5, UV detection) demonstrated disappearance of the starting material which was replaced with two major new spots (R$_f$ approx. 0.5 and 0.4) besides nonpolar byproducts. The mixture was evaporated and the residue chromatographed on SiO$_2$ (23×2.5 cm, CH$_2$Cl$_2$/MeOH/Et$_3$N 93:7:5, then 9:1:1). Fractions containing the two major products were combined, evaporated, and dried (50° C./oil pump vacuum) to yield 358 mg of crude 3-[3-[5-[[1-(tert-butoxycarbonyl)-2(S)-azetidinyl]methoxy]-3-pyridyl]phenyl]propanamine as a yellowish, turbid glass, which was used in the subsequent step without purification.

In a 100 mL round-bottom flask with magnetic stirrer, septum, and balloon (for pressure equalization and exclusion of moisture), 347 mg of the above crude product was dissolved in CH$_2$Cl$_2$ (5 mL) and triethylamine (0.55 mL, 3.9 mmol). The solution was cooled in an ice bath, and neat benzyl chloroformate (0.50 mL, 3.5 mmol) was added dropwise from a syringe in 12 min. The mixture was stirred in the ice bath for 1 h and at room temperature for 5.3 h. Shortly before, TLC (SiO$_2$, EtOAc/hexane 3:1) indicated a major product at R$_f$ approx. 0.35. The excess of benzyl chloroformate was quenched by addition of saturated aqueous NaHCO$_3$ solution (10 mL) and vigorous stirring at room temperature for 30 min. The phases were separated, and the aqueous phase was extracted with CH$_2$Cl$_2$ (2×10 mL). The combined organic phases were dried over MgSO$_4$ and evaporated, and the residue was chromatographed on SiO$_2$ (25×2.5 cm, EtOAc/hexane 2:1, then 4:1). The product-containing fractions were evaporated and dried (50° C./oil pump) to yield 137 mg of the crude product as a yellowish glass. This mate-

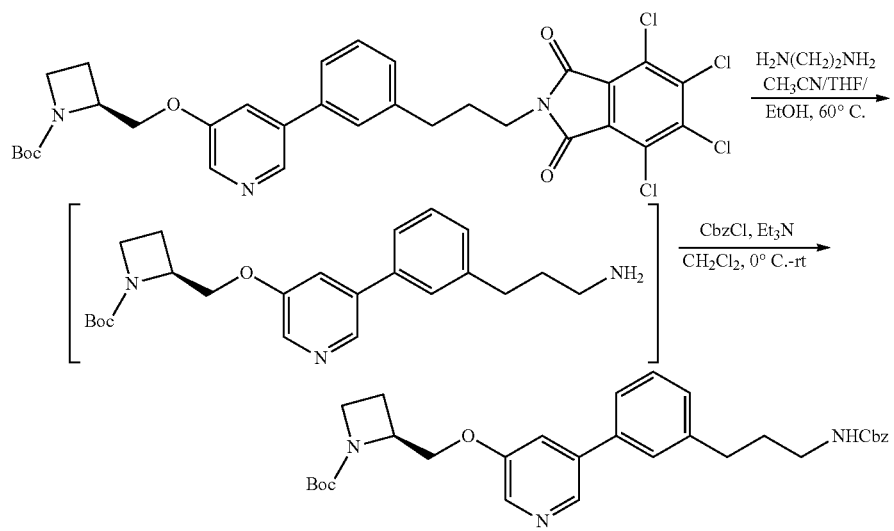

rial, together with another 31 mg previously obtained from a 82 mg run, was dissolved in DMSO (1 mL) and further purified by preparative HPLC (Supelco Discovery C$_{18}$ column, 250×21.2 mm, 5 µm particle size; UV detection at 270 nm; flow 12.5 mL/min; 0-8 min, 20% CH$_3$CN in water, then 20 to 100% within another 40 min; run aborted after elution of major peak and column washed with CH$_3$CN; t$_R$ 39.2-40.6 min). The eluate was partially evaporated to remove CH$_3$CN, and the product was extracted into CH$_2$Cl$_2$ (3×5 mL). The combined organic phases were dried over MgSO$_4$ and evaporated, and the residue was dried (50° C./oil pump vacuum) to yield 135 mg of a colorless glass (39% from a total of 429 mg of the tetrachlorophthalimide precursor). [α]$_D$ –33.2, [α]$_{546}$ –39.5 (c 10.2 g/L, EtOAc). $^1$H NMR (CDCl$_3$, TMS, 400 MHz) δ 8.45 (d, 1H, J=1.4 Hz), 8.32 (d, 1H, J=2.8 Hz), 7.44-7.28 (m, 9H), 7.22 (br d, 1H, J=6.9 Hz), 5.10 (s, 2H), 4.82 (br, 1H), 4.55 (narrow m, 1H), 4.41 (br, 1H), 4.21 (dd, 1H, J=3.0, 9.9 Hz), 3.96-3.87 (m, 2H), 3.27 (q, 2H, J=6.7 Hz), 2.73 (t, 2H, J=7.8 Hz), 2.42-2.27 (m, 2H), 1.90 (quint, 2H, J=7.3 Hz), 1.40 (s, 9H). MS (EI) m/z 531(M$^+$, 6.6%), 475 (15%), 311 (57%), 267 (38%), 198 (17%), 100 (35%), 91 (84%), 57 (100%), 56 (88%).

3-[3-[5-[[1-(tert-Butoxycarbonyl)-2(S)-azetidinyl]methoxy]-3-pyridyl]phenyl]propanamine

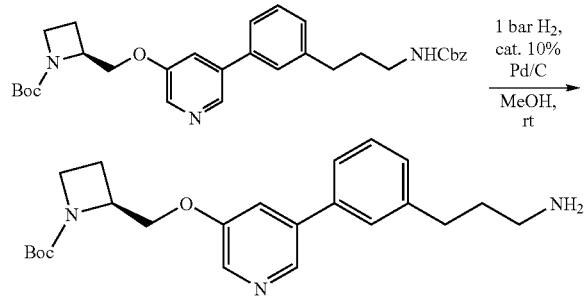

To a solution of benzyl 3-[3-[5-[[1-(tert-butoxycarbonyl)-2(S)-azetidinyl]methoxy]-3-pyridyl]phenyl]propylcarbamate (71.1 mg, 134 μmol) in methanol (3 mL) was added 10% Pd/C (26 mg). The mixture was stirred magnetically under a H$_2$ atmosphere (balloon) at room temperature for 130 min. H$_2$ was replaced by N$_2$, and the catalyst was removed by filtration over a cotton plug. The solution was evaporated and dried (30° C./oil pump vacuum) to yield 47.3 mg (89%) of a colorless film. MS (EI) m/z 397(M$^+$, 4.3%), 341 (4.3%), 311 (17%), 242 (18%), 241 (25%), 198 (10%), 100 (12%), 70 (14%), 57 (100%), 56 (73%).

N-[3-[3-[5-[[1-(tert-Butoxycarbonyl)-2(S)-azetidinyl]methoxy]-3-pyridyl]phenyl]propyl]acetamide

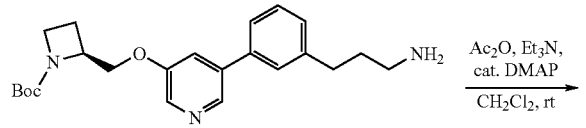

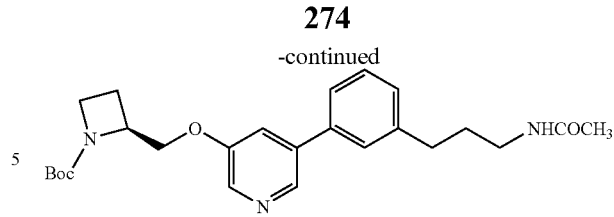

In a 25 mL round-bottom flask with magnetic stirrer, septum, and N$_2$ balloon, acetic anhydride (26 μL, 0.27 mmol, 2.3 equiv.) was added dropwise in 9 min with ice cooling to a solution of 3-[3-[5-[[1-(tert-butoxycarbonyl)-2(S)-azetidinyl]methoxy]-3-pyridyl]phenyl]propanamine (47.3 mg, 119 μmol), triethylamine (75 μL, 0.54 mmol, 4.5 equiv.), and 4-(dimethylamino)pyridine (DMAP; 1.6 mg, 13 μmol, 0.11 equiv.) in anhydrous CH$_2$Cl$_2$ (1 mL). The reaction mixture was stirred at 0° C. for 2.5 h. Shortly before, TLC (SiO$_2$, CH$_2$Cl$_2$/MeOH/Et$_3$N 90:10:5, UV detection) demonstrated disappearance of the starting material. On SiO$_2$ with CH$_2$Cl$_2$/MeOH 9:1, the product spot was detected at R$_f$ approx. 0.45. Methanol (100 μL) was added to the reaction mixture, and stirring was continued at room temperature for 1 h. After evaporation, the residue was chromatographed on SiO$_2$ (19× 1.3 cm, CH$_2$Cl$_2$/MeOH 10:1). The product eluted after a forerun. Pure fractions were evaporated, and the residue was dried (50° C./oil pump vacuum) to yield 52.5 mg (100%) of the acetylation product. [α]$_D$–35.7, [α]$_{546}$–42.2 (c 5.85 g/L, EtOAc). $^1$H NMR (CDCl$_3$, TMS, 400 MHz) δ 8.46 (br s, 1H), 8.33 (d, 1H, J=2.8 Hz), 7.46 (m, 1H), 7.43-7.36 (m, 3H), 7.23 (br d, 1H, J=6.6 Hz), 5.60 (br, 1H), 4.55 (narrow m, 1H), 4.42 (br, 1H), 4.22 (dd, 1H, J=3.2, 10.1 Hz), 3.96-3.87 (m, 2H), 3.32 (q, 2H, J=6.7 Hz), 2.73 (t, 2J, J=7.5 Hz), 2.43-2.27 (m, 2H), 1.97 (s, 3H), 1.90 (quint, 2H, J=7.3 Hz), 1.40 (s, 9H). MS (EI) m/z 439 (M$^+$, 1.4%), 383 (5.9%), 311 (45%), 284 (18%), 283 (22%), 267 (14%), 198 (26%), 100 (25%), 76 (16%), 57 (100%), 56 (75%), 43 (33%).

N-(3-[3-[5-[(2(S)-Azetidinyl)methoxy]-3-pyridyl]phenyl]propyl]acetamide Trifluoroacetate

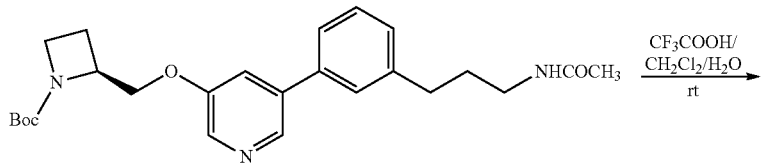

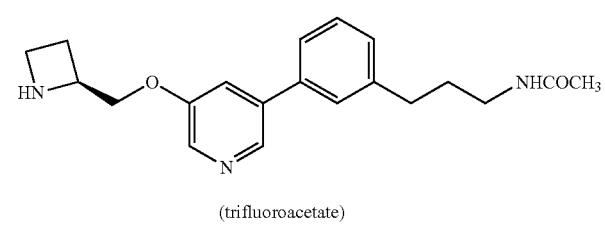

(trifluoroacetate)

In a 15 mL round-bottom flask, a mixture of $CH_2Cl_2$, trifluoroacetic acid, and water (1.1/0.22/0.022 mL) was added to N-[3-[3-[5-[[1-(tert-butoxycarbonyl)-2(S)-azetidinyl]methoxy]-3-pyridyl]phenyl]propyl]acetamide (52.2 mg, 119 μmol). The flask was swirled until the starting material had dissolved, stoppered, and set aside at room temperature for 14.5 h. Shortly before, TLC ($SiO_2$, $CH_2Cl_2$/MeOH/conc. aq. $NH_3$ 84:16:2; UV detection) showed a single spot at $R_f$ approx. 0.4. Evaporation (bath 30° C.) furnished 118 mg of a residue, which was lyophilized from water (3 mL) to yield 84.8 mg of a colorless glass. $[\alpha]_D$–3.5, $[\alpha]_{546}$–4.3 (c 3.45 g/L, MeOH). $^1$H NMR ($CD_3OD$, TMS, 400 MHz) δ 8.74 (s, 1H), 8.57 (s, 1H), 8.28 (s, 1H), 7.63 (s, 1H), 7.60, 7.39 (ABq, 2H, J=7.8 Hz), 7.49 (t, 1H, J=7.8 Hz), approx. 4.95 (m, 1H, overlaps with side band of $CD_3OH$ signal), 4.63, 4.60 (ABq, 2H, $J_{AB}$=11.2 Hz, low-field part d with J=5.5 Hz, high-field part d with J=3.6 Hz), 4.19-4.07 (m, 2H), 3.21 (t, 2H, J=6.9 Hz), 2.80-2.65 (m, 4H containing t at δ 2.76, 2H, J=7.3 Hz), 1.94 (s, 3H), 1.88 (quint, 2H, J=7.3 Hz). Anal. Calcd. for $C_{20}H_{25}N_3O_2 \cdot 3.94 CF_3COOH \cdot 0.38 H_2O$: C, 42.09; H, 3.76; N, 5.28; F, 28.23. Found: C, 41.79; H, 3.43; N, 5.21; F, 27.90.

A small sample of the trifluoroacetate was dissolved in MeOH and filtered over a 3×0.5 cm column of Amberlyst A-26 anion exchange resin (OH$^-$ form). The effluent was used to aquire an EI-MS: no M$^+$ observed; m/z 284 (69%), 283 (43%), 241 (7.8%), 212 (9.7%), 198 (11%), 182 (12%), 70 (15%), 56 (100%), 43 (42%).

Example 23

N-[3-[3-[5-[(2(S)-azetidinyl)methoxy]-3-pyridyl]phenyl]propyl]acetamide

N-[3-[3-[5-[[(tert-Butoxycarbonyl)-2(S)-azetidinyl]methoxy]-3-pyridyl]phenyl]propyl]methanesulfonamide

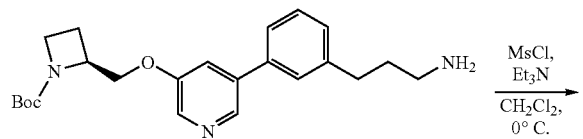

MsCl, Et$_3$N
$CH_2Cl_2$, 0° C.

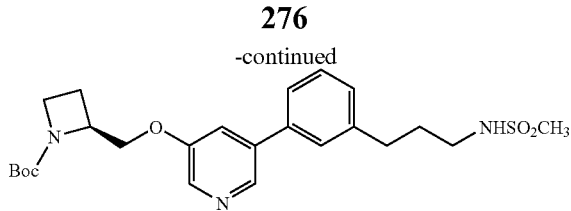

In a 25 mL round-bottom flask with magnetic stirrer, septum, and $N_2$ balloon, methanesulfonyl chloride (12 μL, 0.16 mmol, 1.3 equiv.) was added dropwise in 4 min with ice cooling to a solution of 3-[3-[5-[[1-(tert-butoxycarbonyl)-2(S)-azetidinyl]methoxy]-3-pyridyl]phenyl]propanamine (43.1 mg, 81.1 μmol) and triethylamine (30 μL, 0.22 mmol, 1.8 equiv.) in anhydrous $CH_2Cl_2$ (0.8 mL). The reaction mixture was stirred at 0° C. for 55 min. After 45 min, TLC ($SiO_2$, $CH_2Cl_2$/MeOH/$Et_3N$ 90:10:5, UV detection) demonstrated disappearance of the starting material. On $SiO_2$ with EtOAc, the product spot was detected at $R_f$ approx. 0.25; with MeOAc, at $R_f$ approx. 0.5. Water (100 μL) was added to the reaction mixture, and stirring was continued at room temperature for 1 h. After evaporation, the residue was chromatographed on $SiO_2$ (21×1.3 cm, EtOAc, then MeOAc). Product-containing fractions were evaporated, and the residue was dried (50° C./oil pump) to furnish 54 mg of the sulfonamide, which was taken up in 1 mL of DMSO. The solution was filtered over a cotton plug (0.2 mL rinse) before purification by prep. HPLC (Supelco Discovery $C_{18}$ column, 250×21.2 mm, 5 μm particle size; UV detection at 270 nm; flow 12.5 mL/min; 0-8 min, 20% $CH_3CN$ in water, then 20 to 100% within another 40 min; run aborted after elution of major peak and column washed with $CH_3CN$; $t_R$ 32.0-33.0 min). The eluate was partially evaporated to remove $CH_3CN$, and the product was extracted into $CH_2Cl_2$ (3×8 mL). The combined organic phases were dried over $MgSO_4$ and evaporated, and the residue was dried (50° C./oil pump vacuum) to yield 39.9 mg (78%) of a colorless glass. $[\alpha]_D$–36.3, $[\alpha]_{546}$–43.3 (c 6.0 g/L, EtOAc). $^1$H NMR ($CDCl_3$, TMS, 400 MHz) δ 8.45 (s, 1H), 8.33 (d, 1H, J=2.3 Hz), 7.46-7.37 (m, 4H), 7.23 (d, 1H, J=7.4 Hz), 4.61 (m, 1H), 4.55 (br m, 1H), 4.41 (br, 1H), 4.21 (dd, 1H, J=2.8, 10.1 Hz), 3.96-3.87 (m, 2H), 3.20 (q, 2H, J=6.7 Hz), 2.95 (s, 3H), 2.79 (t, 2H, J=7.6 Hz), 2.43-2.27 (m, 2H), 1.97 (quint, 2H, J=7.2 Hz), 1.40 (s, 9H). MS (EI) m/z 475 (M$^+$, 0.4%), 402 (2.3%), 346 (5.3%), 320 (12%), 319 (31%), 307 (12%), 198 (12%), 113 (14%), 100 (30%), 70 (11%), 57 (94%), 56 (100%).

N-[3-[3-[5-[(2(S)-Azetidinyl)methoxy]-3-pyridyl]phenyl]propyl]acetamide Trifluoroacetate

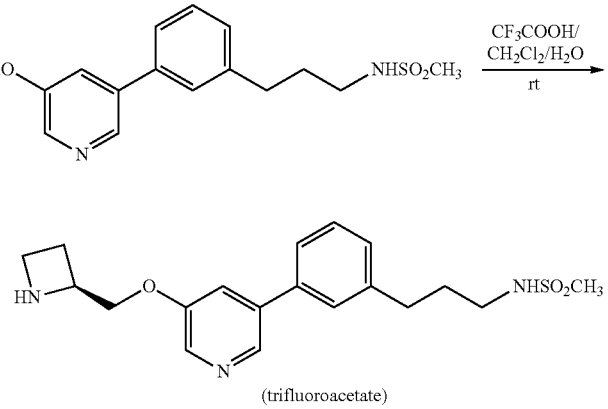

(trifluoroacetate)

In a 10 mL round-bottom flask, a mixture of $CH_2Cl_2$, trifluoroacetic acid, and water (0.8/0.16/0.016 mL) was added to N-[3-[3-[5-[[1-(tert-butoxycarbonyl)-2(S)-azetidinyl]methoxy]-3-pyridyl]phenyl]propyl]methanesulfonamide (39.7 mg, 83.5 μmol). The flask was swirled until the starting material had dissolved, stoppered, and set aside at room temperature for 22 h. Evaporation (bath 30° C.) furnished 88 mg of a residue, which was lyophilized from water (3 mL) to yield 62.3 mg of a colorless glass. $^1$H NMR ($CD_3OD$, TMS, 400 MHz) δ 8.74 (s, 1H), 8.55 (d, 1H, J=2.8), 8.31 (narrow m, 1H), 7.67 (s, 1H), 7.61 (d, 1H, J=7.8 Hz), 7.50 (t, 1H, J=7.6 Hz), 7.40 (d, 1H, J=7.8 Hz), approx. 4.95 (m, 1H, overlaps with side band of $CD_3OH$ signal), 4.64, 4.60 (ABq, 2H, $J_{AB}$=11.2 Hz, low-field part d with J=5.7 Hz, high-field part d with J=3.4 Hz), 4.19-4.07 (m, 2H), 3.08 (t, 2H, J=6.6 Hz), 2.93 (s, 3H), 2.84 (t, 2H, J=7.3 Hz), 2.79-2.65 (m, 2H), 1.93 (quint, 2H, J=6.9 Hz). MS (EI): no M$^+$ observed; m/z 321 (20%), 320 (55%), 319 (77%), 56 (100%). Anal. Calcd. for $C_{19}H_{25}N_3O_3S\cdot3.53CF_3COOH\cdot0.03H_2O$: C, 40.20; H, 3.70; N, 5.40; F, 25.84. Found: C, 40.21; H, 3.88; N, 5.39; F, 26.02.

Example 24

2-[3-[5-[(2(S)-Azetidinyl)methoxy]-3-pyridyl]phenyl]ethanol

3-[[1-(Benzyloxycarbonyl)-2(S)-azetidinyl]methoxy]-5-bromopyridine

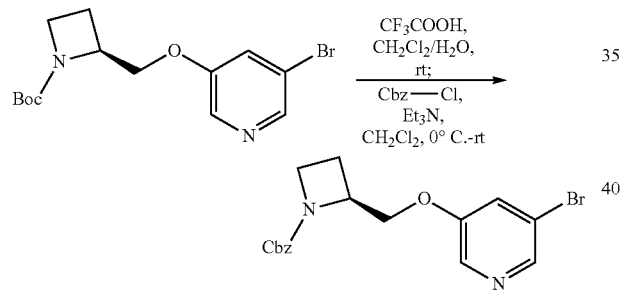

To a solution of 3-bromo-5-[[1-(tert-butoxycarbonyl)-2(S)-azetidinyl]methoxy]pyridine (704 mg, 2.05 mmol) in $CH_2Cl_2$ (20 mL) contained in a 200 mL round-bottom flask with magnetic stirrer was added a mixture of $CF_3COOH$ (4 mL) and water (0.4 mL). The flask was loosely stoppered (some pressure may otherwise build up). The mixture was stirred at room temperature for 15.5 h, then evaporated (bath 30° C.) to leave 4.56 g of a colorless liquid. This residue was taken up in $CH_2Cl_2$ (20 mL) and placed in a round-bottom flask with magnetic stirrer and ice bath. Triethylamine (3.4 mL, 24.5 mmol, 12 equiv.) was added dropwise in 5 min. After 4 min of stirring in the ice bath, benzyl chloroformate (0.44 mL, 3.1 mmol, 1.5 equiv.) was added dropwise in 7 min. The reaction mixture was then stirred at room temperature for 3.5 h. A thin-layer chromatogram taken after 3 h ($SiO_2$, EtOAc/hexane 2:3; product: $R_f$ 0.2) indicated low conversion, most of the balance being baseline material (amine salt; reaction mixture unexpectedly acidic by testing with moist pH paper). After re-cooling in an ice bath, additional triethylamine (1.7 mL, 6 equiv.) and benzyl chloroformate (0.44 mL, 1.5 equiv.) were added. The mixture was stirred at room temperature for 3 h and then evaporated to produce a colorless sludge, which was taken up in water (20 mL) and extracted with EtOAc (3×10 mL). The combined organic phases were without drying evaporated, and the residue was chromatographed on $SiO_2$ (25×2.5 cm, EtOAc/hexane 3:7, then 2:3). The product-containing fractions were evaporated and the residue dried (50° C./oil pump) to obtain 756 mg of a colorless glass.

The crude product was taken up in DMSO (2.5 mL) and in a single injection purified by preparative HPLC (Supelco Discovery $C_{18}$, 250×21.2 mm, 5 μm particle size; UV detection at 270 nm; flow/solvent gradient: 0-12 min, 6 to 12.5 mL/min, 20% $CH_3CN/H_2O$; 12-52 min, 12.5 mL/min, 20-100% $CH_3CN/H_2O$). The product eluted at $t_R$ 36.9-39.6 min. This eluate was partially evaporated to remove $CH_3CN$, and the product was extracted into $CH_2Cl_2$ (3×10 mL). The combined organic phases were dried over $MgSO_4$, evaporated and dried (50° C./oil pump) to obtain 694 mg (90%) of a colorless syrup. $^1$H NMR ($CDCl_3$, TMS, 250 MHz) δ 8.30 (br s, 1H), 8.24 (br s, 1H), 7.36 (br s, 1H), 7.31 (s, 5H), 5.12, 5.05 (ABq, 2H, J=12.3 Hz), 4.60 (m, 1H), 4.34 (br, 1H), 4.10 (br dd, 1H, J=2.0, 10.0 Hz), 3.99 (t, 2H, J=7.5 Hz), 2.49-2.25 (m, 2H). $^{13}$C NMR ($CDCl_3$, 62.5 MHz) δ 156.1, 155.3 (br), 143.2, 136.5, 136.3, 128.4 (2C), 128.1, 127.9 (2C), 124.0, 120.3 (br), 68.5 (br), 66.6, 60.0, 47.3 (br), 19.1. MS (EI) m/z 378/376 (M$^+$, 2.4/2.1%), 175/173 (12/12%), 91 (100%), 65 (9.2%).

3-[[1-(Benzyloxycarbonyl)-2(S)-azetidinyl]methoxy]-5-(trimethylstannyl)pyridine

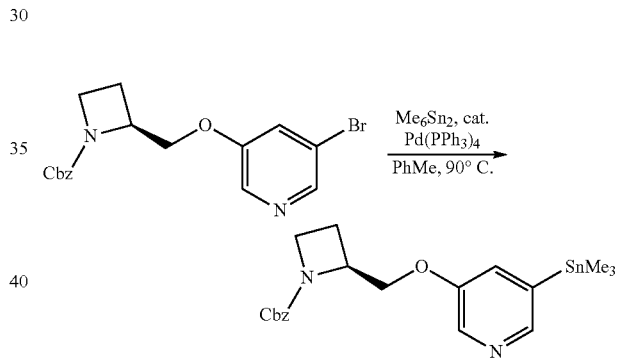

A solution of 3-[[1-(benzyloxycarbonyl)-2(S)-azetidinyl]methoxy]-5-bromopyridine (489 mg, 1.30 mmol) and tetrakis(triphenylphosphine)palladium(0) (45 mg, 39 μmol, 0.03 equiv.) in anhydrous toluene (4 mL) was purged with nitrogen in a 38 mL Chemglass pressure tube. Hexamethyldistannane (0.81 mL, 3.9 mmol, 3.0 equiv.) was added all at once, and the tube was capped and heated to 90° C. for 21.5 hours. After cooling, the heterogeneous reaction mixture (solution and precipitate) was directly loaded onto a silica gel column (26× 3.8 cm), and the product was rapidly eluted with EtOAc/hexane/triethylamine 25:70:5. The product-containing fractions were evaporated and the residue evaporated with EtOAc (to remove residual triethylamine). Drying (30-35° C./oil pump vacuum) yielded 556 mg (93%) of the stannane as a yellowish oil which was suitable for subsequent reactions. Purity by HPLC (Supelco Discovery $C_{18}$, 250×3 mm with guard column, 5 μm particle size, deactivated prior to use with 2 μL of pyridine while eluting with $CH_3CN$; UV detection at 270 nm; flow 0.5 mL/min; gradient from 20 to 100% $CH_3CN$ in water within 20 min, then 15 min $CH_3CN$): 94.7% ($t_R$ 26.2 min).

A small sample was purified by preparative HPLC under the above analytical-scale conditions; $t_R$ 24.5-27.5 min. The eluate was evaporated and dried (35° C./14 torr) in a NaHCO$_3$-washed flask. $^1$H NMR (C$_6$D$_6$, TMS, 400 MHz) δ 8.53 (s, 1H; Sn satellites present but too broad to read coupling constants), 8.47 (br, 1H), 7.30 (br, 1H), 7.22 (br d, 2H, J=7.1 Hz), 7.12-7.00 (m, 3H), 5.08, 5.04 (ABq, 2H, J=12.4 Hz), 4.12 (br, 2H), 3.67 (br m, 2H), 3.54 (br, 1H), 1.77 (br, 1H), 1.65-1.56 (m, 1H), 0.14 (s, 9H, with Sn satellites, J$_{H-Sn}$=55.9 and 53.6 Hz, resp.). MS (EI) m/z 447/445/443 (M$^+$–CH$_3$, 8.9/6.6/3.5%), 403/401/399 (8.4/6.3/3.7%), 91 (100%).

2-[3-[5-[[1-(Benzyloxycarbonyl)-2(S)-azetidinyl]methoxy]-3-pyridyl]phenyl]ethanol

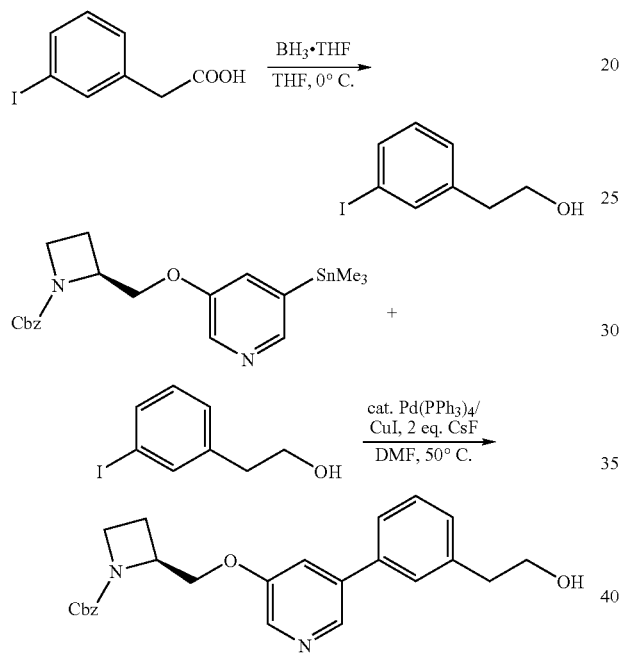

2-(3-Iodophenyl)ethanol was prepared by borane reduction of 3-iodophenylacetic acid in THF in a similar manner as outlined in Example 17, and additionally purified by CC on SiO$_2$ with EtOAc/hexane 2:3.

3-[[1-(Benzyloxycarbonyl)-2(S)-azetidinyl]methoxy]-5-(trimethylstannyl)pyridine (546 mg, 1.19 mmol), 2-(3-iodophenyl)ethanol (294 mg, 1.19 mmol), and anhydrous DMF (4 mL) were placed in a 25 mL round bottom flask with magnetic stirrer. To this mixture were added rapidly CsF (360 mg, 2.37 mmol, 2 equiv.), CuI (23 mg, 0.12 mmol, 0.1 equiv.), and tetrakis(triphenylphosphine)palladium(0) (58 mg, 50 μmol, 42 mequiv.). The flask was fitted with a three-way stopcock with nitrogen balloon, and the atmosphere was exchanged. The reaction mixture was heated at 50° C. for 6 h. The solvent was pumped off at room temperature (water bath) with an oil pump into a −78° C. receiver, and CH$_2$Cl$_2$/MeOH 95:5 was added to the residue, resulting in a solution and a precipitate. TLC (SiO$_2$, CH$_2$Cl$_2$/MeOH 93:7) showed the formation of a product at R$_f$ 0.25 (UV-and KMnO$_4$-active) followed by residual DMF (R$_f$ 0.15; KMnO$_4$ stain only). The crude product was loaded on a silica gel column (24×3.8 cm), which was eluted with CH$_2$Cl$_2$/MeOH 95:5. Inadequate separation from DMF and a weak nonpolar impurity was observed. The eluate was concentrated to a small volume, filtered over a cotton plug, and then fully evaporated to leave 625 mg of an amber oil. This residue was taken up in DMSO (1.8 mL). Further purification was achieved by preparative HPLC in four portions on a Supelco Discovery C$_{18}$ column (250×21.2 mm, 5 μm particle size; UV detection at 270 nm; flow 12.5 mL/min; 8 min elution with 20% CH$_3$CN in water, then 20 to 100% within 40 min; runs aborted after elution of the main peak and column washed with CH$_3$CN). The coupling product eluted at t$_R$ 30.4-31.5 min. The eluate was partially evaporated to remove acetonitrile, and the product was extracted from the residue with CH$_2$Cl$_2$ (3×10 mL). After drying over MgSO$_4$, the combined organic phases were evaporated and dried (50° C./oil pump) to obtain 399 mg (80%) of a glass. [α]$_D$–43.8, [α]$_{546}$–52.0 (c 12.7 g/L, EtOAc). $^1$H NMR (CDCl$_3$, TMS, 400 MHz) δ 8.45 (d, 1H, J=1.4 Hz), 8.29 (br, 1H), 7.46-7.36 (m, 4H), 7.32-7.23 (m, 6H), 5.10, 5.05 (ABq, 2H, J=12.1 Hz), 4.64 (br m, 1H), 4.45 (br, 1H), 4.19 (br d, 1H, J=9.2 Hz), 4.07-3.96 (m, 2H), 3.93 (q, 2H, J=6.1 Hz), 2.96 (t, 2H, J=6.4 Hz), 2.49-2.33 (m, 2H), 1.64 (s, 1H, OH). MS (EI) m/z 418 (M$^+$, 1.2%), 388 (8%), 91 (100%).

2-[3-[5-[(2(S)-Azetidinyl)methoxy]-3-pyridyl]phenyl]ethanol

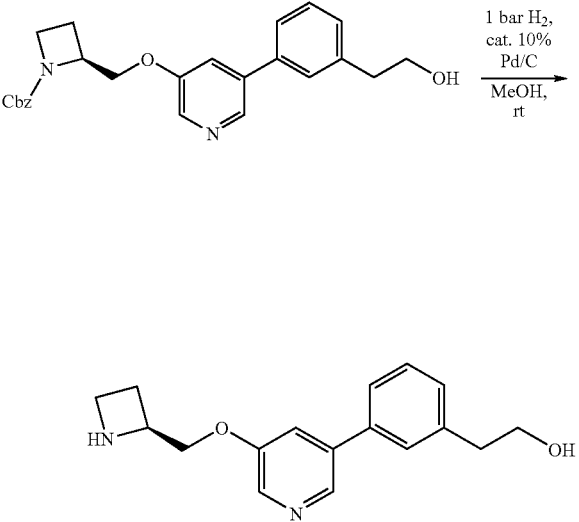

In a 100 mL round-bottom flask with magnetic stirrer and H$_2$ balloon, 2-[3-[5-[[1-(benzyloxycarbonyl)-2(S)-azetidinyl]methoxy]-3-pyridyl]phenyl]ethanol (240 mg, 574 μmol) in MeOH (10 mL) was stirred with 10% Pd/C (50 mg; Alfa Aesar #38305, water content 50%) at room temperature for 130 min. H$_2$ was replaced with Ar, and the catalyst was filtered off over a cotton plug and rinsed with MeOH (2 mL). The solution was evaporated and dried (30° C., oil pump vacuum) to yield the free base as a colorless film. [α]$_D$–1.0, [α]$_{546}$–1.4 (c 7.35 g/L, MeOH). $^1$H NMR (CDCl$_3$, TMS, 400 MHz) δ 8.41 (d, 1H, J=1.8 Hz), 8.28 (d, 1H, J=2.8 Hz), 7.45-7.40 (m, 3H), 7.39 (dd, 1H, J=1.8, 2.8 Hz), 7.28 (dt, 1H, J=6.4 Hz (d), 2.1 Hz (t)), 4.31 (m, 1H), 4.12, 4.08 (ABq, 2H, J=9.4 Hz, low-field part d with J=6.2 Hz, high-field part d with J=4.8 Hz), 3.92 (t, 2H, J=6.6 Hz), 3.72 (q, 1H, J=7.9 Hz), 3.48 (m, 1H), 2.95 (t, 2H, J=6.6 Hz), 2.41, 2.29 (ABq, 2H, J=11.0 Hz, low-field part m, high-field part q with J=8.2 Hz), 2.08 (br, NH, OH, and H₂O). MS (EI) m/z 284 (M⁺, 1.9%), 254 (2.2%), 229 (36%), 228 (56%), 199 (10%), 56 (100%).

2-[3-[5-[(2(S)-Azetidinyl)methoxy]-3-pyridyl]phenyl]ethanol Hydrochloride

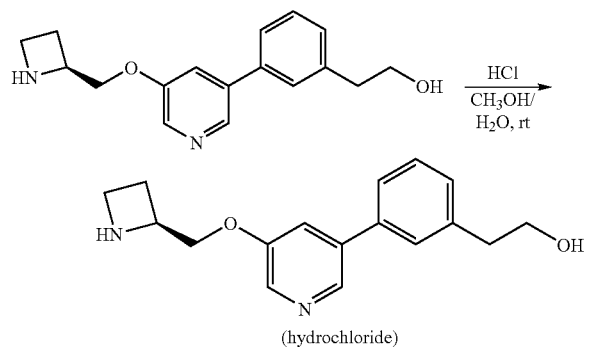

(hydrochloride)

The free base was dissolved in MeOH (0.3 mL). Aqueous hydrochloric acid (1.00M, 1.15 mL, 2 equiv.) and water (10 mL, HPLC grade) were added. Lyophilization yielded 202 mg of the hydrochloride as a colorless foam and droplets. ¹H NMR (CD₃OD, 500 MHz) δ 8.90 (narrow m, 1H), 8.76 (narrow m, 1H), 8.61 (narrow m, 1H), 7.76 (br s, 1H), 7.72 (d, 1H, J=7.7 Hz), 7.56 (t, 1H, J=7.7 Hz), 7.49 (d, 1H, J=7.6 Hz), 5.00 (m, 1H), 4.76, 4.69 (ABq, 2H, J=11.1 Hz, low-field part d with J=5.8 Hz, high-field part d with J=3.0 Hz), 4.17 (m, 2H), 3.87 (t, 2H, J=6.7 Hz), 2.98 (t, 2H, J=6.7 Hz), 2.76 (m, 2H). Anal. Calcd. for $C_{17}H_{20}N_2O_2 \cdot 2.1HCl \cdot 0.7H_2O$: C, 54.66; H, 6.34; N, 7.50; Cl, 19.93. Found: C, 54.85; H, 6.62; N, 7.47; Cl, 20.13.

Example 25 tert-Butyl [3-[5-[(2(S)-Azetidinyl)methoxy]-3-pyridyl]benzyl]carbamate tert-Butyl 3-Iodobenzylcarbamate

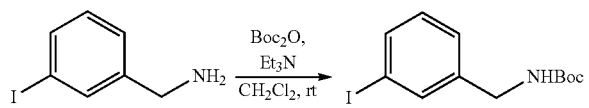 [SMILES: NCc1cccc(I)c1 ; CC(C)(C)OC(=O)NCc1cccc(I)c1]

In a 100 mL round-bottom flask with magnetic stirrer and balloon (for pressure equalization and exclusion of moisture), a solution of di-tert-butyl dicarbonate (0.72 g, 3.3 mmol, 1.2 equiv.) in CH₂Cl₂ (5 mL) was added all at once at room temperature to a solution of 3-iodobenzylamine (641 mg, 2.75 mmol) and triethylamine (0.57 mL, 4.1 mmol, 1.5 equiv.) in CH₂Cl₂ (10 mL). The mixture was stirred at room temperature for 4.5 h. TLC after 3.5 h (SiO₂, EtOAc/hexane/Et₃N 22:78:5) indicated complete conversion of the amine (R_f approx. 0.05), whereas a strongly UV-active impurity (R_f approx. 0.65) remained unchanged, and the product was detected at R_f approx. 0.55. With EtOAc/hexane 1:9 as eluent, product and impurity exhibit R_f values of approx. 0.2 and 0.4, respectively. The reaction mixture was evaporated, and the residue was chromatographed on SiO₂ (26×3.8 cm, EtOAc/hexane 6:94 until the nonpolar impurity was completely eluted, then 1:4). Evaporation and drying (40° C./oil pump) furnished 820 mg (89%) of a colorless solid. Mp 53.5-54.5° C. MS (EI) m/z 333 (M⁺, 0.2%), 277 (33%), 276 (38%), 232 (6.4%), 217 (11%), 150 (5.4%), 106 (19%), 59 (26%), 57 (100%).

tert-Butyl [3-[5-[[1-(Benzyloxycarbonyl)-2(S)-azetidinyl]methoxy]-3-pyridyl]benzyl]carbamate

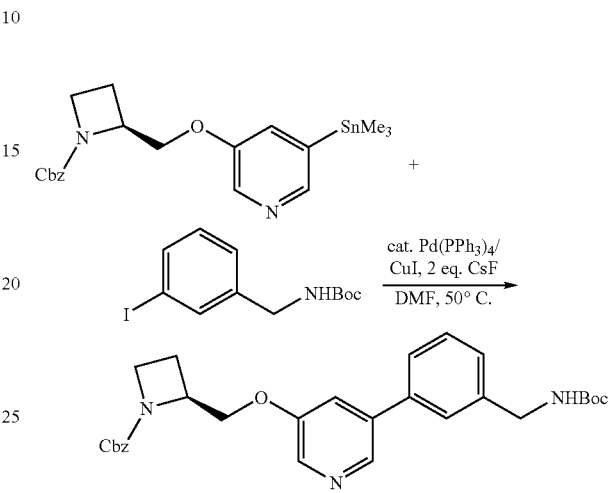

3-[[1-(Benzyloxycarbonyl)-2(S)-azetidinyl]methoxy]-5-(trimethylstannyl)pyridine (682 mg, 1.48 mmol), tert-butyl 3-iodobenzylcarbamate (498 mg, 1.48 mmol), and anhydrous DMF (5 mL) were placed in a 50 mL round-bottom flask with magnetic stirrer. To this mixture were added rapidly CsF (450 mg, 2.96 mmol, 2 equiv.), CuI (29 mg, 0.15 mmol, 0.1 equiv.), and tetrakis(triphenylphosphine)palladium(0) (87 mg, 75 μmol, 0.05 equiv.). The flask was fitted with a three-way stopcock with argon balloon, and the atmosphere was exchanged. The reaction mixture was heated at 50° C. for 6 h, during which time it turned from an olive-colored solution to a dark suspension. The solvent was pumped off at 30° C. with an oil pump into a −78° C. receiver. The residue was stirred with ether (20 mL) to disperse the solid, which was then removed by suction filtration over celite. The filter residue was twice washed with ether (15 mL each), and the combined ether solutions were evaporated. TLC (SiO₂, EtOAc) showed the formation of a major product at R_f 0.5 (UV- and KMnO₄-active) followed by residual DMF (R_f 0.15; KMnO₄ stain only). The crude product was chromatographed on silica gel (20×3.8 cm) with a stepwise gradient of EtOAc/hexane 1:1, 2:1, 3:1, and 4:1. The product-containing eluate fractions were evaporated. The residue was taken up in DMSO (2.2 mL) and further purified by preparative HPLC in a single portion on a Supelco Discovery C₁₈ column (250×21.2 mm, 5 μm particle size; UV detection at 270 nm; flow/solvent gradient: 0-12 min, 6 to 12.5 mL/min (then remaining at this value)/20% CH₃CN in water; 20-100% within 40 min; run aborted after elution of the main peak and column washed with CH₃CN). The product eluted at t_R 39.8-41.9 min. Evaporation and drying (50° C./oil pump) gave 542 mg (73%) of a yellowish glass. $[\alpha]_D$ −44.3, $[\alpha]_{546}$ −52.5 (c 10.5 g/L, EtOAc). ¹H NMR (CDCl₃, 500 MHz) δ 8.48 (s, 1H), 8.32 (br, 1H), 7.51-7.25 (m, 10H), 5.13, 5.09 (ABq, 2H, J=12.4 Hz), 4.96 (br, 1H), 4.67 (br, 1H), approx. 4.5 (very br, 1H), 4.42 (br d, 2H, J=5.3 Hz), 4.22 (br, 1H), 4.08-4.00 (m, 2H), 2.51-2.32

(m, 2H), 1.50 (s, 9H). MS (EI) m/z 503 (M+, 0.6%), 447 (1.5%), 312 (2.4%), 199 (2.6%), 91 (100%), 57 (18%).

tert-Butyl [-3-[5-[(2(S)-Azetidinyl)methoxy]-3-pyridyl]benzyl]carbamate

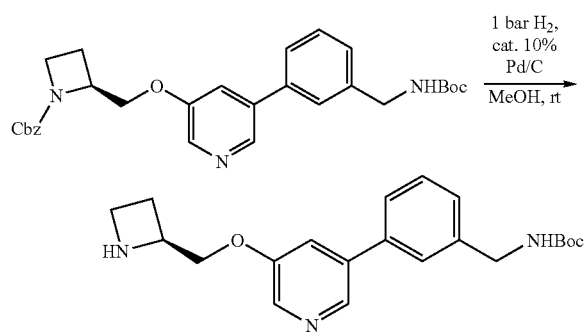

In a 100 mL round-bottom flask with magnetic stirrer and H₂ balloon, tert-butyl [3-[5-[[1-(benzyloxycarbonyl)-2(S)-azetidinyl]methoxy]-3-pyridyl]benzyl]carbamate (91.2 mg, 181 μmol) in MeOH (3 mL) was stirred with 10% Pd/C (19 mg; Alfa Aesar #38305, water content 50%) at room temperature for 2.5 h. H₂ was replaced with Ar, and the catalyst was filtered off over a cotton plug and rinsed with MeOH (1.5 mL). The solution was evaporated and dried (35° C., oil pump vacuum) to yield the free azetidine (67.3 mg, 101%, must contain a trace of solvent) as a colorless film. [α]$_D$0, [α]$_{546}$0 (c 6.4 g/L, MeOH). ¹H NMR (CDCl₃, 500 MHz) δ 8.46 (br s, 1H), 8.32 (br s, 1H, J=2.8 Hz), 7.51-7.34 (m, 5H), 4.98 (br, 1H), 4.42 (narrow m, 1H), 4.34 (m, 1H), 4.18-4.08 (m, 2H), 3.75 (q, 1H, J=7.9 Hz), 3.50 (m, 1H), 2.44 (m, 1H), 2.33 (m, 1H), 1.89 (br, 1H), 1.49 (s, 9H). MS (EI) m/z 369 (M+, 0.1%), 314 (15%), 313 (21%), 257 (23%), 214 (24%), 213 (11%), 70 (11%), 56 (100%).

tert-Butyl [3-[5-[(2(S)-Azetidinyl)methoxy]-3-pyridyl]benzyl]carbamate Hydrochloride

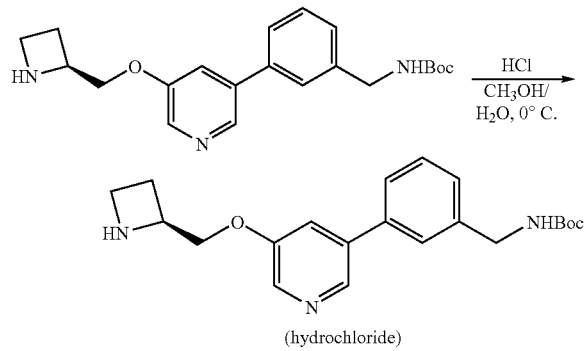

(hydrochloride)

The free base (60.5 mg) was dissolved in MeOH (0.2 mL). Aqueous hydrochloric acid (1.00M, 0.31 mL, 1.9 equiv.) was added dropwise with ice cooling, followed by water (3 mL, HPLC grade) after filtration from a minor turbidity. Lyophilization yielded 68 mg of the hydrochloride as a foam. ¹H NMR (CD₃OD, 500 MHz) δ 8.76 (s, 1H), 8.62 (s, 1H), 8.30 (s, 1H), 7.71 (s, 1H), 7.70 (d, 1H, partially overlapping with the preceding signal), 7.56 (t, 1H, J=7.6 Hz), 7.48 (d, 1H, J=7.6 Hz), 4.97 (m, 1H), 4.76, 4.69 (ABq, 2H, J=11.2 Hz, low-field part d with J=5.9 Hz, high-field part d with J=2.9 Hz), 4.35 (s, 2H), 4.21-4.12 (m, 2H), 2.79-2.70 (m, 2H), 1.48 (s, 9H). Anal. Calcd. for C₂₁H₂₇N₃O₃.1.65HCl.0.7H₂O: C, 57.04; H, 6.85; N, 9.50; Cl, 13.23. Found: C, 57.15; H, 7.07; N, 9.36; Cl, 13.19.

Example 26

N-[3-[5-[(2(S)-Azetidinyl)methoxy]-3-pyridyl]benzyl]acetamide Hydrochloride

3-[5-[[1-(Benzyloxycarbonyl)-2(S)-azetidinyl]methoxy]-3-pyridyl]benzylamine

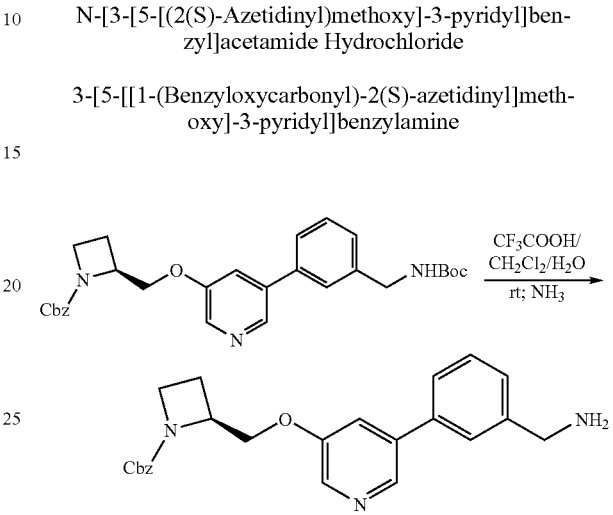

In a 100 mL round-bottom flask, a mixture of trifluoroacetic acid (1.2 mL) and water (0.12 mL) was added to a solution of tert-butyl 3-[5-[[1-(benzyloxycarbonyl)-2(S)-azetidinyl]methoxy]-3-pyridyl]benzylcarbamate (329 mg, 653 μmol) in CH₂Cl₂ (6 mL). The flask was loosely stoppered, and the mixture was stirred magnetically for 7 h. Shortly before, a small aliquot was worked up with aq. NaHCO₃/EtOAc and analyzed by TLC (UV detection; SiO₂, EtOAc: R$_f$ 0; SiO₂, CH₂Cl₂/MeOH/conc. aq. NH₃ 87:13:3: R$_f$ approx. 0.55), indicating complete conversion of the starting material. The mixture was evaporated (40° C./14 torr) to obtain a colorless glass (0.76 g), which was taken up in MeOH (3 mL). The pH was adjusted to approx. 8-9 (indicator paper) by adding a few drops of conc. NH₃, and the solution was evaporated again. The residue was chromatographed on SiO₂ (20×1.9 cm, CH₂Cl₂/MeOH/conc. aq. NH₃ 87:13:3), and the product-containing fractions were evaporated and dried (40° C./oil pump) to obtain 262 mg (99.5%) of the free primary amine as a slightly yellowish glass. ¹H NMR (CDCl₃, 500 MHz) δ 8.50 (s, 1H), 8.32 (br, 1H), 7.56 (s, 1H), 7.51-7.45 (m, 2H), approx. 7.43 (br and overlapping, 1H), 7.40 (m, 1H), 7.32 (br s, 5H), 5.13, 5.08 (ABq, 2H, J=12.3 Hz), 4.67 (m, 1H), approx. 4.5 (br, 1H), 4.22 (br s, 1H), 4.09-4.00 (m, 2H), 3.99 (s, 2H), 2.51-2.37 (m, 2H), 1.64 (br, NH₂ and H₂O). MS (EI) m/z 403 (M+, 5.8%), 312 (6.4%), 200 (5.4%), 199 (4.0%), 91 (100%).

N-[3-[5-[[1-(Benzyloxycarbonyl)-2(S)-azetidinyl]methoxy]-3-pyridyl]benzyl]acetamide

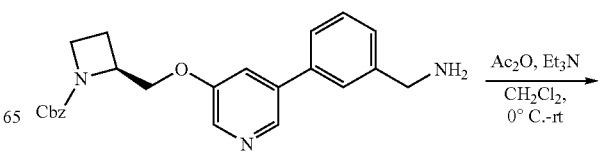

-continued

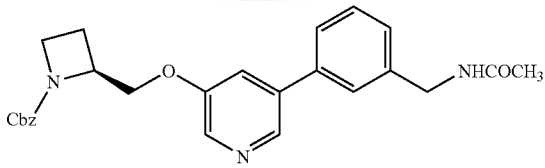

In a 15 mL round-bottom flask with magnetic stirrer, septum, and balloon (for pressure equalization and exclusion of moisture), neat acetic anhydride (23 μL, 0.24 mmol, 1.5 equiv.) was added with ice cooling in 5 min to a solution of 3-[5-[[1-(benzyloxycarbonyl)-2(S)-azetidinyl]methoxy]-3-pyridyl]benzylamine (65.3 mg, 162 μmol) and triethylamine (45 μL, 0.32 mmol, 2 equiv.) in anhydrous $CH_2Cl_2$ (1 mL). Stirring was continued at room temperature for 85 min, while the septum was replaced with a glass stopper to avoid evaporation losses. After 65 min, TLC ($SiO_2$, $CH_2Cl_2$/MeOH 9:1, UV detection) demostrated complete conversion of the starting material ($R_f$ approx. 0.05) to the acetamide ($R_f$ approx. 0.45). Methanol (25 μL) was added, and the reaction mixture was stored at room temperature for 1 h before being directly applied on a $SiO_2$ column (26×1.3 cm; eluent: $CH_2Cl_2$/MeOH 94:6 for a forerun, then 9:1). The product-containing fractions were evaporated and dried (50° C./oil pump) to yield 69.1 mg (96%) of the amide as a colorless glass. $[\alpha]_D$–40.7, $[\alpha]_{546}$–48.3 (c 14.8 g/L, EtOAc). $^1$H NMR ($CDCl_3$, 500 MHz) δ 8.47 (s, 1H), 8.32 (br, 1H), 7.55-7.48 (m, 2H), 7.47 (t, 1H, J=7.5 Hz), approx. 7.4 (br and overlapping, 1H), 7.30 (d, 1H, J=7.4 Hz), 7.31 (br s, 5H), 5.89 (br, 1H), 5.12, 5.07 (ABq, 2H, J=12.3 Hz), 4.67 (br, 1H), 4.54 (d, 2H, J=5.7 Hz), approx. 4.4-4.5 (br, 1H), 4.22 (br, 1H), 4.09-4.00 (m, 2H), 2.51-2.32 (m, 2H), 2.08 (s, 3H). MS (EI) m/z 445 ($M^+$, 8.46%), 354 (2.2%), 312 (2.8%), 310 (5.9%), 242 (6.5%), 199 (5.0%), 91 (100%), 43 (11%).

N-[3-[5-[(2(S)-Azetidinyl)methoxy]-3-pyridyl]benzyl]acetamide Hydrochloride

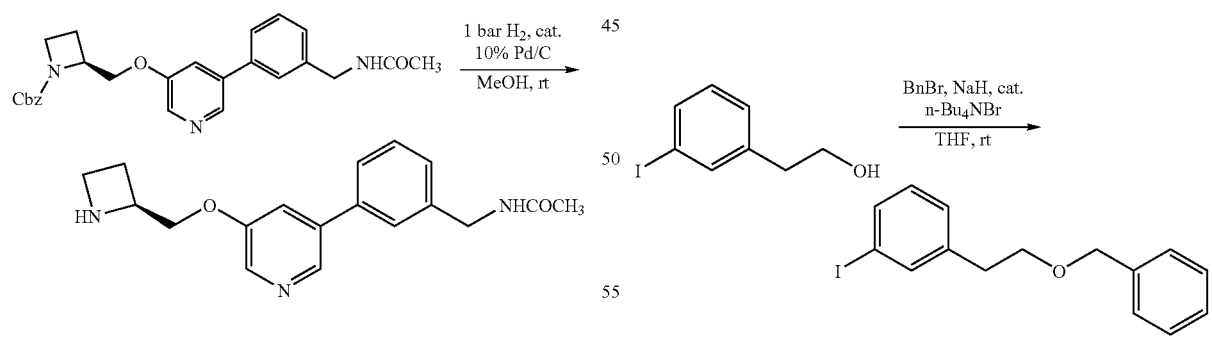

In a 50 mL round-bottom flask with magnetic stirrer and $H_2$ balloon, N-[3-[5-[[1-(benzyloxycarbonyl)-2(S)-azetidinyl]methoxy]-3-pyridyl]benzyl]acetamide (66 mg, 148 μmol) in MeOH (3 mL) was stirred with 10% Pd/C (16 mg; Alfa Aesar #38305, water content 50%) at room temperature for 165 min. $H_2$ was replaced with Ar, and the catalyst was filtered off over a cotton plug and rinsed with MeOH (1 mL). The solution was evaporated and dried (30° C., oil pump vacuum) to yield the free azetidine (46.7 mg, 101%, must contain a trace of solvent) as a colorless film. MS (EI) m/z 312 (M+H$^+$, 0.4%), 311 ($M^+$, 0.5%), 256 (48%), 255 (51%), 226 (8.5%), 197 (13%), 70 (8.7%), 56 (100%), 43 (30%).

N-[3-[5-[(2(S)-Azetidinyl)methoxy]-3-pyridyl]benzyl]acetamide Hydrochloride

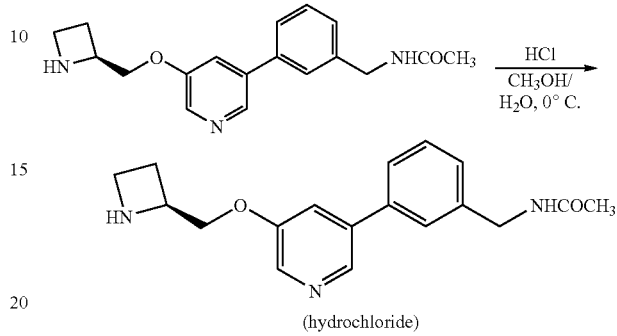

(hydrochloride)

The free base (43.1 mg) was dissolved in MeOH (0.2 mL). Aqueous hydrochloric acid (1.00M, 0.28 mL, 1.9 equiv.) was added followed by water (3 mL, HPLC grade). The solution was filtered from a minor turbidity over cotton and then lyophilized to yield 51.4 mg of the hydrochloride. $^1$H NMR ($CD_3OD$, 500 MHz) δ 8.91 (s, 1H), 8.77 (s, 1H), 8.63 (s, 1H), 7.82 (s, 1H), 7.78 (d, 1H, J=7.6 Hz), 7.60 (t, 1H, J=7.7 Hz), 7.53 (d, 1H, J=7.8 Hz), 5.01 (m, 1H), 4.76, 4.69 (ABq, 2H, J=11.1 Hz, low-field part d with J=5.9 Hz, high-field part d with J=3.0 Hz), 4.50 (s, 2H), 4.20-4.15 (m, 2H), 2.80-2.72 (m, 2H), 2.05 (s, 3H). Anal. Calcd. for $C_{18}H_{21}N_3O_2$.2.15HCl.1.35H$_2$O: C, 52.21; H, 6.29; N, 10.15; Cl, 18.41. Found: C, 52.23; H, 6.66; N, 10.00; Cl, 18.78.

Example 27

3-[((2S)-Azetidinyl)methoxy]-5-[3-[2-(benzyloxy)ethyl]phenyl]pyridine

1-[2-(Benzyloxy)ethyl]-3-iodobenzene

Into a 50-mL 3-necked round-bottom flask under $N_2$ was placed a solution of 2-(3-iodophenyl)ethanol (470 mg, 1.90 mmol) in tetrahydrofuran (10 mL). Sodium hydride (91 mg, 3.8 mmol, 2 equiv.) was added at 0° C. The resulting mixture was warmed to room temperature and stirred at room temperature for 2 h. Benzyl bromide (272 μL, 3.9 mmol, 2.05 equiv.) and tetra-n-butylammonium bromide (61 mg, 0.19 mmol, 0.10 equiv.) were added at room temperature. The resulting solution was stirred for 20 h at room temperature.

The reaction progress was monitored by TLC (EtOAc/petroleum ether 1:30). The reaction was then quenched by the addition of aqueous NH₄Cl (10 mL). The resulting solution was extracted with EtOAc (3×60 mL), and the organic layers were combined and washed with brine (50 mL). The residue was chromatographed on silica gel with EtOAc/petroleum ether 1:20 to give 0.48 g (75%) of 1-[2-(benzyloxy)ethyl]-3-iodobenzene as a colorless oil. ¹H NMR (CDCl₃, 300 MHz) δ 7.62 (s, 1H), 7.58 (d, 1H, J=7.8 Hz), 7.42-7.25 (m, 5H), 7.22 (d, 1H, J=7.8 Hz), 7.05 (t, 1H, J=7.8 Hz), 4.55 (s, 2H), 3.69 (t, 2H, J=6.9 Hz), 2.89 (t, 2H, J=6.9 Hz).

3-[3-[2-(Benzyloxy)ethyl]phenyl]-5-[[1-(tert-butoxycarbonyl)-2(S)-azetidinyl]methoxy]pyridine

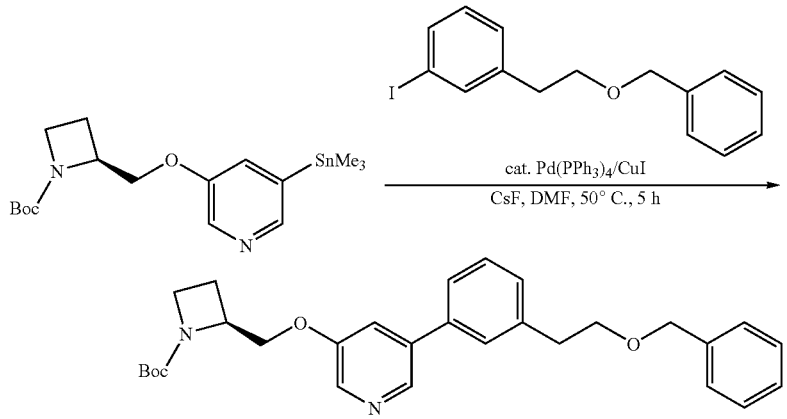

3-[[1-(tert-Butoxycarbonyl)-2(S)-azetidinyl]methoxy]-5-(trimethylstannyl)pyridine (619 mg, 1.45 mmol), 1-[2-(benzyloxy)ethyl]-3-iodobenzene (490 mg, 1.45 mmol), and anhydrous DMF (5.0 mL) were placed in a 25 mL round-bottom flask with magnetic stirrer. To this mixture were rapidly added CsF (441 mg, 2.90 mmol, 2.0 equiv.), CuI (27.5 mg, 0.14 mmol, 0.10 equiv.), and Pd(PPh₃)₄ (84 mg, 0.07 mmol, 0.05 equiv.). The flask was fitted with a three-way stopcock with nitrogen balloon, and the atmosphere was exchanged three times. The reaction mixture was heated at 50° C. for 5 h. TLC analysis of the crude reaction mixture indicated that the aryl iodide was absent. After evaporation of the solvent in vacuo, the residue was chromatographed on silica gel with EtOAc/petroleum ether/Et₃N 2:4:0.05 to give the title compound (400 mg, 58%) as a colorless oil. LC-MS (ESI) m/z 475 (M+H⁺).

3-[((2S)-Azetidinyl)methoxy]-5-[3-[2-(benzyloxy)ethyl]phenyl]pyridine Trifluoroacetate

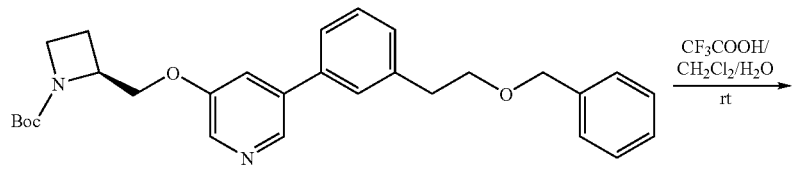

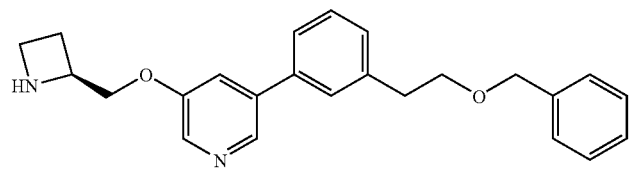

To a solution of 3-[3-[2-(benzyloxy)ethyl]phenyl]-5-[[1-(tert-butoxycarbonyl)-2(S)-azetidinyl]methoxy]pyridine (400 mg, 0.84 mmol) in CH$_2$Cl$_2$ (6.5 mL) were added water (0.13 mL) and CF$_3$COOH (1.3 mL) under nitrogen. The resulting solution was stirred for 20 h at room temperature. After removal of the solvent in vacuo, the residue was purified by preparative HPLC (column: SunFire HPrepC-029 C$_{18}$, 5 μm particle size, 19×100 mm; detector: UV, 220 nm; flow: 20 mL/min; mobile phase: gradient of methanol in water/0.05% CF$_3$COOH) to afford the title compound (250 mg) containing unknown amounts of CF$_3$COOH and water as a colorless oil. $^1$H NMR (CDCl$_3$, 300 MHz) δ 8.47 (s, 1H), 8.32 (s, 1H), 8.05 (s, 1H), 7.57-7.45 (m, 4H), 7.43-7.30 (m, 6H), 4.56 (s, 2H), 4.50-4.38 (m, 2H), 3.82 (m, 1H), 3.77 (t, J=6.9 Hz, 2H), 3.63 (m, 1H), 3.02 (t, J=6.9 Hz, 2H), 2.46-2.38 (m, 2H). LC-MS (ESI) m/z 375 (M+H$^+$).

To a solution of this material (310 mg, 0.83 mmol) in THF (0.6 mL) was added a solution of trifluoroacetic acid (135 μL) in water (3.4 mL) under nitrogen. The resulting solution was stirred for 1 h at room temperature. The solution was diluted with more water (6 mL) and lyophilized. The lyophilization process was repeated four times to afford the trifluoroacetate (400 mg) as a yellowish, brittle foam. $^1$H NMR (CDCl$_3$, 300 MHz) δ 12.3 (very br, 1H), 9.90 (br s, 1H), 9.63 (br s, 1H), 8.62 (s, 1H), 8.43 (s, 1H), 8.02 (s, 1H), 7.54-7.40 (m, 4H), 7.39-7.34 (m, 3H), 7.31-7.25 (m, 2H), 4.96 (m, 1H), 4.57-4.53 (m, 4H), 4.11 (m, 2H), 3.75 (t, J=6.9 Hz, 2H), 3.00 (t, J=6.9 Hz, 2H), 2.68 (m, 2H). LC-MS (ESI) m/z 375 (M+H$^+$). Anal. Calcd. for C$_{24}$H$_{26}$N$_2$O$_2$.2.55CF$_3$COOH.1.3H$_2$O: C, 50.46; H, 4.56; N, 4.07; F, 21.10. Found: C, 50.46; H, 4.25; N, 4.16; F, 20.98.

Example 28

3-[(2(S)-Azetidinyl)methoxy]-5-[3-(phenethoxymethyl)phenyl]pyridine

3-[[1-(tert-Butoxycarbonyl)-2(S)-azetidinyl]methoxy]-5-[3-(phenethoxymethyl)phenyl]pyridine

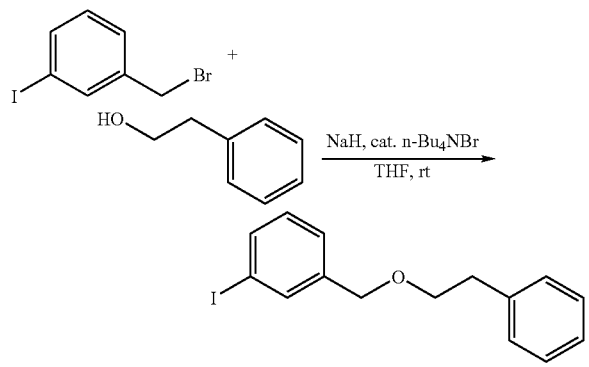

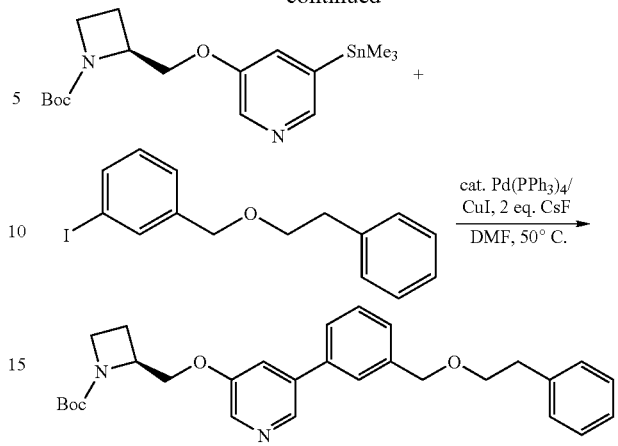

Into a 100 mL round-bottom flask was placed under N$_2$ a solution of 2-phenylethanol (110 mg, 0.90 mmol) in tetrahydrofuran (10 mL). Sodium hydride (26 mg, 1.08 mmol, 1.2 equiv.) was added with ice cooling. The mixture was stirred for 2 h at 25° C., then 3-iodobenzyl bromide (320 mg, 1.08 mmol, 1.2 equiv.) and n-Bu$_4$NBr (30 mg, 0.09 mmol, 0.10 equiv.) were added. The resulting solution was stirred for 20 h at 25° C. The reaction progress was monitored by TLC (SiO$_2$, EtOAc/petroleum ether 1:5). The reaction was quenched by the addition of saturated aqueous NH$_4$Cl solution. The resulting solution was extracted with EtOAc, and the organic layers were combined, dried over Na$_2$SO$_4$, and concentrated under vacuum. The residue was chromatographed on silica gel with EtOAc/petroleum ether 1:20 to obtain 300 mg (99%) of 1-iodo-3-(phenethoxymethyl)benzene as a yellow oil.

A solution/suspension of 1-iodo-3-(phenethoxymethyl)benzene (300 mg, 0.89 mmol, 1.0 equiv.), 3-[[1-(tert-butoxycarbonyl)-2(S)-azetidinyl]methoxy]-5-(trimethylstannyl)pyridine (380 mg, 0.89 mmol), CsF (271 mg, 1.78 mmol, 2.0 equiv.), CuI (17 mg, 0.09 mmol, 0.10 equiv.) and Pd(PPh$_3$)$_4$ (46 mg, 0.04 mmol, 0.05 equiv.) in anhydrous DMF (5 mL) was stirred for 5 h at 50° C. under nitrogen. The reaction progress was monitored by TLC (EtOAc/petroleum ether 1:1). The mixture was concentrated under vacuum, the residue was diluted with water and extracted with EtOAc (2×50 mL), and the combined organic layers were dried over Na$_2$SO$_4$. After concentration in vacuo, the residue was applied onto a silica gel column, which was eluted with EtOAc/petroleum ether/Et$_3$N 3:6:0.5 to give the title compound (230 mg, 55%) as a yellow oil. $^1$H NMR (CDCl$_3$, 300 MHz) δ 8.48 (s, 1H), 8.36 (d, J=2.1 Hz, 1H), 7.53-7.43 (m, 4H), 7.38 (s, 1H), 7.35-7.23 (m, 5H), 4.62 (s, 3H), 4.43 (s, 1H), 4.25 (dd, J=7.5, 3.0 Hz, 1H), 3.94 (t, J=7.5 Hz, 2H), 3.77 (t, J=7.5 Hz, 2H), 2.99 (t, J=7.2 Hz, 2H), 2.43-2.33 (m, 2H), 1.43 (s, 9H). LC-MS (ESI) m/z 475 (M+H$^+$).

3-[(2(S)-Azetidinyl)methoxy]-5-[3-(phenethoxymethyl)phenyl]pyridine Trifluoroacetate

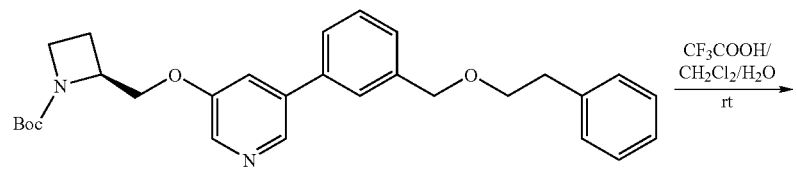

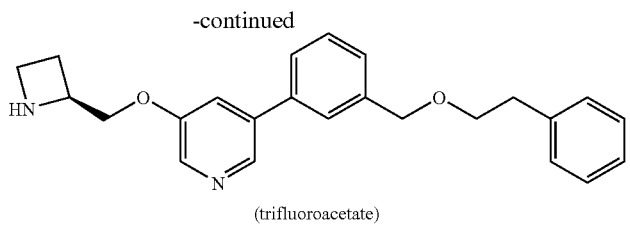

(trifluoroacetate)

Trifluoroacetic acid (1.0 mL) and water (0.11 mL) were added to CH₂Cl₂ (5.5 mL). This mixture was added to 3-[[1-(tert-butoxycarbonyl)-2(S)-azetidinyl]methoxy]-5-[3-(phenethoxymethyl)phenyl]pyridine (230 mg, 485 μmol) in a 25 mL round-bottom flask equipped with a magnetic stirrer under N₂. After stirring at 25° C. for 20 h, TLC analysis of the crude reaction mixture indicated that the starting material had disappeared. The mixture was concentrated under vacuum, and the crude product was purified by preparative HPLC (SunFire Prep C₁₈ column, 19×150 mm, 5 μm particle size; UV detection at 254 nm; flow 20 mL/min; CH₃CN/water gradient with addition of 0.05% CF₃COOH, from 20-40% CH₃CN in 6 min). The eluate was evaporated in vacuo (bath 30° C.) to provide the product (127 mg, yellowish oil) as a partial trifluoroacetate.

To a solution of this material (200 mg) in THF (0.5 mL) was added a solution of CF₃COOH (182 mg) in water (3 mL) under N₂. The resulting solution was stirred for 2 h at ambient temperature and lyophilized. The residue was dissolved in a mixture of CF₃COOH (86 mg) and water (2 mL) and allowed to stand for 1 h before re-lyophilization. The residue was dissolved in 12 mL of water and re-lyophilized again. This process was repeated three times to afford 280 mg of a light-yellow solid. ¹H NMR (CDCl₃, 300 MHz) δ 11.89 (br s, 1H), 9.93 (br s, 1H), 9.64 (br s, 1H), 8.61 (s, 1H), 8.42 (s, 1H), 7.96 (s, 1H), 7.47-7.41 (m, 4H), 7.30-7.17 (m, 5H), 4.95 (br s, 1H), 4.59(m, 4H), 4.10 (br s, 2H), 3.75 (t, J=6.9 Hz, 2H), 2.96 (t, J=6.9 Hz, 2H), 2.69 (br s, 2H). LC-MS (ESI) m/z 375 (M+H⁺). Anal. Calcd. for C₁₇H₂₀N₂O₂.2.7CF₃COOH.1.2H₂O: C, 50.16; H, 4.45; N, 3.98; F, 21.86. Found: C, 49.74; H, 3.97; N, 4.29; F, 21.52.

Example 29

3-[(2(S)-Azetidinyl)methoxy]-5-[3-(3-phenylpropoxy)phenyl]pyridine

1-Iodo-3-(3-phenylpropoxy)benzene

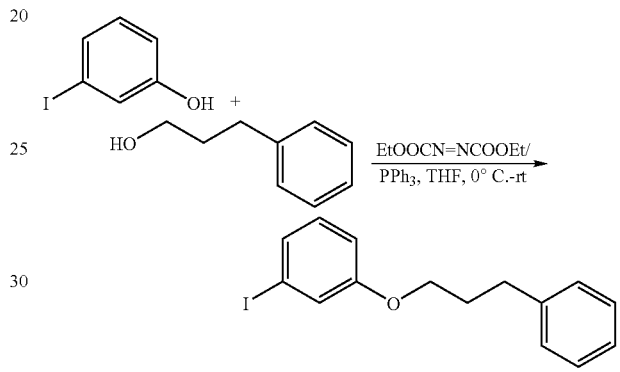

In a 100 mL round-bottom flask was placed 3-phenyl-1-propanol (2.00 g, 14.7 mmol, 1.5 equiv.), 3-iodophenol (2.16 g, 9.82 mmol), triphenylphosphine (3.85 g, 14.7 mmol, 1.5 equiv.) and THF (40 mL). The mixture was stirred in a small ice bath. Neat diethyl azodicarboxylate (2.30 mL, 14.6 mmol, 1.5 equiv.) was added over a period of 30 min. The mixture was stirred in the ice bath for 20 h, then the bath was removed, and stirring was continued for 24 h at room temperature. The resulting mixture was concentrated under vacuum and diluted with EtOAc (200 mL). The solution was washed with brine (60 mL) and dried over Na₂SO₄. After evaporation, the residue was chromatographed on silica gel with EtOAc/petroleum ether 1:50. This resulted in 3.30 g (99%) of 1-iodo-3-(3-phenylpropoxy)benzene as light-yellow oil. ¹H NMR (CDCl₃, TMS, 300 MHz) δ 7.34-7.25 (m, 7H), 6.98 (t, 1H, J=8.0 Hz), 6.84 (dd, 1H, J=2.0, 8.2 Hz), 3.92 (t, 2H, J=6.5 Hz), 2.79 (t, 2H, J=7.7 Hz), 2.08 (m, 2H).

3-[[1-(tert-Butoxycarbonyl)-2(S)-azetidinyl]methoxy]-5-[3-(3-phenylpropoxy)phenyl]pyridine

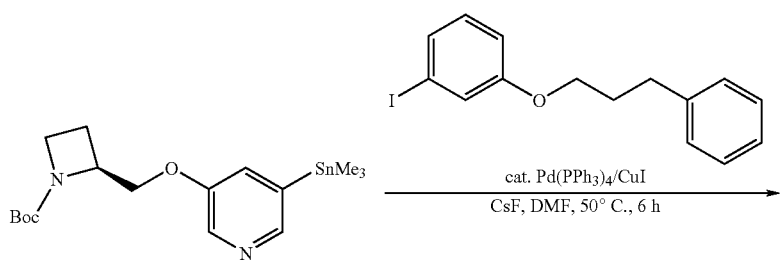

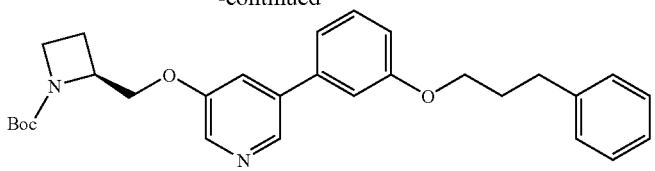

3-[[1-(tert-Butoxycarbonyl)-2(S)-azetidinyl]methoxy]-5-(trimethylstannyl)pyridine (75 mg, 176 μmol), 1-iodo-3-(3-phenylpropoxy)benzene (59 mg, 174 μmol, 1.0 equiv.) and anhydrous DMF (2 mL) were placed in a 25 mL round-bottom flask with magnetic stirrer. To this mixture were added rapidly copper(I) iodide (3.3 mg, 0.02 mmol, 0.10 equiv.), cesium fluoride (53 mg, 0.35 mmol, 2.0 equiv.), and Pd(PPh$_3$)$_4$ (10.1 mg, 0.01 mmol, 0.05 equiv.). The flask was fitted with a three-way stopcock with nitrogen balloon, and the atmosphere was exchanged. The reaction mixture was heated at 50° C. for 6 h. The bulk of solvent was pumped off at room temperature with an oil pump. The reaction progress was monitored by TLC (EtOAc/petroleum ether 1:1). The residue was chromatographed on silica gel with EtOAc/petroleum ether/Et$_3$N 2:3:0.05. This resulted in 55 mg (66%) of 3-[[1-(tert-butoxycarbonyl)-2(S)-azetidinyl]methoxy]-5-[3-(3-phenylpropoxy)phenyl]pyridine as a colorless oil. $^1$H NMR (CDCl$_3$, TMS, 300 MHz) δ 8.48 (s, 1H), 8.33 (s, 1H), 8.02 (s, 1H), 7.57 (br s, 1H), 7.39 (t, 1H, J=8.0 Hz), 7.34-7.19 (m, 4H), 7.16 (d, 1J, J=8.1 Hz), 7.10 (s, 1H), 6.96 (dd, 1H, J=2.1, 8.1 Hz), 4.55 (br m, 1H), 4.43 (br m, 1H), 4.22 (dd, 1H, J=2.5, 10.0 Hz), 4.04 (t, 2H, J=6.3 Hz), 3.91 (t, 2H, J=7.5 Hz), 2.85 (7, 2H, J=7.5 Hz), 2.36 (m, 2H), 2.15 (m, 3H), 1.41 (s, 9H).

3-[(2(S)-Azetidinyl)methoxy]-5-[3-(3-phenylpropoxy)phenyl]pyridine Trifluoroacetate The solution was filtered and evaporated, and the crude material was purified by preparative HPLC (column: SunFire HPrepC-001(T) C$_{18}$, 19×150 mm, particle size 5 μm; detector: UV, 254 nm; flow: 20 mL/min; mobile phase: A, water with 0.05% CF$_3$COOH; B, CH$_3$CN, gradient: 0-6 min, 20-50% B in A; 6-7 min, 50-100% B in A). This resulted in 30 mg of 3-[(2(S)-azetidinyl)methoxy]-5-[3-(3-phenylpropoxy)phenyl]pyridine containing unknown amounts of CF$_3$COOH and water as a colorless oil.

To a solution of this material (250 mg, 0.67 mmol) in tetrahydrofuran (0.5 mL) was added a solution of CF$_3$COOH (0.10 mL, 2.0 equiv.) in water (15 mL). The resulting solution was stirred for 1 h at 20° C. The solution was diluted with more water (6 mL) and lyophilized to obtain 358 mg of the trifluoroacetate as a yellowish solid. $^1$H NMR (300 MHz,

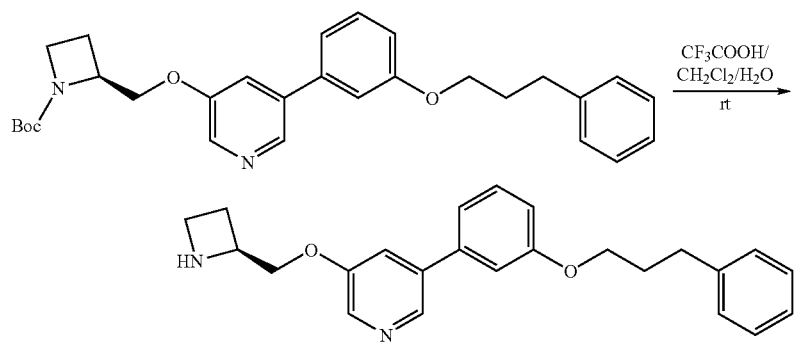

To a solution of 3-[[1-(tert-butoxycarbonyl)-2(S)-azetidinyl]methoxy]-5-[3-(3-phenylpropoxy)phenyl]pyridine (50 mg, 0.11 mmol) in dichloromethane (1.0 mL) was added water (0.02 mL) and CF$_3$COOH (0.2 mL). The resulting solution was stirred for 20 h at 20° C. The reaction progress was monitored by TLC (dichloromethane/methanol 30:1).

CDCl$_3$) δ 12.3 (very br, 1H), 10.0-9.7 (very br, 2H), 8.62 (br, 1H), 8.44 (s, 1H), 8.02 (s, 1H), 7.40 (t, 1H, J=8.0 Hz), 7.32-7.16 (m, 5H), 7.11 (d, 1H, J=7.8 Hz), 7.09 (s, 1H), 7.00 (d, 1H, J=8.1 Hz), 4.97 (br s, 1H), 4.60 (br s, 2H), 4.11 (br s, 2H), 4.01 (t, 2H, J=6.0 Hz), 2.82 (t, 2H, J=7.5 Hz), 2.69 (br s, 2H), 2.12 (m, 2H). LC-MS (ESI) m/z 375 (M+H$^+$). Anal. Calcd. for $C_{24}H_{26}N_2O_2 \cdot 2.45CF_3COOH \cdot 0.65H_2O$: C, 52.15; H, 4.51; N, 4.21. Found: C, 52.03; H, 4.42; N, 4.35.

Example 30

3-[(2(S)-Azetidinyl)methoxy]-5-[4-[2-(benzyloxy)ethyl]phenyl]pyridine

3-[4-[2-(Benzyloxy)ethyl]phenyl]-5-[[1-(tert-butoxycarbonyl)-2(S)-azetidinyl]methoxy]pyridine

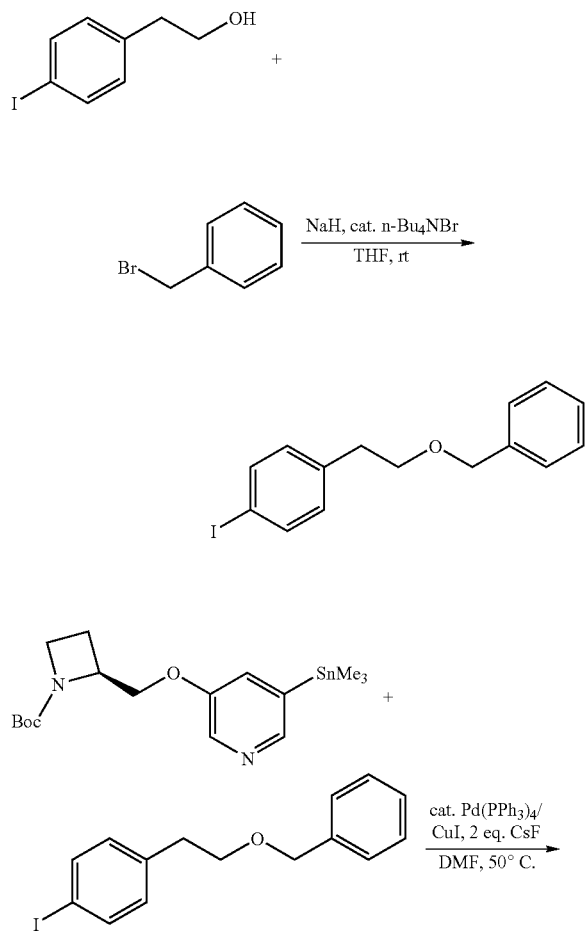

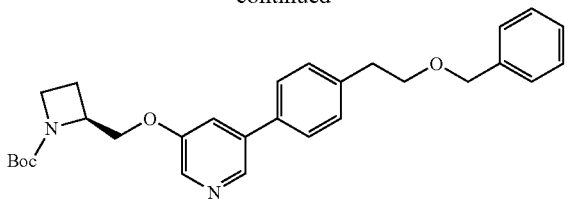

Into a 50-mL 3-necked round-bottom flask under $N_2$ was placed a solution of 2-(4-iodophenyl)ethanol (470 mg, 1.90 mmol) in tetrahydrofuran (10 mL). Sodium hydride (91 mg, 3.8 mmol, 1.2 equiv.) was added at 0° C. The mixture was warmed to room temperature and stirred at room temperature for 2 h. Benzyl bromide (272 µL, 3.9 mmol, 1.2 equiv.) and tetra-n-butylammonium bromide (61 mg, 0.19 mmol, 0.10 equiv.) were added at room temperature. The resulting solution was stirred for 20 h at room temperature. The reaction was then quenched by the addition of 10 mL of aqueous $NH_4Cl$. The solution was extracted with 3×60 mL of EtOAc, and the organic layers were combined and washed with 50 mL of brine. After evaporation, the residue was applied onto a silica gel column, and the product was eluted with EtOAc/petroleum ether 1:20 to furnish 600 mg (94%) of 1-[2-(benzyloxy)ethyl]-4-iodobenzene as a white solid.

A solution/suspension of 3-[[1-(tert-butoxycarbonyl)-2(S)-azetidinyl]methoxy]-5-(trimethylstannyl)pyridine (427 mg, 1.00 mmol), 1-[2-(benzyloxy)ethyl]-4-iodobenzene (338 mg, 1.00 mmol), CsF (304 mg, 2.00 mmol), $Pd(PPh_3)_4$ (58 mg, 0.05 mmol) and CuI (19 mg, 0.10 mmol) in anhydrous DMF (5 mL) was stirred at 50° C. for 5 h under $N_2$. The reaction mixture was cooled and concentrated under vacuum. The residue was applied onto a silica gel column, and the product was eluted with EtOAc/petroleum ether/$Et_3N$ 3:6:0.5 as the eluent to give the title compound (280 mg, 59%) as light-yellow oil. $^1$H NMR (CDCl$_3$, 300 MHz) δ 8.48 (s, 1H), 8.33 (d, J=2.1 Hz, 1H), 7.55 (d, J=8.1 Hz, 2H), 7.48 (s, 1H), 7.37-7.29 (m, 7H), 4.57 (s, 3H), 4.42 (s, 1H), 4.24 (dd, J=7.2, 3.0 Hz, 1H), 3.93 (t, J=7.2 Hz, 2H), 3.75 (t, J=7.2 Hz, 2H), 3.00 (t, J=7.2 Hz, 2H), 2.43-2.30 (m, 2H), 1.42 (s, 9H). LC-MS (ESI) m/z 475 (M+H$^+$).

3-[(2(S)-Azetidinyl)methoxy]-5-[4-[2-(benzyloxy)ethyl]phenyl]pyridine Trifluoroacetate

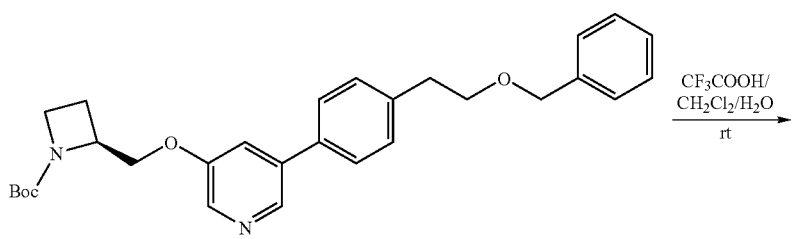

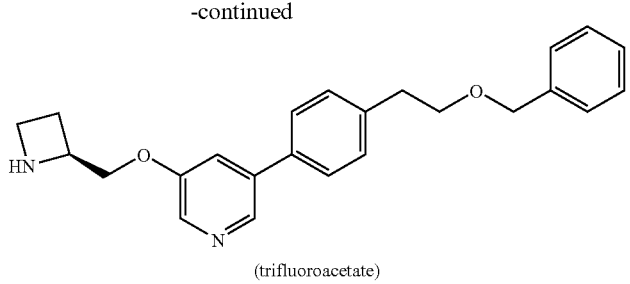

(trifluoroacetate)

Trifluoroacetic acid (1.0 mL) and water (0.11 mL) were added to CH₂Cl₂ (5.5 mL). This mixture was added to 3-[4-[2-(benzyloxy)ethyl]phenyl]-5-[[1-(tert-butoxycarbonyl)-2 (S)-azetidinyl]methoxy]pyridine (220 mg, 0.46 mmol) in a 25 mL round-bottom flask with a magnetic stirrer under N₂. After stirring at 30° C. for 24 h, TLC analysis indicated that the starting material had disappeared. The reaction mixture was concentrated, and the residue was purified by preparative HPLC (SunFire Prep C₁₈ column, 19×150 mm, 5 μm particle size; UV detection at 254 nm; flow 15 mL/min; CH₃CN/water gradient with addition of 0.05% CF₃COOH, from 20-40% CH₃CN in 6 min) to provide the title compound (140 mg, light-yellow solid) as a partial trifluoroacetate.

To a solution of this material (140 mg) in THF (0.5 mL) was added a solution of CF₃COOH (86 mg) in 2 mL of water at room temperature under N₂. The resulting solution was stirred for 2 h at room temperature and lyophilized. The residue was dissolved in a mixture of CF₃COOH (86 mg) and 2 mL of water, allowed to stand for 1 h, and re-lyophilized. The residue was dissolved in 12 mL of water and re-lyophilized three times to afford the product (217 mg) as a white solid. ¹H NMR (CDCl₃, 300 MHz) δ 11.49 (br s, 1H), 9.91 (br s, 1H), 9.70 (br s, 1H), 8.63 (s, 1H), 8.47 (s, 1H), 8.05 (s, 1H), 7.52 (d, J=8.1 Hz, 2H), 7.41 (d, J=8.1 Hz, 2H), 7.35-7.30 (m, 5H), 4.99 (br s, 1H), 4.62 (br s, 2H), 4.54 (s, 2H), 4.12 (br s, 1H), 3.75 (t, J=6.6 Hz, 2H), 2.99 (t, J=6.6 Hz, 2H), 2.70 (br s, 2H). LC-MS (ESI) m/z 375 (M+H⁺). Anal. Calcd. for C₁₇H₂₀N₂O₂.2.8CF₃COOH.0.8H₂O: C, 50.20; H, 4.33; N, 3.96; F, 22.54. Found: C, 50.01; H, 4.13; N, 4.14; F, 22.56.

Example 31

2-[3-[[5-((2S)-Azetidinyl)methoxy]-3-pyridyl]phenethoxy]ethanol tert-Butyl 2-(3-Bromophenethoxy)acetate

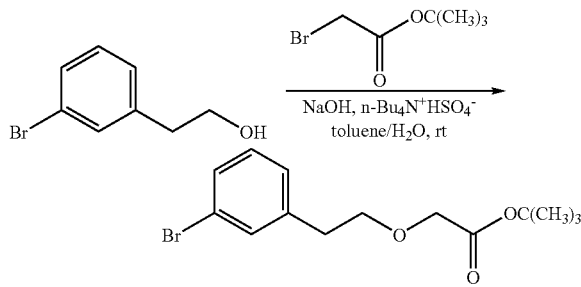

To a mixture of 2-(3-bromophenyl)ethanol (3.40 g, 16.9 mmol), tert-butyl 2-bromoacetate (26.0 g, 133 mmol, 8.0 equiv.), tetra-n-butylammonium hydrogen sulfate (4.52 g, 13.3 mmol, 0.80 equiv.), and 84 mL of toluene was added 267 mL of 5N aqueous NaOH solution. The reaction mixture was stirred at room temperature for 3 h. The aqueous layer was then extracted with four portions of EtOAc, dried (MgSO₄), and evaporated. The residue was purified by CC on silica gel with EtOAc/petroleum ether 1:40 to afford the title compound (4.8 g, 90%) as a colorless oil. ¹H NMR (CDCl₃, 300 MHz) δ 7.42 (s, 1H), 7.35-7.39 (m, 1H), 7.18-7.20 (m, 2H), 3.98 (s, 2H), 3.76 (t, 2H, J=6.9 Hz), 2.94 (t, 2H, J=7.2 Hz), 1.50 (s, 9H).

2-(3-Bromophenethoxy)ethanol

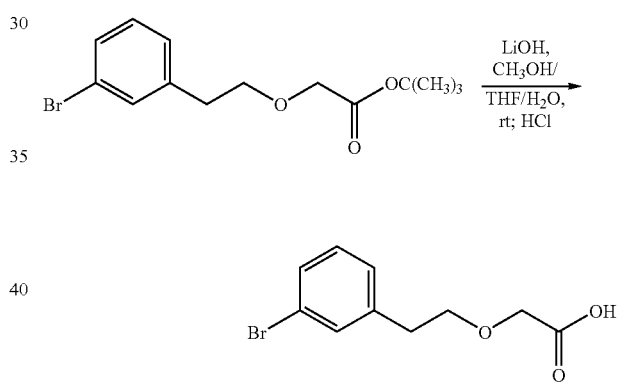

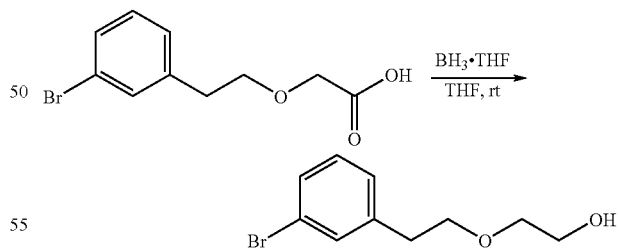

To a solution of tert-butyl 2-(3-bromophenethoxy)acetate (580 mg, 1.84 mmol) in THF/CH₃OH/H₂O (8/4/4 mL) was added LiOH.H₂O (232 mg, 5.5 mmol, 3.0 equiv.) at room temperature. The reaction mixture was stirred for 2 h at room temperature. After concentration under vacuum, the pH of the residual solution was adjusted to 2 with 1M hydrochloric acid. The carboxylic acid was extracted into EtOAc (3×50 mL). The combined organic layers were dried over Na₂SO₄ and concentrated in vacuo to afford 2-(3-bromophenethoxy)acetic acid (470 mg, 99%) as a colorless oil.

A 100 mL three-necked flask was fitted with a dropping funnel, septa and a $N_2$ balloon. The flask was charged with a solution of 2-(3-bromophenethoxy)acetic acid (2.20 g, 8.49 mmol) in anhydrous THF (20 mL) and cooled in an ice bath. Borane-THF complex (1.0 M in THF, 17 mL, 2 equiv.) was added dropwise to the solution of the starting material in 15 min. After 3 h, the reaction was quenched by addition (cautiously at first until $H_2$ evolution has abated) of $THF/H_2O$ (1:1, 30 mL). The resulting mixture was an amber solution together with a colorless precipitate. THF was removed from the solution by partial evaporation, and the product was extracted into ether (200 mL). The organic phase was washed sequentially with water (20 mL) and brine (20 mL), evaporated, and dried over $Na_2SO_4$ to afford the title product (2.00 g, 96%) as a colorless oil. $^1H$ NMR ($CDCl_3$, 300 MHz) δ 7.40 (s, 1H), 7.35-7.39 (m, 1H), 7.17-7.22 (m, 2H), 3.70-3.75 (m, 4H), 3.58 (t, 2H, J=6.9 Hz), 2.90 (t, 2H, J=7.2 Hz).

2-[3-[[5-[1-(tert-Butoxycarbonyl)-(2S)-azetidinyl] methoxy]-3-pyridyl]phenethoxy]ethanol

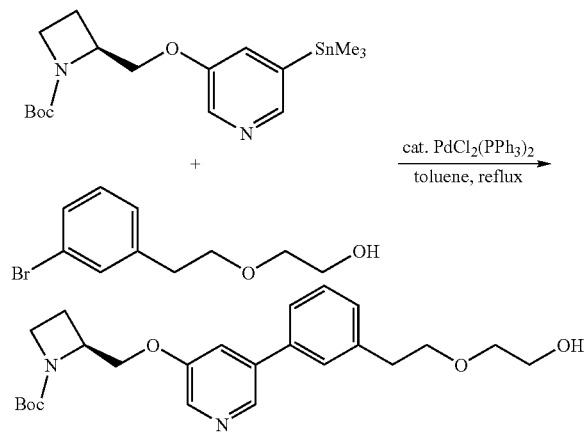

To a solution of 2-(3-bromophenethoxy)ethanol (50 mg, 0.20 mmol) and 3-bromo-5-[[1-(tert-butoxycarbonyl)-2(S)-azetidinyl]methoxy]pyridine (87 mg, 0.20 mmol, 1.0 equiv.) in anhydrous toluene (3 mL) was added bis(triphenylphosphine)palladium(II) chloride (14.3 mg, 20 μmol, 0.10 equiv.) at room temperature under $N_2$. The reaction mixture was heated to reflux for 24 h in an oil bath. After cooling, water was added, and the product was extracted into EtOAc (3×50 mL). The combined organic layers were dried over $Na_2SO_4$ and concentrated under vacuum. The residue was purified by CC on silica gel with EtOAc/petroleum ether as the eluent to give the title product (52 mg, 60%) as a light yellow oil. LC-MS (ESI) m/z 429 ($M+H^+$).

2-[3-[[5-((2S)-Azetidinyl)methoxy]-3-pyridyl] phenethoxy]ethanol Trifluoroacetate

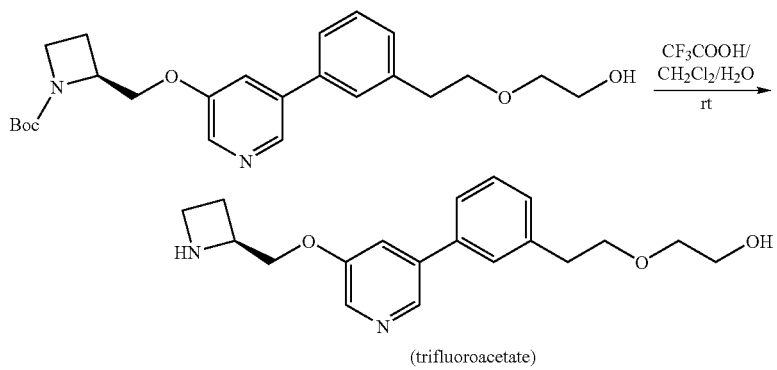

(trifluoroacetate)

To a round-bottom flask containing a solution of 2-[3-[[5-[1-(tert-butoxycarbonyl)-(2S)-azetidinyl]methoxy]-3-pyridyl]phenethoxy]ethanol (150 mg, 350 mmol) in $CH_2Cl_2$/$H_2O$ (6/0.12 mL) was added trifluoroacetic acid (1.5 mL) at 0° C. under $N_2$. The resulting solution was stirred overnight at room temperature. After removal of the solvent, the residue was purified by preparative HPLC (column: SunFire Prep $C_{18}$, 150×19 mm, 5 μm particle size; UV detection at 254 and 220 nm; mobile phase: A, water with 0.05% TFA; B, methanol; 20-70% methanol in 8 min, 70-100% in 1 min, back to 20% in 1 min) The product-containing eluate was evaporated under reduced pressure (bath 30° C.) to remove $CH_3OH$. The residue was basified with saturated aqueous $NaHCO_3$ solution and extracted with EtOAc. The combined organic layers were washed with brine and dried over $Na_2SO_4$. Concentration in vacuo gave 80 mg of the free base as a colorless oil.

To a solution of the free base in methanol/$H_2O$ (0.5/1.5 mL) was added trifluoroacetic acid (61 mg, 0.54 mmol, 2.2 equiv.) at 0° C. under $N_2$. The solution was stirred for 2 h at room temperature and then lyophilized. The lyophilization process was repeated three times to obtain the trifluoroacetate (88 mg) as a colorless oil. $^1H$ NMR ($D_2O$, 300 MHz) δ 8.69 (s, 1H), 8.51 (s, 1H), 8.40 (s, 1H), 7.61-7.45 (m, 4H), 5.10-4.90 (m, 1H), 4.59 (d, 2H, J=4.2 Hz), 4.18-4.00 (m, 2H), 3.81 (t, 2H, J=6.6 Hz), 3.64-3.55 (m, 4H), 2.97 (t, 2H, J=6.6 Hz), 2.72 (q, 2H, J=8.4 Hz). LC-MS (ESI) m/z 329 ($M+H^+$). Anal.

Example 32

1-[3-[5-[(2(S)-Azetidinyl)methoxy]-3-pyridyl]phenyl]-3-phenyl-2(S)-propanol (S)-3-Phenylpropane-1,2-diol

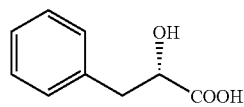
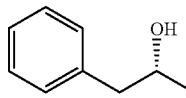

To a solution of (S)-2-hydroxy-3-phenylpropanoic acid (4.98 g, 30.0 mmol) in 100 mL of anhydrous THF was added slowly BH$_3$.THF complex (90 mL, 1M in THF, 3.0 equiv.) with ice cooling under N$_2$. The solution was stirred overnight at room temperature, and the reaction was quenched with water (Caution, copious H$_2$ evolution). After evaporation of the solvent, the residue was diluted with water and extracted with EtOAc (3×50 mL). The combined organic layers were dried over Na$_2$SO$_4$ and concentrated to afford (S)-3-phenylpropane-1,2-diol (4.13 g, 91%) as a colorless oil. LC-MS (ESI) m/z 153 (M+H$^+$).

(S)-2-Benzyloxirane

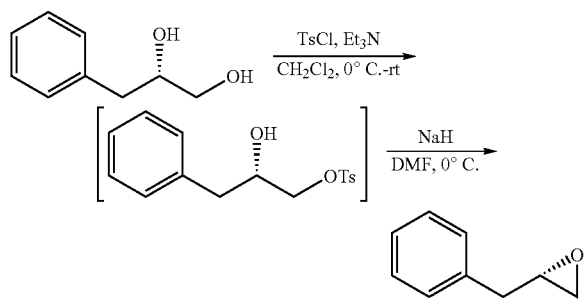

To a stirred solution of (S)-3-phenylpropane-1,2-diol (4.65 g, 30 mmol) and triethylamine (4.6 mL, 33 mmol) in CH$_2$Cl$_2$ (80 mL) at 0° C. was added p-toluenesulfonyl chloride (5.7 g, 30 mmol) under N$_2$. After stirring at room temperature overnight, the mixture was poured into ice water and washed with 1M hydrochloric acid. The aqueous phase was back-extracted with EtOAc. The combined organic layers were washed with saturated aqueous NaHCO$_3$ solution and brine, and dried over Na$_2$SO$_4$ to give the crude tosylate. The tosylate was then dissolved in DMF (30 mL) followed by the addition of sodium hydride (70% oil dispersion, 1.13 g) at 0° C. under N$_2$. After stirring at 0° C. for 2 h, TLC demonstrated complete conversion. The reaction was quenched by addition of water, and the aqueous layer was extracted with EtOAc (3×50 mL). The combined organic layers were dried over anhydrous Na$_2$SO$_4$, the solvent was distilled off under reduced pressure, and the crude product was purified by CC on silica gel with EtOAc/petroleum ether 1:20 to give the epoxide (3.00 g, 75%) as a colorless oil. LC-MS (ESI) m/z 135 (M+H$^+$).

1-(3-Bromophenyl)-3-phenyl-2(S)-propanol

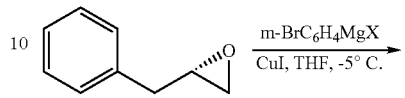
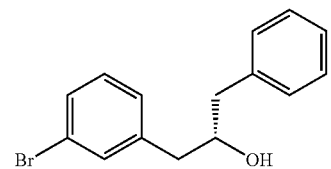

To a dried 100 mL round-bottom flask containing a solution of 3-bromoiodobenzene (5.66 g, 20.0 mmol, 1.0 equiv.) in anhydrous THF (40 mL) was added slowly isopropylmagnesium chloride (10 mL, 2M in hexane) at −40° C. under N$_2$. The solution was stirred at this temperature for 3 h to produce the m-bromophenyl Grignard reagent. Another 100 mL three-necked flask was charged under N$_2$ with CuI (213 mg, 1.12 mmol, 56 mequiv.) and a solution of (S)-2-benzyloxirane (1.50 g, 11.2 mmol, 1.0 equiv.) in dried THF (20 mL). After cooling to −20° C., the above-prepared Grignard reagent was added to this second flask via syringe. The solution was stirred for 2 h at −5° C., during which time the epoxide disappeared. The reaction was quenched with saturated aqueous NH$_4$Cl solution and extracted with EtOAc (3×50 mL). The combined organic layers were washed with brine and dried over Na$_2$SO$_4$. After filtration and concentration, the crude product was purified by CC on silica gel with EtOAc/petroleum ether 1:20-1:5 to give 1-(3-bromophenyl)-3-phenyl-2(S)-propanol (3.00 g, 92%) as a colorless oil. $[\alpha]_D^{25}$+ 2.24 (c 40 g/L, CHCl$_3$); ee 98.7% (HPLC; column: Daicel Chiral-A(IA), 15×0.46 cm, ELS detection, flow 1.0 mL/min, eluent EtOH/hexane 5:95; $t_R$ 7.9 min, opposite enantiomer $t_R$ 7.0 min). $^1$H NMR (CDCl$_3$, 300 MHz) δ 7.42-7.35 (m, 4H), 7.25-7.18 (m, 5H), 4.08 (m, 1H), 2.91-2.71 (m, 4H). LC-MS (ESI) m/z 292 (M+H$^+$).

1-[3-[5-[[1-(tert-Butoxycarbonyl)-2(S)-azetidinyl]methoxy]-3-pyridyl]phenyl]-3-phenyl-2(S)-propanol

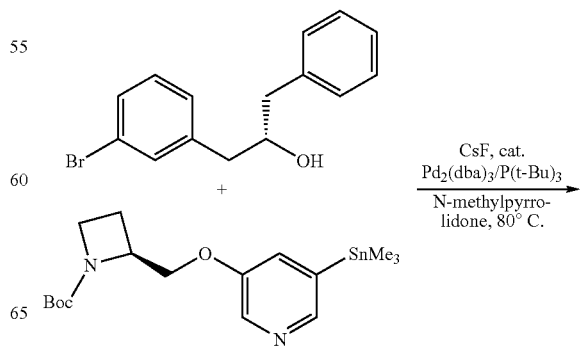

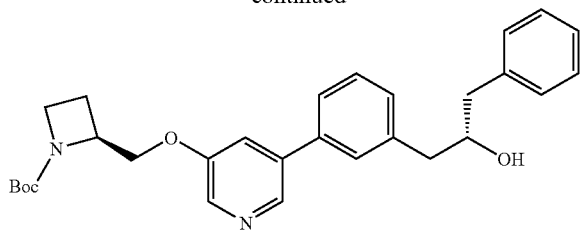

To a solution/suspension of 1-(3-bromophenyl)-3-phenyl-2(S)-propanol (260 mg, 0.89 mmol), 3-[[1-(tert-butoxycarbonyl)-2(S)-azetidinyl]methoxy]-5-(trimethylstannyl)pyridine (417 mg, 0.98 mmol, 1.1 equiv.), $Pd_2dba_3 \cdot CHCl_3$ (13.8 mg, 13.5 μmol, 15 mequiv.) and CsF (270 mg, 1.78 mmol, 2.0 equiv.) in N-methylpyrrolidone (1.0 mL) contained in a dried 100 mL round-bottom flask was added $P(t-Bu)_3$ (10 wt % in hexane, 106 μL, 33 μmol) by syringe at room temperature under $N_2$. The mixture was stirred for 3 h at 80° C., after which time TLC analysis indicated that the starting material had disappeared. After cooling, the reaction was quenched with saturated aqueous $NH_4Cl$ solution, and the mixture was extracted with EtOAc (3×50 mL). The organic layers were combined, dried over anhydrous $Na_2SO_4$, and concentrated under vacuum. The residue was applied onto a silica gel column, which was eluted with $CH_2Cl_2$/MeOH 70:1 to give the product (280 mg, 66%) as a yellow oil. $^1$H NMR ($CDCl_3$, 300 MHz) δ 8.48 (br s, 1H), 8.35 (br s, 1H), 7.52-7.41 (m, 3H), 7.39-7.25 (m, 7H), 4.58 (m, 1H), 4.43 (m, 1H), 4.23 (dd, 1H, J=9.9, 3.0 Hz), 4.15 (m, 1H), 3.94 (t, 2H, J=7.2 Hz), 3.12-2.78 (m, 4H), 2.43-2.27 (m, 2H), 1.58 (OH and water), 1.43 (s, 9H). LC-MS (ESI) m/z 475 (M+H$^+$).

1-[3-[5-[(2(S)-Azetidinyl)methoxy]-3-pyridyl]phenyl]-3-phenyl-2(S)-propanol

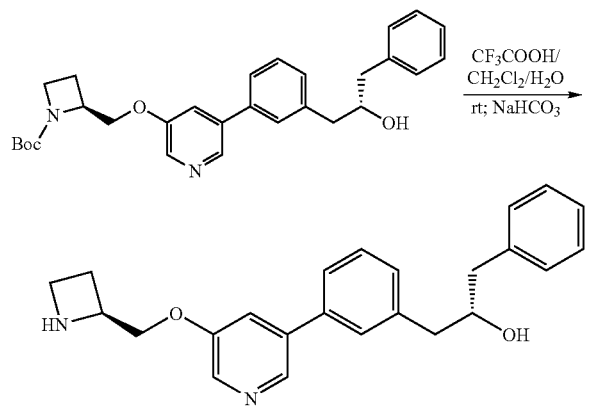

Trifluoroacetic acid (1.6 mL) and water (0.16 mL) were added to $CH_2Cl_2$ (8.0 mL). This mixture was added to a sample of 1-[3-[5-[[1-(tert-butoxycarbonyl)-2(S)-azetidinyl]methoxy]-3-pyridyl]phenyl]-3-phenyl-2(S)-propanol (320 mg, 0.67 mmol) in a 25 mL round-bottom flask with magnetic stirrer under $N_2$. After stirring at room temperature overnight, the solution was concentrated in vacuo, the residue was diluted with water, and the solution was basified with saturated aqueous $NaHCO_3$ solution and extracted with EtOAc (3×50 mL). The combined organic layers were washed with brine and dried over $Na_2SO_4$. After filtration and concentration, the crude product (300 mg) was purified by preparative HPLC (column: SunFire Prep $C_{18}$, 150×19, 5 μm particle size; UV detection at 254 nm; flow 20 mL/min; mobile phase: A, water with 0.05% TFA; B, methanol; 40-100% B in A in 8 min). The product-containing eluate was partially evaporated under reduced pressure to remove MeOH. The residual solution was basified with saturated aqueous $NaHCO_3$ solution and extracted with EtOAc (3×50 mL). The combined organic phases were washed with brine and dried over $Na_2SO_4$. Concentration gave the free amine (130 mg, 52%) as a yellow oil. LC-MS (ESI) m/z 375 (M+H$^+$).

1-[3-[5-[(2(S)-Azetidinyl)methoxy]-3-pyridyl]phenyl]-3-phenyl-2(S)-propanol Hydrochloride

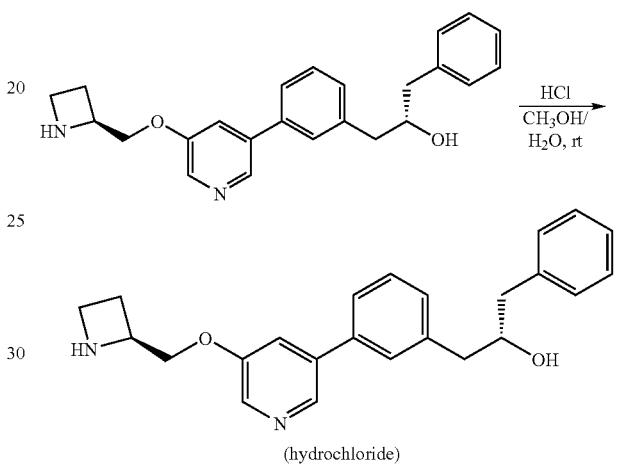

To a solution of 1-[3-[5-[(2(S)-azetidinyl)methoxy]-3-pyridyl]phenyl]-3-phenyl-2(S)-propanol (130 mg, 0.35 mmol) in methanol (1 mL) was added 2M hydrochloric acid (0.53 mL) at 0° C. under $N_2$. The solution was stirred for 2 h at room temperature and then evaporated. Water (8 mL) was added to dissolve the residue, and the solution was lyophilized. The residue was dissolved in 12 mL of water, and the solution was re-lyophilized to give the hydrochloride (145 mg) as a colorless solid. $^1$H NMR ($D_2O$, 300 MHz) δ 8.65 (br s, 1H), 8.49 (br s, 1H), 8.35 (br s, 1H), 7.57-7.46 (m, 3H), 7.42 (m, 1H), 7.33-7.22 (m, 5H), 4.96 (m, 1H), 4.57 (d, 2H, J=3.9 Hz), 4.17-4.03 (m, 3H), 2.99-2.62 (m, 6H). LC-MS (ESI) m/z 375 (M+H$^+$). Anal. Calcd. for $C_{24}H_{26}N_2O_2 \cdot 2.1HCl \cdot 1.25H_2O$: C, 60.87; H, 6.51; N, 5.92; Cl, 15.72. Found: C, 60.87; H, 6.50; N, 5.85; Cl, 15.61.

Example 33

1-[3-[5-[(2(S)-Azetidinyl)methoxy]-3-pyridyl]phenyl]-3-phenyl-2(R)-propanol (R)-3-Phenylpropane-1,2-diol

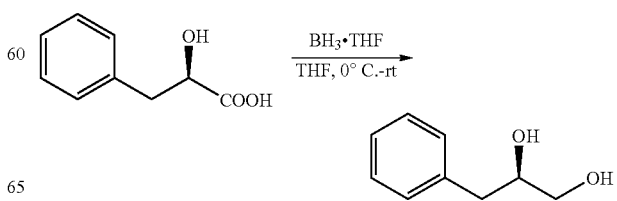

To a solution of (R)-2-hydroxy-3-phenylpropanoic acid (5.0 g, 30.0 mmol) in 100 mL of anhydrous THF was added slowly BH₃.THF complex (90 mL, 1M in THF, 3.0 equiv.) with ice cooling under N₂. The solution was stirred overnight at room temperature, and the reaction was quenched with water (Caution, copious H₂ evolution). After evaporation of the solvent, the residue was diluted with water and extracted with EtOAc (3×50 mL). The combined organic layers were dried over Na₂SO₄ and concentrated to afford (R)-3-phenylpropane-1,2-diol (4.3 g, 94%) as a colorless oil. LC-MS (ESI) m/z 153 (M+H⁺). ¹H NMR (CDCl₃, 300 MHz) δ 7.37-7.23 (m, 5H), 4.02-3.94 (m, 1H), 3.74 (dd, 1H, J=11.1, 3.3 Hz), 3.54 (dd, 1H, J=11.1, 6.9 Hz), 2.85-2.74 (m, 2H).

(R)-2-Benzyloxirane

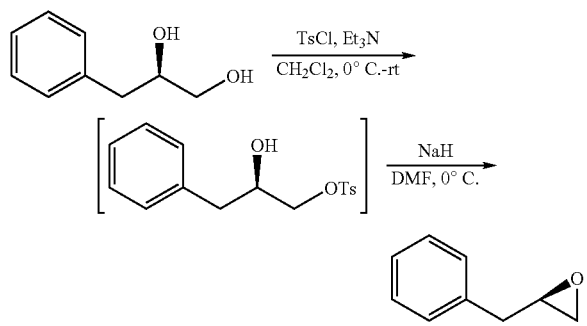

To a stirred solution of (R)-3-phenylpropane-1,2-diol (4.65 g, 30 mmol) and triethylamine (4.6 mL, 33 mmol, 1.1 equiv.) in CH₂Cl₂ (80 mL) at 0° C. was added p-toluenesulfonyl chloride (5.7 g, 30 mmol) under N₂. After stirring at room temperature overnight, the mixture was poured into ice water and washed with 1M hydrochloric acid. The aqueous phase was back-extracted with EtOAc. The combined organic layers were washed with saturated aqueous NaHCO₃ solution and brine, and dried over anhydrous Na₂SO₄ to give the crude tosylate. The tosylate was then dissolved in DMF (30 mL) followed by the addition of sodium hydride (70% oil dispersion, 1.13 g, 33 mmol, 1.1 equiv.) at 0° C. under N₂. After TLC demonstrated complete conversion, the reaction was quenched by addition of water, and the aqueous layer was extracted with ether (3×50 mL). The combined organic layers were dried over Na₂SO₄, the solvent was distilled off under reduced pressure, and the crude product was purified by CC on silica gel with EtOAc/petroleum ether 1:20 to give the epoxide (3.00 g, 75%) as a colorless oil. ¹H NMR (CDCl₃, 300 MHz) δ 7.37-7.24 (m, 5H), 3.21-3.15 (m, 1H), 2.97 (dd, 1H, J=14.4, 5.4 Hz), 2.87-2.81 (m, 2H), 2.58 (dd, 1H, J=5.4, 2.7 Hz).

1-(3-Bromophenyl)-3-phenyl-2(R)-propanol

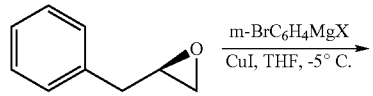

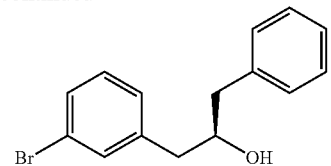

To a dried 100 mL round-bottom flask containing a solution of 3-bromoiodobenzene (5.66 g, 20.0 mmol, 1.0 equiv.) in anhydrous THF (40 mL) was added slowly isopropylmagnesium chloride (10 mL, 2M in hexane) at −40° C. under N₂. The solution was stirred at this temperature for 3 h to produce the m-bromophenyl Grignard reagent. Another 100 mL three-necked flask was charged under N₂ with CuI (213 mg, 1.12 mmol, 56 mequiv.) and a solution of (R)-2-benzyloxirane (1.50 g, 11.2 mmol, 1.0 equiv.) in dried THF (20 mL). After cooling to −20° C., the above-prepared Grignard reagent was added to this second flask via syringe. The solution was stirred for 2 h at −5° C., during which time the epoxide disappeared. The reaction was quenched with saturated aqueous NH₄Cl solution, and the mixture was extracted with EtOAc (3×50 mL). The combined organic layers were washed with brine and dried over Na₂SO₄. After filtration and concentration, the crude product was purified by chroCC-matography on silica gel with EtOAc/petroleum ether 1:20-1:5 to give 1-(3-bromophenyl)-3-phenyl-2(S)-propanol (3.00 g, 92%) as a colorless oil. [α]_D^{25} −2.25 (c 40 g/L, CHCl₃); ee 98% (by chiral HPLC). ¹H NMR (CDCl₃, 300 MHz) δ 7.42-7.19 (m, 9H), 4.16-4.04 (m, 1H), 2.92-2.72 (m, 4H).

1-[3-[5-[[1-(tert-Butoxycarbonyl)-2(S)-azetidinyl]methoxy]-3-pyridyl]phenyl]-3-phenyl-2(R)-propanol

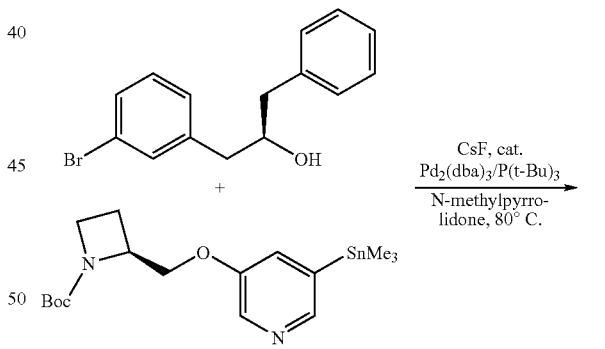

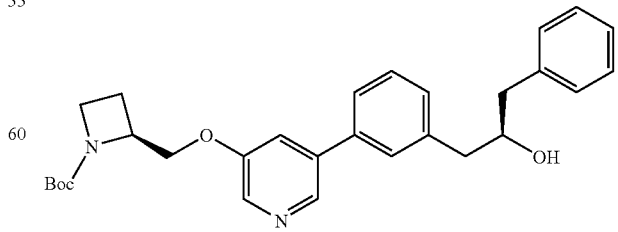

To a solution/suspension of 1-(3-bromophenyl)-3-phenyl-2(R)-propanol (291 mg, 1.00 mmol), 3-[[1-(tert-butoxycarbonyl)-2(S)-azetidinyl]methoxy]-5-(trimethylstannyl)pyridine (427 mg, 1.00 mmol, 1.00 equiv.), Pd$_2$(dba)$_3$.CHCl$_3$ (15.5 mg, 15 μmol, 15 mequiv.) and CsF (304 mg, 2.00 mmol, 2.00 equiv.) in N-methylpyrrolidone (1.0 mL) contained in a dried 100 mL round-bottom flask was added P(t-Bu)$_3$ (10 wt % in hexane, 106 μL) by syringe at room temperature under N$_2$. The mixture was stirred for 3 h at 80° C., after which time TLC analysis indicated that the starting material had disappeared. After cooling, the reaction was quenched with saturated aqueous NH$_4$Cl solution, and the mixture was extracted with EtOAc (3×50 mL). The organic layers were combined, washed with brine, dried over Na$_2$SO$_4$, and concentrated under vacuum. The residue was applied onto a silica gel column, which was eluted with EtOAc/petroleum ether/ aqueous NH$_3$ 1:10:0.1-1:1:0.1 to give the product (381 mg, 80%) as a yellowish oil. $^1$H NMR (CDCl$_3$, 300 MHz) δ 8.47 (s, 1H), 4.34 (s, 1H), 7.47-7.26 (m, 10H), 4.56 (m, 1H), 4.41 (m, 1H), 4.21 (dd, 1H, J=10.0, 3.0 Hz), 4.18-4.11 (m, 2H), 3.93 (t, 2H, J=6.6 Hz), 3.01-2.78 (m, 4H), 2.42-2.20 (m, 2H), 1.42 (s, 9H).

1-[3-[5-[(2(S)-Azetidinyl)methoxy]-3-pyridyl]phenyl]-3-phenyl-2(R)-propanol

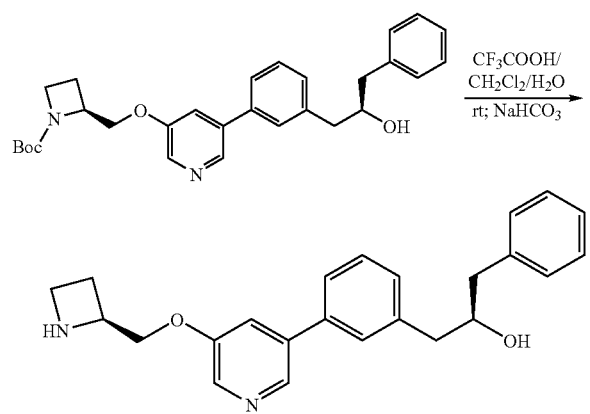

Trifluoroacetic acid (1.6 mL) and water (0.16 mL) were added to CH$_2$Cl$_2$ (8.0 mL). This mixture was added to 1-[3-[5-[[1-(tert-butoxycarbonyl)-2(S)-azetidinyl]methoxy]-3-pyridyl]phenyl]-3-phenyl-2(R)-propanol (381 mg, 0.80 mmol) in a 25 mL round-bottom flask with magnetic stirrer under N$_2$. After stirring at room temperature overnight, the solution was concentrated in vacuo, the residue was diluted with water, and the solution was basified with saturated aqueous NaHCO$_3$ solution and extracted with EtOAc (3×50 mL). The combined organic layers were washed with brine and dried over Na$_2$SO$_4$. After filtration and concentration, the crude product (250 mg) was purified by preparative HPLC (column: SunFire Prep C$_{18}$, 150×19, 5 μm particle size; UV detection at 254 nm; flow 20 mL/min; mobile phase: A, water with 0.05% TFA; B, methanol; 40-70% B in A in 6 min). The product-containing eluate was partially concentrated under reduced pressure to remove MeOH. The residual solution was basified with saturated aqueous NaHCO$_3$ solution and extracted with EtOAc (3×50 mL). The combined organic phases were washed with brine and dried over Na$_2$SO$_4$. Concentration gave the free amine (130 mg, 43%) as a white solid. LC-MS (ESI) m/z 375 (M+H$^+$).

1-[3-[5-[(2(S)-Azetidinyl)methoxy]-3-pyridyl]phenyl]-3-phenyl-2(R)-propanol Hydrochloride

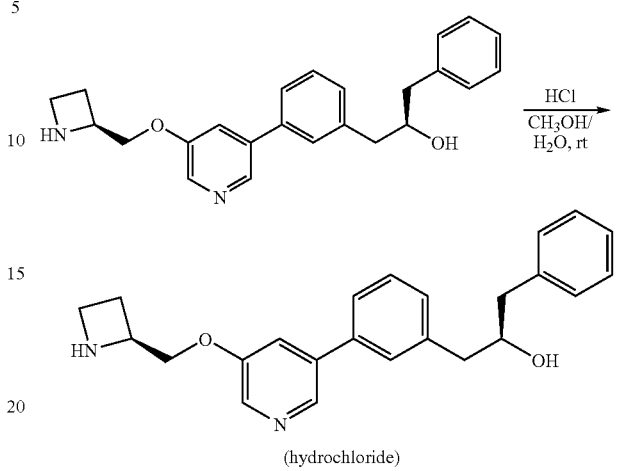

(hydrochloride)

To a solution of 1-[3-[5-[(2(S)-azetidinyl)methoxy]-3-pyridyl]phenyl]-3-phenyl-2(R)-propanol (130 mg, 0.35 mmol) in methanol (1 mL) was added 2M hydrochloric acid (0.4 mL) at 0° C. under N$_2$. The solution was stirred for 2 h at room temperature and then evaporated. Water (8 mL) was added to dissolve the residue, and the solution was lyophilized. The residue was dissolved in 12 mL of water, and the solution was re-lyophilized to give the hydrochloride (145 mg) as a colorless solid. $^1$H NMR (D$_2$O, 300 MHz) δ 8.65 (s, 1H), 8.51 (s, 1H), 8.38 (s, 1H), 7.58-7.47 (m, 3H), 7.42-7.39 (m, 1H), 7.32-7.22 (m, 5H), 4.99-4.94 (m, 1H), 4.57 (d, 2H, J=3.9 Hz), 4.17-4.03 (m, 3H), 2.99-2.63 (m, 6H). Anal. Calcd. for C$_{24}$H$_{26}$N$_2$O$_2$.2.45HCl.1.65H$_2$O: C, 58.41; H, 6.48; N, 5.68; Cl, 17.60. Found: C, 58.51; H, 6.69; N, 5.58; Cl, 17.66.

Example 34

3-[(2(S)-Azetidinyl)methoxy]-5-[3-(2(S)-methoxy-3-phenylpropyl)phenyl]pyridine

1-Bromo-3-(2(S)-methoxy-3-phenylpropyl)benzene

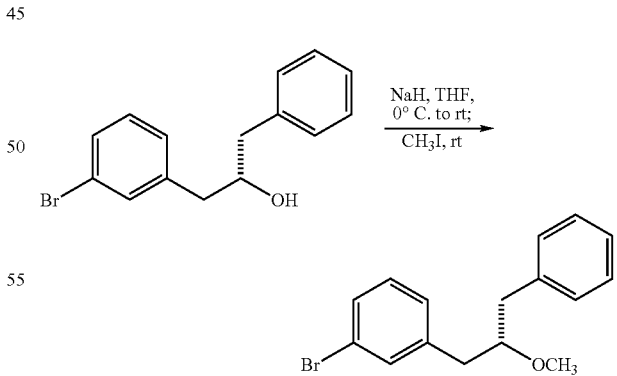

To a solution of 1-(3-bromophenyl)-3-phenyl-2(S)-propanol (365 mg, 1.25 mmol) in 15 mL of anhydrous THF was added NaH (70% dispersion in mineral oil, 100 mg, 2.9 mmol, 2.3 equiv.) at 0° C. under N$_2$. The mixture was warmed to room temperature and stirred for 30 min, then CH$_3$I (1.75 g, 12.3 mmol, 9.8 equiv.) was added at room temperature. The mixture was stirred overnight at room temperature. The reaction was quenched with saturated aqueous NH$_4$Cl solution, and the mixture was extracted with EtOAc (3×50 mL). The combined organic phases were washed with brine and dried over Na$_2$SO$_4$. After filtration and concentration, the residue was purified by CC on silica gel with EtOAc/petroleum ether 1:20 to provide the methyl ether (300 mg, 78%) as a yellow oil. LC-MS (ESI) m/z 306 (M+H$^+$).

3-[[1-(tert-Butoxycarbonyl)-2(S)-azetidinyl]methoxy]-5-[3-(2(S)-methoxy-3-phenylpropyl)phenyl]pyridine

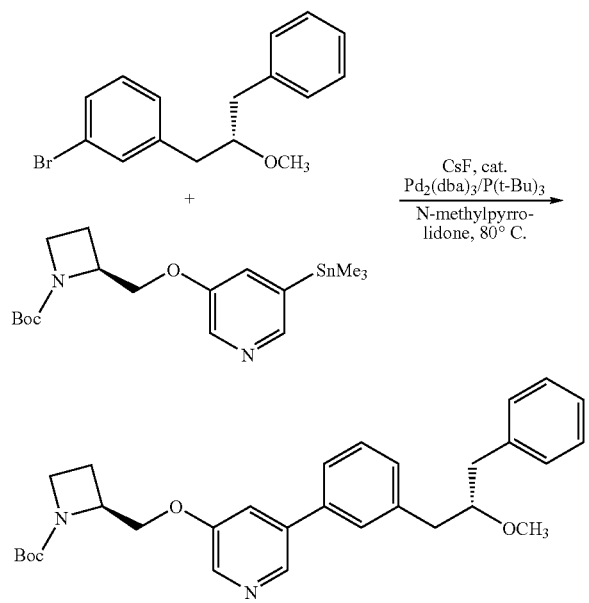

To a solution/suspension of 3-[[1-(tert-butoxycarbonyl)-2(S)-azetidinyl]methoxy]-5-(trimethylstannyl)pyridine (370 mg, 0.87 mmol, 1.1 equiv.), 1-(3-bromophenyl)-3-phenyl-2(S)-propanol (240 mg, 0.79 mmol), CsF (240 mg, 1.58 mmol, 2.0 equiv.) and Pd$_2$(dba)$_3$·CHCl$_3$ (8 mg, 8 μmol, 10 mequiv.) in N-methylpyrrolidone (1.0 mL) was added P(t-Bu)$_3$ (10 wt % in hexane, 33 mequiv.) by syringe at room temperature under N$_2$. The mixture was heated to 80° C. for 3 h, after which time TLC analysis indicated that the starting material had disappeared. After cooling, the reaction was quenched with saturated aqueous NH$_4$Cl solution and extracted with EtOAc (3×50 mL). The combined organic layers were washed with brine and dried over Na$_2$SO$_4$. After filtration and concentration, the residue was purified by CC on silica gel with EtOAc/petroleum ether/conc. aqueous NH$_3$ (10:1:0.1-5:1:0.1) to give the product (290 mg, 76%) as a yellow oil. LC-MS (ESI) m/z 489 (M+H$^+$).

3-[(2(S)-Azetidinyl)methoxy]-5-[3-(2(S)-methoxy-3-phenylpropyl)phenyl]pyridine

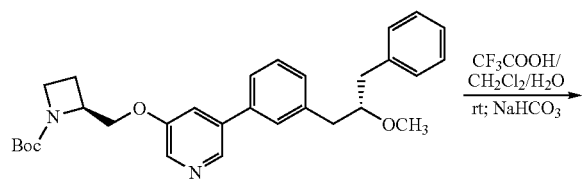

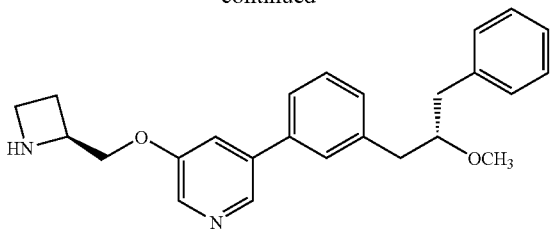

Trifluoroacetic acid (1.6 mL) and water (0.16 mL) were added to 8 mL of CH$_2$Cl$_2$. This mixture was added to 3-[[1-(tert-butoxycarbonyl)-2(S)-azetidinyl]methoxy]-5-[3-(2(S)-methoxy-3-phenylpropyl)phenyl]pyridine (290 mg, 0.59 mmol) at 0° C. under N$_2$. The solution was stirred overnight at room temperature. After concentration in vacuo, the crude product (290 mg) was purified by preparative HPLC (column: SunFire Prep C$_{18}$, 150×19, 5 μm; UV detection, at 254 nm; mobile phase: A, water with 0.05% CF$_3$COOH; B, CH$_3$CN; 20-60% B in A in 8 min). The product-containing eluate was partially evaporated under reduced pressure (bath 30° C.) to remove CH$_3$CN. The pH of the residue was adjusted to 8.0 with saturated aqueous NaHCO$_3$ solution, and the product was extracted into EtOAc (3×60 mL). The combined organic phases were washed with brine and dried over Na$_2$SO$_4$. After filtration and concentration, the free amine (118 mg, 51%) was obtained as a yellow oil. LC-MS (ESI) m/z 389 (M+H$^+$).

3-[(2(S)-Azetidinyl)methoxy]-5-[3-(2(S)-methoxy-3-phenylpropyl)phenyl]pyridine Hydrochloride

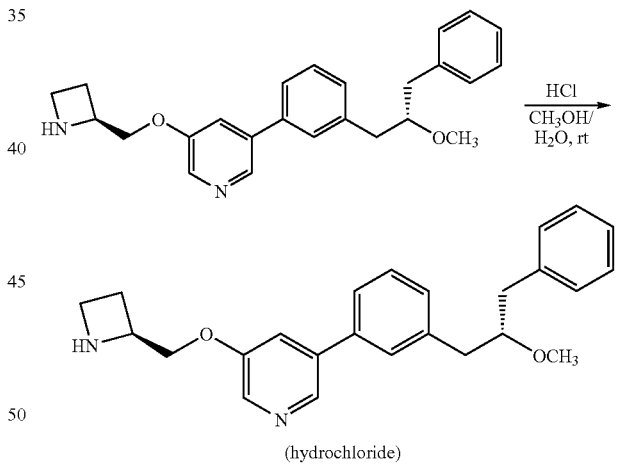

(hydrochloride)

To a solution of 3-[(2(S)-azetidinyl)methoxy]-5-[3-(2(S)-methoxy-3-phenylpropyl)phenyl]pyridine (118 mg, 0.30 mmol) in methanol (1 mL) was added 2M hydrochloric acid (2 mL) at 0° C. under N$_2$. The solution was stirred for 2 h at room temperature and evaporated. The residue was dissolved in 8 mL of water and lyophilized. The lyophilization process was repeated three times to give the hydrochloride (122 mg) as a colorless solid. $^1$H NMR (D$_2$O, 300 MHz) δ 8.63 (br s, 1H), 8.49 (br s, 1H), 8.32 (br s, 1H), 7.56-7.38 (m, 4H), 7.31-7.20 (m, 5H), 4.96 (m, 1H), 4.57 (d, 2H, J=3.6 Hz), 4.17-4.02 (m, 2H), 3.85 (m, 1H) 3.19 (s, 3H), 2.92-2.63 (m, 6H). LC-MS (ESI) m/z 389 (M+H$^+$). Anal. Calcd. for C$_{25}$H$_{28}$N$_2$O$_2$·2.15HCl·1.7H$_2$O: C, 60.35; H, 6.80; N, 5.63; Cl, 15.32. Found: C, 60.44; H, 6.92; N, 5.57; Cl, 15.22.

Example 35

3-[(2(S)-Azetidinyl)methoxy]-5-[3-(2(R)-methoxy-3-phenylpropyl)phenyl]pyridine

1-Bromo-3-(2(R)-methoxy-3-phenylpropyl)benzene

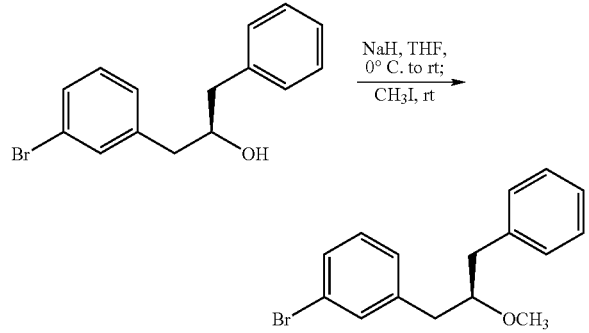

To a solution of 1-(3-bromophenyl)-3-phenyl-2(R)-propanol (437 mg, 1.50 mmol) in 20 mL of anhydrous THF was added NaH (70% dispersion in mineral oil, 64 mg, 1.87 mmol, 1.24 equiv.) at 0° C. under N₂. The mixture was warmed to room temperature and stirred for 30 min, then CH₃I (2.1 g, 15 mmol, 10 equiv.) was added at room temperature. The mixture was stirred for 3 h at room temperature. The reaction was quenched with saturated aqueous NH₄Cl solution, and the mixture was extracted with EtOAc (3×50 mL). The combined organic phases were washed with brine and dried over Na₂SO₄. After filtration and concentration, the residue was purified by CC on silica gel with EtOAc/petroleum ether 1:20 to provide the methyl ether (347 mg, 76%) as a colorless oil. ¹H NMR (CDCl₃, 300 MHz) δ 7.36-7.12 (m, 9H), 3.61 (quintet, 1H, J=6.3 Hz), 3.27 (s, 3H), 2.85 (dd, 1H, J=13.8, 6.6 Hz), 2.75 (dd, 3H, J=12.9, 6.6 Hz).

3-[[1-(tert-Butoxycarbonyl)-2(S)-azetidinyl]methoxy]-5-[3-(2(R)-methoxy-3-phenylpropyl)phenyl]pyridine

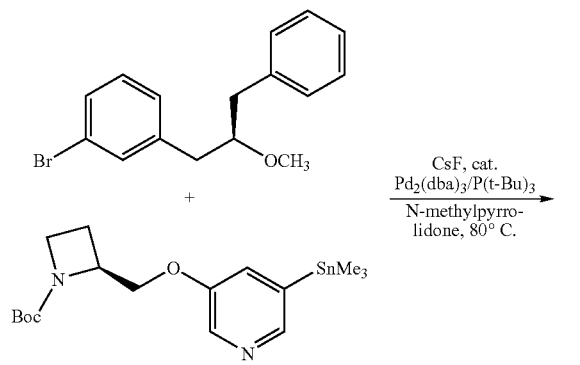

To a solution/suspension of 3-[[1-(tert-butoxycarbonyl)-2(S)-azetidinyl]methoxy]-5-(trimethylstannyl)pyridine (508 mg, 1.19 mmol, 1.05 equiv.), 1-(3-bromophenyl)-3-phenyl-2(R)-propanol (345 mg, 1.13 mmol), CsF (344 mg, 2.26 mmol, 2.0 equiv.) and Pd₂(dba)₃.CHCl₃ (23.4 mg, 22.6 μmol, 20 mequiv.) in N-methylpyrrolidone (1.5 mL) was added P(t-Bu)₃ (10 wt % in hexane, 0.12 mL, 33 mequiv.) by syringe at room temperature under N₂. The mixture was heated to 80° C. for 3 h, after which time TLC analysis indicated that the starting material had disappeared. After cooling, the reaction was quenched with saturated aqueous NH₄Cl solution and extracted with EtOAc (3×50 mL). The combined organic layers were washed with brine and dried over Na₂SO₄. After filtration and concentration, the residue was purified by CC on silica gel with EtOAc/petroleum ether/conc. aqueous NH₃ 10:1:0.1-5:1:0.1 to give the product (470 mg, 85%) as a yellowish oil. LC-MS (ESI) m/z 489 (M+H⁺).

3-[(2(S)-Azetidinyl)methoxy]-5-[3-(2(R)-methoxy-3-phenylpropyl)phenyl]pyridine

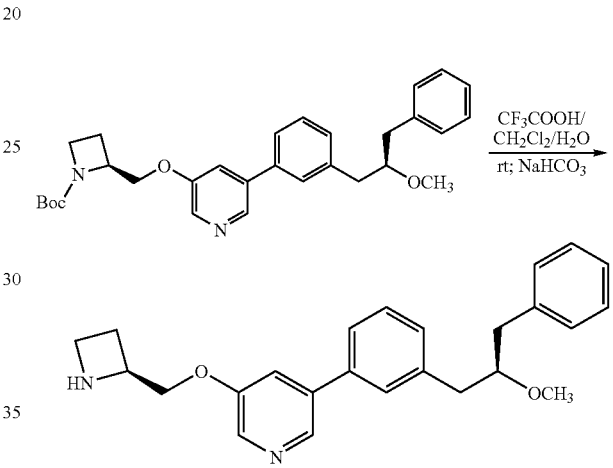

Trifluoroacetic acid (1.6 mL) and water (0.16 mL) were added to 8 mL of CH₂Cl₂. This mixture was added to 3-[[1-(tert-butoxycarbonyl)-2(R)-azetidinyl]methoxy]-5-[3-(2(S)-methoxy-3-phenylpropyl)phenyl]pyridine (470 mg, 0.96 mmol) at 0° C. under N₂. The solution was stirred overnight at room temperature. After concentration in vacuo, the crude product (300 mg) was purified by preparative HPLC (column: SunFire Prep C₁₈, 150×19, 5 μm; UV detection, at 254 nm; mobile phase: A, water with 0.05% CF₃COOH; B, CH₃CN; 18-40% B in A in 6 min, 40-100% in 1 min). The product-containing eluate was partially evaporated under reduced pressure (bath 30° C.) to remove CH₃CN. The pH of the residue was adjusted to 8.0 with saturated aqueous NaHCO₃ solution, and the product was extracted into EtOAc (3×60 mL). The combined organic phases were washed with brine and dried over Na₂SO₄. After filtration and concentration, the free amine (175 mg, 47%) was obtained as a colorless oil. LC-MS (ESI) m/z 389 (M+H⁺).

3-[(2(S)-Azetidinyl)methoxy]-5-[3-(2(R)-methoxy-3-phenylpropyl)phenyl]pyridine Hydrochloride

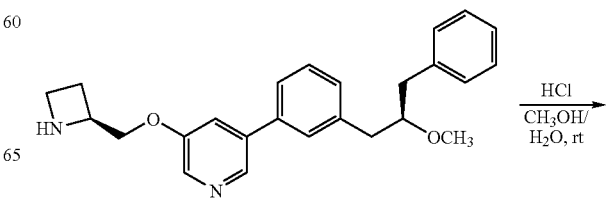

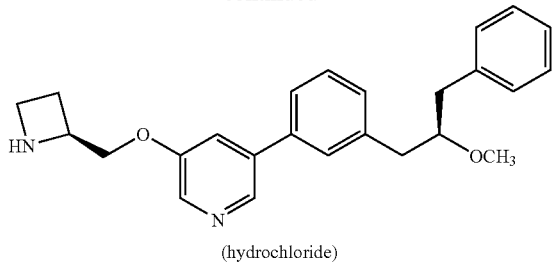

(hydrochloride)

To a solution of 3-[[(2(S)-azetidinyl)methoxy]-5-[3-(2(R)-methoxy-3-phenylpropyl)phenyl]pyridine (175 mg, 0.45 mmol) in methanol (1 mL) was added 2M hydrochloric acid (2 mL) at 0° C. under $N_2$. The solution was stirred for 2 h at room temperature and evaporated. The residue was dissolved in 8 mL of water and lyophilized. The lyophilization process was repeated three times to give the hydrochloride (200 mg) as a colorless solid. $^1$H NMR ($D_2O$, 300 MHz) δ 8.61 (s, 1H), 8.50 (s, 1H), 8.34 (s, 1H), 7.56-7.44 (m, 3H), 7.38-7.35 (m, 1H), 7.29-7.25 (m, 2H), 7.21-7.17 (m, 3H), 4.99-4.94 (m, 1H), 4.57 (d, 1H, J=3.9 Hz), 4.13-4.03 (m, 2H), 3.87-3.81 (m, 1H), 3.18 (s, 3H), 2.92-2.63 (m, 6H). LC-MS (ESI) m/z 389 (M+H$^+$). Anal. Calcd. for $C_{25}H_{28}N_2O_2 \cdot 1.95HCl \cdot 1.15H_2O$: C, 62.51; H, 6.77; N, 5.83; Cl, 14.48. Found: C, 62.48; H, 6.82; N, 5.85; Cl, 14.48.

Example 36

Synthesis of 3-[2-[5-[(2(S)-Azetidinyl)methoxy]-3-pyridyl]ethyl]phenylmethanol and N-[3-[2-[5-[(2(S)-Azetidinyl)methoxy]-3-pyridyl]ethyl]phenylmethyl]methanesulfonamide These compounds are synthesized according to the procedure set forth in Scheme 12.

3-[[1-(tert-Butoxycarbonyl)-2(S)-azetidinyl]methoxy]-5-[(trimethylsilyl)ethynyl]pyridine

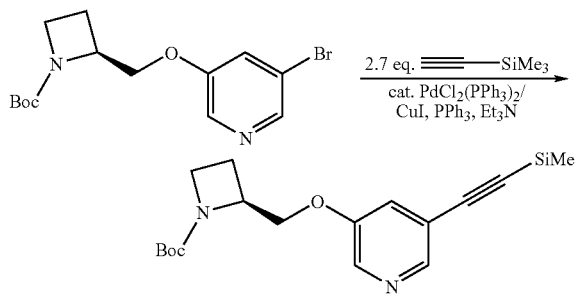

A 50 mL round-bottom flask with stir bar was charged with 3-bromo-5-[[1-(tert-butoxycarbonyl)-2(S)-azetidinyl]methoxy]pyridine (564 mg, 1.64 mmol), copper(I) iodide (25 mg, 0.13 mmol, 0.08 equiv.), bis(triphenylphosphine)palladium (II) chloride (49 mg, 66 μmol, 0.04 equiv.), and triphenylphosphine (34 mg, 0.13 mmol, 0.08 equiv.). Anhydrous triethylamine (5 mL) and trimethylsilylacetylene (0.63 mL, 4.45 mmol, 2.7 equiv.) were added. The flask was equipped with a reflux condenser topped by a $N_2$ balloon, and the reaction mixture was heated to gentle reflux (heating mantle) for 16 h. A black color appeared soon after heating. After cooling, the mixture consisted of an amber solution and a black precipitate. TLC (silica gel, EtOAc/hexane 55:45) demonstrated complete conversion ($R_f$ 0.6; starting material: $R_f$ 0.55). The reaction mixture was evaporated and the residue was taken up in DMPU (0.8 mL+0.4 mL rinse) and was chromatographed on silica gel (25×2.5 cm, EtOAc/hexane 35:65 switching to 45:55 after appearance of the product). After evaporation of the product-containing fractions, the residue was twice evaporated with $CH_3CN$ and the solution before the final evaporation was filtered over a cotton plug to remove a small amount of solid. Drying (50° C./14 torr) afforded 587 mg (99%) of the product as a light-amber glass of sufficient purity to be used in the subsequent step. $^1$H NMR (CDCl$_3$, TMS, 250 MHz) δ 8.30 (d, 1H, J=1.4 Hz), 8.27 (d, 1H, J=2.8 Hz), 7.30 (dd, 1H, 1.6, 2.7 Hz), 4.51 (m, 1H), 4.32 (m, 1H), 4.12 (dd, 1H, J=2.8, 10.1 Hz), 3.88 (t, 2H, J=7.6 Hz), 2.43-2.20 (m, 2H), 1.43 (s, 9H), 0.26 (s, 9H); $^{13}$C NMR (CDCl$_3$, 62.5 MHz) δ 156.1, 154.3, 145.0, 138.1, 133.9, 123.2, 120.3, 101.2, 98.0, 79.6, 68.6, 59.9, 46.9 (br), 28.3, 18.9, 0.1.

3-[[1-(tert-Butoxycarbonyl)-2(S)-azetidinyl]methoxy]-5-ethynylpyridine

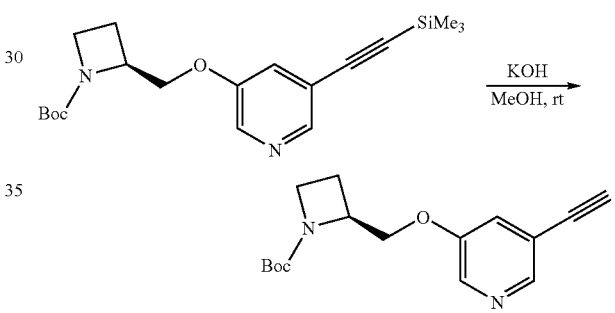

In a 50 mL round-bottom flask with stir bar, a solution of KOH (174 mg) in methanol (4 mL) was added to a solution of 3-[[1-(tert-butoxycarbonyl)-2(S)-azetidinyl]methoxy]-5-[(trimethylsilyl)ethynyl]pyridine (560 mg, 1.55 mmol) in methanol (1 mL). The flask was loosely closed with a rubber stopper, and the mixture was stirred at room temperature for 3 h. A TLC taken after 105 min (silica gel, EtOAc/hexane 55:45) showed traces of starting material ($R_f$ 0.6) and a new spot ($R_f$ 0.5). The mixture was evaporated and the residue directly chromatographed on silica gel (24×2.5 cm, EtOAc/hexane 1:1). The product-containing fractions were evaporated, and the residue was dried (35° C./14 torr) to obtain 473 mg (nominally 106%) of the product, an orange-brown oil which darkened upon standing and appeared to be too unstable for more stringent drying. The excess mass balance was represented by EtOAc as shown by $^1$H NMR. The material was suitable in this form for the subsequent reaction. $^1$H NMR (CDCl$_3$, TMS, 250 MHz) δ 8.36-8.29 (m, 2H), 7.33 (dd, 1H, J=1.6, 2.7 Hz), 4.51 (m, 1H), 4.34 (m, 1H), 4.13 (dd, 1H, J=2.9, 10.1 Hz), 3.89 (t, 2H, J=7.6 Hz), 3.20 (s, 1H), 2.43-2.20 (m, 2H), 1.43 (s, 9H); $^{13}$C NMR (CDCl$_3$, 62.5

MHz) δ 156.0, 154.3 (br), 145.1, 138.4, 123.5, 119.3 (br), 80.4, 80.0, 79.7, 68.7, 59.9, 47.0 (br), 28.3, 18.9.

3-[[5-[[1-(tert-Butoxycarbonyl)-2(S)-azetidinyl]methoxy]-3-pyridyl]ethynyl]phenylmethanol

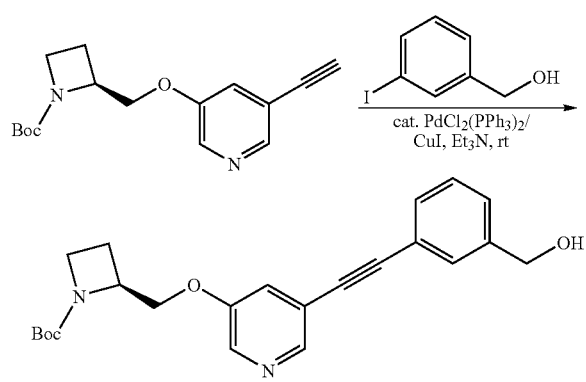

A small resealable tube with stir bar was charged with 3-[[1-(tert-butoxycarbonyl)-2(S)-azetidinyl]methoxy]-5-ethynylpyridine (168 mg, 583 μmol), copper(I) iodide (11 mg, 58 μmol, 0.1 equiv.), and bis(triphenylphosphine)palladium(II) chloride (43 mg, 58 μmol, 0.1 equiv.). To these reactants was added a solution of m-iodobenzyl alcohol (136 mg, 581 μmol, 1 equiv.). The mixture was purged with nitrogen through a needle, then the tube was capped, and the brown suspension was stirred at room temperature for 18.5 h. Solids were removed by suction filtration over celite and were washed with three portions of EtOAc (4 mL each). The solution was evaporated. TLC analysis (silica gel, EtOAc/hexane 3:1) showed, besides some PPh$_3$ and baseline material, a single spot ($R_f$ 0.3). The brown crude product was purified by CC on silica gel (24×2.5 cm, EtOAc/hexane 3:1 changing to 1:0 after appearance of the product). The product-containing fractions were evaporated and dried (50° C./oil pump) to yield 189 mg (82%) of a light-amber glass. $^1$H NMR (CDCl$_3$, TMS, 250 MHz) δ 8.35 (d, 1H, J=1.4 Hz), 8.28 (d, 1H, J=2.7 Hz), 7.57 (narrow m, 1H), 7.49-7.43 (m, 1H), 7.43-7.32 (m, 3H), 4.73 (s, 2H), 4.53 (m, 1H), 4.35, 4.14 (ABq, 2H, J=10.1 Hz, low-field part br d, J=4.3 Hz, high-field part d, J=2.9 Hz), 3.90 (t, 2H, J=7.6 Hz), 2.47-2.21 (m, 3H, apparently including OH), 1.43 (s, 9H); $^{13}$C NMR (CDCl$_3$, 62.5 MHz) δ 156.0, 154.4, 144.3, 141.8, 137.4, 130.3, 129.8, 128.3, 127.2, 123.0, 122.2, 120.5, 92.5, 85.4, 79.7, 68.5, 63.9, 59.8, 46.9 (br), 28.2, 18.8; MS (EI) m/z 394 (M$^+$, 2.7%), 321 (3.8%), 294 (14%), 293 (11%), 265 (10%), 238 (22%), 100 (23%), 57 (100%), 56 (73%).

3-[2-[5-[[1-(tert-Butoxycarbonyl)-2(S)-azetidinyl]methoxy]-3-pyridyl]ethyl]phenylmethanol

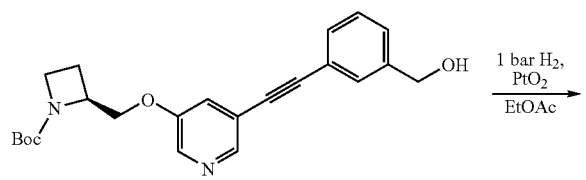

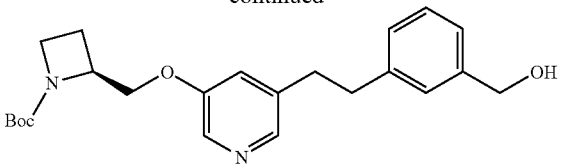

In a 50 mL round-bottom flask, a solution of 3-[[5-[[1-(tert-butoxycarbonyl)-(2S)-azetidinyl]methoxy]-3-pyridyl]ethynyl]phenylmethanol in EtOAc was hydrogenated over PtO$_2$ with stirring at room temperature for 6.25 h. TLC (silica gel, EtOAc/hexane 3:1) showed a new spot ($R_f$ 0.15) in place of the starting material ($R_f$ 0.3), which was accompanied by a nonpolar impurity. The solution was concentrated and filtered over silica gel (11×1.3 cm, EtOAc). Evaporation of the product-containing fractions gave a quantitative yield of crude product, which by $^1$H NMR was shown to be a mixture of two major components in a molar ratio of approx. 4.5-5:1.

Further purification of the product can be achieved by preparative HPLC (acetonitrile/water gradient on C$_{18}$). The product-containing fraction is partially evaporated to remove CH$_3$CN, and the product is extracted into CH$_2$Cl$_2$. The organic phase is dried over MgSO$_4$ and evaporated, and the residue is dried in vacuo to yield the purified product.

3-[2-[5-[(2(S)-Azetidinyl)methoxy]-3-pyridyl]ethyl]phenylmethanol Hydrochloride

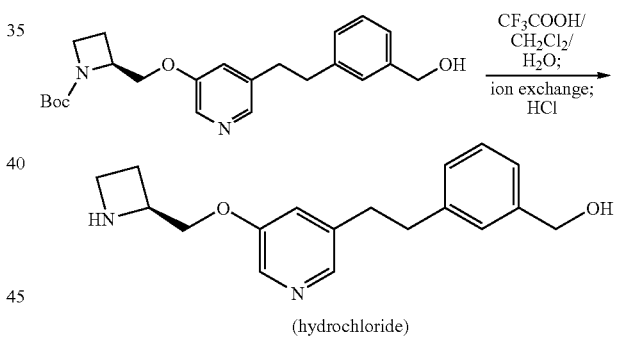

(hydrochloride)

3-[2-[5-[[1-(tert-Butoxycarbonyl)-2(S)-azetidinyl]methoxy]-3-pyridyl]ethyl]phenylmethanol is dissolved in a mixture of trifluoroacetic acid, CH$_2$Cl$_2$, and water. The reaction is allowed to proceed at room temperature until the starting material is no longer detected by TLC. The solvent is evaporated, and the residue is purified by preparative HPLC (for example, acetonitrile/water gradient on C$_{18}$). The product-containing fraction is partially evaporated to remove CH$_3$CN, and the product is extracted into CH$_2$Cl$_2$. The organic phase is dried over MgSO$_4$ and evaporated. The residue is taken up in methanol and adsorbed on a cation exchange column. The column is first eluted with methanol to remove neutral or acidic impurities (including residual trifluoroacetic acid), then with methanolic ammonia to recover the product as free base. After evaporation, this material is dissolved in a small volume of methanol, neutralized with a small excess of hydrochloric acid, diluted with water, and lyophilized to yield the product.

3-[2-[5-[[1-(tert-Butoxycarbonyl)-2(S)-azetidinyl]methoxy]-3-pyridyl]ethyl]phenylmethyl Chloride

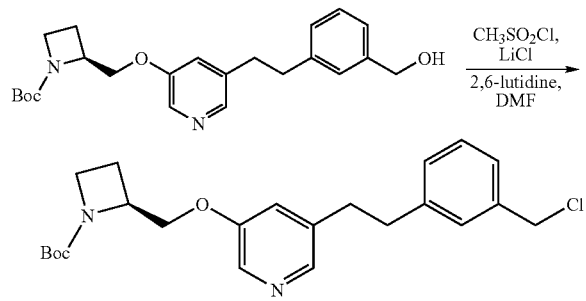

To a solution of 3-[2-[5-[[1-(tert-butoxycarbonyl)-2(S)-azetidinyl]methoxy]-3-pyridyl]ethyl]phenylmethanol, LiCl (1-4 equiv.), and 2,6-lutidine (1-2 equiv.) in DMF is added with stirring, cooling, and exclusion of moisture methanesulfonyl chloride (1-1.5 equiv.). The reaction mixture is stirred at ambient or elevated temperature until the alcohol and the intermediate mesylate have disappeared. The solvent is then distilled into a cooled receiver in an oil pump vacuum. The residue is diluted with EtOAc and aqueous NaHCO$_3$ solution. The phases are separated. The organic phase is washed with brine, dried over MgSO$_4$, and evaporated, and the residue is used directly in the subsequent step. A purer product is obtained by filtration over silica gel with EtOAc or a mixture of EtOAc with a nonpolar solvent. The product is not stable in storage and should be carried forward promptly.

3-[2-[5-[[1-(tert-Butoxycarbonyl)-2(S)-azetidinyl]methoxy]-3-pyridyl]ethyl]phenylmethyl Azide

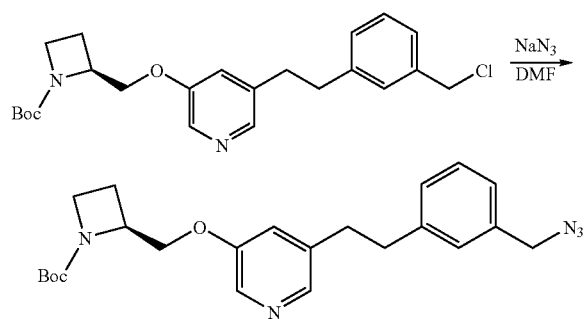

3-[2-[5-[[1-(tert-Butoxycarbonyl)-2(S)-azetidinyl]methoxy]-3-pyridyl]ethyl]phenylmethyl chloride is dissolved in DMF, and sodium azide (1-4 equiv.) is added. The reaction mixture is stirred with exclusion of moisture at ambient or elevated temperature until all starting material has been converted. The solvent is then distilled into a cooled receiver in an oil pump vacuum at a bath temperature of up to 40° C. (caution should be observed not to exceed this temperature, as organic azides may explode upon heating). The residue is diluted with EtOAc and water, and the phases are separated. The organic phase is washed with brine, dried over MgSO$_4$, and evaporated, and the residue is chromatographed on silica gel with EtOAc or a mixture of EtOAc with a nonpolar solvent. Evaporation of the product-containing fractions and drying yields the azide. Before the subsequent step, the azide is preferably evaporated with toluene to remove residual EtOAc, which may react with the amine to be prepared. In order to obtain the following intermediate directly in a form that does not require further purification, it may be convenient to further purify the azide by preparative HPLC (for example, acetonitrile/water gradient on C$_{18}$).

3-[2-[5-[[1-(tert-Butoxycarbonyl)-2(S)-azetidinyl]methoxy]-3-pyridyl]ethyl]phenylmethylamine

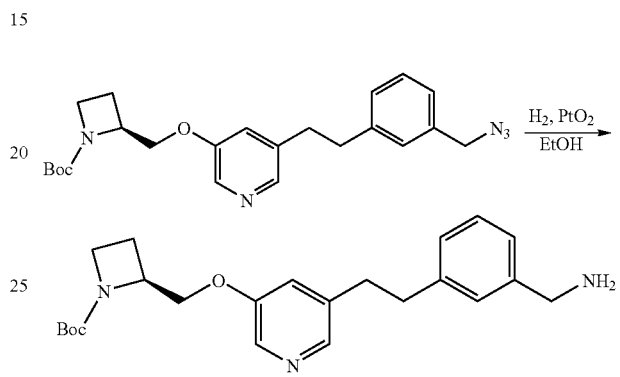

3-[2-[5-[[1-(tert-Butoxycarbonyl)-2(S)-azetidinyl]methoxy]-3-pyridyl]ethyl]phenylmethyl azide is dissolved in ethanol, and a catalytic amount of PtO$_2$ is added. The reaction flask is attached to a H$_2$ balloon by way of a three-way stopcock, and the atmosphere is exchanged. The mixture is stirred at room temperature. The reaction is followed by TLC and terminated by replacing the atmosphere with N$_2$ when the starting material has disappeared. The catalyst is removed by centrifugation or filtration over a filter membrane. The solution is evaporated and the residue used directly in the following step. If desired, the product can be purified by CC on silica gel eluting with CH$_2$Cl$_2$/methanol/Et$_3$N or CH$_2$Cl$_2$/methanol/conc. aqueous NH$_3$, or on deactivated basic alumina with CH$_2$Cl$_2$/methanol.

N-[3-[2-[5-[[1-(tert-Butoxycarbonyl)-2(S)-azetidinyl]methoxy]-3-pyridyl]ethyl]phenylmethyl]methanesulfonamide

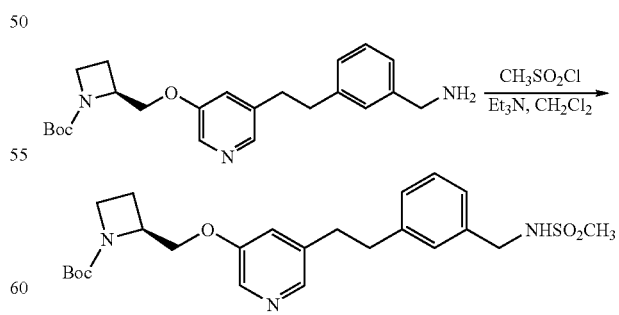

3-[2-[5-[[1-(tert-Butoxycarbonyl)-(2S)-azetidinyl]methoxy]-3-pyridyl]ethyl]phenylmethylamine and triethylamine (1-2 equiv.) are dissolved in anhydrous CH$_2$Cl$_2$, and with exclusion of moisture and ice cooling a solution of methanesulfonyl chloride (1-1.5 equiv.) in CH$_2$Cl$_2$ is added dropwise.

The mixture is stirred in the ice bath until no more starting amine is observed, then diethanolamine (0.2-0.7 equiv.) is added to quench the excess of methanesulfonyl chloride. The reaction mixture is evaporated and the residue chromatographed on silica gel with $CH_2Cl_2$/methanol. The product-containing fractions are evaporated, and the residue is dried in vacuo to obtain the sulfonamide.

N-[3-[2-[5-[(2(S)-Azetidinyl)methoxy]-3-pyridyl]ethyl]phenylmethyl]methanesulfonamide Hydrochloride

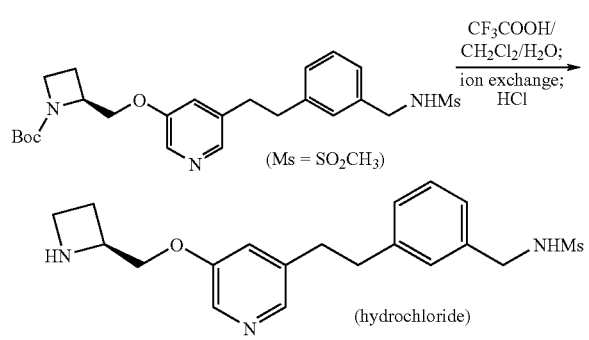

The same procedure as for the conversion of 3-[2-[5-[[1-(tert-butoxycarbonyl)-2(S)-azetidinyl]methoxy]-3-pyridyl]ethyl]phenylmethanol into 3-[2-[5-[(2(S)-azetidinyl)methoxy]-3-pyridyl]ethyl]phenylmethanol hydrochloride is followed in this step.

Example 37

Synthesis of 5-[5-(2(S)-Azetidinylmethoxy)-3-pyridyl]-3-isoxazolylmethanol

The synthesis of this compound was performed according to Scheme 13 as set forth in the following steps.

3-[[1-(tert-Butoxycarbonyl)-2(S)-azetidinyl]methoxy]-5-[3-[(tetrahydro-2H-pyran-2-yloxy)methyl]-5-isoxazolyl]pyridine

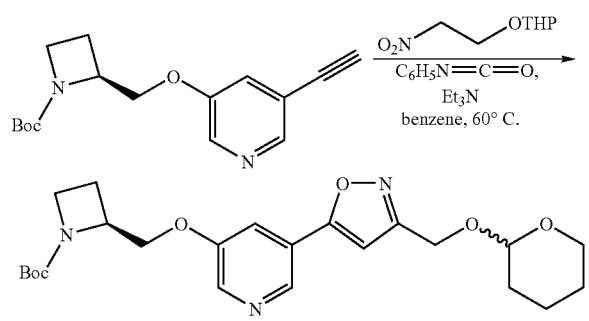

To a solution of 1-nitro-2-(tetrahydro-2H-pyran-2-yloxy)ethane (Basra, S. K.; Drew, M. G. B.; Mann, J.; Kane, P. D. *J. Chem. Soc., Perkin Trans.* 1, 2000, 3592-3598) (0.53 mL, 3.4 mmol, 3.0 equiv.) and 3-[[1-(tert-butoxycarbonyl)-2(S)-azetidinyl]methoxy]-5-ethynylpyridine (330 mg, 1.14 mmol) in dry benzene (11 mL) were added phenyl isocyanate (0.37 mL, 3.4 mmol, 3.0 equiv.) and triethylamine (0.70 mL, 5.0 mmol, 4.4 equiv.). The reaction mixture was stirred at 60° C. for 24 h, then diluted with water, stirred vigorously for 2 h, and extracted with $CH_2Cl_2$. The combined organic phases were dried over $MgSO_4$, filtered, and concentrated in vacuo. The residue was purified by CC on $SiO_2$ with EtOAc/hexane 1:1 to give the isoxazole (420 mg, 82%). $^1$H NMR ($CDCl_3$, 400 MHz) δ 8.64 (br s, 1H), 8.41 (br s, 1H), 7.64 (s, 1H), 6.71 (s, 1H), 4.86 (d, 1H, J=12.0 Hz), 4.77 (t, 1H, J=4.0 Hz), 4.68 (d, 1H, J=12.0 Hz), 4.55 (m, 1H), 4.41 (m, 1H), 4.21 (dd, 1H, J=8.0, 4.0 Hz), 3.91 (t, 3H, J=8.0 Hz), 3.59 (m, 1H), 2.38 (m, 2H), 1.78 (m, 2H), 1.58 (m, 4H), 1.42 (s, 9H).

Synthesis of 5-[5-(2(S)-Azetidinylmethoxy)-3-pyridyl]-3-isoxazolylmethanol Hydrochloride

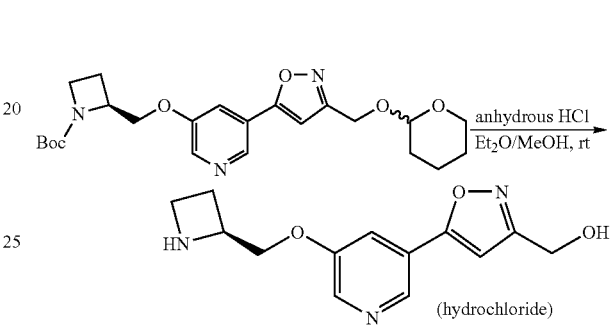

To a solution of 3-[[1-(tert-butoxycarbonyl)-2(S)-azetidinyl]methoxy]-5-[3-[(tetrahydro-2H-pyran-2-yloxy)methyl]-5-isoxazolyl]pyridine (100 mg, 0.22 mmol) in MeOH (31 mL) was added at 0° C. 2M anhydrous HCl in ether (11 mL). The reaction mixture was stirred at room temperature for 12 h, then concentrated in vacuo. The residue was purified by HPLC to give the product as its hydrochloride (70 mg). $^1$H NMR ($CD_3OD$, 400 MHz) δ 9.00 (br s, 1H), 8.77 (br s, 1H), 8.51 (s, 1H), 7.26 (s, 1H), 4.96 (m, 1H), 4.72 (s, 2H), 4.64 (m, 2H), 4.13 (m, 2H), 3.19 (dd, 1H, J=14.4, 7.2 Hz), 2.70 (m, 2H). $^{13}$C NMR ($CDCl_3$, 100 MHz) δ 167.8, 166.7, 140.5, 139.8, 120.3, 119.8, 102.2, 68.6, 60.5, 56.9, 44.9, 32.5, 21.9.

Example 38

[5-[5-[(2(S)-Pyrrolidinyl)methoxy]-3-pyridyl]-3-isoxazolyl]methanol

3-[[1-(tert-Butoxycarbonyl)-2(S)-pyrrolidinyl]methoxy]-5-[(trimethylsilyl)ethynyl]pyridine

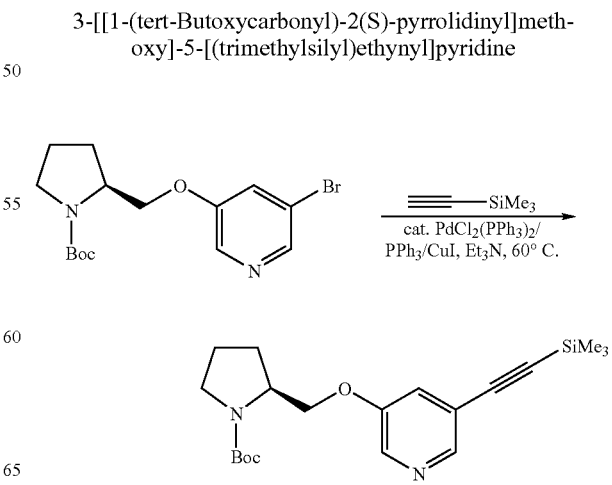

To a stirred solution/suspension of 3-bromo-5-[[1-(tert-butoxycarbonyl)-2(S)-pyrrolidinyl]methoxy]pyridine (300 mg, 0.83 mmol), PPh$_3$ (72 mg, 0.28 mmol, 0.34 equiv.) and CuI (72 mg, 0.37 mmol, 0.45 equiv.) in triethylamine (3.6 mL) was added PdCl$_2$(PPh$_3$)$_2$ (59 mg, 84 μmol, 0.1 equiv.). The mixture was stirred at room temperature for 20 min under argon, and then ethynyltrimethylsilane (356 μL, 1.75 mmol, 2.1 equiv.) was added. The reaction mixture was stirred at 60° C. for 24 h. The reaction was quenched by addition of saturated aqueous NH$_4$Cl solution. The mixture was extracted with CH$_2$Cl$_2$, and the organic phase was dried over MgSO$_4$, filtered, and concentrated in vacuo. The residue was purified by CC on SiO$_2$ eluting with EtOAc/CH$_2$Cl$_2$ 1:10-1:6 to give the silylalkyne (310 mg, 99%). $^1$H NMR (CDCl$_3$, 400 MHz) δ 8.28 (s, 1H), 8.24 (d, 1H, J=2.4 Hz), 7.31 (s, 1H), 4.15 (m, 2H), 4.02 (m, 1H), 3.38 (m, 2H), 1.95 (m, 4H), 1.5 (s, 9H), 0.26 (s, 9H); $^{13}$C NMR (CDCl$_3$, 100 MHz) δ 154.2, 145.0, 144.7, 138.1, 123.1, 122.8, 120.2, 68.6, 68.4, 55.9, 55.4, 46.9, 46.5, 28.6, 28.4, −0.3.

3-[[1-(tert-Butoxycarbonyl)-2(S)-pyrrolidinyl]methoxy]-5-[3-[(tetrahydro-2H-pyran-2-yloxy)methyl]-5-isoxazolyl]pyridine

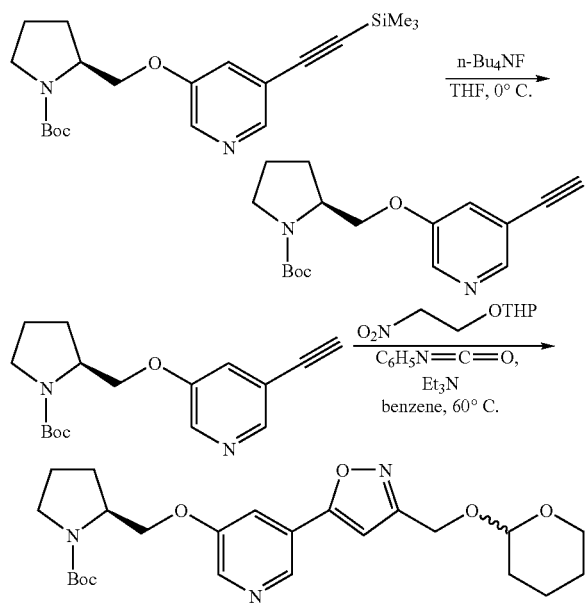

To a solution of 3-[[1-(tert-butoxycarbonyl)-2(S)-pyrrolidinyl]methoxy]-5-[(trimethylsilyl)ethynyl]pyridine (500 mg, 1.3 mmol) in anhydrous THF (43 mL) was added at 0° C. 1.0M tetra-n-butylammonium fluoride solution in THF (4.0 mL, 4.0 mmol). The reaction mixture was stirred at 0° C. for 2 h. The reaction was quenched by addition of saturated aqueous NH$_4$Cl solution. The mixture was extracted with CH$_2$Cl$_2$, and the organic phase was dried over MgSO$_4$, filtered, and concentrated in vacuo. The residue was purified by CC on SiO$_2$ eluting with EtOAc/hexane 1:4 to give 3-[[1-(tert-butoxycarbonyl)-2(S)-pyrrolidinyl]methoxy]-5-ethynylpyridine (470 mg, 98%).

To a solution of 1-nitro-2-(tetrahydro-2H-pyran-2-yloxy)ethane (0.17 mL, 1.12 mmol, 2.0 equiv.) and 3-[[1-(tert-butoxycarbonyl)-2(S)-pyrrolidinyl]methoxy]-5-ethynylpyridine (170 mg, 0.56 mmol) in dry benzene (5.6 mL) were added phenyl isocyanate (122 μL, 1.12 mmol, 2.0 equiv.) and triethylamine (80 μL, 0.57 mmol, 1.0 equiv.). The reaction mixture was stirred at 60° C. for 48 h, then diluted with water and stirred vigorously for 2 h. The mixture was extracted with CH$_2$Cl$_2$. The organic phase was dried over MgSO$_4$, filtered, and concentrated in vacuo. The residue was purified by CC on SiO$_2$ with EtOAc/hexane 1:1 to give 3-[[1-(tert-butoxycarbonyl)-2(S)-pyrrolidinyl]methoxy]-5-[3-[(tetrahydro-2H-pyran-2-yloxy)methyl]-5-isoxazolyl]pyridine (190 mg, 74%). The $^1$H NMR spectrum (CDCl$_3$, 400 MHz) exhibits two sets of signals for two of the heteroaromatic protons: δ 8.53 (br s, 1H), 8.28 (br s, 1H), 7.69 (br s, 1H of the major component), 7.49 (br s, 1H of the minor component), 6.69 (br s, 1H of the major component), 6.65 (br s, 1H of the minor component), 4.75, 4.57 (ABq, 2H, J=12.8 Hz), 4.67 (br s, 1H), 4.23-4.01 (m, 2H), 3.99-3.84 (m, 1H), 3.81 (br t, 1H, J=9.6 Hz), 3.53-3.42 (m, 1H), 3.40-3.20 (m, 2H), 2.03-1.4 (series of overlapping m, 10H), 1.38 (s, 9H).

[5-[5-[(2(S)-Pyrrolidinyl)methoxy]-3-pyridyl]-3-isoxazolyl]methanol Hydrochloride

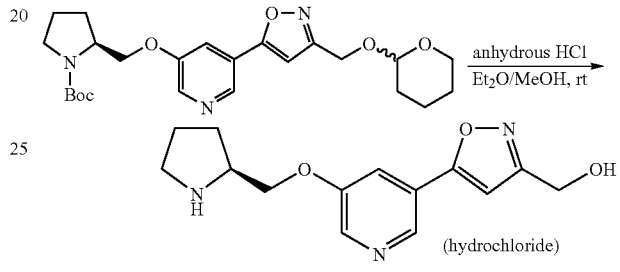

To a solution of 3-[[1-(tert-butoxycarbonyl)-2(S)-pyrrolidinyl]methoxy]-5-[3-[(tetrahydro-2H-pyran-2-yloxy)methyl]-5-isoxazolyl]pyridine (145 mg, 0.31 mmol) in MeOH (10 mL) was added at 0° C. 2M anhydrous HCl in ether (10 mL). The reaction mixture was stirred at room temperature for 12 h, then concentrated in vacuo. The residue was purified by HPLC to give the hydrochloride (90 mg). The $^1$H NMR spectrum (CD$_3$OD, 400 MHz) of this material exhibits signals compatible with the postulated structure, but in addition a second set of signals of somewhat lower intensity for the heteroaromatic protons in close proximity to those of the title compound: δ 9.02 (s, 1H of minor component), 9.01 (s, 1H of major component), 8.74 (narrow m, 1H of minor component), 8.73 (narrow m, 1H of major component), 8.58 (narrow m, 1H of minor component), 8.55 (narrow m, 1H of major component), 7.30 (s, 1H of minor component), 7.28 (s, 1H of major component), 4.74 (s, 2H), 4.71-4.64 (m, 1H), 4.56-4.48 (m, 1H), 4.21-4.32 (m, 1H), 3.49-3.37 (m, 2H), 2.38-2.28 (m, 1H), 2.26-2.06 (m, 2H), 2.04-1.93 (m, 1H).

Example 39

3-[5-[5-[(2(S)-Azetidinyl)methoxy]-3-pyridyl]-3-isoxazolyl]propionic Acid Methyl Ester 3-[5-[5-[[1-(tert-Butoxycarbonyl)-2(S)-azetidinyl]methoxy]-3-pyridyl]-3-isoxazolyl]propionic Acid Methyl Ester

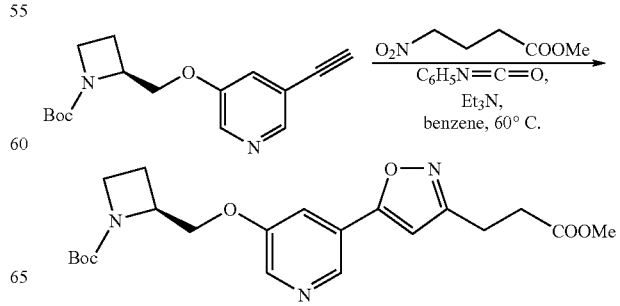

To a solution of methyl 4-nitrobutyrate (306 μL, 2.4 mmol) and 3-[[1-(tert-butoxycarbonyl)-2(S)-azetidinyl]methoxy]-5-ethynylpyridine (230 mg, 798 μmol) in dry benzene (8.0 mL) were added phenyl isocyanate (0.26 mL, 2.4 mmol) and triethylamine (0.22 mL, 1.6 mmol). The reaction mixture was stirred at 60° C. for 24 h, then diluted with water and stirred vigorously for 2 h. The mixture was extracted with $CH_2Cl_2$, and the organic phase was dried over $MgSO_4$, filtered and concentrated in vacuo. The residue was purified by CC on $SiO_2$ eluting with EtOAc/hexane 1:1 to give the isoxazole (283 mg, 85%). $^1$H NMR ($CD_3OD$, 400 MHz) δ 8.50 (br s, 2H), 7.62 (s, 1H), 6.53 (s, 1H), 4.55 (br s, 1H), 4.40 (br s, 1H), 4.21 (dd, 1H, J=10.0, 2.4 Hz), 3.91 (t, 2H, J=7.2 Hz), 3.73 (s, 3H), 3.07 (t, 2H, J=7.2 Hz), 2.80 (t, 2H, J=7.2 Hz), 2.38 (m, 2H), 1.42 (s, 9H). $^{13}$C NMR ($CDCl_3$, 100 MHz) δ 172.8, 167.1, 163.3, 156.3, 155.4, 139.8, 139.5, 124.3, 117.6, 100.9, 80.0, 69.0, 60.1, 52.0, 47.3, 32.1, 28.8, 21.7, 19.2.

3-[5-[5-[(2(S)-Azetidinyl)methoxy]-3-pyridyl]-3-isoxazolyl]propionic Acid Methyl Ester Hydrochloride

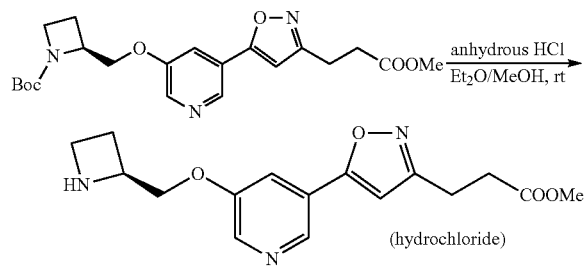

To a solution of 3-[5-[5-[[1-(tert-butoxycarbonyl)-2(S)-azetidinyl]methoxy]-3-pyridyl]-3-isoxazolyl]propionic acid methyl ester (100 mg, 0.24 mmol) in MeOH (34 mL) was added at 0° C. 2M anhydrous HCl in ether (12 mL). The reaction mixture was stirred at 0° C. for 7 h, then concentrated in vacuo. The residue was purified by HPLC to give the hydrochloride (90 mg). $^1$H NMR ($CD_3OD$, 400 MHz) δ 8.70 (s, 1H), 8.46 (s, 1H), 7.93 (d, 1H, J=1.6 Hz), 6.93 (s, 1H), 4.92 (s, 1H), 4.49 (m, 2H), 4.10 (m, 2H), 3.69 (s, 3H), 3.04 (t, 2H, J=7.2 Hz), 2.80 (t, 2H, J=7.2 Hz), 2.70 (m, 2H). $^{13}$C NMR ($CDCl_3$, 100 MHz) δ 174.3, 165.8, 164.6, 158.5, 134.0, 133.1, 129.5, 128.5, 105.8, 70.1, 60.3, 52.5, 45.1, 32.7, 22.6, 22.0.

Example 40

3-[5-[5-[(1-Methyl-2(S)-pyrrolidinyl)methoxy]-3-pyridyl]-3-isoxazolyl]-1-propanol 3-[5-[5-[(1-Methyl-2(S)-pyrrolidinyl)methoxy]-3-pyridyl]-3-isoxazolyl]propionic Acid Methyl Ester

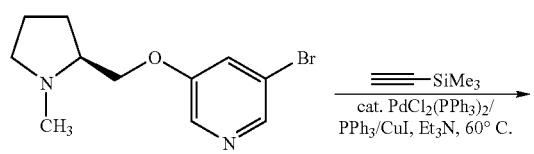

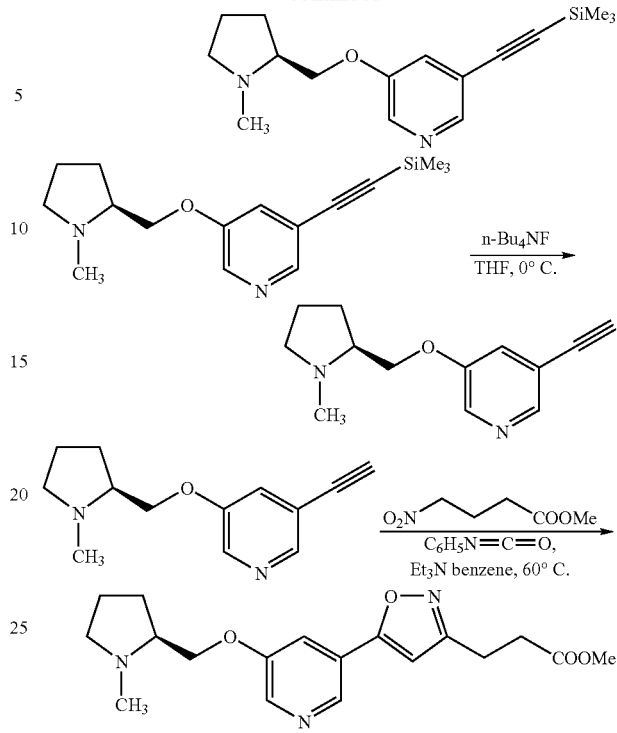

To a stirred solution/suspension of 3-bromo-5-[(1-methyl-2(S)-pyrrolidinyl)methoxy]pyridine (Lin, N. H.; He, Y.; Holladay, M. W.; Ryther, K.; Li, Y. U.S. Pat. No. 5,629,325, 1997) (2.50 g, 9.22 mmol), $PPh_3$ (798 mg, 3.04 mmol, 0.33 equiv.) and CuI (790 mg, 2.52 mmol, 0.27 equiv.) in triethylamine (24 mL) was added $PdCl_2(PPh_3)_2$ (647 mg, 0.92 mmol, 0.1 equiv.). The mixture was stirred at room temperature for 20 min under argon, then ethynyltrimethylsilane (3.9 mL, 27.6 mmol, 3.0 equiv.) was added. The reaction mixture was stirred at 60° C. for 24 h. Saturated aqueous $NH_4Cl$ solution was added, and the mixture was extracted with $CH_2Cl_2$, dried over $MgSO_4$, filtered, and concentrated in vacuo. The residue was purified by CC on $SiO_2$ with $CH_2Cl_2$/MeOH 9:1 to give 3-[[(1-methyl-2(S)-pyrrolidinyl)methoxy]-5-[(trimethylsilyl)ethynyl]pyridine (2.30 g, 86%).

To a solution of this intermediate (30 mg, 0.1 mmol) in anhydrous THF (3.3 mL) was added at 0° C. 1.0M tetra-n-butylammonium fluoride solution in THF (0.3 mL, 0.3 mmol). The reaction mixture was stirred at 0° C. for 1 h. The reaction was quenched by adding saturated aqueous $NH_4Cl$ solution, and the mixture was extracted with $CH_2Cl_2$, dried over $MgSO_4$, filtered, and concentrated in vacuo. The residue was purified by CC on $SiO_2$ with $CH_2Cl_2$/MeOH 9:1 to give 3-[[(1-methyl-2(S)-pyrrolidinyl)methoxy]-5-ethynylpyridine (21 mg, 93%).

To a solution of methyl 4-nitrobutyrate (90 μL, 0.69 mmol, 3.0 equiv.) and 3-[[(1-methyl-2(S)-pyrrolidinyl)methoxy]-5-ethynylpyridine (50 mg, 0.23 mmol) in dry benzene (2.3 mL) were added phenyl isocyanate (80 μL, 0.69 mmol, 3.0 equiv.) and triethylamine (60 μL, 0.46 mmol, 2.0 equiv.). The reaction mixture was stirred at 60° C. for 24 h, then diluted with water and stirred vigorously for 2 h. The mixture was extracted with $CH_2Cl_2$, and the organic phase was dried over $MgSO_4$, filtered and concentrated in vacuo. The residue was purified by CC on $SiO_2$ with $CH_2Cl_2$/MeOH 9:1 to give the isoxazole (80 mg, 98%). $^1$H NMR ($CD_3OD$, 400 MHz) δ 8.58 (s, 1H), 8.39 (s, 1H), 7.57 (s, 1H), 6.51 (s, 1H), 4.09 (dd, 1H, J=9.2, 5.5 Hz), 4.02 (dd, 1H, J=9.2, 5.5 Hz), 3.73 (s, 3H), 3.15 (t, 1H, J=7.2 Hz), 3.07 (t, 2H, J=7.2 Hz), 2.80 (t, 2H, J=7.2 Hz), 2.73 (m, 1H), 2.51 (s, 3H), 2.36 (m, 1H), 2.07 (m, 1H), 1.85 (m, 3H).

Example 41

3-[(1-Methyl-2(S)-pyrrolidinyl)methoxy]-5-[3-(3-phenoxypropyl)-5-isoxazolyl]pyridine Hydrochloride

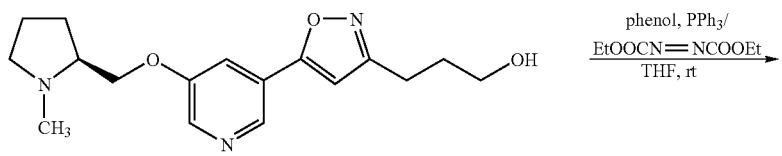

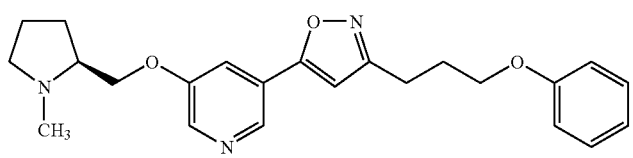

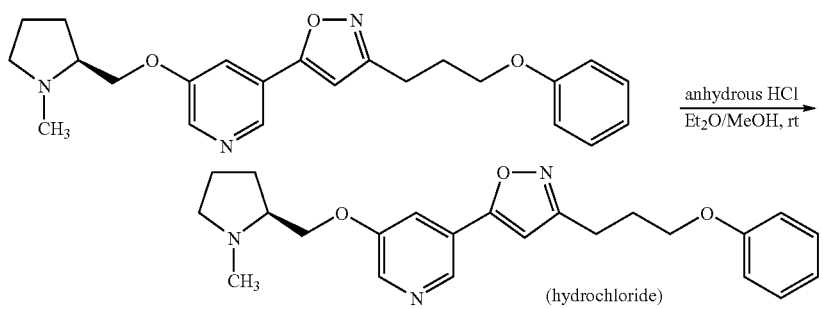

To a solution of 3-[5-[5-[(1-methyl-2(S)-pyrrolidinyl)methoxy]-3-pyridyl]-3-isoxazolyl]-1-propanol (10 mg, 33 µmol), phenol (5 mg, 50 µmol, 1.5 equiv.) and PPh₃ (13 mg, 50 µmol, 1.5 equiv.) in anhydrous THF (0.2 mL) was added diethyl azodicarboxylate (DEAD; 8 µL, 50 µmol, 1.5 equiv.) at 0° C. The mixture was stirred for 1 h at 0° C. and then warmed to room temperature. Stirring was continued for 11 h, then the mixture was concentrated in vacuo. The residue was purified by CC on SiO₂ with CH₂Cl₂/MeOH 9:1 to give 3-[(1-methyl-2(S)-pyrrolidinyl)methoxy]-5-[3-(3-phenoxypropyl)-5-isoxazolyl]pyridine (20 mg, 51%).

To a solution of this base (50 mg, 85 µmol) in MeOH (4.3 mL) at 0° C. was added 2M anhydrous HCl in ether (0.4 mL). The reaction mixture was stirred at 0° C. for 1 h, then concentrated in vacuo to give the hydrochloride (40 mg, 99%). ¹H NMR (CD₃OD, 400 MHz) δ 8.99 (s, 1H), 8.80 (s, 1H), 8.67 (s, 1H), 7.27 (s, 1H), 7.20 (t, 2H, J=8.0 Hz), 6.86 (m, 3H), 4.73 (m, 2H), 4.02 (t, 3H, J=5.6 Hz), 3.76 (m, 1H), 3.26 (m, 2H), 3.07 (s, 3H), 2.94 (t, 2H, J=7.2 Hz), 2.43 (m, 1H), 2.16 (m, 4H). ¹³C NMR (CDCl₃, 100 MHz) δ 162.2, 161.2, 156.6, 156.3, 155.5, 134.7, 134.0, 125.6, 121.9, 116.9, 115.9, 110.7, 98.4, 64.2, 62.8, 53.6, 37.0, 24.1, 22.7, 18.9, 18.8.

Example 42

N-Methyl-3-[5-[5-[(2(S)-azetidinyl)methoxy]-3-pyridyl]-3-isoxazolyl]propionamide Hydrochloride

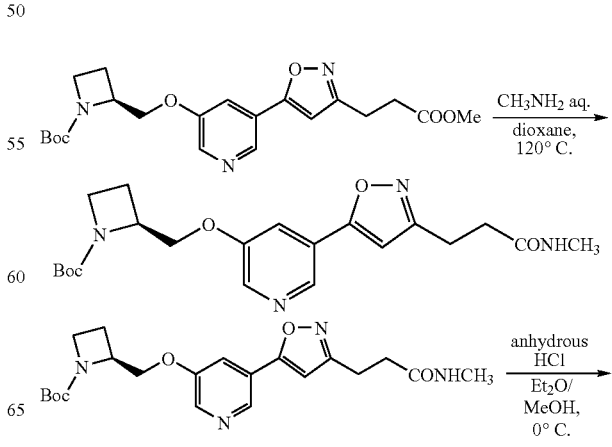

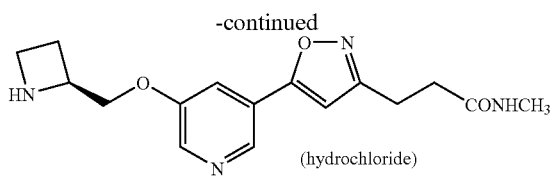

(hydrochloride)

To a solution of 3-[5-[5-[[1-(tert-butoxycarbonyl)-2(S)-azetidinyl]methoxy]-3-pyridyl]-3-isoxazolyl]propionic acid methyl ester (330 mg, 0.79 mmol) in 1,4-dioxane (4 mL) was added 40 wt % solution of methylamine in $H_2O$ (2.7 mL, 31.6 mmol). The mixture was heated at 120° C. for 12 h, cooled, and concentrated. The residue was dissolved in water and extracted with $CH_2Cl_2$. The organic phase was dried over $MgSO_4$, filtered, and concentrated in vacuo. The residue was purified by CC on $SiO_2$ with EtOAc/hexane 2:1 to give N-methyl-3-[5-[5-[[1-(tert-butoxycarbonyl)-2(S)-azetidinyl]methoxy]-3-pyridyl]-3-isoxazolyl]propionamide (217 mg, 66%).

To a solution of the preceding intermediate (200 mg, 0.48 mmol) in MeOH (20 mL) was added at 0° C. 2M anhydrous HCl in ether (10 mL). The reaction mixture was stirred at 0° C. for 7 h, then concentrated in vacuo. The residue was purified by HPLC, and the eluate was concentrated. To the solution of the resulting trifluoroacetate in MeOH (24 mL) at 0° C. was added 2M anhydrous HCl solution in ether (2.4 mL). The reaction mixture was stirred at 0° C. for 1 h, then concentrated in vacuo to give the hydrochloride (120 mg). $^1$H NMR ($CD_3OD$, 400 MHz) δ 9.06 (s, 1H), 8.86 (s, 1H), 8.74 (s, 1H), 7.28 (s, 1H), 5.01 (m, 1H), 4.78 (dd, 1H, J=10.8, 6.0 Hz), 4.70 (dd, 1H, J=11.2, 2.8 Hz), 4.15 (t, 2H, J=8.4 Hz), 3.09 (t, 2H, J=7.2 Hz), 2.70 (m, 7H). $^{13}$C NMR ($CD_3OD$, 100 MHz) δ 178.0, 165.8, 164.4, 158.7, 133.4, 132.4, 129.8, 129.2, 106.0, 70.1, 60.2, 45.0, 34.5, 26.7, 23.2, 21.9.

Example 43

3-[5-[5-[2(S)-Azetidinyl)methoxy]-3-pyridyl]-3-isoxazolyl]-1-(1-pyrrolidinyl)-1-propanone Hydrochloride

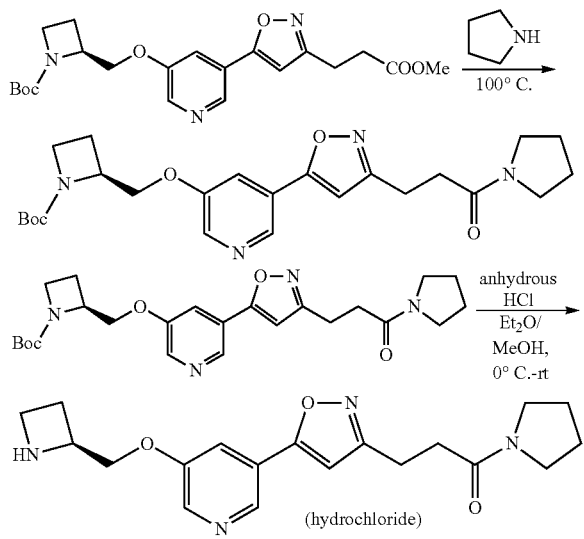

To 3-[5-[5-[[1-(tert-butoxycarbonyl)-2(S)-azetidinyl]methoxy]-3-pyridyl]-3-isoxazolyl]propionic acid methyl ester (210 mg, 0.5 mmol) was added pyrrolidine (1.2 mL, 15 mmol). The mixture was heated at 100° C. for 12 h, cooled, and concentrated. The residue was dissolved in water and extracted with $CH_2Cl_2$. The organic phase was dried over $MgSO_4$, filtered and concentrated in vacuo. The residue was purified by CC on $SiO_2$ with EtOAc/hexane 1:1 to give 3-[5-[5-[[1-(tert-butoxycarbonyl)-2(S)-azetidinyl]methoxy]-3-pyridyl]-3-isoxazolyl]-1-(1-pyrrolidinyl)-1-propanone (230 mg, 99%).

To a solution of this intermediate (230 mg, 0.50 mmol) in MeOH (16 mL) was added at 0° C. 2M anhydrous HCl solution in ether (8 mL). The reaction mixture was stirred at room temperature for 12 h and then concentrated in vacuo. The residue was purified by preparative HPLC to give the hydrochloride (182 mg). $^1$H NMR ($CD_3OD$, 400 MHz) δ 9.05 (s, 1H), 8.85 (s, 1H), 8.71 (s, 1H), 7.28 (br s, 1H), 4.99 (m, 1H), 4.75 (m, 1H), 4.70 (m, 1H), 4.14 (t, 2H, J=7.2 Hz), 3.56 (m, 2H), 3.44 (m, 2H), 3.10 (m, 2H), 2.85 (m, 2H), 2.73 (m, 2H), 1.99 (m, 2H), 1.90 (m, 2H). $^{13}$C NMR ($CD_3OD$, 100 MHz) δ 172.3, 166.2, 164.3, 158.7, 133.7, 132.5, 129.8, 129.0, 106.3, 70.2, 60.3, 48.2, 47.3, 45.1, 33.1, 27.1, 25.5, 22.6, 21.9. Anal. Calcd. for $C_{19}H_{24}N_4O_3$·2.55HCl·1.2$H_2O$: C, 48.45; H, 6.20; N, 11.89; Cl, 19.19. Found: C, 48.60; H, 6.00; N, 11.89; Cl, 19.19.

Example 44

7-[5-[(2(S)-Azetidinyl)methoxy]-3-pyridyl]-7-azabicyclo[2.2.1]heptane

7-[5-[[1-(tert-Butoxycarbonyl)-2(S)-azetidinyl]methoxy]-3-pyridyl]-7-azabicyclo[2.2.1]heptane

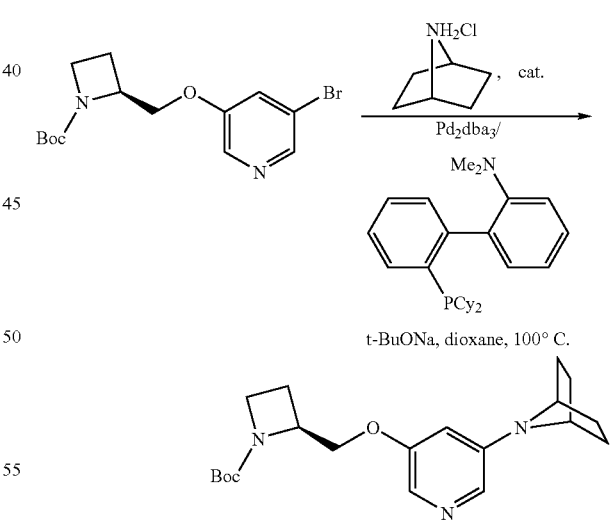

Tris(dibenzylideneacetone)dipalladium(0) (9.0 mg, 10 µmol, 0.02 equiv.) and 2-(dicyclohexylphosphino)-2'-(N,N-dimethylamino)biphenyl (8.1 mg, 20 µmol, 0.04 equiv.) were dissolved in anhydrous dioxane (2 mL) in a 25 mL round bottom flask with a side neck, which was equipped with a condenser. tert-BuONa (135 mg, 1.4 mmol, 2.8 equiv.) was added, and the atmosphere was exchanged with Ar (3 times). The mixture was stirred at 80° C. for 30 min. 7-Azabicyclo[2.2.1]heptane hydrochloride (Ace Synthesis LLC, 21-G Olympia Ave., Suite 30, Woburn, Mass. 01801; 80 mg, 0.60 mmol, 1.2 equiv.) and 3-bromo-5-[[1-(tert-butoxycarbonyl)-2(S)-azetidinyl]methoxy]pyridine (172 mg, 0.50 mmol) in anhydrous dioxane (2 mL) and DMF (0.5 mL) were added via syringe. The mixture was stirred at 100° C. for 40 h and cooled to room temperature. Water (20 mL) was added, and the product was extracted into EtOAc (2×25 mL). The combined organic phases were washed with brine (20 mL), dried over $Na_2SO_4$, and concentrated. The residue was chromatographed on a silica gel column (20×1.0 cm, EtOAc) to give the crude product, which was purified by preparative HPLC (Supelco Discovery $C_{18}$, 250×21.2 mm, 5 μm particle size, UV detection at 270 nm, flow rate 12.5 mL/min, gradient from 20% to 100% $CH_3CN$ in water within 40 min, then 100% $CH_3CN$ for 20 min; $t_R$ 24.8-26.4 min) to give a colorless oil (59 mg, 33%). $[\alpha]_{546}$ −68.1; $[\alpha]_{589}$ −57.0 (c 16.2 g/L, EtOAc). $^1$H NMR ($CDCl_3$, 400 MHz) δ 7.90 (s, 1H), 7.79 (d, 1H, J=1.8 Hz), 6.73 (t, 1H, J=2.3 Hz), 4.53-4.45 (m, 1H), 4.29 (dd, 1H, J=9.6, 5.0 Hz), 4.19 (quint, 2H, J=2.4 Hz), 4.12 (dd, 1H, J=9.6, 2.8 Hz), 3.94-3.85 (m, 2H), 2.40-2.22 (m, 2H), 1.86-1.74 (m, 4H), 1.50-1.43 (m, 4H), 1.42 (s, 9H); MS (EI) m/z 359 ($M^+$, 22%).

7-[5-[(2(S)-Azetidinyl)methoxy]-3-pyridyl]-7-azabicyclo[2.2.1]heptane Trifluoroacetate

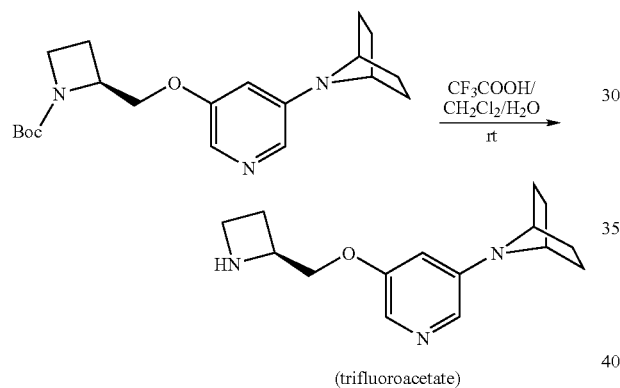

(trifluoroacetate)

A mixture of $CF_3COOH$, $H_2O$, and $CH_2Cl_2$ (10:1:50, 2.44 mL) was added to a 15 mL round bottom flask containing 7-[5-[[1-(tert-butoxycarbonyl)-2(S)-azetidinyl]methoxy]-3-pyridyl]-7-azabicyclo[2.2.1]heptane (90 mg, 0.25 mmol). The flask was capped with a glass stopper, and the reactants were stirred at room temperature for 14 h. The reaction mixture was concentrated with a rotary evaporator (bath up to 35° C.) and was further dried with an oil pump (40° C.). The residue was dissolved in water (2 mL) and lyophilized to give the trifluoroacetate (161 mg, 95%). $^1$H NMR ($CD_3OD$, 400 MHz) δ 8.12 (d, 1H, J=2.3 Hz), 7.95 (d, 1H, J=2.3 Hz), 7.61 (t, 1H, J=2.3 Hz), 4.96-4.90 (m, 1H), 4.56-4.43 (m, 4H), 4.17-4.03 (m, 2H), 2.76-2.59 (m, 2H), 1.90-1.75 (m, 4H), 1.69-1.55 (m, 4H); MS (EI) m/z 259 ($M^+$ of free base, 1.6%). Anal. Calcd. for $C_{15}H_{21}N_3O.3.63CF_3COOH.0.13H_2O$ (FW 675.6): C, 39.57; H, 3.71; N, 6.22; F, 30.62. Found: C, 39.57; H, 3.77; N, 6.32; F 30.64.

Example 45

3-[5-[(2(S)-Pyrrolidinyl)methoxy]-3-pyridyl]-3-azabicyclo[3.2.1]octane

The palladium catalyst A was prepared according to the following Scheme (Biscoe, M. R.; Fors, B. P.; Buchwald, S. L. *J. Am. Chem. Soc.* 2008, 130, 6686-6687):

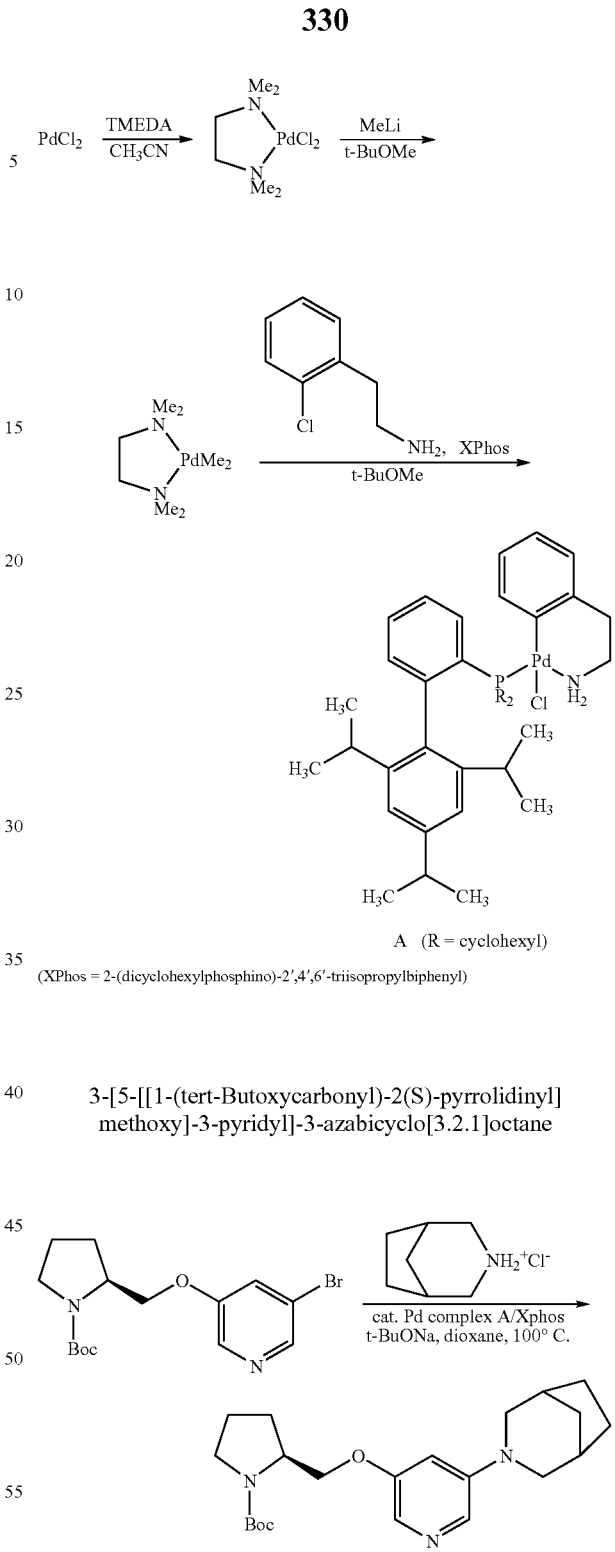

A (R = cyclohexyl)

(XPhos = 2-(dicyclohexylphosphino)-2',4',6'-triisopropylbiphenyl)

3-[5-[[1-(tert-Butoxycarbonyl)-2(S)-pyrrolidinyl]methoxy]-3-pyridyl]-3-azabicyclo[3.2.1]octane Palladium catalyst A (6.2 mg, 7.5 μmol, 83 mequiv.), 2-(dicyclohexylphosphino)-2',4',6'-triisopropylbiphenyl (Xphos, 3.7 mg, 7.5 μmol, 83 mequiv.), tert-BuONa (206 mg, 2.1 mmol, 2.8 equiv.), 3-bromo-5-[[1-(tert-butoxycarbonyl)-2(S)-pyrrolidinyl]methoxy]pyridine (268 mg, 0.75 mmol) and 3-azabicyclo[3.2.1]octane hydrochloride (Arkè Organics srl, Zona Industriale della Botte No. 4, 56012 Fornacette (PI), Italy; 133 mg, 0.90 mmol, 1.2 equiv.) were filled into a 25 mL round bottom-flask with a side neck. The flask was equipped with a stir bar, a condenser, and rubber septa. The atmosphere was exchanged with Ar (3 times), and anhydrous dioxane (3 mL) was added via syringe. The mixture was stirred at 100° C. for 5 h and cooled to room temperature. Water (10 mL) was added to quench the reaction. The product was extracted into EtOAc (40 mL). The organic phase was washed with brine (10 mL), dried over $Na_2SO_4$, and concentrated. The residue was purified by CC ($SiO_2$, 25×2.5 cm, EtOAc) to give the crude product, which was further purified by preparative HPLC (Supelco Discovery $C_{18}$, 250×21.2 mm, 5 µm particle size, UV detection at 270 nm, flow rate 12.5 mL/min, gradient from 20% to 100% $CH_3CN$ in water within 40 min, then 100% $CH_3CN$ for 20 min; $t_R$ 32.6-36.9 min) to give the title compound as a yellowish oil (198 mg, 65%). MS (EI) m/z 387 ($M^+$, 16%).

3-[5-[(2(S)-Pyrrolidinyl)methoxy]-3-pyridyl]-3-azabicyclo[3.2.1]octane Trifluoroacetate

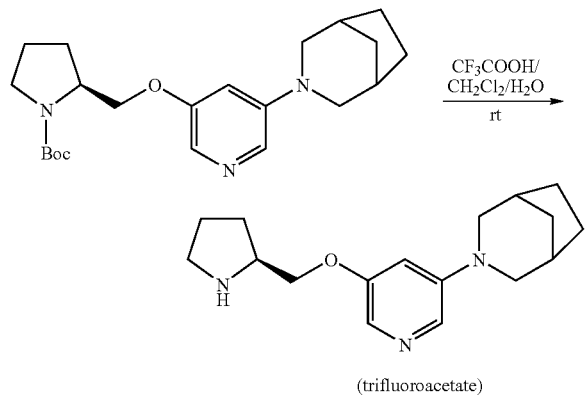

(trifluoroacetate)

A mixture of $CF_3COOH$, $H_2O$, and $CH_2Cl_2$ (10:1:50, 6.1 mL) was added to a 15 mL round-bottom flask containing 3-[5-[[1-(tert-butoxycarbonyl)-2(S)-pyrrolidinyl]methoxy]-3-pyridyl]-3-azabicyclo[3.2.1]octane (182 mg, 446 µmol). The flask was capped with a glass stopper, and the reactants were stirred at room temperature for 14 h. The reaction mixture was concentrated with a rotary evaporator (bath up to 35° C.) and was further dried with an oil pump (40° C.). The residue was purified by preparative HPLC (Supelco Discovery $C_{18}$, 250×21.2 mm, 5 µm particle size, UV detection at 270 nm, flow rate 4.9 mL/min, 8% $CH_3CN$ in water for 10 min followed by gradient from 8% to 25% for 35 min, from 25% to 100% for another 35 min, then 100% $CH_3CN$ for 40 min, both solvents containing 0.1 vol % $CF_3COOH$; $t_R$ 48.8-59.5 min) to give the yellow tifluoroacetate (260 mg, 94%). $^1$H NMR ($CD_3OD$, 500 MHz) δ 8.00 (d, 1H, J=2.2 Hz), 7.89 (d, 1H, J=1.9 Hz), 7.41 (d, 1H, J=2.2 Hz), 4.68 (dt, 1H, $J_1$=10.6 Hz, $J_2$=3.2 Hz), 4.38-4.32 (m, 1H), 4.17-4.07 (m, 1H), 3.64 (d, 2H, J=11.2 Hz), 3.46-3.39 (m, 2H), 3.06 (d, 2H, J=11.2 Hz), 2.49 (s, br, 2H), 2.36-2.27 (m, 1H), 2.24-2.16 (m, 1H), 2.16-2.08 (m, 1H), 2.01-1.91 (m, 1H), 1.88-1.81 (m, 2H), 1.72 (s, br, 2H), 1.65 (d, 2H, J=7.7 Hz); MS (EI) m/z 287 ($M^+$ of free base, 0.8%). Anal. Calcd. for $C_{17}H_{25}N_3O.2.93CF_3COOH$ (FW 621.5): C, 44.18; H, 4.53; N, 6.76; F, 26.87. Found: C, 44.20; H, 4.44; N, 6.73; F, 26.89.

Example 46

3-[5-[(2(S)-Azetidinyl)methoxy]-3-pyridyl]-3-azabicyclo[3.1.0]hexane

3-Azabicyclo[3.1.0]hexane

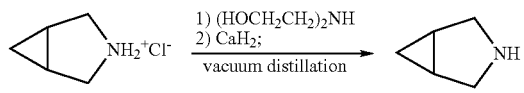

To 3-azabicyclo[3.1.0]hexane hydrochloride (Anichem, Inc., 195 Black Horse Lane, North Brunswick, N.J. 08902; 3.78 g, 31.5 mmol) in a 50 mL round-bottom flask was added diethanolamine (10.0 g, 94.5 mmol, 3.0 equiv.). The flask was equipped with a stir bar and a short path still head with a 25 mL round-bottom flask as receiver. The mixture was heated with a 50 mL heating mantle (at 30% power, thermometer reading of the vapor temperature <30° C.) under reduced pressure (diaphragm pump, approx. 14 torr). The receiver was cooled with a dry ice/acetone bath. Drops condensing on the flask wall and the still head were driven over into the receiver by gentle warming with a heat gun until no further condensate was observed. The collected ice-like solid was warmed to room temperature to give a colorless liquid. Small portions of $CaH_2$ were added until no more bubbles were formed. After cessation of visible gas evolution, the flask was stoppered and left to stand at room temperature overnight. The dried amine was distilled using the same setup as above into a 10 mL round-bottom flask cooled with a dry ice/acetone bath to furnish a volatile, colorless oil (2.41 g, 92%). Density 0.94 g/mL.

3-[5-[[1-(tert-Butoxycarbonyl)-2(S)-azetidinyl]methoxy]-3-pyridyl]-3-azabicyclo[3.1.0]hexane

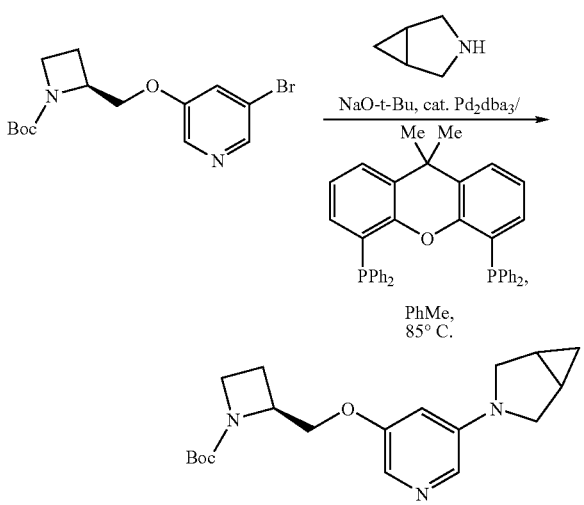

Tris(dibenzylideneacetone)dipalladium(0) (366 mg, 0.40 mmol, 0.02 equiv.), 4,5-bis(diphenylphosphino)-9,9-dimethylxanthene (Xantphos, 716 mg, 1.2 µmol, 0.06 equiv.), tert- BuONa (2.35 g, 24 mmol, 1.2 equiv.) and 3-bromo-5-[[1-(tert-butoxycarbonyl)-2(S)-azetidinyl]methoxy]pyridine (6.86 g, 20 mmol) were filled into a 350 mL Chemglass pressure bottle. Dry toluene (150 mL) was added, and the suspension was purged with Ar for 5 min. 3-Azabicyclo[3.1.0]hexane (1.75 g, 21 mmol, 1.05 equiv.) was added via syringe in one portion. The tube was sealed, and the mixture was stirred at 85° C. for 20 h and cooled to room temperature. The reaction was quenched by addition of water (100 mL), and the product was extracted into EtOAc (3×100 mL). The combined organic phases were concentrated, and the residue was purified by CC (SiO$_2$, 38×3.8 cm, EtOAc/hexanes 3:1) to give the crude amination product, which was purified by preparative HPLC in 19 portions (Supelco Discovery C$_{18}$, 250×21.2 mm, 5 μm particle size, UV detection at 270 nm, flow rate 12.5 mL/min, gradient from 20% to 100% CH$_3$CN in water within 40 min, then 100% CH$_3$CN for 20 min; t$_R$ 24.1-27.2 min) to give a colorless oil (6.00 g, 87%). [α]$_{546}$-76.4; [α]$_{589}$-64.5 (c 8.30 g/L, EtOAc). $^1$H NMR (CDCl$_3$, 400 MHz) δ 7.69 (d, 1H, J=2.3 Hz), 7.62 (d, 1H, J=2.3 Hz), 6.37 (t, 1H, J=2.3 Hz), 4.53-4.46 (m, 1H), 4.29 (dd, 1H, J=9.6, 5.0 Hz), 4.12 (dd, 1H, J=10.1, 2.8 Hz), 3.94-3.85 (m, 2H), 3.51 (d, 2H, J=8.7 Hz), 3.27 (d, 2H, J=8.2 Hz), 2.39-2.22 (m, 2H), 1.76-1.63 (m, 2H) 1.42 (s, 9H), 0.75 (td, 1H, J=7.8, 4.6 Hz), 0.32 (q, 1H, J=4.6 Hz). MS (EI) m/z 345 (M$^+$, 36%), 289 (11%), 288 (21%), 189 (22%), 177 (43%), 176 (72%), 175 (51%), 113 (21%), 70 (20%), 57 (94%), 56 (40%), 41 (100%).

3-[5-[[1-(Benzyloxycarbonyl)-2(S)-azetidinyl]methoxy]-3-pyridyl]-3-azabicyclo[3.1.0]hexane

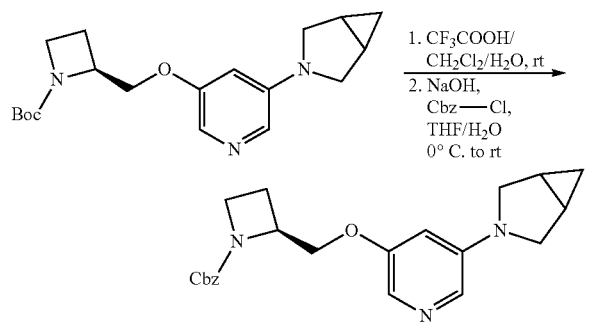

A mixture of CF$_3$COOH, H$_2$O, and CH$_2$Cl$_2$ (10:1:40, 153 mL) was added to a 250 mL round-bottom flask containing 3-[5-[[1-(tert-butoxycarbonyl)-2(S)-azetidinyl]methoxy]-3-pyridyl]-3-azabicyclo[3.1.0]hexane (6.00 g, 15.8 mmol). The flask was capped with a glass stopper, and the reactants were stirred at room temperature for 14 h. The reaction mixture was concentrated with a rotary evaporator (bath up to 35° C.) and was further dried with an oil pump (35° C.). The residue was dissolved in water (30 mL) and THF (100 mL). The mixture was stirred in an ice bath. Aqueous NaOH solution (5 N, approximately 20 mL) was added dropwise to adjust the pH of the solution to 10 (as monitored by spotting a few μL of the solution on pH paper). Benzyl chloroformate (4.9 mL, 31.6 mmol, 2.0 equiv.) was added dropwise over 30 min. During the addition, the pH of the solution was kept between 9 and 10 by gradually adding 5 N NaOH solution (approximately 20 mL). The pH of the solution was adjusted to 10 at the end of the addition. The ice bath was removed, and the mixture was stirred at room temperature for 18 h. The product was extracted into EtOAc (150+2×100 mL). The combined organic phases were concentrated, and the residue was purified by CC (SiO$_2$, 25×3.8 cm, EtOAc/hexanes 3:1) to give the product as a colorless oil (4.00 g, 67%). $^1$H NMR (CDCl$_3$, 500 MHz) δ 7.68 (br s, 1H), 7.63 (s, 1H), 7.38-7.26 (m, 5H), 6.40 (br s, 1H), 5.13 (s, 1H, J=12.2 Hz), 5.09 (s, 1H, J=8.8 Hz), 4.65-4.58 (m, 1H), 4.50-4.23 (m, 1H), 4.17-4.10 (m, 1H), 4.06-3.96 (m, 2H), 3.51 (d, 2H, J=8.8 Hz), 3.40 (d, 1H, J=8.3 Hz), 2.47-2.32 (m, 2H), 1.70 (t, 2H, J=3.4 Hz), 0.79 (td, 1H, J=7.6, 4.9 Hz), 0.33 (q, 1H, J=3.8 Hz). MS (EI) m/z 379 (M$^+$, 10%), 288 (1.9%), 177 (4.8%), 176 (9.1%), 175 (11%), 148 (5.0%), 91 (100%). The product of a second run solidified on standing at room temperature; mp 80-81.5° C.

3-[5-[(2(S)-Azetidinyl)methoxy]-3-pyridyl]-3-azabicyclo[3.1.0]hexane L-Tartrate

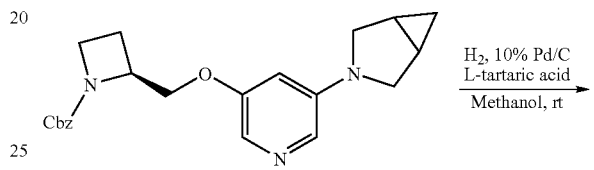

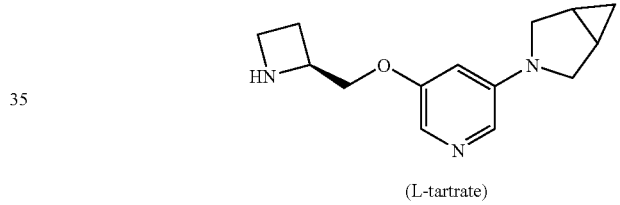

(L-tartrate)

To a solution of 3-[5-[[1-(benzyloxycarbonyl)-2(S)-azetidinyl]methoxy]-3-pyridyl]-3-azabicyclo[3.1.0]hexane (395 mg, 1.04 mmol) in methanol (30 mL) in a 100 mL round-bottom flask were added L-tartaric acid (156 mg, 1.04 mmol) and 10% palladium on carbon (40 mg). The atmosphere was exchanged with H$_2$ (3 times), and the mixture was stirred under H$_2$ (1 bar) for 3 h. The mixture was filtered through a cotton plug, and the filtrate was concentrated. The residue was further dried with an oil pump at room temperature to give the product as a brittle, tan foam (404 mg, 91%). Anal. Calcd. for C$_{14}$H$_{19}$N$_3$.O1.09C$_6$H$_4$O$_6$.1.06H$_2$O (FW 428.0): C, 51.52; H, 6.51; N, 9.82. Found: C, 51.61; H, 6.60; N, 9.72.

3-[5-[(2(S)-Azetidinyl)methoxy]-3-pyridyl]-3-azabicyclo[3.1.0]hexane Trifluoroacetate

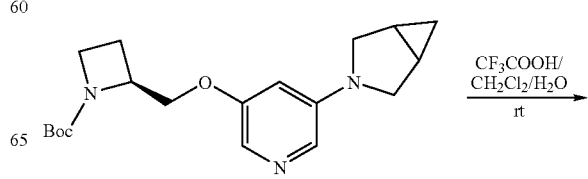

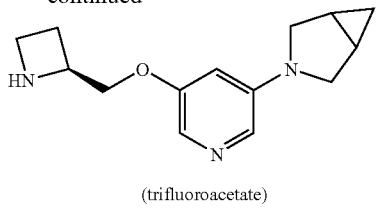

(trifluoroacetate)

A mixture of CF₃COOH, H₂O, and CH₂Cl₂ (10:1:50, 2.44 mL) was added to a 15 mL round-bottom flask containing 3-[5-[[1-(tert-butoxycarbonyl)-2(S)-azetidinyl]methoxy]-3-pyridyl]-3-azabicyclo[3.1.0]hexane (74 mg, 214 µmol). The flask was capped with a glass stopper, and the reactants were stirred at room temperature for 14 h. The reaction mixture was concentrated with a rotary evaporator (bath up to 35° C.) and was further dried with an oil pump (40° C.). The residue was dissolved in water (2 mL) and lyophilized to give the trifluoroacetate (116 mg, 92%). $^1$H NMR (CD₃OD, 400 MHz) δ 7.85 (d, 1H, J=2.3 Hz), 7.75 (d, 1H, J=1.8 Hz), 7.17 (t, 1H, J=2.1 Hz), 4.98-4.90 (m, 1H), 4.55-4.46 (m, 2H), 4.17-4.03 (m, 2H), 3.60 (d, 2H, J=9.6 Hz), 3.47 (d, 2H, J=9.6 Hz), 2.76-2.60 (m, 2H), 1.86-1.80 (m, 2H), 0.89 (td, 1H, J=7.8, 5.0 Hz), 0.32 (q, 1H, J=4.3 Hz). MS (EI) m/z 245 (M⁺ of free base, 14%). Anal. Calcd. for C₁₄H₁₉N₃O.2.96CF₃COOH.0.36H₂O (FW 589.3): C, 40.60; H, 3.88; N, 7.13; F, 28.63. Found: C, 40.59; H, 3.64; N, 7.07; F 28.60.

Example 47

3-[5-[(2(R)-Azetidinyl)methoxy]-3-pyridyl]-3-azabicyclo[3.1.0]hexane

3-[5-[[1-(tert-Butoxycarbonyl)-2(R)-azetidinyl]methoxy]-3-pyridyl]-3-azabicyclo[3.1.0]hexane

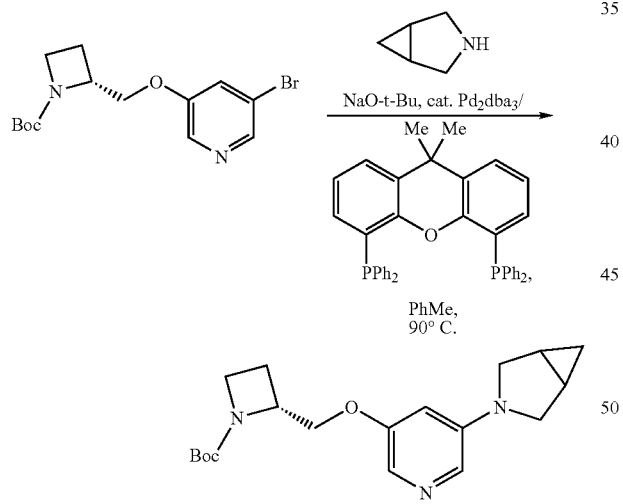

Tris(dibenzylideneacetone)dipalladium(0) (9.0 mg, 10 µmol, 0.02 equiv.), 4,5-bis(diphenylphosphino)-9,9-dimethylxanthene (Xantphos, 18 mg, 30 µmol, 0.06 equiv.), tert-BuONa (59 mg, 0.60 mmol, 1.2 equiv.) and 3-bromo-5-[[1-(tert-butoxycarbonyl)-2(R)-azetidinyl]methoxy]pyridine (172 mg, 0.50 mmol) were filled into a 10 mL resealable tube with a screw-cap. Dry toluene (2 mL) was added, and the suspension was purged with Ar for 5 min. 3-Azabicyclo[3.1.0]hexane (49 µL, 0.55 mmol, 1.1 equiv.) was added via syringe in one portion. The tube was sealed, and the mixture was stirred at 90° C. for 18 h, cooled to room temperature, and separated by CC (SiO₂, 25×1.0 cm, EtOAc/hexane 3:1). The crude product was purified by preparative HPLC (Supelco Discovery C₁₈, 250×21.2 mm, 5 µm particle size, UV detection at 270 nm, flow rate 12.5 mL/min, gradient from 20% to 100% CH₃CN in water within 40 min, then 100% CH₃CN for 20 min; $t_R$ 24.3-26.5 min) to give a yellowish oil (141 mg, 82%). [α]₅₄₆+78.7; [α]₅₈₉+66.6 (c 4.70 g/L, EtOAc). $^1$H NMR (CDCl₃, 500 MHz) δ 7.71 (s, 1H), 7.63 (s, 1H), 6.41 (s, 1H), 4.55-4.48 (m, 1H), 4.35-4.27 (m, 1H), 4.14 (dd, 1H, J=9.9, 2.7 Hz), 3.95-3.86 (m, 2H), 3.52 (d, 2H, J=8.9 Hz), 3.30 (d, 2H, J=8.5 Hz), 2.41-2.25 (m, 2H), 1.69 (t, 2H, J=3.9 Hz) 1.44 (s, 9H), 0.77 (td, 1H, J=7.8, 5.1 Hz), 0.34 (q, 1H, J=4.2 Hz). MS (EI) m/z 345 (M⁺, 33%).

3-[5-[(2(R)-Azetidinyl)methoxy]-3-pyridyl]-3-azabicyclo[3.1.0]hexane Trifluoroacetate

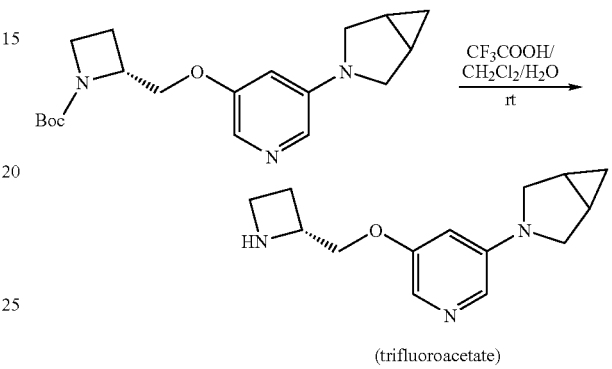

(trifluoroacetate)

A mixture of CF₃COOH, H₂O, and CH₂Cl₂ (10:1:40, 4.11 mL) was added to a 15 mL round-bottom flask containing 3-[5-[[1-(tert-butoxycarbonyl)-2(R)-azetidinyl]methoxy]-3-pyridyl]-3-azabicyclo[3.1.0]hexane (131 mg, 379 µmol). The flask was capped with a glass stopper, and the reactants were stirred at room temperature for 14 h. The reaction mixture was concentrated with a rotary evaporator (bath up to 35° C.) and further dried with an oil pump (30° C.). The residue was dissolved in water (1.5 mL) and lyophilized to give the trifluoroacetate as a yellow oil (240 mg, 99%). $^1$H NMR (CD₃OD, 500 MHz) δ 7.87 (s, 1H), 7.77 (d, 1H, J=1.9 Hz), 7.20 (d, 1H, J=1.8 Hz), 4.92-4.85 (m, 1H), 4.58-4.49 (m, 2H), 4.18-4.07 (m, 2H), 3.63 (d, 2H, J=9.8 Hz), 3.49 (d, 2H, J=9.4 Hz), 2.78-2.63 (m, 2H), 1.86 (t, 2H, J=3.6 Hz), 0.92 (td, 1H, J=7.5, 5.0 Hz), 0.29 (q, 1H, J=4.2 Hz). MS (EI) m/z 245 (M⁺, 27%). Anal. Calcd. for C₁₄H₁₉N₃O.3.33CF₃COOH.0.73H₂O: C, 38.88; H, 3.76; N, 6.58; F, 29.74. Found: C, 38.93; H, 3.71; N, 6.53; F, 29.69).

Example 48

3-[5-[(2(S)-Pyrrolidinyl)methoxy]-3-pyridyl]-3-azabicyclo[3.1.0]hexane

3-[5-[[1-(tert-Butoxycarbonyl)-2(S)-pyrrolidinyl]methoxy]-3-pyridyl]-3-azabicyclo[3.1.0]hexane

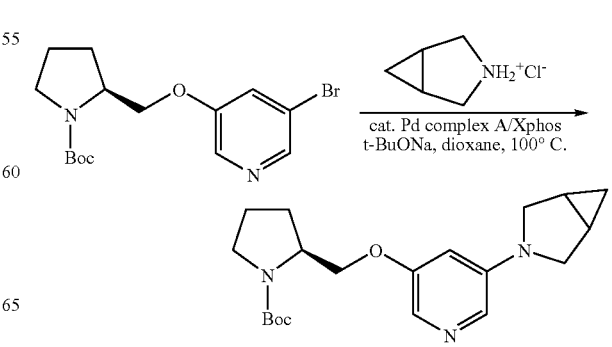

Palladium catalyst A (see Example 45; 6.2 mg, 7.5 μmol, 0.1 equiv.), 2-(dicyclohexylphosphino)-2',4',6'-triisopropylbiphenyl (Xphos, 3.7 mg, 7.5 μmol, 0.1 equiv.), tert-BuONa (206 mg, 2.1 mmol, 2.8 equiv.), 3-bromo-5-[[1-(tert-butoxycarbonyl)-2(S)-pyrrolidinyl]methoxy]pyridine (268 mg, 0.75 mmol) and 3-azabicyclo[2.1.0]hexane hydrochloride (108 mg, 0.90 mmol, 1.2 equiv.) were filled into a 25 mL round-bottom flask with a side neck. The flask was equipped with a stir bar, a condenser, and rubber septa. The atmosphere was exchanged with Ar (3 times), and anhydrous dioxane (3 mL) was added via syringe. The mixture was stirred at 100° C. for 5 h and cooled to room temperature. Water (10 mL) was added to quench the reaction. The product was extracted with EtOAc (40 mL). The organic phase was washed with brine (10 mL), dried over $Na_2SO_4$, and concentrated. The residue was purified by CC ($SiO_2$, 25×2.5 cm, EtOAc) to give the crude product, which was purified by preparative HPLC (Supelco Discovery $C_{18}$, 250×21.2 mm, 5 μm particle size, UV detection at 270 nm, flow rate 4.9 mL/min, 20% of acetonitrile in water for 10 min followed by gradient from 20% to 100% within 80 min, then 100% acetonitrile for 30 min; $t_R$ 72.0-79.2 min) to give the product as a yellowish oil (119 mg, 44%). MS (EI) m/z 359 (M+, 16%).

3-[5-[(2(S)-Pyrrolidinyl)methoxy]-3-pyridyl]-3-azabicyclo[3.1.0]hexane Trifluoroacetate

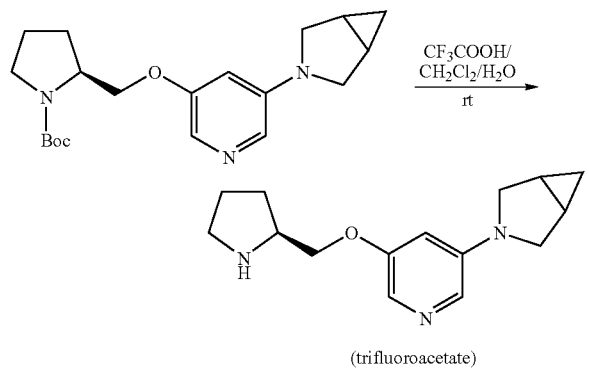

(trifluoroacetate)

A mixture of $CF_3COOH$, $H_2O$, and $CH_2Cl_2$ (10:1:50, 6.1 mL) was added to a 15 mL round-bottom flask containing 3-[5-[[1-(tert-butoxycarbonyl)-2(S)-pyrrolidinyl]methoxy]-3-pyridyl]-3-azabicyclo[3.1.0]hexane (159 mg, 443 μmol). The flask was capped with a glass stopper, and the reactants were stirred at room temperature for 14 h. The reaction mixture was concentrated with a rotary evaporator (bath up to 35° C.) and was further dried with an oil pump (40° C.). The residue was dissolved in water (1 mL) and lyophilized to give the trifluoroacetate (299 mg, 92%). $^1$H NMR ($CD_3OD$, 500 MHz) δ 7.83 (s, 1H), 7.76 (d, 1H, J=1.5 Hz), 7.15 (s, 1H), 4.54 (dd, 1H, J=10.7, 3.4 Hz), 4.35 (dd, 1H, J=10.6, 8.2 Hz), 4.14-4.08 (m, 1H), 3.62 (d, 2H, J=9.8 Hz), 3.49 (d, 2H, J=9.3 Hz), 3.45-3.40 (m, 2H), 2.36-2.28 (m, 1H), 2.24-2.16 (m, 1H), 2.16-2.08 (m, 1H), 2.00-1.92 (m, 1H), 1.88-1.83 (m, 2H), 0.91 (dd, 1H, J=12.9, 7.7 Hz), 0.28 (q, 1H, J=4.4 Hz). Anal. Calcd. for $C_{15}H_{21}N_3O\cdot3.65CF_3COOH$ (FW 675.5): C, 39.65; H, 3.68; N, 6.22; F, 30.80. Found: C, 39.77; H, 3.68; N, 6.36; F, 30.97.

Example 49

3-(1-Indolinyl)-5-[(2(S)-pyrrolidinyl)methoxy]pyridine

3-[[1-(tert-Butoxycarbonyl)-2(S)-pyrrolidinyl]methoxy]-5-(1-indolinyl)pyridine

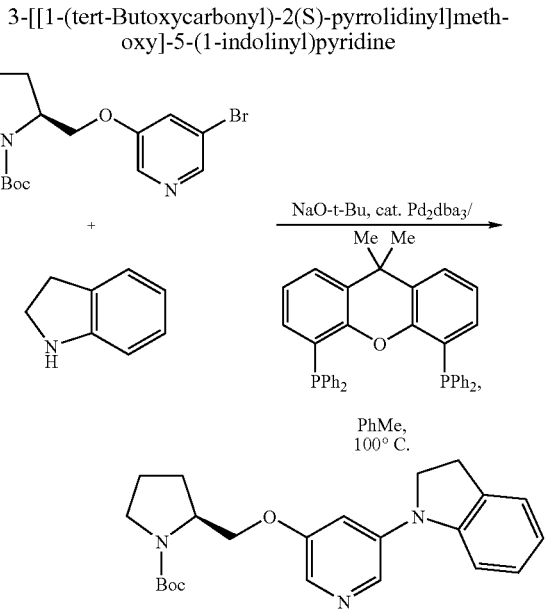

To a solution of 3-bromo-5-[[1-(tert-butoxycarbonyl)-2(S)-pyrrolidinyl]methoxy]pyridine (70 mg, 0.20 mmol) and indoline (25 μL, 0.22 mmol, 1.1 equiv.) in anhydrous toluene (2 mL) were added successively sodium tert-butoxide (29 mg, 0.3 mmol, 1.5 equiv.), tris(dibenzylideneacetone)dipalladium(0) (3.7 mg, 4.0 μmol, 0.02 equiv.), and 4,5-bis(diphenylphosphino)-9,9-dimethylxanthene (Xantphos; 6.9 mg, 12 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over $Na_2SO_4$, and evaporated. The residue was purified by CC ($SiO_2$, $CH_2Cl_2$/EtOAc 4:1, then 1:1). The product (71 mg, 90%) was obtained as a bright yellow oil. $^1$H NMR ($CDCl_3$, 400 MHz) δ 8.19 (s, 1H), 7.91 (s, 1H), 7.20-7.00 (m, 4H), 6.79 (t, 1H, J=6.8 Hz), 4.11 (m, 2H), 3.90-3.86 (m, 3H), 3.41 (m, 2H), 3.13 (t, 2H, J=8.4 Hz), 2.02 (m, 3H), 1.86 (m, 1H), 1.46 (s, 9H); $^{13}$C NMR ($CDCl_3$, 100 MHz) δ 155.6, 146.0, 141.4, 132.1, 131.5, 130.1, 129.1, 127.3, 125.3, 120.0, 109.4, 108.7, 68.5, 56.1, 51.9, 47.1, 46.8, 28.9, 28.6, 28.2, 24.0.

3-(1-Indolinyl)-5-[(2(S)-pyrrolidinyl)methoxy]pyridine Hydrochloride

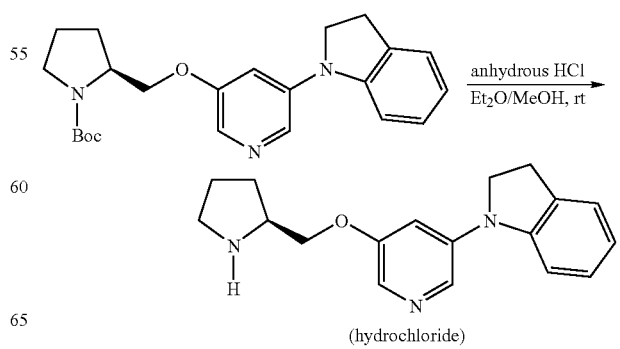

(hydrochloride)

To a solution of 3-[[N-(tert-butoxycarbonyl)-2(S)-pyrrolidinyl]methoxy]-5-(1-indolinyl)pyridine (71 mg, 0.18 mmol) in MeOH (0.2 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. After lyophilization from water, the hydrochloride (71 mg) was obtained as yellow solid. $[\alpha]^{20}_D$+7.0 (c 1.0 g/L, MeOH). $^1$H NMR (D$_2$O, 400 MHz) δ 7.97 (s, 1H), 7.83 (s, 1H), 7.41 (s, 1H), 7.12 (d, 1H, J=7.2 Hz), 7.05 (m, 2H), 6.82 (t, 1H, J=7.2 Hz), 4.45 (dd, 1H, J=3.2 Hz, J=10.4 Hz), 4.31 (dd, 1H, J=7.6 Hz, J=10.4 Hz), 4.15 (m, 1H), 3.78 (t, 2H, J=8.4 Hz), 3.45 (t, 2H, J=7.2 Hz), 3.01 (t, 2H, J=8.4 Hz), 2.32 (m, 1H), 2.14 (m, 2H), 1.97 (m, 1H). $^{13}$C NMR (D$_2$O, 100 MHz) δ 156.2, 142.5, 141.9, 132.2, 126.7, 125.3, 121.9, 121.5, 118.2, 114.2, 109.6, 67.3, 58.1, 51.0, 45.6, 26.6, 25.5, 23.0. HRMS (ESI) calcd for $C_{18}H_{22}N_3O$ (M+H$^+$) m/z 296.1763, found 296.1758. Anal. Calcd. for $C_{18}H_{21}N_3O$·3.0HCl·0.1H$_2$O: C, 53.18; H, 6.00; N, 10.34; Cl, 26.16. Found: C, 53.27; H, 6.18; N, 10.26; Cl, 26.03.

Example 50

3-(1,3-Dihydro-2H-isoindol-2-yl)-5-[(2(S)-pyrrolidinyl)methoxy]pyridine

3-[[1-(tert-Butoxycarbonyl)-2(S)-pyrrolidinyl]methoxy]-5-(1,3-dihydro-2H-isoindol-2-yl)pyridine

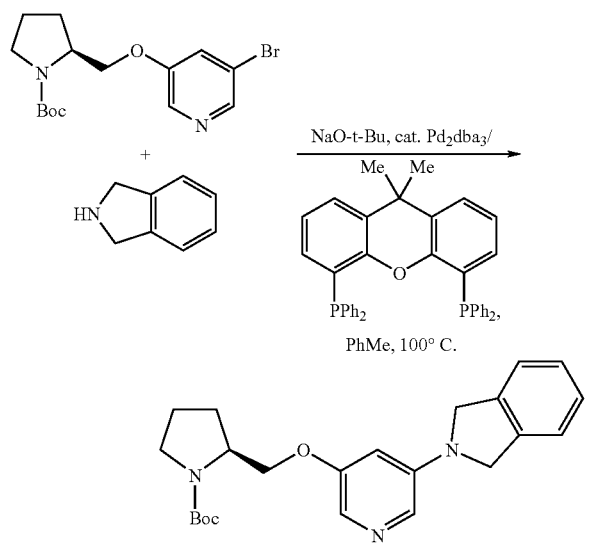

To a solution of 3-bromo-5-[[1-(tert-butoxycarbonyl)-2(S)-pyrrolidinyl]methoxy]pyridine (89 mg, 0.25 mmol) and isoindoline (31 μL, 0.28 mmol, 1.1 equiv.) in anhydrous toluene (2 mL) were added successively sodium tert-butoxide (36 mg, 0.38 mmol, 1.5 equiv.), tris(dibenzylideneacetone)dipalladium(0) (4.6 mg, 5.0 μmol, 0.02 equiv.), and 4,5-bis(diphenylphosphino)-9,9-dimethylxanthene (Xantphos; 8.7 mg, 15 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over Na$_2$SO$_4$, and evaporated. The residue was purified by CC (SiO$_2$, CH$_2$Cl$_2$/EtOAc 4:1, then 3:2). The product (67 mg) was obtained as a pale yellow oil. $^1$H NMR (CDCl$_3$, 400 MHz) δ 7.73 (m, 2H), 7.27 (m, 4H), 6.63-6.41 (m, 1H), 4.85 (s, 4H), 4.10 (m, 2H), 3.96 (m, 1H), 3.41 (m, 2H), 2.02 (m, 3H), 1.85 (m, 1H), 1.47 (s, 9H).

3-(1,3-Dihydro-2H-isoindol-2-yl)-5-[(2(S)-pyrrolidinyl)methoxy]pyridine Hydrochloride

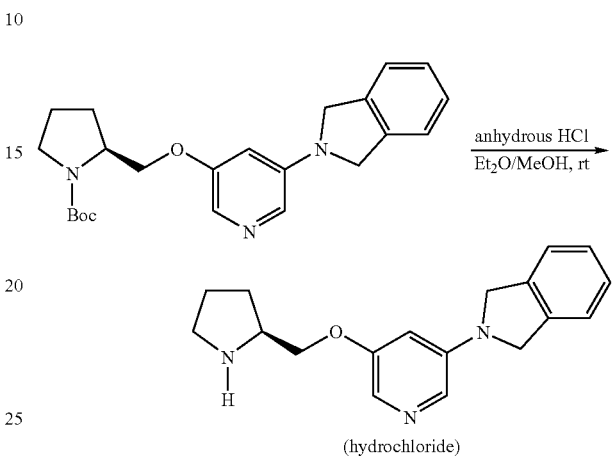

(hydrochloride)

To a solution of 3-[[1-(tert-butoxycarbonyl)-2(S)-pyrrolidinyl]methoxy]-5-(1,3-dihydro-2H-isoindol-2-yl)pyridine (266 mg, 0.67 mmol) in MeOH (0.5 mL) was added 2N anhydrous HCl/ether (2 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (column: ACE AQ, 150×21.2 mm; UV detection at 254 and 280 nm; flow 10.0 mL/min; 0-50% CH$_3$CN in water [both containing 0.05 vol % of CF$_3$COOH] in 25 min, to 100% in another 5 min; $t_R$ 17.5-20.0 min) to obtain the trifluoroacetate (178 mg). This salt (61 mg) was treated with PL-HCO3 MP anion exchange resin (Polymer Laboratories) in MeOH to afford the free amine, which was dissolved in MeOH (0.2 mL) and treated again with 2N anhydrous HCl/ether (1 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the hydrochloride (49 mg) was obtained as a grey solid. $[\alpha]^{20}_D$+1.1 (c 0.90 g/L, MeOH). $^1$H NMR (D$_2$O, 400 MHz) δ 7.54 (s, 1H), 7.40 (s, 1H), 7.17 (m, 4H), 6.83 (s, 1H), 4.38 (m, 1H), 4.22 (m, 5H), 4.10 (m, 1H), 3.46 (t, 2H, J=7.2 Hz), 2.33 (m, 1H), 2,18 (m, 2H), 1.98 (m, 1H). $^{13}$C NMR (D$_2$O, 100 MHz) δ 157.3, 156.1, 144.9, 134.9, 127.2, 122.0, 115.9, 109.8, 67.0, 58.1, 52.9, 45.6, 25.4, 23.0. HRMS (ESI) calcd for $C_{18}H_{22}N_3O$ (M+H$^+$) m/z 296.1763, found 296.1761. Anal. Calcd. for $C_{18}H_{21}N_3O$·2.9HCl·0.2H$_2$O: C, 53.42; H, 6.05; N, 10.38; Cl, 25.40. Found: C, 53.56; H, 6.22; N, 10.31, Cl, 25.48.

Example 51

Synthesis of 3-[4-[2-(Benzyloxy)ethyl]-1-piperidinyl]-5-[(2(S)-pyrrolidinyl)methoxy]pyridine 1-(tert-Butoxycarbonyl)-4-[2-(benzyloxy)ethyl]piperidine

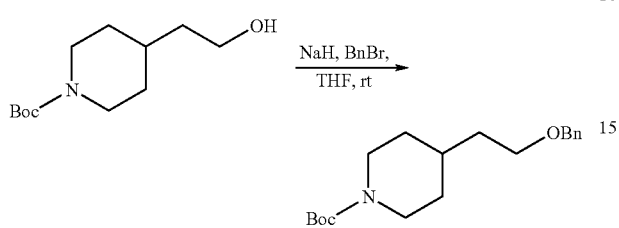

A solution of 1-(tert-butoxycarbonyl)-4-(2-hydroxyethyl)piperidine (5.03 g, 22.0 mmol) in anhydrous THF (73 mL) was cooled to 0° C., and NaH (60% dispersion in oil, 1.85 g, 44 mmol, 2 equiv.) was added all at once. Alkoxide formation was effected by stirring at room temperature for 2 h under $N_2$, then benzyl bromide (3.9 mL, 33 mmol, 1.5 equiv.) and tetra-n-butylammonium iodide (0.81 g, 2.2 mmol, 0.1 equiv.) were added. The mixture was stirred at room temperature for 20 h. At this point, TLC ($SiO_2$, EtOAc/hexane 1:1) indicated essentially complete conversion of the alcohol ($R_f$ approx. 0.3) to the benzyl ether ($R_f$ approx. 0.88). Saturated aqueous $NH_4Cl$ solution was added, and the product was extracted into EtOAc. The organic layer was dried over $MgSO_4$ and concentrated. The residue was chromatographed on $SiO_2$ with EtOAc/hexane increasing the proportion of EtOAc stepwise from 5% to 10%, 30%, and eventually 50%. Mixed fractions with nonpolar and polar impurities were chromatographed again. Overall, 5.7 g (81%) of the benzyl ether was obtained after evaporation. $^1$H NMR (CDCl$_3$, 400 MHz) δ 7.48-7.20 (m, 5H), 4.45 (s, 2H), 4.10-4.04 (m, 2H), 3.46 (t, 2H, J=6.0 Hz), 2.64 (m, 2H), 1.61-1.50 (m, 5H), 1.43 (s, 9H), 1.18-1.07 (m, 2H).

4-[2-(Benzyloxy)ethyl]piperidine

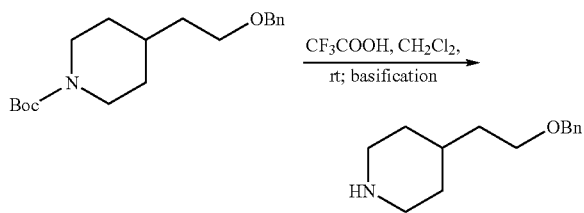

Trifluoroacetic acid (11.5 mL) was added dropwise to the solution of 1-(tert-butoxycarbonyl)-4-[2-(benzyloxy)ethyl]piperidine (4.15 g, 13.0 mmol) in $CH_2Cl_2$ (45 mL) at 0° C. under $N_2$. The solution was stirred overnight at room temperature. After evaporation, the mixture was dissolved in water, and the solution was washed with hexane before basification with saturated aqueous $NaHCO_3$ solution. The mixture was extracted three times with EtOAc, and the combined organic phases were dried over $Na_2SO_4$ and evaporated to afford the product (2.70 g, 95%) as a colorless solid. $^1$H NMR (CDCl$_3$, 400 MHz) δ 7.8 (br, 1H), 7.38-7.13 (m, 5H), 4.49 (s, 2H), 5.31 (t, 2H, J=6.0 Hz), 3.36 (m, 2H), 2.82 (m, 2H), 1.86-1.74 (m, 3H), 1.63-1.46 (m, 4H). MS (EI) m/z 220 (M+H$^+$, 0.4%), 218 (M$^+$–H, 0.9%), 128 (100%), 112 (20%), 91 (64%), 84 (17%), 82 (25%), 65 (13%).

3-[4-[2-(Benzyloxy)ethyl]-1-piperidinyl]-5-[[-1-(tert-butoxycarbonyl)-2(S)-pyrrolidinyl]methoxy]pyridine

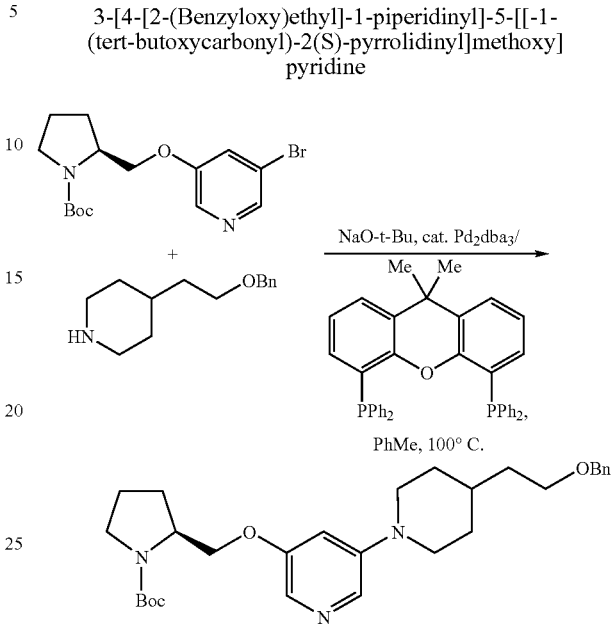

To a mixture of 3-bromo-5-[[1-(tert-butoxycarbonyl)-2(S)-pyrrolidinyl]methoxy]pyridine (72 mg, 0.20 mmol) and 4-[2-(benzyloxy)ethyl]piperidine (44 mg, 0.20 mmol) in anhydrous toluene (2.0 mL) were added successively sodium tert-butoxide (29 mg, 0.30 mmol, 1.5 equiv.), tris(dibenzylideneacetone)dipalladium(0) (3.7 mg, 4.0 μmol, 0.02 equiv.), and 4,5-bis(diphenylphosphino)-9,9-dimethylxanthene (Xantphos; 6.9 mg, 12 μmol, 0.06 equiv.). The mixture was degassed and purged with Ar (3 cycles), then warmed to 98-100° C. for 4 h. After cooling to room temperature, the mixture was diluted with EtOAc and washed with brine. The solution was dried over $Na_2SO_4$ and evaporated, and the residue was purified by CC ($SiO_2$, $CH_2Cl_2$/EtOAc 4:1 followed by $CH_2Cl_2$/MeOH 10:1) to recover first unreacted 3-bromo-5-[1-(tert-butoxycarbonyl)-2(S)-pyrrolidinyl]methoxy]pyridine (14 mg) and subsequently 3-[4-[2-(benzyloxy)ethyl]-1-piperidinyl]-5-[[1-(tert-butoxycarbonyl)-2(S)-pyrrolidinyl]methoxy]pyridine (67 mg, 85%) as a pale yellow oil. $^1$H NMR (CDCl$_3$, 400 MHz) δ 7.91-7.78 (m, 2H), 7.37-7.21 (m, 5H), 6.86-6.68 (m, 1H), 4.51 (s, 2H), 4.15 (m, 2H), 3.93-3.82 (m, 1H), 3.67 (m, 2H), 3.54 (t, 2H, J=6.0 Hz), 3.41 (m, 2H), 2.74 (m, 2H), 2.02-1.83 (m, 4H), 1.80-1.62 (m, 2H), 1.61-1.58 (m, 3H), 1.47 (s, 9H), 1.38-1.26 (m, 2H).

3-[4-[2-(Benzyloxy)ethyl]-1-piperidinyl]-5-[(2(S)-pyrrolidinyl)methoxy]pyridine Hydrochloride

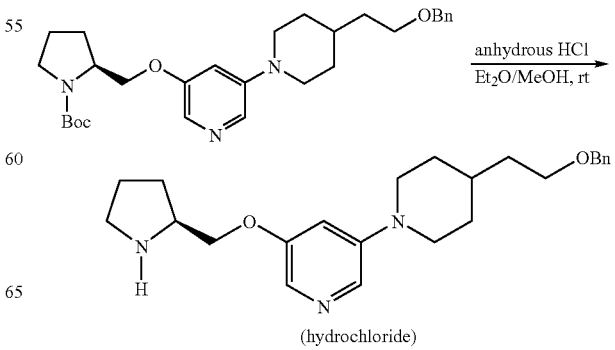

To a solution of 3-[4-[2-(benzyloxy)ethyl]-1-piperidinyl]-5-[[1-(tert-butoxycarbonyl)-2(S)-pyrrolidinyl]methoxy]pyridine (120 mg, 0.24 mmol) in MeOH (0.5 mL) was added 2N anhydrous HCl/ether (2 mL) under Ar at room temperature. The mixture was stirred at room temperature overnight. After the solvent was evaporated, the residue was dissolved in deionized water. The aqueous solution was washed three times with EtOAc, then filtered over a cotton plug. The water was removed under reduced pressure at 35° C., and the residue was purified by preparative HPLC (ACE AQ 150×21.2 mm; UV detection at 254 and 280 nm; flow 10.0 mL/min; gradient of 0 to 50% $CH_3CN$ in water [both containing 0.05 vol % $CF_3COOH$] in 25 min, to 100% in another 5 min; $t_R$ 12.8-19.4 min) to obtain, after evaporation, the trifluoroacetate (131 mg). This salt was treated with PL-HCO3 MP anion exchange resin (Polymer Laboratories) in MeOH to afford the free amine, which was dissolved in MeOH (0.5 mL) and treated again with 2N anhydrous HCl/ether (2 mL) under Ar protection at room temperature. The mixture was stirred at room temperature overnight. After the solvent was evaporated, the residue was dissolved in deionized water (approx. 25 mL). The solution was filtered over a cotton plug, and the water was removed under reduced pressure at 35° C. After lyophilization from water, the hydrochloride (103 mg) was obtained as a yellow glass. $[\alpha]^{20}_D$+1.8 (c 0.555 g/L, MeOH). $^1$H NMR ($D_2O$, 400 MHz) δ 7.89 (s, 1H), 6.67 (s, 1H), 7.32 (s, 1H), 7.26-7.18 (m, 5H), 4.49 (m, 3H), 4.37 (m, 1H), 4.17 (m, 1H), 3.63 (m, 2H), 3.44 (t, 2H, J=6.8 Hz), 3.27 (t, 2H, J=6.8 Hz), 2.82 (m, 2H), 2.16-2.13 (m, 1H), 2.02-1.93 (m, 2H), 1.90-1.79 (m, 1H), 1.60 (m, 2H), 1.42 (m, 1H), 1.38 (m, 2H), 1.11 (m, 2H). $^{13}$C NMR ($D_2O$, 100 MHz) δ 156.4, 148.8, 137.0, 128.2, 128.0, 127.7, 121.8, 117.3, 114.3, 72.0, 67.2, 58.1, 47.5, 45.6, 34.5, 31.2, 30.0, 25.4, 23.0. HRMS (ESI) calcd for $C_{24}H_{34}N_3O_2$ (M+H$^+$) m/z 396.2651, found 396.2637. Anal. Calcd. for $C_{24}H_{33}N_3O_2$·3.0HCl·0.85$H_2O$: C, 55.41; H, 7.30; N, 8.08; Cl, 20.44. Found: C, 55.64; H, 7.57; N, 8.21; Cl, 20.43.

Example 52

3-[4-[2-(3-Pyridylmethoxy)ethyl]-1-piperidinyl]-5-[(2(S)-pyrrolidinyl)methoxy]pyridine 1-(tert-Butoxycarbonyl)-4-[2-(3-pyridylmethoxy)ethyl]piperidine A solution of 1-(tert-butoxycarbonyl)-4-(2-hydroxyethyl)piperidine (459 mg, 2.0 mmol) in anhydrous DMF (10 mL) was cooled to 0° C., and NaH (60% dispersion in oil, 200 mg, 5 mmol, 2.5 equiv.) was added all at once. Alkoxide formation was effected by stirring at room temperature for 2 h under $N_2$, then 3-picolyl chloride hydrochloride (345 mg, 2.1 mmol, 1.05 equiv.) and tetra-n-butylammonium iodide (7.4 mg, 20 µmol, 0.01 equiv.) were added. The mixture was warmed to 80° C. and stirred at that temperature for 4 h. After cooling to room temperature, $H_2O$ was added, and the product was extracted into EtOAc. The organic layer was dried over $Na_2SO_4$ and concentrated. The residue was purified by CC ($SiO_2$, EtOAc/hexane 1:1) to afford 1-(tert-butoxycarbonyl)-4-[2-(3-pyridylmethoxy)ethyl]piperidine (574 mg, 80%) after evaporation as a colorless oil. $^1$H NMR (CDCl$_3$, 400 MHz) δ 8.39 (s, 1H), 8.33 (d, 1H, J=4.8 Hz), 7.54 (d, 1H, J=8.0 Hz), 7.11 (m, 1H), 4.71 (s, 2H), 3.89 (m, 2H), 3.46 (t, 2H, J=6.4 Hz), 2.74 (m, 2H), 1.44 (m, 3H), 1.31 (m, 2H), 1.24 (s, 9H), 0.88 (m, 2H); $^{13}$C NMR (CDCl$_3$, 100 MHz) δ 154.6, 149.1, 149.0, 136.2, 133.2, 123.5, 78.9, 59.2, 42.8, 39.0, 32.3, 31.9, 28.2.

4-[2-(3-Pyridylmethoxy)ethyl]piperidine

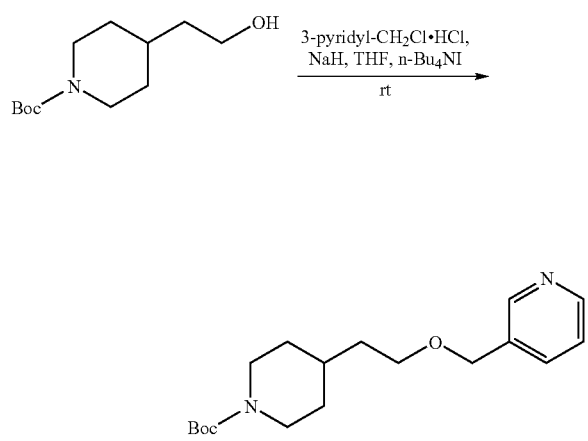

To a solution of 1-(tert-butoxycarbonyl)-4-[2-(3-pyridylmethoxyl)ethyl]piperidine (413 mg, 1.29 mmol) in dioxane (0.2 mL) was added 4N HCl/dioxane (1 mL, 4.0 mmol). The solution was stirred overnight. After evaporation, the residue was dissolved in deionized water. EtOAc was used to wash the aqueous layer before the pH was altered to approx. 9-10. The aqueous layer was extracted three times with $CH_2Cl_2$, and the combined organic phases were dried over $Na_2SO_4$. After evaporation, 4-[2-(3-pyridylmethoxy)ethyl]piperidine (100 mg, 35%) was obtained as a colorless oil. $^1$H NMR (CDCl$_3$, 400 MHz) δ 8.40 (m, 2H), 7.53 (d, 1H, J=7.6 Hz), 7.14 (m, 1H), 4.37 (s, 2H), 3.40 (t, 2H, J=6.0 Hz), 2.91 (d, 2H, J=12.0 Hz), 2.45 (t, 2H, J=11.6 Hz), 2.27 (s, 1H), 1.52 (d, 2H, J=12.4 Hz), 1.43 (m, 3H), 1.01 (m, 2H).

3-[[1-(tert-Butoxycarbonyl)-2(S)-pyrrolidinyl]methoxy]-5-[4-[2-(3-pyridylmethoxy)ethyl]-1-piperidinyl]pyridine

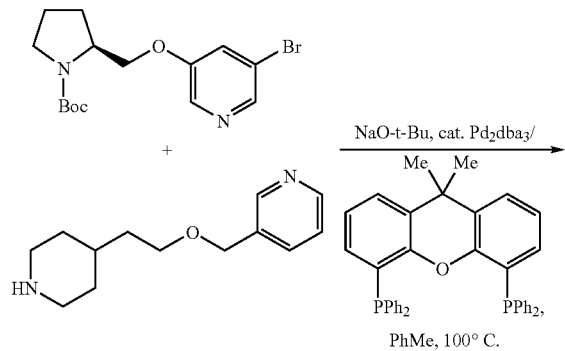

4-[2-(3-pyridylmethoxy)ethyl]piperidine (99.8 mg, 0.45 mmol, 1.1 equiv.) in anhydrous toluene (2 mL) were added successively potassium tert-butoxide (75 mg, 0.61 mmol, 1.5 equiv.), tris(dibenzylideneacetone)dipalladium(0) (7.5 mg, 8.0 μmol, 0.02 equiv.), and 4,5-bis(diphenylphosphino)-9,9-dimethylxanthene (Xantphos; 14.3 mg, 24 μmol, 0.06 equiv.). The mixture was degassed and purged with Ar (3 cycles), then warmed by microwave irradiation under Ar. After reaction for 30-40 minutes at 130° C., the mixture was cooled to room temperature, diluted with EtOAc, and washed with brine. The solution was dried over $Na_2SO_4$ and evaporated, and the residue was purified by CC ($SiO_2$, $CH_2Cl_2$/EtOAc 4:1 followed by $CH_2Cl_2$/MeOH 10:1). The product (182 mg, 89%) was obtained as a pale yellow oil. $^1$H NMR ($CDCl_3$, 400 MHz) δ 8.56 (br, 2H), 7.80 (m, 3H), 7.46 (m, 1H), 6.94 (m, 1H), 4.51 (s, 2H), 4.12 (m, 2H), 3.83 (m, 1H), 3.66 (m, 2H), 3.54 (m, 2H), 3.39 (m, 2H), 2.76 (t, 2H, J=11.2 Hz), 2.01-1.80 (m, 5H), 1.63 (m, 4H), 1.46 (s, 9H), 1.33 (m, 2H).

3-[4-[2-(3-Pyridylmethoxy)ethyl]-1-piperidinyl]-5-[(2(S)-pyrrolidinyl)methoxy]pyridine Hydrochloride

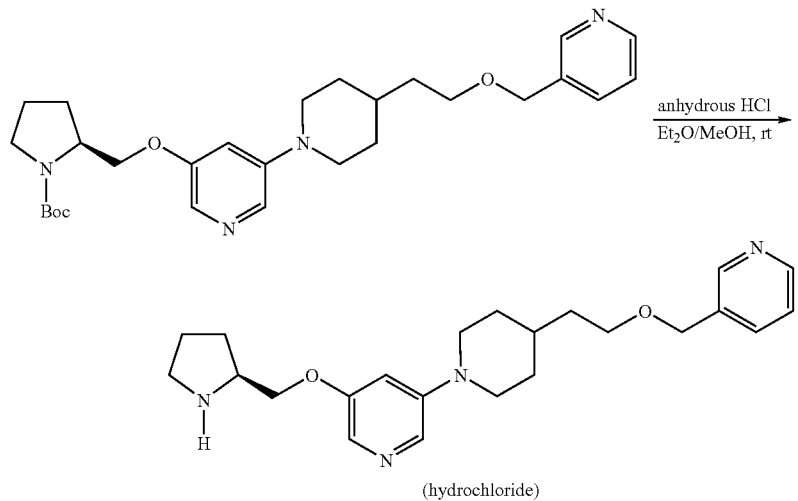

(hydrochloride)

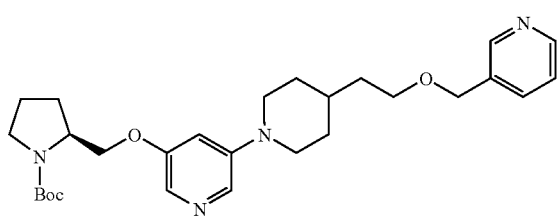

-continued

To a solution of 3-bromo-5-[[1-(tert-butoxycarbonyl)-2(R)-pyrrolidinyl]methoxy]pyridine (147 mg, 0.41 mmol) and To a solution of 3-[[1-(tert-butoxycarbonyl)-2(S)-pyrrolidinyl]methoxy]-5-[4-[2-(3-pyridylmethoxy)ethyl]-1-piperidinyl]pyridine (182 mg, 0.37 mmol) in dioxane (0.2 mL) was added 4N anhydrous HCl/dioxane (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (ACE AQ 150×21.2 mm; UV detection at 254 nm and 280 nm; flow 10.0 mL/min; 8-100% MeOH in water [both containing 0.1 vol % of $CF_3COOH$] in 30 min, then 100% for another 3 min; $t_R$ 15.8-17.8 min) to obtain the trifluoroacetate. This salt was treated with PL-HCO3 MP anion exchange resin (Polymer Laboratories) in MeOH to afford the free amine, which was dissolved in MeOH (0.5 mL) and treated again with 2N anhydrous HCl/ether (2 mL) under Ar protection at room temperature. The mixture was stirred at room temperature overnight. After the solvent was evaporated, the residue was dissolved in deionized water. After the solution was filtered over a cotton plug, the water was removed under reduced pressure at 35° C. After lyophilization from water, the product (53 mg) was obtained as a yellow glass. $^1$H NMR (D$_2$O, 400 MHz) δ 8.81 (s, 1H), 8.77 (d, 1H, J=6.0 Hz), 8.63 (d, 1H, J=8.0 Hz), 8.11 (dd, 1H, J=6.0, 8.0 Hz), 8.02 (d, 1H, J=2.4 Hz), 7.83 (d, 1H, J=2.0 Hz), 7.51 (t, 1H, J=2.0 Hz), 4.82 (s, 2H), 4.55 (dd, 1H, J=3.2, 11.2 Hz), 4.35 (dd, 1H, J=7.6, 11.2 Hz), 4.15 (m, 1H), 3.85 (d, 2H, J=12.8 Hz), 3.75 (t, 2H, J=6.4 Hz), 3.43 (t, 2H, J=7.2 Hz), 3.04 (m, 2H), 2.31 (m, 1H), 2.12 (m, 2H), 1.97 (m, 1H), 1.85 (d, 2H, J=12.8 Hz), 1.70 (m, 1H), 1.66 (m, 2H), 1.34 (m, 2H); $^{13}$C NMR (D$_2$O, 100 MHz) δ 156.5, 149.1, 145.7, 140.0, 139.4, 138.3, 126.9, 121.9, 117.3, 114.3, 68.4, 67.8, 67.2, 58.1, 47.4, 45.6, 34.5, 31.2, 30.0, 25.4, 23.1.

Example 53

3-[3(R)-[3-(Benzyloxy)propyl]-1-pyrrolidinyl]-5-[(2(S)-pyrrolidinyl)methoxy]pyridine

(E)-Butyl 3-(1H-Pyrrol-3-yl)acrylate

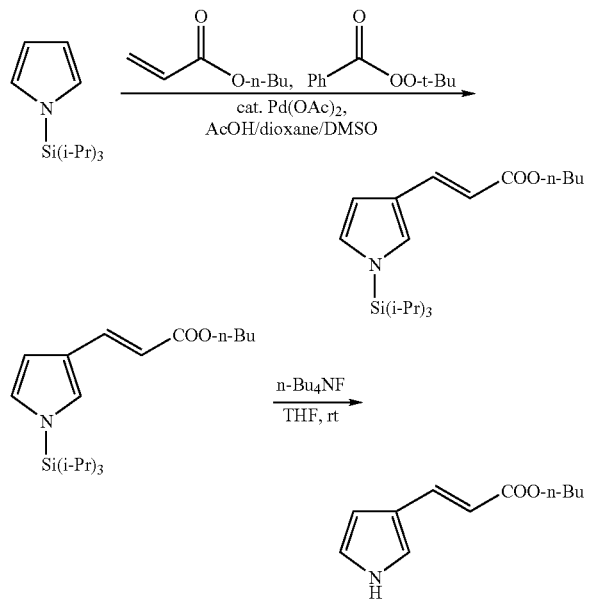

Palladium(II) acetate (0.05 equiv.) was added to a solution of n-butyl acrylate (0.27 mL, 1.5 mmol, 0.50 equiv.), 1-(triisopropylsilyl)-1H-pyrrole (1.34 g, 3.00 mmol), and tert-butyl peroxybenzoate (0.56 mL, 1.5 mmol, 0.50 equiv.), in acetic acid/dioxane/dimethylsulfoxide (0.23/0.69/0.08 mL). The mixture was stirred at 35° C. for 24 h, diluted with diethyl ether (200 mL) and water (20 mL), and filtered through a plug of celite. The organic phase was separated and washed with saturated NaHCO$_3$ solution (2×30 mL) and water (30 mL). The combined aqueous layers were further extracted with CH$_2$Cl$_2$. The combined organic extracts were dried over MgSO$_4$, filtered, and concentrated in vacuo. The residue was purified by CC (SiO$_2$, EtOAc/petroleum ether 1:20) to give (E)-butyl 3-[1-(triisopropylsilyl)-1H-pyrrol-3-yl]acrylate (0.70 g, 67%) as a light-yellow oil.

To a solution of (E)-butyl 3-[1-(triisopropylsilyl)-1H-pyrrol-3-yl]acrylate (10.0 g, 28.7 mmol) in 200 mL of THF was added tetra-n-butylammonium fluoride trihydrate (7.5 g, 23.8 mmol, 0.83 equiv.) at room temperature under N$_2$. The solution was stirred for 30 min at room temperature, diluted with EtOAc (500 mL), and washed with water (2×100 mL). The organic layer was dried over Na$_2$SO$_4$ and concentrated under vacuum. The residue was applied onto a silica gel column, which was eluted with EtOAc/petroleum ether 1:5 to afford (E)-butyl 3-(1H-pyrrol-3-yl)acrylate (4.0 g, 72%) as a light yellow solid. LC-MS (ESI) m/z 194 (M+H$^+$).

Butyl 3-(1H-Pyrrol-3-yl)propionate

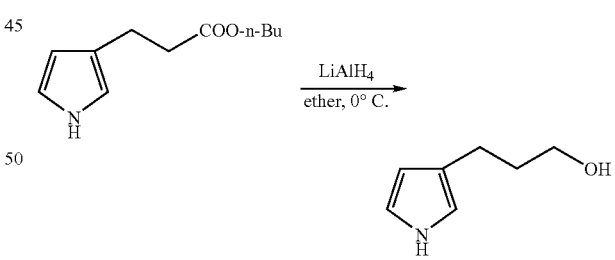

To a solution of (E)-butyl 3-(1H-pyrrol-3-yl)acrylate (2.0 g, 10.4 mmol) in 50 mL of THF was added Pd (10% on activated carbon; 0.50 g). The solution was deoxygenated under vacuum, and H$_2$ was introduced to the reaction flask from a balloon. The process was repeated three times, and the reaction mixture was stirred for 4 h at room temperature. The mixture was filtered through celite, and the filtrate was evaporated under reduced pressure to yield butyl 3-(1H-pyrrol-3-yl)propionate (2.0 g, 99%) as a light-yellow oil. LC-MS (ESI) m/z 196 (M+H$^+$).

3-(1H-Pyrrol-3-yl)-1-propanol

To a solution of butyl 3-(1H-pyrrol-3-yl)propionate (14.1 g, 72.3 mmol) in ether (400 mL) was added LiAlH$_4$ (4.12 g, 108 mmol, 1.50 equiv.) at 0° C. under N$_2$. The solution was stirred for 2 h at 0° C., and the reaction was cautiously quenched with saturated aqueous NH$_4$Cl. The resulting solution was extracted with ether (3×150 mL). The combined organic layers were dried and concentrated under vacuum to give 3-(1H-pyrrol-3-yl)-1-propanol (8.0 g, 89%) as a light-yellow oil. $^1$H NMR (CDCl$_3$, 300 MHz) δ 8.11 (br, 1H), 6.76

(s, 1H), 6.63 (s, 1H), 6.14 (s, 1H), 3.73 (t, 2H, J=6.6 Hz), 2.62 (t, 2H, J=7.5 Hz), 1.85-1.94 (m, 2H). LC-MS (ESI) m/z 126 (M+H⁺).

3-(3-Pyrrolidinyl)-1-propanol

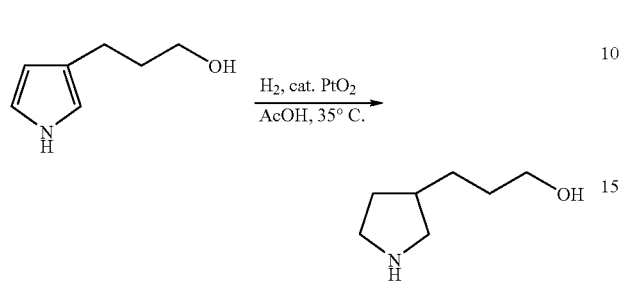

A solution of 3-(1H-pyrrol-3-yl)-1-propanol (400 mg, 3.20 mmol) in 5 mL of freshly distilled glacial acetic acid containing 40 mg of platinum(IV) oxide was hydrogenated with a H₂ balloon for 2 h at 35° C. The catalyst was removed by filtration, and the solvent was evaporated. The residue was heated under reflux for 0.5 h with 4 mL of 30% aqueous NaOH solution to saponify any acetate ester that may have formed. The mixture was extracted with CH₂Cl₂, and the organic phase was concentrated to obtain the crude pyrrolidine (0.35 g, 85%) as a light-yellow oil, which could be used without purification in the following step. ¹H NMR (CDCl₃, 300 MHz) δ 3.66 (t, 2H, J=6.3 Hz), 2.62 (dd, 1H, J=7.2, 10.5 Hz), 2.91-2.99 (m, 2H), 2.51 (dd, 1H, J=7.2, 10.8 Hz), 1.93-2.15 (m, 2H), 1.56-1.65 (m, 2H), 1.46 (t, 2H, J=7.2 Hz), 1.37-1.41 (m, 2H). LC-MS (ESI) m/z 130 (M+H⁺).

3-[1-(tert-Butoxycarbonyl)-3-pyrrolidinyl]-1-propanol

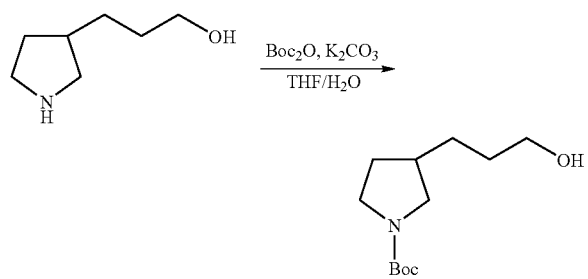

To a solution of 3-(3-pyrrolidinyl)-1-propanol (1.60 g, 12.4 mmol) and K₂CO₃ (5.0 g, 36 mmol, 2.9 equiv.) in THF/H₂O (80/80 mL) was added di-tert-butyl dicarbonate (3.4 mL, 14.8 mmol, 1.2 equiv.) at room temperature under N₂. The solution was stirred for 16 h at room temperature. Saturated aqueous NH₄Cl solution (30 mL) was added. The mixture was extracted with EtOAc, and the organic phase was concentrated under vacuum. The residue was purified by CC (SiO₂, EtOAc/petroleum ether 1:2) to afford a light-yellow solid (1.60 g, 56%). ¹H NMR (CDCl₃, 300 MHz) δ 3.68 (t, 2H, J=6.3 Hz), 3.57 (dd, 1H, J=7.5, 10.5 Hz), 3.44-3.51 (m, 1H), 3.22-3.31 (m, 1H), 2.90 (dd, 1H, J=8.7, 10.5 Hz), 2.09-2.17 (m, 1H), 1.97-2.06 (m, 1H), 1.57-1.69 (m, 3H), 1.49-1.53 (m, 2H), 1.48 (s, 9H). LC-MS (ESI) m/z 230 (M+H⁺).

tert-Butyl 3-[3-(Benzyloxy)propyl]pyrrolidine-1-carboxylate

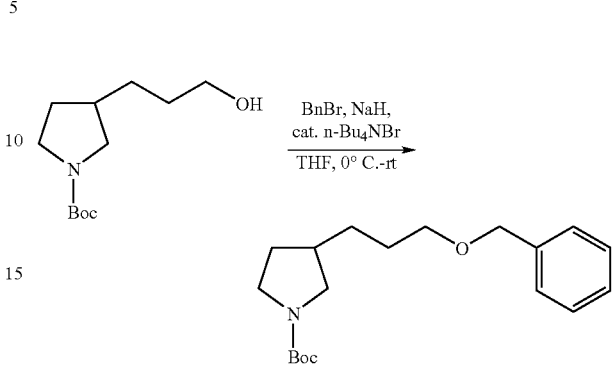

NaH (0.92 g, 38 mmol, 1.7 equiv.) was added to a solution of 3-[1-(tert-butoxycarbonyl)-3-pyrrolidinyl]-1-propanol (5.11 g, 22.3 mmol) in anhydrous THF (180 mL) at 0° C. under N₂. The mixture was warmed to room temperature and stirred for about 2 h. Then benzyl bromide (3.2 mL, 26.9 mmol, 1.2 equiv.) and tetra-n-butylammonium bromide (0.72 g, 2.2 mmol, 0.10 equiv.) were added at room temperature. The solution was stirred for 20 h at room temperature, after which time period the reaction was completed as judged by TLC analysis (SiO₂, EtOAc/petroleum ether 1:10). The reaction was then quenched by the addition of 20 mL of saturated aqueous NH₄Cl solution. The product was extracted into EtOAc (3×60 mL), and the combined organic layers were washed with brine. After concentration in vacuo, the residue was applied onto a silica gel column, which was eluted with EtOAc/petroleum ether 1:20-1:10 to provide the product (6.20 g, 87%) as a colorless oil. ¹H NMR (CDCl₃, 300 MHz) δ 7.30-7.37 (m, 5H), 4.52 (s, 2H), 3.42-3.57 (m, 4H), 3.23-3.30 (m, 1H), 2.89 (dd, 1H, J=10.5, 8.7 Hz), 2.06-2.12 (m, 1H), 1.96-2.01 (m, 1H), 1.61-1.69 (m, 2H), 1.47-1.51 (m, 3H), 1.48 (s, 9H).

tert-Butyl 3(R)-(3-(Benzyloxy)propyl)pyrrolidine-1-carboxylate and tert-Butyl 3(S)-(3-(Benzyloxy)propyl)pyrrolidine-1-carboxylate

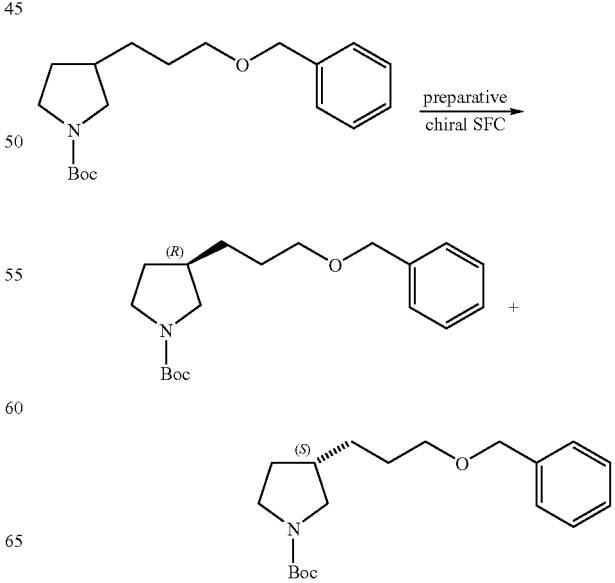

The racemate (5.0 g) was separated by preparative supercritical fluid chromatography (column: Chiralcel OJ-H-SFC, 25×2.1 cm, 5 μm particle size; UV detection at 220 nm; flow 40 g/min; mobile phase: CO$_2$/MeOH 95:5). The R-isomer [1.8 g; t$_R$ 9.90 min; [α]$_D^{26}$+14.0 (c 20 g/L, CHCl$_3$); enantiomeric excess 99.5%] and S-isomer [1.8 g; t$_R$ 11.48 min; [α]$_D^{26}$−13.5 (c 20 g/L, CHCl$_3$); enantiomeric excess 99.0%] were obtained as colorless oils. Analytical HPLC of the racemate on a 250×4.6 mm Chiralcel OJ-H column run with EtOH/hexane 8:92 at a flow of 1.0 mL/min with UV detection at 210 nm shows two peaks with retention times of 7.38 and 8.45 min.

The absolute configuration of the individual enantiomers was established by independent synthesis of the dextrorotatory isomer from commercially available 1-(tert-butoxycarbonyl)pyrrolidine-2(R)-carboxylic acid ((R)—N-Boc-beta-proline) as shown below.

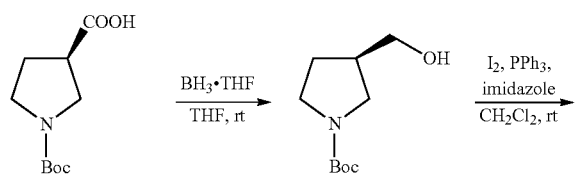

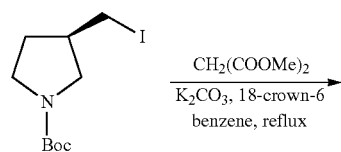

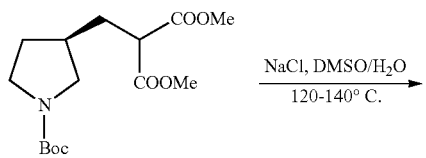

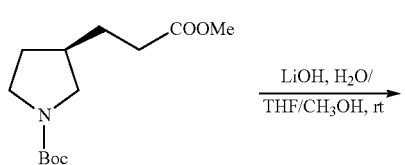

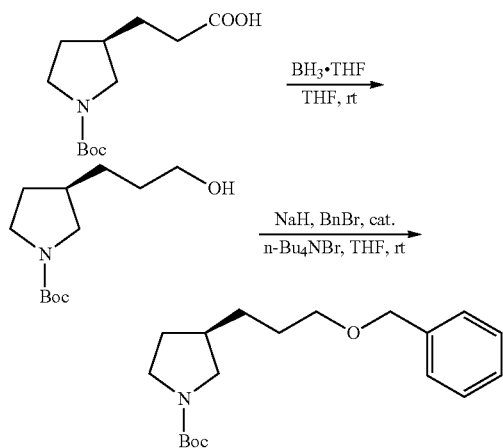

3(R)-[3-(Benzyloxy)propyl]pyrrolidine

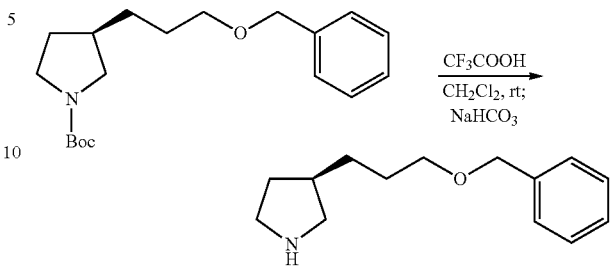

To a solution of tert-butyl 3(R)-[3-(benzyloxy)propyl]pyrrolidine-1-carboxylate (170 mg, 0.53 mmol) in 2 mL of CH$_2$Cl$_2$ was added CF$_3$COOH (0.5 mL) at room temperature under N$_2$. The solution was stirred for 3 h at room temperature and then concentrated under vacuum. To the residue was added 20 mL of water, and the solution was washed with 30 mL of petroleum ether. The aqueous layer was adjusted to pH 8.0 with 2M aqueous NaHCO$_3$ solution. The product was extracted into CH$_2$Cl$_2$ (3×40 mL), and the combined organic layers were dried over Na$_2$SO$_4$ and concentrated in vacuo to give the free amine (115 mg, 99%) as a yellowish oil. LC-MS (ESI) m/z 220 (M+H$^+$).

3-[3(R)-[3-(Benzyloxy)propyl]-1-pyrrolidinyl]-5-[[1-(tert-butoxycarbonyl)-2(S)-pyrrolidinyl]methoxy]pyridine

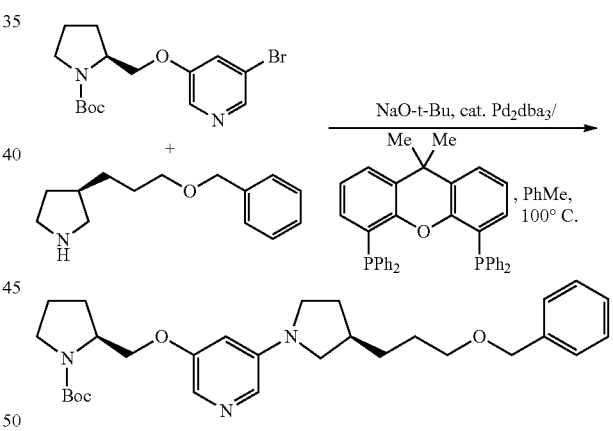

To a solution of 3(R)-[3-(benzyloxy)propyl]pyrrolidine (350 mg, 1.60 mmol) and 3-bromo-5-[[1-(tert-butoxycarbonyl)-2(S)-pyrrolidinyl]methoxy]pyridine (627 mg, 1.76 mmol, 1.1 equiv.) in 10 mL of anhydrous toluene were added successively at room temperature sodium tert-butoxide (307 mg, 3.20 mmol, 2.0 equiv.), tris(dibenzylideneacetone)dipalladium(0) (99 mg, 0.10 mmol, 0.06 equiv.) and 4,5-bis(diphenylphosphino)-9,9-dimethylxanthene (Xantphos, 111 mg, 0.19 mmol, 0.12 equiv.). The mixture was degassed and purged with nitrogen (3 cycles) and then heated to 98-100° C. After 4 h, the mixture was cooled to room temperature, diluted with EtOAc, and washed with brine. After drying over Na$_2$SO$_4$, the solvent was evaporated, and the residue was purified by CC (SiO$_2$, CH$_2$Cl$_2$/EtOAc 8:1 to 3:1) to obtain the product (791 mg, 63%) as a light yellow oil. LC-MS (ESI) m/z 496 (M+H$^+$).

3-[3(R)-[3-(Benzyloxy)propyl]-1-pyrrolidinyl]-5-[(2 (S)-pyrrolidinyl)methoxy]pyridine

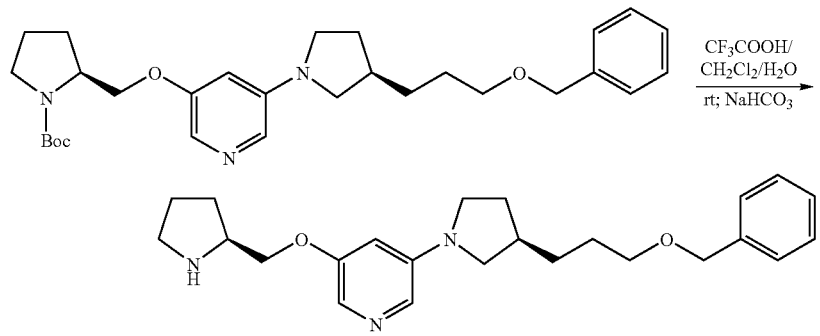

To a 25 mL round-bottom flask containing a solution of 3-[3(R)-[3-(benzyloxy)propyl]-1-pyrrolidinyl]-5-[[1-(tert-butoxycarbonyl)-2(S)-pyrrolidinyl]methoxy]pyridine (500 mg, 1.01 mmol) in CH$_2$Cl$_2$/H$_2$O (7.5/0.15 mL) was added CF$_3$COOH (1.5 mL) at 0° C. under N$_2$. The reaction mixture was stirred for 3 h at room temperature. After evaporation under reduced pressure, the crude product (500 mg) was purified by preparative HPLC (column: SunFire Prep C$_{18}$, 150×19 mm, 5 μm particle size; UV detection at 220 and 254 nm; flow 20 mL/min; mobile phase: A, water with 0.05% CF$_3$COOH; B, methanol; 40-100% of B in A in 8 min, back to 40% in 1 min). The eluate was partially evaporated under reduced pressure (bath 30° C.) to remove CH$_3$OH. The residue was basified with saturated aqueous NaHCO$_3$ solution and extracted with EtOAc. The combined organic layers were washed with brine and dried over Na$_2$SO$_4$. After concentration in vacuo, the free base (280 mg, 70%) was obtained as a light-yellow solid. $^1$H NMR (CDCl$_3$, 300 MHz) δ 7.65 (s, 1H), 7.61 (s, 1H), 7.37-7.33 (m, 5H), 6.33 (s, 1H), 4.54 (s, 2H), 4.01-3.97 (m, 2H), 3.69-3.59 (m, 1H), 3.53 (t, J=6.3 Hz, 2H), 3.50-3.20 (m, 4H), 3.09-3.06 (m, 2H), 2.90 (t, 1H, J=6.3 Hz), 2.38-2.10 (m, 2H), 2.03-1.83 (m, 3H), 1.79-1.51 (m, 5H). LC-MS (ESI) m/z 396 (M+H$^+$).

3-[3(R)-[3-(Benzyloxy)propyl]-1-pyrrolidinyl]-5-[(2 (S)-pyrrolidinyl)methoxy]pyridine Hydrochloride

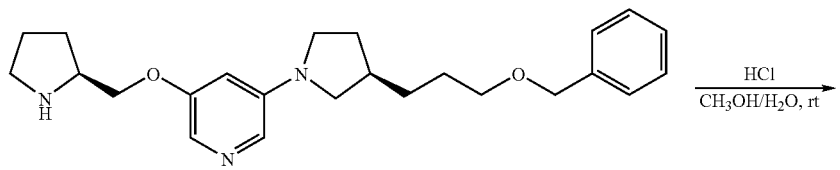

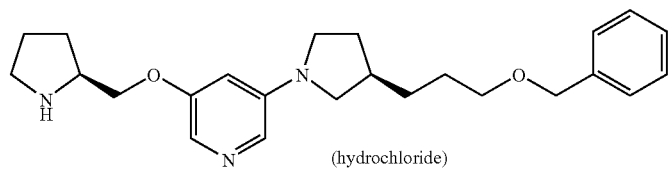
(hydrochloride)

To a solution of 3-[3(R)-[3-(benzyloxy)propyl]-1-pyrrolidinyl]-5-[(2(S)-pyrrolidinyl)methoxy]pyridine (210 mg, 0.53 mmol) in methanol (0.4 mL) was added 2 N hydrochloric acid (0.88 mL, 3.3 equiv.) under N$_2$. The mixture was stirred for 4 h at room temperature. After evaporation in vacuo, the residue was diluted with water (12 mL) and lyophilized. The lyophilization process was repeated three times to obtain the hydrochloride (250 mg) as a yellowish solid. $^1$H NMR (D$_2$O, 300 MHz) δ 7.56 (s, 1H), 7.51 (s, 1H), 7.37-7.27 (m, 5H), 6.92 (s, 1H), 4.48 (s, 2H), 4.47 (dd, 1H, J=6.6, 9.9 Hz), 4.25 (dd, 1H, J=7.5, 10.5 Hz), 4.07-4.03 (m, 1H), 3.54 (t, 2H, J=6.3 Hz), 3.45-3.24 (m, 5H), 2.89 (t, 1H, J=8.4 Hz), 2.03-1.95 (m, 5H), 1.91-1.80 (m, 1H), 1.74-1.51 (m, 3H), 1.48-1.38 (m, 2H). LC-MS (ESI) m/z 396 (M+H⁺). Anal. Calcd. for C$_{24}$H$_{33}$N$_3$O$_2$.2.05HCl.0.6H$_2$O: C, 59.92; H, 7.59; N, 8.73; Cl, 15.11. Found: C, 59.86; H, 8.08; N, 8.63; Cl, 15.57.

Example 54

3-[1-[5-[(2(S)-Pyrrolidinyl)methoxy]-3-pyridyl]-3 (S)-pyrrolidinyl]-1-propanol

3-[1-[5-[(2(S)-Pyrrolidinyl)methoxy]-3-pyridyl]-3 (S)-pyrrolidinyl]-1-propanol

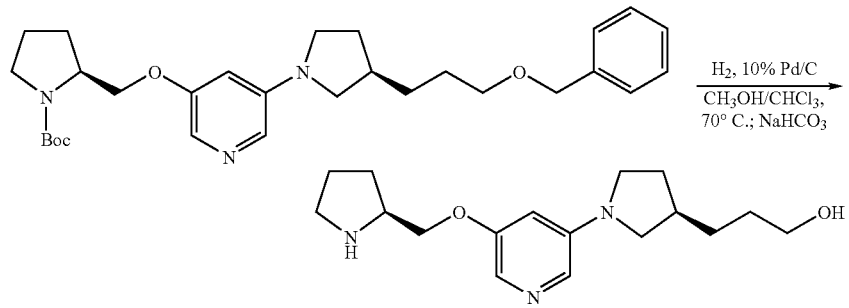

In a 100 mL round-bottom flask with reflux condenser, 10% palladium on carbon (100 mg) was added to a solution of 3-[3(R)-[3-(benzyloxy)propyl]-1-pyrrolidinyl]-5-[[1-(tert-butoxycarbonyl)-2(S)-pyrrolidinyl]methoxy]pyridine (500 mg, 1.01 mmol) in a mixed solvent of methanol/CHCl$_3$ (40/5 mL). The reaction mixture was deoxygenated under vacuum, then H$_2$ was admitted from a balloon placed above the condenser. The process was repeated three times, and the reaction mixture was stirred for 16 h at 70° C. in an oil bath. After cooling, the mixture was filtered through celite, and the filtrate was evaporated under reduced pressure. The crude product (340 mg) was purified by preparative HPLC (column: SunFire Prep C$_{18}$, 100×19 mm, 5 µm particle size; UV detection at 220 nm; flow 20 mL/min; mobile phase: A, water with 0.05% CF$_3$COOH; B, CH$_3$OH; 15 to 100% B in A within 7 min). The eluate was partially evaporated under reduced pressure (bath 30° C.) to remove CH$_3$OH. The residue was basified with saturated aqueous NaHCO$_3$ solution and extracted with EtOAc. The combined organic layers were washed with brine and dried. After concentration in vacuo, the free base (250 mg, 81%) was obtained as a light-yellow oil. ¹H NMR (CD$_3$OD, 300 MHz) δ 7.54 (s, 1H), 7.50 (s, 1H), 6.53 (s, 1H), 4.10-4.04 (m, 1H), 3.99-3.97 (m, 1H), 3.61 (t, 2H, J=6.0 Hz), 3.53-3.50 (m, 2H), 3.35-3.30 (m, 1H), 3.00-2.94 (m, 3H), 2.38-2.18 (m, 2H), 2.09-1.95 (m, 2H), 1.91-1.81 (m, 2H), 1.71-1.51 (m, 6H). LC-MS (ESI) m/z 306 (M+H⁺).

3-[1-[5-[(2(S)-Pyrrolidinyl)methoxy]-3-pyridyl]-3 (R)-pyrrolidinyl]-1-propanol Hydrochloride

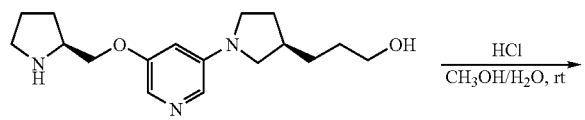

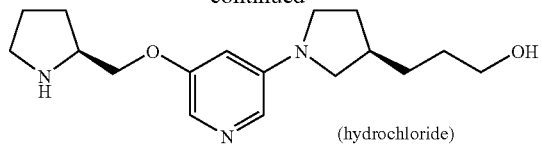

To a solution of 3-[1-[5-[(2(S)-pyrrolidinyl)methoxy]-3-pyridyl]-3(R)-pyrrolidinyl]-1-propanol (120 mg, 0.39 mmol) in methanol (0.3 mL) was added 2N hydrochloric acid (0.64 mL, 3.3 equiv.) under N$_2$. The reaction mixture was stirred for 4 h at room temperature. After evaporation in vacuo, the residue was diluted with water (12 mL) and lyophilized. The lyophilization process was repeated three times to obtain the hydrochloride (150 mg) as a light-yellow solid. ¹H NMR (D$_2$O, 300 MHz) δ 7.56 (s, 1H), 7.53 (s, 1H), 6.95 (s, 1H), 4.44 (d, 1H, J=10.5 Hz), 4.24 (t, 1H, J=8.1 Hz), 4.06-4.04 (m, 1H), 3.57-3.26 (m, 7H), 2.92 (t, 1H, J=8.7 Hz, 1H), 2.32-1.98 (m, 5H), 1.97-1.83 (m, 1H), 1.68-1.54 (m, 5H). LC-MS (ESI) m/z 306 (M+H⁺). Anal. Calcd. for C$_{17}$H$_{27}$N$_3$O$_2$.2.3HCl.1.0H$_2$O: C, 50.13; H, 7.75; N, 10.32. Found: C, 50.15; H, 7.85; N, 10.20.

Example 55

3-[3(S)-[3-(Benzyloxy)propyl]-1-pyrrolidinyl]-5-[(2 (S)-pyrrolidinyl)methoxy]pyridine 3(S)-[3-(Benzyloxy)propyl]pyrrolidine

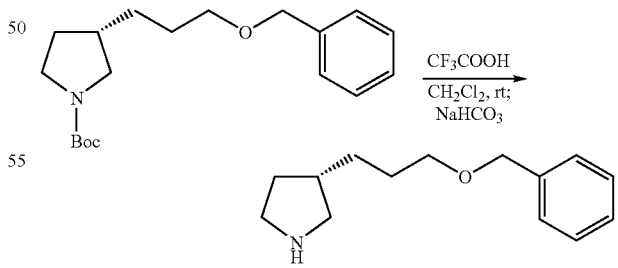

To a solution of tert-butyl 3(S)-[3-(benzyloxy)propyl]pyrrolidine-1-carboxylate (495 mg, 1.55 mmol) in 6 mL of CH$_2$Cl$_2$ was added CF$_3$COOH (1.5 mL) at room temperature under N$_2$. The resulting solution was stirred for 3 h at room temperature and then concentrated under vacuum. To the residue was added 20 mL of water, and the solution was washed with 30 mL of petroleum ether. The water layer was adjusted to pH 8.0 with 2 M aqueous NaHCO₃ solution and extracted with CH₂Cl₂ (3×40 mL). The organic layers were dried over Na₂SO₄ and concentrated in vacuo to give 3(S)-[3-(benzyloxy)propyl]pyrrolidine (330 mg, 97%) as a yellowish oil. LC-MS (ESI) m/z 220 (M+H⁺).

3-[3(S)-[3-(Benzyloxy)propyl]-1-pyrrolidinyl]-5-[[1-(tert-butoxycarbonyl)-2(S)-pyrrolidinyl]methoxy]pyridine

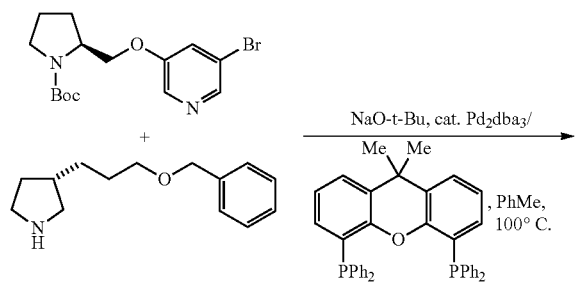

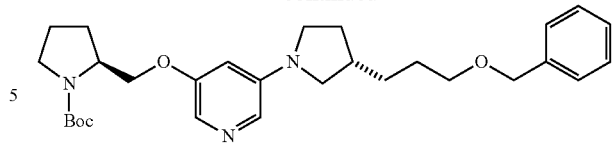

To a solution of 3(S)-[3-(benzyloxy)propyl]pyrrolidine (330 mg, 1.51 mmol) and 3-bromo-5-[[1-(tert-butoxycarbonyl)-2(S)-pyrrolidinyl]methoxy]pyridine (592 mg, 1.66 mmol, 1.1 equiv.) in 10 mL of anhydrous toluene were added successively at room temperature sodium tert-butoxide (290 mg, 3.02 mmol, 2.0 equiv.), tris(dibenzylideneacetone)dipalladium(0) (94 mg, 0.09 mmol, 0.06 equiv.), and 4,5-bis(diphenylphosphino)-9,9-dimethylxanthene (Xantphos, 105 mg, 0.18 mmol, 0.12 equiv.). The mixture was degassed and purged with nitrogen (3 cycles) and then heated to 98-100° C. After 4 h, the mixture was cooled to room temperature, diluted with EtOAc, and washed with brine. After drying over Na₂SO₄, the solvent was evaporated, and the residue was purified by CC (SiO₂, CH₂Cl₂/EtOAc 8:1 to 3:1) to obtain the title product (746 mg, 68%) as a light yellow oil. LC-MS (ESI) m/z 496 (M+H⁺).

3-[3(S)-[3-(Benzyloxy)propyl]-1-pyrrolidinyl]-5-[(2(S)-pyrrolidinyl)methoxy]pyridine

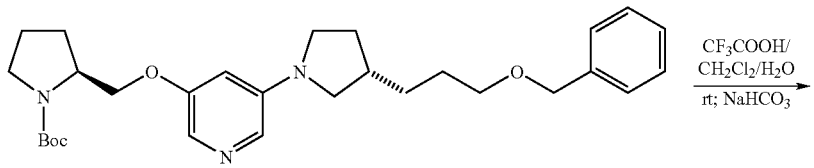

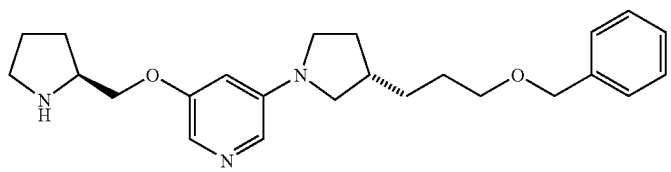

To a 25 mL round-bottom flask containing a solution of 3-[3(S)-[3-(benzyloxy)propyl]-1-pyrrolidinyl]-5-[[1-(tert-butoxycarbonyl)-2(S)-pyrrolidinyl]methoxy]pyridine (500 mg, 1.01 mmol) in $CH_2Cl_2/H_2O$ (7.5/0.15 mL) was added $CF_3COOH$ (1.5 mL) at 0° C. under $N_2$. The reaction mixture was stirred for 3 h at room temperature. After evaporation under reduced pressure, the crude product (310 mg) was purified by preparative HPLC (column: SunFire Prep $C_{18}$, 150×19 mm, 5 μm particle size; UV detection at 270 nm; flow 20 mL/min; mobile phase: A, water with 0.05% $CF_3COOH$; B, methanol; 40-50% B in A in 6 min, 50-100% in 1 min, back to 40% in 1 min). The eluate was partially evaporated under reduced pressure (bath 30° C.) to remove $CH_3OH$. The residue was washed with saturated aqueous $NaHCO_3$ solution and extracted with EtOAc. The combined organic layers were washed with brine and dried. After concentrated in vacuo, the free amine (280 mg, 70%) was obtained as light-yellow solid. $^1H$ NMR ($CDCl_3$, 300 MHz) δ 7.66 (s, 1H), 7.61 (s, 1H), 7.37-7.30 (m, 5H), 6.34 (s, 1H), 4.54 (s, 2H), 4.01-3.94 (m, 2H), 3.54-3.49 (m, 3H), 3.48-3.22 (m, 3H), 3.12-3.00 (m, 2H), 2.91 (t, 1H, J=9.6 Hz), 2.36-2.23 (m, 1H), 2.21-2.10 (m, 1H), 2.06-1.79 (m, 3H), 1.76-1.50 (m, 6H). LC-MS (ESI) m/z 396 (M+H$^+$).

3-[3(S)-[3-(Benzyloxy)propyl]-1-pyrrolidinyl]-5-[(2 S)-pyrrolidinyl)methoxy]pyridine Hydrochloride

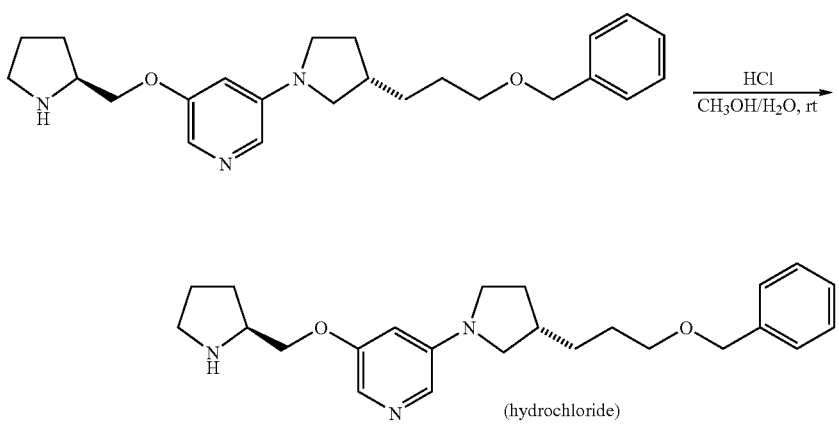

To a solution of 3-[3(S)-[3-(benzyloxy)propyl]-1-pyrrolidinyl]-5-[(2(S)-pyrrolidinyl)methoxy]pyridine (150 mg, 0.38 mmol) in methanol (0.3 mL) was added 2 N hydrochloric acid (0.63 mL, 3.3 equiv.) under $N_2$. The reaction mixture was stirred for 4 h at room temperature. After evaporation in vacuo, the residue was diluted with water (12 mL) and lyophilized. The lyophilization process was repeated three times to obtain the hydrochloride (170 mg, 88%) as a yellowish solid. $^1H$ NMR ($D_2O$, 300 MHz) δ 7.56 (s, 1H), 7.50 (s, 1H), 7.34-7.30 (m, 5H), 6.92 (s, 1H), 4.47 (s, 2H), 4.44 (dd, 1H, J=10.5, 3.3 Hz), 4.24 (dd, 1H, J=10.5, 7.5 Hz), 4.06-4.03 (m, 1H), 3.53 (t, 2H, J=6.3 Hz), 3.44-3.23 (m, 5H), 2.89 (t, 1H, J=8.4 Hz), 2.03-1.95 (m, 5H), 1.91-1.80 (m, 1H), 1.74-1.51 (m, 3H), 1.48-1.38 (m, 2H). LC-MS (ESI) m/z 396 (M+H$^+$). Anal. Calcd. for $C_{24}H_{33}N_3O_2 \cdot 2.3HCl \cdot 1.65H_2O$: C, 56.62; H, 7.64; N, 8.25; Cl, 16.02. Found: C, 56.53; H, 7.93; N, 8.51; Cl, 16.31.

Example 56

3-[1-[5-[(2(S)-Pyrrolidinyl)methoxy]-3-pyridyl]-3-(S)-pyrrolidinyl]-1-propanol

3-[1-[5-[(2(S)-Pyrrolidinyl)methoxy]-3-pyridyl]-3-(S)-pyrrolidinyl]-1-propanol

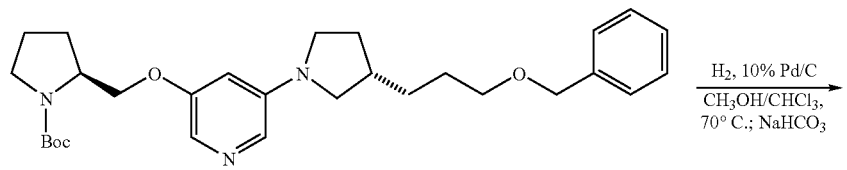

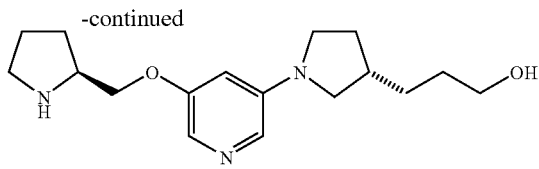

In a 100 mL round-bottom flask with reflux condenser, 10% palladium on carbon (100 mg) was added to a solution of 3-[3(S)-[3-(benzyloxy)propyl]-1-pyrrolidinyl]-5-[[1-(tert)-butoxycarbonyl)-2(S)-pyrrolidinyl]methoxy]pyridine (500 mg, 1.01 mmol) in a mixed solvent of methanol/CHCl$_3$ (40/5 mL). The reaction mixture was deoxygenated under vacuum, then H$_2$ was admitted from a balloon placed above the condenser. The process was repeated three times, and the reaction mixture was stirred for 16 h at 70° C. in an oil bath. After cooling, the mixture was filtered through celite, and the filtrate was evaporated under reduced pressure. The crude product (290 mg) was purified by preparative HPLC (column: SunFire Prep C$_{18}$, 100×19 mm, 5 μm particle size; UV detection at 220 nm; flow 20 mL/min; mobile phase: A, water with 0.05% CF$_3$COOH; B, CH$_3$OH; 15 to 100% B in A within 7 min). The eluate was partially evaporated under reduced pressure (bath 30° C.) to remove CH$_3$OH. The residue was basified with saturated aqueous NaHCO$_3$ solution and extracted with EtOAc. The combined organic layers were washed with brine and dried. After concentration in vacuo, the free base (280 mg, 91%) was obtained as a light-yellow oil. $^1$H NMR (CD$_3$OD, 300 MHz) δ 7.54 (s, 1H), 7.50 (s, 1H), 6.53 (s, 1H), 4.10-4.04 (m, 1H), 3.99-3.97 (m, 1H), 3.61 (t, 2H, J=6.0 Hz), 3.53-3.50 (m, 2H), 3.35-3.30 (m, 1H), 3.02-2.91 (m, 3H), 2.38-2.18 (m, 2H), 2.09-1.95 (m, 2H), 1.91-1.81 (m, 2H), 1.71-1.31 (m, 6H). LC-MS (ESI) m/z 306 (M+H$^+$).

3-[1-[5-[(2(S)-Pyrrolidinyl)methoxy]-3-pyridyl]-3 (S)-pyrrolidinyl]-1-propanol Hydrochloride

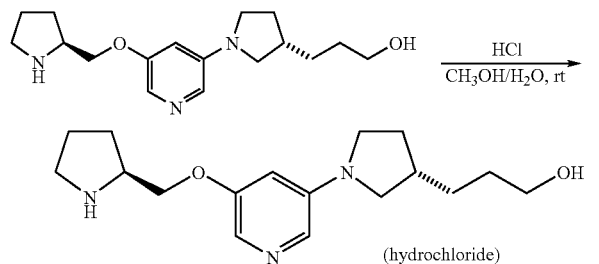

To a solution of 3-[1-[5-[(2(S)-pyrrolidinyl)methoxy]-3-pyridyl]-3(S)-pyrrolidinyl]-1-propanol (200 mg, 0.66 mmol) in methanol (0.5 mL) was added 2N hydrochloric acid (1.1 mL, 3.3 equiv.) under N$_2$. The reaction mixture was stirred for 4 h at room temperature. After evaporation in vacuo, the residue was diluted with water (12 mL) and lyophilized. The lyophilization process was repeated three times to obtain the hydrochloride (210 mg) as a light-yellow solid. $^1$H NMR (D$_2$O, 300 MHz) δ 7.57 (s, 1H), 7.54 (s, 1H), 6.95 (s, 1H), 4.51 (d, 1H, J=10.5 Hz), 4.24 (t, 1H, J=9.0 Hz), 4.07-4.05 (m, 1H), 3.57-3.26 (m, 7H), 2.93 (t, 1H, J=9.0 Hz, 1H), 2.33-1.99 (m, 5H), 1.98-1.84 (m, 1H), 1.69-1.55 (m, 5H). LC-MS (ESI) m/z 306 (M+H$^+$). Anal. Calcd. for C$_{17}$H$_{27}$N$_3$O$_2$.5.2HCl: C, 41.25; H, 6.56; N, 8.49. Found: C, 41.35; H, 6.64; N, 8.34.

Example 57

3-[4-[(2-Cyclohexyloxy)ethyl]-1-piperidinyl]-5-[(2 (S)-pyrrolidinyl)methoxy]pyridine 4-[2-(Cyclohexyloxy)ethyl]piperidine

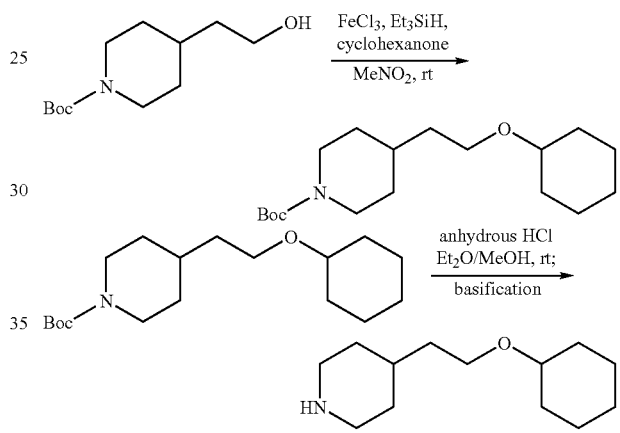

A solution of 1-(tert-butoxycarbonyl)-4-(2-hydroxyethyl) piperidine (229 mg, 1.0 mmol) and cyclohexanone (86 μL, 0.83 mmol) in MeNO$_2$ (2 mL), followed by Et$_3$SiH (160 μL, 1.0 mmol) were added successively to a suspension of FeCl$_3$ (35 mg, 0.20 mmol) in MeNO$_2$ (3 mL) at room temperature under Ar protection. After the mixture was stirred at rt for 112 h, the reaction was quenched by addition of phosphate buffer (pH 7). The mixture was extracted with CH$_2$Cl$_2$, and the organic layer was dried over Na$_2$SO$_4$. After evaporation, the residue was purified by CC (SiO$_2$, hexane/EtOAc 10:1 to 6:1) to afford 1-(tert-butoxycarbonyl)-4-[2-(cyclohexyloxy) ethyl]piperidine together with a with by-product (182 mg total) as a colorless oil. This mixture was used in the following step without further purification.

To a solution of 1-(tert-butoxycarbonyl)-4-[2-(cyclohexyloxy)ethyl]piperidine (182 mg, 0.59 mmol) in MeOH (2 mL) was added 2N anhydrous HCl/ether (0.75 mL, 1.5 mmol). The reaction mixture was stirred overnight. After evaporation, the residue was dissolved in deionized water. EtOAc was used to wash the aqueous layer before the pH was altered to approx. 9-10. The aqueous layer was extracted three times with CH$_2$Cl$_2$ and dried over Na$_2$SO$_4$. After evaporation, the product (38.0 mg, 30%) was obtained as a colorless oil. $^1$H NMR (CDCl$_3$, 400 MHz) δ 3.46-3.29 (m, 2H), 3.16 (1, 2H), 3.02 (m, 2H), 2.56 (m, 2H), 2.17 (br, 1H), 1.88 (m, 2H), 1.71-1.64 (m, 4H), 1.52-1.42 (m, 4H), 1.25-1.22 (m, 3H), 1.99-1.13 (m, 2H), 1.11-1.08 (m, 2H); $^{13}$C NMR (CDCl$_3$, 100 MHz) δ 64.8, 46.3, 37.0, 33.2, 32.8, 32.0, 27.2, 25.4, 23.9.

3-[4-[(2-Cyclohexyloxy)ethyl]-1-piperidinyl]-5-[(2(S)-pyrrolidinyl)methoxy]pyridine Hydrochloride

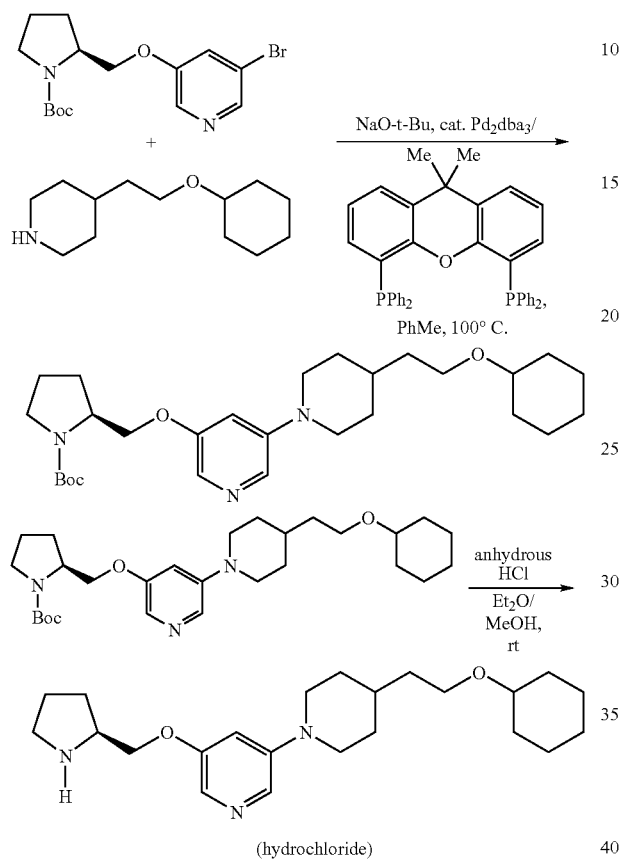

To a solution of 3-bromo-5-[[1-(tert-butoxycarbonyl)-2(S)-pyrrolidinyl]methoxy]pyridine (89 mg, 0.25 mmol) and 4-[2-(cyclohexyloxy)ethyl]piperidine (64 mg, 0.30 mmol, 1.2 equiv.) in anhydrous toluene (3 mL) were added successively sodium tert-butoxide (36 mg, 0.38 mmol, 1.5 equiv.), tris(dibenzylideneacetone)dipalladium(0) (4.6 mg, 5.0 µmol, 0.02 equiv.), and 4,5-bis(diphenylphosphino)-9,9-dimethylxanthene (Xantphos; 8.7 mg, 15 µmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over Na$_2$SO$_4$, and evaporated. The residue was purified by CC on SiO$_2$ with CH$_2$Cl$_2$/EtOAc 4:1 followed by CH$_2$Cl$_2$/MeOH 12:1. 3-[[1-(tert-Butoxycarbonyl)-2(S)-pyrrolidinyl]methoxy]-5-[[4-(2-cyclohexyloxy)ethyl]-1-piperidinyl]pyridine (102 mg, 84%) was obtained as a pale yellow oil.

To a solution of this intermediate (102 mg, 0.21 mmol) in MeOH (0.2 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. to obtain the crude hydrochloride. The residue was purified by preparative HPLC (ACE AQ 150×21.2 mm; UV detection at 254 and 280 nm; flow 10.0 mL/min; gradient of 0 to 50% CH$_3$CN in water [both containing 0.05 vol % CF$_3$COOH] in 25 min, to 100% in another 5 min; $t_R$ 19.3-22.0 min) and the eluate evaporated to obtain the trifluoroacetate (112 mg). This salt was treated with PL-HCO3 MP anion exchange resin (Polymer Laboratories) in MeOH to afford the free amine, which was dissolved in MeOH (0.2 mL), and treated again with 2N anhydrous HCl/ether (1 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the hydrochloride (74 mg) was obtained as a yellow glass. [α]$^{20}_D$+2.0 (c 1.5 g/L, MeOH). $^1$H NMR (D$_2$O, 400 MHz) δ 8.00 (d, 1H, J=1.6 Hz), 7.81 (s, 1H), 7.49 (s, 1H), 4.51 (dd, 1H, J=3.2 Hz, J=10.8 Hz), 4.32 (dd, 1H, J=7.6 Hz, J=10.4 Hz), 4.13 (m, 1H), 3.82 (d, 2H, J=12.8 Hz), 3.57 (t, 2H, J=6.4 Hz), 3.40 (t, 2H, J=6.8 Hz), 3.30 (m, 1H), 3.00 (t, 2H, J=11.6 Hz), 2.25 (m, 1H), 2.10 (m, 2H), 1.90 (m, 3H), 1.81 (d, 2H, J=12.4 Hz), 1.65 (m, 3H), 1.45 (m, 3H), 1.30-1.09 (m, 7H). $^{13}$C NMR (D$_2$O, 100 MHz) δ 156.5, 149.0, 121.8, 117.3, 114.3, 77.8, 67.2, 64.7, 58.1, 47.5, 45.6, 34.9, 31.3 (2C), 30.0, 25.4, 24.8, 23.4, 23.1. HRMS (ESI) calcd for C$_{23}$H$_{38}$N$_3$O$_2$ (M+H$^+$) m/z 388.2964, found 388.2954. Anal. Calcd. for C$_{23}$H$_{37}$N$_3$O$_2$.2.9HCl.0.6H$_2$O: C, 54.80; H, 8.22; N, 8.34. Found: C, 54.79; H, 8.30; N, 8.20.

Example 58

3-[4-(2-Phenoxyethyl)-1-piperidinyl]-5-[(2(S)-pyrrolidinyl)methoxy]pyridine 1-(tert-Butoxycarbonyl)-4-(2-iodoethyl)piperidine

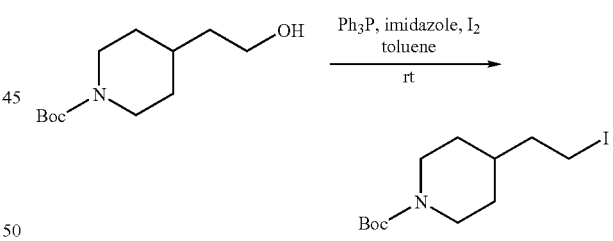

To a solution of 1-(tert-butoxycarbonyl)-4-(2-hydroxyethyl)piperidine (458 mg, 2.0 mmol), Ph$_3$P (785 mg, 3.0 mmol, 1.5 equiv.) and imidazole (204 mg, 3.0 mmol, 1.5 equiv.) in toluene (10 mL) was added I$_2$ (761 mg, 3.0 mmol, 1.5 equiv.) at 0° C. The mixture was allowed to stand at room temperature overnight, before it was quenched with saturated Na$_2$S$_2$O$_3$ solution. The product was extracted into CH$_2$Cl$_2$, and the organic layer was washed with brine and dried over Na$_2$SO$_4$. After concentration, the residue was purified by CC (SiO$_2$, hexane/EtOAc 8:1, then 4:1). After removal of the solvents, 1-(tert-butoxycarbonyl)-4-(2-iodoethyl)piperidine (560 mg, 83%) was obtained as a colorless oil. $^1$H NMR (CDCl$_3$, 400 MHz) δ 4.09 (br, 2H), 3.21 (t, 2H, J=7.2 Hz), 2.70 (t, 2H, J=12.0 Hz), 1.77 (q, 2H, J=7.2 Hz), 1.65 (d, 2H, J=12.8 Hz), 1.56 (m, 1H), 1.45 (s, 9H), 1.11 (m, 2H).

1-(tert-Butoxycarbonyl)-4-[2-phenoxyethyl]piperidine

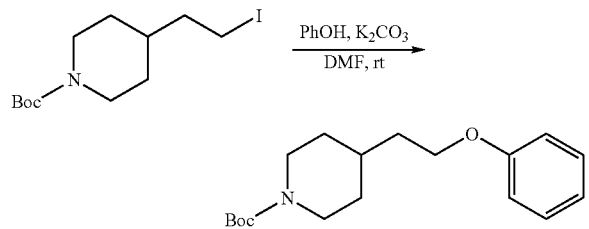

To a solution of 1-(tert-butoxycarbonyl)-4-(2-iodoethyl)piperidine (339 mg, 1.0 mmol) and phenol (188 mg, 1.0 mmol) in DMF (5 mL) was added anhydrous $K_2CO_3$ (828 mg, 6.0 mmol) at room temperature under Ar protection. After stirring overnight, the reaction mixture was poured into 2N aqueous NaOH. The mixture was extracted three times with EtOAc, and the combined organic layers were washed with brine and dried over $Na_2SO_4$. After evaporation, the residue was purified by CC ($SiO_2$, hexane/EtOAc 8:1, then 4:1) to afford 1-(tert-butoxycarbonyl)-4-(2-phenoxyethyl)piperidine (220 mg, 72%) as a white solid. $^1H$ NMR ($CDCl_3$, 400 MHz) δ 7.27 (t, 2H, J=7.6 Hz), 6.95-6.88 (m, 3H), 4.10 (m, 2H), 3.99 (t, 2H, J=6.0 Hz), 2.70 (m, 2H), 1.72-1.63 (m, 5H), 1.47 (s, 9H), 1.23-1.15 (m, 2H). $^{13}C$ NMR ($CDCl_3$, 100 MHz) δ 158.5, 154.4, 129.0, 120.2, 144.0, 78.8, 64.8, 43.5, 35.4, 32.6, 31.7, 28.1.

4-(2-Phenoxyethyl)piperidine

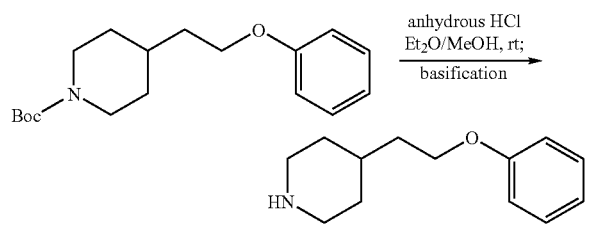

To a solution of 1-(tert-butoxycarbonyl)-4-(2-phenoxyethyl)piperidine (220 mg, 0.72 mmol) in MeOH (2 mL) was added 2N anhydrous HCl/ether (0.5 mL, 1.0 mmol). The reaction mixture was stirred overnight. After evaporation, the residue was dissolved in deionized water. EtOAc was used to wash the aqueous layer before the pH was altered to approx. 9-10. The aqueous layer was extracted three times with $CH_2Cl_2$ and dried over $Na_2SO_4$. After evaporation, 4-(2-phenoxyethyl)piperidine (131.5 mg, 89%) was obtained as a colorless oil. $^1H$ NMR ($CDCl_3$, 400 MHz) δ 7.23 (m, 2H), 6.96 (m, 1H), 6.85 (m, 2H), 3.95 (m, 2H), 3.27 (m, 2H), 2.71 (m, 3H), 1.92 (m, 2H), 1.56 (m, 3H), 1.42 (m, 2H).

3-[[1-(tert-Butoxycarbonyl)-2(S)-pyrrolidinyl]methoxy]-5-[4-(2-phenoxyethyl)-1-piperidinyl]pyridine

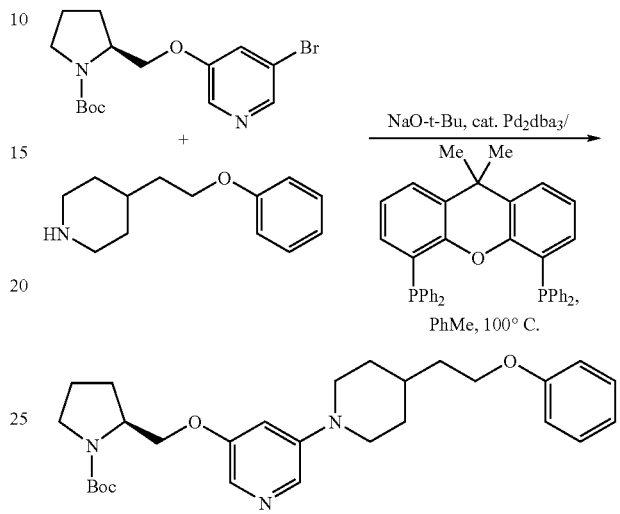

To a solution of 3-bromo-5-[[1-(tert-butoxycarbonyl)-2(S)-pyrrolidinyl]methoxy]pyridine (212 mg, 0.59 mmol) and 4-(2-phenoxyethyl)piperidine (134 mg, 0.65 mmol, 1.1 equiv.) in anhydrous toluene (5 mL) were added successively sodium tert-butoxide (85 mg, 0.89 mmol, 1.5 equiv.), tris(dibenzylideneacetone)dipalladium(0) (10.8 mg, 12 μmol, 0.02 equiv.), and 4,5-bis(diphenylphosphino)-9,9-dimethylxanthene (Xantphos; 20.6 mg, 37 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over $Na_2SO_4$, and evaporated. The residue was purified by CC on $SiO_2$ with $CH_2Cl_2$/EtOAc 4:1, then 1:1. The product (150 mg, 53%) was obtained as a pale yellow oil. $^1H$ NMR ($CDCl_3$, 400 MHz) δ 7.93-7.79 (m, 2H), 7.28 (t, 2H, J=8.0 Hz), 6.96-6.69 (m, 4H), 4.12 (m, 2H), 4.03 (t, 2H, J=6.0 Hz), 3.93-3.83 (m, 1H), 3.70 (m, 2H), 3.40 (m, 2H), 2.77 (m, 2H), 2.04-1.87 (m, 3H), 1.87-1.80 (m, 3H), 1.78-1.75 (m, 3H), 1.47 (s, 9H), 1.43-1.30 (m, 2H); $^{13}C$ NMR ($CDCl_3$, 100 MHz) δ 158.5, 155.1, 154.3, 148.0, 131.7, 130.9, 129.1, 127.8, 126.6, 120.2, 114.0, 108.7, 108.2, 79.4, 79.0, 68.4, 67.9, 64.8, 55.6, 48.7, 46.5, 46.2, 35.3, 32.2, 31.4, 28.1, 27.7, 23.4, 22.5.

3-[4-(2-Phenoxyethyl)-1-piperidinyl]-5-[(2(S)-pyrrolidinyl)methoxy]pyridine Hydrochloride

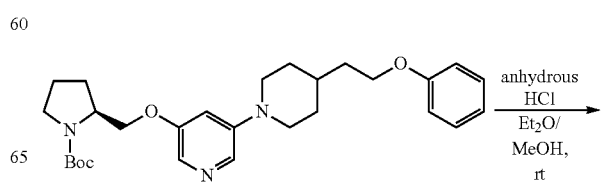

-continued

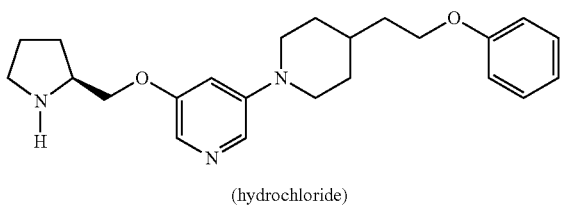

(hydrochloride)

To a solution of 3-[[1-(tert-butoxycarbonyl)-2(S)-pyrrolidinyl]methoxy]-5-[4-(2-phenoxyethyl)-1-piperidinyl]pyridine (150 mg, 0.31 mmol) in MeOH (0.5 mL) was added 2N anhydrous HCl/ether (2 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C., and the residue was purified by HPLC (ACE AQ 150×21.2 mm; UV detection at 254 and 280 nm; flow 10.0 mL/min; gradient of 0 to 50% $CH_3CN$ in water [both containing 0.05 vol % $CF_3COOH$] in 25 min, to 100% in another 5 min; $t_R$ 13.6-19.7 min) to obtain, after evaporation, the trifluoroacetate (131 mg). This salt was treated with PL-HCO3 MP anion exchange resin (Polymer Laboratories) in MeOH. to afford the free amine. The solution was evaporated, and the residue was dissolved in MeOH (0.5 mL) and treated again with 2N anhydrous HCl/ether (2 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the hydrochloride (117 mg) was obtained as a colorless solid. $[\alpha]^{20}_D$+2.6 (c 6.9 g/L, MeOH). $^1$H NMR ($D_2O$, 400 MHz) δ 7.59 (s, 1H), 7.13 (s, 1H), 6.92 (m, 2H), 6.57 (m, 3H), 4.22 (m, 1H), 4.08 (m, 1H), 3.88 (m, 1H), 3.60 (m, 2H), 3.41 (m, 2H), 3.18 (m, 2H, J=6.8 Hz), 2.52 (m, 2H), 2.04-2.00 (m, 1H), 2.00-1.80 (m, 2H), 1.78-1.62 (m, 1H), 1.43 (m, 2H), 1.31 (m, 3H), 0.93 (m, 2H). $^{13}$C NMR ($D_2O$, 100 MHz) δ 157.9, 156.4, 148.5, 129.1, 121.2, 120.4, 117.2, 114.0, 67.3, 65.2, 58.0, 47.0, 45.5, 34.4, 31.1, 30.1, 25.4, 23.0. HRMS (ESI) calcd for $C_{23}H_{32}N_3O_2$ (M+H$^+$) m/z 382.2495, found 382.2484. Anal. Calcd. for $C_{23}H_{31}N_3O_2 \cdot 2.2HCl \cdot 0.7H_2O$: C, 58.24; H, 7.35; N, 8.86; Cl, 16.44. Found: C, 58.36; H, 7.33; N, 8.80; Cl, 16.12.

Example 59

3-[4-[2-(Benzyloxy)ethyl]-1-piperidinyl]-5-[(1-methyl-2(S)-pyrrolidinyl)methoxy]pyridine Hydrochloride

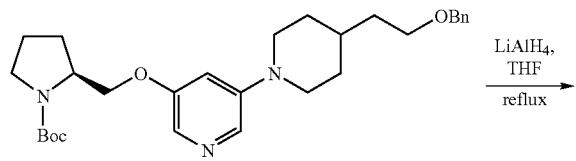

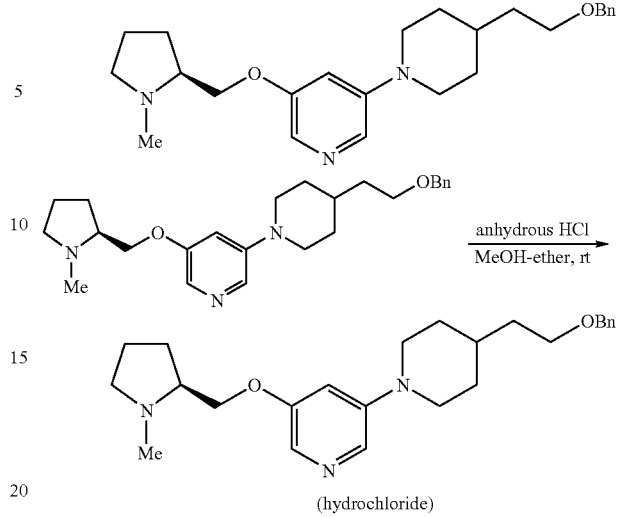

(hydrochloride)

To a suspension of lithium aluminum hydride (60 mg, 1.59 mmol, 5.0 equiv.) in THF (5 mL) was added a solution of 3-[4-[2-(benzyloxy)ethyl]-1-piperidinyl]-5-[(2(S)-pyrrolidinyl)methoxy]pyridine (156 mg, 0.32 mmol) in THF (1 mL). The mixture was refluxed for 1.5 h and then cooled to room temperature. To a flask containing 4-5 g of $Na_2SO_4$ was added with stirring 40-50 mL of ether followed by the cooled reaction mixture. Water was subsequently added dropwise to quench residual hydride. When no more gas was generated, the mixture was filtered, and the solid phase was washed with $CH_2Cl_2$/MeOH 4:1 (100-150 mL). Solvent removal furnished crude 3-[4-[2-(benzyloxy)ethyl]-1-piperidinyl]-5-[(1-methyl-2(S)-pyrrolidinyl)methoxy]pyridine (106 mg, 81%), which could be used in the following step without further purification.

To a solution of the above crude intermediate (106 mg, 0.26 mmol) in MeOH (1 mL) was added 2N anhydrous HCl/ether (2 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (ACE AQ 150× 21.2 mm; UV detection at 254 and 280 nm; flow 10.0 mL/min; gradient of 0 to 50% $CH_3CN$ in water [both containing 0.05 vol % $CF_3COOH$] in 25 min, to 100% in another 5 min; $t_R$ 15.0-19.4 min) to obtain the trifluoroacetate (141 mg). This salt was treated with PL-HCO3 MP anion exchange resin (Polymer Laboratories) in MeOH to afford the free amine, which was dissolved in MeOH (0.2 mL), and treated again with 2N anhydrous HCl/ether (1 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the hydrochloride (114 mg) was obtained as a yellow glass. $^1$H NMR (CDCl$_3$, 400 MHz) δ 7.87 (s, 1H), 7.74 (s, 1H), 7.37 (s, 1H), 7.24 (m, 5H), 4.47 (dd, 1H, J=2.8 Hz, J=10.8 Hz), 4.39 (s, 2H), 4.33 (dd, 1H, J=6.0 Hz, J=11.2 Hz), 3.85 (m, 1H), 3.67 (m, 3H), 3.48 (t, 2H, J=6.8 Hz), 3.17 (m, 1H), 2.95 (s, 3H), 2.85 (m, 2H), 2.32 (m, 1H), 2.12 (m, 1H), 2.00 (m, 2H), 1.65 (d, 2H, J=12.0 Hz), 1.50 (m, 1H), 1.41 (m, 2H), 1.10 (m, 2H). $^{13}$C NMR (CDCl$_3$, 100 MHz) δ 156.3, 148.8, 137.0, 128.2, 127.9, 127.7, 121.8, 117.1, 114.1, 72.0, 67.2, 66.9, 65.9, 56.8, 47.3, 40.1, 34.5, 31.2, 30.0, 25.5, 21.7. HRMS (ESI) calcd for $C_{25}H_{36}N_3O_2$ (M+H$^+$) m/z 410.2808, found 410.2797. Anal. Calcd. for $C_{25}H_{35}N_3O_2 \cdot 3.25HCl \cdot 1.8H_2O$: C, 53.57; H, 7.53; N, 7.50; Cl, 20.56. Found: C, 53.42, H, 7.36; N, 7.50, Cl, 20.39.

Example 60

3-[(2(S)-Azetidinyl)methoxy]-5-[4-[2-(benzyloxy)ethyl]-1-piperidinyl]pyridine

3-[4-[2-(Benzyloxy)ethyl]-1-piperidinyl]-[[1-(tert-butoxycarbonyl)-2(S)-azetidinyl]methoxy]pyridine

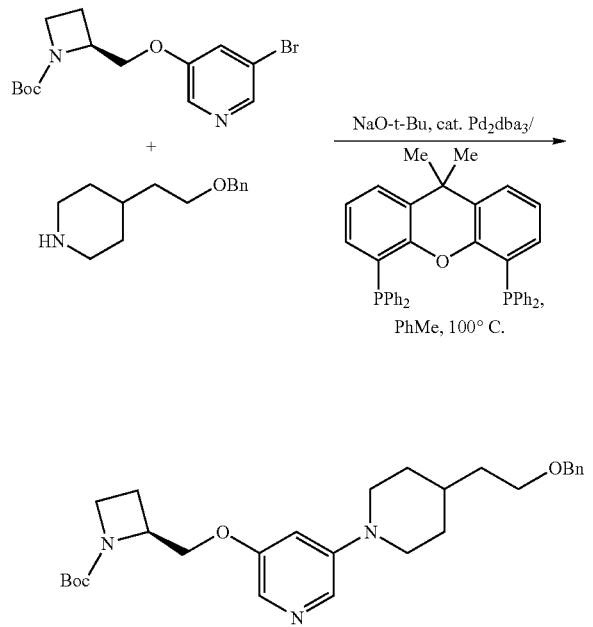

To a mixture of 3-bromo-5-[[1-(tert-butoxycarbonyl)-2(S)-azetidinyl]methoxy]pyridine (203 mg, 0.59 mmol) and 4-[2-(benzyloxy)ethyl]piperidine (143 mg, 0.65 mmol, 1.1 equiv.) in anhydrous toluene (2 mL) were added successively sodium tert-butoxide (85 mg, 0.89 mmol, 1.5 equiv.), tris(dibenzylideneacetone)dipalladium(0) (10.8 mg, 12 μmol, 0.02 equiv.), and 4,5-bis(diphenylphosphino)-9,9-dimethylxanthene (Xantphos; 20.5 mg, 35 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over $Na_2SO_4$, and evaporated. The residue was purified by CC on $SiO_2$ with $CH_2Cl_2$/EtOAc 4:1 followed by $CH_2Cl_2$/MeOH 10:1. The product (211 mg) was obtained as a pale yellow oil. $^1$H NMR (CDCl$_3$, 400 MHz) δ 7.92 (s, 1H), 7.76 (s, 1H), 7.27 (m, 5H), 6.71 (s, 1H), 4.47 (m, 3H), 4.26 (m, 1H), 4.07 (m, 1H), 3.85 (m, 2H), 3.63 (d, 2H, J=12.4 Hz), 3.50 (t, 2H, J=6.0 Hz), 2.70 (s, 2H, J=12.0 Hz), 2.26 (m, 2H), 1.74 (d, 2H, J=12.8 Hz), 1.57 (m, 3H), 1.38 (s, 9H), 1.23 (m, 2H); $^{13}$C NMR (CDCl$_3$, 100 MHz) δ 156.2, 155.6, 148.3, 138.5, 132.0, 131.8, 131.7, 128.4, 127.6 (2C), 127.3, 109.0, 79.6, 73.0, 68.7, 67.7, 60.2, 49.1, 36.2, 32.5, 31.8, 31.5, 28.5, 19.2.

3-[(2(S)-Azetidinyl)methoxy]-5-[4-[2-(benzyloxy)ethyl]-1-piperidinyl]pyridine Hydrocloride

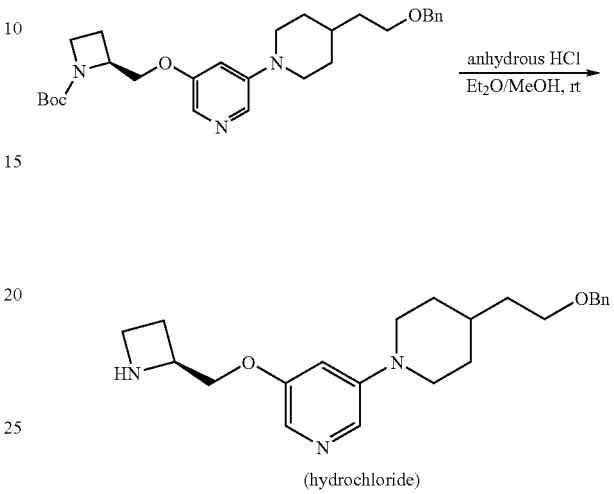

To a solution of crude 3-[4-[2-(benzyloxy)ethyl]-1-piperidinyl]-5-[[1-(tert-butoxycarbonyl)-2(S)-azetidinyl]methoxy]pyridine (97 mg, 0.20 mmol) in MeOH (0.2 mL) was added 2N anhydrous HCl/ether (1.5 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (ACE AQ 150×21.2 mm; UV detection at 254 and 280 nm; flow 10.0 mL/min; gradient of 0 to 50% $CH_3CN$ in water [both containing 0.05 vol % $CF_3COOH$] in 25 min, to 100% in another 5 min; $t_R$ 14.7-17.7 min) to obtain the trifluoroacetate (150 mg). This salt was treated with PL-HCO3 MP anion exchange resin (Polymer Laboratories) in MeOH to afford the free amine, which was dissolved in MeOH (0.2 mL) and treated again with 2N anhydrous HCl/ether (1 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the hydrochloride (86 mg) was obtained as a yellow glass. $[\alpha]^{23}_D$ −9.1 (c 2.20 g/L, MeOH). $^1$H NMR (CDCl$_3$, 400 MHz) δ 7.94 (s, 1H), 7.81 (s, 1H), 7.47 (s, 1H), 7.32 (m, 5H), 4.93 (m, 1H), 4.47 (s, 2H), 4.44 (m, 2H), 4.07 (m, 2H), 3.76 (d, 2H, J=13.2 Hz), 3.57 (t, 2H, J=6.4 Hz), 2.93 (m, 2H), 2.65 (q, 2H, J=8.4 Hz), 1.73 (d, 2H, J=12.4 Hz), 1.52 (m, 1H), 1.51 (m, 2H), 1.21 (m, 2H). $^{13}$C NMR (CDCl$_3$, 100 MHz) δ 156.5, 149.0, 137.0, 128.2, 128.0, 127.8, 121.8, 117.2, 114.2, 72.0, 67.2, 67.0, 58.3, 47.4, 43.3, 34.5, 31.2, 30.0, 19.9. HRMS (ESI) calcd for $C_{23}H_{32}N_3O_2$ (M+H$^+$) m/z 382.2495, found 382.2491. Anal. Calcd. for $C_{23}H_{31}N_3O_2 \cdot 2.95HCl \cdot 0.3H_2O$: C, 55.87; H, 7.04; N, 8.50; Cl, 21.15. Found C, 55.84; H, 7.03; N, 8.36, Cl, 21.30.

Example 61

3-[4-[2-(Benzyloxy)ethyl]-1-piperidinyl]-5-[(1-methyl-2(S)-azetidinyl)methoxy]pyridine 3-[4-[2-(Benzyloxy)ethyl]-1-piperidinyl]-5-[(1-methyl-2(S)-azetidinyl)methoxy]pyridine

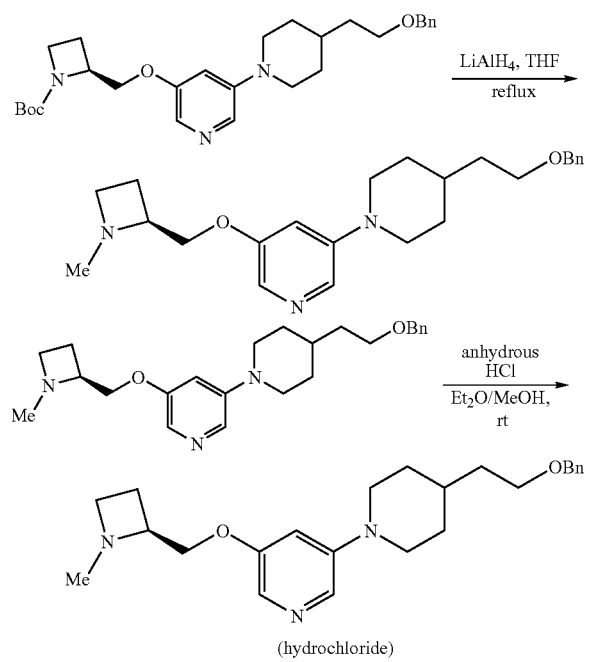

(hydrochloride)

To a suspension of lithium aluminum hydride (45 mg, 1.2 mmol, 5.0 equiv.) in THF (1.5 mL) was added a solution of 3-[4-[2-(benzyloxy)ethyl]-1-piperidinyl]-5-[[1-(tert-butoxycarbonyl)-2(S)-azetidinyl]methoxy]pyridine (115 mg, 0.24 mmol) in THF (0.5 mL). The mixture was refluxed for 1 h, then cooled to room temperature. To a flask containing 4-5 g of $Na_2SO_4$ was added with stirring 40-50 mL of $Et_2O$ followed by the cooled reaction mixture. Water was subsequently added dropwise to quench residual hydride. When no more gas was generated, the mixture was filtered, and the solid phase was washed with $CH_2Cl_2$/MeOH 4:1 (100-150 mL). Solvent removal furnished crude 3-[4-[2-(benzyloxy) ethyl]-1-piperidinyl]-5-[(1-methyl-2(S)-azetidinyl)methoxy]pyridine (97 mg, 100%), which was used in the following step without purification.

To a solution of 3-[4-[2-(benzyloxy)ethyl]-1-piperidinyl]-5-[(1-methyl-2(S)-azetidinyl)methoxy]pyridine (97 mg, 0.25 mmol) in MeOH (0.2 mL) was added 2N anhydrous HCl/ether (1.5 mL) under Ar at room temperature. The mixture was stirred at room temperature overnight. After the solvent was evaporated, the residue was dissolved in deionized water (25 mL). The aqueous solution was washed twice with EtOAc, then filtered over a cotton plug. The water was removed under reduced pressure at 35° C. The residue was purified by HPLC (ACE AQ 150×21.2 mm; UV detection at 254 and 280 nm; flow 10.0 mL/min; 0 to 50% $CH_3CN$ in water [both containing 0.05 vol % $CF_3COOH$] in 30 min, to 100% in another 5 min; $t_R$ 17.6-20.4 min) to obtain the trifluoroacetate (156 mg). This salt was treated with PL-HCO3 MP anion exchange resin (Polymer Laboratories) in MeOH to afford the free amine, which was dissolved in MeOH (0.2 mL) and treated again with 2N anhydrous HCl/ether (1 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the product (63 mg) was obtained as a yellow glass. $[\alpha]^{23}_D$ −16.0 (c 0.50 g/L, MeOH). $^1$H NMR ($CDCl_3$, 400 MHz) δ 7.90 (s, 1H), 7.77 (s, 1H), 7.42 (s, 1H), 7.29 (m, 5H), 4.74 (m, 1H), 4.39 (m, 4H), 4.19 (m, 1H), 3.93 (m, 1H), 3.70 (d, 2H, J=12.8 Hz), 3.51 (t, 2H, J=6.4 Hz), 2.83 (m, 5H), 2.56 (m, 2H), 1.67 (d, 2H, J=12.8 Hz), 1.58 (m, 1H), 1.43 (m, 2H), 1.18 (m, 2H), $^{13}$C NMR ($CDCl_3$, 100 MHz) δ 156.3, 148.8, 137.0, 128.2, 128.0, 127.7, 122.0, 117.3, 114.3, 72.0, 67.7, 67.2, 66.2, 52.9, 47.5, 40.5, 34.5, 31.2, 30.0, 17.5. HRMS (ESI) calcd for $C_{24}H_{34}N_3O_2$ (M+H$^+$) m/z 396.2651, found 396.2647. Anal. Calcd. for $C_{24}H_{33}N_3O_2 \cdot 3.1HCl \cdot 0.05H_2O$: C, 56.58; H, 7.16; N, 8.25. Found: C, 56.65; H, 7.21; N, 8.16.

Example 62

3-[4-[2-(Benzyloxy)ethyl]-1-piperidinyl]-5-[(2(R)-pyrrolidinyl)methoxy]pyridine

3-Bromo-5-[[1-(tert-butoxycarbonyl)-2(R)-pyrrolidinyl]methoxy]pyridine

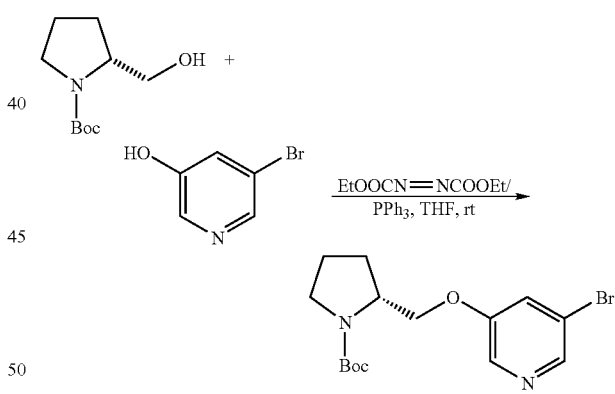

To a solution of [1-(tert-butoxycarbonyl)-2(R)-pyrrolidinyl]methanol (524 mg, 2.60 mmol, 1.5 equiv.), 5-bromo-3-pyridinol (302 mg, 1.74 mmol) and $Ph_3P$ (682 mg, 2.60 mmol, 1.5 equiv.) in THF (15 mL) was added diethyl azodicarboxylate (410 μL, 2.60 mmol, 1.5 equiv.) at room temperature under Ar protection. After stirring overnight, the solvent was removed. The residue was diluted with hexane/EtOAc 4:1, and the solution was washed with brine and dried over $Na_2SO_4$. After evaporation, the residue was purified by CC ($SiO_2$, $CH_2Cl_2$/EtOAc 4:1) to afford the product (462 mg, 95%) as a pale yellow oil. $[\alpha]^{23}_D$ +18.6 (c 6.3 g/L, $CHCl_3$). $^1$H NMR ($CDCl_3$, 400 MHz) δ 8.23 (m, 2H), 7.42 (m, 1H), 4.26 (m, 2H), 3.99 (m, 1H), 3.34 (m, 2H), 1.88 (m, 4H), 1.41 (s, 9H); $^{13}$C NMR ($CDCl_3$, 100 MHz) δ 155.5, 154.9, 143.2, 142.9, 136.8, 136.5, 124.2, 120.6, 80.2, 79.8, 69.0, 56.1, 55.6, 47.2, 46.8, 28.7, 28.2, 28.0, 24.1, 23.1.

3-[4-[2-(Benzyloxy)ethyl]-1-piperidinyl]-5-[[1-(tert-butoxycarbonyl)-2(R)-pyrrolidinyl]methoxy]pyridine

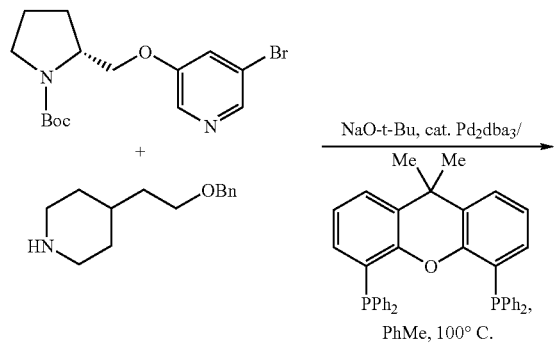

To a solution of 4-[2-(benzyloxy)ethyl]piperidine (1.80 g, 8.21 mmol) and 3-bromo-5-[1-(tert-butoxycarbonyl)-2(S)-pyrrolidinyl]pyridine (3.15 g, 8.82 mmol, 1.07 equiv.) in 50 mL of anhydrous toluene were added successively at room temperature sodium tert-butoxide (0.92 g, 9.6 mmol, 1.2 equiv.), tris(dibenzylideneacetone)dipalladium(0)-chloroform adduct (166 mg, 0.16 mmol, 0.02 equiv.) and 4,5-bis(diphenylphosphino)-9,9-dimethylxanthene (Xantphos, 278 mg, 0.48 mmol, 0.06 equiv.). The mixture was degassed and purged with $N_2$ (3 cycles) and then heated to 100° C. for 6 h. After cooling, the solvent was evaporated. The residue was diluted with water and extracted with EtOAc. The organic layers were combined and washed with brine. After drying, the solvent was evaporated, and the residue was purified by CC ($SiO_2$, EtOAc/petroleum ether 10:1 to 1:1) to afford the product (2.70 g, 66%) as a yellowish oil. $^1$H NMR ($CDCl_3$, 400 MHz) δ 7.94 (m, 1H), 7.75 (s, 1H), 7.28 (m, 5H), 6.86 (m, 1H), 4.49 (s, 2H), 4.13 (m, 2H), 3.81 (m, 1H), 3.66 (m, 2H), 3.52 (t, 2H, J=6.0 Hz), 3.39 (m, 2H), 2.72 (m, 2H), 2.05 (m, 3H), 1.85 (m, 1H), 1.76 (d, 2H, J=12.8 Hz), 1.58 (m, 3H), 1.45 (s, 9H), 1.30 (m, 2H). LC-MS (ESI) m/z 496 (M+H$^+$).

3-[4-[2-(Benzyloxy)ethyl]-1-piperidinyl]-5-[(2(R)-pyrrolidinyl)methoxy]pyridine Hydrochloride

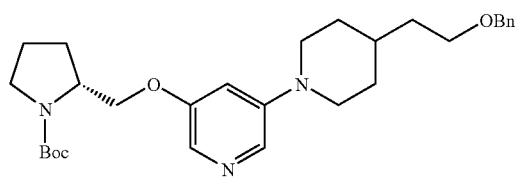

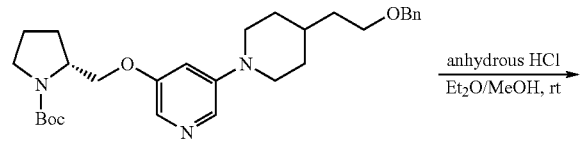

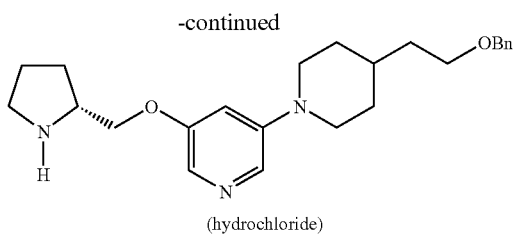
(hydrochloride)

To a solution of 3-[4-[2-(benzyloxy)ethyl]-1-piperidinyl]-5-[[1-(tert-butoxycarbonyl)-2(R)-pyrrolidinyl]methoxy]pyridine (112 mg, 0.23 mmol) in MeOH (0.3 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (ACE AQ 150×21.2 mm; UV detection at 254 and 280 nm; flow 10.0 mL/min; 0 to 50% $CH_3CN$ in water [both containing 0.05 vol % $CF_3COOH$] in 25 min, to 100% in another 5 min; $t_R$ 16.4-19.4 min) to obtain the trifluoroacetate (151 mg). This salt was treated with PL-HCO3 MP anion exchange resin (Polymer Laboratories) in MeOH to afford the free amine, which was dissolved in MeOH (0.2 mL) and treated again with 2N anhydrous HCl/ether (1 mL) under Ar protection at room temperature. The mixture was stirred at room temperature overnight. After the solvent was evaporated, the residue was dissolved in deionized water. After the solution was filtered over a cotton plug, the water was removed under reduced pressure at 35° C. After lyophilization from water, the hydrochloride (68 mg) was obtained as a yellow glass. $[\alpha]^{22}_D$ –5.3 (c 0.94 g/L, MeOH). $^1$H NMR ($CDCl_3$, 400 MHz) δ 7.90 (s, 1H), 7.74 (s, 1H), 7.39 (s, 1H), 7.30 (m, 5H), 4.46 (m, 3H), 4.26 (m, 1H), 4.07 (m, 1H), 3.72 (m, 2H), 3.53 (t, 2H, J=6.4 Hz), 3.36 (t, 2H, J=7.2 Hz), 2.89 (m, 2H), 2.22 (m, 1H), 2.07 (m, 2H), 1.89 (m, 1H), 1.71 (m, 2H), 1.50 (m, 1H), 1.48 (m, 2H), 1.19 (m, 2H). $^{13}$C NMR ($CDCl_3$, 100 MHz) δ 156.4, 148.8, 137.0, 128.2, 128.0, 127.7, 121.7, 117.2, 114.2, 72.0, 67.2, 58.0, 47.4, 45.5, 34.5, 31.2, 30.0, 25.4, 23.0. HRMS (ESI) calcd for $C_{24}H_{34}N_3O_2$ (M+H$^+$) m/z 396.2651, found 396.2649. Anal. Calcd. for $C_{24}H_{33}N_3O_2$·3.15 HCl·0.85$H_2O$: C, 54.83; H, 7.26; N, 7.99; Cl, 21.24. Found: C, 54.77; H, 7.21; N, 7.99, Cl, 21.34.

3-[4-[2-(Benzyloxy)ethyl]-1-piperidinyl]-5-[2(R)-pyrrolidinyl)methoxy]pyridine, free base

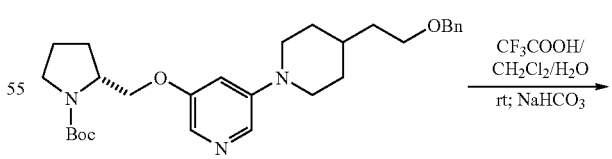

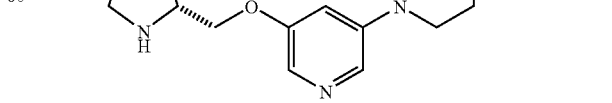

Trifluoroacetic acid (8.6 mL) and water (0.86 mL) were added to $CH_2Cl_2$ (43 mL). This mixture was added to a solution of 3-[4-[2-(benzyloxy)ethyl]-1-piperidinyl]-5-[[1-(tert-butoxycarbonyl)-2(R)-pyrrolidinyl]methoxy]pyridine (2.20 g, 4.44 mmol) in CH$_2$Cl$_2$ (5 mL) at room temperature under N$_2$. After stirring overnight, the mixture was concentrated in vacuo, and the residue was purified by preparative HPLC (column: SunFire Prep C$_{18}$, 150×19 mm, 5 μm particle size; UV detection at 254 nm; mobile phase: A, water with 0.05% CF$_3$COOH; B, methanol; 40-50% B in A in 6 min, 50-100% in 1 min, back to 40% in 1 min). The product-containing fractions were combined and partially evaporated in an oil pump vacuum (bath 30° C.) to remove methanol. The pH of the residual solution was adjusted to 8 with saturated aqueous NaHCO$_3$ solution. The product was extracted into EtOAc (3×80 mL). The combined organic layers were washed with brine and dried over Na$_2$SO$_4$. After filtration and concentration, the free base (1.40 g, 80%) was obtained as a yellow solid. $^1$H NMR (CDCl$_3$, 300 MHz) δ 7.89 (s, 1H), 7.74 (s, 1H), 7.40-7.30 (m, 5H), 6.84 (s, 1H), 4.52 (s, 2H), 4.39-4.25 (m, 2H), 3.69 (m, 1H), 3.67 (m, 2H), 3.55 (t, 2H, J=6.0 Hz), 3.41-3.32 (m, 2H), 2.78 (m, 2H), 2.62 (br s, 1H), 2.23-1.94 (m, 4H), 2.23 (m, 2H), 1.82-1.57 (m, 3H), 1.35-1.27 (m, 2H). LC-MS (ESI) m/z 396 (M+H$^+$).

3-[4-[2-(Benzyloxy)ethyl]-1-piperidinyl]-5-[(2(R)-pyrrolidinyl)methoxy]pyridine D-Tartrate

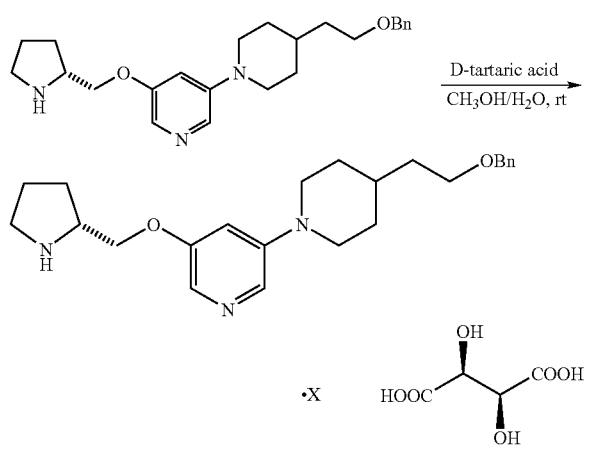

To a solution of 3-[4-[2-(benzyloxy)ethyl]-1-piperidinyl]-5-[(2(R)-pyrrolidinyl)methoxy]pyridine (2.3 g, 5.8 mmol) in methanol (15 mL) was added D-tartaric acid (1.3 g, 8.7 mmol, 1.5 equiv.) at room temperature under N$_2$. The resulting solution was stirred for 6 h at room temperature, and then methyl tert-butyl ether was added slowly until an emulsion was formed. The emulsion was allowed to stand overnight whereon crystallization of the salt took place. Filtration afforded the D-tartrate (2.5 g) as a colorless solid. The mother liquor was concentrated in vacuo, and the residue was recrystallized to give additional D-tartrate (0.7 g). $^1$H NMR (D$_2$O, 300 MHz) δ 7.91 (br s, 1H), 7.73 (br s, 1H), 7.31 (m, 5H), 7.29 (br s, 1H), 4.47 (s, 2H), 4.40 (dd, 1H, J=10.5, 3.3 Hz), 4.28 (s, 2H), 4.40 (dd, 1H, J=10.2, 7.8 Hz), 4.07-4.03 (m, 1H), 3.70 (m, 2H), 3.58 (t, 2H, J=6.3 Hz), 3.34 (t, 2H, J=6.9 Hz), 2.86 (m, 2H), 2.23-2.19 (m, 1H), 2.09-2.01 (m, 2H), 1.91-1.84 (m, 1H), 1.70 (m, 2H), 1.59 (m, 1H), 1.54-1.47 (m, 2H), 1.27-1.14 (m, 2H). LC-MS (ESI) m/z 396 (M+H$^+$). Anal. (a) first crystal crop: Calcd. for C$_{24}$H$_{33}$N$_3$O$_2$.1.15C$_4$H$_6$O$_6$.0.1H$_2$O: C, 60.27; H, 7.09; N, 7.37. Found: C, 60.26; H, 6.99; N, 7.40. (b) second crystal crop: Calcd. for C$_{24}$H$_{33}$N$_3$O$_2$.1.3C$_4$H$_6$O$_6$.0.1H$_2$O: C, 59.20, H, 6.98; N, 7.09. Found: C, 59.10; H, 6.98; N, 7.22.

Example 63

3-[4-[2-(Benzyloxy)ethyl]-1-piperidinyl]-5-[(1-methyl-2(R)-pyrrolidinyl)methoxy]pyridine Hydrochloride

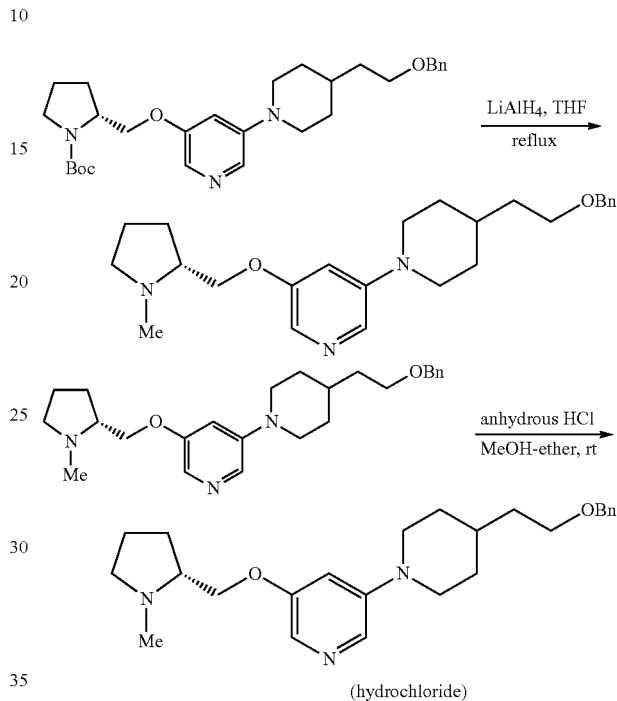

To a suspension of lithium aluminum hydride (46.4 mg, 1.22 mmol, 5 equiv.) in THF (2 mL) was added a solution of 3-[4-[2-(benzyloxy)ethyl]-1-piperidinyl]-5-[[1-(tert-butoxycarbonyl)-2(R)-pyrrolidinyl]methoxy]pyridine (121 mg, 0.24 mmol) in THF (0.5 mL). The resulting mixture was refluxed for 1.5 h, then cooled to room temperature. To a flask containing 4-5 g of Na$_2$SO$_4$ was added with stirring 40-50 mL of Et$_2$O followed by the cooled reaction mixture. Water was subsequently added dropwise to quench the reaction. When no more gas was generated, the mixture was filtered, and the solid phase was washed with CH$_2$Cl$_2$/MeOH 4:1 (100-150 mL). Solvent removal furnished crude 3-[4-[2-(benzyloxy)ethyl]-1-piperidinyl]-5-[(1-methyl-2(R)-pyrrolidinyl)methoxy]pyridine (110 mg), which could be used in the following step without purification.

To a solution of this intermediate (110 mg, 0.26 mmol) in MeOH (0.2 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by preparative HPLC (ACE AQ 150×21.2 mm; UV detection at 254 and 280 nm; flow 10.0 mL/min; 0 to 50% CH$_3$CN in water [both containing 0.05 vol % CF$_3$COOH] in 30 min, to 100% in another 5 min; t$_R$ 16.5-19.3 min) to obtain the trifluoroacetate (103 mg). This salt was treated with PL-HCO3 MP anion exchange resin (Polymer Laboratories) in MeOH to afford the free amine, which was disolved in MeOH (0.2 mL), and treated again with 2N anhydrous HCl/ether (1 mL) under Ar protection at room temperature. The mixture was stirred at room temperature overnight. After the solvent was evaporated, the residue was dissolved in deionized water. After the solution was filtered over a cotton plug, the water was removed under reduced pressure at 35° C. After lyophilization from water, the hydrochloride (67 mg) was obtained as a yellow glass. $[\alpha]^{22}_D$ –6.0 (c 0.50 g/L, MeOH). $^1$H NMR (CDCl$_3$, 400 MHz) δ 7.90 (s, 1H), 7.76 (s, 1H), 7.39 (s, 1H), 7.26 (m, 5H), 4.49 (dd, 1H, J=2.8 Hz, J=10.8 Hz), 4.43 (s, 2H), 4.35 (dd, 1H, J=6.0 Hz, J=11.2 Hz), 3.87 (m, 1H), 3.70 (m, 3H), 3.52 (t, 2H, J=6.8 Hz), 3.19 (m, 1H), 2.97 (s, 3H), 2.89 (m, 2H), 2.33 (m, 1H), 2.13 (m, 1H), 2.02 (m, 2H), 1.69 (d, 2H, J=12.0 Hz), 1.49 (m, 1H), 1.44 (m, 2H), 1.16 (m, 2H). $^{13}$C NMR (CDCl$_3$, 100 MHz) δ 156.3, 148.8, 137.0, 128.2, 128.0, 127.7, 121.9, 117.1, 114.2, 72.0, 67.2, 67.0, 65.8, 56.8, 47.4, 40.1, 34.5, 31.2, 30.0, 25.5, 21.7. HRMS (ESI) calcd for C$_{25}$H$_{36}$N$_3$O$_2$ (M+H$^+$) m/z 410.2808, found 410.2800. Anal. Calcd. for C$_{25}$H$_{35}$N$_3$O$_2$.3.2HCl.1.4H$_2$O: C, 54.45; H, 7.49; N, 7.62. Found: C, 54.46; H, 7.55; N, 7.56.

Example 64

3-[(2(R)-Azetidinyl)methoxy]-5-[4-[2-(benzyloxy)ethyl]-1-piperidinyl]pyridine 3-[4-[2-(Benzyloxy)ethyl]-1-piperidinyl]-5-[[1-(tert-butoxycarbonyl)-2(R)-azetidinyl]methoxy]pyridine

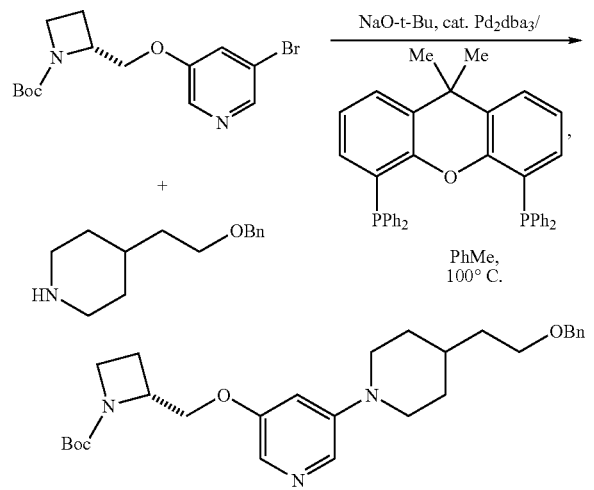

To a solution of 4-[2-(benzyloxy)ethyl]piperidine (330 mg, 1.50 mmol) and 3-bromo-5-[1-(tert-butoxycarbonyl)-2(S)-pyrrolidinyl]pyridine (568 mg, 1.65 mmol, 1.1 equiv.) in 15 mL of anhydrous toluene were added successively sodium tert-butoxide (288 mg, 3.00 mmol, 2.0 equiv.), 4,5-bis(diphenylphosphino)-9,9-dimethylxanthene (Xantphos, 104 mg, 0.18 mmol, 0.12 equiv.) and tris(dibenzylideneacetone)dipalladium(0)-chloroform adduct (93 mg, 0.09 mmol, 0.06 equiv.). The mixture was stirred for 5 h at 100° C. under N$_2$. The solvent was removed under vacuum, and the residue was diluted with water. The solution was extracted with EtOAc, and the combined organic phases were washed with brine, dried over Na$_2$SO$_4$, and concentrated in vacuo. The residue was purified by CC on silica gel with EtOAc/CH$_2$Cl$_2$ 1:5-1:2 to provide the product (320 mg, 44%) as a yellowish oil. LC-MS (ESI) m/z 482 (M+H$^+$).

3-[(2(R)-Azetidinyl)methoxy]-5-[4-[2-(benzyloxy)ethyl]-1-piperidinyl]pyridine

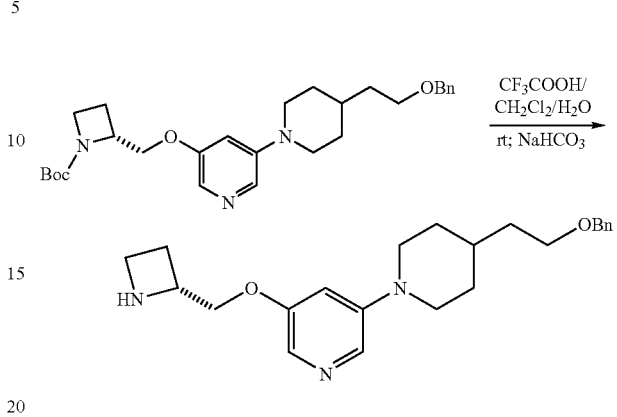

Trifluoroacetic acid (1.5 mL) and water (0.15 mL) were added to CH$_2$Cl$_2$ (7.5 mL). This mixture was added to 3-[4-[2-(benzyloxy)ethyl]-1-piperidinyl]-5-[[1-(tert-butoxycarbonyl)-2(R)-azetidinyl]methoxy]pyridine (260 mg, 0.54 mmol) in a 25 mL round-bottom flask with a magnetic stirrer under N$_2$. After stirring overnight at room temperature, TLC analysis of the crude reaction mixture indicated that the starting material had disappeared. The mixture was concentrated, and the residue was purified by preparative HPLC (column: SunFire Prep C$_{18}$, 150×19 mm, 5 μm particle size; UV detection at 270 nm; mobile phase: A, water with 0.05% CF$_3$COOH; B, methanol; 40-50% B in A in 6 min, up to 100% in 1 min, back to 40% in 1 min). The eluate was partially evaporated under reduced pressure (bath 30° C.) to remove CH$_3$OH. The residue was basified with saturated aqueous NaHCO$_3$ solution and extracted with EtOAc. The combined organic layers were washed with brine and dried. After concentrated in vacuo, the free base (130 mg, 63%) was obtained as a yellow oil. $^1$H NMR (CDCl$_3$, 300 MHz) δ 7.97 (s, 1H), 7.79 (s, 1H), 7.38-7.28 (m, 5H), 6.78 (s, 1H), 4.53 (s, 2H), 4.43-4.41 (m, 1H), 4.15-4.09 (m, 2H), 3.85-3.82 (m, 1H), 3.70-3.66 (m, 2H), 3.58-3.50 (m, 2H), 2.79-2.71 (dd, 2H, J=7.2 Hz, 2.1 Hz), 2.47-2.39 (m, 2H), 1.82-1.78 (d, 2H, J=1.2 Hz), 1.64-1.58 (m, 3H), 1.40-1.27 (m, 3H). LC-MS (ESI) m/z 382 (M+H$^+$).

3-[(2(R)-Azetidinyl)methoxy]-5-[4-[2-(benzyloxy)ethyl]-1-piperidinyl]pyridine Hydrochloride

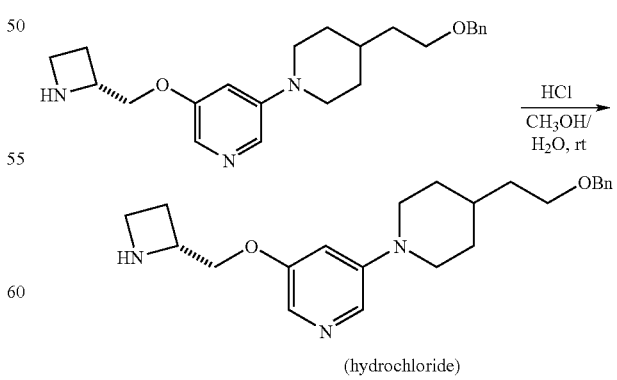

(hydrochloride)

Hydrochloric acid (2M, 0.77 mL, 4.5 equiv.) was added to a solution of 3-[(2(R)-azetidinyl)methoxy]-5-[4-[2-(benzyloxy)ethyl]-1-piperidinyl]pyridine (130 mg, 0.34 mmol) in methanol/water (⅓ mL) under N$_2$. The solution was stirred overnight at room temperature and lyophilized. The lyophilization process was repeated three times to afford the hydrochloride (150 mg) as a yellow solid. $^1$H NMR (D$_2$O, 300 MHz) δ 7.93 (s, 1H), 7.78 (s, 1H), 7.45 (s, 1H), 7.34 (s, 5H), 4.92-4.87 (s, 1H), 4.48 (s, 2H), 4.43-4.41 (m, 2H), 4.10-3.99 (m, 2H), 3.78-3.73 (m, 2H), 3.59-3.55 (m, 2H), 2.97-2.89 (t, 2H, J=12.0 Hz), 2.62 (dd, 2H, J=8.4 Hz), 1.74-1.69 (m, 2H), 1.61-1.58 (m, 1H), 1.53-1.47 (m, 2H), 1.26-1.19 (m, 2H). LC-MS (ESI) m/z 382 (M+H$^+$). Anal. Calcd. for C$_{23}$H$_{31}$N$_3$O$_2$.2.3HCl.1.45H$_2$O: C, 56.21; H, 7.42; N, 8.55; Cl, 16.59. Found: C, 56.31; H, 7.63; N, 8.56; Cl, 16.75.

Example 65

3-[4-[(2-Phenylethoxy)methyl]-1-piperidinyl]-5-[(2 (S)-pyrrolidinyl)methoxy]pyridine 1-(tert-Butoxycarbonyl)-4-[(phenylacetoxy)methyl] piperidine

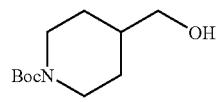

+

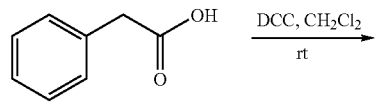

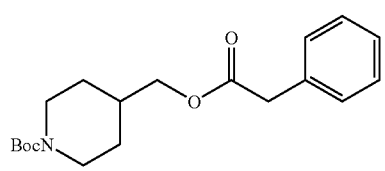

To a mixture of phenylacetic acid (312 mg, 2.29 mmol, 1.2 equiv.) and 1-(tert-butoxycarbonyl)-4-(2-hydroxymethyl)piperidine (411 mg, 1.90 mmol) in CH$_2$Cl$_2$ (10 mL) were added DCC (473 mg, 2.29 mmol, 1.2 equiv.) and DMAP (12.1 mg, 95 μmol, 0.05 equiv.). The mixture was allowed to stand overnight. After filtration, the liquid phase was washed with brine and dried over Na$_2$SO$_4$. After the solvent was removed, the residue was purified by CC (SiO$_2$, hexane/EtOAc 4:1) to obtain, after evaporation, 1-(tert-butoxycarbonyl)-4-[phenylacetoxy)methyl]piperidine (562 mg, 89%) as a colorless oil. $^1$H NMR (CDCl$_3$, 400 MHz) δ 7.31 (m, 5H), 4.12 (d, 2H, J=14.4 Hz), 3.94 (d, 2H, J=6.4 Hz), 3.62 (s, 2H), 2.66 (t, 2H, J=13.2 Hz), 1.77 (m, 1H), 1.64 (m, 3H), 1.45 (s, 9H), 1.24 (m, 1H), 1.12 (m, 2H).

4-[(2-Phenylethoxy)methyl]piperidine

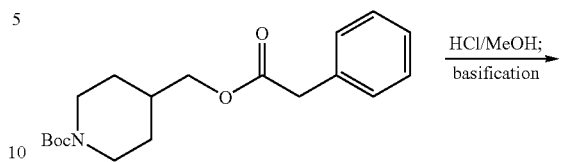

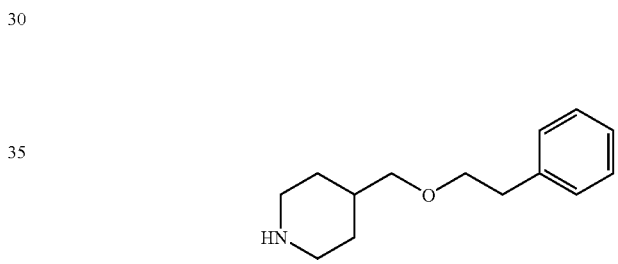

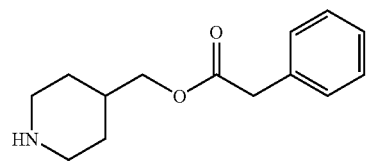

To a solution of 1-(tert-butoxycarbonyl)-4-[(phenylacetoxy)methyl]piperidine (318 mg, 0.95 mmol) in MeOH (0.2 mL) was added 2N anhydrous HCl/ether (1.5 mL, 3.0 mmol). The reaction mixture was stirred overnight. After evaporation, the residue was dissolved in deionized water. EtOAc was used to wash the aqueous layer before the pH was altered to approx. 9-10. The aqueous layer was extracted three times with CH$_2$Cl$_2$ and dried over Na$_2$SO$_4$. After evaporation, 4-[(phenylacetoxy)methyl]piperidine (173 mg, 78%) was obtained as a colorless oil.

In a oven-dried flask, 4-[(phenylacetoxy)methyl]piperidine (53 mg, 0.23 mmol) and InBr$_3$ (161 mg, 0.46 mmol) were dissolved in toluene (1.5 mL). After degassing and replacement of the atmosphere with Ar, Et$_3$SiH (145 μL, 0.91 mmol, 4.0 equiv.) was added. The mixture was stirred at 90° C. for 4 h. After cooling to room temperature, the reaction was quenched with 1N HCl. The aqueous layer was washed with EtOAc, and its pH was raised to 9-10. After extraction with CH$_2$Cl$_2$, the organic layer was dried with Na$_2$SO$_4$. The solvent was removed to furnish 4-[(2-phenylethoxy)methyl]piperidine (30 mg, 59%) as a colorless oil. $^1$H NMR (CDCl$_3$, 400 MHz) δ 7.22 (m, 5H), 3.61 (t, 2H, J=7.2 Hz), 3.26 (d, 2H, J=6.0 Hz), 3.07 (d, 2H, J=12.0 Hz), 2.87 (t, 2H, J=7.2 Hz), 2.59 (t, 2H, J=11.6 Hz), 2.31 (br, 1H), 1.70 (m, 3H), 1.09 (m, 2H).

3-[4-[(2-Phenylethoxy)methyl]-1-piperidinyl]-5-[(2(S)-pyrrolidinyl)methoxy]pyridine Hydrochloride

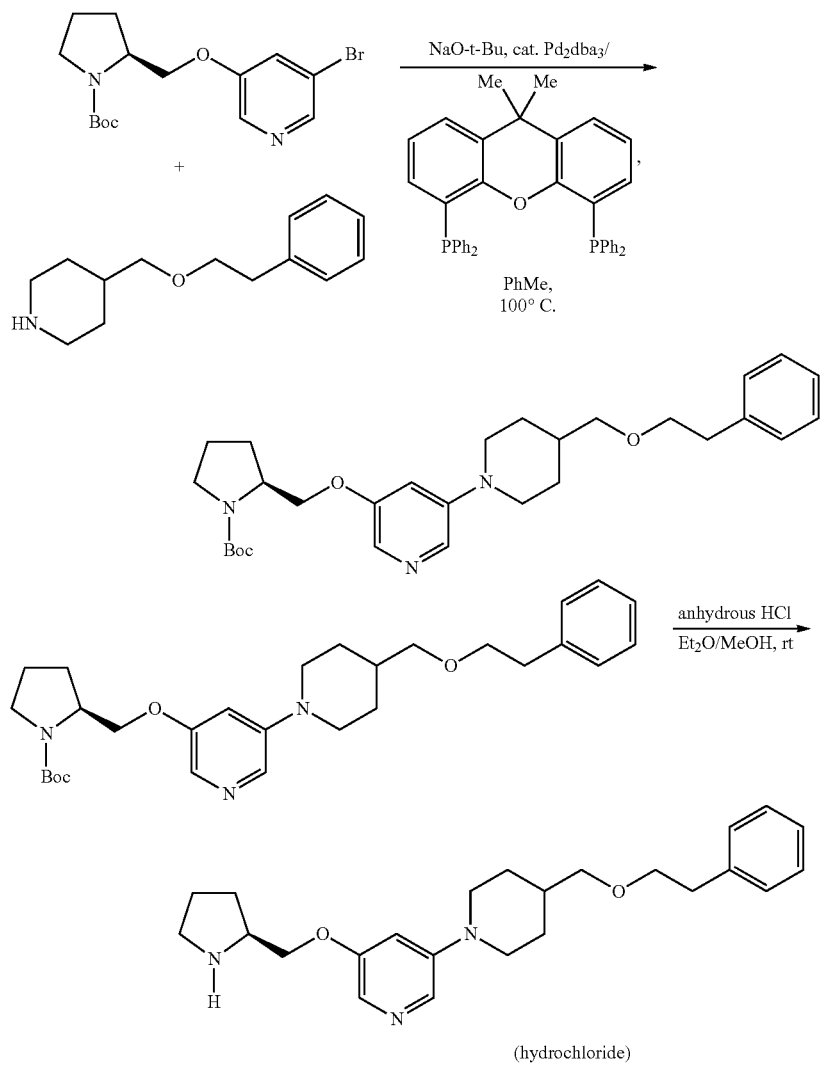

(hydrochloride)

To a solution of 3-bromo-5-[[1-(tert-butoxycarbonyl)-2(R)-pyrrolidinyl]methoxy]pyridine (160 mg, 0.45 mmol) and 4-[2-(phenylethoxy)methyl]piperidine (98 mg, 0.45 mmol) in anhydrous toluene (2 mL) were added successively sodium tert-butoxide (64 mg, 0.67 mmol), tris(dibenzylideneacetone)dipalladium(0) (8.2 mg, 9.0 µmol, 0.02 equiv.), and 4,5-bis(diphenylphosphino)-9,9-dimethylxanthene (Xantphos; 15.5 mg, 27 µmol, 0.06 equiv.). The mixture was degassed and purged with Ar (3 cycles), then warmed to 98-100° C. for 4 h. After cooling to room temperature, the mixture was diluted with EtOAc and washed with brine. The solution was dried over $Na_2SO_4$ and evaporated, and the residue was purified by CC on $SiO_2$ with $CH_2Cl_2$/EtOAc 4:1, then 1:1. 3-[[1-(tert-Butoxycarbonyl)-2(S)-pyrrolidinyl]methoxy]-5-[4-[(2-phenylethoxy)methyl]-1-piperidinyl]pyridine (174 mg, 78%) was obtained as a pale yellow oil.

To a solution of this intermediate (174 mg, 0.35 mmol) in MeOH (0.4 mL) was added 2N anhydrous HCl/ether (1 mL) under Ar at room temperature. The mixture was stirred at room temperature overnight. After the solvent was evaporated, the residue was dissolved in deionized water (25 mL). The aqueous solution was washed twice with EtOAc, then filtered over a cotton plug. The water was removed under reduced pressure at 35° C. The residue was purified by preparative HPLC (ACE AQ 150×21.2 mm; UV detection at 254 nm and 280 nm; flow 10.0 mL/min; 8% to 100% MeOH in water [both containing 0.05 vol % of $CF_3COOH$] in 30 min, then 100% for another 3 min) to obtain the trifluoroacetate. This salt was treated with PL-HCO3 MP anion exchange resin (Polymer Laboratories) in MeOH to afford the free amine, which was dissolved in MeOH (0.5 mL) and treated again with 2N anhydrous HCl/ether (2 mL) under Ar protection at room temperature. The mixture was stirred at room temperature overnight. After the solvent was evaporated, the residue was dissolved in deionized water. After the solution was filtered over a cotton plug, the water was removed under reduced pressure at 35° C. After lyophilization from water, the hydrochloride (132 mg) was obtained as a yellow glass. $^1$H NMR ($D_2O$, 400 MHz) δ 7.88 (d, 1H, J=2.4 Hz), 7.77 (d, 1H, J=2.0 Hz), 7.39 (s, 1H), 7.24 (m, 5H), 4.46 (dd, 1H, J=3.2

Hz, J=10.4 Hz), 4.29 (dd, 1H, J=7.6 Hz, J=10.4 Hz), 4.10 (m, 1H), 3.74 (d, 2H, J=12.8 Hz), 3.66 (t, 2H, J=6.8 Hz), 3.40 (t, 2H, J=6.8 Hz), 3.30 (d, 2H, J=6.4 Hz), 2.90 (t, 2H, J=12.4 Hz), 2.78 (t, 2H, J=6.4 Hz), 2.26 (m, 1H), 2.11 (m, 2H), 1.93 (m, 1H), 1.78 (m, 1H), 1.68 (d, 2H, J=12.4 Hz), 1.13 (m, 2H); $^{13}C$ NMR ($D_2O$, 100 MHz) δ 156.5, 148.9, 138.6, 128.5, 128.1, 125.9, 121.5, 117.0, 114.0, 74.4, 71.0, 67.2, 58.1, 46.8, 45.6, 34.8, 34.3, 26.9, 25.4, 23.1. Anal. Calcd. for $C_{24}H_{33}N_3O_2 \cdot 2.85HCl \cdot 1.95H_2O$: C, 53.92; H, 7.49; N, 7.86; Cl, 18.90. Found: C, 53.84; H, 7.17; N, 7.80; Cl, 18.58.

Example 66

3-[4-(4-Phenylbutyl)-1-piperidinyl]-5-[(2(S)-pyrrolidinyl)methoxy]pyridine 1-(tert-Butoxycarbonyl)-4-(4-phenylbutylidene)piperidine

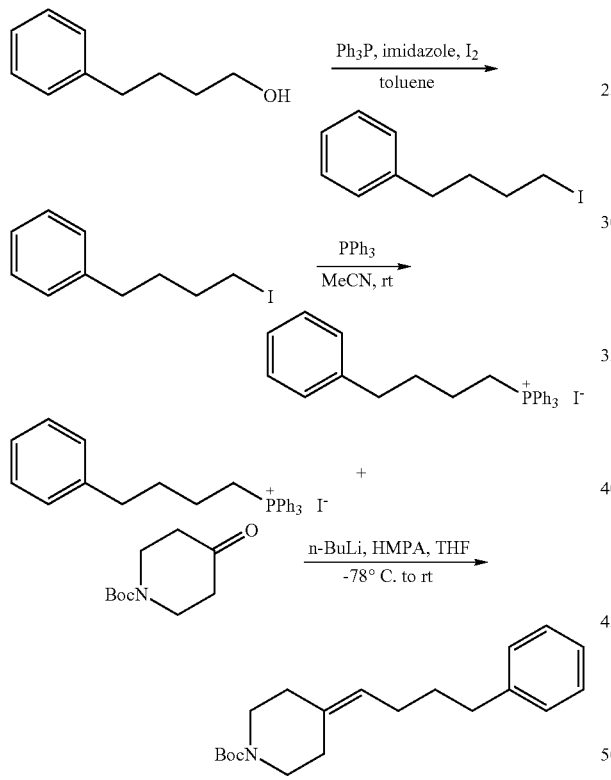

To a mixture of 4-phenyl-1-butanol (601 mg, 4.0 mmol), $Ph_3P$ (1.57 g, 6.0 mmol, 1.5 equiv.) and imidazole (409 mg, 6.0 mmol, 1.5 equiv.) in toluene (20 mL) was added $I_2$ (1.52 g, 6.0 mmol, 1.5 equiv.) at 0° C. The mixture was allowed to stand overnight, and the reaction was quenched with saturated $Na_2S_2O_3$ solution. The mixture was extracted with hexane/EtOAc 10:1, and the organic layer was washed with brine and dried over $Na_2SO_4$. After concentration, the residue was filtrated through Celite, and the Celite was washed with hexane. After removal of the solvent, (4-iodobutyl)benzene (1.04 g, 100%) was obtained as a pale yellow oil, which was used in the subsequent step without purification.

A solution of (4-iodobutyl)benzene (1.04 g, 4.0 mmol) and $Ph_3P$ (1.05 g, 4.0 mmol) in $CH_3CN$ (20 mL) was stirred for 48 h and then washed with hexane. The solvent was removed to afford triphenyl(4-phenylbutyl)phosphonium iodide (1.30 g, 62%) as a white foam, which was used in the following step without purification.

To a solution of triphenyl(4-phenylbutyl)phosphonium iodide (975 mg, 1.87 mmol) in THF (8 mL) under Ar at −78° C. was added HMPA (1 mL) followed by n-BuLi (1.6 M in hexane; 1.28 mL, 2.05 mmol, 1.1 equiv.). After stirring at room temperature for 2 h, the mixture was cooled to −78° C. again, and tert-butyl 4-oxopiperidine-1-carboxylate (409 mg, 2.05 mmol, 1.1 equiv.) in THF (2 mL) was added. The mixture was allowed to warm to room temperature and to stand for 2 days. The reaction was quenched with $H_2O$, and the mixture was extracted three times with EtOAc. The combined organic layers were washed with brine and dried over $Na_2SO_4$. After concentration, the residue was purified by CC ($SiO_2$, hexane/EtOAc 10:1) to obtain 1-(tert-butoxycarbonyl)-4-(4-phenylbutylidene)piperidine (216 mg, 37%) as a pale yellow oil. $^1H$ NMR ($CDCl_3$, 400 MHz) δ 7.25 (m, 2H), 7.15 (m, 3H), 5.22 (t, 1H, J=7.2 Hz), 3.55 (m, 4H), 2.60 (t, 2H, J=8.0 Hz), 2.15 (m, 4H), 2.03 (m, 2H), 1.66 (m, 2H), 1.46 (s, 9H).

1-(tert-Butoxycarbonyl)-4-(4-phenylbutyl)piperidine

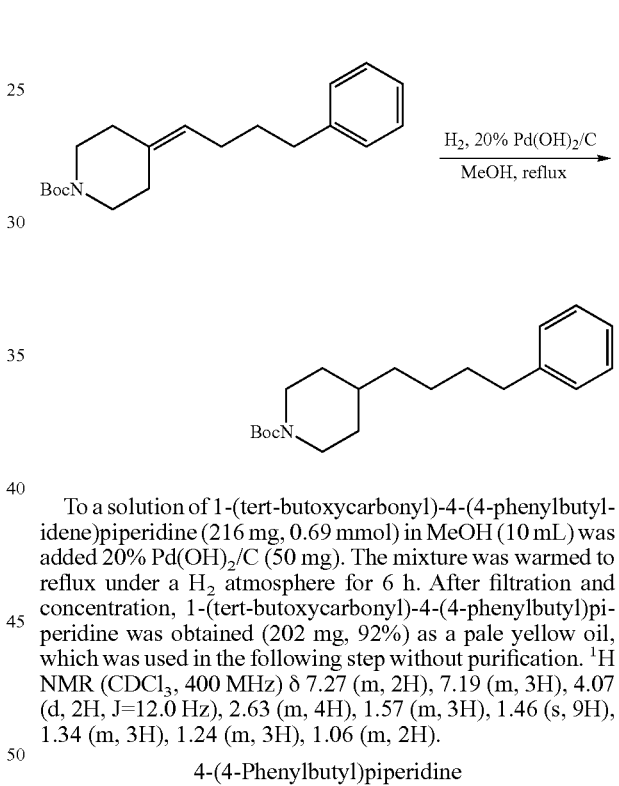

To a solution of 1-(tert-butoxycarbonyl)-4-(4-phenylbutylidene)piperidine (216 mg, 0.69 mmol) in MeOH (10 mL) was added 20% $Pd(OH)_2/C$ (50 mg). The mixture was warmed to reflux under a $H_2$ atmosphere for 6 h. After filtration and concentration, 1-(tert-butoxycarbonyl)-4-(4-phenylbutyl)piperidine was obtained (202 mg, 92%) as a pale yellow oil, which was used in the following step without purification. $^1H$ NMR ($CDCl_3$, 400 MHz) δ 7.27 (m, 2H), 7.19 (m, 3H), 4.07 (d, 2H, J=12.0 Hz), 2.63 (m, 4H), 1.57 (m, 3H), 1.46 (s, 9H), 1.34 (m, 3H), 1.24 (m, 3H), 1.06 (m, 2H).

4-(4-Phenylbutyl)piperidine

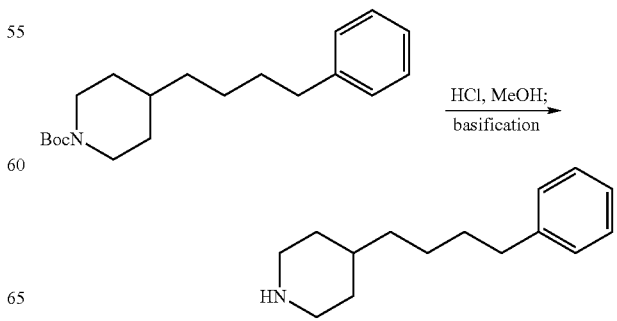

To a solution of 1-(tert-butoxycarbonyl)-4-(4-phenylbutyl) piperidine (202 mg, 636 μmol) in MeOH (1 mL) was added 2N anhydrous HCl/ether (1.5 mL, 3.0 mmol). The solution was stirred overnight and then evaporated. The residue was dissolved in deionized water. EtOAc was used to wash the aqueous layer before the pH was altered to approx. 9-10. The aqueous layer was extracted three times with $CH_2Cl_2$ and dried over $Na_2SO_4$. After evaporation, 4-(4-phenylbutyl)piperidine (83.4 mg, 60%) was obtained as a colorless oil. $^1$H NMR (CDCl$_3$, 400 MHz) δ 7.28 (m, 2H), 7.18 (m, 3H), 3.05 (m, 2H), 2.57 (m, 4H), 2.41 (br, 1H), 1.61 (m, 3H), 1.25 (m, 8H).

3-[4-(4-Phenylbutyl)-1-piperidinyl]-5-[(2(S)-pyrrolidinyl)methoxy]pyridine Hydrochloride

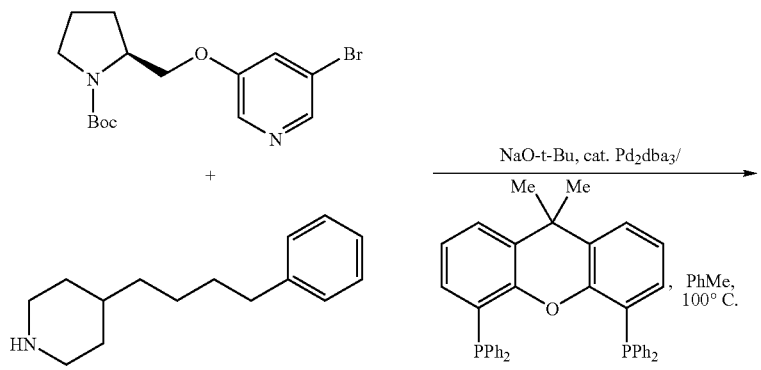

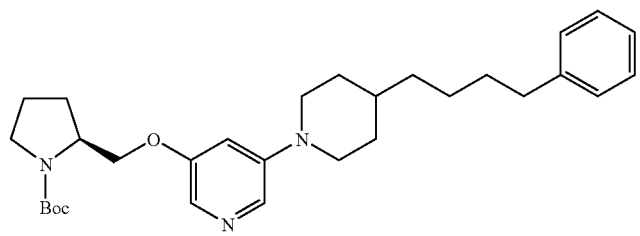

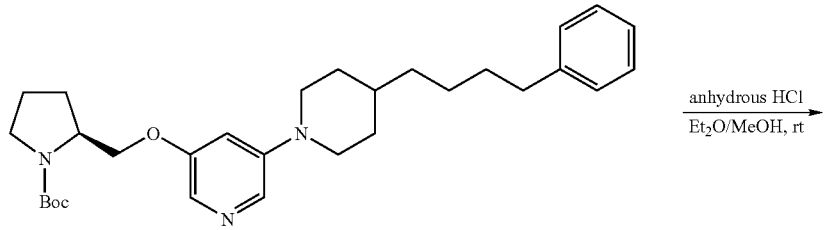

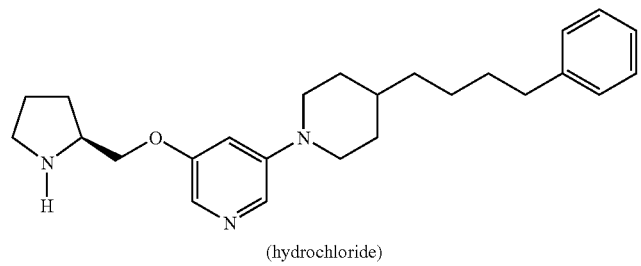

(hydrochloride)

To a mixture of 3-bromo-5-[[1-(tert-butoxycarbonyl)-2 (R)-pyrrolidinyl]methoxy]pyridine (125 mg, 350 µmol) and 4-(4-phenylbutyl)piperidine (83.4 mg, 384 µmol, 1.1 equiv.) in anhydrous toluene (2 mL) were added successively potassium tert-butoxide (64 mg, 0.52 mmol, 1.5 equiv.), tris(dibenzylideneacetone)dipalladium(0) (6.4 mg, 7.0 µmol, 0.02 equiv.), and 4,5-bis(diphenylphosphino)-9,9-dimethylxanthene (Xantphos; 12.1 mg, 21 µmol, 55 mequiv.). The mixture was degassed and purged with Ar (3 cycles), then warmed by microwave irradiation under Ar. After reaction for 30-40 minutes at 130° C., the mixture was cooled to room temperature, diluted with EtOAc, and washed with brine. The solution was dried over $Na_2SO_4$ and evaporated, and the residue was purified by CC on $SiO_2$ with $CH_2Cl_2$/EtOAc 3:2. 3-[[1-(tert-Butoxycarbonyl)-2(S)-pyrrolidinyl]methoxy]-5-[4-(4-phenylbutyl)-1-piperidinyl]pyridine (128 mg, 74%) was obtained as a pale yellow oil.

To a solution of this intermediate (128 mg, 0.26 mmol) in MeOH (0.5 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by preparative HPLC (ACE AQ 150×21.2 mm; UV detection at 254 and 280 nm; flow 17.0 mL/min; 0% to 60% MeOH in water [both containing 0.05 vol % $CF_3COOH$] in 20 min, to 100% in another 5 min, 100% for a final 5 min; $t_R$ 22.8-24.8 min) to obtain the trifluoroacetate. This salt was treated with PL-HCO3 MP anion exchange resin (Polymer Laboratories) in MeOH to afford the free amine, which was dissolved in MeOH (0.5 mL) and treated again with 2N anhydrous HCl/ether (1 mL) under Ar protection at room temperature. The mixture was stirred at room temperature overnight. After the solvent was evaporated, the residue was dissolved in deionized water. After the solution was filtered over a cotton plug, the water was removed under reduced pressure at 35° C. After lyophilization from water, the hydrochloride (45 mg) was obtained as a yellow glass. $^1$HNMR ($D_2O$, 400 MHz) δ 7.88 (s, 1H), 7.82 (d, 1H, J=1.6 Hz), 7.39 (s, 1H), 7.14 (m, 2H), 7.06 (m, 3H), 4.46 (dd, 1H, J=3.2, 10.8 Hz), 4.31 (dd, 1H, J=7.6, 10.4 Hz), 4.11 (m, 1H), 3.70 (d, 2H, J=12.4 Hz), 3.41 (t, 2H, J=7.2 Hz), 2.77 (t, 2H, J=11.6 Hz), 2.46 (t, 2H, J=7.2 Hz), 2.26 (m, 1H), 2.12 (m, 2H), 1.93 (m, 1H), 1.65 (d, 2H, J=11.6 Hz), 1.45 (m, 2H), 1.43 (m, 7H); $^{13}$C NMR ($D_2O$, 100 MHz) δ 156.5, 149.0, 142.3, 127.9, 125.2, 121.3, 113.9, 67.4, 58.0, 47.1, 45.6, 35.4, 35.1, 34.1, 31.0, 30.5, 25.5, 25.4, 23.1.

Example 67
3-[4-[2-(2-Phenylethoxy)ethyl]-1-piperidinyl]-5-[(2 (S)-pyrrolidinyl)methoxy]pyridine 1-(tert-Butoxycarbonyl)-4-[2-(phenylacetoxy)ethyl] piperidine

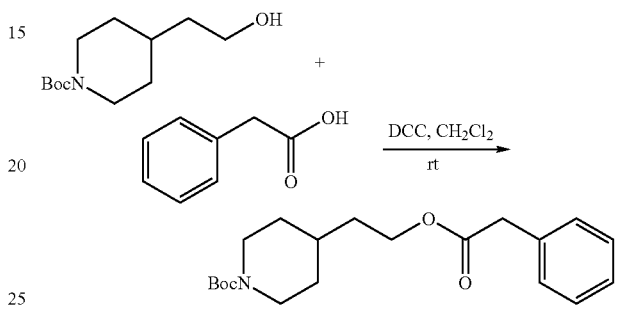

To a mixture of phenylacetic acid (327 mg, 2.40 mmol, 1.2 equiv.) and 1-(tert-butoxycarbonyl)-4-(2-hydroxyethyl)piperidine (459 mg, 2.00 mmol) in $CH_2Cl_2$ (10 mL) were added DCC (495 mg, 2.40 mmol, 1.2 equiv.) and DMAP (12.2 mg, 100 µmol, 0.1 equiv.). The reaction mixture was allowed to stand overnight. After filtration, the liquid phase was washed with brine and dried over $Na_2SO_4$. After the solvent was removed, the residue was purified by CC ($SiO_2$, hexane/EtOAc 4:1). The ester (672 mg, 97%) was obtained as a colorless oil. $^1$H NMR ($CDCl_3$, 400 MHz) δ 7.31 (m, 5H), 4.14 (t, 2H, J=6.8 Hz), 4.03 (d, 2H, J=13.2 Hz), 3.61 (s, 2H), 2.60 (dt, 2H, J=2.0, 12.8 Hz), 1.56 (m, 5H), 1.45 (s, 9H), 1.06 (m, 2H).

3-[4-[2-(2-Phenylethoxy)ethyl]-1-piperidinyl]-5-[(2 (S)-pyrrolidinyl)methoxy]pyridine Hydrochloride

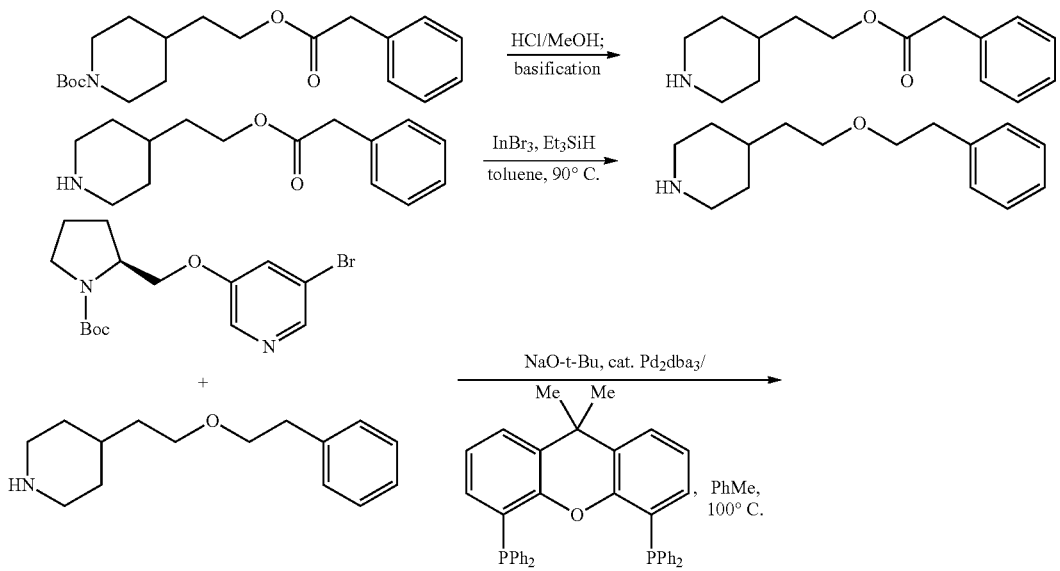

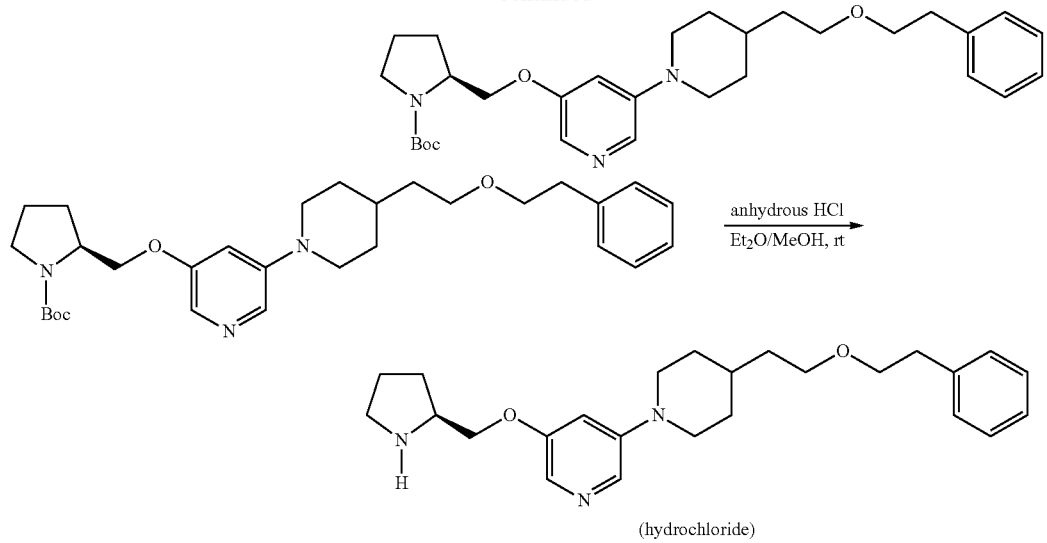

(hydrochloride)

To a solution of 1-(tert-butoxycarbonyl)-4-[2-(phenylacetoxy)ethyl]piperidine (431 mg, 1.24 mmol) in MeOH (0.2 mL) was added 2N anhydrous HCl/ether (1.5 mL, 3.0 mmol). The reaction mixture was stirred overnight. After evaporation, the residue was dissolved in deionized water. EtOAc was used to wash the aqueous layer before the pH was altered to approx. 9-10. The aqueous layer was extracted three times with $CH_2Cl_2$, and the combined organic phases were dried over $Na_2SO_4$. After evaporation, 4-[2-(phenylacetoxy)ethyl]piperidine (268 mg, 87%) was obtained as a colorless oil.

In a oven-dried flask, 4-[2-(phenylacetoxy)ethyl]piperidine (101 mg, 0.41 mmol) and $InBr_3$ (290 mg, 0.82 mmol, 2 equiv.) were dissolved in toluene (2 mL). After degassing and replacement of the atmosphere with Ar, $Et_3SiH$ (260 μL, 1.64 mmol, 4 equiv.) was added. The mixture was stirred at 90° C. for 4 h. After cooling to room temperature, the reaction was quenched with 1N HCl. After the aqueous layer was washed with EtOAc, its pH was raised to 9-10. After extraction with $CH_2Cl_2$, the organic layer was dried with $Na_2SO_4$. The solvent was removed to afford 4-[2-(2-phenylethoxy)ethyl]piperidine (40 mg, 42%) as a colorless oil.

To a solution of 3-bromo-5-[[1-(tert-butoxycarbonyl)-2(R)-pyrrolidinyl]methoxy]pyridine (118 mg, 0.33 mmol) and 4-[2-(2-phenylethoxy)ethyl]piperidine (77 mg, 0.33 mmol) in anhydrous toluene (2 mL) were added successively sodium tert-butoxide (48 mg, 0.50 mmol, 1.5 equiv.), tris(dibenzylideneacetone)dipalladium(0) (6.1 mg, 6.6 μmol, 0.02 equiv.), and 4,5-bis(diphenylphosphino)-9,9-dimethylxanthene (Xantphos; 11.5 mg, 20 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over $Na_2SO_4$, and evaporated. The residue was purified by CC on $SiO_2$ with $CH_2Cl_2$/EtOAc 4:1, then 1:1. 3-[[1-(tert-Butoxycarbonyl)-2(S)-pyrrolidinyl]methoxy]-5-[4-[2-(2-phenylethoxy)ethyl]-1-piperidinyl]pyridine (96 mg, 57%) was obtained as a pale-yellow oil.

To a solution of this intermediate (96 mg, 0.19 mmol) in MeOH (0.2 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by preparative HPLC (ACE AQ 150×21.2 mm; UV detection at 254 nm and 280 nm; flow 10.0 mL/min; 8% to 100% MeOH in water [both containing 0.1 vol % of $CF_3COOH$] in 30 min, then 100% for another 3 min; $t_R$ 20.7-23.6 min) to obtain the trifluoroacetate. This salt was treated with PL-HCO3 MP anion exchange resin (Polymer Laboratories) in MeOH to afford the free amine, which was dissolved in MeOH (0.5 mL) and treated again with 2N anhydrous HCl/ether (2 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the hydrochloride (74 mg) was obtained as a yellow glass. $^1$H NMR ($D_2O$, 400 MHz) δ 7.97 (d, 1H, J=2.0 Hz), 7.82 (d, 1H, J=2.0 Hz), 7.46 (t, 1H, J=2.0 Hz), 7.31 (m, 5H), 4.53 (dd, 1H, J=3.2, 10.4 Hz), 4.35 (dd, 1H, J=7.6, 10.4 Hz), 4.17 (m, 1H), 3.77 (m, 4H), 3.56 (t, 2H, J=6.0 Hz), 3.45 (t, 2H, J=7.2 Hz), 2.90 (m, 4H), 2.32 (m, 1H), 2.15 (m, 2H), 2.01 (m, 1H), 1.71 (d, 2H, J=12.8 Hz), 1.48 (m, 3H), 1.20 (m, 2H); $^{13}$C NMR ($D_2O$, 100 MHz) δ 156.5, 149.1, 138.9, 128.5, 128.2, 126.0, 121.7, 117.0, 114.0, 70.5, 67.5, 67.2, 58.1, 47.3, 45.6, 34.8, 34.3, 31.2, 29.9, 25.4, 23.1. Anal. Calcd. for $C_{25}H_{35}N_3O_2 \cdot 1.60HCl \cdot 0.1H_2O$: C, 63.93; H, 7.90; N, 8.95. Found: C, 64.26; H, 8.02; N, 8.63.

Example 68

3-[3(S)-[3-(Benzyloxy)propyl]-1-piperidinyl]-5-[(2(S)-pyrrolidinyl)methoxy]pyridine

3-[1-(tert-Butoxycarbonyl)-3-piperidinyl]-1-propanol

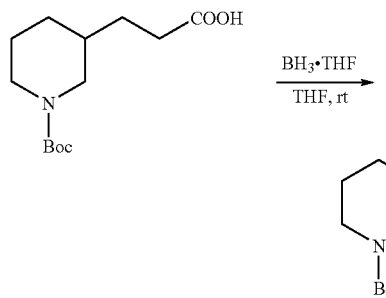

To a solution of commercially available 3-[1-(tert-butoxycarbonyl)-3-piperidinyl]propionic acid (2.57 g, 10.0 mmol) in 100 mL of anhydrous THF was added slowly a solution of $BH_3 \cdot THF$ complex in THF (1.0 M, 20 mL, 2.0 equiv) at room temperature under $N_2$. The solution was stirred for 16 h at room temperature. Water was added carefully (hydrogen evolution!), and the resulting solution was concentrated under reduced pressure. The residue was diluted with water and extracted with EtOAc. The combined organic layers were washed with brine and dried over $Na_2SO_4$. The solvent was removed under reduced pressure to give the alcohol (2.35 g, 97%) as a colorless oil. LC-MS (ESI) m/z 244 (M+H⁺).

tert-Butyl 3-[3-(Benzyloxy)propyl]piperidine-1-carboxylate

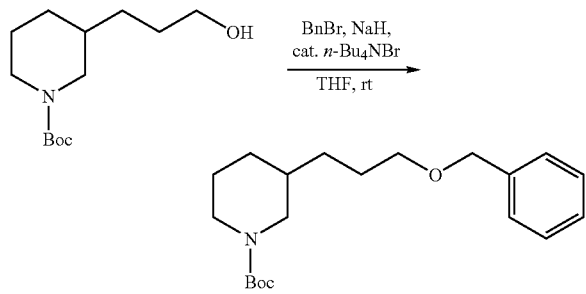

NaH (150 mg, 6.25 mmol, 1.7 equiv.) was added to a solution of 3-[1-(tert-butoxycarbonyl)-3-piperidinyl]-1-propanol (900 mg, 3.70 mmol) in THF (10 mL) with ice cooling under $N_2$. The solution was stirred for 2 h at room temperature. Then benzyl bromide (950 mg, 5.55 mmol, 1.5 equiv.) and n-Bu₄NBr (119 mg, 0.37 mmol, 0.10 equiv.) were added. The reaction was allowed to proceed with stirring for 20 h at room temperature and then quenched with water. The mixture was extracted with EtOAc, and the combined organic layers were dried over $Na_2SO_4$ and concentrated under vacuum. The residue was applied onto a silica gel column, and the product was eluted with EtOAc/petroleum ether 1:50 to give the benzyl ether (0.91 g, 74%) as a yellow oil. ¹H NMR (CDCl₃, 300 MHz) δ 7.39-7.28 (m, 5H), 4.52 (s, 2H), 3.95-3.91 (m, 2H), 3.48 (t, 2H, J=6.6 Hz), 2.76 (td, 1H, J=13.2, 3.0 Hz), 2.46 (td, 1H, J=13.2, 2.4 Hz), 1.86-1.81(m, 1H), 1.72-1.61 (m, 3H), 1.47 (s, 11H), 1.42-1.22 (m, 2H), 1.14-1.06 (m, 1H). LC-MS (ESI) m/z 334 (M+H⁺).

tert-Butyl 3(S)-[3-(Benzyloxy)propyl]piperidine-1-carboxylate and tert-Butyl 3(R)-[3-(Benzyloxy)propyl]piperidine-1-carboxylate

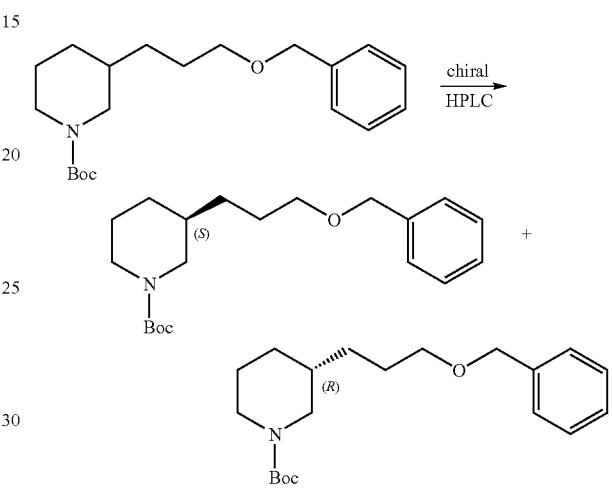

Racemic tert-butyl 3-[3-(benzyloxy)propyl]piperidine-1-carboxylate (910 mg) was resolved into its enantiomers by preparative HPLC under the following conditions: column, Chiralcel OJ-H-SFC, 25×2.1 cm, 5 μm particle size; UV detection at 210 nm; mobile phase, hexane/ethanol 98:2, isocratic. Fractions containing the individual enantiomers were evaporated under reduced pressure (bath 30° C.). The S-isomer [190 mg, $t_R$=6.76 min, $[\alpha]_D^{26}$–20.0 (c 20 g/L, CHCl₃), ee>99.9%] and the R-isomer [50 mg, $t_R$=8.13 min, $[\alpha]_D^{26}$+ 20.3 (c 20 g/L, CHCl₃), ee>99%] were obtained as light-yellow oils. The mass balance was recovered as mixed fraction.

Alternatively, the resolution can also be effected by preparative SFC under the following conditions: column, Chiralcel OJ-H-SFC, 25×2.1 cm, 5 μm particle size; UV detection at 254 nm; flow 1.5 mL/min; mobile phase, $CO_2$/methanol 93:7.

In another variant of this method, the sequence of the borane reduction/benzylation steps and of the enantiomer resolution by preparative HPLC was reversed as shown below. Both enantiomers of 3-[1-(tert-butoxycarbonyl)-3-piperidinyl]propionic acid were transformed into the enantiomeric hydrochlorides of 3-(3-piperidinyl)propionic acid, which exhibited opposite optical rotations of equal absolute value. Of these, the R-enantiomer was identified by the positive sign of its optical rotation, as has been reported in the literature (Brehm, R.; Ohnhäuser, D.; Gerlach, H. *Helv. Chim. Acta* 1987, 70, 1981-1987). The N-Boc precursor leading to this enantiomer was subjected to borane reduction and benzylation to arrive at tert-butyl 3(R)-[3-(benzyloxy)propyl] piperidine-1-carboxylate which was found dextrorotatory, whereby the

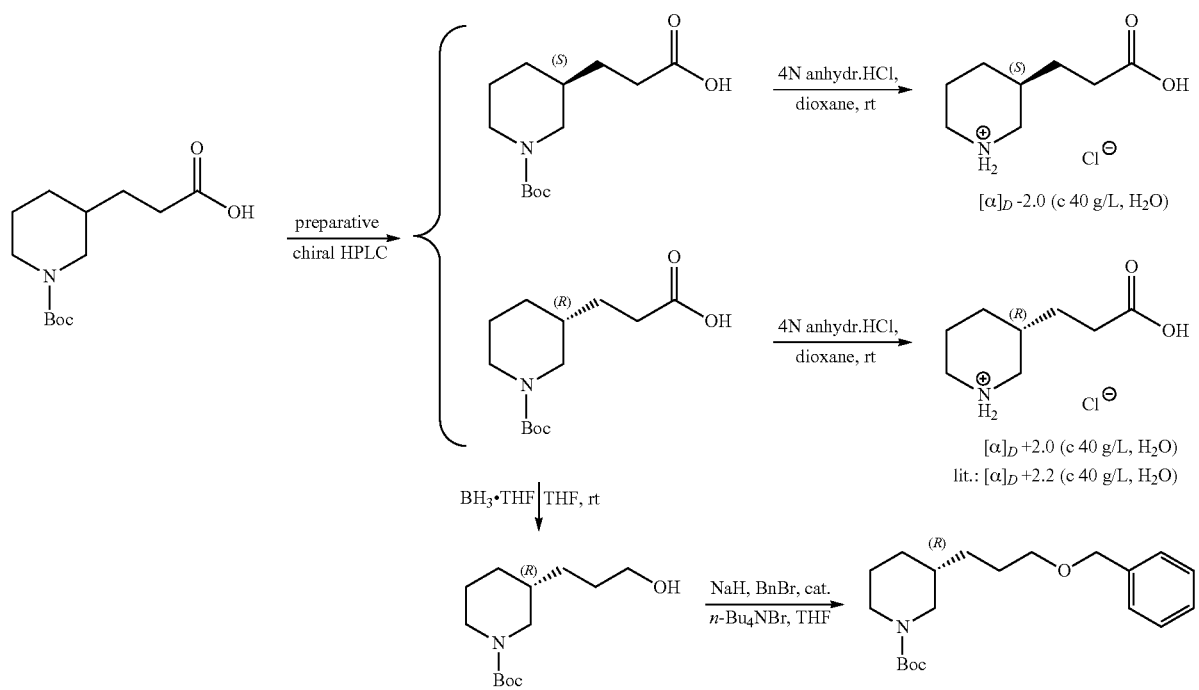

assignment of R-configuration to the dextrorotatory enantiomer obtained by resolution of racemic tert-butyl 3-[3-(benzyloxy)propyl]piperidine-1-carboxylate was confirmed.

3(S)-[3-(Benzyloxy)propyl]piperidine

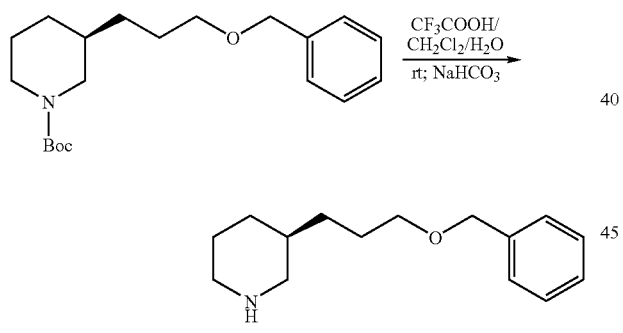

To a solution of tert-butyl 3(S)-[3-(benzyloxy)propyl]piperidine-1-carboxylate (280 mg, 0.84 mmol) in $CH_2Cl_2/H_2O$ (6 mL/0.5 mL) was added $CF_3COOH$ (1.92 g, 16.8 mmol, 20 equiv.) at 0° C. under $N_2$. The solution was stirred overnight at room temperature. After concentration under reduced pressure, water was added, and the solution was washed with hexane. The aqueous phase was basified with saturated $NaHCO_3$ solution and extracted with EtOAc. The combined organic layers were washed with brine and dried over $Na_2SO_4$. The solvent was removed in vacuo to give 3(S)-[3-(benzyloxy)propyl]piperidine (190 mg, 97%) as a yellow oil. LC-MS (ESI) m/z 234 (M+H$^+$).

3-[3(S)-[3-(Benzyloxy)propyl]-1-piperidinyl]-5-[1-(tert-butoxycarbonyl)-2(S)-pyrrolidinyl)methoxy]pyridine

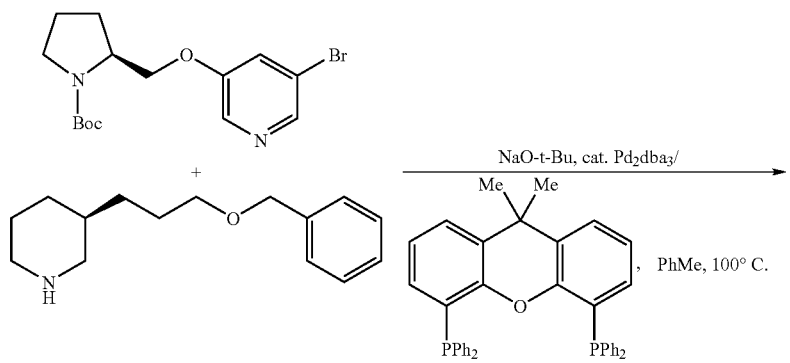

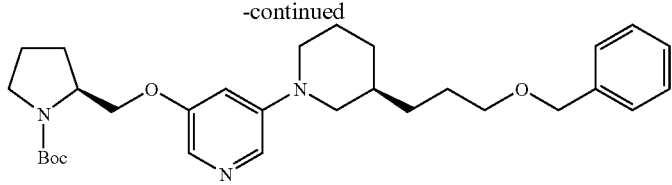

In a 100 mL round-bottom flask under $N_2$, a solution/suspension of 3(S)-[3-(benzyloxy)propyl]piperidine (250 mg, 1.07 mmol), 3-bromo-5-[1-(tert-butoxycarbonyl)-2(S)-pyrrolidinyl]pyridine (570 mg, 1.60 mmol, 1.5 equiv.), sodium tert-butoxide (150 mg, 1.56 mmol, 1.50 equiv.), tris(dibenzylideneacetone)dipalladium(0) (18 mg, 20 μmol, 0.02 equiv.) and 4,5-bis(diphenylphosphino)-9,9-dimethylxanthene (Xantphos; 37 mg, 60 μmol, 0.06 equiv.) in 20 mL of anhydrous toluene was stirred for 4 h at 100° C. After this time period, the reaction was complete as judged by TLC analysis. After concentration in vacuo, the pH of the solution was adjusted to 5 with saturated aqueous $NH_4Cl$ solution. The solution was extracted with EtOAc, and the combined organic layers were washed with brine and dried. The solvent was removed under reduced pressure. The residue was applied onto a silica gel column, and the product was eluted with EtOAc/petroleum ether 1:10-1:1 to give the title product (350 mg, 64%) as a yellow oil. LC-MS (ESI) m/z 510 (M+H⁺).

3-[3(S)-[3-(Benzyloxy)propyl]-1-piperidinyl]-5-[(2(S)-pyrrolidiinyl)methoxy]pyridine

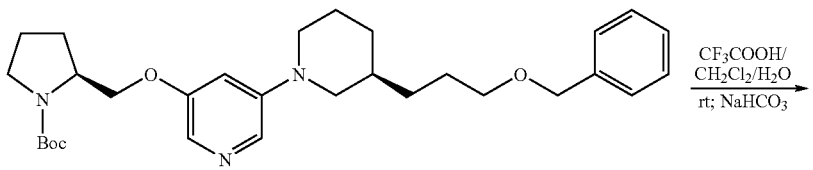

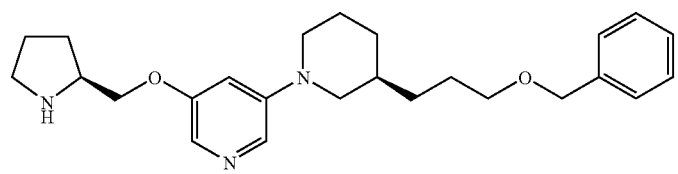

To a 100 mL three-necked round-bottom flask containing a solution of 3-[3(S)-[3-(benzyloxy)propyl]-1-piperidinyl]-5-[1-(tert-butoxycarbonyl)-2(S)-pyrrolidinyl)methoxy]pyridine (300 mg, 0.59 mmol) in CH₂Cl₂/H₂O (5 mL) was added CF₃COOH (1.35 g, 11.8 mmol, 20 equiv.) at 0° C. under N₂. The solution was stirred overnight at room temperature. After concentration in vacuo, the residue was purified by preparative HPLC (column: SunFire Prep C₁₈, 150×19 mm, particle size 5 μm; UV detection at 270 nm; flow 20 mL/min; mobile phase: A, water with 0.05% CF₃COOH; B, methanol; 40-60% B in A in 6 min, 60-100% in 1 min, back to 40% in 1 min). The eluate was partially evaporated under reduced pressure (bath 30° C.) to remove CH₃OH. The residue was basified with saturated aqueous NaHCO₃ solution and extracted with EtOAc. The organic layers were washed with brine and dried. After concentrated in vacuo, the free base (160 mg, 66%) was obtained as a yellowish oil. ¹H NMR (CDCl₃, 300 MHz) δ 7.95 (br s, 1H), 7.77 (br s, 1H), 7.37-7.28 (m, 5H), 6.73-6.71 (br s, 1H), 4.53 (s, 2H), 4.00-3.91 (m, 2H), 3.63-3.56 (m, 3H), 3.50 (t, J=6.6 Hz, 2H), 3.08-3.00 (m, 2H), 2.73 (m, 1H), 2.47-2.39 (m, 2H), 2.01-1.62 (m, 10H), 1.41-1.29 (m, 2H), 1.18-1.02 (m, 1H). LC-MS (ESI) m/z 410 (M+H⁺).

3-[3(S)-[3-(Benzyloxy)propyl]-1-piperidinyl]-5-[(2(S)-pyrrolidinyl)methoxy]pyridine Hydrochloride

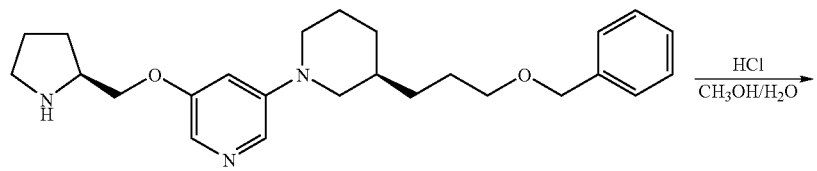

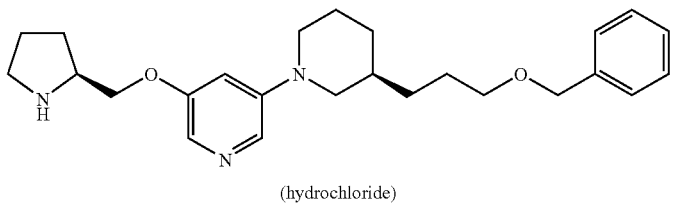

(hydrochloride)

To a solution of 3-[3(S)-[3-(benzyloxy)propyl]-1-piperidinyl]-5-[(2(S)-pyrrolidinyl)methoxy]pyridine (160 mg, 0.39 mmol) in CH₃OH (0.5 mL) was added 2 N hydrochloric acid (0.88 mL, 4.5 equiv.) at 0° C. under N₂. The solution was stirred for 4 h at room temperature. Water (20 mL) was added, and the solution was lyophilized. The residue was dissolved in 12 mL of water and re-lyophilized. This process was repeated three times to afford the hydrochloride (189 mg) as a yellowish solid. ¹H NMR (D₂O, 300 MHz) δ 7.88 (d, 1H, J=2.1 Hz), 7.69 (d, 1H, J=1.8 Hz), 7.38-7.27 (m, 6H), 4.48 (narrow ABq, 2H), 4.44, 4.23 (ABq, 2H, J_{AB}=10.5 Hz, low-field part d with J=3.3 Hz, high-field part d with J=7.5 Hz), 4.06 (m, 1H), 3.66 (m, 2H), 3.52 (t, 2H, J=6.3 Hz), 3.35 (t, 2H, J=7.2 Hz), 2.96 (td, 1H, J=10.5 (t), 3.0 Hz(d)), 2.69 (dd, 1H, J=10.5, 12.9 Hz), 2.29-2.17 (m, 1H), 2.16-1.97 (m, 2H), 1.96-1.76 (m, 2H), 1.76-1.42 (m, 5H), 1.37-1.08 (m, 3H). LC-MS (ESI) m/z 410 (M+H⁺). Anal. Calcd. for C₂₅H₃₅N₃O₂.2.5HCl.0.55H₂O: C, 58.80; H, 7.62; N, 8.23. Found: C, 58.54; H, 7.89; N, 8.51.

Example 69

3-[3(R)-[(3-Phenylpropoxy)methyl]-1-pyrrolidinyl]-5-[(2(S)-pyrrolidinyl)methoxy]pyridine 1-(tert-Butoxycarbonyl)-3(R)-pyrrolidinylmethanol

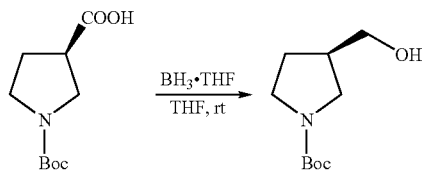 [SMILES: "BH3·THF" ; CC(C)(C)OC(=O)N1CC[C@@H](C(=O)O)C1 ; CC(C)(C)OC(=O)N1CC[C@@H](CO)C1]

To a solution of 1-(tert-butoxycarbonyl)pyrrolidine-3(R)-carboxylic acid (800 mg, 3.72 mmol) in 20 mL of anhydrous THF was added dropwise BH₃.THF complex (1M in THF, 7.4 mL, 2.0 equiv.) at 0° C. under N₂. The resulting solution was stirred for 4 h at room temperature. The reaction was then quenched with water. The mixture was concentrated under vacuum and extracted with EtOAc. The combined organic layers were dried over Na₂SO₄ and concentrated in vacuo. The residue was applied onto a silica gel column, which was eluted with EtOAc/petroleum ether 1:5 to give the title compound (720 mg, 96%) as a colorless oil. LC-MS (ESI) m/z 202 (M+H⁺).

tert-Butyl 3(R)-[(3-Phenylpropoxy)methyl]pyrrolidine-1-carboxylate

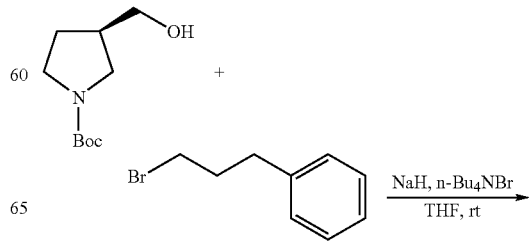

-continued

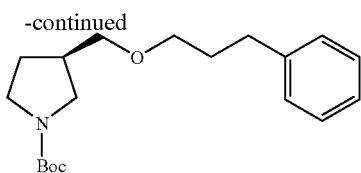

NaH (170 mg, 7.1 mmol, 2.0 equiv.) was added to a solution of 1-(tert-butoxycarbonyl)-3(R)-pyrrolidinylmethanol (500 mg, 2.49 mmol) in anhydrous THF (40 mL) with ice cooling under N$_2$. The solution was stirred for 2 h at room temperature. (3-Bromopropyl)benzene (590 mg, 2.96 mmol, 1.2 equiv.) and n-Bu$_4$NBr (80 mg, 0.25 mmol, 0.10 equiv.) were added, and the mixture was stirred overnight at 25° C. The reaction was then quenched with water. After concentration under vacuum, the solution was extracted with EtOAc. The combined organic layers were dried over Na$_2$SO$_4$ and concentrated in vacuo. The residue was applied onto a silica gel column, which was eluted with EtOAc/petroleum ether 1:10 to afford the product (500 mg, 63%) as a yellowish oil. $^1$H NMR (CDCl$_3$, 300 MHz) δ 7.33-7.19 (m, 5H), δ 3.55-3.31 (m, 7H), δ 3.11 (dd, 1H, J=10.8, 6.9 Hz), 2.71 (t, 2H) 2.48 (m, 1H), 1.87-2.01 (m, 3H), 1.71-1.64 (m, 1H), 1.48 (s, 9H). LC-MS (ESI) m/z 320 (M+H$^+$).

3(R)-[(3-Phenylpropoxy)methyl]pyrrolidine

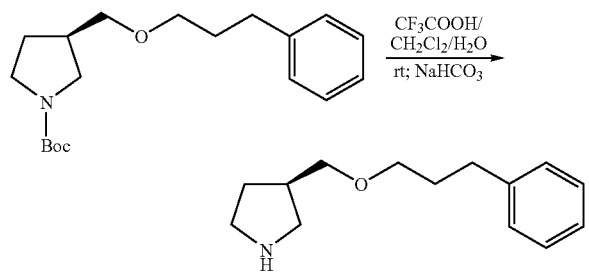

To a solution of tert-butyl 3(R)-[(3-phenylpropoxy)methyl]pyrrolidine-1-carboxylate (600 mg, 1.88 mmol) in CH$_2$Cl$_2$ (15 mL) was added a mixture of CF$_3$COOH (4.62 g, 40.5 mmol, 21.6 equiv.) and water (0.3 mL) at 0° C. under N$_2$. The solution was stirred overnight at room temperature. After concentration in vacuo, water was added, and the solution was washed with hexane. The water phase was basified with saturated aqueous NaHCO$_3$ solution and extracted with EtOAc. The combined organic phases were dried and concentrated to obtain the product (220 mg, 53%) as a yellow oil. LC-MS (ESI) m/z 220 (M+H$^+$).

3-[[1-(tert-Butoxycarbonyl)-2(S)-pyrrolidinyl]methoxy]-5-[3(R)-[(3-phenylpropoxy)methyl]-1-pyrrolidinyl]pyridine

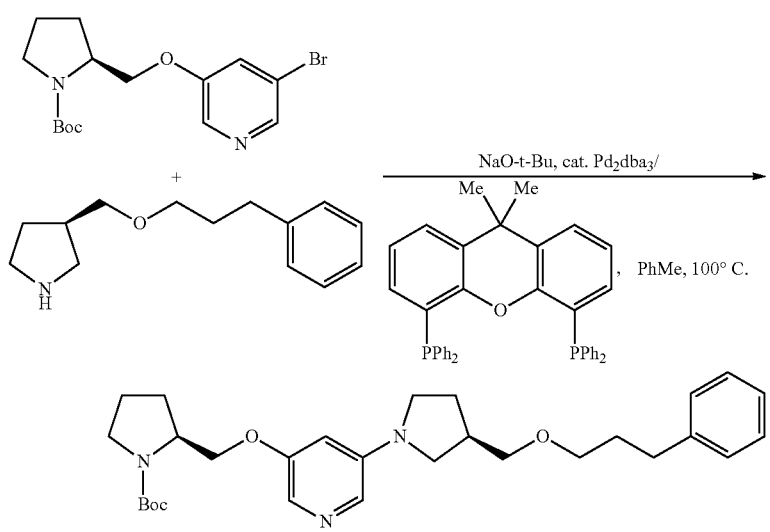

To a solution of 3(R)-[(3-phenylpropoxy)methyl]pyrrolidine (220 mg, 1.00 mmol, 1.50 equiv.) and 3-bromo-5-[[1-(tert-butoxycarbonyl)-2(S)-pyrrolidinyl]methoxy]pyridine (240 mg, 0.67 mmol) in toluene (15 mL) were added sodium tert-butoxide (96 mg, 1.00 mmol, 1.5 equiv.), tris(dibenzylideneacetone)dipalladium(0) (12 mg, 13.4 μmol, 0.02 equiv.) and 4,5-bis(diphenylphosphino)-9,9-dimethylxanthene (Xantphos, 23 mg, 40 μmol, 0.06 equiv.) under N$_2$. The mixture was stirred for 4 h at 100° C. After concentration in vacuo, the residue was diluted with water and extracted with EtOAc. The combined organic layers were dried and concentrated under reduced pressure. The residue was applied onto a silica gel column, which was eluted with EtOAc/petroleum ether 1:1 to afford the product (300 mg, 90%) as a yellow oil. $^1$H NMR (CDCl$_3$, 300 MHz) δ 7.68 (br s, 1H), 7.63 (br s, 1H), 7.37-7.19 (m, 5H), 6.43 (br s, 1H), 4.18-4.10 (m, 2H), 3.90 (br s, 1H), 3.49-3.29 (m, 9H), 3.13 (dd, 1H, J=9.0, 6.6 Hz), 2.74-2.61 (m, 3H), 2.20-2.12 (m, 1H), 2.06 (m, 2H), 1.99-1.82 (m, 5H). LC-MS (ESI) m/z 496 (M+H$^+$).

3-[3(R)-[(3-Phenylpropoxy)methyl]-1-pyrrolidinyl]-5-[(2(S)-pyrrolidinyl)methoxy]pyridine

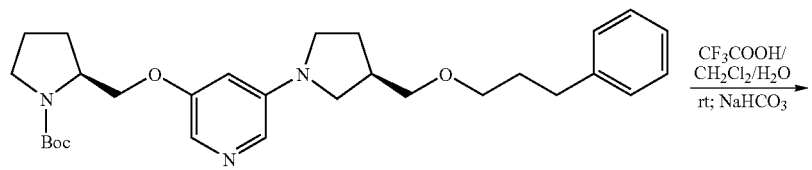

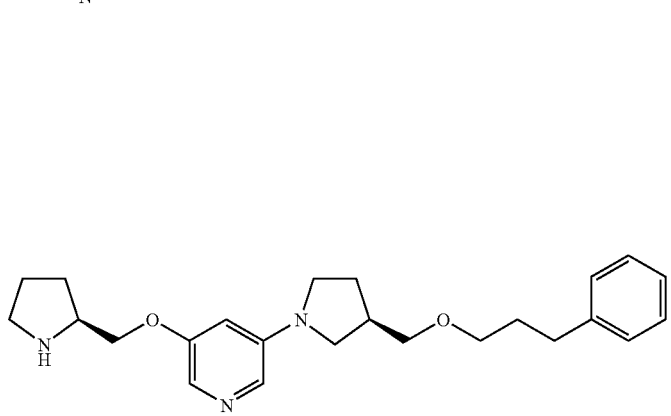

To a solution of 3-[[1-(tert-butoxycarbonyl)-2(S)-pyrrolidinyl]methoxy]-5-[3(R)-[(3-phenylpropoxy)methyl]-1-pyrrolidinyl]pyridine (280 mg, 0.56 mmol) in $CH_2Cl_2$ (5 mL) was added a mixture of $CF_3COOH$ (1 mL) and water (0.1 mL) under $N_2$. The solution was stirred overnight at room temperature. After concentration under vacuum, the crude product was purified by preparative HPLC (column: SunFire Prep $C_{18}$, 150×19 mm, 5 μm particle size; UV detection at 270 nm; flow 20 mL/min; mobile phase: A, water with 0.05% TFA; B, MeOH; 0-6 min, 40% to 50% B in A; 6-7 min, 50%; 7-8 min, 100%). The eluate was partially evaporated under reduced pressure (bath 30° C.) to remove $CH_3OH$. The residue was basified with saturated aqueous $NaHCO_3$ solution and extracted with EtOAc. The combined organic layers were washed with brine and dried. After concentration in vacuo, the free base (150 mg, 67%) was obtained as a yellowish oil. $^1$H NMR ($CDCl_3$, 300 MHz) δ 7.67 (d, 1H, J=2.1 Hz), 7.64 (d, 1H, J=2.1 Hz), 7.32-7.19 (m, 5H), 6.37 (t, 1H, J=2.1 Hz), 4.03-3.96 (m, 2H), 3.64-3.60 (m, 1H), 3.49-3.29 (m, 7H), 3.13-3.01 (m, 3H), 2.90 (br s, 1H), 2.74-2.63 (m, 3H), 2.19-2.13 (m, 1H), 2.04-1.88 (m, 6H), 1.69-1.57 (m, 1H). LC-MS (ESI) m/z 396 (M+H$^+$).

3-[3(R)-[(3-Phenylpropoxy)methyl]-1-pyrrolidinyl]-5-[2(S)-pyrrolidinyl)methoxy]pyridine Hydrochloride

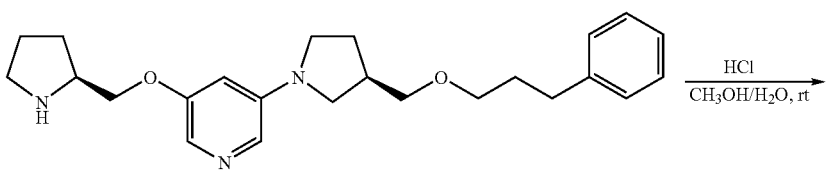

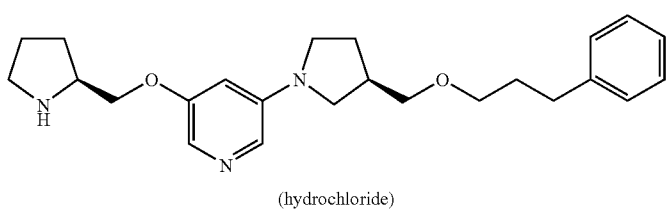

(hydrochloride)

Into a 10 mL round-bottom flask was placed a solution of 3-[3(R)-[(3-phenylpropoxy)methyl]-1-pyrrolidinyl]-5-[(2(S)-pyrrolidinyl)methoxy]pyridine (91 mg, 0.23 mmol) in CH$_3$OH (2 mL). To this solution was added 1 mL of hydrochloric acid (2N) at 0° C. under N$_2$. The solution was stirred for 2 h at room temperature and lyophilized. The residue was dissolved in 12 mL of water and re-lyophilized. The re-lyophilization process was repeated three times to afford the hydrochloride (115 mg) as a yellow solid. $^1$H NMR (D$_2$O, 300 MHz) δ 7.58 (d, 1H, J=1.5 Hz), 7.52 (d, 1H, J=1.5 Hz), 7.25-7.13 (m, 5H), 6.93 (s, 1H), 4.43 (dd, 1H, J=10.8, 3.6 Hz), 4.22 (dd, 1H, J=10.8, 7.5 Hz), 4.06-4.01 (m, 1H), 3.48-3.27 (m, 9H), 3.07 (dd, 1H, J=9.9, 6.0 Hz), 2.64-2.55 (m, 3H), 2.24-1.98 (m, 4H), 1.89-1.71 (m, 4H). LC-MS (ESI) m/z 396 (M+H$^+$). Anal. Calcd. for C$_{24}$H$_{33}$N$_3$O$_2$·1.9HCl·1.4H$_2$O: C, 58.82; H, 7.75; N, 8.57. Found: C, 59.12; H, 8.07; N, 8.26.

Example 70

4-[2-[1-[5-[(2(S)-Pyrrolidinyl)methoxy]-3-pyridyl]-4-piperidinyl]ethoxy]phenol tert-Butyl 4-[2-[4-(Benzyloxy)phenoxy]ethyl]piperidine-1-carboxylate

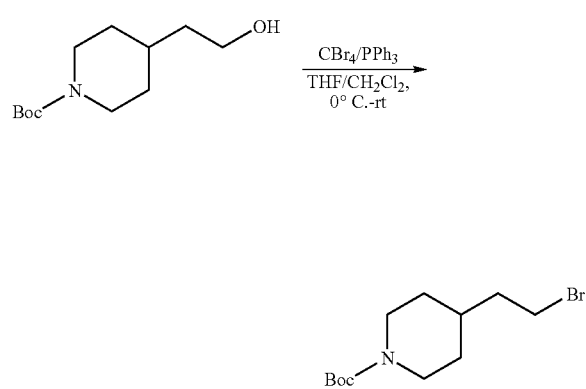

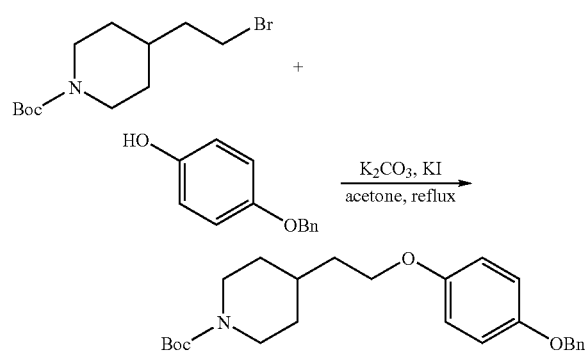

Into a 100-mL round-bottom flask was placed a solution of 2-[1-(tert-butoxycarbonyl)-4-piperidinyl]ethanol (1.10 g, 4.80 mmol) and tetrabromomethane (2.40 g, 7.24 mmol, 1.86 equiv.) in tetrahydrofuran (30 mL). Triphenylphosphine (1.26 g, 4.80 mmol, 1.00 equiv.) in CH$_2$Cl$_2$ was added slowly under N$_2$ at 0° C. The resulting solution was stirred overnight at 30° C. and then concentrated under vacuum. The residue was applied onto a silica gel column, which was eluted with EtOAc/petroleum ether 1:10 to 1:5. This resulted in 1.22 g (87%) of the bromide as a colorless oil.

A solution/suspension of tert-butyl 4-(2-bromoethyl)piperidine-1-carboxylate (1.22 g, 4.18 mmol), 4-(benzyloxy)phenol (1.01 g, 5.04 mmol, 1.20 equiv.), K$_2$CO$_3$ (830 mg, 6.01 mmol, 1.40 equiv.) and KI (75 mg, 0.45 mmol, 0.11 equiv.) in acetone was heated to reflux under N$_2$ overnight. After cooling to room temperature, the mixture was diluted with 100 mL of EtOAc, and the solids were filtered off. The filtrate was concentrated under vacuum, and the residue was applied onto a silica gel column, which was eluted with ethyl acetate/petroleum ether (1:5) to afford the product (1.25 g, 73%) as a white solid. $^1$H NMR (CDCl$_3$, 300 MHz) δ 7.43-7.29 (m, 5H), 6.90 (d, 2H, J=6.6 Hz), 5.01 (s, 2H), 4.08 (d, 2H, J=7.2 Hz), 3.95 (t, 1H, J=4.2 Hz), 2.70 (t, 2H, J=9.6 Hz), 1.71-1.69 (m, 5H), 1.45 (s, 9H), 1.20-1.15 (m, 2H). LC-MS (ESI) m/z 434 (M+Na$^+$).

4-[2-[4-(Benzyloxy)phenoxy]ethyl]piperidine

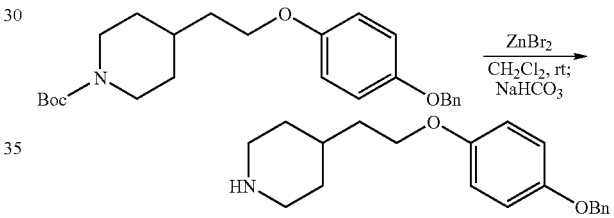

Anhydrous ZnBr$_2$ (1.10 g, 4.88 mmol, 2.0 equiv.) was added to a solution of tert-butyl 4-[2-[4-(benzyloxy)phenoxy]ethyl]piperidine-1-carboxylate (1.00 g, 2.43 mmol) in CH$_2$Cl$_2$ (20 mL) under N$_2$. The mixture was stirred overnight at room temperature, diluted with CH$_2$Cl$_2$ (300 mL), and washed with saturated aqueous NaHCO$_3$ solution and brine. The organic layer was dried over anhydrous Na$_2$SO$_4$. After filtration and concentration, the crude product was purified by preparative HPLC (column: SunFire Prep C18, 100×19 mm, 5 μm particle size; UV detection at 220 nm; flow 18 mL/min; mobile phase: CH$_3$CN in water with 0.05% CF$_3$COOH; 5-30% CH$_3$CN in 6 min.) The eluate was partially evaporated under reduced pressure (bath 30° C.) to remove CH$_3$OH. The residue was basified with aqueous NaHCO$_3$ solution and extracted with EtOAc. The combined organic layers were washed with brine and dried. After concentration in vacuo, the free base was obtained as a white solid. $^1$H NMR (CDCl$_3$, 300 MHz) δ 7.46-7.31 (m, 5H), 6.93 (d, 2H, J=9.0 Hz), 6.83 (d, 2H, J=9.0 Hz), 5.03 (s, 2H), 3.97 (t, 2H, J=6.0 Hz), 3.12 (d, 2H, J=11.7 Hz), 2.64 (t, 2H, J=12 Hz), 2.27 (br s, 1H), 1.78-1.69 (m, 5H), 1.25-1.17 (m, 2H). LC-MS (ESI) m/z 312 (M+H$^+$).

3-[4-[2-[4-(Benzyloxy)phenoxy]ethyl]-1-piperidinyl]-5-[[1-(tert-butoxycarbonyl)-2(S)-pyrrolidinyl]methoxy]pyridine

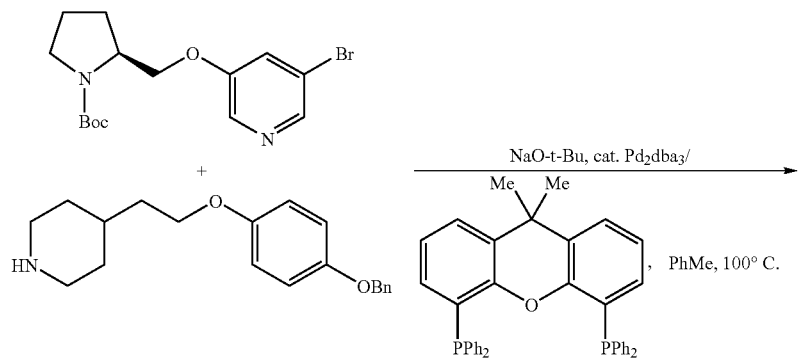

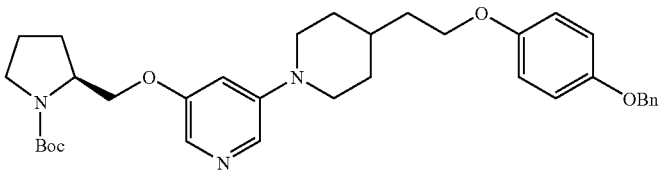

A solution/suspension of 4-[2-[4-(benzyloxy)phenoxy]ethyl]piperidine (220 mg, 0.71 mmol), 3-bromo-5-[[1-(tert-butoxycarbonyl)-2(S)-pyrrolidinyl]methoxy]pyridine (277 mg, 0.78 mmol, 1.1 equiv.), sodium tert-butoxide (136 mg, 1.42 mmol, 2.0 equiv.), tris(dibenzylideneacetone)dipalladium(0)-chloroform adduct (45 mg, 40 µmol, 0.06 equiv.), and 4,5-bis(diphenylphosphino)-9,9-dimethylxanthene (Xantphos, 50 mg, 90 µmol, 0.12 equiv.) in anhydrous toluene (20 mL) was stirred overnight at 100° C. under $N_2$. After cooling to room temperature, the mixture was concentrated under vacuum, and the residue was taken up in 500 mL of EtOAc and washed with brine. The organic layer was dried and concentrated in vacuo, and the residue was applied onto a silica gel column, which was eluted with EtOAc/$CH_2Cl_2$ 1:5 to 1:2 to provide the title compound (300 mg, 72%) as a yellow oil. $^1$H NMR (CDCl$_3$, 300 MHz) δ 7.90 (s, 1H), 7.67 (s, 1H), 7.46-7.34 (m, 5H), 7.08 (s, 1H), 6.93 (d, 2H, J=9.3 Hz), 6.85 (d, 2H, J=9.3 Hz), 5.02 (s, 2H), 4.18-4.13 (m, 3H), 4.00 (t, 2H, J=5.7 Hz), 3.76 (m, 2H), 3.41 (m, 2H), 2.83 (s, 2H), 2.07-2.03 (m, 2H), 1.90-1.72 (m, 3H), 1.77 (m, 3H), 1.49 (s, 9H), 1.40-1.30 (m, 2H), 1.28-1.26 (m, 1H). LC-MS (ESI) m/z 588 (M+H$^+$).

3-[4-[2-(4-Hydroxyphenoxy)ethyl]-1-piperidinyl]-5-[[1-(tert-butoxycarbonyl)-2(S)-pyrrolidinyl]methoxy]pyridine

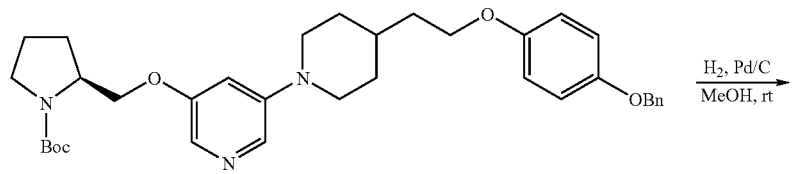

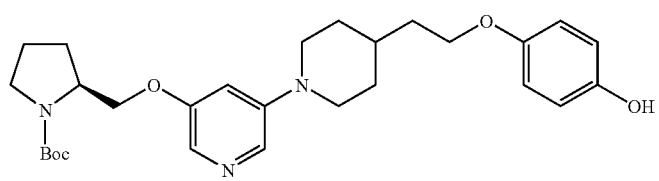

A mixture of 3-[4-[2-[4-(benzyloxy)phenoxy]ethyl]-1-piperidinyl]-5-[[1-(tert-butoxycarbonyl)-2(S)-pyrrolidinyl]methoxy]pyridine (300 mg, 0.51 mmol) and palladium on carbon (60 mg) in MeOH/CH$_2$Cl$_2$ (20/7 mL) was stirred at room temperature overnight under H$_2$. TLC analysis of the reaction mixture indicated that the starting material had disappeared. The solids were filtered off, and the filtrate was concentrated under vacuum to provide the title compound (260 mg, 92%) as a yellow solid. $^1$H NMR (DMSO-d$_6$, 300 MHz) δ 8.88 (s, 1H), 7.91 (s, 1H), 7.70 (s, 1H), 6.97 (s, 1H), 6.75 (d, 2H, J=8.7 Hz), 6.66 (d, 2H, J=9.0 Hz), 4.05-4.01 (m, 3H), 3.92-3.90 (m, 2H), 3.77 (m, 2H), 3.32 (m, 2H), 2.74-2.71 (m, 2H), 1.99-1.65 (m, 7H), 1.40 (s, 9H), 1.38-1.18 (m, 4H). LC-MS (ESI) m/z 498 (M+H$^+$).

4-[2-[1-[5-[(2(S)-Pyrrolidinyl)methoxy]-3-pyridyl]-4-piperidinyl]ethoxy]phenol

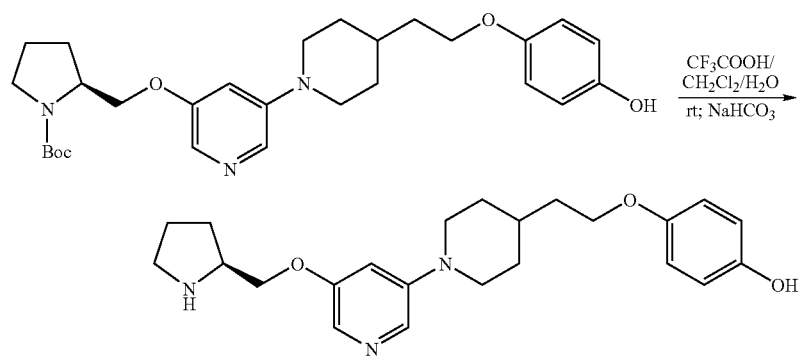

Trifluoroacetic acid (1.5 mL) was added slowly to a solution of 3-[4-[2-(4-hydroxyphenoxy)ethyl]-1-piperidinyl]-5-[[1-(tert-butoxycarbonyl)-2(S)-pyrrolidinyl]methoxy]pyridine (260 mg) in CH$_2$Cl$_2$/H$_2$O (7.5/0.15 mL) at room temperature under N$_2$. The solution was stirred overnight at room temperature. After removing the solvent, the residue was purified by preparative HPLC (column: SunFire Prep C$_{18}$, 100×19 mm, 5 µm particle size; UV detection at 254 nm; flow 18 mL/min; mobile phase: A, water with 0.05% CF$_3$COOH; B, CH$_3$CN; 5% to 30% B in A in 6 min). The eluate was partially evaporated under reduced pressure (bath 30° C.) to remove CH$_3$CN. The residue was basified with saturated aqueous NaHCO$_3$ solution and extracted with EtOAc. The combined organic layers were washed with brine 4-[2-[1-[5-[(2(S)-Pyrrolidinyl)methoxy]-3-pyridiyl]-4-piperidinyl]ethoxy]phenol Hydrochloride

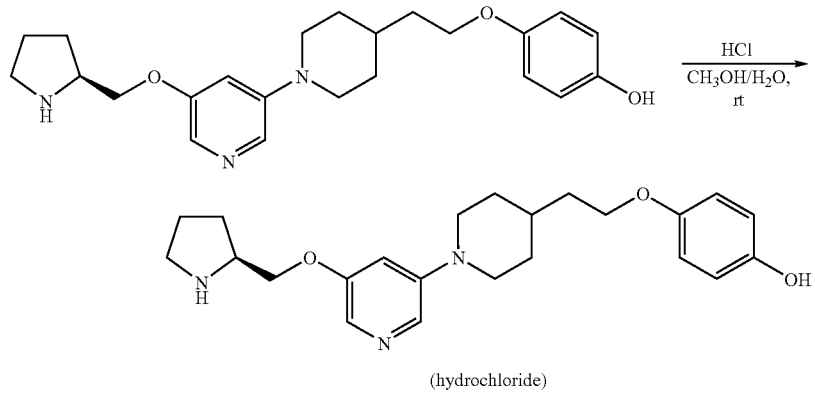

(hydrochloride)

Hydrochloric acid (2N; 0.96 mL, 4.5 equiv.) was added to a solution of 4-[2-[1-[5-[(2(S)-pyrrolidinyl)methoxy]-3-pyridyl]-4-piperidinyl]ethoxy]phenol (170 mg, 0.43 mmol) in a mixture of 1 mL of MeOH and 5 mL of water under $N_2$. The solution was stirred overnight at room temperature and then lyophilized. The residue was dissolved in 8 mL of water and re-lyophilized. The lyophilization process was repeated four times to afford the hydrochloride (176 mg) as a yellowish solid. $^1$H NMR ($D_2O$, 300 MHz) δ 7.90 (d, 1H, J=2.1 Hz), 7.71 (d, 1H, J=1.8 Hz), 6.82 (d, 2H, J=9.0 Hz), 6.74 (d, 2H, J=9.0 Hz), 4.45 (m, 1H), 4.41-4.20 (m, 1H), 4.06-3.97 (m, 3H), 3.75 (d, 2H, J=13.2 Hz), 3.33 (t, 2H, J=7.2 Hz), 2.92 (t, 2H, J=12.9 Hz), 2.22-2.08 (m, 1H), 2.08-2.00 (m, 2H), 1.40 (s, 9H), 1.89-1.85 (m, 1H), 1.84-1.76 (m, 3H), 1.65-1.61 (m, 2H), 1.27-1.23 (m, 2H). LC-MS (ESI) m/z 398 (M+H$^+$). Anal. Calcd. for $C_{23}H_{31}N_3O_3$·2.45HCl·2.7H$_2$O: C, 51.59; H, 7.31; N, 7.85; Cl, 16.22. Found: C, 51.40; H, 7.47; N, 8.03; Cl, 16.26.

Example 71

3-[4-[2-(4-Chlorobenzyloxy)ethyl]-1-piperidinyl]-5-[(2(S)-pyrrolidinyl)methoxy]pyridine 1-(tert-Butoxycarbonyl)-4-[2-(4-chlorobenzyloxy)ethyl]piperidine

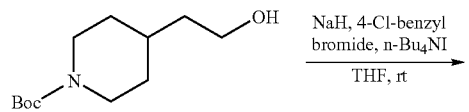

NaH, 4-Cl-benzyl
bromide, n-Bu$_4$NI
THF, rt

-continued

A solution of 1-(tert-butoxycarbonyl)-4-(2-hydroxyethyl)piperidine (708 mg, 3.09 mmol) in anhydrous THF (15 mL) was cooled to 0° C., and NaH (60% dispersion in oil, 148 mg, 3.7 mmol, 1.2 equiv.) was added all at once. Alkoxide formation was effected by stirring at room temperature for 2 h under $N_2$, then 4-chlorobenzyl chloride (597 mg, 3.7 mmol, 1.2 equiv.) and tetra-n-butylammonium iodide (114 mg, 0.31 mmol, 0.1 equiv.) were added. The mixture was stirred at room temperature for 20 h. Saturated aqueous NH$_4$Cl solution was added, and the product was extracted into EtOAc. The organic layer was dried over Na$_2$SO$_4$ and concentrated. The residue was purified by CC (SiO$_2$, hexane/EtOAc 4:1) to afford, after evaporation, 1-(tert-butoxycarbonyl)-4-[2-(4-chlorobenzyloxy)ethyl]piperidine (974 mg, 89%) as a pale yellow oil. $^1$H NMR (CDCl$_3$, 400 MHz) δ 7.30 (d, 2H, J=8.4 Hz), 7.24 (d, 2H, J=6.8 Hz), 4.45 (s, 2H), 4.05 (d, 2H, J=13.2 Hz), 3.49 (t, 2H, J=6.0 Hz), 2.67 (t, 2H, J=12.8 Hz), 1.63 (d, 2H, J=13.6 Hz), 1.55 (m, 3H), 1.44 (s, 9H), 1.11 (m, 2H).

3-[4-[2-(4-Chlorobenzyloxy)ethyl]-1-piperidinyl]-5-[(2(S)-pyrrolidinyl)methoxy]pyridine Hydrochloride

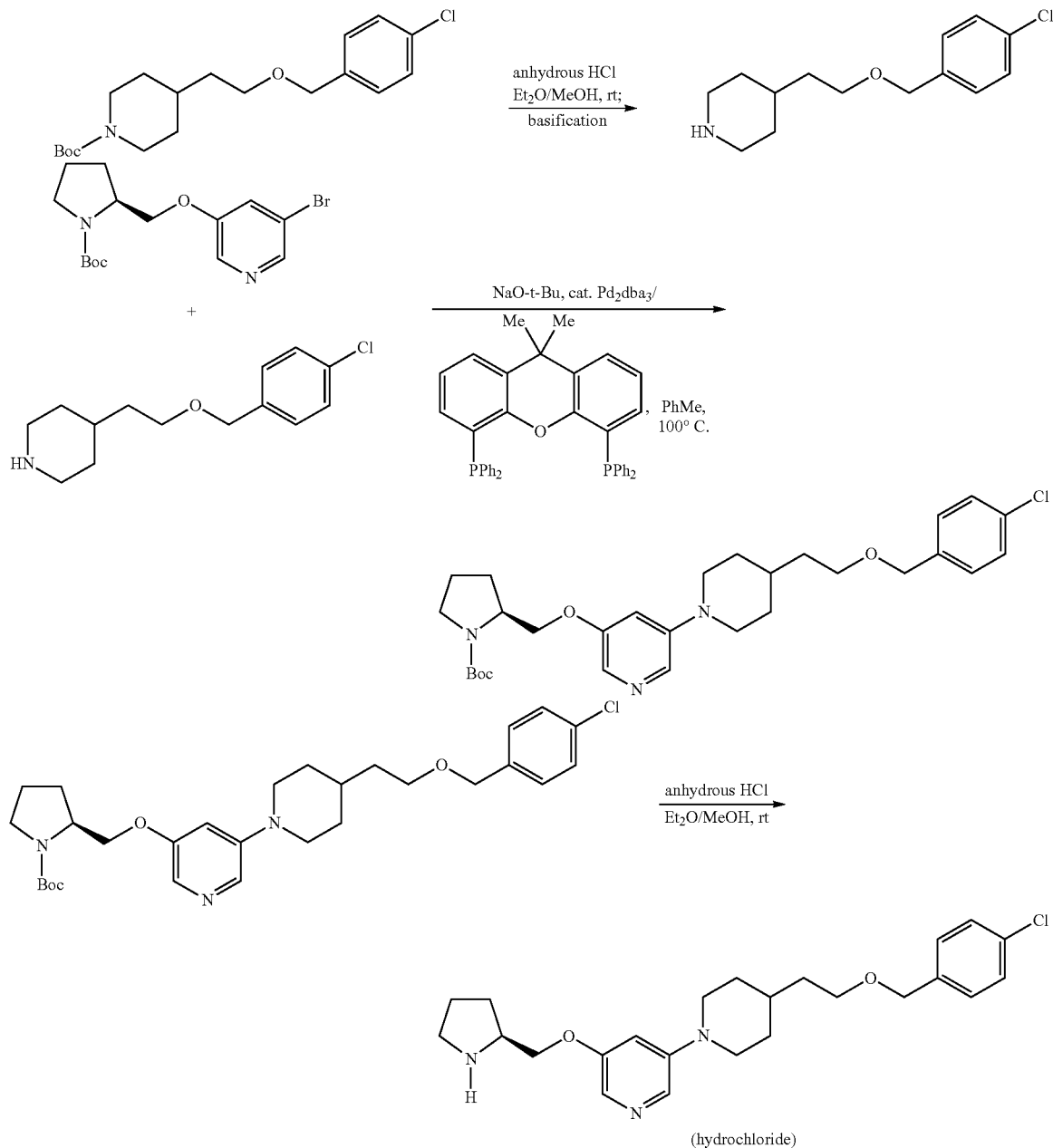

(hydrochloride)

To a solution of 1-(tert-butoxycarbonyl)-4-[2-(4-chlorobenzyloxy)ethyl]piperidine (760 mg, 0.47 mmol) in MeOH (0.5 mL) was added 2N anhydrous HCl/ether (1.5 mL, 3.0 mmol). The reaction mixture was stirred overnight, then evaporated, and the residue was dissolved in deionized water. EtOAc was used to wash the aqueous layer before the pH was altered to approx. 9-10. The aqueous layer was extracted three times with $CH_2Cl_2$, and the combined organic phases were dried over $Na_2SO_4$. After evaporation, 4-[2-(4-chlorobenzyloxy)ethyl]piperidine (531 mg, 97%) was obtained as a colorless oil.

To a solution of 3-bromo-5-[[1-(tert-butoxycarbonyl)-2(R)-pyrrolidinyl]methoxy]pyridine (346 mg, 0.97 mmol) and 4-[2-(4-chlorobenzyloxy)ethyl]piperidine (270 mg, 1.06 mmol, 1.1 equiv.) in anhydrous toluene (6 mL) were added successively sodium tert-butoxide (139 mg, 1.45 mmol, 1.5 equiv.), tris(dibenzylideneacetone)dipalladium(0) (17.7 mg, 19 μmol, 0.02 equiv.), and 4,5-bis(diphenylphosphino)-9,9-dimethylxanthene (Xantphos; 33.6 mg, 58 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over $Na_2SO_4$, and evaporated. The residue was purified by CC on $SiO_2$ with $CH_2Cl_2$/EtOAc 4:1, then 1:1. After evaporation, 3-[[1-(tert-butoxycarbonyl)-

2(S)-pyrrolidinyl]methoxy]-5-[4-[2-(4-chlorobenzyloxy)ethyl]-1-piperidinyl]pyridine (437 mg, 85%) was obtained as a pale yellow oil.

To a solution of this intermediate (437 mg, 0.82 mmol) in MeOH (0.5 mL) was added 2N anhydrous HCl/ether (1.5 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (ACE AQ 150× 21.2 mm; UV detection at 254 nm and 280 nm; flow 10.0 mL/min; 8% to 100% MeOH in water [both containing 0.05 vol % of $CF_3COOH$] in 30 min, then 100% for another 3 min; $t_R$ 21.7-34.0 min) to obtain the trifluoroacetate. This salt was treated with PL-HCO3 MP anion exchange resin (Polymer Laboratories) in MeOH to afford the free amine, which was dissolved in MeOH (0.5 mL), and treated again with 2N anhydrous HCl/ether (2 mL) under Ar protection at room temperature. The mixture was stirred at room temperature overnight. After the solvent was evaporated, the residue was dissolved in deionized water. After the solution was filtered over a cotton plug, the water was removed under reduced pressure at 35° C. After lyophilization from water, the final compound (395 mg) was obtained as a yellow glass. $^1$H NMR ($D_2O$, 400 MHz) δ 7.90 (s, 1H), 7.71 (s, 1H), 7.38 (s, 1H), 7.34 (d, 2H, J=8.4 Hz), 7.28 (d, 2H, J=8.4 Hz), 4.42 (s, 3H), 4.23 (dd, 1H, J=7.6, 10.4 Hz), 4.04 (m, 1H), 3.72 (d, 2H, J=12.8 Hz), 3.55 (t, 2H, J=6.4 Hz), 3.33 (t, 2H, 6.8 Hz), 2.91 (t, 2H, J=11.2 Hz), 2.20 (m, 1H), 2.04 (m, 2H), 1.86 (m, 1H), 1.69 (d, 2H, J=13.2 Hz), 1.60 (m, 1H), 1.48 (m, 2H), 1.17 (m, 2H). $^{13}$C NMR ($D_2O$, 100 MHz) δ 156.4, 148.9, 136.2, 132.4, 129.2, 128.0, 121.4, 117.0, 113.9, 71.1, 67.3, 67.2, 58.0, 47.1, 45.6, 34.7, 31.3, 30.1, 25.5, 23.0; HRMS (ESI) calcd for $C_{24}H_{33}ClN_3O_2$ (M+H$^+$) m/z 430.2261, found 430.2268. Anal. Calcd. for $C_{24}H_{32}ClN_3O_2 \cdot 3.3HCl \cdot 2.4H_2O$: C, 48.57; H, 6.81; N, 7.08; Cl, 25.68. Found C, 48.44; H, 6.63; N, 6.98; Cl, 25.65.

Example 72

3-[4-[2-(4-Fluorobenzyloxy)ethyl]-1-piperidinyl]-5-[(2(S)-pyrrolidinyl)methoxy]pyridine 1-(tert-Butoxycarbonyl)-4-[2-(4-fluorobenzyloxy)ethyl]piperidine

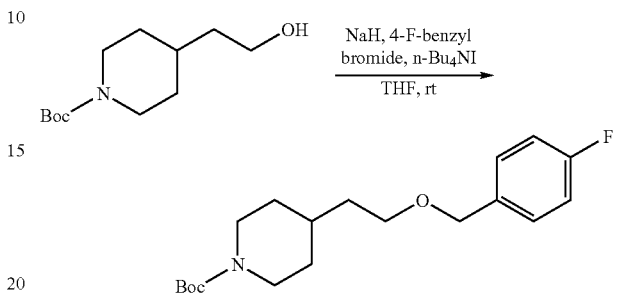

To a solution of 1-(tert-butoxycarbonyl)-4-(2-hydroxyethyl)piperidine (195 mg, 0.85 mmol) in THF (5 mL) was added sodium hydride (60% dispersion in oil, 41 mg, 1.02 mmol, 1.2 equiv.). After stirring at room temperature for 2 h, 4-fluorobenzyl bromide (127 μL, 1.02 mmol, 1.2 equiv.) was added. The reaction mixture was allowed to stand overnight. After quenching with $H_2O$, the phases were separated, and the aqueous layer was extracted with EtOAc. The combined organic layer was washed with brine and dried over $Na_2SO_4$. After the solvent was removed, the residue was purified by CC ($SiO_2$, hexane/EtOAc 4:1) to afford 1-(tert-butoxycarbonyl)-4-[2-(4-fluorobenzyloxy)ethyl]piperidine (257 mg, 90%) as a colorless oil. $^1$H NMR (400 MHz, CDCl$_3$) δ 7.28 (dd, 2H, J=8.0 Hz, J=5.2 Hz), 7.01 (t, 2H, J=8.4 Hz), 4.61 (s, 2H), 4.05 (d, 2H, J=12.8 Hz), 3.48 (t, 2H, J=6.0 Hz), 2.66 (t, 2H, J=12.4 Hz), 1.55 (m, 5H), 1.44 (s, 9H), 1.10 (m, 2H).

3-[4-[2-(4-Fluorobenzyloxy)ethyl]-1-piperidinyl]-5-[(2(S)-pyrrolidinyl)methoxy]pyridine Hydrochloride

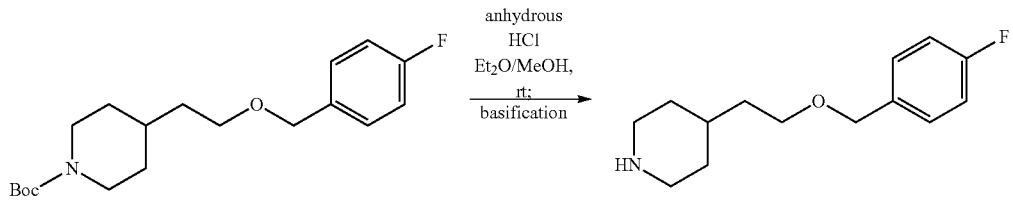

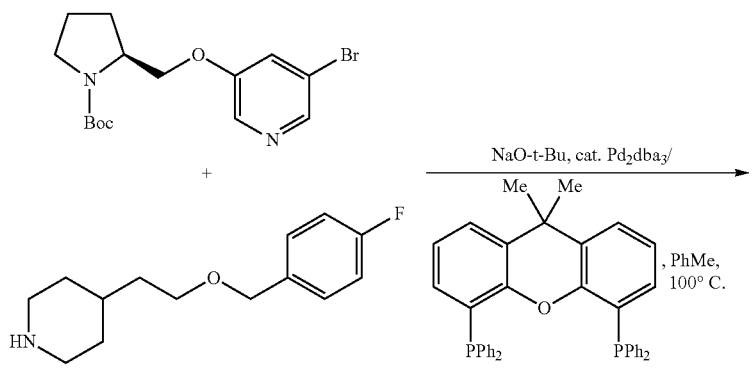

-continued

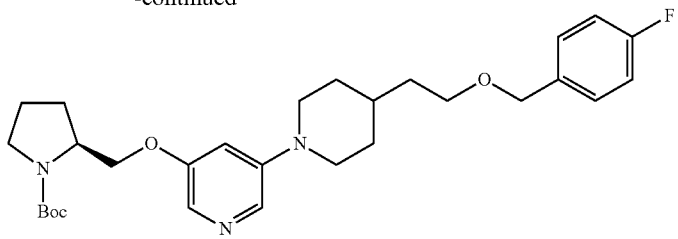

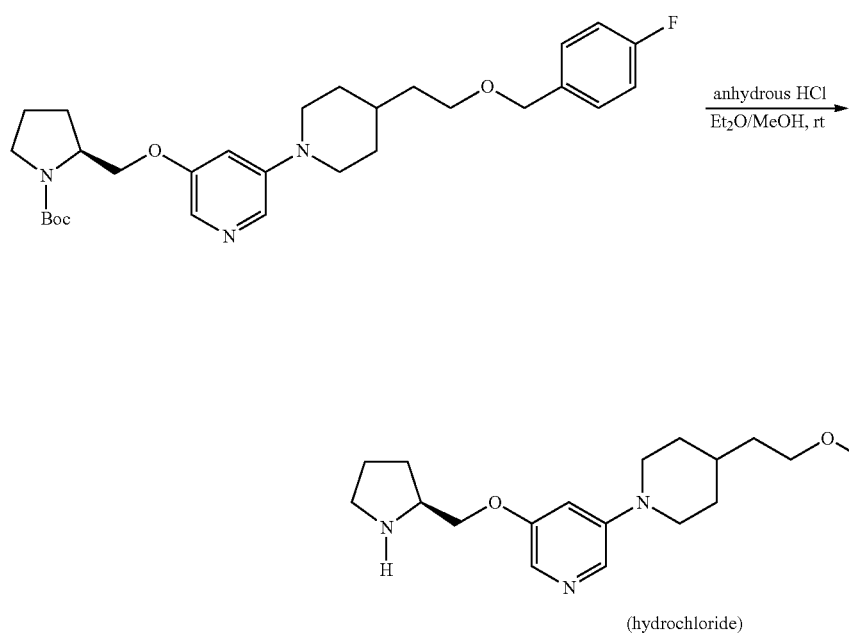

(hydrochloride)

To a solution of 1-(tert-butoxycarbonyl)-4-[2-(4-fluorobenzyloxy)ethyl]piperidine (257 mg, 0.76 mmol) in MeOH (0.5 mL) was added 2N anhydrous HCl/ether (1.0 mL, 2.0 mmol). The reaction mixture was stirred overnight. After evaporation, the residue was dissolved in deionized water. EtOAc was used to wash the aqueous layer before the pH was altered to approx. 9-10. The aqueous layer was extracted three times with $CH_2Cl_2$, and the combined organic phases were dried over $Na_2SO_4$. After evaporation, 4-[2-(4-fluorobenzyloxy)ethyl]piperidine (150 mg, 83% yield) was obtained as a colorless oil.

To a solution of 3-bromo-5-[[1-(tert-butoxycarbonyl)-2 (R)-pyrrolidinyl]methoxy]pyridine (264 mg, 0.74 mmol) and 4-[2-(4-fluorobenzyloxy)ethyl]piperidine (193 mg, 0.81 mmol, 1.1 equiv.) in anhydrous toluene (4 mL) were added successively sodium tert-butoxide (106 mg, 1.11 mmol, 1.5 equiv.), tris(dibenzylideneacetone)dipalladium(0) (13.5 mg, 15 μmol, 0.02 equiv.), and 4,5-bis(diphenylphosphino)-9,9-dimethylxanthene (Xantphos; 25.6 mg, 44 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over $Na_2SO_4$, and evaporated. The residue was purified by CC on $SiO_2$ with $CH_2Cl_2$/EtOAc 4:1, then 1:1. 3-[[1-(tert-Butoxycarbonyl)-2(S)-pyrrolidinyl] methoxy]-5-[4-[2-(4-fluorobenzyloxy)ethyl]-1-piperidinyl] pyridine (305 mg, 80%) was obtained as a pale yellow oil.

To a solution of this intermediate (305 mg, 0.59 mmol) in MeOH (0.2 mL) was added 2N anhydrous HCl/ether (1.5 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (ACE AQ 150× 21.2 mm; UV detection at 254 nm and 280 nm; flow 10.0 mL/min; 8% to 100% MeOH in water [both containing 0.05 vol % of $CF_3COOH$] in 30 min, then 100% for another 3 min; $t_R$ 15.0-23.9 min) to obtain the trifluoroacetate (232 mg). This salt was treated with PL-HCO3 MP anion exchange resin (Polymer Laboratories) in MeOH to afford the free amine, which was dissolved in MeOH (0.5 mL) and treated again with 2N anhydrous HCl/ether (2 mL) under Ar protection at room temperature. The mixture was stirred at room temperature overnight. After the solvent was evaporated, the residue was dissolved in deionized water. After the solution was filtered over a cotton plug, the water was removed under reduced pressure at 35° C. After lyophilization from water, the hydrochloride (154 mg) was obtained as a yellow glass.
$^1$H NMR ($D_2O$, 400 MHz) δ 7.74 (s, 1H), 7.65 (s, 1H), 7.25 (s, 1H), 7.04 (m, 2H), 6.76 (t, 2H, J=8.8 Hz), 4.30 (d, 1H, J=8.0 Hz), 4.16 (m, 3H), 3.92 (m, 1H), 3.53 (d, 2H, J=12.0 Hz), 3.22 (m, 4H), 2.66 (t, 2H, J=12.0 Hz), 2.08 (m, 1H), 1.92 (m, 2H), 1.72 (m, 1H), 1.48 (d, 2H, J=12.8 Hz), 1.35 (m, 1H), 1.24 (m, 2H), 0.98 (m, 2H); $^{13}$C NMR (D$_2$O, 100 MHz) δ 163.1, 160.6, 156.7, 148.7, 133.7, 129.8, 121.8, 117.8, 114.8, 71.4, 67.6, 67.4, 58.3, 47.7, 45.8, 34.9, 31.4, 30.3, 35.7, 23.3. HRMS (ESI) calcd for C$_{24}$H$_{33}$FN$_3$O$_2$ (M+H$^+$) m/z 414.2557, found 414.2552. Anal. Calcd. for C$_{24}$H$_{32}$FN$_3$O$_2$.3.35HCl.1.9H$_2$O: C, 50.58; H, 6.92; N, 7.37; Cl, 20.84. Found: C, 50.69; H, 6.82; N, 7.29, Cl, 20.72.

Example 73

3-[(2(S)-Pyrrolidinyl)methoxy]-5-[4-[2-[4-(trifluoromethyl)benzyloxy]ethyl]-1-piperidinyl]pyridine 1-(tert-Butoxycarbonyl)-4-[2-[4-(trifluoromethyl)benzyloxy]ethyl]piperidine

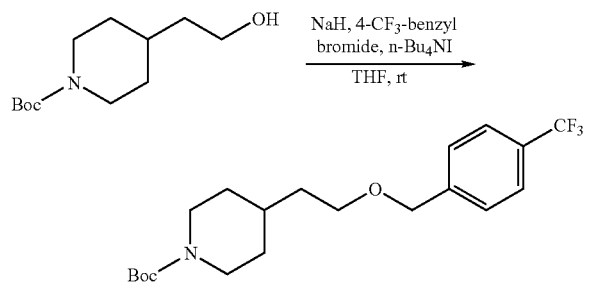

A solution of 1-(tert-butoxycarbonyl)-4-(2-hydroxyethyl)piperidine (302 mg, 1.32 mmol) in anhydrous THF (10 mL) was cooled to 0° C., and NaH (60% dispersion in oil, 63 mg, 1.58 mmol, 1.2 equiv.) was added all at once. Alkoxide formation was effected by stirring at room temperature for 2 h under N$_2$, then 4-(trifluoromethyl)benzyl bromide (378 mg, 1.58 mmol, 1.2 equiv.) was added. The mixture was stirred at room temperature overnight. Saturated aqueous NH$_4$Cl solution was added, and the product was extracted into EtOAc. The organic layer was dried over Na$_2$SO$_4$ and concentrated. The residue was purified by CC (SiO$_2$, EtOAc/hexane 1:4) to afford the ether (496 mg, 97%) after evaporation. $^1$H NMR (CDCl$_3$, 400 MHz) δ 7.59 (d, 2H, J=8.4 Hz), 7.43 (d, 2H, J=8.0 Hz), 4.54 (s, 2H), 4.06 (d, 2H, J=13.2 Hz), 5.31 (t, 2H, J=6.4 Hz), 2.68 (t, 2H, J=12.8 Hz), 1.58 (m, 5H), 0.89 (m, 2H).

4-[2-[4-(Trifluoromethyl)benzyloxy]ethyl]piperidine

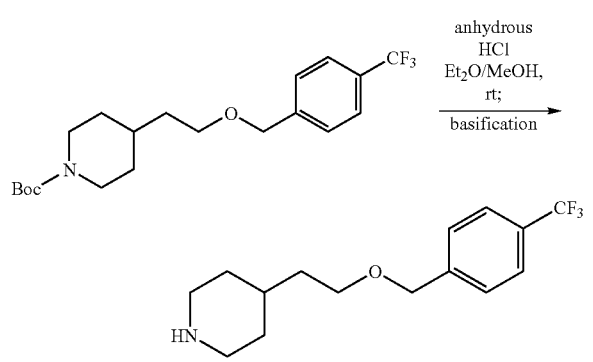

To a solution of 1-(tert-butoxycarbonyl)-4-[2-[4-(trifluoromethyl)benzyloxy]ethyl]piperidine (496 mg, 1.28 mmol) in MeOH (0.5 mL) was added 2N anhydrous HCl/ether (2.0 mL, 4.0 mmol). The reaction mixture was stirred overnight. After evaporation, the residue was dissolved in deionized water. EtOAc was used to wash the aqueous layer before the pH was altered to approx. 9-10. The aqueous layer was extracted three times with CH$_2$Cl$_2$ and dried over Na$_2$SO$_4$. After evaporation, 4-[2-[4-(trifluoromethyl)benzyloxy]ethyl]piperidine (321 mg, 87%) was obtained as a colorless oil. $^1$H NMR (CDCl$_3$, 400 MHz) δ 7.56 (d, 2H, J=8.4 Hz), 7.41 (d, 2H, J=8.0 Hz), 4.51 (s, 2H), 3.50 (t, 2H, J=6.0 Hz), 3.39 (br, 1H), 3.07 (d, 2H, J=12.0 Hz), 2.59 (t, 2H, J=11.6 Hz), 1.66 (d, 2H, J=12.8 Hz), 1.54 (m, 3H), 1.20 (m, 2H).

3-[[1-(tert-Butoxycarbonyl)-2(S)-pyrrolidinyl]methoxy]-5-[4-[2-[4-(trifluoromethyl)benzyloxy]ethyl]-1-piperidinyl]pyridine

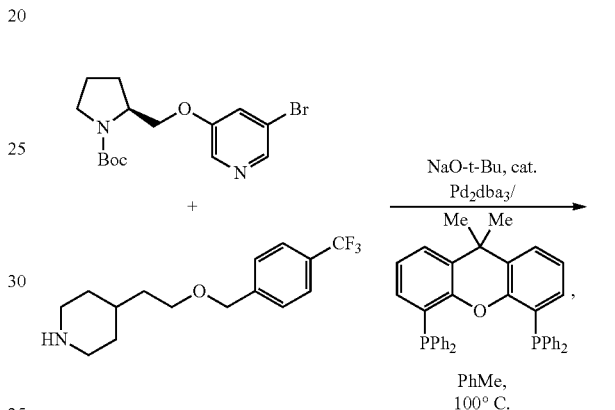

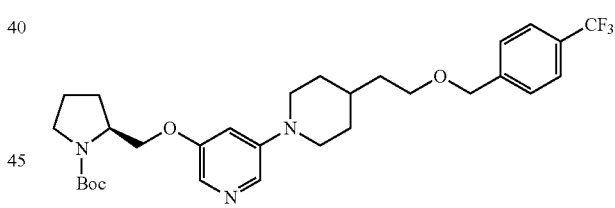

To a solution of 3-bromo-5-[[1-(tert-butoxycarbonyl)-2(R)-pyrrolidinyl]methoxy]pyridine (210 mg, 0.59 mmol) and 4-[2-[4-(trifluoromethyl)benzyloxy]ethyl]piperidine (186 mg, 0.65 mmol, 1.1 equiv.) in anhydrous toluene (2 mL) were added successively sodium tert-butoxide (93 mg, 0.97 mmol, 1.5 equiv.), tris(dibenzylideneacetone)dipalladium(0) (11.8 mg, 13 µmol, 0.02 equiv.), and 4,5-bis(diphenylphosphino)-9,9-dimethylxanthene (Xantphos; 22.4 mg, 39 µmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over Na$_2$SO$_4$, and evaporated. The residue was purified by CC on SiO$_2$ with CH$_2$Cl$_2$/EtOAc 4:1, then 1:1. The product (371 mg, 100%) was obtained as a dark yellow oil.

3-[(2(S)-Pyrrolidinyl)methoxy]-5-[4-[2-[4-(trifluoromethyl)benzyloxy]ethyl]-1-piperidinyl]pyridine Hydrochloride

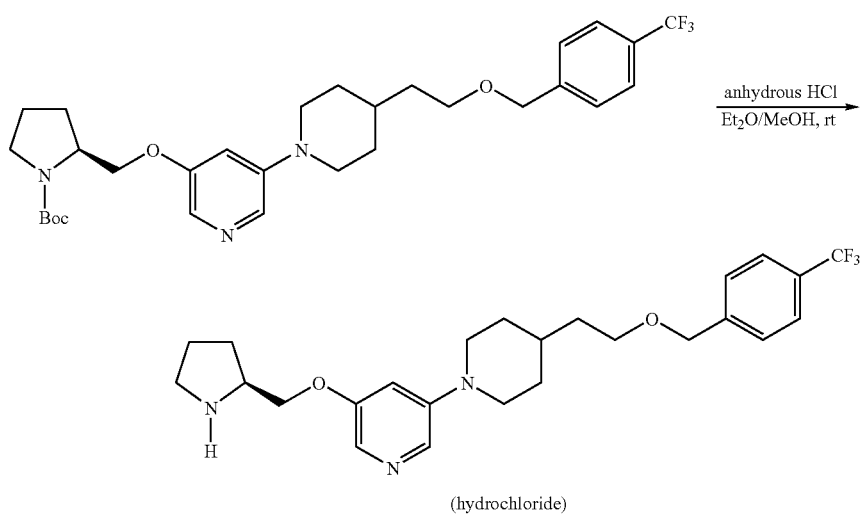

To a solution of 3-[[1-(tert-butoxycarbonyl)-2(S)-pyrrolidinyl]methoxy]-5-[4-[2-[4-(trifluoromethyl)benzyloxy]ethyl]-1-piperidinyl]pyridine (371 mg, 0.80 mmol) in MeOH (0.2 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (ACE AQ 150×21.2 mm; UV detection at 254 nm and 280 nm; flow 10.0 mL/min; 8% to 100% MeOH in water [both containing 0.05 vol % of $CF_3COOH$] in 30 min, then 100% for another 3 min; $t_R$ 18.9-21.9 min) to obtain the trifluoroacetate. This salt was treated with PL-HCO3 MP anion exchange resin (Polymer Laboratories) in MeOH to afford the free amine, which was dissolved in MeOH (0.5 mL) and treated again with 2N anhydrous HCl/ether (2 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the hydrochloride (74 mg) was obtained as a yellow glass. $^1$HNMR ($D_2O$, 400 MHz) δ 8.00 (d, 1H, J=2.0 Hz), 7.83 (d, 1H, J=2.0 Hz), 7.71 (d, 2H, J=8.0 Hz), 7.55 (d, 2H, J=8.0 Hz), 7.48 (d, 1H, J=2.0 Hz), 4.62 (s, 2H), 4.55 (dd, 1H. J=3.2 Hz, J=10.4 Hz), 4.36 (dd, 1H, J=7.6 Hz, J=10.4 Hz), 4.16 (m, 1H), 3.82 (d, 2H, J=12.8 Hz), 3.65 (t, 2H, J=6.4 Hz), 3.45 (t, 2H, J=7.2 Hz), 2.98 (m, 2H), 2.32 (m, 1H), 2.16 (m, 2H), 1.98 (m, 1H), 1.78 (d, 2H, J=12.8 Hz), 1.61 (m, 1H), 1.58 (m, 2H), 1.28 (m, 2H); $^{13}$C NMR ($D_2O$, 100 MHz) δ 156.5, 149.0, 142.1, 127.4, 124.6, 121.3, 117.0, 113.9, 71.0, 67.5, 67.4, 58.0, 47.0, 45.6, 34.8, 31.3, 30.2, 25.5, 23.1. Anal. Calcd. for $C_{24}H_{32}F_3N_3O_2 \cdot 2.50HCl \cdot 0.5H_2O$: C, 52.25; H, 6.49; F, 10.33; N, 7.62; Cl, 16.07. Found: C, 53.37; H, 6.26; N, 7.31; Cl, 15.64.

Example 74

3-[4-[2-(4-Methylbenzyloxy)ethyl]-1-piperidinyl]-5-[(2(S)-pyrrolidinyl)methoxy]pyridine

1-(tert-Butoxycarbonyl)-4-[2-(4-methylbenzyloxy)ethyl]piperidine

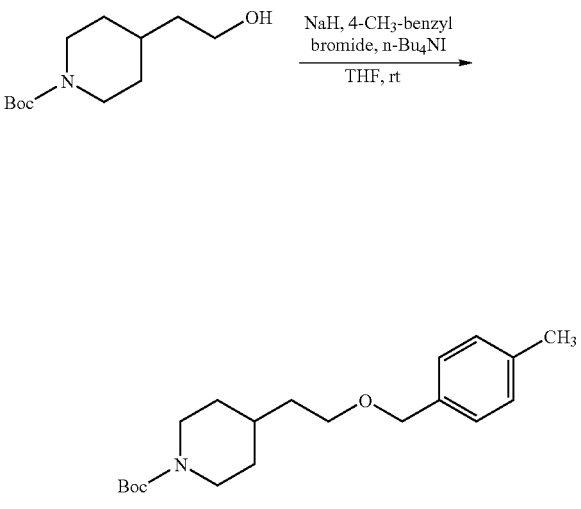

A solution of 1-(tert-butoxycarbonyl)-4-(2-hydroxyethyl)piperidine (328 mg, 1.43 mmol) in anhydrous THF (10 mL) was cooled to 0° C., and NaH (60% dispersion in oil, 69 mg, 1.71 mmol, 1.2 equiv.) was added all at once. Alkoxide formation was effected by stirring at room temperature for 2 h under $N_2$, then 4-methylbenzyl bromide (317 mg, 1.71 mmol, 1.2 equiv.) was added. The mixture was stirred at room temperature overnight. Saturated aqueous $NH_4Cl$ solution was added, and the product was extracted into EtOAc. The organic layer was dried over $Na_2SO_4$ and concentrated. The residue was purified by CC ($SiO_2$, EtOAc/hexane 1:4) to afford 1-(tert-butoxycarbonyl)-4-[2-(4-methylbenzyloxy)ethyl]piperidine (470 mg, 99%) after evaporation. $^1$H NMR ($CDCl_3$, 400 MHz) δ 7.21 (d, 2H, J=8.0 Hz), 7.14 (d, 2H, J=8.0 Hz), 4.45 (s, 2H), 4.04 (d, 2H, J=13.6 Hz), 3.48 (t, 2H, J=6.4 Hz), 2.66 (t, 2H, J=13.6 Hz), 2.32 (s, 3H), 1.60 (m, 2H), 1.54 (m, 3H), 1.44 (s, 9H), 1.10 (m, 2H).

4-[2-(4-Methylbenzyloxy)ethyl]piperidine

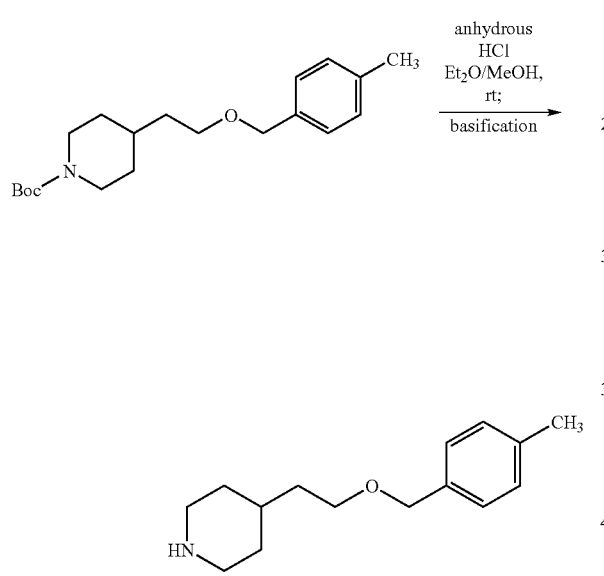

To a solution of 1-(tert-butoxycarbonyl)-4-[2-(4-methylbenzyloxy)ethyl]piperidine (470 mg, 1.41 mmol) in MeOH (0.5 mL) was added 2N anhydrous HCl/ether (2 mL, 4.0 mmol). The reaction mixture was stirred overnight. After evaporation, the residue was dissolved in deionized water. EtOAc was used to wash the aqueous layer before the pH was altered to approx. 9-10. The aqueous layer was extracted three times with $CH_2Cl_2$ and dried over $Na_2SO_4$. After evaporation, 4-[2-(4-methylbenzyloxy)ethyl]piperidine (269 mg, 82%) was obtained as a colorless oil. $^1$H NMR ($CDCl_3$, 400 MHz) δ 7.20 (d, 2H, J=7.6 Hz), 7.13 (d, 2H, J=8.0 Hz), 4.44 (s, 2H), 3.47 (t, 2H, 6.0 Hz), 3.02 (d, 2H, J=12.0 Hz), 2.53 (m, 3H), 2.33 (s, 3H), 1.64 (d, 2H, J=12.4 Hz), 1.51 (m, 3H), 1.06 (m, 2H).

3-[[1-(tert-Butoxycarbonyl)-2(S)-pyrrolidinyl]methoxy]-5-[4-[2-(4-methylbenzyloxy)ethyl]-1-piperidinyl]pyridine

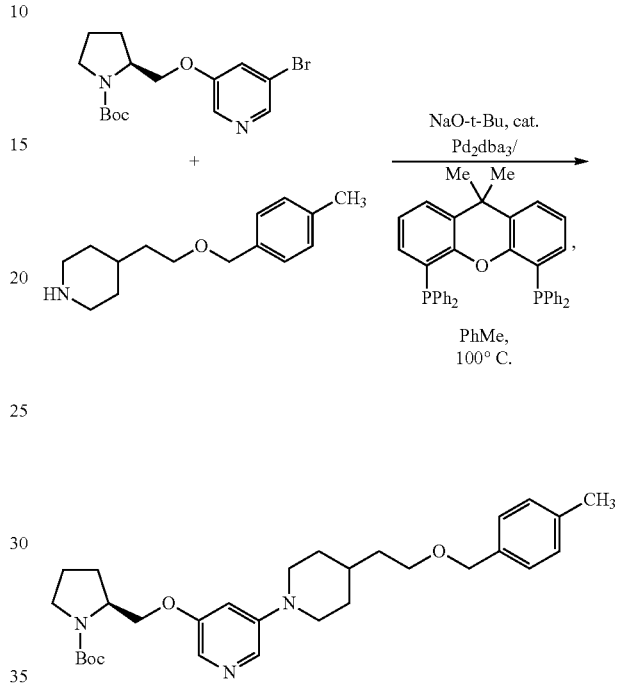

To a solution of 3-bromo-5-[[1-(tert-butoxycarbonyl)-2(R)-pyrrolidinyl]methoxy]pyridine (254 mg, 0.71 mmol) and 4-[2-(4-methylbenzyloxy)ethyl]piperidine (182 mg, 0.78 mmol, 1.1 equiv.) in anhydrous toluene (2 mL) were added successively sodium tert-butoxide (102 mg, 1.07 mmol), tris(dibenzylideneacetone)dipalladium(0) (13.0 mg, 14 μmol, 0.02 equiv.), and 4,5-bis(diphenylphosphino)-9,9-dimethylxanthene (Xantphos; 24.7 mg, 43 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over $Na_2SO_4$, and evaporated. The residue was purified by CC on $SiO_2$ with $CH_2Cl_2$/EtOAc 4:1, then 1:1. The product (231 mg, 64%) was obtained as a pale yellow oil.

3-[4-[2-(4-Methylbenzyloxy)ethyl]-1-piperidinyl]-5-[(2(S)-pyrrolidinyl)methoxy]pyridine Hydrochloride

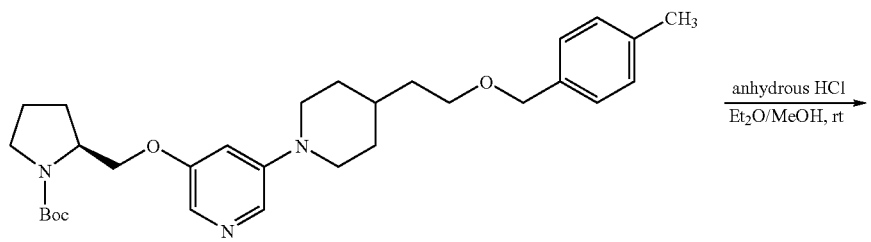

-continued

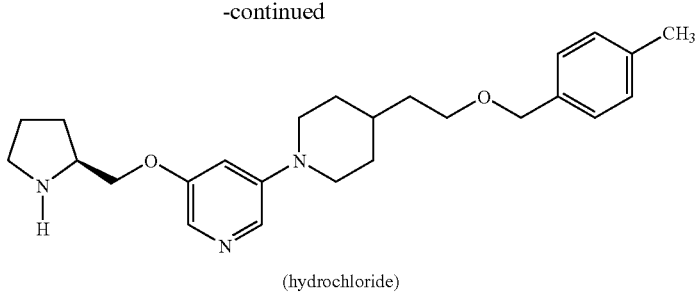

(hydrochloride)

To a solution of 3-[[1-(tert-butoxycarbonyl)-2(S)-pyrrolidinyl]methoxy]-5-[4-[2-(4-methylbenzyloxy)ethyl]-1-piperidinyl]pyridine (231 mg, 0.45 mmol) in MeOH (0.2 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. The residue was purified by HPLC (ACE AQ 150×21.2 mm; UV detection at 254 nm and 280 nm; flow 10.0 mL/min; 8% to 100% MeOH in water [both containing 0.05 vol % of $CF_3COOH$] in 30 min, then 100% for another 3 min; $t_R$ 14.8-22.2 min) to obtain the trifluoroacetate. This salt was treated with PL-HCO3 MP anion exchange resin (Polymer Laboratories) in MeOH to afford the free amine, which was dissolved in MeOH (0.5 mL), and treated again with 2N anhydrous HCl/ether (2 mL) under Ar protection at room temperature. The mixture was stirred at room temperature overnight. After the solvent was evaporated, the residue was dissolved in deionized water. After the solution was filtered over a cotton plug, the water was removed under reduced pressure at 35° C. After lyophilization from water, the hydrochloride (188 mg) was obtained as a yellow glass. $^1$HNMR ($D_2O$, 400 MHz) δ 7.84 (s, 1H), 7.76 (s, 1H), 7.36 (s, 1H), 7.09 (d, 2H, J=7.6 Hz), 7.02 (d, 2H, J=8.0 Hz), 4.42 (dd, 1H, J=3.2, 10.8 Hz), 4.27 (m, 3H), 4.06 (m, 1H), 3.66 (d, 2H, J=12.8 Hz), 3.39 (m, 4H), 2.78 (t, 2H, J=11.6 Hz), 2.22 (m, 1H), 2.15 (s, 3H), 2.05 (m, 2H), 1.88 (m, 1H), 1.62 (d, 2H, J=12.4 Hz), 1.50 (m, 1H), 1.40 (m, 2H), 1.09 (m, 2H); $^{13}$C NMR ($D_2O$, 100 MHz) δ 156.5, 148.8, 137.3, 134.2, 128.6, 127.8, 121.5, 117.2, 114.1, 71.8, 67.3, 67.0, 58.0, 47.2, 45.6, 34.7, 31.2, 30.1, 25.5, 23.0, 20.1. Anal. Calcd. for $C_{25}H_{35}N_3O_2 \cdot 3.10HCl \cdot 1.75H_2O$: C, 54.19; H, 7.57; N, 7.58; Cl, 19.83. Found: C, 54.23; H, 7.44; N, 7.52; Cl, 19.72.

Example 75

3-[4-(2-Hydroxyethyl)-1-piperidinyl]-5-[(2(S)-pyrrolidinyl)methoxy]pyridine

4-[2-(4-Methoxybenzyloxy)ethyl]piperidine

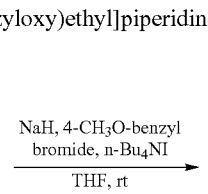 NaH, 4-$CH_3$O-benzyl bromide, n-$Bu_4$NI
―――――→
THF, rt

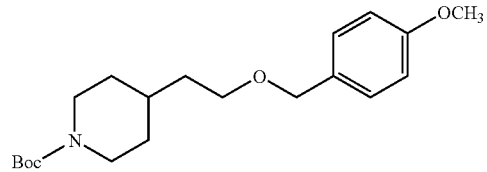

NaH (60% dispersion in oil, 98 mg, 2.4 mmol, 1.2 equiv.) was added to a solution of 1-(tert-butoxycarbonyl)-4-(2-hydroxyethyl)piperidine (468 mg, 2.0 mmol) in THF (10 mL) at 0° C. under Ar protection. The mixture was warmed to room temperature and stirred at that temperature for 3 h. 1-(Bromomethyl)-4-methoxybenzene (353 µL, 2.4 mmol, 1.2 equiv.) was added at room temperature. After stirring for 20 h, the reaction was quenched with saturated aqueous $NH_4Cl$ solution. The mixture was extracted three times with EtOAc, and the combined organic layers were washed with brine and dried over $Na_2SO_4$. The solvent was removed, and the residue was purified by CC ($SiO_2$, hexane/EtOAc 10:1 to 4:1) to afford the product (268 mg, 38%) as a yellow oil. $^1$H NMR ($CDCl_3$, 400 MHz) δ 7.22 (d, 2H, J=8.4 Hz), 6.85 (d, 2H, J=8.8 Hz), 4.40 (s, 2H), 4.05 (m, 2H), 3.76 (m, 4H), 3.45 (t, 2H, J=6.0 Hz), 2.65 (m, 2H), 1.62-1.50 (m, 5H), 1.44 (s, 9H), 1.08 (m, 2H).

3-[[N-(tert-Butoxycarbonyl)-2(S)-pyrrolidinyl]methoxy]-5-[4-[2-(4-methoxybenzyloxy)ethyl]-1-piperidinyl]pyridine

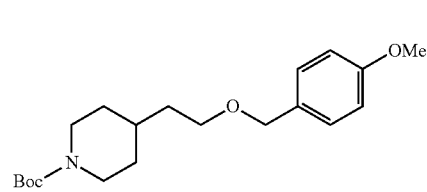 anhydrous HCl
$Et_2O$/MeOH,
rt;
basification
―――――→

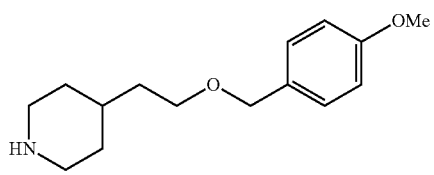

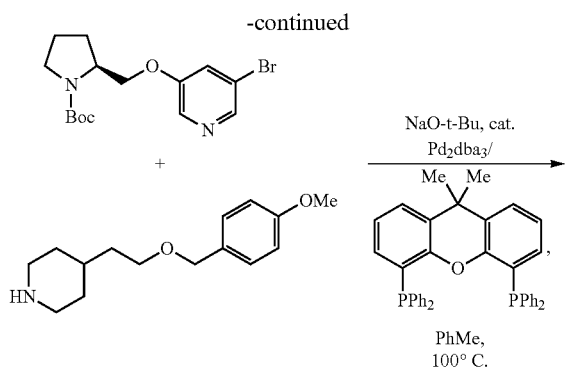

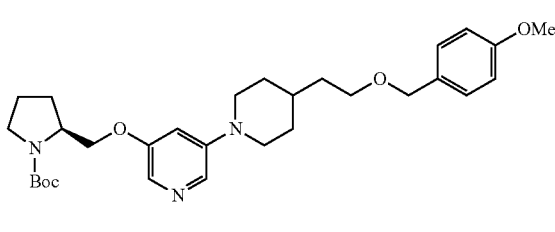

To a solution of 4-[2-(4-methoxybenzyloxy)ethyl]piperidine (268 mg, 0.77 mmol) in MeOH (2 mL) was added 2N anhydrous HCl/ether (0.75 mL, 1.54 mmol). The reaction mixture was stirred overnight. After evaporation, the residue was dissolved in deionized water. EtOAc was used to wash the aqueous layer before the pH was altered to approx. 9-10. The aqueous layer was extracted three times with CH₂Cl₂ and dried over Na₂SO₄. After evaporation, 4-[2-(4-methoxybenzyloxy)ethyl]piperidine (112 mg, 58%) was obtained as a colorless oil.

To a solution of 3-bromo-5-[[1-(tert-butoxycarbonyl)-2(S)-pyrrolidinyl]methoxy]pyridine (112 mg, 0.31 mmol) and 4-[2-(4-methoxybenzyloxy)ethyl]piperidine (86 mg, 0.34 mmol, 1.1 equiv.) in anhydrous toluene (2 mL) were added successively sodium tert-butoxide (45 mg, 0.47 mmol, 1.5 equiv.), Pd₂dba₃ (5.7 mg, 6.0 μmol, 0.02 equiv.), and 4,5-bis(diphenylphosphino)-9,9-dimethylxanthene (Xantphos; 10.8 mg, 19 μmol, 0.06 equiv.). The mixture was degassed and purged with Ar (3 cycles), then warmed to 98-100° C. for 4 h. After cooling to room temperature, the mixture was diluted with EtOAc, and the solution was washed with brine, dried over Na₂SO₄, and evaporated. The residue was purified by CC on SiO₂ with CH₂Cl₂/EtOAc 3:2, then 1:2. The product (137 mg, 84%) was obtained as a pale yellow oil. $^1$H NMR (CDCl₃, 400 MHz) δ 8.23-7.30 (m, 3H), 7.24 (d, 2H, J=8.4 Hz), 6.86 (d, 2H, J=8.4 Hz), 4.41 (s, 2H), 4.10 (m, 2H), 3.90-3.80 (m, 1H), 3.78 (s, 3H), 3.65 (m, 2H), 3.49 (t, 2H, J=6.0 Hz), 3.39 (m, 2H), 2.72 (m, 2H), 2.02 (m, 3H), 1.84 (m, 1H), 1.75 (d, 2H, J=12.4 Hz), 1.55 (m, 3H), 1.45 (s, 9H), 1.31 (m, 2H).

3-[4-(2-Hydroxyethyl)-1-piperidinyl]-5-[(2(S)-pyrrolidinyl)methoxy]pyridine Hydrochloride

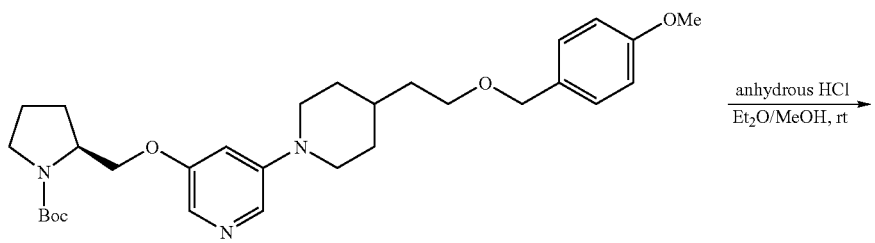

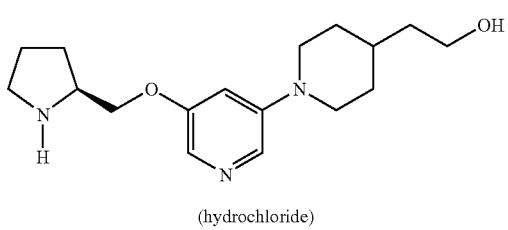

(hydrochloride)

To a solution of 3-[[N-(tert-butoxycarbonyl)-2(S)-pyrrolidinyl]methoxy]-5-[4-[2-(4-methoxybenzyloxy)ethyl]-1-piperidinyl]pyridine (92 mg, 0.18 mmol) in MeOH (0.2 mL) was added 2N anhydrous HCl/ether (1 mL) under Ar at room temperature. The mixture was stirred at room temperature overnight. After the solvent was evaporated, the residue was dissolved in deionized water. The aqueous solution was washed twice with EtOAc, then filtered over a cotton plug. The water was removed under reduced pressure at 35° C. to obtain the crude hydrochloride. This material was purified by preparative HPLC (ACE AQ 150×21.2 mm; UV detection at 254 and 280 nm; flow 10.0 mL/min; 0 to 50% $CH_3CN$ in water [both containing 0.05 vol % $CF_3COOH$] in 25 min, to 100% in another 5 min; $t_R$ 13.1-14.8 min), and the eluate was evaporated to obtain the trifluoroacetate. This salt was treated with PL-HCO3 MP anion exchange resin (Polymer Laboratories) in MeOH to afford free amine, which was dissolved in MeOH (0.2 mL) and treated again with 2N anhydrous HCl/ether (1 mL) under Ar protection at room temperature. The mixture was stirred at room temperature overnight. After the solvent was evaporated, the residue was dissolved in deionized water. The solution was filtered over a cotton plug, and the water was removed under reduced pressure at 35° C. After lyophilization from water, the hydrochloride (42 mg) was obtained as a yellow glass. $[\alpha]^{20}_D$ +1.1 (c 0.90 g/L, MeOH). $^1H$ NMR ($D_2O$, 400 MHz) δ 8.00 (d, 1H, J=2.0 Hz), 7.81 (d, 1H, J=1.6 Hz), 4.52 (dd, 1H, J=3.2, 10.4 Hz), 4.32 (dd, 1H, J=7.6, 10.4 Hz), 4.13 (m, 1H), 4.82 (d, 2H, J=12.8 Hz), 3.64 (t, 2H, J=6.8 Hz), 3.40 (t, 2H, J=6.8 Hz), 3.01 (m, 2H), 2.27 (m, 1H), 2.10 (m, 2H), 1.94 (m, 1H), 1.82 (d, 2H, J=12.0 Hz), 1.65 (m, 1H), 1.49 (q, 2H, J=6.4 Hz), 1.28 (m, 2H); $^{13}C$ NMR ($D_2O$, 100 MHz) δ 156.5, 149.0, 122.0, 117.4, 114.4, 67.2, 58.7, 58.1, 47.6, 45.6, 37.2, 30.8, 30.0, 25.4, 23.0; HRMS (ESI) calcd for $C_{17}H_{28}N_3O_2$ $(M+H^+)$ m/z 306.2182, found 306.2178.

Example 76

In Vitro Binding Assay for Nicotinic Acetylcholine Receptor Ligands

All binding assays were performed according to procedures set forth in the University of North Carolina at Chapel Hill National Institute of Mental Health Psychoactive Drug Screening Program Assay Protocol Book (pp. 50-54; PI: Bryan L. Roth MD, PhD).

Nicotinic receptors: α2β2, α2β4, α3β2, α3β4, α4β2, α4β4, endogenous α4β2. Assay buffer: 50 mM Tris-HCl, pH 7.4. Membrane fraction source: Stably transfected cell lines (e.g., HEK293, COS, CHO, NIH3T3) (α2β2, α2β4, α3β2, α3β4, α4β2, α4β4) or rat forebrain (α4β2). Protocol adapted from Xiao et al. *Mol Pharm* 54(2):322-333 (1998).

Experimental Procedure and Data Analysis

Solutions of the compounds to be tested were prepared as a 1-mg/ml stock in assay buffer or DMSO according to the solubility of the compound. A similar stock solution of a reference compound (positive control) [(−)-nicotine] was also prepared. Eleven dilutions (5×assay concentration) of the test and reference compound were prepared in assay buffer by serial dilution: 0.05 nM, 0.5 nM, 1.5 nM, 5 nM, 15 nM, 50 nM, 150 nM, 500 nM, 1.5 μM, 5 μM, 50 μM (thus, the corresponding assay concentrations spanned from 10 pM to 10 μM and included semilog points in the range where high-to-moderate affinity ligands compete with radioligand for binding sites).

Radioligand ($[^3H]$epibatidine) was diluted to 2.5 nM (five times the assay concentration) in assay buffer. Aliquots (50 μl) of radioligand were dispensed into the wells of a 96-well plate containing 100 μl of assay buffer. Then, duplicate 50-μl aliquots of the test and reference compound dilutions were added.

Finally, crude membrane fractions of cells expressing recombinant target (prepared from 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; typically, one 10-cm plate provides sufficient material for 24 wells) were resuspended in 3 ml of chilled assay buffer and homogenized by several passages through a 26 gauge needle, then 50 μl were dispensed into each well.

The 250-μl reactions were incubated at room temperature and shielded from light (to prevent photolysis of light-sensitive ligands) for 4 hours, then harvested by rapid filtration onto Whatman GF/B glass fiber filters pre-soaked with 0.5% polyethyleneimine using a 96-well Brandel harvester. Four rapid 500-μl washes were performed with chilled Standard Binding Buffer to reduce non-specific binding. Filters were placed in 6-ml scintillation tubes and allowed to dry overnight. The next day, 4 ml of EcoScint scintillation cocktail (National Diagnostics) were added to each tube. The tubes were capped, labeled, and counted by liquid scintillation counting.

Raw data (dpm) representing total radioligand binding (i.e., specific+non-specific binding) were plotted as a function of the logarithm of the molar concentration of the competitor (i.e., test or reference compound). Non-linear regression of the normalized (i.e., percent radioligand binding compared to that observed in the absence of test or reference compound) raw data was performed in Prism 4.0 (GraphPad) using the built-in three parameter logistic model describing ligand competition binding to radioligand-labeled sites:

$$y = \text{bottom} + [(\text{top}-\text{bottom})/(1+10^{x-\log IC_{50}})]$$

where bottom is the residual radioligand binding measured in the presence of 10 μM reference compound (i.e., non-specific binding) and top is the total radioligand binding observed in the absence of competitor. The log $IC_{50}$ (i.e., the log of the ligand concentration that reduces radioligand binding by 50%) was thus estimated from the data and used to obtain the $K_i$ by applying the Cheng-Prusoff approximation:

$$K_i = IC_{50}/(1+[\text{ligand}]/K_D)$$

where [ligand] is the assay radioligand concentration and $K_D$ is the affinity constant of the radioligand for the target receptor.

$K_i$ values for nicotinic acetylcholine receptor ligands of the present invention are shown in Table 1.

TABLE 1

| Compound | $K_i$ (nM) | | | | | | |
|---|---|---|---|---|---|---|---|
| | α2β2 | α2β4 | α3β2 | α3β4 | α4β2 | α4β2*++ | α4β4 |
| [structure with azetidine-CH2-O-pyridine-cyclopropyl-CH2CH2-OH] ·2HCl | 0.9 | 62 | 5.1 | 640 | 0.3 | 1.2 | 83 |
| [structure with azetidine-CH2-O-pyridine-cyclopropyl-(CH2)4-OH] ·2HCl | 0.6 | 120 | 6.5 | 10000 | 0.5 | 1.4 | 240 |
| [structure with azetidine-CH2-O-pyridine-cyclopropyl-CH2CH2-F] ·2HCl | 6.4 | 660 | 34 | >10000 | 1 | 11 | 1300 |

++For receptor nomenclature, see Lucas, R., et al., Pharmacological Reviews, June 1999, 51(2), 397-401.

Thus, the nicotinic acetylcholine receptor ligands of the invention demonstrate binding to nicotinic acetylcholine receptors.

Example 77

In Vitro Affinity of Nicotinic Acetylcholine Receptor Ligands for α-Bungarotoxin-insensitive (α4β2) Neuronal Nicotinic Receptor The affinity of nicotinic acetylcholine receptor ligands for the agonist site of the α-Bungarotoxin-insensitive nicotinic receptor in the rat cerebral cortex were determined according to procedures set forth in the Cerep SOP No. 1A076 (Catalog ref. 807-n1).

Nicotinic receptors: α-Bungarotoxin-insensitive central nicotinic receptor (α4β2). Assay buffer: 50 mM Tris-HCl, pH 7.4, 120 mM NaCl, 5 mM KCl, 1 mM $MgCl_2$ and 2 mM $CaCl_2$. Membrane fraction source: homogenates of rat cerebral cortex. Protocol adapted from Pabreza et al. *Mol Pharm* 39:9-12 (1991).

Experimental Procedure and Data Analysis

Membrane homogenates of cerebral cortex (800 μg protein) were incubated for 75 min at 4° C. with 1.5 nM [$^3$H] cytisine in the absence or presence of 100 nM of the test compound in a buffer containing 50 mM Tris-HCl buffer (pH 7.4) containing 120 mM NaCl, 5 mM KCl, 1 mM $MgCl_2$ and 2 mM $CaCl_2$.

Non-specific binding was determined in the presence of 10 μM nicotine.

Following incubation, the samples were filtered rapidly under vacuum through glass fiber filters (Filtermat B, Wallac) presoaked with 0.3% PEI and rinsed several times with ice-cold 50 mM Tris-HCl using a 48-sample cell harvester (Mach II, Tomtec). The filters were dried, then counted for radioactivity in a scintillation counter (Betaplate 1204, Wallac) using a solid scintillator (Meltilex B/HS, Wallac).

The specific ligand binding to the receptors is defined as the difference between the total binding and the nonspecific binding determined in the presence of 10 μM nicotine.

The results were expressed as a percent inhibition of the control radioligand specific binding obtained in the presence of the test compound: (100–((measured specific binding/control specific binding)×100)).

The standard reference compound was nicotine, which was tested in each experiment at several concentrations to obtain a competition curve from which its $IC_{50}$ was calculated.

The compounds whose structure appear in Examples 2, 11, 12, 14, 15c, 15d, 19, 22, 24, 27, 37, 41, 46, 49, and 51 showed greater than 50% inhibition (ranging from 59% to 100% inhibition) of the control radioligand specific binding at a concentration of 100 nM. The compounds whose structure is shown in Examples 58, 62, 70, and 72, using the same binding procedure, at a concentration of 100 nM, showed inhibition ranging from 8% to 28%. The compound of Example 71, which is also an intermediate that can be used to synthesize additional analogs described herein such as the compound in Example 70, showed no binding activity at a concentration of 100 nM.

Thus, the nicotinic acetylcholine receptor ligands of the invention demonstrate binding to central nicotinic acetylcholine receptors.

Example 78

Effect of Nicotinic Acetylcholine Receptor Ligands on the Forced Swim Test in Mice Subjects. The subjects were male Balb/cJ mice obtained from Jackson Laboratory, Bar Harbor, Me. Mice were housed 4 per cage under controlled conditions of temperature, relative humidity and light-dark cycle with free access to food and water.

Procedures. Procedures were based on those previously described (Porsolt et al., 1977). Mice were individually placed into clear glass cylinders (i.e., 15 cm tall×10 cm wide, 1 L beakers) containing 23±1° C. water 12 cm deep (approximately 800 mL). The time the animal spent immobile was recorded over a 6 min trial. Immobility was described as the postural position of floating in the water.

Drugs. The test compounds were AMOP—H—OH, the compounds whose structure appear in Example 2, 4, 8, 15c, 15d, 24, 46, 49, 51, 58, 62, 72, and sertraline (a known SSRI antidepressant). The mice were injected intraperitoneally (i.p.) 30 minutes before the start of the test. In another set of experiments, the test compounds were administered orally (p.o.) 30 minutes before the start of the test. The test compounds were the compounds whose structure appear in Examples 2, 10, 12, 15c, 24, 27, 46, 49, 51, 52, and 62.

Statistics. The length of time spent floating was analyzed by Analysis of Variance (ANOVA) with dose of drug as the between-subject factor and time spent immobile across the 6 min test as the dependent variable. Post-hoc comparisons between the treatment groups and control group were made using Fisher's PLSD test. A significance level of 5% was used throughout.

TABLE 2

Forced Swim Test in Mice

| Compound Administered | Dose (mg/kg i.p.) | Average Immobility Time (seconds) |
|---|---|---|
| Vehicle | 0 | 126.3 |
| Sertraline | 20 | 11.9** |
| AMOP-H-OH | 0.3 | 116.7 |
| AMOP-H-OH | 1 | 20.2** |
| AMOP-H-OH | 3 | 2.9** |
| AMOP-H-OH | 10 | 5.3** |

The number of mice/group was 10 except for the vehicle group which had 9 mice.

Results marked with a double asterisk (**) are those that were shown to be significantly different from vehicle.

AMOP—H—OH (structure shown below) showed positive effects in the forced swim test as indicated by a reduction in immobility time (Table 2). The reference compound sertraline showed a very similar result to that observed with AMOP—H—OH.

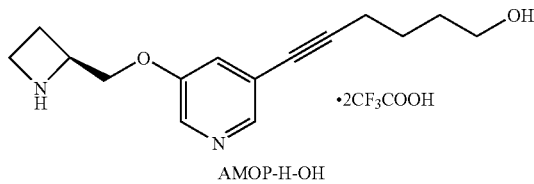 [SMILES: OCCCCC#Cc1cncc(OC[C@@H]2CCN2)c1]

AMOP-H-OH

TABLE 3

Forced Swim Test in Mice

| Compound Administered | Dose (mg/kg i.p.) | Average Immobility Time (seconds) |
|---|---|---|
| Vehicle | 0 | 133.3 |
| AMOP-H—OH | 3 | 0** |
| Compound in Example 15c | 5 | 110.6 |
| Compound in Example 15c | 10 | 105.1** |

All groups had 10 mice. Results marked with a double asterisk (**) are those that were shown to be significantly different from vehicle.

TABLE 4

Forced Swim Test in Mice

| Compound Administered | Dose (mg/kg i.p.) | Average Immobility Time (seconds) |
|---|---|---|
| Vehicle | 0 | 115.2 |
| Sertraline | 10 | 23.7** |
| Compound in Example 15c | 10 | 85.3** |
| Compound in Example 15c | 20 | 49.7** |

All groups had 10 mice. Results marked with a double asterisk (**) are those that were shown to be significantly different from vehicle.

The compound whose structure is shown in Example 15c (structure shown below) showed positive effects in the forced swim test as indicated by a reduction in immobility time (Table 3 and Table 4).

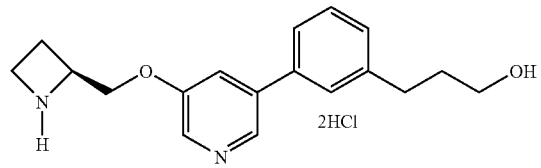 [SMILES: OCCCc1cccc(-c2cncc(OC[C@@H]3CCN3)c2)c1 ; "2HCl"]

TABLE 5

Forced Swim Test in Mice

| Compound Administered | Dose (mg/kg i.p.) | Average Immobility Time (seconds) |
|---|---|---|
| Vehicle | 0 | 104.9 |
| Sertraline | 10 | 47.8** |
| Compound in Example 2 | 10 | 44** |
| Compound in Example 2 | 20 | 7** |

All groups had 10 mice. Results marked with a double asterisk (**) are those that were shown to be significantly different from vehicle.

The compound from Example 2, a nicotinic acetylcholine receptor ligand of the present invention having the structure:

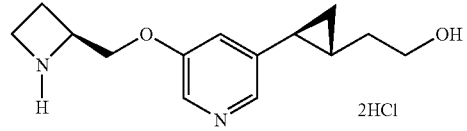 [SMILES: OCC[C@H]1C[C@@H]1c1cncc(OC[C@@H]2CCN2)c1 ; "2HCl"]

showed positive effects in the forced swim test as indicated by a reduction in immobility time (Table 5). The reference compound sertraline showed a very similar result to that observed with Compound 22 (Table 5).

The compounds whose structure is shown in Examples 2, 4, 8, 15c, 15d, 24, 46, 49, 51, 58, 62, and 72 showed activity in the Forced Swim test as indicated by an average reduction in immobility time of the mice ranging from 22.0 to 85.7 seconds compared to the use of a vehicle that was selected from one of water, saline or 2% pharmasolve solution, at a dose of 10 mg/kg dose (i.p.).

The compound whose structure is shown in Examples 2, 10, 12, 24, 27, 46, 49, 51, 52, and 62 were administered p.o. in the Forced Swim test using water as the vehicle for comparison. At a dose of 10 mg/kg (p.o.) these compounds showed an average reduction in immobility time ranging from 21.2 to 114.2 seconds compared to the average immobility time for the vehicle. The compound of Example 15c at a dose of 10 mg/kg (p.o.) did not show any change in immobility time compared to the vehicle and at a dose of 20 mg/kg (p.o.) showed a reduction in immobility time of 24.5 seconds compared to the immobility time for the vehicle.

What is claimed is:

1. A compound of formula I:

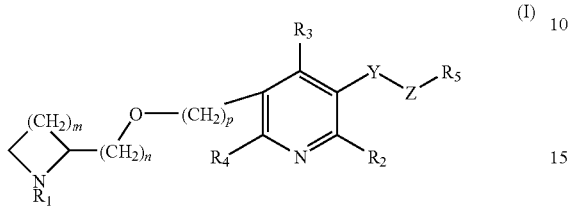

wherein $R_1$ is hydrogen, $C_1$-$C_6$ straight chain alkyl, $C_3$-$C_6$ branched chain alkyl, allyl, or $C_3$-$C_6$ cycloalkyl;

$R_2$, $R_3$ and $R_4$ are each independently hydrogen, $C_1$-$C_6$ straight chain alkyl, $C_3$-$C_6$ branched chain alkyl, $C_3$-$C_6$ cycloalkyl or $C_1$-$C_6$ alkyl substituted with one or more fluorine atoms;

Y is a bond, or —$(CH_2)_q$—, optionally substituted with one or two groups independently selected from methyl, ethyl, propyl, isopropyl, and cyclopropyl;

Z is cyclopropyl, and wherein said cyclopropyl is optionally substituted with one or two $C_1$-$C_3$ alkyl groups;

$R_5$ is $C_1$-$C_6$ straight chain alkyl; $C_3$-$C_6$ branched chain alkyl; $C_1$-$C_6$ hydroxyalkyl; alkoxyalkyl in which the alkoxy and alkyl portions each independently contain from 1 to 6 carbon atoms; $C_1$-$C_6$ fluoroalkyl; arylalkyl in which the alkyl portion contains from 1 to 6 carbon atoms; arylalkoxy in which the alkoxy portion contains from 1 to 6 carbon atoms; aryl; biaryl; heteroarylalkyl in which the alkyl portion contains from 1 to 6 carbon atoms; heteroarylalkoxy in which the alkoxy portion contains from 1 to 6 carbon atoms; —$(CH_2)_{1-6}$—O—$(CH_2)_{0-6}$-aryl; —$(CH_2)_{1-6}$—O—$(CH_2)_{0-6}$-heteroaryl; —$(CH_2)_{0-6}$—O—$(CH_2)_{0-6}$—$C_3$-$C_6$ cycloalkyl; heteroaryl; or a four- to six-membered saturated heterocycle, with the proviso that $R_5$ is not arylalkoxy or heteroarylalkoxy when Z is $C_3$-cycloalkyl;

wherein $R_5$ is optionally substituted with one or two substituents independently selected from $C_1$-$C_6$ straight chain alkyl; $C_3$-$C_6$ branched chain alkyl; $C_1$-$C_6$ fluoroalkyl; $C_1$-$C_6$ hydroxyalkyl; aryloxy; heteroaryloxy; $C_3$-$C_6$ cycloalkyloxy; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —$NH_2$; $C_1$-$C_6$ alkylthio; —$CF_3$; $C_1$-$C_6$ monoalkylamino; $C_1$-$C_6$ dialkylamino; carboxyl; and $C_2$-$C_6$ alkoxycarbonyl;

and wherein if $R_5$ comprises an aryl group or a heteroaryl group, then $R_5$ is optionally substituted with one or two substituents selected from $C_1$-$C_6$ straight chain alkyl; $C_3$-$C_6$ branched chain alkyl; $C_1$-$C_6$ fluoroalkyl; $C_1$-$C_6$ hydroxyalkyl; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —$NH_2$; $C_1$-$C_6$ alkylthio; —$CF_3$; $C_1$-$C_6$ monoalkylamino; $C_1$-$C_6$ dialkylamino; carboxyl; $C_2$-$C_6$ alkoxycarbonyl; Cl and $OCF_3$;

or $R_5$ is —$(CH_2)_rNR'R^{vi}$; —$(CH_2)_rC(O)NR'R^{vi}$; —$(CH_2)_r$ $C(O)OR^{ix}$; —$(CH_2)_rSR^{viii}$; —$(CH_2)_rSO_2R^{ix}$ or —$(CH_2)_rSOR^{ix}$;

wherein:

$R^v$ and $R^{vi}$ are each independently hydrogen, $C_1$-$C_6$ straight chain alkyl; $C_3$-$C_6$ branched chain alkyl; $C_3$-$C_6$ cycloalkyl; aryl; arylalkyl in which the alkyl portion contains 1 to 6 carbon atoms; —$(CO)R^{vii}$; —$(CO)OR^{vii}$; —$SO_2R^{vii}$; or $R^v$ and $R^{vi}$ form a four- to six-membered saturated heterocyclic ring having a single nitrogen atom; wherein if one of $R^v$ and $R^{vi}$ is —$(CO)R^{vii}$ or —$SO_2R^{vii}$, the other is not —$(CO)R^{vii}$ or —$SO_2R^{vii}$;

$R^{vii}$ is $C_1$-$C_6$ straight chain alkyl which is optionally substituted with one or two hydroxyl groups; $C_3$-$C_6$ branched chain alkyl which is optionally substituted with one or two hydroxyl groups; $C_3$-$C_6$ cycloalkyl, wherein when the cycloalkyl group contains more than 3 carbon atoms, it is optionally substituted with one or two hydroxyl groups; aryl which is optionally substituted with 1 or 2 fluorine atoms, one hydroxyl group, one hydroxyl group and one fluorine atom, $C_1$-$C_6$ straight chain alkyl, $C_3$-$C_6$ branched chain alkyl or $C_3$-$C_6$ cycloalkyl, and wherein if the $C_1$-$C_6$ straight chain alkyl group, the $C_3$-$C_6$ branched chain alkyl group or the $C_3$-$C_6$ cycloalkyl group is substituted, then no more than one heteroatom selected from the oxygen atom in the hydroxyl group and the sulfur atom in —$SO_2R^{vii}$ is bound to any single carbon atom; arylalkyl in which the alkyl portion contains from 1 to 6 carbon atoms; heteroaryl; or heteroarylalkyl in which the alkyl portion contains from 1 to 6 carbon atoms; or when $R^v$ is not H and $R^{vi}$ is either —$(CO)R^{vii}$ or —$SO_2R^{vii}$, $R^v$ and $R^{vii}$ can be taken together to form a 4- to 7-membered ring;

$R^{viii}$ is hydrogen, $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —$(CH_2)_rSR^{viii}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; or $R^{viii}$ is —$C(O)R^x$;

$R^{ix}$ is $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —$(CH_2)_rSO_2R^{ix}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, one hydroxyl group and one fluorine atom, or $C_1$-$C_6$ hydroxyalkyl; heteroaryl that is optionally substituted with 1 or 2 fluorine atoms, one hydroxyl group, one hydroxyl group and one fluorine atom, or $C_1$-$C_6$ hydroxyalkyl, wherein the number of substituents does not exceed the number of available C—H and N—H bonds; or arylalkyl in which the alkyl portion contains from 1 to 6 carbon atoms and the aryl portion is optionally substituted with 1 or 2 fluorine atoms, one hydroxyl group, one hydroxyl group and one fluorine atom, or $C_1$-$C_6$ hydroxyalkyl;

$R^x$ is $C_1$-$C_6$ straight chain alkyl optionally substituted with one or two hydroxyl groups or $C_1$-$C_6$ alkoxy groups, wherein if the $C_1$-$C_6$ alkyl group is substituted, then no more than one heteroatom selected from the oxygen atom in the hydroxyl group and the oxygen atom in the alkoxy group is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; arylalkyl in which the alkyl portion contains from 1 to 6 carbon atoms and in which the aryl portion is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; $C_1$-$C_6$ monoalkylamino; or $C_1$-$C_6$ dialkylamino;

wherein if $R_5$ contains at least one saturated carbon atom and said $R_5$ is substituted with two substituents independently selected from $C_1$-$C_6$ alkoxy, alkoxyalkoxy in which the alkoxy portions each independently contain from 1 to 6 carbon atoms, F, —OH, —NH$_2$, $C_1$-$C_6$ monoalkylamino, $C_1$-$C_6$ dialkylamino, and $C_1$-$C_6$ alkylthio, then said two substituents are not bound to the same saturated carbon atom;

m is 1;

n is an integer ranging from 1 to 2;

p is an integer ranging from 0 to 2;

wherein when n is 2 or p is 2, the carbon atom linked to the oxygen atom can be substituted with a $C_1$-$C_6$ straight chain alkyl group or a $C_3$-$C_6$ branched chain alkyl group;

q is an integer ranging from 1 to 5;

r is an integer ranging from 0 to 5;

and pharmaceutically acceptable derivatives thereof.

2. A compound of formula I:

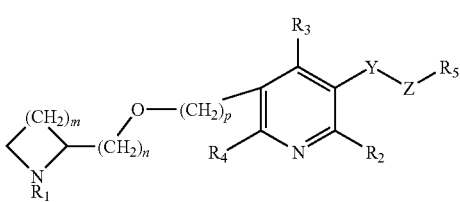

(I)

wherein $R_1$ is hydrogen, $C_1$-$C_6$ straight chain alkyl, $C_3$-$C_6$ branched chain alkyl, allyl, or $C_3$-$C_6$ cycloalkyl;

$R_2$, $R_3$ and $R_4$ are each independently hydrogen, $C_1$-$C_6$ straight chain alkyl, $C_3$-$C_6$ branched chain alkyl, $C_3$-$C_6$ cycloalkyl or $C_1$-$C_6$ alkyl substituted with one or more fluorine atoms;

Y is a bond, or —(CH$_2$)$_q$—, optionally substituted with one or two groups independently selected from methyl, ethyl, propyl, isopropyl, and cyclopropyl;

Z is cyclopropyl, and wherein said cyclopropyl is optionally substituted with $C_1$-$C_3$ alkyl;

$R_5$ is $C_1$-$C_6$ straight chain alkyl; $C_3$-$C_6$ branched chain alkyl; $C_1$-$C_6$ hydroxyalkyl; alkoxyalkyl in which the alkoxy and alkyl portions each independently contain from 1 to 6 carbon atoms; $C_1$-$C_6$ fluoroalkyl; arylalkyl in which the alkyl portion contains from 1 to 6 carbon atoms; arylalkoxy in which the alkoxy portion contains from 1 to 6 carbon atoms, with the proviso that $R_5$ is not arylalkoxy when Z is $C_3$-cycloalkyl; aryl; biaryl; heteroarylalkyl in which the alkyl portion contains from 1 to 6 carbon atoms; heteroarylalkoxy in which the alkoxy portion contains from 1 to 6 carbon atoms; —(CH$_2$)$_{1-6}$—O—(CH$_2$)$_{0-6}$-aryl; —(CH$_2$)$_{1-6}$—O—(CH$_2$)$_{0-6}$-heteroaryl; —(CH$_2$)$_{0-6}$—O—(CH$_2$)$_{0-6}$—$C_3$-$C_6$ cycloalkyl; heteroaryl; or four- to six-membered saturated heterocycle;

wherein $R_5$ is optionally substituted with one or two substituents independently selected from $C_1$-$C_6$ straight chain alkyl; $C_3$-$C_6$ branched chain alkyl; $C_1$-$C_6$ fluoroalkyl; $C_1$-$C_6$ hydroxyalkyl; aryloxy; heteroaryloxy; $C_3$-$C_6$ cycloalkyloxy; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —NH$_2$; $C_1$-$C_6$ alkylthio; —CF$_3$; $C_1$-$C_6$ monoalkylamino; $C_1$-$C_6$ dialkylamino; carboxyl; and $C_2$-$C_6$ alkoxycarbonyl;

and wherein if $R_5$ comprises an aryl group or a heteroaryl group, then $R_5$ is optionally substituted with one or two substituents selected from $C_1$-$C_6$ straight chain alkyl; $C_3$-$C_6$ branched chain alkyl; $C_1$-$C_6$ fluoroalkyl; $C_1$-$C_6$ hydroxyalkyl; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —NH$_2$; $C_1$-$C_6$ alkylthio; —CF$_3$; $C_1$-$C_6$ monoalkylamino; $C_1$-$C_6$ dialkylamino; carboxyl; $C_2$-$C_6$ alkoxycarbonyl; Cl and OCF$_3$;

or $R_5$ is —(CH$_2$)$_r$NR$^v$R$^{vi}$; —(CH$_2$)$_r$C(O)NR$^v$R$^{vi}$; —(CH$_2$)$_r$C(O)OR$^{ix}$; —(CH$_2$)$_r$SR$^{viii}$; —(CH$_2$)$_r$SO$_2$R$^{ix}$ or —(CH$_2$)$_r$SOR$^{ix}$;

wherein:

R$^v$ and R$^{vi}$ are each independently hydrogen, $C_1$-$C_6$ straight chain alkyl; $C_3$-$C_6$ branched chain alkyl; $C_3$-$C_6$ cycloalkyl; aryl; arylalkyl in which the alkyl portion contains 1 to 6 carbon atoms; —(CO)R$^{vii}$; —(CO)OR$^{vii}$; —SO$_2$R$^{vii}$; or R$^v$ and R$^{vi}$ form a four- to six-membered saturated heterocyclic ring having a single nitrogen atom; wherein if one of R$^v$ and R$^{vi}$ is —(CO)R$^{vii}$ or —SO$_2$R$^{vii}$, the other is not —(CO)R$^{vii}$ or —SO$_2$R$^{vii}$;

R$^{vii}$ is $C_1$-$C_6$ straight chain alkyl which is optionally substituted with one or two hydroxyl groups; $C_3$-$C_6$ branched chain alkyl which is optionally substituted with one or two hydroxyl groups; $C_3$-$C_6$ cycloalkyl, wherein when the cycloalkyl group contains more than 3 carbon atoms, it is optionally substituted with one or two hydroxyl groups; aryl which is optionally substituted with 1 or 2 fluorine atoms, one hydroxyl group, one hydroxyl group and one fluorine atom, $C_1$-$C_6$ straight chain alkyl, $C_3$-$C_6$ branched chain alkyl or $C_3$-$C_6$ cycloalkyl, and wherein if the $C_1$-$C_6$ straight chain alkyl group, the $C_3$-$C_6$ branched chain alkyl group or the $C_3$-$C_6$ cycloalkyl group is substituted, then no more than one heteroatom selected from the oxygen atom in the hydroxyl group and the sulfur atom in —SO$_2$R$^{vii}$ is bound to any single carbon atom; arylalkyl in which the alkyl portion contains from 1 to 6 carbon atoms; heteroaryl; or heteroarylalkyl in which the alkyl portion contains from 1 to 6 carbon atoms; or when $R^v$ is not H and $R^{vi}$ is either —(CO)$R^{vii}$ or —SO$_2$$R^{vii}$, $R^v$ and $R^{vii}$ can be taken together to form a 4- to 7-membered ring;

$R^{viii}$ is hydrogen, $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —(CH$_2$)$_r$S$R^{viii}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; or $R^{viii}$ is —C(O)$R^x$;

$R^{ix}$ is $C_1$-$C_6$ straight chain alkyl optionally substituted with one or two hydroxyl groups or $C_1$-$C_6$ alkoxy groups, wherein if the $C_1$-$C_6$ straight chain alkyl group is substituted, then no more than one heteroatom selected from the oxygen atom in the hydroxyl group, the oxygen atom in the alkoxy group and the sulfur atom in —(CH$_2$)$_r$SO$_2$$R^{ix}$ is bound to any single carbon atom; $C_3$-$C_6$ branched chain alkyl; $C_3$-$C_6$ cycloalkyl; aryl that is optionally substituted with 1 or 2 fluorine atoms, one hydroxyl group, one hydroxyl group and one fluorine atom, or $C_1$-$C_6$ hydroxyalkyl; heteroaryl that is optionally substituted with 1 or 2 fluorine atoms, one hydroxyl group, one hydroxyl group and one fluorine atom, or $C_1$-$C_6$ hydroxyalkyl, wherein the number of substituents does not exceed the number of available C—H and N—H bonds; or arylalkyl in which the alkyl portion contains from 1 to 6 carbon atoms and the aryl portion is optionally substituted with 1 or 2 fluorine atoms, one hydroxyl group, one hydroxyl group and one fluorine atom, or $C_1$-$C_6$ hydroxyalkyl;

$R^x$ is $C_1$-$C_6$ straight chain alkyl optionally substituted with one or two hydroxyl groups or $C_1$-$C_6$ alkoxy groups, wherein if the $C_1$-$C_6$ alkyl group is substituted, then no more than one heteroatom selected from the oxygen atom in the hydroxyl group and the oxygen atom in the alkoxy group is bound to any single carbon atom; $C_3$-$C_6$ branched chain alkyl; $C_3$-$C_6$ cycloalkyl; aryl that is optionally substituted with 1 or 2 fluorine atoms, one hydroxyl group, or one hydroxyl group and one fluorine atom; arylalkyl in which the alkyl portion contains from 1 to 6 carbon atoms and in which the aryl portion is optionally substituted with 1 or 2 fluorine atoms, one hydroxyl group, or one hydroxyl group and one fluorine atom; heteroaryl that is optionally substituted with 1 or 2 fluorine atoms, one hydroxyl group, or one hydroxyl group and one fluorine atom, wherein the number of substituents does not exceed the number of available C—H and N—H bonds; $C_1$-$C_6$ monoalkylamino; or $C_1$-$C_6$ dialkylamino;

wherein if $R_5$ contains at least one saturated carbon atom and said $R_5$ is substituted with two substituents independently selected from $C_1$-$C_6$ alkoxy, alkoxyalkoxy in which the alkoxy portions each independently contain from 1 to 6 carbon atoms, F, —OH, —NH$_2$, $C_1$-$C_6$ monoalkylamino, $C_1$-$C_6$ dialkylamino, and $C_1$-$C_6$ alkylthio, then said two substituents are not bound to the same saturated carbon atom;

m is 1;

n is an integer ranging from 1 to 2;

p is an integer ranging from 0 to 2;

wherein when n is 2 or p is 2, the carbon atom linked to the oxygen atom can be substituted with a $C_1$-$C_6$ straight chain alkyl group or a $C_3$-$C_6$ branched chain alkyl group;

q is an integer ranging from 1 to 5;

r is an integer ranging from 0 to 5;

and pharmaceutically acceptable derivatives thereof; and with the proviso that when m is 1 and Y is a bond, $R_5$ is not —(CH$_2$)$_r$N$R^v$$R^{vi}$ when $R^v$ and $R^{vi}$ are each independently hydrogen, $C_1$-$C_6$ straight chain alkyl, $C_3$-$C_6$ branched chain alkyl or $C_3$-$C_6$ cycloalkyl.

3. The compound of claim 1, wherein Z is a 1,2-disubstituted cyclopropyl ring and $R_5$ is $C_1$-$C_6$ hydroxyalkyl.

4. The compound of claim 1, wherein Y is a bond.

5. The compound of claim 1, wherein Z is a 1,2-disubstituted cyclopropyl group.

6. The compound of claim 1, wherein $R_5$ is $C_1$-$C_6$ hydroxyalkyl.

7. The compound of claim 1, wherein Y is a bond, Z is a 1,2-disubstituted cyclopropyl ring and $R_5$ is $C_1$-$C_6$ hydroxyalkyl.

8. The compound of claim 1, wherein Y is —CH$_2$—, Z is a 1,2-disubstituted cyclopropyl ring and $R_5$ is —CH$_2$OH.

9. The compound of claim 1, wherein Y is —(CH$_2$)$_2$—, Z is a 1,2-disubstituted cyclopropyl ring and $R_5$ is —(CH$_2$)$_2$OH.

10. The compound of claim 1, wherein Y is a bond, n is 1, p is 0, $R_2$, $R_3$ and $R_4$ are each hydrogen, Z is a 1,2-disubstituted cyclopropyl ring and $R_5$ is —CH$_2$CH$_2$OH.

11. The compound of claim 1, wherein Y is a bond, n is 1, p is 0, $R_2$, $R_3$ and $R_4$ are each hydrogen, Z is a 1,2-disubstituted cyclopropyl ring and $R_5$ is $C_1$-$C_6$ fluoroalkyl.

12. The compound of claim 1, wherein Y is a bond, n is 1, p is 0, $R_2$, $R_3$ and $R_4$ are each hydrogen, Z is a 1,2-disubstituted cyclopropyl ring and $R_5$ is —CH$_2$CH$_2$F.

13. The compound of claim 1, wherein Y is a bond, Z is a 1,2-disubstituted cyclopropyl ring, and $R_5$ is —CH$_2$OCH$_3$, —CH$_2$CH$_2$OCH$_3$ or —CH$_2$CH$_2$OCH$_2$CF$_3$.

14. The compound of claim 1, wherein Y is a bond, n is 1, p is 0, $R_1$, $R_2$, $R_3$, and $R_4$ are each hydrogen, Z is a 1,2-disubstituted cyclopropyl ring, and $R_5$ is $C_1$-$C_6$ hydroxyalkyl.

15. The compound of claim 1, wherein Y is a bond, n is 1, p is 0, $R_1$, $R_2$, $R_3$, and $R_4$ are each hydrogen, Z is a 1,2-disubstituted cyclopropyl ring, and $R_5$ is alkoxyalkyl in which the alkoxy and the alkyl portions each independently contain from 1 to 6 carbon atoms and said alkoxyalkyl is optionally substituted with one or two substituents independently selected from $C_1$-$C_6$ straight chain alkyl; $C_3$-$C_6$ branched chain alkyl; $C_1$-$C_6$ fluoroalkyl; $C_1$-$C_6$ hydroxyalkyl; aryloxy; heteroaryloxy; $C_3$-$C_6$ cycloalkyloxy; $C_1$-$C_6$ alkoxy; alkoxyalkyl in which the alkoxy and alkyl portions each independently contain from 1 to 6 carbon atoms; alkoxyalkoxy in which the alkoxy portions each independently contain from 1 to 6 carbon atoms; F; —OH; —NH$_2$; $C_1$-$C_6$ alkylthio; —CF$_3$; $C_1$-$C_6$ monoalkylamino; $C_1$-$C_6$ dialkylamino; carboxyl; and $C_2$-$C_6$ alkoxycarbonyl.

16. The compound of claim 1, wherein Y is a bond, n is 1, p is 0, $R_1$, $R_2$, $R_3$, and $R_4$ are each hydrogen, Z is a 1,2-disubstituted cyclopropyl ring, and $R_5$ is —CH$_2$CH$_2$OH.

17. The compound of claim 1, wherein said compound is 2-[(1R,2S)-2-[5-(2(S)-azetidinyl)methoxy]-3-pyridyl]cyclopropyl]ethanol and pharmaceutically acceptable salts thereof.

18. The compound of claim 1, wherein said compound is 3-[(2(S)-azetidinyl)methoxy]-5 -[(1S,2R)-2-(2-fluoroethyl)cyclopropyl]pyridine and pharmaceutically acceptable salts thereof.

19. The compound of claim 1, wherein said compound is 3-[(2(S)-azetidinyl)methoxy]-5-[(1S,2R)-2-(2-methoxyethyl)cyclopropyl]pyridine and pharmaceutically acceptable salts thereof.

\* \* \* \* \*